US008501750B2

(12) United States Patent
Kuroita et al.

(10) Patent No.: US 8,501,750 B2
(45) Date of Patent: Aug. 6, 2013

(54) HETEROCYCLIC COMPOUND AND USE THEREOF

(75) Inventors: Takanobu Kuroita, Osaka (JP); Hideyuki Igawa, Osaka (JP); Hiroki Sakamoto, Osaka (JP); Kouhei Asano, Osaka (JP); Minoru Sasaki, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 688 days.

(21) Appl. No.: 12/451,602

(22) PCT Filed: May 20, 2008

(86) PCT No.: PCT/JP2008/059286
§ 371 (c)(1),
(2), (4) Date: Nov. 20, 2009

(87) PCT Pub. No.: WO2008/143262
PCT Pub. Date: Nov. 27, 2008

(65) Prior Publication Data
US 2010/0137281 A1    Jun. 3, 2010

(30) Foreign Application Priority Data

May 21, 2007 (JP) .................................. 2007-134840

(51) Int. Cl.
| C07D 495/04 | (2006.01) |
| A61K 31/519 | (2006.01) |
| C07D 239/545 | (2006.01) |
| C07D 513/04 | (2006.01) |
| C07D 471/02 | (2006.01) |
| C07D 243/06 | (2006.01) |
| C07D 235/00 | (2006.01) |
| A61K 31/4365 | (2006.01) |
| A61K 31/5513 | (2006.01) |
| A61K 31/4188 | (2006.01) |
| A61K 31/506 | (2006.01) |

(52) U.S. Cl.
USPC ........ 514/260.1; 544/278; 544/255; 544/117; 544/310; 546/113; 514/300; 514/220; 514/387; 514/234.2; 514/274; 540/495; 548/303.7

(58) Field of Classification Search
USPC ...................... 544/278; 514/260.1
See application file for complete search history.

(56) References Cited

U.S. PATENT DOCUMENTS

| 5,162,326 A | 11/1992 | Naka et al. |
| 5,243,054 A | 9/1993 | Naka et al. |
| 5,284,661 A | 2/1994 | Morimoto et al. |
| 5,304,565 A | 4/1994 | Morimoto et al. |
| 5,354,766 A | 10/1994 | Naka et al. |
| 5,389,641 A | 2/1995 | Naka et al. |
| 5,463,073 A | 10/1995 | Takehiko et al. |
| 5,583,141 A | 12/1996 | Naka et al. |
| 5,736,555 A | 4/1998 | Naka et al. |
| 5,883,111 A | 3/1999 | Naka et al. |
| 6,100,252 A | 8/2000 | Naka et al. |

FOREIGN PATENT DOCUMENTS

| EP | 520423 | * 12/1992 |
| JP | 04-330072 A | 11/1992 |
| JP | 05-059062 A | 3/1993 |
| JP | 05-155862 A | 6/1993 |
| JP | 05-163267 A | 6/1993 |
| JP | 05-271228 A | 10/1993 |
| JP | 07-061986 A | 3/1995 |
| WO | WO 2006/130901 A1 | 12/2006 |

OTHER PUBLICATIONS

International Search Report mailed Aug. 5, 2008, in prior PCT/JP2008/059286, five pages.
Ferrari et al,. "Development of tetrazole bioisosteres in angiotensin II antagonists," Bioorganic & Medicinal Chemistry Letters, 1994, 4(1):45-50.

* cited by examiner

*Primary Examiner* — Susanna Moore
(74) *Attorney, Agent, or Firm* — Foley & Lardner LLP

(57) ABSTRACT

Heterocyclic compounds, pharmaceutical agent and methods thereof, having superior pharmacological action and/or physicochemical properties, which are useful for the prophylaxis or treatment of circulatory diseases such as hypertension, cardiac diseases, arteriosclerosis, renal diseases and cerebral apoplexy and/or metabolic diseases such as hyperlipidemia, obesity and diabetes and/or central nervous disorders such as cerebral infarction, and/or mental diseases such as dementia depression and depression.

10 Claims, No Drawings

HETEROCYCLIC COMPOUND AND USE THEREOF

TECHNICAL FIELD

The present invention relates to a novel heterocyclic compound having superior properties as a pharmaceutical agent, a production method thereof and use thereof. More particularly, the present invention relates to a heterocyclic compound having a particular structure, which has an angiotensin II receptor antagonistic action (particularly, AT1 receptor antagonistic action) and a peroxisomal proliferator-activated receptor (PPAR) agonistic action (inclusive of partial agonistic action) in combination, shows superior pharmacological actions such as strong and sustained hypotensive action, insulin sensitizing activity and the like and superior properties such as good crystallinity and stability and the like, and is useful as an agent for the prophylaxis or treatment of circulatory diseases such as hypertension, cardiac diseases (cardiac hypertrophy, cardiac failure, cardiac infarction and the like), arteriosclerosis, renal diseases (diabetic nephropathy, chronic glomerulonephritis and the like), cerebral apoplexy and the like and/or metabolic diseases such as hyperlipidemia (inclusive of hyper-triglycerid(TG)-emia, hypercholesterolemia, hypoHDL-emia, postprandial hyperlipemia and the like), obesity, diabetes and the like, central nervous disorders such as cerebral infarction and the like, mental diseases such as dementia, depression and the like, and the like, or a salt thereof, or a prodrug thereof, a production method thereof, use thereof and the like.

BACKGROUND OF THE INVENTION

JP-A-4-330072 describes a compound represented by the formula

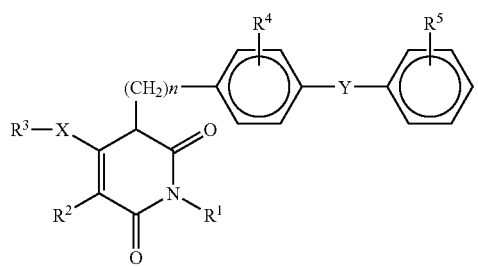

wherein $R^1$ is a hydrogen atom or an optionally substituted hydrocarbon residue; $R^2$ is a hydrogen atom, halogen, nitro group, optionally substituted amino group, formyl group or an optionally substituted hydrocarbon residue; $R^3$ is an optionally substituted hydrocarbon residue; $R^4$ is a hydrogen atom, halogen or nitro group; $R^5$ is a residue capable of forming or convertible to an anion; X is a bond or a spacer having one atomic length and containing an oxygen atom, a nitrogen atom or a sulfur atom; Y is a direct bond or a spacer having atomic length of two or less between the phenylene group and the phenyl group; n is an integer of 1 or 2; or a salt thereof, and that the compound has an angiotensin II antagonistic action and a hypotensive action, and is useful as a therapeutic agent for circulatory diseases (see patent document 1).

JP-A-7-61986 describes a compound represented by the formula

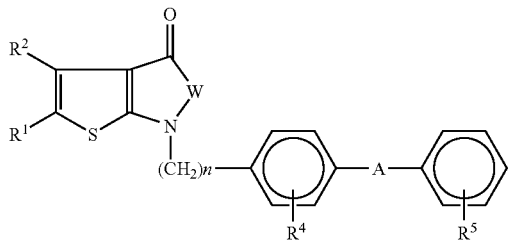

wherein W is a group represented by the formula

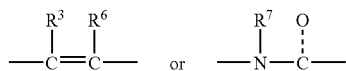

$R^1$ and $R^2$ are each independently a hydrogen atom, halogen, a cyano group, a nitro group, an acylamino group or an optionally substituted hydrocarbon residue; $R^3$ is a hydrogen atom, an optionally substituted alkyl group or alkenyl group, or —COD wherein D is a hydrogen atom, an alkoxy group, a hydroxyl group, halogen or an optionally substituted amino group, $R^4$ is a hydrogen atom, halogen or a nitro group; $R^5$ is a residue capable of forming or convertible to an anion; $R^6$ is a hydrogen atom or an optionally substituted alkyl group or alkenyl group; $R^7$ is an optionally substituted hydrocarbon residue; A is a direct bond or a spacer having atomic length of two or less between the phenylene group and the phenyl group; n is an integer of 1 or 2, or a salt thereof, and that the compound has an angiotensin II antagonistic action and a hypotensive action, and is useful as a therapeutic agent for circulatory diseases (see patent document 2).

JP-A-5-155862 describes a compound represented by the formula

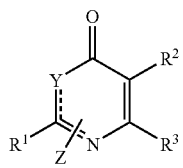

wherein $R^1$ is an optionally substituted hydrocarbon residue optionally bonded via a hetero atom; $R^2$ and $R^3$ are each independently a hydrogen atom, a cyano group, a nitro group, —CO-D wherein D is an alkoxy group, a hydroxyl group, halogen or an optionally substituted amino group, or an optionally substituted lower alkyl group, or $R^2$ and $R^3$ may be bonded to each other to form a benzene ring optionally having substituent(s); Y is N or CH; Z shows that a group represented by the formula

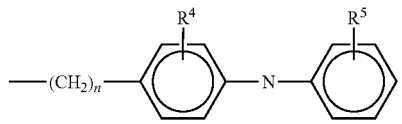

wherein R⁴ is a hydrogen atom, halogen or a nitro group; R⁵ is a residue capable of forming or convertible to an anion; X is a direct bond or a spacer having atomic length of two or less between the phenylene group and the phenyl group; and n is an integer of 1 or 2, is bonded to a ring via a ring nitrogen atom; and a broken line shows the presence of one double bond, or a salt thereof, and that the compound has an angiotensin II antagonistic action and a hypotensive action, and is useful as a therapeutic agent for circulatory diseases (see patent document 3).

JP-A-5-59062 describes a compound represented by the formula

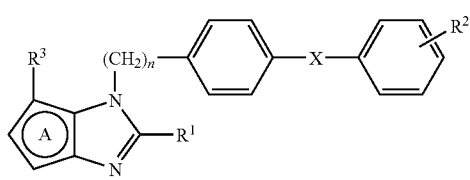

wherein ring A is a thiophene ring optionally further having substituent(s); $R^1$ is a hydrogen atom, or an optionally substituted hydrocarbon residue optionally bonded via a hetero atom; $R^2$ and $R^3$ are each independently a residue capable of forming or convertible to an anion; X a direct bond or a spacer having atomic length of two or less between the phenylene group and the phenyl group; n is an integer of 1 or 2, or a salt thereof, and that the compound has an angiotensin II antagonistic action and hypotensive action, and is useful as a therapeutic agent for circulatory disease (see patent document 4).

JP-A-5-163267 describes a compound represented by the formula

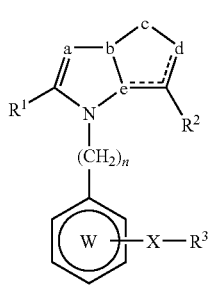

wherein $R^1$ is an optionally substituted hydrocarbon residue optionally bonded via a hetero atom; $R^2$ is a residue capable of forming or convertible to an anion; $R^3$ is an optionally substituted aromatic hydrocarbon residue or an optionally substituted heterocyclic residue; X is a direct bond or a spacer having atomic length of two or less; W is an optionally substituted aromatic hydrocarbon residue or an optionally substituted heterocyclic residue; a, c and d are each independently a carbon atom or a hetero atom, each of which may be substituted; b and e are each independently a carbon atom or a nitrogen atom, each of which may be substituted, or a salt thereof, and that the compound has an angiotensin II antagonistic action and a hypotensive action, and is useful as a therapeutic agent for circulatory diseases (see patent document 5).

JP-A-5-271228 describes a compound represented by the formula

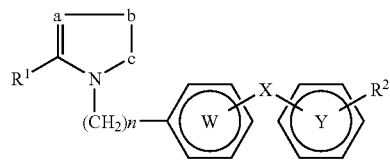

wherein $R^1$ is an optionally substituted hydrocarbon residue optionally bonded via a hetero atom; $R^2$ is an optionally substituted 5- to 7-membered heterocyclic residue; X is a direct bond or a spacer having atomic length of two or less between ring Y and ring W; W and Y are each independently an aromatic hydrocarbon residue or a heterocyclic residue, each of which may be substituted; n is an integer of 1 or 2; a and b constituting the heterocyclic residue are each independently a carbon atom or a hetero atom, each of which may be substituted; c is a carbon atom or a hetero atom, each of which may be substituted, or substituents on the adjacent two ring-constituting atoms may be bonded to each other to form a 5- or 6-membered ring together with the ring-constituting atoms in a group represented by the formula

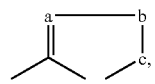

or a salt thereof, and that the compound has an angiotensin II antagonistic action, a hypotensive action and a central nervous system action, and is useful as a therapeutic agent for circulatory diseases, Alzheimer's disease, senile dementia and the like (see patent document 6).

WO 2006/130901 discloses that embusartan (the following structural formula), which is an AT1 antagonist, is a full agonist of PPARγ (see patent document 7).

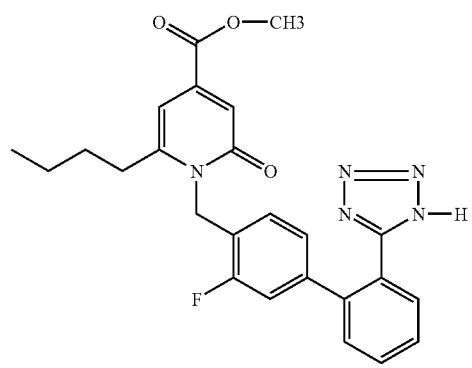 [SMILES: CCCCc1cc(C(=O)OC)cc(=O)n1Cc1ccc(-c2ccccc2-c2nnn[nH]2)cc1F]

patent document 1: U.S. Pat. No. 5,162,326
patent document 2: U.S. Pat. No. 5,284,661
patent document 3: U.S. Pat. No. 5,304,565
patent document 4: U.S. Pat. No. 5,463,073
patent document 5: U.S. Pat. No. 5,389,641
patent document 6: EP-A-0520423
patent document 7: WO 2006/130901

DISCLOSURE OF THE INVENTION

Problems to be Solved by the Invention

An object of the present invention is to provide a compound having a superior pharmacological action, physicochemical properties and the like, which is useful as an agent for the prophylaxis or treatment of circulatory diseases such as hypertension, cardiac diseases (cardiac hypertrophy, cardiac failure, cardiac infarction and the like), arteriosclerosis, renal diseases (diabetic nephropathy, chronic glomerulonephritis and the like), cerebral apoplexy and the like and/or metabolic diseases such as hyperlipidemia (inclusive of hyper-triglycerid(TG)-emia, hypercholesterolemia, hypoHDL-emia, postprandial hyperlipemia and the like), obesity, diabetes and the like, central nervous disorders such as cerebral infarction and the like, mental diseases such as dementia, depression and the like, and the like.

Means of Solving the Problems

The present inventors have first found that a heterocyclic compound represented by the following formula (I) has an angiotensin II receptor antagonistic action (particularly, AT1 receptor antagonistic action) and a peroxisomal proliferator-activated receptor (PPAR) agonistic action (including partial agonistic action), and is useful for the prophylaxis or treatment of circulatory diseases such as hypertension, cardiac diseases (cardiac hypertrophy, cardiac failure, cardiac infarction and the like), arteriosclerosis, renal diseases (diabetic nephropathy, chronic glomerulonephritis and the like), cerebral apoplexy and the like and/or metabolic diseases such as hyperlipidemia (inclusive of hyper-triglycerid(TG)-emia, hypercholesterolemia, hypoHDL-emia, postprandial hyperlipemia and the like), obesity, diabetes and the like, central nervous disorders such as cerebral infarction and the like, mental diseases such as dementia, depression and the like, and the like. Based on this finding, they have conducted intensive studies and completed the present invention.

Accordingly, the present invention relates to

[1] a compound represented by the formula (I):

(I)

wherein a group represented by the formula:

is a group represented by the formula (a):

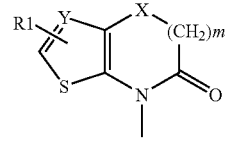
(a)

wherein,

R1 is a hydrogen atom, a $(C_1-C_6)$alkyl group optionally having substituent(s), a $(C_2-C_6)$alkenyl group optionally having substituent(s), a $(C_3-C_6)$cycloalkyl group optionally having substituent(s), a $(C_1-C_6)$alkoxy group optionally having substituent(s), a $(C_1-C_6)$alkylthio group optionally having substituent(s), a $(C_1-C_6)$alkylsulfinyl group optionally having substituent(s), or a $(C_1-C_6)$alkylsulfonyl group optionally having substituent(s);

X is a group represented by the formula: CO—X1, S(O)n-X1 or (R2)C=C(R3) wherein X1 is a group represented by the formula: N(R4) or (R5)C(R6) wherein R4 and R5 are each a hydrogen atom, a $(C_1-C_6)$alkyl group optionally having substituent(s), or a cyclic group optionally having substituent(s), and R6 is a $(C_1-C_6)$alkyl group optionally having substituent(s), R2 is a hydrogen atom, a $(C_1-C_6)$alkyl group optionally having substituent(s), a $(C_1-C_6)$alkoxy group optionally having substituent(s), a $(C_1-C_6)$alkylthio group optionally having substituent(s), a $(C_1-C_6)$alkylsulfinyl group optionally having substituent(s), or a $(C_1-C_6)$alkylsulfonyl group optionally having substituent(s), R3 is a hydrogen atom, a $(C_1-C_6)$alkyl group optionally having substituent(s), or a cyclic group optionally having substituent(s), and n is 1 or 2;

Y is N or a group represented by the formula: C(R7) wherein R7 is a hydrogen atom, or a $(C_1-C_6)$alkyl group optionally having substituent(s); and m is 0 or 1, provided when m is 1, R3 or R4 is optionally bonded to a carbon atom, which is adjacent to the nitrogen atom or carbon atom bonded thereto, to form a ring, a group represented by the formula (b):

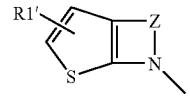
(b)

wherein,

R1' is as defined for the aforementioned R1; and

Z is a group represented by the formula: (R8)N—CO or N=C(R9) wherein R8 is a hydrogen atom, a $(C_1-C_6)$alkyl group optionally having substituent(s), or a cyclic group optionally having substituent(s), and R9 is a $(C_1-C_6)$alkoxy group optionally having substituent(s), a $(C_1-C_6)$alkylthio group optionally having substituent(s), a $(C_1-C_6)$alkylsulfinyl group optionally having substituent(s), or a $(C_1-C_6)$alkylsulfonyl group optionally having substituent(s), a group represented by the formula (c):

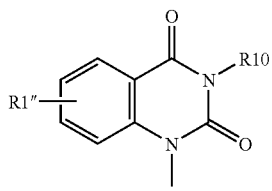

wherein,
R1" is as defined for the aforementioned R1; and
R10 is a hydrogen atom, a $(C_1-C_6)$alkyl group optionally having substituent(s), or a cyclic group optionally having substituent(s), or
a group represented by the formula (d):

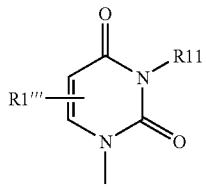

wherein,
R1''' is as defined for the aforementioned R1; and
R11 is a hydrogen atom, a $(C_1-C_6)$alkyl group having substituent(s), or a cyclic group optionally having substituent(s); and
R is a group represented by the formula:

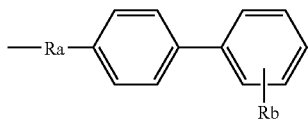

wherein,
Ra is a $(C_1-C_6)$alkylene group optionally having substituent(s), or a group represented by the formula: —O—Rc—, -Rc-O—, —N(Rd)-Rc- or -Rc-N(Rd)- wherein Rc is a bond, or a $(C_1-C_6)$alkylene group optionally having substituent(s), and Rd is a $(C_1-C_6)$alkyl group optionally having substituent(s), or a $(C_3-C_6)$cycloalkyl group optionally having substituent(s); and
Rb is a group represented by the formula:

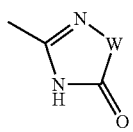

wherein W is an oxygen atom or a sulfur atom, which optionally has substituent(s), wherein the biphenyl group optionally further having substituent(s),
or a salt thereof (hereinafter to be also referred to as compound (I)),

[2] the compound of the above-mentioned [1], which is represented by the formula:

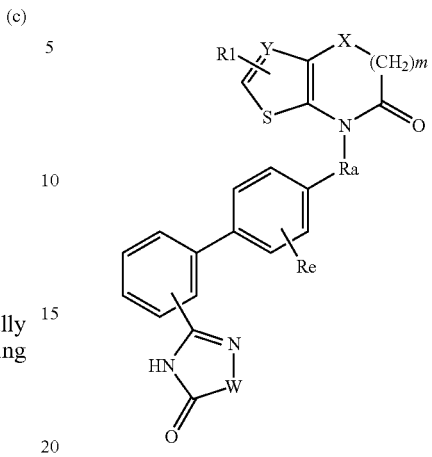

wherein R1, Ra, W, X, Y and m are each as defined in the above-mentioned [1], and Re is a hydrogen atom or halogen,
[3] the compound of the above-mentioned [2], wherein R1 is a $(C_1-C_6)$alkyl group optionally having substituent(s), a $(C_2-C_6)$alkenyl group optionally having substituent(s), or a $(C_3-C_6)$cycloalkyl group optionally having substituent(s);
Ra is a methylene group;
W is O;
X is CO—N(R4) wherein R4 is as defined in the above-mentioned [1];
Y is C(R7) wherein R7 is as defined in the above-mentioned [1];
Re is a hydrogen atom or halogen; and
m is 0,
[4] 6-ethyl-3-[2-(4-methoxyphenyl)-2-oxoethyl]-1-{[2'-(5-oxo-4,5-dihydro-1,2,4-oxadiaiol-3-yl)biphenyl-4-yl]methyl}thieno[2,3-d]pyrimidine-2,4(1H,3H)-dione or a salt thereof,
[5] 6-ethyl-3-[2-(3-fluoro-4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione or a salt thereof,
[6] 6-ethyl-3-[2-(2-fluoro-4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione or a salt thereof,
[7] 6-ethyl-1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione or a salt m thereof,
[8] 6-cyclopropyl-1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H, 3H)-dione or a salt thereof,
[9] a prodrug of the compound of the above-mentioned [1],
[10] a pharmaceutical agent comprising the compound of the above-mentioned [1] or a prodrug thereof as an active ingredient,
[11] the pharmaceutical agent of the above-mentioned [10], which has an angiotensin II receptor inhibitory activity and/or a peroxisomal proliferator-activated receptor agonistic activity,
[12] the pharmaceutical agent of the above-mentioned [10], which is a prophylactic or therapeutic agent for a circulatory disease,

[13] the pharmaceutical agent of the above-mentioned [10], which is a prophylactic or therapeutic agent for hypertension, a cardiac disease, arteriosclerosis, a renal disease, cerebral apoplexy, hyperlipidemia, obesity and/or diabetes,

[14] a method of inhibiting an angiotensin II receptor and/or activating a peroxisomal proliferator-activated receptor in a mammal, which comprises administering the compound of the above-mentioned [1] or a prodrug thereof to said mammal,

[15] a method of preventing or treating a circulatory disease in a mammal, which comprises administering the compound of the above-mentioned [1] or a prodrug thereof to said mammal,

[16] a method of preventing or treating hypertension, a cardiac disease, arteriosclerosis, a renal disease, cerebral apoplexy, hyperlipidemia, obesity and/or diabetes in a mammal, which comprises administering the compound of the above-mentioned [1] or a prodrug thereof to said mammal,

[17] use of the compound of the above-mentioned [1] or a prodrug thereof for the production of an agent having an angiotensin II receptor inhibitory activity and/or a peroxisomal proliferator-activated receptor agonistic activity,

[18] use of the compound of the above-mentioned [1] or a prodrug thereof for the production of an agent for the prophylaxis or treatment of a circulatory disease,

[19] use of the compound of the above-mentioned [1] or a prodrug thereof for the production of an agent for the prophylaxis or treatment of hypertension, a cardiac disease, arteriosclerosis, a renal disease, cerebral apoplexy, hyperlipidemia, obesity and/or diabetes, and the like.

Effect of the Invention

The compound of the present invention is useful as a medicament such as an agent for the prophylaxis or treatment of circulatory diseases such as hypertension, cardiac diseases (cardiac hypertrophy, cardiac failure, cardiac infarction and the like), arteriosclerosis, renal diseases (diabetic nephropathy, chronic glomerulonephritis and the like), cerebral apoplexy and the like and/or metabolic diseases such as hyperlipidemia (inclusive of hyper-triglycerid(TG)-emia, hypercholesterolemia, hypoHDL-emia, postprandial hyperlipemia and the like), obesity, diabetes and the like, central nervous disorders such as cerebral infarction and the like, mental diseases such as dementia, depression and the like, and the like.

DETAILED DESCRIPTION OF THE INVENTION

The definition of each symbol used in the present specification is described in detail in the following.

In the present specification, the "halogen" is fluorine, chlorine, bromine or iodine.

In the present specification, the "$(C_1-C_6)$alkyl group" is, for example, methyl, ethyl, propyl, isopropyl, butyl, isobutyl, sec-butyl, tert-butyl, pentyl, isopentyl, neopentyl, tert-pentyl, hexyl, 2,2-dimethylbutyl, 3,3-dimethylbutyl, 2-ethylbutyl or the like.

In the present specification, the "$(C_2-C_6)$alkenyl group" is, for example, vinyl, allyl, propenyl, isopropenyl, but-3-en-1-yl, pent-4-en-1-yl, hex-5-en-1-yl or the like.

In the present specification, the "$(C_2-C_6)$alkynyl group" is, for example, ethynyl, prop-2-yn-1-yl, but-3-yn-1-yl, pent-4-yn-1-yl, hex-5-yn-1-yl or the like.

In the present specification, the "$(C_3-C_6)$cycloalkyl group" is cyclopropyl, cyclobutyl, cyclopentyl or cyclohexyl.

In the present specification, the "$(C_6-C_{14})$aryl group" is, for example, phenyl, naphthyl (e.g., 1-naphthyl, 2-naphthyl), anthryl, phenanthryl or the like.

In the present specification, the "$(C_7-C_{16})$aralkyl group" is, for example, benzyl, 1-phenylethyl, 2-phenylethyl, naphthylmethyl (1-naphthylmethyl, 2-naphthylmethyl), 3-phenylpropyl, 4-phenylbutyl, 5-phenylpentyl or the like.

In the present specification, the "$(C_1-C_6)$alkoxy group" is, for example, methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, 2-ethylbutoxy or the like.

In the present specification, the "optionally halogenated $(C_1-C_6)$alkyl group" is the above-mentioned "$(C_1-C_6)$alkyl group" optionally substituted by 1 to 5 of the above-mentioned "halogen". For example, methyl, ethyl, propyl, isopropyl, butyl, tert-butyl, isobutyl, trifluoromethyl and the like can be mentioned.

In the present specification, the "optionally halogenated $(C_1-C_6)$alkoxy group" is the above-mentioned "$(C_1-C_6)$alkoxy group" optionally substituted by 1 to 5 of the above-mentioned "halogen". For example, methoxy, ethoxy, propoxy, isopropoxy, butoxy, tert-butoxy, trifluoromethoxy, 2-fluoroethoxy, trifluoroethoxy and the like can be mentioned.

In the present specification, the "heterocyclic group" is, unless otherwise specified, aromatic heterocyclic group and nonaromatic heterocyclic group can be mentioned.

Here, as the aromatic heterocyclic group, for example, a 4- to 7-membered (preferably 5- or 6-membered) monocyclic aromatic heterocyclic group and a condensed aromatic heterocyclic group, each containing, as ring-constituting atom besides carbon atom, 1 to 4 hetero atoms selected from oxygen atom, sulfur atom and nitrogen atom, can be mentioned. As the condensed aromatic heterocyclic group, for example, a group induced from a ring obtained by condensation of a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), 5-membered aromatic heterocycle containing one sulfur atom (e.g., thiophene) and a benzene ring and the like can be mentioned.

The "aromatic heterocyclic group" is, for example, a monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl or the like; or an aromatic fused heterocyclic group such as benzofuranyl, isobenzofuranyl, benzo[b]thienyl, indolyl, isoindolyl, 1H-indazolyl, benzimidazolyl, benzoxazolyl, benzo[d]isoxazolyl, benzothiazolyl, benzo[d]isothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-a]pyridazinyl, imidazo[1,2-a]pyrimidinyl, 1,2,4-triazolo[4,3-a]pyridyl, 1,2,4-triazolo[4,3-b]pyridazinyl or the like.

As the nonaromatic heterocyclic group, for example, 4- to 7-membered (preferably 5- or 6-membered) monocyclic nonaromatic heterocyclic group and condensed nonaromatic heterocyclic group, each of which containing, as ring-constituting atom besides carbon atom, 1 to 4 hetero atoms selected from oxygen atom, sulfur atom and nitrogen atom, can be mentioned. As the condensed nonaromatic heterocyclic group, for example, a group induced from a ring obtained by condensation of a ring corresponding to the 4- to 7-membered monocyclic nonaromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), 5-membered aromatic heterocycle containing one sulfur atom (e.g., thiophene) and a benzene ring, and a group obtained by partial saturation of the group, and the like can be mentioned.

The "nonaromatic heterocyclic group" is, for example, a monocyclic nonaromatic heterocyclic group such as azetidinyl, oxetanyl, thietanyl, pyrrolidinyl, tetrahydrofuryl, thiolanyl, imidazolidinyl, pyrazolidinyl, oxazolidinyl, thiazolidinyl, piperidyl, tetrahydropyranyl, morpholinyl, thiomorpholinyl, piperazinyl or the like; or a nonaromatic fused heterocyclic group such as isochromanyl, dihydrobenzopyranyl, isochromenyl, chromenyl (2H-chromenyl, 4H-chromenyl), 1,2,3,4-tetrahydroisoquinolyl, 1,2,3,4-tetrahydroquinolyl, 2,3-dihydrobenzofuranyl, benzo[1,3]dioxolyl or the like.

In the present specification, the "$(C_3$-$C_6)$cycloalkyloxy group" is cyclopropyloxy, cyclobutyloxy, cyclopentyloxy or cyclohexyloxy.

In the present specification, the "$(C_6$-$C_{14})$aryloxy group" is, for example, phenoxy, 1-naphthyloxy, 2-naphthyloxy or the like.

In the present specification, the "$(C_7$-$C_{16})$aralkyloxy group" is, for example, benzyloxy, phenethyloxy or the like.

In the present specification, the "$(C_1$-$C_6)$alkylamino group" is, for example, an amino group monosubstituted by the above-mentioned "$(C_1$-$C_6)$alkyl group". Specific examples thereof include methylamino, ethylamino, propylamino, isopropylamino, butylamino, isobutylamino, sec-butylamino, tert-butylamino, pentylamino, isopentylamino, neopentylamino, tert-pentylamino, hexylamino and the like.

In the present specification, the "di$(C_1$-$C_6)$alkylamino group" is, for example, an amino group disubstituted by the above-mentioned "$(C_1$-$C_6)$alkyl group". Specific examples thereof include dimethylamino, diethylamino, N-ethyl-N-methylamino and the like.

In the present specification, the "$(C_6$-$C_{14})$arylamino group" is, for example, an amino group monosubstituted by the above-mentioned "$(C_6$-$C_{14})$aryl group". Specific examples thereof include phenylamino, 1-naphthylamino, 2-naphthylamino and the like.

In the present specification, the "di$(C_6$-$C_{14})$arylamino group" is, for example, an amino group disubstituted by the above-mentioned "$(C_6$-$C_{14})$aryl group". Specific examples thereof include diphenylamino, dinaphthylamino and the like.

In the present specification, the "$(C_7$-$C_{16})$aralkylamino group" is, for example, an amino group monosubstituted by the above-mentioned "$(C_7$-$C_{16})$aralkyl group". Specific examples thereof include benzylamino, phenethylamino and the like.

In the present specification, the "di$(C_7$-$C_{16})$aralkylamino group" is, for example, an amino group disubstituted by the above-mentioned "$(C_7$-$C_{16})$aralkyl group". Specific examples thereof include dibenzylamino, diphenethylamino and the like.

In the present specification, the "N—$(C_1$-$C_6)$alkyl-N—$(C_6$-$C_{14})$arylamino group" is, for example, an amino group substituted by the above-mentioned "$(C_1$-$C_6)$alkyl group" and the above-mentioned "$(C_6$-$C_{14})$aryl group". Examples thereof include N-methyl-N-phenylamino, N-ethyl-N-phenylamino and the like.

In the present specification, the "N—$(C_1$-$C_6)$alkyl-N—$(C_7$-$C_{16})$aralkylamino group" is, for example, an amino group substituted by the above-mentioned "$(C_1$-$C_6)$alkyl group" and the above-mentioned "$(C_7$-$C_{16})$aralkyl group". Examples thereof include N-methyl-N-benzylamino, N-ethyl-N-benzylamino and the like.

In the present specification, the "$(C_1$-$C_6)$alkyl-carbonylamino group" is, for example, acetylamino, propanoylamino, butanoylamino, 2-methylpropanoylamino, pentanoylamino, 3-methylbutanoylamino, 2,2-dimethylpropanoylamino or the like.

In the present specification, the "$(C_1$-$C_6)$alkylthio group" is, for example, methylthio, ethylthio, propylthio, isopropylthio, butylthio, sec-butylthio, tert-butylthio or the like.

In the present specification, the "$(C_1$-$C_6)$alkylsulfinyl group" is, for example, methylsulfinyl, ethylsulfinyl, propylsulfinyl, isopropylsulfinyl, butylsulfinyl, sec-butylsulfinyl, tert-butylsulfinyl or the like.

In the present specification, the "$(C_1$-$C_6)$alkylsulfonyl group" is, for example, methylsulfonyl, ethylsulfonyl, propylsulfonyl, isopropylsulfonyl, butylsulfonyl, sec-butylsulfonyl, tert-butylsulfonyl or the like.

In the present specification, the "$(C_1$-$C_6)$alkylsulfonyloxy group" is, for example, methylsulfonyloxy, ethylsulfonyloxy, propylsulfonyloxy, isopropylsulfonyloxy, butylsulfonyloxy, sec-butylsulfonyloxy, tert-butylsulfonyloxy or the like.

In the present specification, the "optionally esterified carboxy group" is, for example,
(1) a carboxy group;
(2) a $(C_1$-$C_6)$alkoxy-carbonyl group (e.g., methoxycarbonyl, ethoxycarbonyl, propoxycarbonyl, tert-butoxycarbonyl);
(3) a $(C_6$-$C_{14})$aryloxy-carbonyl group (e.g., phenoxycarbonyl);
(4) a $(C_7$-$C_{16})$aralkyloxy-carbonyl group (e.g., benzyloxycarbonyl, phenethyloxycarbonyl);
or the like.

In the present specification, the "$(C_1$-$C_6)$alkyl-carbonyl group" is, for example, acetyl, propanoyl, butanoyl, 2-methylpropanoyl, pentanoyl, 3-methylbutanoyl, 2,2-dimethylpropanoyl or the like.

In the present specification, the "$(C_1$-$C_6)$alkyl-carbonyloxy group" is, for example, acetyloxy, propanoyloxy, butanoyloxy, 2-methylpropanoyloxy, pentanoyloxy, 3-methylbutanoyloxy, 2,2-dimethylpropanoyloxy or the like.

In the present specification, the "$(C_3$-$C_{10})$cycloalkyl-carbonyl group" is, for example, cyclopentylcarbonyl, cyclohexylcarbonyl, adamantylcarbonyl or the like.

In the present specification, the "$(C_6$-$C_{14})$aryl-carbonyl group" is, for example, benzoyl, 1-naphthoyl, 2-naphthoyl or the like.

In the present specification, the "$(C_7$-$C_{16})$aralkyl-carbonyl group" is, for example, phenylacetyl, 3-phenylpropanoyl or the like.

In the present specification, the "$(C_1$-$C_6)$alkoxy-carbonyl group" is, for example, methoxycarbonyl, ethoxycarbonyl, propoxycarbonyl, tert-butoxycarbonyl or the like.

In the present specification, the "$(C_6$-$C_{14})$aryloxy-carbonyl group" is, for example, phenoxycarbonyl, 1-naphthyloxycarbonyl, 2-naphthyloxycarbonyl or the like.

In the present specification, the "$(C_7$-$C_{16})$aralkyloxy-carbonyl group" is, for example, benzyloxycarbonyl, phenethyloxycarbonyl or the like.

In the present specification, the "heterocycle" of the "heterocycle-carbonyl group" is, for example, a ring corresponding to the aromatic or nonaromatic heterocyclic group exemplified as the aforementioned heterocyclic group. Specific examples of the "heterocycle-carbonyl group" include benzofuranylcarbonyl, thienylcarbonyl, benzoimidazolylcarbonyl, pyrimidinylcarbonyl, 1-pyrrolidinylcarbonyl, piperidinocarbonyl, 1-piperazinylcarbonyl, morpholinocarbonyl, thiomorpholinocarbonyl and the like.

The "heterocycle" of the "heterocycle-carbonyl group" is optionally further substituted by 1 to 3 substituents selected from the group consisting of a $(C_1-C_6)$alkyl group, halogen and a heterocyclic group.

In the present specification, the "$(C_1-C_6)$alkyl-carbamoyl group" is, for example, a carbamoyl group monosubstituted by the above-mentioned "$(C_1-C_6)$alkyl group". Specific examples thereof include methylcarbamoyl, ethylcarbamoyl and the like, in addition to the carbonyl group.

In the present specification, the "di$(C_1-C_6)$alkyl-carbamoyl group" is, for example, a carbamoyl group disubstituted by the above-mentioned "$(C_1-C_6)$alkyl group". Specific examples thereof include dimethylcarbamoyl, diethylcarbamoyl, N-ethyl-N-methylcarbamoyl and the like.

In the present specification, the "$(C_6-C_{14})$aryl-carbamoyl group" is, for example, a carbamoyl group monosubstituted by the above-mentioned "$(C_6-C_{14})$aryl group". Specific examples thereof include phenylcarbamoyl, 1-naphthylcarbamoyl, 2-naphthylcarbamoyl and the like.

In the present specification, the "di$(C_6-C_{14})$aryl-carbamoyl group" is, for example, a carbamoyl group disubstituted by the above-mentioned "$(C_6-C_{14})$aryl group". Specific examples thereof include diphenylcarbamoyl, dinaphthylcarbamoyl and the like.

In the present specification, the "$(C_1-C_6)$alkylsulfamoyl group" is, for example, a sulfamoyl group monosubstituted by the above-mentioned "$(C_1-C_6)$alkyl group". Specific examples thereof include methylsulfamoyl, ethylsulfamoyl and the like.

In the present specification, the "di$(C_1-C_6)$alkylsulfamoyl group" is, for example, a sulfamoyl group disubstituted by the above-mentioned "$(C_1-C_6)$alkyl group". Specific examples thereof include dimethylsulfamoyl, diethylsulfamoyl, N-ethyl-N-methylsulfamoyl and the like.

In the present specification, the "$(C_6-C_{14})$arylsulfamoyl group" is, for example, a sulfamoyl group monosubstituted by the above-mentioned "$(C_6-C_{14})$aryl group". Specific examples thereof include phenylsulfamoyl, 1-naphthylsulfamoyl, 2-naphthylsulfamoyl and the like.

In the present specification, the "di$(C_6-C_{14})$arylsulfamoyl group" is, for example, a sulfamoyl group disubstituted by the above-mentioned "$(C_6-C_{14})$aryl group". Specific examples thereof include diphenylsulfamoyl, dinaphthylsulfamoyl and the like.

Of the formula (I), a group represented by the formula

is a group represented by any of the following formulas (a)-(d):

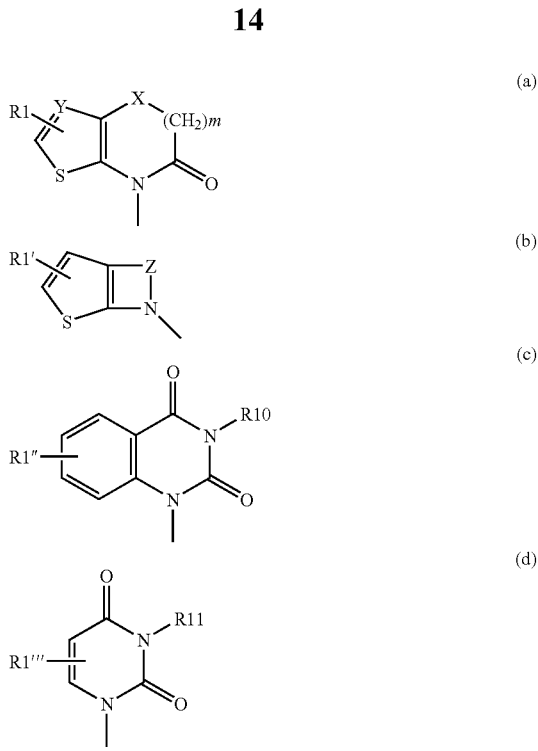

The groups represented by the formulas (a)-(d) are explained in the following.

(a group represented by the formula (a):)

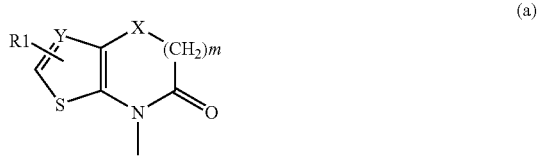

R1 is a hydrogen atom, a $(C_1-C_6)$alkyl group optionally having substituent(s), a $(C_2-C_6)$alkenyl group optionally having substituent(s), a $(C_3-C_6)$cycloalkyl group optionally having substituent(s), a $(C_1-C_6)$alkoxy group optionally having substituent(s), a $(C_1-C_6)$alkylthio group optionally having substituent(s), a $(C_1-C_6)$alkylsulfinyl group optionally having substituent(s), or a $(C_1-C_6)$alkylsulfonyl group optionally having substituent(s).

In the present specification, the "$(C_1-C_6)$alkyl group" of the "$(C_1-C_6)$alkyl group optionally having substituent(s)", the "$(C_2-C_6)$alkenyl group" of the "$(C_2-C_6)$alkenyl group optionally having substituent(s)", the "$(C_1-C_6)$alkoxy group" of the "$(C_1-C_6)$alkoxy group optionally having substituent(s)", the "$(C_1-C_6)$alkylthio group" of the "$(C_1-C_6)$alkylthio group optionally having substituent(s)", the "$(C_1-C_6)$alkylsulfinyl group" of the "$(C_1-C_6)$alkylsulfinyl group optionally having substituent(s)", and the "$(C_1-C_6)$alkylsulfonyl group" of the "$(C_1-C_6)$alkylsulfonyl group optionally having substituent(s)" each optionally have 1 to 5, preferably 1 to 3, substituents at substitutable positions.

Such substituent includes, for example, a group consisting of
(1) halogen,
(2) a hydroxy group,
(3) an amino group,
(4) a nitro group, (5) a cyano group,
(6) an imino group optionally having substituent(s),
(7) a $(C_1-C_3)$alkylidene group optionally having substituent(s),
(8) an optionally halogenated $(C_1-C_6)$alkoxy group,
(9) a $(C_3-C_6)$cycloalkyloxy group,
(10) a $(C_6-C_{14})$aryloxy group,
(11) a $(C_7-C_{16})$aralkyloxy group,
(12) a $(C_1-C_6)$alkylamino group,
(13) a di$(C_1-C_6)$alkylamino group,
(14) a $(C_6-C_{14})$arylamino group,
(15) a di$(C_6-C_{14})$arylamino group,
(16) a $(C_7-C_{16})$aralkylamino group,
(17) a di$(C_7-C_{16})$aralkylamino group,
(18) an N—$(C_1-C_6)$alkyl-N—$(C_6-C_{14})$arylamino group,
(19) an N—$(C_1-C_6)$alkyl-N—$(C_7-C_{16})$aralkylamino group,
(20) a $(C_1-C_6)$alkyl-carbonylamino group,
(21) a $(C_1-C_6)$alkylthio group,
(22) a $(C_1-C_6)$alkylsulfinyl group,
(23) a $(C_1-C_6)$alkylsulfonyl group,
(24) a $(C_1-C_6)$alkylsulfonyloxy group,
(25) an optionally esterified carboxy group,
(26) a $(C_1-C_6)$alkyl-carbonyl group optionally having substituent(s),
(27) a $(C_1-C_6)$alkyl-carbonyloxy group,
(28) a $(C_3-C_{10})$cycloalkyl-carbonyl group,
(29) a $(C_6-C_{14})$aryl-carbonyl group optionally having substituent(s),
(30) a $(C_7-C_{16})$aralkyl-carbonyl group,
(31) a $(C_1-C_6)$ alkoxy-carbonyl group,
(32) a heterocycle-carbonyl group,
(33) a carbamoyl group,
(34) a thiocarbamoyl group,
(35) a $(C_1-C_6)$alkyl-carbamoyl group,
(36) a di$(C_1-C_6)$alkyl-carbamoyl group,
(37) a $(C_6-C_{14})$aryl-carbamoyl group optionally substituted by 1 to 3 $(C_1-C_6)$alkoxy groups,
(38) a di$(C_6-C_{14})$aryl-carbamoyl group,
(39) a sulfamoyl group,
(40) a $(C_1-C_6)$alkylsulfamoyl group,
(41) a di$(C_1-C_6)$alkylsulfamoyl group,
(42) a $(C_6-C_{14})$arylsulfamoyl group,
(43) a di$(C_6-C_{14})$arylsulfamoyl group,
(44) a cyclic group optionally having substituent(s) and the like (hereinafter to be also referred to as substituent group A).

The "imino group optionally having substituent(s)" is, for example, an imino group optionally substituted by
(1) a hydroxy group; or
(2) a $(C_1-C_6)$alkoxy group (e.g., methoxy, ethoxy, isopropyloxy) optionally substituted by 1 to 3 substituents selected from the group consisting of
 (i) a carboxy group,
 (ii) a $(C_6-C_{14})$aryl group (e.g., phenyl),
 (iii) a $(C_1-C_6)$alkoxy-carbonyl group (e.g., ethoxycarbonyl), and
 (iv) a $(C_1-C_3)$alkylidene group (e.g., methylidene).

The "$(C_1-C_3)$alkylidene group" of the "$(C_1-C_3)$alkylidene group optionally having substituent(s)" is, for example, methylidene($CH_2$=), ethylidene ($CH_3CH$=) or propylidene ($CH_3CH_2CH$=).

The "$(C_1-C_3)$alkylidene group" optionally has 1 to 3 substituents at substitutable positions. Such substituent includes, for example, an optionally esterified carboxy group and the like.

The "$(C_1-C_6)$alkyl-carbonyl group" of the "$(C_1-C_6)$alkyl-carbonyl group optionally having substituent(s)" optionally has 1 to 5, preferably 1 to 3, substituents at substitutable positions. Such substituent includes, for example,
(1) halogen;
(2) a hydroxy group;
(3) a $(C_1-C_6)$alkoxy group optionally substituted by 1 to 3 substituents selected from
 (i) halogen (e.g., fluorine),
 (ii) a hydroxy group,
 (iii) a $(C_3-C_6)$cycloalkyl group (e.g., cyclopropyl), and
 (iv) a di$(C_1-C_6)$alkylamino group (e.g., dimethylamino);
(4) an amino group;
(5) a $(C_1-C_6)$alkylamino group;
(6) a di$(C_1-C_6)$alkylamino group;
(7) a $(C_1-C_6)$alkylthio group;
(8) a $(C_1-C_6)$alkylsulfonyl group;
(9) a $(C_3-C_6)$cycloalkyl group;
(10) a $(C_1-C_6)$alkyl-carbonyl group;
(11) a $(C_1-C_6)$alkyl-carbonyloxy group;
(12) an optionally esterified carboxy group; and the like.

The "$(C_6-C_{14})$aryl-carbonyl group" of the "$(C_6-C_{14})$aryl-carbonyl group optionally having substituent(s)" optionally has 1 to 5, preferably 1 to 3, substituents at substitutable positions. Such substituent includes, for example,
(1) halogen (e.g., fluorine);
(2) a hydroxy group;
(3) an optionally halogenated $(C_1-C_6)$alkyl group;
(4) a $(C_1-C_6)$alkoxy group optionally substituted by 1 to 3 substituents selected from
 (i) halogen (e.g., F),
 (ii) a hydroxy group,
 (iii) a $(C_3-C_6)$cycloalkyl group (e.g., cyclopropyl), and
 (iv) a di$(C_1-C_6)$alkylamino group (e.g., dimethylamino);
(5) an amino group;
(6) a $(C_1-C_6)$alkylamino group;
(7) a di$(C_1-C_6)$alkylamino group;
(8) a $(C_1-C_6)$alkylthio group;
(9) a $(C_1-C_6)$alkylsulfonyl group;
(10) a $(C_3-C_6)$cycloalkyl group;
(11) a $(C_1-C_6)$alkyl-carbonyl group;
(12) a $(C_1-C_6)$alkyl-carbonyloxy group;
(13) an optionally esterified carboxy group; and the like.

As the "cyclic group optionally having substituent(s)", those similar to the below-mentioned "cyclic group optionally having substituent(s)" for R4 can be mentioned.

The "$(C_3-C_6)$cycloalkyl group" of the "$(C_3-C_6)$cycloalkyl group optionally having substituent(s)" for R1 optionally has 1 to 5, preferably 1 to 3, substituents at substitutable positions. Such substituent includes, for example, the below-mentioned substituent group C.

R1 is preferably
(1) a hydrogen atom;
(2) a $(C_1-C_6)$alkyl group optionally substituted by 1 to 3 substituents selected from (i) halogen (e.g., fluorine), (ii) a hydroxy group, and (iii) a $(C_1-C_6)$alkoxy group;
(3) a $(C_2-C_6)$alkenyl group;
(4) an optionally halogenated (e.g., fluorine) $(C_1-C_6)$alkoxy group; or
(5) a $(C_3-C_6)$cycloalkyl group (e.g., cyclopropyl).

X is the formula: CO—X1, S(O)n-X1, or (R2)C=C(R3).
X1 is N(R4) or (R5)C(R6). That is, in the formula (a), —X—$(CH_2)m$- moiety is
(1) —CO—N(R4)-$(CH_2)m$-;
(2) —CO—(R5)C(R6)-$(CH_2)m$-;
(3) —S(O)n-N(R4)-$(CH_2)m$;
(4) —S (O)n-(R5)C(R6)-$(CH_2)m$-; or
(5) —(R2)C=C(R3)-$(CH_2)m$- (wherein n is 1 or 2, and m is 0 or 1).

In the formula, —X—(CH$_2$)m- moiety is preferably
(1) —CO—N(R4)-(CH$_2$)m-;
(2) —CO—(R5)C(R6)-(CH$_2$)m-; or
(3) —(R2)C═C(R3)-(CH$_2$)m- (wherein m is 0 or 1).

In the above-mentioned formula, R4 and R5 are each a hydrogen atom, a (C$_1$-C$_6$)alkyl group optionally having substituent(s), or a cyclic group optionally having substituent(s).

The "(C$_1$-C$_6$)alkyl group" of the "(C$_1$-C$_6$)alkyl group optionally having substituent(s)" for R4 is optionally substituted by 1 to 5, preferably 1 to 3, substituents selected from the above-mentioned substituent group A at substitutable positions.

Such substituent is preferably
(1) a hydroxy group;
(2) an amino group;
(3) an imino group optionally substituted by
  (a) a hydroxy group, or
  (b) a (C$_1$-C$_6$)alkoxy group (e.g., methoxy, ethoxy, isopropyloxy) optionally substituted by 1 to 3 substituents selected from the group consisting of (i) a carboxy group, (ii) a (C$_6$-C$_{14}$)aryl group (e.g., phenyl), (iii) a (C$_1$-C$_6$)alkoxy-carbonyl group (e.g., ethoxycarbonyl), and (iv) a (C$_1$-C$_3$)alkylidene group (e.g., methylidene);
(4) a (C$_1$-C$_3$)alkylidene group (e.g., methylidene) optionally substituted by a (C$_1$-C$_6$)alkoxy-carbonyl group (e.g., ethoxycarbonyl);
(5) a (C$_1$-C$_6$)alkoxy group (e.g., methoxy, ethoxy);
(6) a (C$_6$-C$_{14}$)aryloxy group (e.g., phenoxy);
(7) a (C$_6$-C$_{14}$)arylamino group (e.g., phenylamino);
(8) a (C$_1$-C$_6$)alkylsulfonyloxy group (e.g., methylsulfonyloxy);
(9) a (C$_1$-C$_6$)alkoxy-carbonyl group (e.g., ethoxycarbonyl);
(10) a (C$_1$-C$_6$)alkyl-carbonyl group (e.g., acetyl, 2,2-dimethylpropanoyl) optionally substituted by 1 to 3 substituents selected from
  (a) a hydroxy group, and
  (b) a (C$_1$-C$_6$)alkyl-carbonyloxy group (e.g., acetyloxy);
(11) a (C$_1$-C$_6$)alkyl-carbonyloxy group (e.g., acetyloxy);
(12) a (C$_3$-C$_{10}$)cycloalkyl-carbonyl group (e.g., cyclohexylcarbonyl, adamantylcarbonyl);
(13) a (C$_6$-C$_{14}$)aryl-carbonyl group (e.g., benzoyl, naphthoyl) optionally substituted by 1 to 3 substituents selected from
  (a) halogen (e.g., F, Cl, Br),
  (b) a carboxy group,
  (c) a (C$_1$-C$_6$)alkyl group (e.g., methyl, ethyl),
  (d) a (C$_1$-C$_6$)alkoxy group (e.g., methoxy, ethoxy) optionally substituted by 1 to 3 substituents selected from (i) halogen (e.g., F), (ii) hydroxy, (iii) a (C$_3$-C$_6$)cycloalkyl group (e.g., cyclopropyl), and (iv) a di(C$_1$-C$_6$)alkylamino group (e.g., dimethylamino), and
  (e) a (C$_1$-C$_6$)alkoxy-carbonyl group (e.g., methoxycarbonyl);
(14) a heterocycle-carbonyl group (e.g., aromatic-carbonyl group (e.g., pyridylcarbonyl, thienylcarbonyl, benzofuranylcarbonyl, benzoimidazolylcarbonyl), nonaromatic heterocycle-carbonyl group (e.g., morpholinocarbonyl)) optionally substituted by 1 to 3 substituents selected from (i) halogen (e.g., Cl, Br), (ii) a (C$_1$-C$_6$)alkyl group (e.g., methyl, ethyl) and (iii) an aromatic heterocyclic group (e.g., pyridyl);
(15) a (C$_6$-C$_{14}$)aryl-carbamoyl group optionally substituted by 1 to 3 (C$_1$-C$_6$)alkoxy groups (e.g., methoxyphenylcarbamoyl);
(16) a (C$_3$-C$_6$)cycloalkyl group (e.g., cyclopropyl) optionally substituted by (C$_6$-C$_{14}$)aryl (e.g., phenyl) optionally substituted by 1 to 3 (C$_1$-C$_6$)alkoxy groups (e.g., methoxy);
(17) a (C$_6$-C$_{14}$)aryl group (e.g., phenyl, naphthyl) optionally substituted by 1 to 3 substituents selected from
  (a) halogen (e.g., F, Cl),
  (b) a (C$_1$-C$_6$)alkyl group, and
  (c) a (C$_1$-C$_6$)alkoxy group (e.g., methoxy);
(18) a heterocyclic group (aromatic heterocyclic group (e.g., thienyl, imidazolyl, pyridyl, pyrazinyl, benzofuranyl, benzimidazolyl, benzo[d]isoxazolyl) or nonaromatic heterocyclic group (e.g., oxetanyl, pyrrolidinyl, piperidyl, tetrahydropyranyl, morpholinyl, piperazinyl)) optionally substituted by 1 to 3 substituents selected from
  (a) halogen (e.g., F, Cl, Br),
  (b) a hydroxy group,
  (c) a (C$_1$-C$_6$)alkyl group optionally substituted by 1 to 3 substituents selected from (i) a hydroxy group and (ii) a (C$_1$-C$_6$)alkoxy group (e.g., methyl, methoxymethyl, hydroxymethyl), and
  (d) a (C$_1$-C$_6$)alkyl-carbonyl group (e.g., methylcarbonyl);
(hereinafter to be also referred to as substituent group B) and the like.

The "cyclic group" of the "cyclic group optionally having substituent(s)" for R4 is, for example, a cyclic hydrocarbon group or a heterocyclic group.

The "cyclic hydrocarbon group" is, for example, an alicyclic hydrocarbon group consisting of 3 to 14 carbon atoms, aromatic hydrocarbon group consisting of 6 to 14 carbon atoms or the like.

The "alicyclic hydrocarbon group" is, for example, a (C$_3$-C$_6$)cycloalkyl group (e.g., cyclopropyl, cyclobutyl, cyclopentyl, cyclohexyl), a (C$_3$-C$_6$)cycloalkenyl group (e.g., cyclopentenyl, cyclohexenyl), a (C$_5$-C$_{14}$)cycloalkadienyl group (e.g., 2,4-cyclopentadienyl, 1,3-cyclohexadienyl), an indanyl group, an adamantyl group or the like.

The "aromatic hydrocarbon group" is, for example, a (C$_6$-C$_{14}$)aryl group (e.g., phenyl, naphthyl, anthryl, phenanthryl) or the like.

As the "heterocyclic group", the aforementioned aromatic heterocyclic group (e.g., pyridyl, pyridazinyl, oxazolyl, quinolyl, pyrimidinyl, pyrazolyl) and nonaromatic heterocyclic group (e.g., 2,3-dihydrobenzofuranyl) can be mentioned.

The "cyclic group" of the "cyclic group optionally having substituent(s)" for R4 is preferably
(1) a (C$_3$-C$_6$)cycloalkyl group;
(2) a (C$_3$-C$_6$)cycloalkenyl group;
(3) an indanyl group;
(4) a (C$_6$-C$_{14}$)aryl group;
(5) a heterocyclic group
or the like.

The "cyclic group" of the "cyclic group optionally having substituent(s)" for R4 optionally has 1 to 5, preferably 1 to 3, substituents at substitutable positions. Such substituent includes, for example,
(1) halogen,
(2) an oxo group,
(3) a hydroxy group,
(4) an amino group,
(5) a nitro group,
(6) a cyano group,
(7) a (C$_1$-C$_6$)alkyl group,
(8) a (C$_2$-C$_6$)alkenyl group,
(9) a (C$_2$-C$_6$)alkynyl group,
(10) a (C$_3$-C$_6$)cycloalkyl group,
(11) a (C$_6$-C$_{14}$)aryl group optionally substituted by 1 to 3 (C$_1$-C$_6$)alkoxy groups,
(12) a (C$_7$-C$_{16}$)aralkyl group,
(13) a heterocyclic group,
(14) a (C$_1$-C$_6$)alkoxy group,

(15) a $(C_3\text{-}C_6)$cycloalkyloxy group,
(16) a $(C_6\text{-}C_{14})$aryloxy group,
(17) a $(C_7\text{-}C_{16})$aralkyloxy group,
(18) a $(C_1\text{-}C_6)$alkylamino group,
(19) a di$(C_1\text{-}C_6)$alkylamino group,
(20) a $(C_6\text{-}C_{14})$arylamino group,
(21) a di$(C_6\text{-}C_{14})$arylamino group,
(22) a $(C_7\text{-}C_{16})$aralkylamino group,
(23) a di$(C_7\text{-}C_{16})$aralkylamino group,
(24) an N—$(C_1\text{-}C_6)$alkyl-N—$(C_6\text{-}C_{14})$arylamino group,
(25) an N—$(C_1\text{-}C_6)$alkyl-N—$(C_7\text{-}C_{16})$aralkylamino group,
(26) a $(C_1\text{-}C_6)$alkyl-carbonylamino group,
(27) a $(C_1\text{-}C_6)$alkylthio group,
(28) a $(C_1\text{-}C_6)$alkylsulfinyl group,
(29) a $(C_1\text{-}C_6)$alkylsulfonyl group,
(30) an optionally esterified carboxy group,
(31) a $(C_1\text{-}C_6)$alkyl-carbonyl group,
(32) a $(C_3\text{-}C_6)$cycloalkyl-carbonyl group,
(33) a $(C_6\text{-}C_{14})$aryl-carbonyl group,
(34) a $(C_7\text{-}C_{16})$aralkyl-carbonyl group,
(35) a heterocycle-carbonyl group,
(36) a carbamoyl group,
(37) a thiocarbamoyl group,
(38) a $(C_1\text{-}C_6)$alkyl-carbamoyl group,
(39) a di$(C_1\text{-}C_6)$alkyl-carbamoyl group,
(40) a $(C_6\text{-}C_{14})$aryl-carbamoyl group optionally substituted by 1 to 3 $(C_1\text{-}C_6)$alkoxy groups,
(41) a di$(C_6\text{-}C_{14})$aryl-carbamoyl group,
(42) a sulfamoyl group,
(43) a $(C_1\text{-}C_6)$alkylsulfamoyl group,
(44) a di$(C_1\text{-}C_6)$alkylsulfamoyl group,
(45) a $(C_6\text{-}C_{14})$arylsulfamoyl group,
(46) a di$(C_6\text{-}C_{14})$arylsulfamoyl group,
(hereinafter to be also referred to as substituent group C) and the like.

Of the substituents mentioned above, the "$(C_1\text{-}C_6)$alkyl group", "$(C_2\text{-}C_6)$alkenyl group", "$(C_2\text{-}C_6)$alkynyl group", and "$(C_1\text{-}C_6)$alkoxy group" are each optionally substituted by 1 to 3 substituents selected from
(1) a $(C_1\text{-}C_6)$alkoxy group optionally substituted by 1 to 3 $(C_1\text{-}C_6)$lkoxy groups,
(2) a hydroxy group,
(3) halogen,
(4) a $(C_1\text{-}C_6)$alkylamino group,
(5) a di$(C_1\text{-}C_6)$alkylamino group,
(6) a $(C_3\text{-}C_6)$cycloalkyl group, and,
(7) a $(C_1\text{-}C_6)$alkoxy-carbonyl group.

The substituent of the "cyclic group optionally having substituent(s)" for R4 preferably includes
(1) halogen,
(2) a cyano group,
(3) an optionally halogenated $(C_1\text{-}C_6)$alkyl group,
(4) a $(C_6\text{-}C_{14})$aryl group,
(5) a $(C_1\text{-}C_6)$alkoxy group,
(6) an optionally esterified carboxy group (e.g., carboxy group, $(C_1\text{-}C_6)$alkoxy-carbonyl group),
and the like.

The "cyclic group optionally having substituent(s)" for R4 is preferably
(1) a $(C_3\text{-}C_6)$cycloalkyl group (e.g., cyclopropyl);
(2) a $(C_6\text{-}C_{14})$aryl group (e.g., phenyl) optionally substituted by 1 to 3 substituents selected from
  (a) halogen (e.g., Cl),
  (b) an optionally halogenated $(C_1\text{-}C_6)$alkyl group (e.g., trifluoromethyl),
  (c) a $(C_1\text{-}C_6)$alkoxy group (e.g., isopropyloxy),
  (d) a carboxy group, and
  (e) a $(C_1\text{-}C_6)$alkoxy-carbonyl group (e.g., methoxycarbonyl);
(3) a heterocyclic group (aromatic heterocyclic group (e.g., pyridyl, pyridazinyl, oxazolyl, quinolyl, pyrimidinyl, pyrazolyl) or nonaromatic heterocyclic group (e.g., 2,3-dihydrobenzofuranyl)) optionally substituted by 1 to 3 substituents selected from
  (a) halogen (e.g., Cl),
  (b) a cyano group,
  (c) a $(C_1\text{-}C_6)$alkyl group (e.g., methyl),
  (d) a $(C_6\text{-}C_{14})$aryl group (e.g., phenyl), and
  (e) a $(C_1\text{-}C_6)$alkoxy group (e.g., methoxy);
and the like.

R4 is preferably
(1) a hydrogen atom;
(2) a $(C_1\text{-}C_6)$alkyl group optionally substituted by 1 to 3 substituents selected from the above-mentioned substituent group B;
(3) a $(C_3\text{-}C_6)$cycloalkyl group (e.g., cyclopropyl);
(4) a $(C_6\text{-}C_{14})$aryl group (e.g., phenyl) optionally substituted by 1 to 3 substituents selected from
  (a) halogen (e.g., Cl),
  (b) an optionally halogenated $(C_1\text{-}C_6)$alkyl group (e.g., trifluoromethyl),
  (c) a $(C_1\text{-}C_6)$alkoxy group (e.g., isopropyloxy),
  (d) a carboxy group, and
  (e) a $(C_1\text{-}C_6)$alkoxy-carbonyl group (e.g., methoxycarbonyl); or
(5) a heterocyclic group (aromatic heterocyclic group (e.g., pyridyl, pyridazinyl, oxazolyl, quinolyl, pyrimidinyl, pyrazolyl) or nonaromatic heterocyclic group (e.g., 2,3-dihydrobenzofuranyl)) optionally substituted by 1 to 3 substituents selected from
  (a) halogen (e.g., Cl),
  (b) a cyano group,
  (c) a $(C_1\text{-}C_6)$alkyl group,
  (d) a $(C_6\text{-}C_{14})$aryl group (e.g., phenyl), and
  (e) a $(C_1\text{-}C_6)$alkoxy group (e.g., methoxy).

As the "$(C_1\text{-}C_6)$alkyl group optionally having substituent(s)" for R5, those similar to the "$(C_1\text{-}C_6)$alkyl group optionally having substituent(s)" for R1 can be mentioned.

As the "$(C_1\text{-}C_6)$alkyl group optionally having substituent(s)" for R5, a $(C_1\text{-}C_6)$alkyl group is preferable.

As the "cyclic group optionally having substituent(s)" for R5, those similar to the "cyclic group optionally having substituent(s)" for R4 can be mentioned.

R5 is preferably
(1) a hydrogen atom, or
(2) a $(C_1\text{-}C_6)$alkyl group.

R6 is a $(C_1\text{-}C_6)$alkyl group optionally having substituent(s).

As the "$(C_1\text{-}C_6)$alkyl group optionally having substituent(s)" for R6, those similar to the "$(C_1\text{-}C_6)$alkyl group optionally having substituent(s)" for R1 can be mentioned.

R6 is preferably a $(C_1\text{-}C_6)$alkyl group optionally substituted by a $(C_6\text{-}C_{14})$aryl group (e.g., phenyl).

R2 is a hydrogen atom, a $(C_1\text{-}C_6)$alkyl group optionally having substituent(s), a $(C_1\text{-}C_6)$alkoxy group optionally having substituent(s), a $(C_1\text{-}C_6)$alkylthio group optionally having substituent(s), a $(C_1\text{-}C_6)$alkylsulfinyl group optionally having substituent(s), or a $(C_1\text{-}C_6)$alkylsulfonyl group optionally having substituent(s).

As the "(C₁-C₆)alkyl group optionally having substituent(s)" for R2, those similar to the "(C₁-C₆)alkyl group optionally having substituent(s)" for R1 can be mentioned.

As the "(C₁-C₆)alkoxy group optionally having substituent(s)" for R2, those similar to the "(C₁-C₆)alkoxy group optionally having substituent(s)" for R1 can be mentioned.

As each of the "(C₁-C₆)alkylthio group optionally having substituent(s)", "(C₁-C₆)alkylsulfinyl group optionally having substituent(s)", and "(C₁-C₆)alkylsulfonyl group optionally having substituent(s)" for R2, those similar to the "(C₁-C₆)alkylthio group optionally having substituent(s)", "(C₁-C₆)alkylsulfinyl group optionally having substituent(s)", and "(C₁-C₆)alkylsulfonyl group optionally having substituent(s)" for R1 can be mentioned.

R2 is preferably
(1) a hydrogen atom,
(2) a (C₁-C₆)alkyl group, or
(3) a (C₁-C₆)alkoxy group.

R3 is a hydrogen atom, a (C₁-C₆)alkyl group optionally having substituent(s), or a cyclic group optionally having substituent(s).

As the "(C₁-C₆)alkyl group optionally having substituent(s)" for R3, those similar to the "(C₁-C₆)alkyl group optionally having substituent(s)" for R1 can be mentioned.

As the "(C₁-C₆)alkyl group optionally having substituent(s)" for R3, a (C₁-C₆)alkyl group optionally substituted by a (C₆-C₁₄)aryl group (e.g., phenyl) is preferable.

As the "cyclic group optionally having substituent(s)" for R3, those similar to the "cyclic group optionally having substituent(s)" for R4 can be mentioned.

R3 is preferably a (C₁-C₆)alkyl group optionally substituted by a (C₆-C₁₄)aryl group (e.g., phenyl).

Y is a nitrogen atom or formula: C(R7).

Here, R7 is a hydrogen atom, or a (C₁-C₆)alkyl group optionally having substituent(s).

Y is preferably C(R7).

As the "(C₁-C₆)alkyl group optionally having substituent(s)" for R7, those similar to the "(C₁-C₆)alkyl group optionally having substituent(s)" for R1 can be mentioned.

R7 is preferably
(1) a hydrogen atom, or
(2) a (C₁-C₆)alkyl group.

m is 0 or 1.

Here, when m is 1, R3 or R4 is optionally bonded to a carbon atom, which is adjacent to the nitrogen atom or carbon atom bonded thereto, to form a ring.

As such a ring, for example, (C₅-C₇)cycloalkane, (C₅-C₇)cycloalkene, (C₅-C₇)cycloalkadiene, a benzene ring, and 5- to 7-membered aromatic and nonaromatic heterocycles (when R4 forms the ring, it contains at least one nitrogen atom) can be mentioned.

As each of the above-mentioned (C₅-C₇)cycloalkane, (C₅-C₇)cycloalkene, (C₅-C₇)cycloalkadiene, a benzene ring, a 5- to 7-membered monocyclic aromatic heterocycle or a 5- to 7-membered monocyclic nonaromatic heterocycle, a 5- to 7-membered ring which is selected from the (C₃-C₆)cycloalkyl group, the (C₃-C₆)cycloalkenyl group, the (C₅-C₁₄)cycloalkadienyl group, as well as the monocyclic aromatic heterocyclic group and the monocyclic nonaromatic heterocyclic group (when R4 forms the ring, it contains at least one nitrogen atom), which have been exemplified as the "cyclic group" of the "cyclic group optionally having substituent(s)" for R4, can be mentioned.

When m is 1, the ring formed by R4 is preferably monocyclic nonaromatic heterocycle (e.g., pyrrolidine) containing at least one nitrogen atom.

m is preferably 0.

(a group represented by the formula (b):)

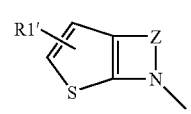

R1' is a hydrogen atom, a (C₁-C₆)alkyl group optionally having substituent(s), a (C₂-C₆)alkenyl group optionally having substituent(s), a (C₃-C₆)cycloalkyl group optionally having substituent(s), a (C₁-C₆)alkoxy group optionally having substituent(s), a (C₁-C₆)alkylthio group optionally having substituent(s), a (C₁-C₆)alkylsulfinyl group optionally having substituent(s), or a (C₁-C₆)alkylsulfonyl group optionally having substituent(s). As each of these groups, those similar to R1 in the above-mentioned formula (a) can be mentioned.

R1' is preferably a (C₁-C₆)alkyl group.

Z is the formula: (R8)N—CO or N═C(R9). Namely, the part represented by

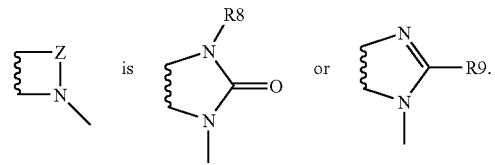

R8 is hydrogen, a (C₁-C₆)alkyl group optionally having substituent(s), or a cyclic group optionally having substituent(s).

As the "(C₁-C₆)alkyl group optionally having substituent(s)" for R8, those similar to the "(C₁-C₆)alkyl group optionally having substituent(s)" for R1 in the above-mentioned formula (a) can be mentioned.

As the "(C₁-C₆)alkyl group optionally having substituent(s)" for R8, a (C₁-C₆)alkyl group substituted by a (C₆-C₁₄)aryl group (e.g., phenyl) optionally substituted by halogen is preferable.

As the "cyclic group optionally having substituent(s)" for R8, those similar to the "cyclic group optionally having substituent(s)" for R4 of the above-mentioned formula (a) can be mentioned.

R8 is preferably a (C₁-C₆)alkyl group substituted by a (C₆-C₁₄)aryl group (e.g., phenyl) optionally substituted by halogen.

R9 is a (C₁-C₆)alkoxy group optionally having substituent(s), a (C₁-C₆)alkylthio group optionally having substituent(s), a (C₁-C₆)alkylsulfinyl group optionally having substituent(s), or a (C₁-C₆)alkylsulfonyl group optionally having substituent(s).

As the "(C₁-C₆)alkoxy group optionally having substituent(s)" for R9, those similar to the "(C₁-C₆)alkoxy group optionally having substituent(s)" for R1 can be mentioned.

As the "(C₁-C₆)alkoxy group optionally having substituent(s)" for R9, (C₁-C₆)alkoxy group and the like are preferable.

As each of the "(C₁-C₆)alkylthio group optionally having substituent(s)", "(C₁-C₆)alkylsulfinyl group optionally having substituent(s)", and "($C_1$-$C_6$)alkylsulfonyl group optionally having substituent(s)" for R9, those similar to the "($C_1$-$C_6$)alkylthio group optionally having substituent(s)", "($C_1$-$C_6$)alkylsulfinyl group optionally having substituent(s)", and "($C_1$-$C_6$)alkylsulfonyl group optionally having substituent(s)" for R1 can be mentioned.

R9 is preferably a ($C_1$-$C_6$)alkoxy group.

(a group represented by the formula (c):)

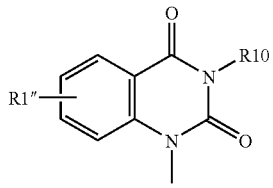

R1" is a hydrogen atom, a ($C_1$-$C_6$)alkyl group optionally having substituent(s), a ($C_2$-$C_6$)alkenyl group optionally having substituent(s), a ($C_3$-$C_6$)cycloalkyl group optionally having substituent(s), a ($C_1$-$C_6$)alkoxy group optionally having substituent(s), a ($C_1$-$C_6$)alkylthio group optionally having substituent(s), a ($C_1$-$C_6$)alkylsulfinyl group optionally having substituent(s), or a ($C_1$-$C_6$)alkylsulfonyl group optionally having substituent(s). As each of these groups, those similar to R1 in the above-mentioned formula (a) can be mentioned.

R1" is preferably
(1) a ($C_1$-$C_6$)alkyl group; or
(2) a ($C_2$-$C_6$)alkenyl group.

R10 is a hydrogen atom, a ($C_1$-$C_6$)alkyl group optionally having substituent(s), or a cyclic group optionally having substituent(s).

As the "($C_1$-$C_6$)alkyl group optionally having substituent(s)" for R10, those similar to the "($C_1$-$C_6$)alkyl group optionally having substituent(s)" for R1 in the above-mentioned formula (a) can be mentioned.

As the "($C_1$-$C_6$)alkyl group optionally having substituent(s)" for R10, a ($C_1$-$C_6$)alkyl group substituted by a ($C_6$-$C_{14}$)aryl group (e.g., phenyl) and the like are preferable.

As the "cyclic group optionally having substituent(s)" for R10, those similar to the "cyclic group optionally having substituent(s)" for R4 of the above-mentioned formula (a) can be mentioned.

R10 is preferably a ($C_1$-$C_6$)alkyl group substituted by a ($C_6$-$C_{14}$)aryl group (e.g., phenyl).

(a group represented by the formula (d):)

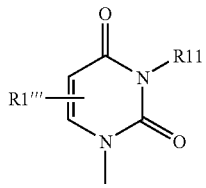

R1'" is a hydrogen atom, a ($C_1$-$C_6$)alkyl group optionally having substituent(s), a ($C_2$-$C_6$)alkenyl group optionally having substituent(s), a ($C_3$-$C_6$)cycloalkyl group optionally having substituent(s), a ($C_1$-$C_6$)alkoxy group optionally having substituent(s), a ($C_1$-$C_6$)alkylthio group optionally having substituent(s), a ($C_1$-$C_6$)alkylsulfinyl group optionally having substituent(s), or a ($C_1$-$C_6$)alkylsulfonyl group optionally having substituent(s). As each of these groups, those similar to R1 in the above-mentioned formula (a) can be mentioned.

R1'" is preferably
(1) a ($C_1$-$C_6$)alkyl group; or
(2) an optionally halogenated (e.g., fluorine) ($C_1$-$C_6$)alkoxy group.

R11 is a hydrogen atom, a ($C_1$-$C_6$)alkyl group having substituent(s), or a cyclic group optionally having substituent(s).

The substituent of the "($C_1$-$C_6$)alkyl group having substituent(s)" for R11 is, for example, the above-mentioned substituent group A.

As the "($C_1$-$C_6$)alkyl group having substituent(s)" for R11, a ($C_1$-$C_6$)alkyl group substituted by (i) a ($C_6$-$C_{14}$)aryl-carbonyl group (e.g., benzoyl) optionally having substituent(s), or (ii) a ($C_1$-$C_6$)alkyl-carbonyl group (e.g., 2,2-dimethylpropanoyl) and the like are preferable.

Here, the substituent of the "($C_6$-$C_{14}$)aryl-carbonyl group (e.g., benzoyl) optionally having substituent(s)" is preferably a ($C_1$-$C_6$)alkoxy group.

As the "cyclic group optionally having substituent(s)" for R11, those similar to the "cyclic group optionally having substituent(s)" for R4 of the above-mentioned formula (a) can be mentioned.

R11 is preferably (i) ($C_6$-$C_{14}$)aryl-carbonyl (e.g., benzoyl) substituted by a ($C_1$-$C_6$)alkoxy group, or (ii) a ($C_1$-$C_6$)alkyl group substituted by a ($C_1$-$C_6$)alkyl-carbonyl group (e.g., 2,2-dimethylpropanoyl).

In the formula (I), R is a group represented by the formula:

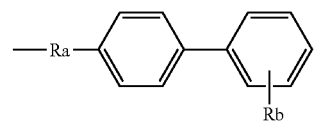

wherein the biphenyl group optionally further has substituent(s).

Ra is a ($C_1$-$C_6$)alkylene group optionally having substituent(s), or the formula: —O—Rc-, —N(Rd)-Rc- or -Rc-N(Rd)-. Here, Rc is a bond or a ($C_1$-$C_6$)alkylene group optionally having substituent(s). Rd is a ($C_1$-$C_6$)alkyl group optionally having substituent(s), or a ($C_3$-$C_6$)cycloalkyl group optionally having substituent(s).

The "($C_1$-$C_6$)alkylene group" of the "($C_1$-$C_6$)alkylene group optionally having substituent(s)" for Ra or Rc may be a straight chain or a branched chain and, for example, methylene, ethylene, —(CH$_2$)$_3$—, —(CH$_2$)$_4$—, —(CH$_2$)$_5$—, —(CH$_2$)$_6$—, —CH$_3$)—, —C(CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$— and the like can be mentioned.

The "($C_1$-$C_6$)alkylene group" of the "($C_1$-$C_6$)alkylene group optionally having substituent(s)" for Ra or Rc optionally has 1 to 3 substituents at substitutable positions.

Such substituent includes, for example,
(1) halogen (e.g., F, Cl, Br),
(2) an oxo group,
(3) a hydroxy group,
(4) a nitro group,
(5) a cyano group,
(6) an optionally halogenated ($C_1$-$C_6$)alkoxy group (e.g., methoxy, ethoxy, trifluoromethoxy),
(7) an amino group,
(8) a ($C_1$-$C_6$)alkylamino group (e.g., methylamino),
(9) a di($C_1$-$C_6$)alkylamino group (e.g., dimethylamino),
(10) a ($C_1$-$C_6$)alkyl-carbonylamino group (e.g., acetylamino), or the like.

As the "$(C_1-C_6)$alkyl group optionally having substituent(s)" for Rd, those similar to the "$(C_1-C_6)$alkyl group optionally having substituent(s)" for R1 can be mentioned.

The "$(C_3-C_6)$cycloalkyl group" of the "$(C_3-C_6)$cycloalkyl group optionally having substituent(s)" for Rd optionally has 1 to 5, preferably 1 to 3, substituents at substitutable positions. Such substituent includes, for example, the above-mentioned substituent group C.

Ra is preferably a $(C_1-C_4)$alkylene group, more preferably methylene.

In a group represented by the formula:

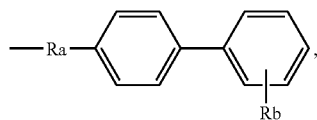

the biphenyl moiety optionally further has 1 to 3 substituents besides —Ra and —Rb at substitutable positions.

Such substituent includes, for example,
(1) halogen (e.g., F, Br),
(2) a hydroxy group,
(3) a nitro group,
(4) a cyano group,
(5) an optionally halogenated $(C_1-C_6)$alkyl group,
(6) an optionally halogenated $(C_1-C_6)$alkoxy group,
(7) an amino group,
(8) a $(C_1-C_6)$alkylamino group,
(9) a di$(C_1-C_6)$alkylamino group,
(10) a $(C_1-C_6)$alkyl-carbonylamino group,
or the like.

The further substituent is preferably
(1) halogen (e.g., F, Br),
(2) a $(C_1-C_6)$alkyl group (e.g., methyl, butyl),
(3) a $(C_1-C_6)$alkoxy group (e.g., methoxy),
or the like.

It is particularly preferably halogen.

Preferable specific examples of a biphenyl group optionally having substituent(s) include

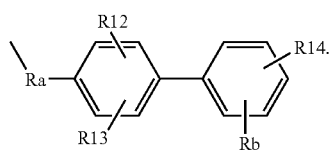

Here, Ra is as defined above. Rb is as mentioned below.

R12, R13 and R14 are each a hydrogen atom or those similar to the aforementioned further substituent. R12, R13 and R14 may be the same or different.

R12, R13 and R14 are preferably each independently
(1) a hydrogen atom;
(2) halogen (e.g., F, Br);
(3) a $(C_1-C_6)$alkyl group (e.g., methyl, butyl); or
(4) a $(C_1-C_6)$alkoxy group (e.g., methoxy),
more preferably each independently a hydrogen atom or fluorine.

Preferable other specific examples of a biphenyl group optionally having substituent(s) include

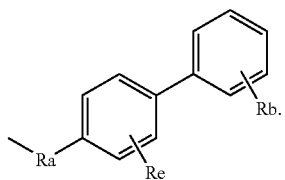

Here, Ra is as defined above. Rb is as mentioned below.

Re is a hydrogen atom or halogen (e.g., F, Br).

Rb is a group represented by the formula:

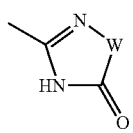

wherein W is an oxygen atom or a sulfur atom, particularly preferably an oxygen atom.

The group represented by the above-mentioned formula has a tautomer shown below, which is encompassed in the above-mentioned formula.

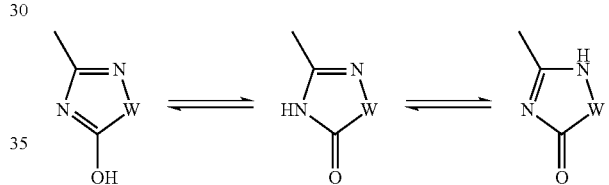

In addition, the group represented by the above-mentioned formula optionally further has, besides an oxo group, 1 or 2 substituents selected from the above-mentioned substituent group C at substitutable positions. Preferably specific examples include

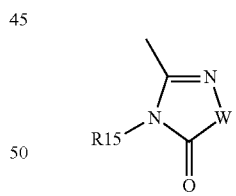

wherein each symbol is as defined above.

Here, R15 is, for example, a substituent similar to the above-mentioned substituent exemplified for group C.

R15 is preferably
(1) a hydrogen atom; or
(2) a $(C_1-C_6)$alkyl group optionally substituted by a $(C_1-C_6)$ alkoxy group optionally substituted by 1 to 3 $(C_1-C_6)$ alkoxy groups (e.g., (2-methoxyethoxy)methyl); more preferably a hydrogen atom.

The position of substitution of Rb may be any of ortho, metha and para. It is particularly preferably the ortho-position, namely,

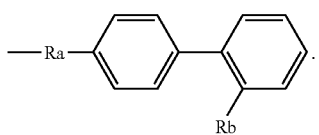

Preferably specific examples of R include

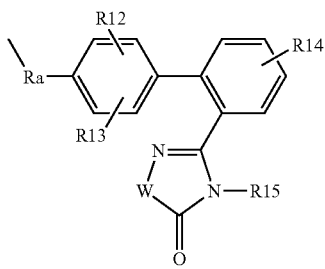

wherein each symbol is as defined above.

Preferable other specific examples of R include,

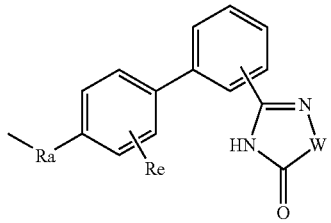

wherein each symbol is as defined above.

Preferably embodiment of compound (I) includes the following.

[Compound A1]

Compound (I) wherein, in the formula (I), a group represented by

is a group represented by the formula:

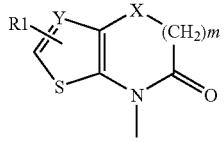

(a)

wherein each symbol is as defined above,

R is a group represented by

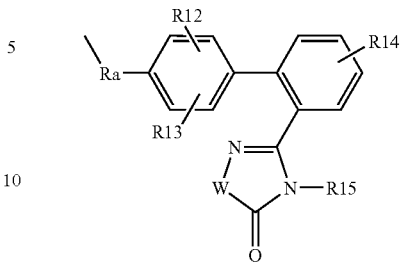

wherein each symbol is as defined above, or a group represented by

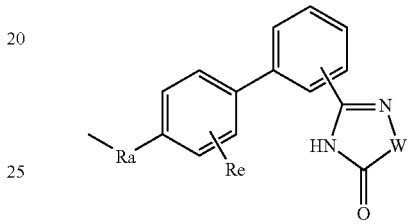

wherein each symbol is as defined above.

[Compound A2]

Compound A1 wherein

R1 is (1) a hydrogen atom;
(2) a ($C_1$-$C_6$)alkyl group optionally substituted by 1 to 3 substituents selected from (i) halogen (e.g., fluorine), (ii) a hydroxy group, and (iii) a ($C_1$-$C_6$)alkoxy group;
(3) a ($C_2$-$C_6$)alkenyl group;
(4) an optionally halogenated (e.g., fluorine) ($C_1$-$C_6$)alkoxy group; or (5) a ($C_3$-$C_6$)cycloalkyl group (e.g., cyclopropyl), Y is a nitrogen atom or C(R7) (preferably C(R7)) (wherein R7 is a hydrogen atom or a ($C_1$-$C_6$)alkyl group), X is (1) CO—N(R4)

wherein R4 is (i) a hydrogen atom;
(ii) a ($C_1$-$C_6$)alkyl group optionally substituted by 1 to 3 substituents selected from the above-mentioned substituent group B;
(iii) a ($C_3$-$C_6$)cycloalkyl group (e.g., cyclopropyl);
(iv) a ($C_6$-$C_{14}$)aryl group (e.g., phenyl) optionally substituted by 1 to 3 substituents selected from
  (a) halogen (e.g., Cl),
  (b) an optionally halogenated ($C_1$-$C_6$)alkyl group (e.g., trifluoromethyl),
  (c) a ($C_1$-$C_6$)alkoxy group (e.g., isopropyloxy),
  (d) a carboxy group, and
  (e) a ($C_1$-$C_6$)alkoxy-carbonyl group (e.g., methoxycarbonyl);
(v) a heterocyclic group (aromatic heterocyclic group (e.g., pyridyl, pyridazinyl, oxazolyl, quinolyl, pyrimidinyl, pyrazolyl) or a nonaromatic heterocyclic group (e.g., 2,3-dihydrobenzofuranyl)) optionally substituted by 1 to 3 substituents selected from
  (a) halogen (e.g., Cl),
  (b) a cyano group,
  (c) a ($C_1$-$C_6$)alkyl group, (d) a ($C_6$-$C_{14}$)aryl group (e.g., phenyl), and
(e) a ($C_1$-$C_6$)alkoxy group (e.g., methoxy);
(2) CO—(R5)C(R6)
wherein R5 is (i) a hydrogen atom, or (ii) a ($C_1$-$C_6$)alkyl group, and R6 is a ($C_1$-$C_6$)alkyl group optionally substituted by a ($C_6$-$C_{14}$)aryl group (e.g., phenyl); or
(3) (R2)C=C(R3)
wherein R2 is (i) a hydrogen atom, (ii) a ($C_1$-$C_6$)alkyl group, or (iii) a ($C_1$-$C_6$)alkoxy group, and R3 is a ($C_1$-$C_6$)alkyl group optionally substituted by a ($C_6$-$C_{14}$)aryl group (e.g., phenyl),
m is 0 or 1 (preferably, 0)
(wherein when m is 1, R3 or R4 is optionally bonded to a carbon atom, which is adjacent to the nitrogen atom or carbon atom bonded thereto, to form a ring),
Ra is a ($C_1$-$C_4$)alkylene group (preferably methylene),
R12, R13 and R14 are each independently
(1) a hydrogen atom;
(2) halogen (e.g., F, Br);
(3) a ($C_1$-$C_6$)alkyl group (e.g., methyl, butyl); or
(4) a ($C_1$-$C_6$)alkoxy group (e.g., methoxy),
preferably, each independently a hydrogen atom or fluorine,
W is an oxygen atom or a sulfur atom (preferably, oxygen atom), and
R15 is
(1) a hydrogen atom; or
(2) a ($C_1$-$C_6$)alkyl group optionally substituted by a ($C_1$-$C_6$) alkoxy group optionally substituted by 1 to 3 ($C_1$-$C_6$) alkoxy groups (e.g., (2-methoxyethoxy)methyl),
preferably, a hydrogen atom.

[Compound B1]
Compound (I) wherein, in the formula (I), a group represented by

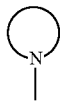

is a group represented by the formula:

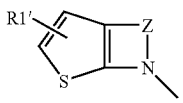
(b)

wherein each symbol is as defined above,
R is a group represented by

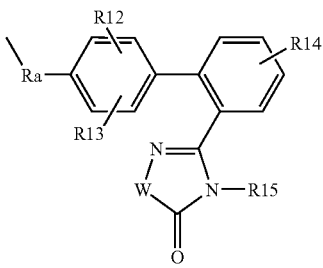

wherein each symbol is as defined above, or a group represented by

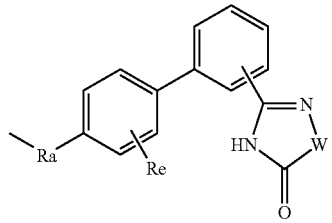

wherein each symbol is as defined above.

[Compound B2]
Compound B1 wherein
R1' is a ($C_1$-$C_6$)alkyl group,
Z is
(1) (R8)N—CO
wherein R8 is a ($C_1$-$C_6$)alkyl group substituted by a ($C_6$-$C_{14}$) aryl group (e.g., phenyl) optionally substituted by halogen; or
(2) N=C(R9)
wherein R9 is a ($C_1$-$C_6$)alkoxy group,
Ra is a ($C_1$-$C_4$)alkylene group (preferably methylene),
R12, R13 and R14 are each independently
(1) a hydrogen atom;
(2) halogen (e.g., F, Br);
(3) a ($C_1$-$C_6$)alkyl group (e.g., methyl, butyl); or
(4) a ($C_1$-$C_6$)alkoxy group (e.g., methoxy),
preferably, each independently a hydrogen atom or fluorine,
W is an oxygen atom or a sulfur atom (preferably, oxygen atom),
R15 is
(1) a hydrogen atom; or
(2) a ($C_1$-$C_6$)alkyl group optionally substituted by a ($C_1$-$C_6$) lkoxy group optionally substituted by 1 to 3 ($C_1$-$C_6$)alkoxy groups (e.g., (2-methoxyethoxy)methyl),
preferably, a hydrogen atom.

[Compound C1]
Compound (I) wherein, in the formula (I), a group represented by

is a group represented by the formula:

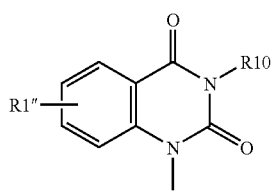
(c)

wherein each symbol is as defined above,

R is a group represented by

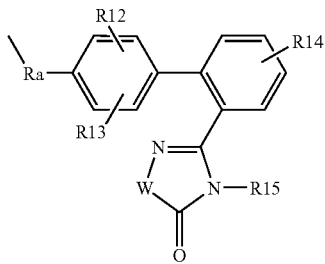

wherein each symbol is as defined above, or a group represented by

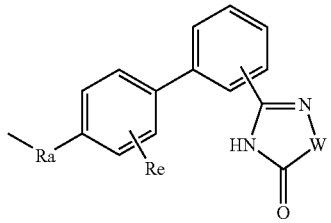

wherein each symbol is as defined above.
[Compound C2]
Compound C1 wherein
R1″ is
(1) a ($C_1$-$C_6$)alkyl group; or
(2) a ($C_2$-$C_6$)alkenyl group,
R10 is a ($C_1$-$C_6$)alkyl group substituted by a ($C_6$-$C_{14}$)aryl group (e.g., phenyl),
Ra is a ($C_1$-$C_4$)alkylene group (preferably methylene),
R12, R13 and R14 are each independently
(1) a hydrogen atom;
(2) halogen (e.g., F, Br);
(3) a ($C_1$-$C_6$)alkyl group (e.g., methyl, butyl); or
(4) a ($C_1$-$C_6$)alkoxy group (e.g., methoxy),
preferably, each independently a hydrogen atom or fluorine,
W is an oxygen atom or a sulfur atom (preferably, oxygen atom),
R15 is
(1) a hydrogen atom; or
(2) a ($C_1$-$C_6$)alkyl group optionally substituted by a ($C_1$-$C_6$) lkoxy group optionally substituted by 1 to 3 ($C_1$-$C_6$)alkoxy groups (e.g., (2-methoxyethoxy)methyl),
preferably, a hydrogen atom.
[Compound D1]
Compound (I) wherein, in the formula (I), a group represented by

is a group represented by the formula:

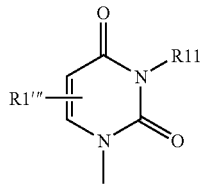

wherein each symbol is as defined above,
R is a group represented by

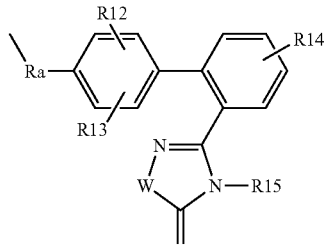

wherein each symbol is as defined above, or a group represented by

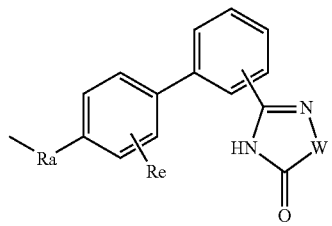

wherein each symbol is as defined above.
[Compound D2]
Compound D1 wherein
R1‴ is
(1) a ($C_1$-$C_6$)alkyl group; or
(2) a optionally halogenated (e.g., fluorine) ($C_1$-$C_6$)alkoxy group,
R11 is
(1) a ($C_6$-$C_{14}$)aryl-carbonyl (e.g., benzoyl) substituted by a ($C_1$-$C_6$)alkoxy group; or
(2) a ($C_1$-$C_6$)alkyl group substituted by a ($C_1$-$C_6$)alkyl-carbonyl group (e.g., 2,2-dimethylpropanoyl),
Ra is a ($C_1$-$C_4$)alkylene group (preferably methylene),
R12, R13 and R14 are each independently
(1) a hydrogen atom;
(2) halogen (e.g., F, Br);
(3) a ($C_1$-$C_6$)alkyl group (e.g., methyl, butyl); or
(4) a ($C_1$-$C_6$)alkoxy group (e.g., methoxy),
preferably, each independently a hydrogen atom or fluorine,
W is an oxygen atom or a sulfur atom (preferably, oxygen atom),
R15 is
(1) a hydrogen atom; or
(2) a ($C_1$-$C_6$)alkyl group optionally substituted by a ($C_1$-$C_6$) lkoxy group optionally substituted by 1 to 3 ($C_1$-$C_6$)alkoxy groups (e.g., (2-methoxyethoxy)methyl),
preferably, a hydrogen atom.

As the salt of a compound represented by the formula (I), a pharmacologically acceptable salt and the like can be mentioned. Examples thereof include acid addition salt with an acid such as trifluoroacetic acid, acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydroiodic acid, sulfamic acid, sulfuric acid and the like; salt with a metal such as sodium, potassium, magnesium, calcium and the like; salt with an organic base such as trimethylamine, triethylamine, pyridine, picoline, N-methylpyrrolidine, N-methylpiperidine, N-methylmorpholine and the like, and the like.

A prodrug of the compound (I) means a compound which is converted to the compound (I) with a reaction due to an enzyme, a gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc. A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxo1-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug of the compound (I) may also be one which is converted into the compound (I) under a physiological condition, such as those described in IYAKUHIN no KAIHATSU (Development of Pharmaceuticals), Vol. 7, Design of Molecules, p. 163-198, 1990, Published by HIROKAWA SHOTEN.

When the compound (I) has isomers such as optical isomer, stereoisomer, positional isomer, rotational isomer and the like, and any isomers and mixture of isomers are encompassed in the compound (I). For example, when the compound (I) has an optical isomer, an optical isomer resolved from a racemate is also encompassed in the compound (I). These isomers can be obtained as independent products by a synthesis means or a separation means (e.g., concentration, solvent extraction, column chromatography, recrystallization and the like), and the like known per se.

The compound (I) may be a crystal or an amorphous form. When the compound (I) is a crystal, both a single crystal and crystal mixtures are encompassed in the compound (I). Crystals can be produced by crystallization according to crystallization methods known per se.

The compound (I) may be a solvate (e.g., hydrate etc.) or a non-solvate, both of which are encompassed in the compound (I).

The compound (I) may be labeled with an isotope (e.g., $^3$H, $^{14}$C, $^{35}$S, $^{125}$I and the like) and the like.

Since the compound of the present invention has a strong angiotensin II antagonistic activity (particularly, AT1 receptor antagonistic activity), the compound of the present invention is useful as an agent for the prophylaxis or treatment of a disease (or a disease whose onset is promoted) developed by the contraction or growth of blood vessels or organ disorder, which expresses via an angiotensin II receptor, or due to the presence of angiotensin II, or a factor induced by the presence of angiotensin II, in mammals (e.g., human, monkey, cat, pig, horse, bovine, mouse, rat, guinea pig, dog, rabbit etc.).

As such diseases, for example, hypertension, blood pressure circadian rhythm abnormality, heart diseases (e.g., cardiac hypertrophy, acute heart failure, chronic heart failure including congestive heart failure, impaired vasodilation, systolic failure, cardiac myopathy, angina pectoris, myocarditis, atrial fibrillation, arrhythmia, tachycardia, myocardial infarction etc.), cerebrovascular disorders (e.g., asymptomatic cerebrovascular disorder, transient cerebral ischemia, cerebral apoplexy, cerebrovascular dementia, hypertensive encephalopathy, cerebral infarction etc.), cerebral edema, cerebral circulatory disorder, migraine, stress-related headache, tension headache, recurrence and sequela of cerebrovascular disorders (e.g., neurotic symptom, psychic symptom, subjective symptom, disorder in daily living activities etc.), ischemic peripheral circulation disorder, myocardial ischemia, venous insufficiency, progression of cardiac insufficiency after myocardial infarction, renal diseases (e.g., nephritis, glomerulonephritis, glomerulosclerosis, renal failure, thrombotic vasculopathy, complication of dialysis, organ dysfunction including nephropathy by irradiation etc.), arteriosclerosis including atherosclerosis (e.g., aneurysm, coronary sclerosis, cerebral arteriosclerosis, peripheral arterial sclerosis etc.), vascular hypertrophy, vascular hypertrophy or obliteration and organ disorders after intervention (e.g., percutaneous transluminal coronary angioplasty, stenting, coronary angioscopy, intravascular ultrasound, intracoronary thrombolysis etc.), vascular re-obliteration and restenosis after bypass, polycythemia, hypertension, organ disorder and vascular hypertrophy after transplantation, rejection after transplantation, ocular diseases (e.g., glaucoma, ocular hypertension etc.), thrombosis, multiple organ disorder, endothelial dysfunction, hypertensive tinnitus, other cardiovascular diseases (e.g., deep vein thrombosis, obstructive peripheral circulatory disorder, arteriosclerosis obliterans, thromboangiitis obliterans, ischemic cerebral circulatory disorder, Raynaud's disease, Buerger's disease etc.), metabolic syndrome, metabolic and/or nutritional disorders (e.g., obesity, impaired glucose tolerance, hyperinsulinemia, hyperlipidemia (including hyper-triglycerid(TG)-emia, hypercholesterolemia, hypoHDL-emia, postprandial hyperlipemia etc.), hyperuricacidemia, hyperkalemia, hypernatremia etc.), glaucoma, nerve degeneration diseases (e.g., Alzheimer's disease, Parkinson's disease, amyotrophic lateral sclerosis, AIDS encephalopathy etc.), central nervous system disorders (e.g., disorders such as cerebral hemorrhage, cerebral infarction etc., and their sequela and complication, ischemic disorder, head injury, spinal injury, cerebral edema, sensory malfunction, sensory functional disorder, autonomic nervous system disorder, autonomic nervous system malfunction, multiple sclerosis etc.), dementia (cerebrovascular dementia, senile dementia and the like), defects of memory, disorder of consciousness, amnesia, anxiety symptom, catatonic symptom, discomfort mental state, psychopathies (e.g., depression, mania, insomnia, epilepsy, alcoholism etc.), cerebral paralysis, inflammatory diseases (e.g., arthritis such as chronic rheumatoid arthritis, osteoarthritis, rheumatoid myelitis, periostitis etc.; inflammation after operation and trauma; remission of swelling; pharyngitis; cystitis; pneumonia; atopic dermatitis; inflammatory intestinal diseases such as Crohn's disease, ulcerative colitis etc.; meningitis; inflammatory ocular disease; pulmonary sarcoidosis such as pneumonia, pulmonary silicosis, pulmonary sarcoidosis, pulmonary tuberculosis etc.), allergic diseases (e.g., allergic rhinitis, conjunctivitis, gastrointestinal allergy, pollinosis, anaphylaxis etc.), chronic obstructive pulmonary disease, interstitial pneumonia, carinni pneumonia, collagen diseases (e.g., systemic lupus erythematosus, scleroderma, polyarteritis etc.), hepatic diseases (e.g., hepatitis including chronic hepatitis, hepatic cirrhosis etc.), portal hypertension, digestive system disorders (e.g., gastritis, gastric ulcer, gastric cancer, gastric disorder after operation, dyspepsia, esophageal ulcer, pancreatitis, colon polyp, cholelithiasis, hemorrhoidal disease, varices ruptures of esophagus and stomach etc.), blood and/or hematopoietic diseases (e.g., erythrocytosis, vascular purpura, autoimmune hemolytic anemia, disseminated intravascular coagulation syndrome, multiple myelopathy etc.), bone diseases (e.g., fracture, refracture, osteoporosis, osteomalacia, bone Paget's disease, sclerosing myelitis, chronic rheumatoid arthritis, osteoarthritis of the knee and joint tissue dysfunction and the like caused by diseases similar to these etc.), solid tumor, tumors (e.g., malignant melanoma, malignant lymphoma, cancer of digestive organs (e.g., stomach, intestine etc.) etc.), cancer and cachexia following cancer, metastasis cancer, endocrinopathy (e.g., Addison's disease, Cushing's syndrome, pheochromocytoma, primary aldosteronism etc.), Creutzfeldt-Jakob-disease, urinary organ and/or male genital diseases (e.g., cystitis, prostatic hypertrophy, prostatic cancer, sex infectious disease etc.), female disorders (e.g., climacteric disorder, gestosis, endometriosis, hysteromyoma, ovarian disease, breast disease, sex infectious disease etc.), disease relating to environment and occupational factors (e.g., radiation hazard, hazard by ultraviolet, infrared or laser beam, altitude sickness etc.), sleep apnea syndrome, respiratory diseases (e.g., chronic obstructive pulmonary diseases, bronchial asthma, cold syndrome, pneumonia, asthma, pulmonary hypertension, pulmonary thrombosis and pulmonary embolism etc.), infectious diseases (e.g., viral infectious diseases with cytomegalovirus, influenza virus, herpes virus etc., rickettsiosis, bacterial infectious disease etc.), toxemias (e.g., sepsis, septic shock, endotoxin shock, Gram-negative sepsis, toxic shock syndrome etc.), otorhinolaryngological diseases (e.g., Meniere's syndrome, tinnitus, dysgeusia, vertigo, disequilibrium, dysphagia etc.), skin diseases (e.g., keloid, hemangioma, psoriasis etc.), intradialytic hypotension, myasthenia gravis, systemic diseases such as chronic fatigue syndrome and the like can be mentioned.

Since the compound of the present invention can maintain a certain hypotensive action through day and night, the dose and frequency can be reduced as compared to the administration of a compound other than the present invention, and moreover, elevation of blood pressure before and after awakening, which is particularly problematic in patients with hypertension, can be suppressed more effectively.

In addition, long-term suppression of action of angiotensin II by the compound of the present invention results in the improvement or suppression of promotion of disorder or abnormality in the biofunction and physiological action, that causes adult disorders and various diseases linked with aging and the like, which in turn leads to the primary and secondary prophylaxis of diseases or clinical conditions caused thereby or suppression of the progression thereof. As the disorder or abnormality in the biofunction and physiological action, for example, disorder or abnormality in automatic controlling capability of cerebral circulation and/or renal circulation, disorder of circulation (e.g., peripheral, cerebral, microcirculation etc.), disorder of blood-brain-barrier, salt sensitivity, abnormal state of coagulation and fibrinolysis system, abnormal state of blood and blood cell components (e.g., accentuation of platelet aggregation action, malfunction of erythrocyte deformability, accentuation of leukocyte adhesiveness, rise of blood viscosity etc.), production and function accentuation of growth factor and cytokines (e.g., PDGF, VEGF, FGF, interleukin, TNF-α, MCP-1 etc.), accentuation of production and infiltration of inflammatory cells, accentuation of production of free radical, liposteatosis accentuation, endothelial function disorder, endothelium, cell and organ dysfunction, edema, cell morphogenesis change of smooth muscle etc. (morphogenesis to proliferation type etc.), production and function accentuation of vasoactive substance and thrombosis inducers (e.g., catecholamine, endothelin, thromboxane $A_2$ etc.), abnormal constriction of blood vessel etc., metabolic disorder (serum lipid abnormalities, dysglycemia etc.), abnormal growth of cell etc., angiogenesis (including abnormal vasculogenesis during abnormal capillary reticular formation in adventitial coat of arteriosclerotic lesion) and the like can be mentioned. Among them, the compound of the present invention can be used as an agent for the primary and secondary prophylaxis or treatment of organ disorders associated with various diseases (e.g., cerebrovascular disorder and organ disorder associated therewith, organ disorder associated with cardiovascular disease, organ disorder associated with diabetes, organ disorder after intervention etc.). In particular, since the compound of the present invention has an activity of inhibiting proteinuria, the compound of the present invention can beused as an agent for protecting kidney. Therefore, the compound of the present invention can be advantageously used when the patients with obesity, insulin resistance, impaired glucose tolerance, diabetes or hyperinsulinemia have concurrently developed the above-mentioned diseases or clinical condition. Moreover, the onset of hypertension and diabetes in such patients can be prevented.

The compound of the present invention can be used as insulin sensitizer, agent for enhancing insulin sensitivity, retinoid related receptor function regulator, peroxisomal proliferator-activated receptor ligand, retinoid X receptor ligand and the like. As used herein, the function regulator means both agonist and antagonist.

The compound of the present invention has hypoglycemic action, hypolipidemic action, insulin resistance improving action, insulin sensitizing action and peroxisomal proliferator-activated receptor (hereinafter sometimes to be abbreviated as PPAR) γ (GenBank Accession No. L40904) agonistic action. As used herein, PPARγ may form a heterodimer receptor with retinoid X receptor (hereinafter sometimes to be abbreviated as RXR) α (GenBank Accession No. X52773), RXRβ (GenBank Accession No. M84820) or RXRγ (GenBank Accession No. U38480).

The compound of the present invention particularly shows a selective partial agonistic action on PPARγ.

It has been reported that a selective partial agonist for PPARγ does not accompany side effects such as body weight increase, adipocyte accumulation, cardiac hypertrophy and the like, as compared to a full agonist for PPARγ (e.g., thiazolidinedione compound) (Molecular Endocrinology, vol. 17, No. 4, page 662, 2003). Therefore, the compound of the present invention is useful as a hypoglycemic agent that does not accompany side effects such as body weight increase, adipocyte accumulation, cardiac hypertrophy and the like, as compared to a full agonist for PPARγ.

Since the compound of the present invention normalizes the intracellular insulin signal transduction mechanism, which mainly causes insulin resistance, thereby reducing insulin resistance and enhancing insulin action, and has a glucose tolerance improvement action. Therefore, the compound of the present invention or a salt thereof or a prodrug thereof (containing the compound of the present invention) can be used for mammals (e.g., human, monkey, cat, pig, horse, bovine, mouse, rat, guinea pig, dog, rabbit etc.) as an improving agent or an agent for the prophylaxis and/or treatment of the diseases in which insulin resistance is involved.

The compound of the present invention can be used, for example, as an agent for the prophylaxis or treatment of, diabetes (e.g., type 1 diabetes, type 2 diabetes, gestational diabetes, obesity type diabetes); an agent for the prophylaxis or treatment of hyperlipidemia (including hypertriglycerid (TG)-emia, hypercholesterolemia, hypoHDL-emia, postprandial hyperlipemia etc.); an insulin sensitizer; an agent for enhancing insulin sensitivity; an agent for the prophylaxis or treatment of impaired glucose tolerance (IGT); an agent for the prophylaxis or treatment of metabolic syndrome; and an agent for preventing progression from impaired glucose tolerance to diabetes. In addition, the compound of the present invention can be used, for example, as an agent for the prophylaxis or treatment of hyperinsulinemia, hypertension associated with insulin resistance, hypertension associated with impaired glucose tolerance, hypertension associated with diabetes (e.g., type 2 diabetes and the like), hypertension associated with hyperinsulinemia, hypertension associated with obesity, insulin resistance associated with hypertension, impaired glucose tolerance associated with hypertension, diabetes associated with hypertension, hyperinsulinemia associated with hypertension, and obesity associated with hypertension. Moreover, the compound of the present invention can also be used for the treatment of patients with diabetes, who shows a normal high blood pressure value, or patients with hypertension, who show a normal high blood glucose value.

The compound of the present invention can be also used as an agent for the prophylaxis or treatment of, for example, diabetic complications [e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, skin and soft tissue infection, lower limb infection), diabetic gangrene, xerostomia, lowered sense of hearing, cerebrovascular disease, peripheral circulatory disturbance], obesity, osteoporosis, cachexia (e.g., cancer cachexia, tuberculous cachexia, diabetic cachexia, hemopathic cachexia, endocrinopathic cachexia, infectious cachexia, cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, end-stage renal disease), muscular dystrophy, cardiac failure, myocardial infarction, angina pectoris, cerebrovascular disease (e.g., cerebral infarction, cerebral apoplexy), insulin resistant syndrome, syndrome X, metabolic syndrome (clinical conditions showing at least three selected from hyper-triglycerid(TG)-emia, hypo-HDL-cholesterolemia (HDL-C), hypertension, abdominal obesity and impaired glucose tolerance), hyperinsulinemia, hyperinsulinemia-induced sensory disorder, tumor (e.g., leukemia, breast cancer, prostate cancer, skin cancer), irritable bowel syndrome, acute or chronic diarrhea, inflammatory diseases (e.g., arteriosclerosis (e.g., atherosclerosis etc.), rheumatoid arthritis, spondylitis deformans, osteoarthritis, lumbago, gout, postoperative or traumatic inflammation, swelling, neuralgia, pharyngolaryngitis, cystitis, hepatitis (including nonalcoholic steatohepatitis), pneumonia, pancreatitis, inflammatory colitis, ulcerative colitis), visceral obesity syndrome and the like.

The compound of the present invention can be used for the improvement of symptoms associated with peptic ulcer, acute or chronic gastritis, biliary dyskinesia, cholecystitis or the like, such as abdominal pain, nausea, vomiting, epigastric discomfort and the like.

The compound of the present invention is also used as an agent for the prophylaxis or treatment of inflammatory diseases in which TNF-α is involved. Here, the inflammatory diseases in which TNF-α is involved means inflammatory diseases developed by the presence of TNF-α, and treated by a TNF-α suppressing effect. Examples of such inflammatory diseases include diabetic complications (e.g., retinopathy, nephropathy, neuropathy, macroangiopathy etc.), chronic rheumatoid arthritis, spondylitis deformans, osteoarthritis, lumbago, gout, postoperative or traumatic inflammation, swelling, neuralgia, pharyngolaryngitis, cystitis, hepatitis, pneumonia, gastric mucosal injury (including aspirin-induced gastric mucosal injury), myocarditis, cardiomyopathy, cardiac failure, ischemic cardiac diseases and the like.

The compound of the present invention has an apoptosis inhibitory activity, and can be used as an agent for the prophylaxis or treatment of diseases mediated by promotion of apoptosis. Examples of the diseases mediated by promotion of apoptosis include viral diseases (e.g., AIDS, fulminant hepatitis etc.), neurodegenerative diseases (e.g., Alzheimer's disease, Parkinson's disease, amyotrophic lateral sclerosis, retinitis pigmentosa, cerebellar degeneration etc.), myelodysplasia (e.g., aplastic anemia etc.), ischemic diseases (e.g., myocardial infarction, cerebral apoplexy etc.), chronic cardiac failure such as congestion and the like, hepatic diseases (e.g., alcoholic hepatitis, hepatitis B, hepatitis C etc.), joint diseases (e.g., osteoarthritis etc.), atherosclerosis and the like.

The compound of the present invention can be used for reducing visceral fats, inhibiting accumulation of visceral fats, ameliorating glycometabolism, ameliorating lipid metabolism, ameliorating insulin resistance, inhibiting oxidized LDL production, ameliorating lipoprotein metabolism, ameliorating coronary artery metabolism, preventing or treating cardiovascular complications, preventing or treating heart failure complications, preventing hypertension, preventing diabetes, lowering blood remnant, preventing or treating anovulation, preventing or treating hirsutism, preventing or treating hyperandrogenism, and the like.

The compound of the present invention is also used for the secondary prevention of various diseases mentioned above (e.g., cardiovascular event such as myocardial infarction etc.) and suppression of progression thereof.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a casual blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) reported new diagnostic criteria of diabetes in 1997 and WHO in 1998.

According to these reports, diabetes is a condition showing a fasting blood glucose level (glucose concentration of intravenous plasma) of not less than 126 mg/dl and a-75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of less than 140 mg/dl is called IFG (Impaired Fasting Glycemia).

The compound of the present invention can also be used as an agent for improving or the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria, or further, as an agent for treating hypertension of hypertensive patients having not less than the above-mentioned diagnostic criteria (e.g., fasting blood sugar level of 126 mg/dl). Moreover, the compound of the present invention can prevent progression of borderline type, impaired glucose tolerance, IFG (Impaired Fasting Glucose) or IFG (Impaired Fasting Glycemia) into diabetes.

The compound of the present invention is effective as a drug for the suppression or improvement of cardiac hypofunction, progression of cardiac remodeling and aggravation of conditions in, or a drug for the suppression of recurrence or decreased survival rate of patients having cardiac disease (e.g., cardiac hypertrophy, acute cardiac failure, chronic cardiac failure including congestive cardiac failure, impaired vasodilation, cardiomyopathy, angina pectoris, myocarditis, atrial fibrillation, arrhythmia, tachycardia, myocardial infarction and the like) with diabetes. In addition, it is effective for the prevention of the onset of a cardiac disease (e.g., cardiac hypertrophy, acute cardiac failure, chronic cardiac failure including congestive cardiac failure, impaired vasodilation, cardiomyopathy, angina pectoris, myocarditis, atrial fibrillation, arrhythmia, tachycardia, myocardial infarction and the like) and hypertension and a cerebrovascular disorder (e.g., asymptomatic cerebrovascular disorder, transient cerebral ischemic attack, cerebral apoplexy, cerebrovascular dementia, hypertensive encephalopathia, cerebral infarction and the like) in diabetic patients.

Since the compound of the present invention has an activity of inhibiting body weight gain, the compound of the present invention can be used as a body weight gain inhibitor to mammals. Target mammals may be any mammals of which body weight gain is to be avoided. The mammals may have a risk of body weight gain genetically or may be suffering from lifestyle-related diseases such as diabetes, hypertension and/or hyperlipidemia (hyper-triglycerid(TG)-emia, hypercholesterolemia, hypoHDL-emia, postprandial hyperlipemia etc.) and the like. The body weight gain may be caused by excessive feeding or diet without nutrient balance, or may be derived from combination drug, for example, agents for enhancing insulin sensitivity having PPARγ-agonistic activity such as troglitazone, rosiglitazone, englitazone, ciglitazone, pioglitazone etc. and the like. In addition, body weight gain may be preliminary to obesity, or may be body weight gain of obesity patients. Here, obesity is defined that BMI (body mass index; body weight (kg)/[height (m)]$^2$) is not less than 25 for Japanese (criterion by Japan Society for the Study of Obesity), or not less than 30 for westerner (criterion by WHO).

The compound of the present invention is useful as an agent for the prophylaxis or treatment of metabolic syndrome. Because patients with metabolic syndrome have an extreme high incidence of cardiovascular diseases as compared to patients with single lifestyle-related diseases, the prophylaxis or treatment of metabolic syndrome is quite important to prevent cardiovascular diseases.

Criteria for diagnosis of metabolic syndrome are announced by WHO in 1999, and by NCEP in 2001. According to the criterion of WHO, patients with at least two of abdominal obesity, dyslipidemia (high TG or low HDL) and hypertension in addition to hyperinsulinemia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in the United. States, patients with at least three of abdominal obesity, hypertriglyceridemia, hypo-HDL cholesterolemia, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can be used for treating patients of hypertension with metabolic syndrome.

Since the compound of the present invention has an anti-inflammatory action, the compound of the present invention can be used as an anti-inflammatory agent for preventing or treating inflammatory diseases. Examples of inflammatory diseases include inflammatory diseases due to various diseases such as arthritis (e.g chronic rheumatoid arthritis, osteoarthritis, rheumatoid myelitis, gouty arthritis, synovitis), asthma, allergic diseases, arteriosclerosis including atherosclerosis (aneurysm, coronary sclerosis, cerebral arterial sclerosis, peripheral arterial sclerosis etc.), digestive tract disease such as inflammatory intestine disease (e.g. Crohn's disease, ulcerative colitis), diabetic complication (diabetic neuropathy, diabetic vascular disorder), atopic dermatitis, chronic obstructive pulmonary disease, systemic lupus erythematosus, visceral inflammatory disease (nephritic, hepatitis), autoimmune hemolytic anemia, psoriasis, nervous degenerative disease (e.g. Alzheimer's disease, Parkinson's diseases, amyotrophic lateral sclerosis, AIDS encephalopathy), central nervous disorder (e.g. cerebrovascular disorder such as cerebral hemorrhage and cerebral infarct, head trauma, spinal damage, cerebral edema, multiple sclerosis), meningitis, angina pectoris, cardiac infarct, myocarditis, congestive cardiac failure, vascular hypertrophy or occlusion and organ disorder after intervention (percutaneous transluminal coronary angioplasty, stenting, coronary angioscopy, intravascular ultrasound, intracoronary thrombolysis etc), vascular reocclusion or restenosis after bypass operation, endothelial functional disorder, other circulatory disease (intermittent claudication, obstructive peripheral circulatory disorder, arteriosclerosis obliterans, thromboangiitis obliterans, ischemic cerebral circulatory disorder, Raynaud's disease, Buerger's disease), inflammatory ocular disease, pulmonary sarcoidosis (e.g chronic pneumonia, silicosis, pulmonary sarcoidosis, pulmonary tuberculosis), endometritis, toxemia (e.g. sepsis, septic shock, endotoxin shock, gram negative sepsis, toxin shock syndrome), cachexia (e.g cachexia due to infection, carcinomatous cachexia, cachexia due to acquired immunodeficiency syndrome), cancer, Addison's disease, Creutzfeldt-Jakob disease, virus infection (e.g. infection of virus such as cytomegalovirus, influenza virus, herpes virus etc.), disseminated intravascular coagulation.

In addition, since the compound of the present invention has an analgesic action, the compound of the present invention can be also used as an analgesic agent for preventing or treating pain. Examples of pain diseases include acute pain due to inflammation, pain associated with chronic inflammation, pain associated with acute inflammation, pain after operation (pain of incisional, deep pain, organ pain, chronic pain after operation etc.), muscular pain (muscular pain associated with chronic pain disease, shoulder stiffness etc.), arthralgia, toothache, gnathicarthralgia, headache (migraine, catatonic headache, headache associated with fever, headache associated hypertension), organ pain (cardiac pain, angina pain, abdominal pain, renal pain, ureterane pain, bladder pain), pain in obstetrics area (mittelschmerz, dysmenorrheal, labor pain), neuralgia (disc hernia, nerve root pain, neuralgia after herpes zoster, trigeminal neuralgia), carcinomatous pain, reflex sympathetic atrophy, complex local pain syndrome, and the like. The compound of the present invention is effective in alleviate directly and rapidly various pains such as nervous pain, carcinomatous pain and inflammatory pain, and exhibits the particularly excellent analgesic effect to patients and pathologies in which a pain sense threshold is lowered (e.g., hypertension, diabetes and the like, and complications thereof and the like).

The compound of the present invention is particularly useful as an analgesic agent for pain associated with chronic inflammation or headache associated with hypertension, or as an agent for preventing or treating inflammatory disease or pain due to (1) arteriosclerosis including atherosclerosis, (2) vascular hypertrophy, occlusion or organ disorder after intervention, (3) reocclusion, restenosis or endothelial functional disorder after bypass operation, (4) intermittent claudication, (5) obstructive peripheral circulatory disorder, or (6) arteriosclerosis obliterans.

The content of the compound of the present invention in a pharmaceutical composition is generally about 0.01—about 99.9 wt %, preferably about 0.1—about 50 wt %, relative to the entire preparation.

The dose of the compound of the present invention is determined in consideration of age, body weight, general health condition, sex, diet, administration time, administration method, clearance rate, combination of drugs, the level of disease for which the patient is under treatment then, and other factors.

While the dose varies depending on the target disease, condition, subject of administration, administration method and the like, for oral administering the compound of the present invention as a therapeutic agent for essential hypertension in adult, the daily dose of 0.1-600 mg is preferably administered in a single dose or in 2 or 3 portions.

In addition, since the compound of the present invention is superior in safety, it can be administered for a long period.

The compound of the present invention can be used in combination with pharmaceutical agents such as a therapeutic agent for diabetes, a therapeutic agent for diabetic complications, an anti-hyperlipidemia agent, an anti-arteriosclerotic agent, an anti-hypertensive agent, an anti-obesity agent, a diuretic, an antigout agent, an antithrombotic agent, an anti-inflammatory agent, a chemotherapeutic agent, an immunotherapeutic agent, a therapeutic agent for osteoporosis, an anti-dementia agent, an erectile dysfunction amelioration agent, a therapeutic agent for urinary incontinence/urinary frequency and the like (hereinafter to be abbreviated as a concomitant drug). These concomitant drugs may be low-molecular-weight compounds, high-molecular-weight proteins, polypeptides, antibodies, vaccines and the like. In this case, the administration mode of the compound of the present invention and the concomitant drug is not particularly restricted, and it is sufficient that the compound of the present invention and the concomitant drug are combined in administration. Examples of such administration mode include the following:

(1) administration of a single preparation obtained by simultaneously processing the compound of the present invention and the concomitant drug, (2) simultaneous administration of .two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like. The dose of the concomitant drug can be appropriately determined based on the dose clinically employed. The mixing ratio of the compound of the present invention and the concomitant drug can be appropriately selected according to the administration subject, administration route, target disease, condition, combination, and other factors. In cases where the administration subject is human, for example, the concomitant drug may be used in an amount of 0.01 to 100 parts by weight per part by weight of the compound of the present invention.

Examples of other therapeutic agents for diabetes include insulin preparations (e.g., animal insulin preparations extracted from pancreas of bovine and swine; human insulin preparations genetically synthesized using *Escherichia coli*, yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Netoglitazone (MCC-555), Rivoglitazone (CS-011), FK-614, compounds described in WO01/38325, Tesaglitazar (AZ-242), Ragaglitazar (NN-622), Muraglitazar (BMS-298585), Edaglitazone (BM-13-1258), Metaglidasen (MBX-102), Naveglitazar (LY-519818), MX-6054, LY-510929, AMG131 (T-131) or a salt thereof, THR-0921), α-glucosidase inhibitors (e.g., voglibose, acarbose, miglitol, emiglitate), biguanides (e.g., phenformin, metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Vidagliptin (LAF237), P32/98, Sitagliptin (MK-431), P93/01, PT-100, Saxagliptin (BMS-477118), T-6666, TS-021), β3 agonists (e.g., AJ-9677), GPR40 agonists, GLP-1 receptor agonists [e.g., GLP-1, GLP-1MR agent, NN-2211, AC-2993 (exendin-4), BIM-51077, Aib(8, 35)hGLP-1(7,37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095), 11β-hydroxysteroid dehydrogenase inhibitors BVT-3498), adiponectin or agonists thereof, IKK inhibitors (e.g., AS-2868), leptin resistance improving drugs, somatostatin receptor agonists (compounds described in WO01/25228, WO03/42204, WO98/44921, WO98/45285, WO99/22735 etc.), glucokinase activators (e.g., Ro-28-1675), ACC$_2$(acetyl-CoA carboxylase2) inhibitor and the like.

Examples of the therapeutic agents for diabetic complications include aldose reductase inhibitors (e.g., tolrestat, epalrestat, zenarestat, zopolrestat, minalrestat, fidarestat, CT-112, ranirestat (AS-3201)), neurotrophic factors and enhancers thereof (e.g., NGF, NT-3, BDNF, neurotrophin production/secretion promoting agents described in WO01/14372 (e.g., 4-(4-chlorophenyl)-2-(2-methyl-1-imidazolyl)-5-[3-(2-methylphenoxy)propyl]oxazole)), PKC inhibitors (e.g., ruboxistaurin mesylate), AGE inhibitors (e.g., ALT946, pimagedine, N-phenacylthiazolium bromide (ALT766), EXO-226, Pyridorin, pyridoxamine), active oxygen scavengers (e.g., thioctic acid), cerebral vasodilators (e.g., tiapride, mexiletine), somatostatin receptor agonists (e.g., BIM23190), and apoptosis signal regulating kinase-1 (ASK-1) inhibitors.

Examples of the anti-hyperlipidemia agents include statin compounds which are cholesterol synthesis inhibitors (e.g., cerivastatin, pravastatin, simvastatin, lovastatin, atorvastatin, fluvastatin, itavastatin or salts thereof (e.g., sodium salt etc.) etc.), squalene synthetase inhibitors (e.g. TAK-475 etc.) or fibrate compounds having a triglyceride lowering effect (e.g., bezafibrate, clofibrate, simfibrate, clinofibrate etc.), cholesterol absorption inhibitor (e.g., Zetia), anion exchange resin (e.g., colestyramine), probucol, nicotinic acid drug (e.g., nicomol, niceritrol), phytosterol (e.g., soysterol, γ-oryzanol), EPA, DHA and the like.

Examples of the anti-arteriosclerotic agents include an acyl-Coenzyme A cholesterol acyltransferase (ACAT) inhibitor (e.g. melinamide, Avasimabe, Eflucimibe etc.) and a lipid rich plaque regressing agent (e.g compounds described in WO 02/06264, WO 03/059900 etc.) and the like.

Examples of the anti-hypertensive agents include angiotensin converting enzyme inhibitors (e.g., captopril, enalapril, delapril etc.), angiotensin II antagonists (e.g., candesartan cilexetil, candesartan, losartan, losartan potassium, eprosartan, valsartan, termisartan, irbesartan, tasosartan, olmesartan, olmesartan medoxomil etc.), calcium antagonists (e.g., manidipine, nifedipine, amlodipine, efonidipine, nicardipine etc.), β-blocker (e.g., metoprolol, atenolol, propranolol, carvedilol, pindolol etc.), clonidine and the like.

Examples of the anti-obesity agents include anti-obesity agents acting on the central nervous system (e.g., dexfenfluramine, fenfluramine, phentermine, sibutramine, amfepramone, dexamphetamine, mazindol, phenylpropanolamine, clobenzorex etc.), MCH receptor antagonists (e.g., SB-568849; SNAP-7941; compounds described in WO01/82925 and WO01/87834), neuropeptide Y antagonists (e.g., CP-422935), cannabinoid receptor antagonists (e.g., SR-141716, SR-147778); ghrelin antagonists; 11β-hydroxysteroid dehydrogenase inhibitors (e.g., BVT-3498), pancreatic lipase inhibitors (e.g., orlistat etc.), β3 agonists (e.g., CL-316243, SR-58611-A, UL-TG-307, SB-226552, AJ-9677, BMS-196085, AZ40140 etc.), peptide anorexiants (e.g., leptin, CNTF (Ciliary Neurotropic Factor) etc.), cholecystokinin agonists (e.g., lintitript, FPL-15849 etc.), feeding deterrent (e.g., P-57) and the like.

Examples of the diuretics include xanthine derivatives (e.g., sodium salicylate and theobromine, calcium salicylate and theobromine etc.), thiazide preparations (e.g., ethiazide, cyclopenthiazide, trichloromethiazide, hydrochlorothiazide, hydroflumethiazide, benzylhydrochlorothiazide, penflutiazide, poly 5 thiazide, methyclothiazide etc.), anti-aldosterone preparations (e.g., spironolactone, triamterene etc.), carbonate dehydratase inhibitors (e.g., acetazolamide and the like), chlorobenzenesulfonamide preparations (e.g., chlortalidone, mefruside, indapamide etc.), azosemide, isosorbide, etacrynic acid, piretanide, bumetanide, furosemide and the like.

Examples of the antigout agents include allopurinol, probenecid, colchicine, benzbromarone, febuxostat, citrate and the like.

Examples of the antithrombotic agents include anticoagulating agent [e.g., heparin sodium, heparin potassium, warfarin potassium (warfarin), anti-thrombin drug (e.g., argatroban), activated blood coagulation factor X inhibitor (e.g., compounds described in WO 2004/048363 etc.) and the like], thrombolytic agent [e.g., tPA, urokinase], antiplatelet agent [e.g., aspirin, sulfinpyrazone (Anturan), dipyridamole (Persantin), ticlopidine (Panaldine), cilostazol (Pletal), GPIIb/IIIa antagonist (e.g., ReoPro), clopidogrel etc.], and the like.

Examples of the anti-inflammatory agents include nonsteroidal anti-inflammatory agents, such as acetaminophen, fenasetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizol, tiaramide hydrochloride, zaltoprofen, gabexate mesylate, camostat mesylate, ulinastatin, colchicine, probenecid, sulfinpyrazone, benzbromarone, allopurinol, sodium gold thiomalate, sodium hyaluronate, sodium salicylate, morphine hydrochloride, salicylic acid, atropine, scopolamine, morphine, pethidine, levorphanol, ketoprofen, naproxen, oxymorphone and their salts etc., and the like.

Examples of the chemotherapeutic agents include alkylating agents (e.g., cyclophosphamide, ifosfamide etc.), metabolic antagonists (e.g., methotrexate, 5-fluorouracil etc.), antitumor antibiotics (e.g., mitomycin, adriamycin etc.), plant-derived antitumor agent (e.g., vincristine, vindesine, Taxol etc.), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivative, Picibanil etc.), polysaccharides having immunity potentiating activity (e.g., lentinan, schizophyllan, krestin etc.), cytokines obtained by genetic engineering techniques (e.g., interferon, interleukin (IL) etc.), colony stimulating factors (e.g., granulocyte colony stimulating factor, erythropoietin etc.) and the like, with preference given to IL-1, IL-2, IL-12 and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium and the like.

Examples of the anti-dementia agents include tacrine, donepezil, rivastigmine, galanthamine and the like.

Examples of the erectile dysfunction amelioration agents include apomorphine, PDE5 (phosphodiesterase 5) inhibitors (e.g., sildenafil citrate) and the like.

Examples of the therapeutic agents for urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin etc.) [Cancer Research, Vol. 49, pages 5935-5939, 1989], progesterone derivatives (e.g., megestrol acetate) [Journal of Clinical Oncology, Vol. 12, pages 213-225, 1994], glucosteroids (e.g., dexamethasone etc.), metoclopramide agents, tetrahydrocannabinol agents (publications are all as mentioned above), fat metabolism improving agents (e.g., eicosapentanoic acid etc.) [British Journal of Cancer, Vol. 68, pages 314-318, 1993], growth hormones, IGF-1, or antibodies against a cachexia-inducing factor such as TNF-α, LIF, IL-6, oncostatin M, drugs for suppressing production thereof and the like, can be used in combination with the compound of the present invention.

Furthermore, examples of the concomitant drug include nerve regeneration promoting drugs (e.g., Y-128, VX853, prosaptide), antidepressants (e.g., desipramine, amitriptyline, imipramine), antiepileptics (e.g., lamotrigine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin), α2 receptor agonists (e.g., clonidine), local analgesics (e.g., capsaicin), antianxiety drugs (e.g., benzodiazepines), dopamine agonists (e.g., apomorphine), midazolam, ketoconazole and the like.

The concomitant drug preferably includes a diuretic, an insulin preparation, an insulin sensitizer, an α-glucosidase inhibitor, a biguanide agent, an insulin secretagogue (preferably sulfonylurea agent) and the like. Particularly, a diuretic such as hydrochlorothiazide and the like and an insulin sensitizer such as pioglitazone hydrochloride and the like are preferable.

The above-mentioned concomitant drug may be a combination of two or more kinds thereof combined at appropriate ratios.

When the compound of the present invention is used in combination with a concomitant drug, the amount of each drug can be reduced within a safe range in consideration of the opposite effect of these drugs. Particularly, the dose of the insulin sensitizer, insulin secretagogue and biguanide can be reduced from conventional level. As a result, the side effects possibly caused by the combination of these drugs can be prevented safely. In addition, the dose of the therapeutic agent for diabetic complications, anti-hyperlipidemia agent or anti-hypertensive agent can be reduced and, as a result, the side effects possibly caused by these drugs can be effectively prevented.

Since the compound of the present invention potentiates hypoglycemic activity of other insulin sensitizers, a combined use of the compound of the present invention or a salt thereof or a prodrug thereof (particularly, the compound of the present invention) and other insulin sensitizers (preferably pioglitazone hydrochloride) markedly enhances a prophylactic and/or therapeutic effect against diseases in which insulin resistance is involved, such as type II diabetes and the like.

In the pharmaceutical agent of the present invention, the compound (I) can be administered orally or parenterally as it is or after mixing with a pharmacologically acceptable carrier.

The dosage form of a pharmaceutical agent containing compound (I) of the present invention when used for oral administration include tablet (including sugar-coated tablet, film-coated tablet, sublingual tablet, orally disintegrating tablet), pill, granule, powder, capsule (including soft capsule, microcapsule), syrup, emulsion, suspension, film (e.g., orally disintegrating film) and the like, and the dosage form thereof for parenteral administration is, for example, injection, injecting agent, instillation, suppository and the like. In addition, it is effective to make a sustained release preparation by combining with a suitable base (e.g., polymer of butyric acid, polymer of glycolic acid, copolymer of butyric acid-glycolic acid, a mixture of polymer of butyric acid and polymer of glycolic acid, polyglycerol fatty acid ester etc.).

As a method to produce the compound (I) in the above-mentioned dosage form, a known production method generally used in the pertinent field can be applied. When the above-mentioned dosage form is produced, suitable amounts of an excipient, a binder, a disintegrant, a lubricant, a sweetener, is a surfactant, a suspending agent, an emulsifier and the like generally used in the pertinent field are appropriately added as necessary, and produced.

When the compound (I) is prepared into a tablet, for example, it can be produced by adding an excipient, a binder, a disintegrant, a lubricant and the like, and when a pill and a granule are to be prepared, they can be produced by adding an excipient, a binder, a disintegrant and the like. When a powder and a capsule are to be prepared, they can be produced by adding an excipient and the like, and when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, saccharose, microcrystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound (I) is produced in the above-mentioned dosage form, a suitable amount of a colorant, a preservative, an aromatic, a corrigent, a stabilizer, a thickening agent and the like typically used in the field of preparation can be added on demand.

When the compound (I) is administered parenterally, it is generally administered in the form of a liquid formulation (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg of body weight, which is preferably given by intravenous injection. As the injection, intravenous injection as well as subcutaneous injection, intracutaneous injection, intramuscular injection, instillation and the like are mentioned, and as a sustained release preparation, iontophoresis transdermal agent and the like are mentioned. Such injections are prepared by methods known per se, or by dissolving, suspending or emulsifying the compound (I) in a sterilized aqueous solution or oily liquid. As an aqueous solution for injection, physiological saline, isotonic solutions containing glucose or other auxiliary drugs (e.g., D-sorbitol, D-mannitol, sodium chloride and the like) and the like can be mentioned, and they can be used in combination with suitable solubilizing agents, such as alcohols (e.g., ethanol), polyalcohols (e.g., propylene glycol, polyethylene glycol), non-ionic surfactants (e.g., polysorbate 80, HCO-50) and the like. As an oily liquid, sesame oil, soybean oil and the like can be mentioned, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like may be mixed therewith. A prepared injection is generally filled in an ampoule.

Production Method

The production methods of the compound of the present invention are explained in the following.

The compound represented by the formula (I) of the present invention (compound (I)) can be produced, for example, by the method shown below or a method analogous thereto and the like.

In the following synthetic methods, the starting compounds may be used in the form of salt and, as such salt, those exemplified as the salt of the compound represented by the aforementioned formula (I) can be used.

Unless otherwise specified, the starting compound is easily commercially available, or can be produced by a method known per se or a method analogous thereto.

In the formula (I), the biphenyl moiety of the group represented by R:

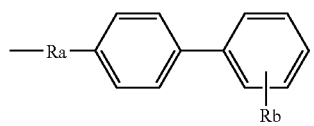

wherein each symbol is as defined above, optionally further has substituent(s), as mentioned above. In each of the following methods, the parts in the resulting product and starting material compounds thereof, which correspond to the above-mentioned biphenyl moiety, optionally further have substituent(s), unless otherwise specified.

While the yield of compound (I) obtained by each of the following methods may vary depending on the reaction conditions used, compound (I) can be obtained easily at a high purity from the resultant products by a conventional separation and purification means (recrystallization, column chromatography and the like).

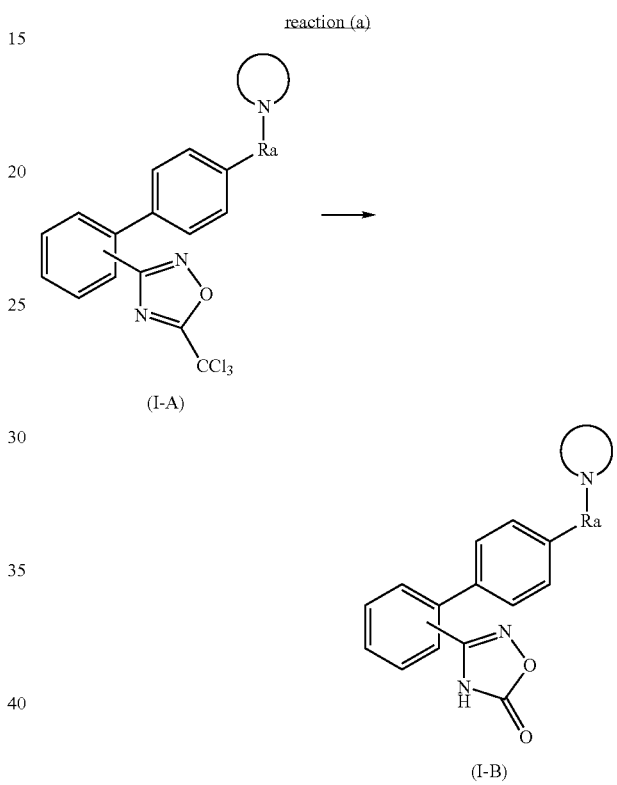

wherein each symbol is as defined above.

In reaction (a), 5-trichloromethyloxadiazole compound (I-A) obtained in the below-mentioned reaction (i) or a reaction analogous thereto is reacted in the presence of an aqueous alkaline solution to give oxadiazolone compound (I-B). Generally, the reaction is performed in an inert solvent using about 1 to 3 molar equivalents of the aqueous alkaline solution relative to compound (I-A).

Examples of such solvent include ethers such as 1,4-dioxane, tetrahydrofuran and the like; alcohols such as methanol, ethanol and the like; water and the like. These solvents may be used as a mixture of two or more kinds thereof at an appropriate ratio.

Examples of the alkali to be used for alkaline aqueous solution include sodium hydroxide, potassium hydroxide, lithium hydroxide, sodium carbonate, potassium carbonate and the like.

The reaction temperature is generally about −50° C. to about 150° C., preferably about 0° C. to about 60° C.

The reaction time is generally about 0.5 to about 20 hr.

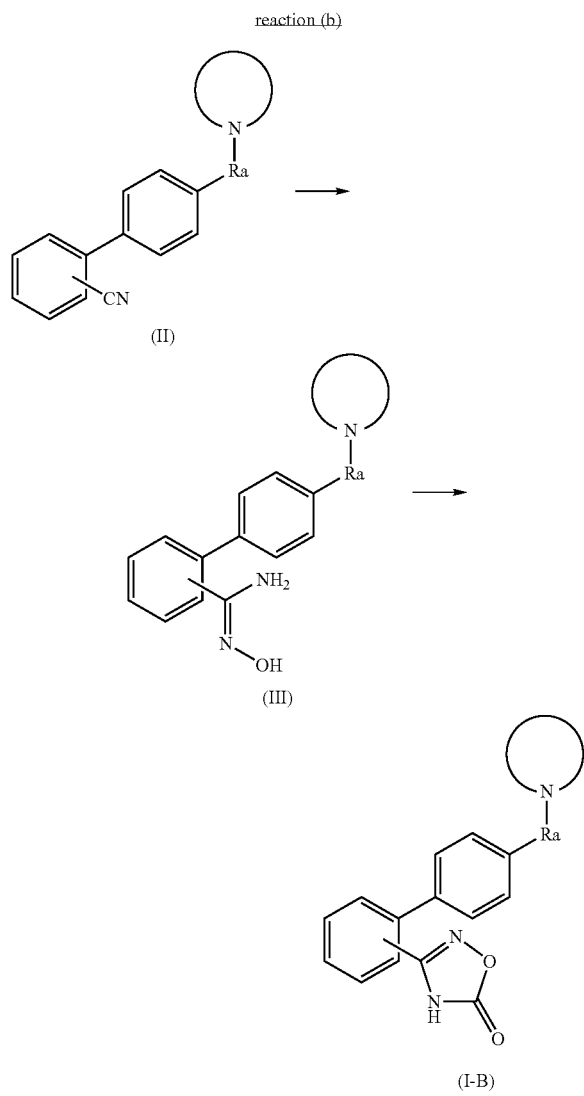

wherein each symbol is as defined above.

In reaction (b), cyano compound (II) obtained in the below-mentioned reactions (g) to (j) or a reaction analogous thereto is converted to amidoxime compound (III), which is then subjected to ring closure to give oxadiazolone compound (I-B).

The reaction to obtain compound (III) is performed in an inert organic solvent using about 1 to 20 mol of hydroxylamine per 1 mol of compound (II).

Examples of such solvent include sulfoxides such as dimethyl sulfoxide and the like; amides such as N,N-dimethylformamide, N,N-dimethylacetamide and the like; alcohols such as methanol, ethanol and the like; ethers such as 1,4-dioxane, tetrahydrofuran etc. and the like. These solvents may be used as a mixture of two or more kinds thereof at an appropriate ratio.

When an inorganic acid salt such as hydroxylamine hydrochloride, hydroxylamine sulfate and the like, or an organic acid salt such as hydroxylamine oxalate and the like is used as hydroxylamine, the reaction is performed in the presence of an equivalent amount or a small excess of a suitable base such as potassium carbonate, sodium hydrogen carbonate, sodium hydroxide, triethylamine, sodium methoxide, sodium hydride and the like.

When an inorganic acid salt or organic acid salt of hydroxylamine is used, the reaction may be performed with addition of about 5 to 20% of water to an organic solvent.

The reaction temperature is generally about −50° C. to about 150° C., preferably about 25° C. to about 100° C.

The reaction time is generally about 3 to about 48 hr.

The reaction to obtain oxadiazolone compound (I-B) from amidoxime compound (III) is performed using about 1 to 2 molar equivalents of a carbonylation reagent relative to amidoxime compound (III) in a solvent that does not adversely influence the reaction in the presence of an equivalent amount or a small excess of a base.

Examples of the carbonylation reagent include N,N'-carbonyldiimidazole, triphosgene, methyl chlorocarbonate, ethyl chlorocarbonate and the like.

Examples of the base include organic amines such as triethylamine, pyridine, diisopropylethylamine, 1,8-diazabicyclo[5.4.0]undec-7-ene and the like; inorganic salts such as potassium carbonate, sodium carbonate etc. and the like.

Examples of the solvent include halogenated carbons such as dichloromethane, chloroform, carbon tetrachloride and the like; amides such as N,N-dimethylformamide, N,N-dimethylacetamide and the like; ethers such as diethyl ether, 1,4-dioxane, tetrahydrofuran etc. and the like. These solvents may be used as a mixture of two or more kinds thereof at an appropriate ratio.

The reaction temperature is generally about −50° C. to about 100° C., preferably about 0° C. to about 50° C.

The reaction time is generally about 0.1 to about 5 hr.

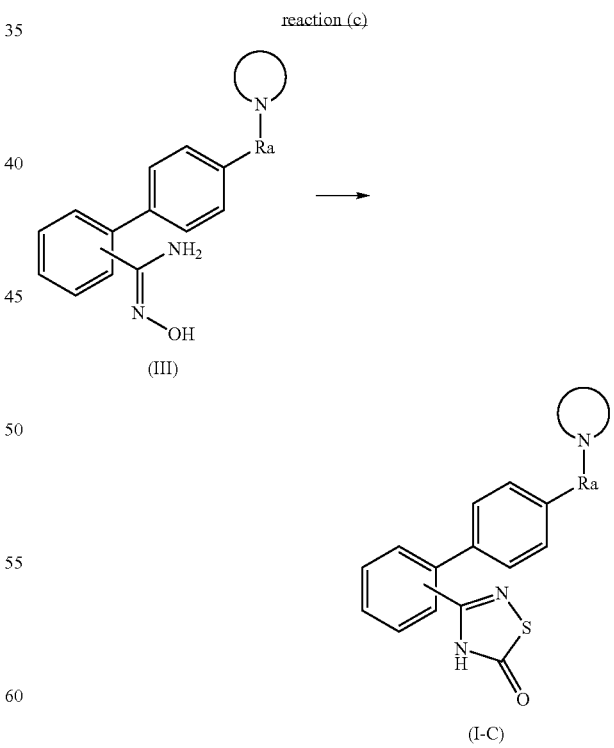

wherein each symbol is as defined above.

In reaction (c), amidoxime compound (III) obtained in reaction (b) or a reaction analogous thereto is subjected to ring closure to give thiadiazolone compound (I-C).

The reaction to obtain compound (I-C) is performed using about 1 to 2 mol of 1,1'-thiocarbonyldiimidazole per 1 mol of compound (III) in the presence of Lewis acid in an organic solvent that does not adversely influence the reaction.

The Lewis acid is not particularly limited as long as the is reaction proceeds and, for example, boron trifluoride diethyl ether complex, tin(II) chloride, zinc chloride, copper(I) chloride, silica gel and the like can be mentioned. The amount of the Lewis acids to be used is preferably about 1 to 3 mol per 1 mol of compound (III).

Examples of the solvent include halogenated carbons such as dichloromethane, chloroform, carbon tetrachloride and the like; amides such as N,N-dimethylformamide, N,N-dimethylacetamide and the like; sulfoxides such as dimethyl sulfoxide and the like; ethers such as diethyl ether, 1,4-dioxane, tetrahydrofuran etc. and the like. These solvents may be used as a mixture of two or more kinds thereof at an appropriate ratio.

The reaction temperature is generally about −50° C. to about 100° C., preferably about 0° C. to about 50° C.

The reaction time is generally about 0.1 to about 5 hr.

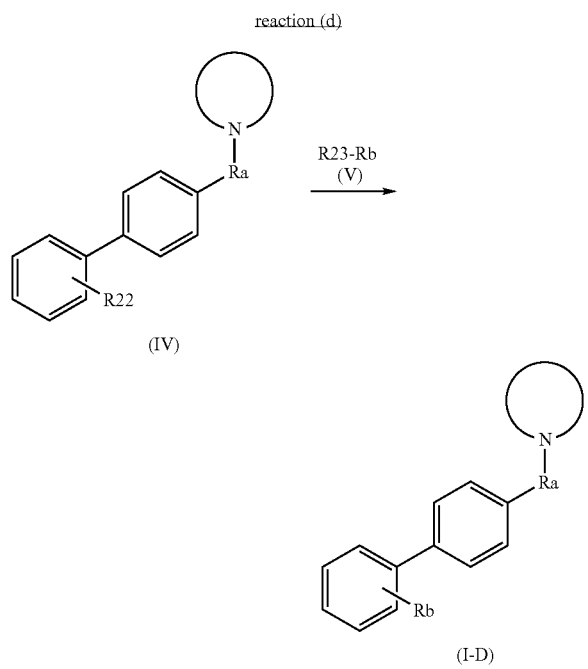

wherein each symbol is as defined above, R22 and R23 are leaving groups (e.g., halogen atom such as chlorine, bromine, iodine and the like; substituted sulfonic acid ester such as trifluoromethanesulfonic acid ester and the like, and the like), or a metal (e.g., potassium, sodium, lithium, magnesium, copper, mercury, zinc, thallium, boron, tin and the like).

In reaction (d), compound (IV) obtained by the below-mentioned reaction (i) or a reaction analogous thereto is reacted with compound (V) to give compound (I-D).

The reaction to obtain compound (I-D) is performed by reacting 1 mol of compound (IV) with about 1-3 mol of compound (V) in an organic solvent that does not adversely influence the reaction.

Examples of such solvent include ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide and the like; and the like. As the solvent, two or more kinds of these solvents may be used in the form of a mixture at any ratio.

In the above-mentioned reaction (d), when R22 of compound (IV) is a leaving group, and R23 of compound (V) is a metal, the reaction can also be promoted by performing the reaction according to a method known per se, for example, the method described in Journal of the American Chemical Society, vol. 124, page 7421 (2002) and the like, or a method analogous thereto in the presence of a metal catalyst.

Examples of the metal catalyst include palladium compound (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), copper compounds (e.g., copper powder, copper(I) chloride, copper(I) iodide, copper(I) acetate and the like), nickel compounds (e.g., tetrakis(triphenylphosphine)nickel and the like), rhodium compounds (e.g., tris(triphenylphosphine)rhodium chloride and the like), platinum compounds and the like.

The amount of the metal catalyst to be used is about 0.000001 molar-5 molar equivalents, preferably 0.0001 molar-1 molar equivalent, relative to compound (IV).

The above-mentioned reaction may be performed in the presence of a base and a ligand. Examples of the base include metal alkoxides such as potassium phenoxide, sodium tert-butoxide and the like; inorganic salts such as potassium carbonate, sodium carbonate, cesium carbonate, potassium phosphate and the like; and the like. Examples of the ligand include organic phosphorus compounds such as triphenylphosphine, tri-tert-butylphosphine, tricyclohexylphosphine, BINAP(2,2'-bis(diphenylphosphino)-1,1'-binaphthyl) and the like; organic amine compounds such as N,N'-dimethyl-cyclohexane-1,2-diamine, 2,2-bipyridyl and the like; and the like.

When a metal catalyst unstable to oxygen is used for this reaction, the reaction is preferably performed under an inert gas (e.g., argon, nitrogen and the like) atmosphere.

The reaction temperature is generally about −50° C. to about 150° C., preferably about −10° C. to about 120° C.

The reaction time is generally about 0.5 to about 20 hr.

In the above-mentioned reaction (d), when R22 of compound (IV) is a metal, and R23 of compound (V) is a leaving group, the reaction can also be promoted by performing the reaction according to a method known per se, for example, the method described in Journal of the American Chemical Society, vol. 124, page 7421 (2002) and the like, or a method analogous thereto in the presence of a metal catalyst.

Examples of the metal catalyst include palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), copper compounds (e.g., copper powder, copper(I) chloride, copper(I) iodide, copper(I) acetate and the like), nickel compounds (e.g., tetrakis(triphenylphosphine)nickel and the like), rhodium compounds (e.g., tris(triphenylphosphine)rhodium chloride and the like), platinum compound and the like.

The amount of the metal catalyst to be used is about 0.000001 mol-5 molar equivalents, preferably 0.0001 mol-1 molar equivalent, relative to compound (IV).

The above-mentioned reaction may be performed in the presence of a base and a ligand. Examples of the base include metal alkoxides such as potassium phenoxide, sodium tert-butoxide and the like; inorganic salts such as potassium carbonate, sodium carbonate, cesium carbonate, potassium phosphate and the like; and the like. Examples of the ligand include organic phosphorus compounds such as triphenylphosphine, tri-tert-butylphosphine, tricyclohexylphosphine, BINAP(2,2'-bis(diphenylphosphino)-1,1'-binaphthyl) and the like; organic amine compounds such as N,N'-dimethyl-cyclohexane-1,2-diamine, 2,2-bipyridyl and the like; and the like.

When a metal catalyst unstable to oxygen is used for this reaction, the reaction is preferably performed under an inert gas (e.g., argon, nitrogen and the like) atmosphere.

The reaction temperature is generally about −50° C. to about 150° C., preferably about −10° C. to about 120° C.

The reaction time is generally about 0.5 to about 20 hr.

Compound (V) used as a starting material compound in the above-mentioned reaction can be produced according to a method known per se.

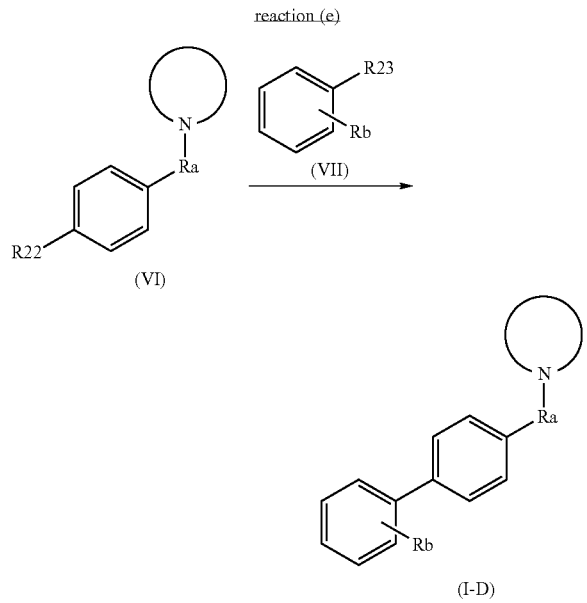

wherein each symbol is as defined above.

In reaction (e), compound (VI) obtained according to the below-mentioned reaction (i) or a reaction analogous thereto is reacted with compound (VII) to give compound (I-D). This reaction can be performed by a method similar to the method described in reaction (d).

Compound (VII) used as a starting material compound in the above-mentioned reaction can be produced according to a method known per se.

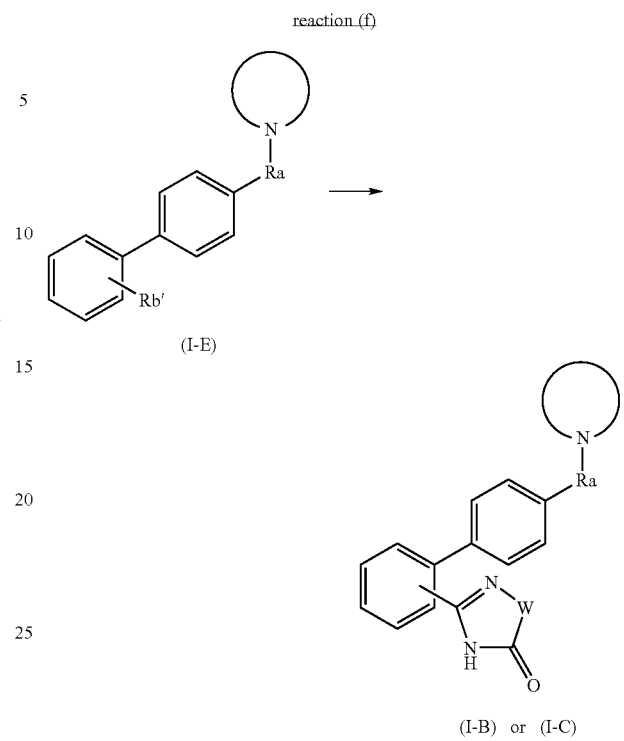

wherein each symbol is as defined above, Rb' is an oxadiazolone ring or thiadiazolone ring protected by a suitable protecting group (e.g., triphenylmethyl, methoxymethyl, methoxyethoxymethyl and 2-tetrahydropyranyl and the like).

In reaction (f), the protecting group of the Rb' moiety of compound (I-E) obtained according to the below-mentioned reaction (i) or a reaction analogous thereto is removed to give compound (I-B) or (I-C).

In the above-mentioned reaction (f), deprotection conditions vary depending on the protecting group to be used. When the protecting group is, for example, triphenylmethyl, methoxymethyl, methoxyethoxymethyl, 2-tetrahydropyranyl and the like, deprotection is performed in water-containing alcohols (e.g., methanol, ethanol and the like) containing about 0.5N-2N hydrochloric acid, sulfuric acid or acetic acid or a mixture of trifluoroacetic acid and water (1:2-5).

The reaction temperature is generally about −50° C. to about 150° C., preferably about 0° C. to about 60° C.

The reaction time is generally about 0.5 to about 20 hr.

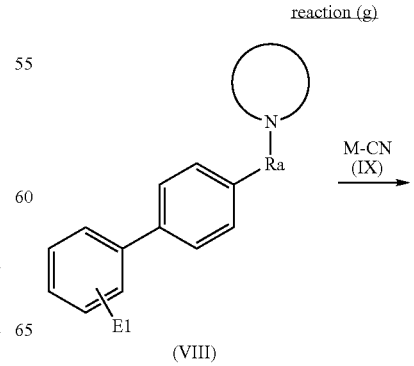

-continued

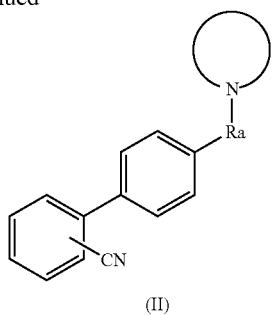

(II)

wherein each symbol is as defined above, E1 is a leaving group (e.g., halogen atom such as chlorine, bromine, iodine and the like, and the like; substituted sulfonic acid ester such as trifluoromethanesulfonic acid ester and the like, and the like), M is a metal (e.g., potassium, sodium, lithium, magnesium, copper, mercury, zinc, thallium, boron, tin, silicon and the like).

In the above-mentioned reaction (g), cyano compound (II) is obtained from compound (VIII) obtained according to the below-mentioned reaction (i) or a reaction analogous thereto. The amount of compound (IX) to be used is preferably about 1 to about 5 molar equivalents relative to compound (VIII).

In the above-mentioned reaction (g), the reaction to obtain compound (II) from compound (VIII) is performed in a solvent that does not adversely influence the reaction. Preferable examples of such solvent include alcohols (e.g., methanol, ethanol, ethylene glycol and the like), ethers (e.g., diethyl ether, tetrahydrofuran, 1,4-dioxane, 1,2-dimethoxyethane and the like), amides (e.g., N,N-dimethylformamide, N,N-dimethylacetamide, N-methylpyrrolidone and the like), aromatic hydrocarbons (e.g., toluene, xylene and the like) and the like. These solvents may be used in a mixture of two or more kinds thereof at an appropriate ratio. In addition, water may be added at an appropriately ratio.

In the above-mentioned reaction (g), the reaction to obtain compound (II) from compound (VIII) can be performed by a method known per se, for example, the method described in Tetrahedron Letters, vol. 40, page 8193 (1999) and the like, or a method analogous thereto. In addition, the reaction can also be promoted by performing the method in the presence of a metal catalyst. Examples of the metal catalyst include palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), copper compounds (e.g., copper powder, copper(I) chloride, copper(I) iodide, copper(I) acetate and the like), nickel compounds (e.g., tetrakis(triphenylphosphine)nickel and the like), rhodium compounds (e.g., tris(triphenylphosphine)rhodium chloride and the like), platinum compounds and the like.

The amount of the metal catalyst to be used is about 0.000001 molar-5 molar equivalents, preferably 0.0001 molar-1 molar equivalent, relative to compound (VIII).

The above-mentioned reaction may be performed in the presence of a ligand. Examples of the ligand include organic phosphorus compounds such as triphenylphosphine, tri-tert-butylphosphine, tricyclohexylphosphine, BINAP(2,2'-bis(diphenylphosphino)-1,1'-binaphthyl) and the like; organic amine compounds such as N,N'-dimethyl-cyclohexane-1,2-diamine, 2,2-bipyridyl and the like; and the like.

When a metal catalyst unstable to oxygen is used in this reaction, the reaction is preferably performed in an inert gas (e.g., argon, nitrogen and the like) atmosphere.

The reaction temperature is generally about −50° C. to about 300° C., preferably about −10° C. to about 150° C.

The reaction time is generally about 0.5 to about 20 hr.

Compound (IX) used as a starting material compound in the above-mentioned reaction can be produced according to a method known per se.

reaction (h)

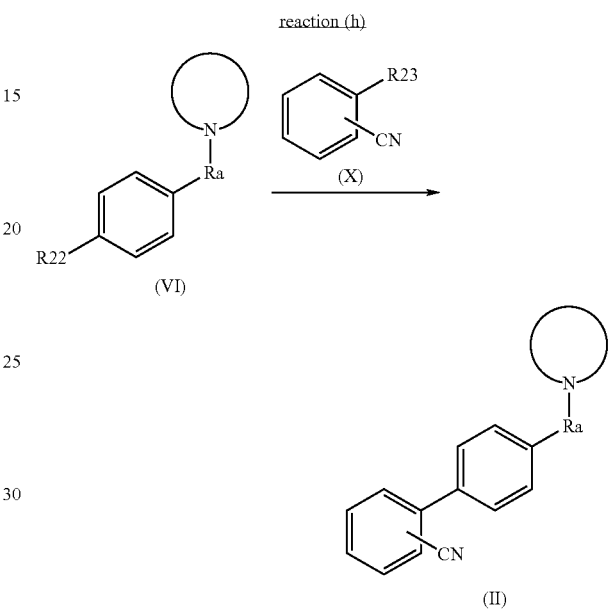

wherein each symbol is as defined above.

The above-mentioned reaction (h) can be performed by a method similar to the method described in reaction (d).

Compound (VI) used as a starting material compound in the above-mentioned reaction can be produced, for example, according to the below-mentioned reaction (i) or a reaction analogous thereto. Moreover, compound (X) can be produced according to a method known per se.

reaction (i)

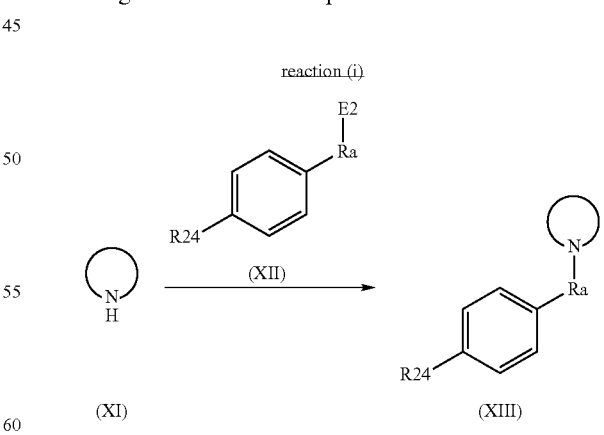

wherein each symbol is as defined above, E2 is a leaving group (e.g., halogen atom such as chlorine, bromine, iodine and the like; substituted sulfonic acid ester such as trifluoromethanesulfonic acid ester and the like; hydroxy group and the like), R24 is a leaving group (e.g., halogen atom such as chlorine, bromine, iodine and the like, and the like; substituted sulfonic acid ester such as trifluoromethanesulfonic acid ester and the like, and the like), metal (e.g., potassium, sodium, lithium, magnesium, copper, mercury, zinc, thallium, boron, tin, silicon and the like) or the formula:

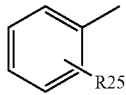

wherein R25 is a cyano group, a 5-trichloromethyl-1,2,4-oxadiazol-3-yl group or a leaving group (e.g., halogen atom such as chlorine, bromine, iodine and the like, and the like).

In reaction (i), compound (XI) is reacted with compound (XII) to give compound (XIII). Generally, the reaction is performed using about 1-3 mol of compound (XII) per 1 mol of compound (XI) in an organic solvent that does not adversely influence the reaction.

In reaction (i), when E2 is halogen atom or substituted sulfonic acid ester, the reaction is performed according to a conventional method in a solvent that does not adversely influence the reaction in the presence of base.

Examples of the base include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide etc. and the like.

The amount of the bases to be used is preferably about 1 to about 5 molar equivalents relative to compound (XI).

Examples of the solvent that does not adversely influence the reaction include aromatic hydrocarbons such as benzene, toluene, xylene and the like; nitriles such as acetonitrile, propionitrile and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide etc. and the like. These solvents may be used as a mixture of two or more kinds thereof at an appropriate ratio.

The reaction temperature is generally about −50° C. to about 150° C., preferably about −10° C. to about 100° C.

The reaction time is generally about 0.5 to about 20 hr.

In reaction (i), when E2 is a hydroxy group, this reaction is performed by a method known per se, for example, the method described in Synthesis, p. 1 (1981) and the like or a method analogous thereto. That is, this reaction is generally performed in the presence of an organic phosphorus compound and an azo reagent, in a solvent that does not adversely influence the reaction.

Examples of the organic phosphorus compound include triphenylphosphine, tri(n-butyl)phosphine and the like.

Examples of the azo reagent include diethyl azodicarboxylate, diisopropyl azodicarboxylate, azodicarbonyldipiperadine and the like.

The amount of the organic phosphorus compound and azo reagent to be used is preferably about 1 to about 5 molar equivalents relative to compound (XI).

Examples of the solvent that does not adversely influence the reaction include ethers such as diethyl ether, tetrahydrofuran, 1,4-dioxane and the like; halogenated hydrocarbons such as chloroform, dichloromethane and the like; aromatic hydrocarbons such as benzene, toluene, xylene and the like; amides such as N,N-dimethylformamide and the like; sulfoxides such as dimethyl sulfoxide and the like, and the like. These solvents may be used as a mixture of two or more kinds thereof at an appropriate ratio.

The reaction temperature is generally about −50° C. to about 150° C., preferably about −10° C. to about 100° C.

The reaction time is generally about 0.5 to about 20 hr.

Compound (XI) and compound (XII) used as starting material compounds in the above-mentioned reaction can be produced according to a method known per se.

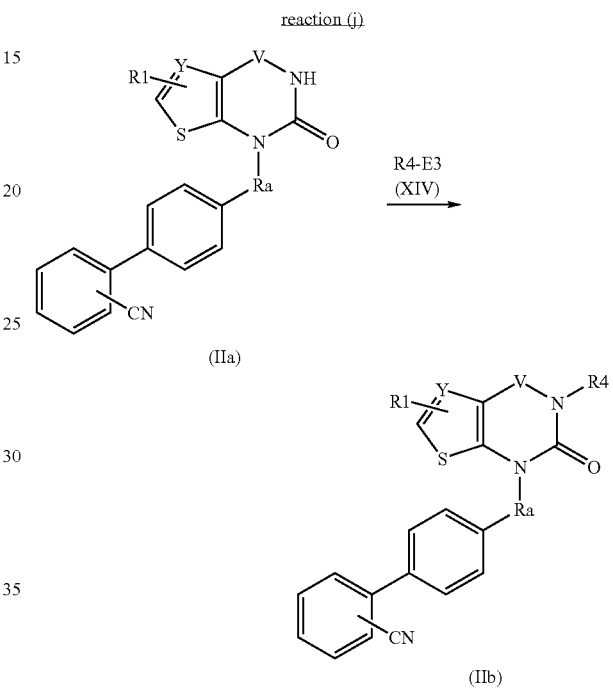

wherein each symbol is as defined above, E3 is a leaving group (e.g., halogen atom such as chlorine, bromine, iodine and the like; substituted sulfonic acid esters such as methanesulfonic acid ester, p-toluenesulfonic acid ester and the like; a hydroxy group; boronic acid or boric acid ester and the like), V is a group of the formula: CO or the formula: S(O)n wherein n is 1 or 2).

Reaction (j) shows a method of producing compound (IIb) wherein the formula:

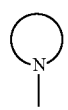

is the formula:

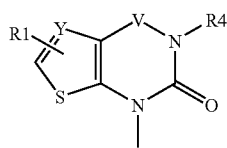

wherein each symbol is as defined above, from among the starting material compounds (II) used for the above-mentioned reaction (b), which includes reacting compound (IIa) with compound (XIV).

When E3 is a halogen atom, a substituted sulfonic acid ester or a hydroxy group, the above-mentioned reaction (j) can be performed by a method similar to the method shown in reaction (i).

Particularly when E3 is a halogen atom or a substituted sulfonic acid ester, and R4 is an aryl group, reaction (j) can be also promoted by a method known per se, for example, the method described in Journal of the American Chemical Society, vol. 124, p. 7421 (2002) and the like or a method analogous thereto, in the presence of a metal catalyst. Examples of the metal catalyst include palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), copper compounds (e.g., copper powder, copper(I) chloride, copper(I) iodide, copper (I) acetate and the like), nickel compounds (e.g., tetrakis (triphenylphosphine)nickel and the like), rhodium compounds (e.g., tris(triphenylphosphine)rhodium chloride and the like), platinum compounds and the like.

The amount of the metal catalyst to be used is about 0.000001 molar-5 molar equivalents, preferably 0.0001 molar-1 molar equivalent, relative to compound (IIa).

The above-mentioned reaction may be performed using a base and a ligand. Examples of the base include metal alkoxides such as potassium phenoxide, sodium tert-butoxide and the like; inorganic salts such as potassium carbonate, sodium carbonate, cesium carbonate, potassium phosphate etc., and the like. Examples of the ligand include organic phosphorus compounds such as triphenylphosphine, tri-tert-butylphosphine, tricyclohexylphosphine, BINAP (2,2'-bis(diphenylphosphino)-1,1'-binaphthyl) and the like; organic amine compounds such as N,N'-dimethyl-cyclohexane-1,2-diamine, 2,2'-bipyridyl and the like, and the like.

When a metal catalyst unstable to oxygen is used, this reaction is preferably performed under an inert gas (e.g., argon, nitrogen and the like) atmosphere.

The reaction temperature is generally about −50° C. to about 150° C., preferably about −10° C. to about 100° C.

The reaction time is generally about 0.5 to about 20 hr.

In reaction (j), when E3 is a boronic acid or a boronic acid ester, this reaction is performed by a method known per se, for example, the method described in Tetrahedron Letters, vol. 39, p. 2933 (1998) and the like or a method analogous thereto, in the presence of a base and a metal catalyst, in a solvent that does not adversely influence the reaction.

Examples of the base include inorganic salts such as potassium carbonate, sodium carbonate, cesium carbonate and the like; metal alkoxides such as sodium methoxide, sodium ethoxide, potassium tert-butoxide and the like; amines such as pyridine,. triethylamine, N,N-dimethylaniline, 1,8-diazabicyclo[5.4.0]undec-7-ene etc. and the like. These bases may be used as a mixture of two or more kinds thereof at an appropriate ratio.

Examples of the metal catalyst include copper or salts thereof (e.g., copper(II) acetate, copper(II) chloride and the like), palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), nickel compounds (e.g., tetrakis(triphenylphosphine)nickel and the like), rhodium compounds (e.g., tris(triphenylphosphine)rhodium chloride and the like), platinum compounds and the like. Of these, copper or salts thereof is preferable.

Examples of the solvent that does not adversely influence the reaction include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide etc. and the like. These solvents may be used as a mixture of two or more kinds thereof at an appropriate ratio.

When copper or a salt thereof is used as a metal catalyst, this reaction is preferably performed under an air atmosphere or an oxygen atmosphere. When a metal catalyst unstable to oxygen is used, this reaction is preferably performed under an inert gas (e.g., argon, nitrogen and the like) atmosphere. In addition, this reaction may be performed using molecular sieves.

The amount of the metal catalyst to be used is about 0.000001 molar-5 molar equivalents, preferably 0.0001 molar-1 molar equivalent, relative to compound (IIa).

The reaction temperature is generally about 0° C. to about 200° C., preferably 10° C. to about 100° C.

The reaction time is generally about 2 to about 96 hr.

Compound (IIa) used as a starting material compound in the above-mentioned reaction can be produced, for example, according to the aforementioned reactions (g)-(i), or a reaction analogous thereto. Compound (XIV) can be produced according to a method known per se.

In each of the aforementioned reactions (a) to (j), when the starting compound has a hydroxy group, an amino group, a carboxyl group or a carbonyl group as a substituent, a protecting group generally used in the peptide chemistry and the like may be introduced into these groups. By removing the protecting group as necessary after the reaction, the object compound can be obtained.

Examples of the protecting group of hydroxy group include $(C_1-C_6)$alkyl group (e.g., methyl, ethyl, propyl, isopropyl, butyl, tert-butyl), phenyl group, trityl group, $(C_7-C_{10})$ aralkyl group (e.g., benzyl), formyl group, $(C_1-C_6)$alkyl-carbonyl group (e.g., acetyl, propionyl), benzoyl group, $(C_7-C_{10})$aralkyl-carbonyl group (e.g., benzylcarbonyl), 2-tetrahydropyranyl group, 2-tetrahydrofuranyl group, silyl group (e.g., trimethylsilyl, triethylsilyl, dimethylphenylsilyl, tert-butyldimethylsilyl, tert-butyldiethylsilyl), $(C_2-C_6)$alkenyl group (e.g., 1-allyl) and the like. These groups are optionally substituted by 1 to 3 substituents selected from halogen atom (e.g., fluorine, chlorine, bromine, iodine), $(C_1-C_6)$alkyl group (e.g., methyl, ethyl, propyl), $(C_1-C_6)$alkoxy group (e.g., methoxy, ethoxy, propoxy), nitro group and the like.

Examples of the amino-protecting group include formyl group, $(C_1-C_6)$alkyl-carbonyl group (e.g., acetyl, propionyl), $(C_1-C_6)$alkoxy-carbonyl group (e.g., methoxycarbonyl, ethoxycarbonyl, tert-butoxycarbonyl), benzoyl group, $(C_7-C_{10})$aralkyl-carbonyl group (e.g., benzylcarbonyl), $(C_7-C_{14})$ aralkyloxy-carbonyl group (e.g., benzyloxycarbonyl, 9-fluorenylmethoxycarbonyl), trityl group, phthaloyl group, N,N-dimethylaminomethylene group, silyl group (e.g., trimethylsilyl, triethylsilyl, dimethylphenylsilyl, tert-butyldimethylsilyl, tert-butyldiethylsilyl), $(C_2-C_6)$alkenyl group (e.g., 1-allyl) and the like. These groups are optionally substituted by 1 to 3 substituents selected from halogen atom (e.g., fluorine, chlorine, bromine, iodine), $(C_1-C_6)$lkoxy group (e.g., methoxy, ethoxy, propoxy), nitro group and the like.

Examples of the protecting group of carboxy group include ($C_1$-$C_6$)alkyl group (e.g., methyl, ethyl, propyl, isopropyl, butyl, tert-butyl), ($C_7$-$C_{10}$)aralkyl group (e.g., benzyl), phenyl group, trityl group, silyl group (e.g., trimethylsilyl, triethylsilyl, dimethylphenylsilyl, tert-butyldimethylsilyl, tert-butyldiethylsilyl, tert-butyldiphenylsilyl), ($C_2$-$C_6$)lkenyl group (e.g., 1-allyl) and the like. These groups are optionally substituted by 1 to 3 substituents selected from halogen atom (e.g., fluorine, chlorine, bromine, iodine), ($C_1$-$C_6$)alkoxy group (e.g., methoxy, ethoxy, propoxy), nitro group and the like.

Examples of the protecting group of carbonyl group include cyclic acetal (e.g., 1,3-dioxane), acyclic acetal (e.g., di-($C_1$-$C_6$)alkyl acetal) and the like.

These protecting groups can be removed according to a method known per se, for example, the method described in Protective Groups in Organic Synthesis, John Wiley and Sons (1980) and the like. For example, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide and the like) and the like, reduction method and the like can be used.

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, (+)-cinchonine, (−)-cinchonidine, brucine, etc.) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (phosphate buffer, etc.) and organic solvents (ethanol, methanol, isopropanol, acetonitrile, trifluoroacetic acid, diethylamine, etc.) solely or in admixture to separate the optical isomer.

3) Diastereomer Method

A method wherein a racemic mixture is prepared into a diastereomeric mixture by chemical reaction with an optically active reagent, which is made into a single substance by a typical separation means (a fractional recrystallization method, a chromatography method, etc.) and the like, and is subjected to a chemical treatment such as hydrolysis and the like to separate an optically active reagent moiety, whereby an optical isomer is obtained. For example, when compound (I) contains hydroxy, or primary or secondary amino in a molecule, the compound and an optically active organic acid (MTPA [α-methoxy-α-(trifluoromethyl)phenylacetic acid], (−)-menthoxyacetic acid, etc.) and the like are subjected to condensation reaction to give diastereomers in the ester form or in the amide form, respectively. When compound (I) has a carboxylic acid group, this compound and an optically active amine or an alcohol reagent are subjected to condensation reaction to give diastereomers in the amide form or in the ester form, respectively. The separated diastereomer is converted to an optical isomer of the original compound by acid hydrolysis or base hydrolysis.

EXAMPLE

The present invention is described in detail by way of the following Experimental Examples, Reference Examples, Examples and Formulation Examples, which are not to be construed as limitative.

In the following Reference Examples and Examples, the room temperature means 1° C.-30° C.

As for NMR spectra, the chemical shift was indicated by δ, and a coupling constant was indicated by Hz. The numeric value in parenthesis with regard to a mixed solvent is a volumetric mixing ratio of each solvent. Moreover, "%" in the solution represents the number of grams in 100 ml of a solution.

The abbreviations used in the present specification mean the following.
s: singlet
d: doublet
t: triplet
q: quartet
dd: double doublet
dt: double triplet
dq: double quartet
td: triple doublet
qd: quadruple doublet
ddd: double double doublet
m: multiplet
br: broad
J: coupling constant
ADDP: 1,1'-(azodicarbonyl)dipiperidine
Boc: tert-butoxycarbonyl group
$CDCl_3$: deuterated chloroform
DMSO-$d_6$: dimethyl sulfoxide-$d_6$
$^1$H NMR: proton nuclear magnetic resonance
Ms: mesyl group (methanesulfonyl group)
TBS: tert-butyl(dimethyl)silyl
THF: tetrahydrofuran
TIPS: triisopropylsilyl In the following Reference Examples and Examples, purification by preparative HPLC was performed under the following conditions.
instrument: high-throughput purification system (Gilson Inc.)
column: YMC CombiPrep ODS-A S-5 μm, 50×20 mm or YMC
Hydrosphere C18 S-5 μm solvent: SOLUTION A; 0.1% aqueous trifluoroacetic acid solution, SOLUTION B; 0.1% trifluoroacetic acid acetonitrile solution, or SOLUTION A; water, SOLUTION B; acetonitrile, or SOLUTION A; 0.1% aqueous formic acid solution, SOLUTION B; 0.1% formic acid acetonitrile solution typical gradient cycle: 0 min (SOLUTION A/SOLUTION B=98/2), 1.00 min (SOLUTION A/SOLUTION B=98/2), 5.20 min (SOLUTION A/SOLUTION B=0/100), 6.40 min (SOLUTION A/SOLUTION B=0/100), 6.50 min (SOLUTION A/SOLUTION B=98/2), 6.60 min (SOLUTION A/SOLUTION B=98/2)

flow rate: 25 mL/min detection method: UV 220 nm

Reference Example 1

3-butyl-6-ethylthieno[2,3-d]pyrimidine-2,4(1H,3H)-dione

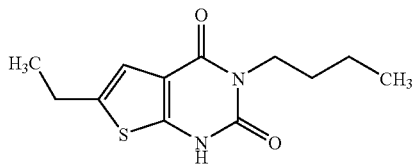 [SMILES: CCCCn1c(=O)[nH]c2sc(CC)cc2c1=O]

To a mixture of methyl 2-amino-5-ethylthiophene-3-carboxylate (2.5 g), 1-isocyanatobutane (1.52 mL) and tetrahydrofuran (20 ml) was added sodium hydride (1.2 g), and the mixture was stirred at 60° C. for. 5 hr. The reaction mixture was diluted with water, and the mixture was adjusted to pH 4 with 1N hydrochloric acid, the precipitated solid was collected by filtration. The obtained solid was recrystallized from ethyl acetate to give the title compound as colorless crystals (1.85 g, 54%).

$^1$H NMR (400 MHz, CDCl$_3$)δ0.96 (3H, t, J=7.2), 1.31 (3H,t, J=7.2), 1.36-1.45 (2H, m), 1.62-1.70 (2H, m), 2.77 (2H, q, J=7.6), 4.02(2H, t, J=7.6), 6.96 (1H, s), 10.3 (1H, br)

Reference Example 2

3-benzyl-6-ethylthieno[2,3-d]pyrimidine-2,4(1H, 3H)-dione

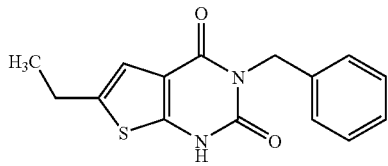 [SMILES: CCc1cc2c(=O)n(Cc3ccccc3)c(=O)[nH]c2s1]

To a mixture of methyl 2-amino-5-ethylthiophene-3-carboxylate (5 g), (isocyanatomethyl)benzene (3.33 mL) and tetrahydrofuran (50 mL) was added sodium hydride (1.18 g), and the mixture was stirred at 60° C. for 5 hr. The reaction mixture was diluted with water, and the mixture was adjusted to pH 4 with 1N hydrochloric acid, and extracted with ethyl acetate. The obtained ethyl acetate layer was washed with saturated brine, and dried over anhydrous magnesium sulfate. The solvent was evaporated under reduced pressure. The obtained residue was recrystallized from ethyl acetate to give the title compound as colorless crystals (2.1 g, 25%).

$^1$H NMR (400 MHz, CDCl$_3$)δ1.30 (3H, t, J=7.2), 2.77 (2H,q, J=7.6), 5.19 (2H, s), 7.22-7.31 (3H, m), 7.49 (2H, d, J=7.6), 10.4 (1H,br)

Reference Example 3 methyl 2-[(ethoxycarbonyl)amino]-5-ethylthiophene-3-carboxylate

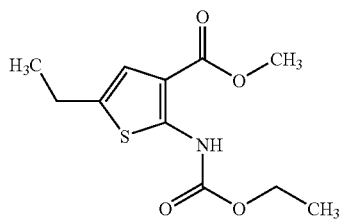 [SMILES: CCOC(=O)Nc1sc(CC)cc1C(=O)OC]

A mixture of methyl 2-amino-5-ethylthiophene-3-carboxylate (7.07 g), ethyl chloroformate (4.4 mL) and toluene (100 mL) was stirred at 100° C. for 3 hr. The reaction mixture was concentrated under reduced pressure, and the obtained residue was purified by silica gel column chromatography to give the title compound as colorless oil (9 g, 92%).

$^1$H NMR (300 MHz, CDCl$_3$)δ1.28 (3H, t, J=7.6), 1.33 (3H,t, J=7.6), 2.71 (2H, dq, J=7.2, 1.2), 3.85 (3H, s), 4.27 (2H, q, J=7.2),6.81 (1H, s), 10.1 (1H, br)

Reference Example 4 ethyl (5-ethyl-3-{[(2-hydroxyethyl)amino]carbonyl}-2-thienyl) carbamate

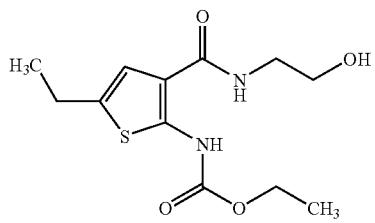

A mixture of methyl 2-[(ethoxycarbonyl)amino]-5-ethylthiophene-3-carboxylate (3 g) and ethanolamine (3.5 mL) was stirred at 130° C. for 2 hr. The reaction mixture was diluted with methylene chloride, washed with water and saturated brine, and dried over anhydrous magnesium sulfate. The solvent was evaporated under reduced pressure. The obtained residue was purified by silica gel column chromatography to give the title compound as colorless crystals (0.22 g, 8%).

$^1$H NMR (300 MHz, CDCl$_3$)δ1.26-1.34 (6H, m), 2.54-2.56 (1H,m), 2.72 (2H, dq, J=7.6, 0.8), 3.57 (2H, q, J=5.6), 3.81 (2H, q, J=4.8),4.25 (2H, q, J=7.2), 6.24 (1H, br), 6.56 (1H, s), 10.9 (1H br)

Reference Example 5 ethyl (3-{[(2-{[tert-butyl(dimethyl)silyl]oxy}ethyl)amino]carbonyl}-5-ethyl-2-thienyl)carbamate

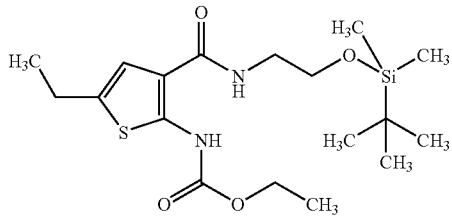 [SMILES: CCOC(=O)Nc1sc(CC)cc1C(=O)NCCO[Si](C)(C)C(C)(C)C]

A mixture of ethyl (5-ethyl-3-{[(2-hydroxyethyl)amino]carbonyl}-2-thienyl)carbamate (0.22 g), tert-butyl(chloro)dimethylsilane (0.15 mL), triethylamine (0.1 g), N,N-dimethylpyridin-4-amine (0.012 g) and methylene chloride (10 mL) was stirred at room temperature for 2 hr. The reaction mixture was diluted with ethyl acetate, washed with water and saturated brine, and dried over anhydrous magnesium sulfate. The solvent was evaporated under reduced pressure. The precipitated solid was collected by filtration to give the title compound as colorless crystals (0.35 g, 95%).

$^1$H NMR (300 MHz CDCl$_3$)δ0.07 (6H, s), 0.93 (9H, s),1.24-1.32 (6H, m), 2.72 (2H, q, J=7.2), 3.49-3.53 (2H, m), 3.76 (2H, t, J=4.8), 4.24 (2H, q, J=7.2), 6.20 (1H, br), 6.50 (1H, s), 11.0 (1H, br)

Reference Example 6

3-(2-{[tert-butyl(dimethyl)silyl]oxy}ethyl)-6-ethylthieno[2,3-d]pyrimidine-2,4(1H,3H)-dione

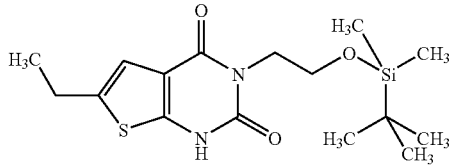 [SMILES: CCc1cc2c(=O)n(CCO[Si](C)(C)C(C)(C)C)c(=O)[nH]c2s1]

A mixture of ethyl (3-{[(2-{[tert-butyl(dimethyl)silyl]oxy}ethyl)amino]carbonyl}-5-ethyl-2-thienyl)carbamate (0.35 g) and N,N-dimethylformamide (5 mL) was stirred at 150° C. for 1 day. The reaction mixture was diluted with ethyl acetate, washed with water and saturated brine, and dried over anhydrous magnesium sulfate. The solvent was evaporated under reduced pressure. The obtained residue was purified by silica gel column chromatography to give the title compound as colorless crystals (0.14 g, 45%).

$^1$H NMR (300 MHz, CDCl$_3$)δ0.05 (6H, s), 0.87 (9H, s), 1.32(3H, t, J=7.6), 2.78 (2H, dq, J=7.6, 0.8), 3.86 (2H, t, J=6.4), 4.21 (2H,t, J=6.4), 6.97 (1H, s)

Reference Example 7

3-cyclopropyl-6-ethylthieno[2,3-d]pyrimidine-2,4(1H,3H)-dione

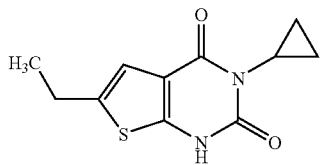 [SMILES: CCc1cc2c(=O)n(C3CC3)c(=O)[nH]c2s1]

To a solution (40 mL) of methyl 2-amino-5-ethylthiophene-3-carboxylate (0.5 g) in methylene chloride were added triphosgene (0.8 g) and triethylamine (0.6 mL), and the mixture was stirred at room temperature for 2 hr. To the reaction mixture was added cyclopropylamine (1.88 mL), and the mixture was further stirred at room temperature for 1 hr. The reaction mixture was washed with water and saturated brine, and dried over anhydrous magnesium sulfate. The solvent was evaporated under reduced pressure. The obtained solid was dissolved in methanol (20 sodium methoxide (28% methanol solution, 0.64 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.28 g, 88%).

$^1$H NMR (400 MHz, CDCl$_3$)δ0.83-0.88 (2H, m), 1.17-1.22 (2H,m), 1.30 (3H, t, J=7.6), 2.72-2.80 (3H, m), 6.94 (1H, s), 10.2 (1H, s)

Reference Example 8

3-[2-(3,4-dimethoxyphenyl)ethyl]-6-ethylthieno[2,3-d]pyrimidine-2,4(1H,3H)-dione

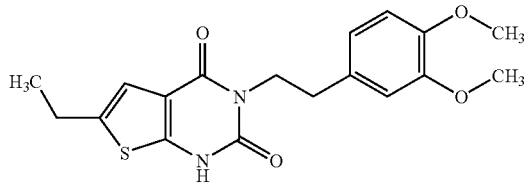 [SMILES: CCc1cc2c(=O)n(CCc3ccc(OC)c(OC)c3)c(=O)[nH]c2s1]

To a solution (40 mL) of methyl 2-amino-5-ethylthiophene-3-carboxylate (0.5 g) in methylene chloride were added triphosgene (0.32 g) and triethylamine (0.59 mL), and the mixture was stirred at room temperature for 2 hr. To the reaction mixture was added 2-(3,4-dimethoxyphenyl)ethanamine (1.36 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (28% methanol solution, 1.3 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.92 g, 95%).

$^1$H NMR (400 MHz, CDCl$_3$)δ1.32 (3H, t, J=7.6), 2.78 (2H,q, J=7.6), 2.90-2.94 (2H, m), 3.86 (3H, s), 3.88 (3H, s), 4.19-4.23 (2H, m),6.78-6.88 (3H, m), 6.79 (1H, s)

Reference Example 9

6-ethyl-3-(2-phenylethyl)thieno[2,3-d]pyrimidine-2,4(1H,3H)-dione

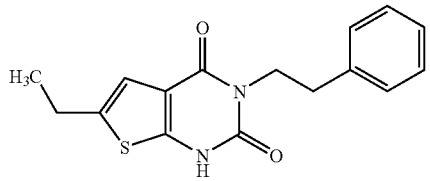 [SMILES: CCc1cc2c(=O)n(CCc3ccccc3)c(=O)[nH]c2s1]

To a solution (40 mL) of methyl 2-amino-5-ethylthiophene-3-carboxylate (0.5 g) in methylene chloride were added triphosgene (0.32 g) and triethylamine (0.59 mL), and the mixture was stirred at room temperature for 2 hr. To the reaction mixture was added 2-phenylethanamine (1.03 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (28% methanol solution, 1.3 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.81 g, 99%).

$^1$H NMR (400 MHz, CDCl$_3$)δ1.31 (3H, t, J=7.6), 2.78 (2H,q, J=7.6), 2.95-2.99 (2H, m), 4.21-4.25 (2H, m), 6.97 (1H, s), 7.17-7.34 (5H,m)

Reference Example 10

6-ethyl-3-(2-morpholin-4-ylethyl)thieno[2,3-d]pyrimidine-2,4(1H,3H)-dione

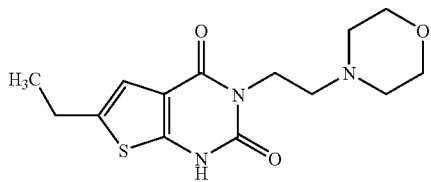 [SMILES: CCc1cc2c(=O)n(CCN3CCOCC3)c(=O)[nH]c2s1]

To a solution (40 mL) of methyl 2-amino-5-ethylthiophene-3-carboxylate (0.5 g) in methylene chloride were added triphosgene (0.32 g) and triethylamine (0.59 mL), and the mixture was stirred at room temperature for 2 hr. To the reaction mixture was added 2-morpholin-4-ylethanamine (1.06 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (28% methanol solution, 1.3 g) was added, and-the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.56 g, 67%).

$^1$H NMR (400 MHz, CDCl$_3$)δ1.27 (3H, t, J=7.6), 2.69 (2H,q, J=7.6), 2.66-2.79 (4H, m), 2.87-2.90 (2H, m), 3.76-3.82 (4H, m), 4.19-4.22(2H, m), 6.71 (1H, s)

Reference Example 11

3-(2-anilinoethyl)-6-ethylthieno[2,3-d]pyrimidine-2,4(1H,3H)-dione

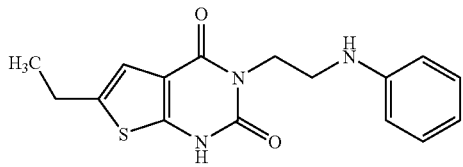 [SMILES: CCc1cc2c(=O)n(CCNc3ccccc3)c(=O)[nH]c2s1]

To a solution (40 mL) of methyl 2-amino-5-ethylthiophene-3-carboxylate (0.5 g) in methylene chloride were added triphosgene (0.32 g) and triethylamine (0.59 mL), and the mixture was stirred at room temperature for 2 hr. To the reaction mixture was added N-phenylethane-1,2-diamine (1 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (28% methanol solution, 1.3 g) was added, and the mixture was stirred at 60° C. for 2 hr. The reaction mixture was concentrated under reduced pressure, and the obtained residue was extracted with 1N hydrochloric acid and ethyl acetate. The ethyl acetate layer was washed with saturated brine, and dried over anhydrous magnesium sulfate. The solvent was evaporated under reduced pressure. The obtained solid was recrystallized from tetrahydrofuran-hexane to give the title compound as colorless crystals (0.22 g, 25%).

$^1$H NMR (400 MHz, CDCl$_3$)δ1.31 (3H, t, J=7.2), 2.78 (2H,q, J=7.2), 3.47 (2H, t, J=6.4), 4.32 (2H, t, J=6.4), 6.64-6.70 (3H, m),6.96 (1H, s), 7.15 (2H, t, J=7.2), 9.49 (1H, br)

Reference Example 12

6-ethyl-3-pyridin-2-ylthieno[2,3-d]pyrimidine-2,4(1H,3H)-dione

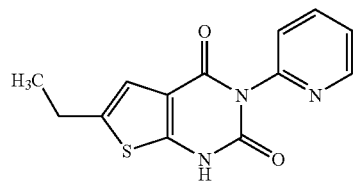

To a solution (40 mL) of methyl 2-amino-5-ethylthiophene-3-carboxylate (0.5 g) in methylene chloride were added triphosgene (0.32 g) and triethylamine (0.59 mL), and the mixture was stirred at room temperature for 2 hr. To the reaction mixture was added pyridin-2-amine (0.76 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (28% methanol solution, 1.3 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.52 g, 70%).

$^1$H NMR (300 MHz, DMSO-d$_6$)δ1.04-1.27 (3H, m), 2.55-2.73(2H, m), 6.57 (1H, s), 7.10 (1H, d, J=7.9), 7.24-7.39 (1H, m), 7.72-7.94 (1H,m), 8.48 (1H, dd, J=4.9, 1.1)

Reference Example 13

6-ethyl-3-(3-phenylpropyl)thieno[2,3-d]pyrimidine-2,4(1H,3H)-dione

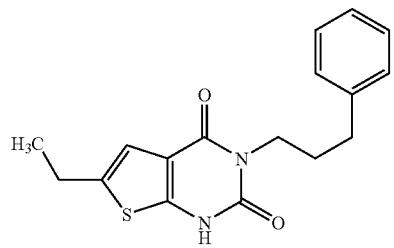 [SMILES: CCc1cc2c(=O)n(CCCc3ccccc3)c(=O)[nH]c2s1]

To a solution (40 mL) of methyl 2-amino-5-ethylthiophene-3-carboxylate (0.5 g) in methylene chloride were added triphosgene (0.32 g) and triethylamine (0.59 mL), and the mixture was stirred at room temperature for 2 hr. To the reaction mixture was added 3-phenylpropan-1-amine (1 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (28% methanol solution, 1.3 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.81 g, 95%).

$^1$H NMR (400 MHz, CDCl$_3$)δ1.31 (3H, t, J=7.6), 2.00-2.07 (2H, m), 2.70-2.80 (4H, m), 4.08 (2H, t, J=7.2), 6.95 (1H, s), 7.14-7.30 (5H,m), 10.2 (1H, br)

Reference Example 14

6-ethyl-3-phenylthieno[2,3-d]pyrimidine-2,4(1H,3H)-dione

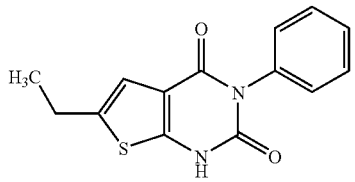 [SMILES: CCc1cc2c(=O)n(-c3ccccc3)c(=O)[nH]c2s1]

To a solution (40 mL) of methyl 2-amino-5-ethylthiophene-3-carboxylate (0.5 g) in methylene chloride were added triphosgene (0.32 g) and triethylamine (0.59 mL), and the mixture was stirred at room temperature for 2 hr. To the reaction mixture was added aniline (0.74 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (0.73 g) was added, and the mixture was stirred at 60° C. for 2 hr. The reaction mixture was concentrated under reduced pressure, and the obtained residue was extracted with 1N hydrochloric acid and ethyl acetate. The ethyl acetate layer was washed with saturated brine, and dried over anhydrous magnesium sulfate. The solvent was evaporated under reduced pressure. The precipitated solid was collected by filtration to give the title compound as a colorless solid (0.34 g, 46%).

$^1$H NMR (400 MHz, DMSO-d$_6$)δ1.23 (3H, t, J=7.2), 2.76 (2H, q, J=7.6), 6.91 (1H, s), 7.25-7.28 (2H, m), 7.38-7.48 (3H, m), 12.2 (1H,s)

Reference Example 15

6-ethyl-3-(2-methoxyethyl)thieno[2,3-d]pyrimidine-2,4(1H,3H)-dione

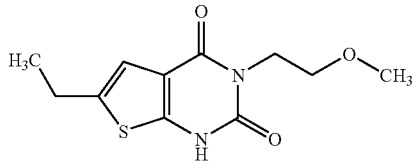

To a solution (40 mL) of methyl 2-amino-5-ethylthiophene-3-carboxylate (0.5 g) in methylene chloride were added triphosgene (0.32 g) and triethylamine (0.59 mL), and the mixture was stirred at room temperature for 2 hr. To the reaction mixture was added 2-methoxyethanamine (0.61 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (0.73 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.56 g, 81%).

$^1$H NMR (400 MHz, CDCl$_3$)δ1.30 (3H, t, J=7.6), 2.77 (2H,q, J=7.2), 3.39 (3H, s), 3.69 (2H, t, J=5.6), 4.27 (2H, q, J=6.0), 6.95(1H, s), 10.3 (1H, br)

Reference Example 16 tert-butyl [2-(6-ethyl-2,4-dioxo-1,4-dihydrothieno[2,3-d]pyrimidin-3(2H)-yl)ethyl]carbamate

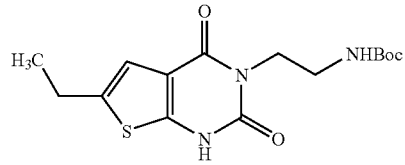 [SMILES: CCc1cc2c(=O)n(CCNC(=O)OC(C)(C)C)c(=O)[nH]c2s1]

To a solution (40 mL) of methyl 2-amino-5-ethylthiophene-3-carboxylate (0.5 g) in methylene chloride were added triphosgene (0.32 g) and triethylamine (0.59 mL), and the mixture was stirred at room temperature for 2 hr. To the reaction mixture was added tert-butyl (2-aminoethyl)carbamate (1 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (0.73 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.7 g, 77%).

$^1$H NMR (400 MHz, CDCl$_3$)δ1.30 (3H, t, J=7.2), 1.35 (9H,s), 2.76 (2H, q, J=7.2), 3.46-3.51 (2H, m), 4.15-4.18 (2H, m), 5.09 (1H, s),6.94 (1H, s), 10.7 (1H, s)

Reference Example 17

6-ethyl-3-(2-pyridin-2-ylethyl)thieno[2,3-d]pyrimidine-2,4(1H,3H)-dione

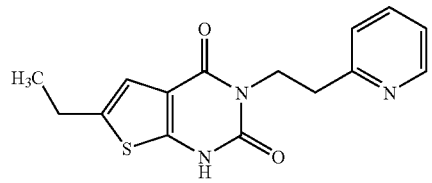 [SMILES: CCc1cc2c(=O)n(CCc3ccccn3)c(=O)[nH]c2s1]

To a solution (40 mL) of methyl 2-amino-5-ethylthiophene-3-carboxylate (0.5 g) in methylene chloride were added triphosgene (0.32 g) and triethylamine (0.59 mL), and the mixture was stirred at room temperature for 2 hr. To the reaction mixture was added 2-pyridin-2-ylethanamine (0.97 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (0.73 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.81 g, 99%).

$^1$H NMR (400 MHz, DMSO-d$_6$)δ1.20 (3H, t, J=7.6), 2.72 (2H, q, J=7.6), 3.33-3.36 (2H, m), 4.24-4.26 (2H, m), 6.79 (1H, s), 7.86-7.92(2H, m), 8.43 (1H, t, J=8.0), 8.68-8.80 (1H, m), 12.3 (1H, s)

Reference Example 18

5-methyl-3-(2-phenylethyl)thieno[2,3-d]pyrimidine-2,4(1H,3H)-dione

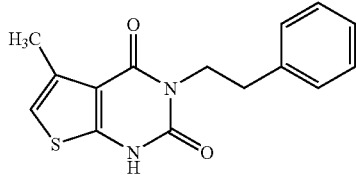 [SMILES: Cc1csc2[nH]c(=O)n(CCc3ccccc3)c(=O)c12]

To a solution (150 mL) of ethyl 2-amino-4-methylthiophene-3-carboxylate (2 g) in methylene chloride were added triphosgene (1.39 g) and triethylamine (2.38 mL), and the mixture was stirred at room temperature for 2 hr. To the reaction mixture was added 2-phenylethanamine (4.09 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (80 mL), sodium methoxide (5.2 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (3.09 g, 100%).

$^1$H NMR (400 MHz, CDCl$_3$)δ2.51 (3H, s), 2.95-2.99 (2H, m),2.95-2.99 (2H, m), 4.20-4.25 (2H, m), 6.42 (1H, s), 7.17-7.36 (5H, m), 10.5(1H, br)

Reference Example 19

6-ethyl-3-[(5-methylpyrazin-2-yl)methyl]thieno[2,3-d]pyrimidine-2,4(1H,3H)-dione

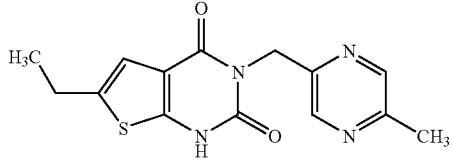 [SMILES: CCc1cc2c(=O)n(Cc3cnc(C)cn3)c(=O)[nH]c2s1]

To a solution (40 mL) of methyl 2-amino-5-ethylthiophene-3-carboxylate (0.5 g) in methylene chloride were added triphosgene (0.32 g) and triethylamine (0.59 mL), and the mixture was stirred at room temperature for 2 hr. To the reaction mixture was added 1-(5-methylpyrazin-2-yl)methanamine (1 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (0.73 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.82 g, 100%).

$^1$H NMR (400 MHz, DMSO-d$_6$)δ1.22 (3H, t, J=7.6), 2.45 (3H, s), 2.75 (2H, d, J=7.6), 5.16 (2H, s), 6.88 (1H, s), 8.39 (1H, s), 8.51(1H, s), 12.4 (1H, s)

Reference Example 20

3-(2-phenylethyl)thieno[2,3-d]pyrimidine-2,4(1H,3H)-dione

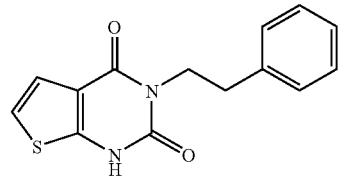 [SMILES: O=c1[nH]c2sccc2c(=O)n1CCc1ccccc1]

To a solution (150 mL) of ethyl 2-amino-4-methylthiophene-3-carboxylate (3 g) in methylene chloride were added triphosgene (2.45 g) and triethylamine (4.21 mL), and the mixture was stirred at room temperature for 2 hr. To the reaction mixture was added 2-phenylethanamine (7.2 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (100 mL), sodium methoxide (9.2 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (5.2 g, 100%).

$^1$H NMR (300 MHz, DMSO-d$_6$)δ2.79-2.85 (2H, m), 3.99-4.05(2H, m), 7.07-7.31 (7H, m), 12.2 (1H, s)

Reference Example 21

3-benzyl-6-methoxy-5-methylthieno[2,3-d]pyrimidine-2,4(1H,3H)-dione

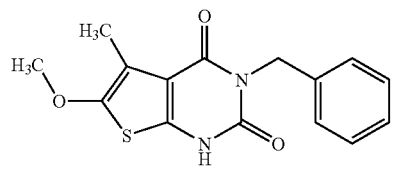 [SMILES: COc1sc2[nH]c(=O)n(Cc3ccccc3)c(=O)c2c1C]

To a solution (30 mL) of ethyl 2-amino-5-methoxy-4-methylthiophene-3-carboxylate (1.0 g) in methylene chloride were added triphosgene (1.8 g) and triethylamine (3.0 mL), and the mixture was stirred at room temperature for 2 hr. To the reaction mixture was added 1-phenylmethanamine (1.5 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (15 mL), sodium methoxide (1.0 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (1.2 g, 84%).

$^1$H NMR (400 MHz, CDCl$_3$)δ2.32 (3H, s), 3.85 (3H, s), 5.17(2H, s), 7.17-7.39 (3H, m), 7.42-7.56 (2H, m)

Reference Example 22

6-methoxy-5-methyl-3-(2-phenylethyl)thieno[2,3-d]pyrimidine-2,4(1H,3H)-dione

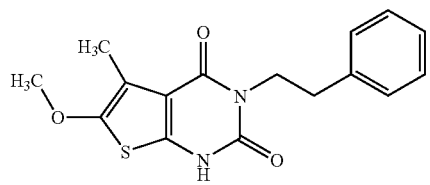 [SMILES: COc1sc2[nH]c(=O)n(CCc3ccccc3)c(=O)c2c1C]

To a solution (30 mL) of ethyl 2-amino-5-methoxy-4-methylthiophene-3-carboxylate (1.0 g) in methylene chloride were added triphosgene (1.8 g) and triethylamine (3.0 mL), and the mixture was stirred at room temperature for 2 hr. To the reaction mixture was added 2-phenylethanamine (1.69 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (15 mL), sodium methoxide (1.0 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (1.2 g, 82%).

$^1$H NMR (300 MHz, CDCl$_3$)δ2.35 (3H, s), 2.90-3.04 (2H, m),3.85 (3H, s), 4.13-4.24 (2H, m), 7.11-7.42 (5H, m)

Reference Example 23

6-methoxy-5-methyl-3-[(1S)-1-phenylethyl]thieno[2,3-d]pyrimidine-2,4(1H,3H)-dione

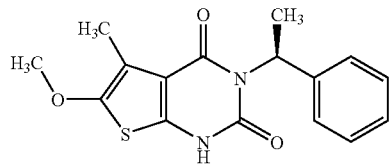 [SMILES: COc1sc2[nH]c(=O)n([C@@H](C)c3ccccc3)c(=O)c2c1C]

To a solution (30 mL) of ethyl 2-amino-5-methoxy-4-methylthiophene-3-carboxylate (1.0 g) in methylene chloride were added triphosgene (1.8 g) and triethylamine (3.0 mL), and the mixture was stirred at room temperature for 2 hr. To the reaction mixture was added (1S)-1-phenylethanamine (1.7 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (15 mL), sodium methoxide (1.0 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.43 g, 29%).

$^1$H NMR (300 MHz, CDCl$_3$)δ1.89 (3H, d, J=7.2), 2.31 (3H,s), 3.85 (3H, s), 6.34 (1H, m), 7.19-7.33 (4H, m), 7.44 (1H, d, J=7.2), 10.84(1H, br)

Reference Example 24

6-methoxy-5-methyl-3-[(1R)-1-phenylethyl]thieno[2,3-d]pyrimidine-2,4(1H,3H)-dione

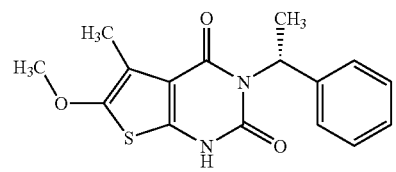 [SMILES: COc1sc2[nH]c(=O)n([C@H](C)c3ccccc3)c(=O)c2c1C]

To a solution (30 mL) of ethyl 2-amino-5-methoxy-4-methylthiophene-3-carboxylate (1.0 g) in methylene chloride were added triphosgene (1.8 g) and triethylamine (3.0 mL), and the mixture was stirred at room temperature for 2 hr. To the reaction mixture was added (1R)-1-phenylethanamine (1.7 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (15 mL), sodium methoxide (1.0 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.62 g, 42%).

$^1$H NMR (300 MHz, CDCl$_3$)δ1.89 (3H, d, J=6.9), 2.31 (3H,s), 3.84 (3H, s), 6.35 (1H, m), 7.19-7.45 (5H, m), 10.46 (1H, br)

Reference Example 25

6-methoxy-5-methyl-3-(2-morpholin-4-ylethyl)thieno[2,3-d]pyrimidine-2,4(1H,3H)-dione

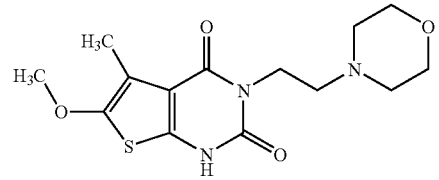 [SMILES: COc1sc2[nH]c(=O)n(CCN3CCOCC3)c(=O)c2c1C]

To a solution (30 mL) of ethyl 2-amino-5-methoxy-4-methylthiophene-3-carboxylate (1.0 g) in methylene chloride were added triphosgene (1.8 g) and triethylamine (3.0 mL), and the mixture was stirred at room temperature for 2 hr. To the reaction mixture was added 2-morpholin-4-ylethanamine (1.8 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (15 mL), sodium methoxide (1.0 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.51 g, 34%).

$^1$H NMR (300 MHz, CDCl$_3$)δ2.32 (3H, s), 2.75-3.35 (6H, m),3.85 (3H, s), 3.70-3.98 (4H, m), 4.26 (2H, t, J=6.0)

Reference Example 26

6-methyl-3-(2-phenylethyl)thieno[2,3-d]pyrimidine-2,4(1H,3H)-dione

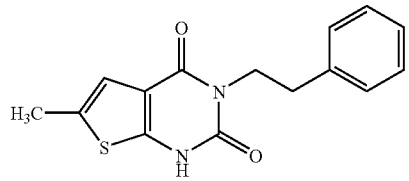 [SMILES: Cc1cc2c(=O)n(CCc3ccccc3)c(=O)[nH]c2s1]

To a solution (200 mL) of methyl 2-amino-5-methylthiophene-3-carboxylate (3.8 g) in methylene chloride were added triphosgene (2.8 g) and triethylamine (4.8 mL), and the mixture was stirred at room temperature for 2 hr. To the reaction mixture was added 2-phenylethanamine (8.3 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (150 mL), sodium methoxide (10.6 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (5.04 g, 80%).

$^1$H NMR (400 MHz, CDCl$_3$)δ2.44 (3H, s), 2.96-3.00 (2H, m),4.24-4.28 (2H, m), 6.95 (1H, s), 6.95-7.35 (5H, m), 11.1 (1H, s).

Reference Example 27

6-ethyl-3-(6-methoxypyridazin-3-yl)thieno[2,3-d]pyrimidine-2,4(1H,3H)-dione

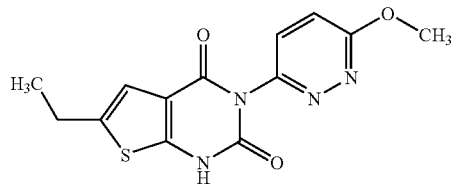 [SMILES: CCc1cc2c(=O)n(-c3ccc(OC)nn3)c(=O)[nH]c2s1]

To a solution (80 mL) of methyl 2-amino-5-ethylthiophene-3-carboxylate (1 g) in methylene chloride were added triphosgene (0.7 g) and triethylamine (1.19 mL), and the mixture was stirred at room temperature for 2 hr. To the reaction mixture was added 6-methoxypyridazin-3-amine (2 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (50 mL), sodium methoxide (3 g) was added, and the mixture was stirred at 60° C. for 2 hr. The reaction mixture was neutralized with hydrochloric acid (10% methanol solution), insoluble material was filtered off, and the solvent was evaporated under reduced pressure. The obtained residue was purified by silica gel column chromatography to give the title compound as colorless crystals (0.45 g, 27%).

$^1$H NMR (300 MHz, CDCl$_3$)δ1.24 (3H, t, J=7.6), 2.78. (2H,q, J=7.6), 4.09 (3H, s), 6.95 (1H, s), 7.43 (1H, d, J=9.2), 7.76 (1H, d, J=9.2), 12.5 (1H, s)

Reference Example 28

6-ethyl-3-[2-(2-thienyl)ethyl]thieno[2,3-d]pyrimidine-2,4(1H,3H)-dione

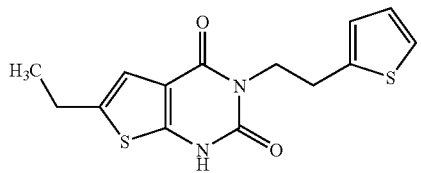 [SMILES: CCc1cc2c(=O)n(CCc3cccs3)c(=O)[nH]c2s1]

To a solution (50 mL) of methyl 2-amino-5-ethylthiophene-3-carboxylate (0.5 g) in methylene chloride were added triphosgene (0.35 g) and triethylamine (0.56 mL), and the mixture was stirred at room temperature for 2 hr. To the reaction mixture was added 2-(2-thienyl)ethanamine (1 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (28% methanol solution, 1.3 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.26 g, 31%).

$^1$H NMR (300 MHz, DMSO-d$_6$)δ1.22 (3H, t, J=7.5),2.63-2.85 (2H, m), 2.95-3.17 (2H, m), 3.90-4.20 (2H, m), 6.70-7.03 (3H, m),7.35 (1H, dd, J=5.1, 1.3), 12.2 (1H, s)

Reference Example 29

6-ethyl-3-(5-methylisoxazol-3-yl)thieno[2,3-d]pyrimidine-2,4(1H,3H)-dione

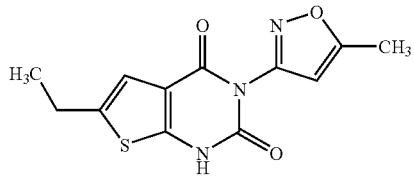 [SMILES: CCc1cc2c(=O)n(-c3cc(C)on3)c(=O)[nH]c2s1]

To a solution (40 mL) of methyl 2-amino-5-ethylthiophene-3-carboxylate (0.63 g) in methylene chloride were added triphosgene (0.44 g) and triethylamine (0.76 mL), and the mixture was stirred at room temperature for 2 hr. To the reaction mixture was added 5-methylisoxazol-3-amine (1 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (40 mL), sodium methoxide (28% methanol solution, 1.6 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.94 g, 100%).

¹H NMR (300 MHz, DMSO-d₆)δ1.23 (3H, t, J=7.5), 2.48 (3H, s), 2.76 (2H, q, J=7.5), 6.39 (1H, s), 6.92 (1H, s), 12.7 (1H, s)

Reference Example 30

6-ethyl-3-quinolin-3-ylthieno[2,3-d]pyrimidine-2,4(1H,3H)-dione

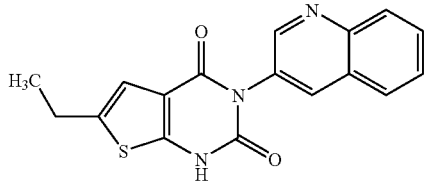 [SMILES: CCc1cc2c(=O)n(-c3cnc4ccccc4c3)c(=O)[nH]c2s1]

To a solution (40 mL) of methyl 2-amino-5-ethylthiophene-3-carboxylate (0.5 g) in methylene chloride were added triphosgene (0.35 g) and triethylamine (0.6 mL), and the mixture was stirred at room temperature for 2 hr. To the reaction mixture was added quinolin-3-amine (1 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (25 mL), sodium methoxide (28% methanol solution, 1.3 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.87 g, 100%).

¹H NMR (300 MHz, DMSO-d₆)δ1.25 (3H, t, J=7.4), 2.78 (2H, q, J=7.4), 6.94 (1H, s), 7.64-7.73 (1H, m), 7.81-7.88 (1H, m), 8.06 (2H,dd, J=17.0, 7.9), 8.37 (1H, d, J=2.3), 8.79 (1H, d, J=2.4)

Reference Example 31

3-(4,6-dimethoxypyrimidin-2-yl)-6-ethylthieno[2,3-d]pyrimidine-2,4(1H,3H)-dione

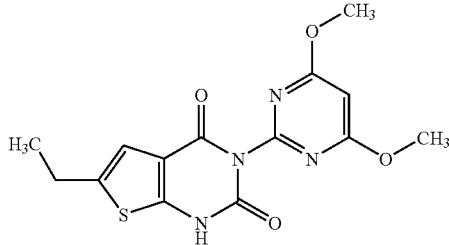 [SMILES: CCc1cc2c(=O)n(-c3nc(OC)cc(OC)n3)c(=O)[nH]c2s1]

To a solution (40 mL) of methyl 2-amino-5-ethylthiophene-3-carboxylate (0.5 g) in methylene chloride were added triphosgene (0.35 g) and triethylamine (0.6 mL), and the mixture was stirred at room temperature for 2 hr. To the reaction mixture was added 4,6-dimethoxypyrimidin-2-amine (1 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (40 mL), sodium methoxide (1 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.9 g, 100%).

¹H NMR (300 MHz, DMSO-d₆)δ1.23 (3H, t, J=7.5), 2.77 (2H, q, J=7.5), 3.88 (6H, s), 6.42 (1H, s), 6.90 (1H, s), 12.4 (1H, s)

Reference Example 32

3-(2-morpholin-4-ylethyl)-6-propylthieno[2,3-d]pyrimidine-2,4(1H,3H)-dione

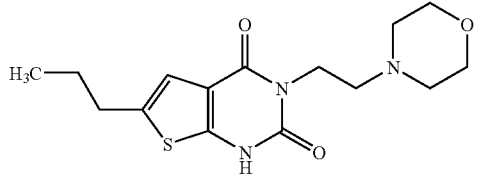 [SMILES: CCCc1cc2c(=O)n(CCN3CCOCC3)c(=O)[nH]c2s1]

To a solution (30 mL) of methyl 2-amino-5-propylthiophene-3-carboxylate (1.0 g) in methylene chloride were added triphosgene (1.8 g) and triethylamine (3.0 mL), and the mixture was stirred at room temperature for 2 hr. To the reaction mixture was added 2-morpholin-4-ylethanamine (2.3 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (15 mL), sodium methoxide (1.0 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (1.5 g, 72%).

¹H NMR (300 MHz, CDCl₃)δ0.96 (3H, t, J=7.2), 1.61-1.68 (2H, m), 2.65 (2H, t, J=7.2), 2.85-3.14 (6H, m), 3.90 (4H, br), 4.27 (2H, t,J=3.0), 6.81 (1H, s)

Reference Example 33

6-isopropyl-3-(2-morpholin-4-ylethyl)thieno[2,3-d]pyrimidine-2,4(1H,3H)-dione

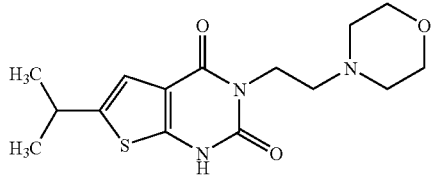 [SMILES: CC(C)c1cc2c(=O)n(CCN3CCOCC3)c(=O)[nH]c2s1]

To a solution (15 mL) of methyl 2-amino-5-isopropylthiophene-3-carboxylate (1.0 g) in methylene chloride were added triphosgene (1.8 g) and triethylamine (3.0 mL), and the mixture was stirred at room temperature for 2 hr. To the reaction mixture was added 2-morpholin-4-ylethanamine (2.3 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (15 mL), sodium methoxide (1.0 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.29 g, 32%).

$^1$H NMR (300 MHz, CDCl$_3$)δ1.28 (6H, d, J=6.9), 2.80 (4H,br), 2.90-3.05 (3H, m), 3.82 (4H, br), 4.22 (2H, t, J=6.0), 6.77 (1H, s)

Reference Example 34 methyl 2-amino-5-cyclopropylthiophene-3-carboxylate

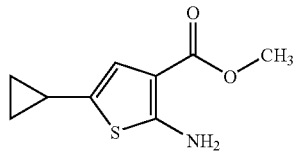

To a mixture of ethyl cyanoacetate (8.1 mL), sulfur (3.0 g) and N,N-dimethylformamide (20 mL) was added a solution of cyclopropylacetoaldehyde (7.8 g) in N,N-dimethylformamide (10 mL), and the mixture was stirred at room temperature for 3 hr. The reaction mixture was diluted with water, washed successively with water and saturated brine, and dried over anhydrous magnesium sulfate. The solvent was evaporated under reduced pressure. The obtained residue was purified by silica gel column chromatography to give the title compound as colorless crystals (3.9 g, 19%).

$^1$H NMR (300 MHz, CDCl$_3$)δ0.59-0.64 (2H, m), 0.81-0.87 (2H,m), 1.72-1.87 (1H, m), 3.77 (3H, s), 5.78 (2H, br), 6.57 (1H, s)

Reference Example 35

6-cyclopropyl-3-(2-phenylethyl)thieno[2,3-d]pyrimidine-2,4(1H,3H)-dione

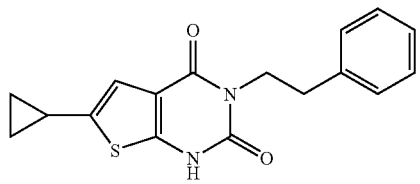 [SMILES: O=c1[nH]c2sc(C3CC3)cc2c(=O)n1CCc1ccccc1]

To a solution (15 mL) of methyl 2-amino-5-cyclopropylthiophene-3-carboxylate (0.5 g) in methylene chloride were added triphosgene (0.9 g) and triethylamine (1.5 mL), and the mixture was stirred at room temperature for 2 hr. To the reaction mixture was added 2-phenylethanamine (0.92 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (10 mL), sodium methoxide (0.5 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.86 g, 100%).

$^1$H NMR (300 MHz, DMSO-d$_6$)δ0.67-0.72 (2H, m), 0.94-0.99(2H, m), 2.05 (1H, m), 2.82 (2H, t, J=6.9), 4.02 (2H, t, J=6.9), 6.83 (1H,s), 7.17-7.32 (5H, m), 12.1 (1H, br)

Reference Example 36

6-cyclopropyl-3-(2-morpholin-4-ylethyl)thieno[2,3-d]pyrimidine-2,4(1H,3H)-dione

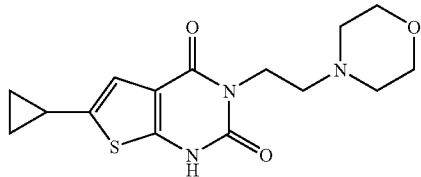 [SMILES: O=c1[nH]c2sc(C3CC3)cc2c(=O)n1CCN1CCOCC1]

To a solution (15 mL) of methyl 2-amino-5-cyclopropylthiophene-3-carboxylate (0.5 g) in methylene chloride were added triphosgene (0.98 g) and triethylamine (1.7 mL), and the mixture was stirred at room temperature for 2 hr. To the reaction mixture was added 2-morpholin-4-ylethanamine (0.99 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (10 mL), sodium methoxide (0.5 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.76 g, 84%).

$^1$H NMR (300 MHz, DMSO-d$_6$)δ0.66-0.72 (2H, m), 0.94-1.01(2H, m), 2.05 (1H, m), 2.49 (4H, br), 3.18 (2H, br), 3.55 (4H, br), 3.97 (2H,t, J=3.3), 6.83 (1H, s), 12.0 (1H, br)

Reference Example 37

3-(2-phenylethyl)-6-propylthieno[2,3-d]pyrimidine-2,4(1H,3H)-dione

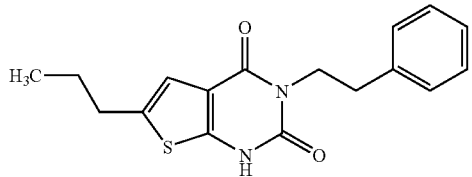 [SMILES: CCCc1cc2c(=O)n(CCc3ccccc3)c(=O)[nH]c2s1]

To a solution (15 mL) of methyl 2-amino-5-propylthiophene-3-carboxylate (0.5 g) in methylene chloride were added triphosgene (0.98 g) and triethylamine (1.7 mL), and the mixture was stirred at room temperature for 2 hr. To the reaction mixture was added 2-phenylethanamine (0.91 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (10 mL), sodium methoxide (0.5 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.71 g, 90%).

¹H NMR (300 MHz, DMSO-d₆)δ0.92 (3H, t, J=7.2),1.42-1.71 (2H, m), 2.70 (2H, t, J=7.2), 2.83 (2H, t, J=8.1), 4.03 (2H, t, J=8.1), 6.88 (1H, s), 7.18-7.33 (5H, m), 12.1 (1H, s)

Reference Example 38

6-isopropyl-3-(2-phenylethyl)thieno[2,3-d]pyrimidine-2, 4(1H,3H)-dione

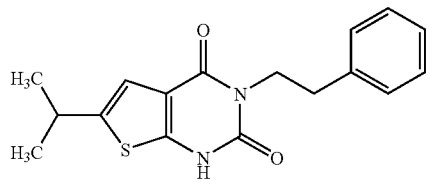 [SMILES: CC(C)c1cc2c(=O)n(CCc3ccccc3)c(=O)[nH]c2s1]

To a solution (15 mL) of methyl 2-amino-5-isopropylthiophene-3-carboxylate (0.5 g) in methylene chloride were added triphosgene (0.98 g) and triethylamine (1.7 mL), and the mixture was stirred at room temperature for 2 hr. To the reaction mixture was added 2-phenylethanamine (0.91 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (10 mL), sodium methoxide (0.54 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (0.43 g, 54%).

¹H NMR (300 MHz, DMSO-d₆)δ1.25 (6H, d, J=6.9), 2.82 (2H, t, J=8.1), 3.09 (1H, m), 4.03 (2H, t, J=8.1), 6.87 (1H, s), 7.17-7.33(5H, m), 12.2 (1H, br)

Reference Example 39

4'-{[6-ethyl-3-(2-hydroxyethyl)-2,4-dioxo-3,4-dihydrothieno[2,3-d]pyrimidin-1(2H)-yl]methyl}biphenyl-2-carbonitrile

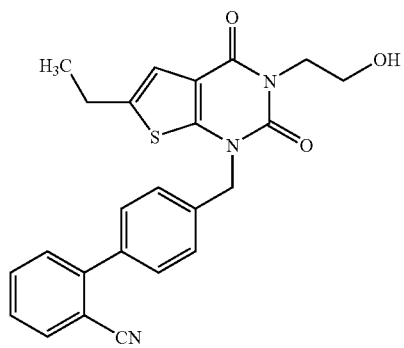 [SMILES: CCc1cc2c(=O)n(CCO)c(=O)n(Cc3ccc(-c4ccccc4C#N)cc3)c2s1]

To a solution (350 mL) of methyl 2-amino-5-ethylthiophene-3-carboxylate (15 g) in methylene chloride were added triphosgene (10.4 g) and triethylamine (17.9 mL), and the mixture was stirred at room temperature for 2 hr. To the reaction mixture was added 2-aminoethanol (14.7 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (200 mL), sodium methoxide (28% methanol solution, 18.1 g) was added, and the mixture was stirred at 60° C. for 2 hr. The reaction mixture was neutralized with hydrochloric acid (10% methanol solution), insoluble material was filtered off, and the solvent was evaporated under reduced pressure. The obtained residue was dissolved in acetonitrile (150 mL), 4'-(bromomethyl)biphenyl-2-carbonitrile (12.5 g) and potassium carbonate (11.5 g) were added, and the mixture was stirred at 50° C. for 3 hr. Insoluble material was filtered off, and the solvent was evaporated under reduced pressure. The obtained residue was purified by silica gel column chromatography to give the title compound as a colorless solid (10.2 g, 30%).

¹H NMR (300 MHz, CDCl₃)δ1.30 (3H, t, J=7.5), 2.71-2.83 (2H, m), 3.89-3.98 (2H, m), 4.30-4.40 (2H, m), 5.20 (2H, s), 7.03 (1H, t, J=1.2), 7.40-7.59 (6H, m), 7.61-7.68 (1H, m), 7.77 (1H, dd, J=7.7, 0.9)

Reference Example 40

4'-{[6-ethyl-3-[2-(2-formyl-1H-imidazol-1-yl)ethyl]-2,4-dioxo-3,4-dihydrothieno[2,3-d]pyrimidin-1(2H)-yl]methyl}biphenyl-2-carbonitrile

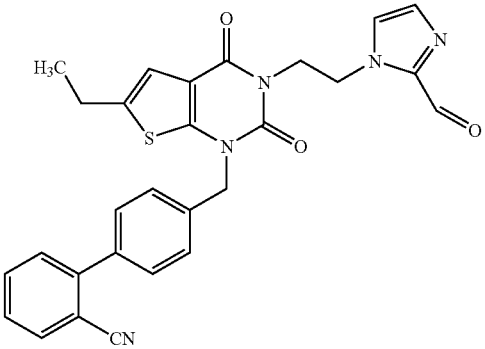 [SMILES: CCc1cc2c(=O)n(CCn3ccnc3C=O)c(=O)n(Cc3ccc(-c4ccccc4C#N)cc3)c2s1]

A mixture of 4'-{[6-ethyl-3-(2-hydroxyethyl)-2,4-dioxo-3,4-dihydrothieno[2,3-d]pyrimidin-1(2H)-yl] methyl}biphenyl-2-carbonitrile (6 g), triethylamine (2.13 mL), methanesulfonylchloride (1.19 mL), N,N-dimethylpyridin-4-amine (0.0084 g) and methylene chloride (300 mL) was stirred at room temperature for 3 hr. The reaction mixture was washed successively with water and saturated brine, and dried over anhydrous magnesium sulfate. The solvent was evaporated under reduced pressure. The obtained residue was dissolved in N,N-dimethylformamide (20 mL), 1H-imidazole-2-carbaldehyde (0.68 g) and sodium hydride (0.28 g) were added, and the mixture was stirred at 60° C. for 1 hr. The reaction mixture was diluted with chloroform, washed successively with 5% aqueous potassium hydrogensulfate solution and saturated brine, and dried over anhydrous magnesium sulfate. The solvent was evaporated under reduced pressure. The obtained ethyl acetate layer was washed with saturated brine, and dried over anhydrous magnesium sulfate. The solvent was evaporated under reduced pressure. The residue was purified by silica gel column chromatography to give the title compound as colorless crystals (2.3 g, 69%).

$^1$H NMR (300 MHz, CDCl$_3$)δ1.29 (3H, t, J=7.8), 2.75 (2H,q, J=7.8), 4.51-4.55 (2H, m), 4.75-4.79 (2H, m), 5.09 (2H, s), 6.97 (2H, s),7.20 (1H, s), 7.42-7.76 (7H, m), 7.77 (1H, m), 9.80 (1H, s)

Reference Example 41

4'-{[6-ethyl-3-{2-[2-(hydroxymethyl)-1H-imidazol-1-yl]ethyl}-2,4-dioxo-3,4-dihydrothieno[2,3-d]pyrimidin-1(2H)-yl]methyl}biphenyl-2-carbonitrile

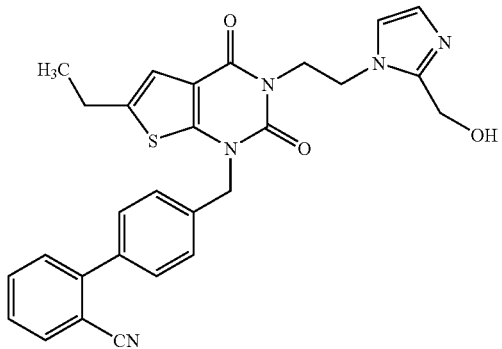 [SMILES: CCc1cc2c(=O)n(CCn3ccnc3CO)c(=O)n(Cc3ccc(-c4ccccc4C#N)cc3)c2s1]

To a solution (40 mL) of 4'-{[6-ethyl-3-[2-(2-formyl-1H-imidazol-1-yl)ethyl]-2,4-dioxo-3,4-dihydrothieno[2,3-d]pyrimidin-1(2H)-yl]methyl}biphenyl-2-carbonitrile (2.2 g) in methanol was added sodium borohydride (0.27 g), and the mixture was stirred at room temperature for 1 hr. The solvent was evaporated under reduced pressure, and the residue was extracted with water and ethyl acetate. The obtained ethyl acetate layer was washed with saturated brine, and dried over anhydrous magnesium sulfate. The solvent was evaporated under reduced pressure. The residue was purified by silica gel column chromatography to give the title compound as colorless crystals (2.0 g, 91%).

$^1$H NMR (300 MHz, CDCl$_3$)δ1.29 (3H, t, J=7.5), 2.75 (2H,q, J=7.5), 4.32-4.36 (2H, m), 4.45-4.49 (2H, m), 4.74 (2H, s), 5.12 (2H, s),6.81 (1H, s), 6.88 (1H, s), 6.99 (1H, s), 7.40-7.67 (7H, m), 7.74-7.77 (1H, m)

Reference Example 42

4'-{[3-{2-[2-({[tert-butyl(dimethyl)silyl]oxy}methyl)-1H-imidazol-1-yl]ethyl}-6-ethyl-2,4-dioxo-3,4-dihydrothieno[2,3-d]pyrimidin-1(2H)-yl]methyl}biphenyl-2-carbonitrile

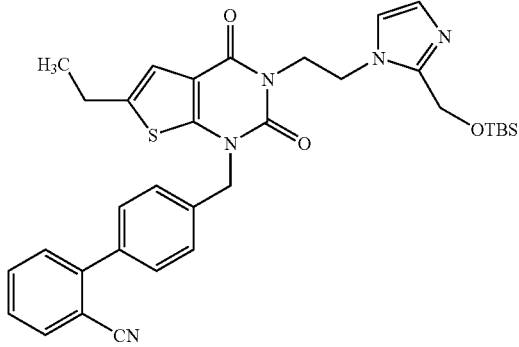 [SMILES: CCc1cc2c(=O)n(CCn3ccnc3CO[Si](C)(C)C(C)(C)C)c(=O)n(Cc3ccc(-c4ccccc4C#N)cc3)c2s1]

A mixture of 4'-{[6-ethyl-3-{2-[2-(hydroxymethyl)-1H-imidazol-1-yl]ethyl}-2,4-dioxo-3,4-dihydrothieno[2,3-d]pyrimidin-1(2H)-yl]methyl}biphenyl-2-carbonitrile (0.5 g), tert-butyl(chloro)dimethylsilane (0.18 g), triethylamine (0.16 mL) and methylene chloride (20 mL) was stirred at room temperature for 4 hr. The reaction mixture was washed successively with water and saturated brine, and dried over anhydrous magnesium sulfate. The solvent was evaporated under reduced pressure. The obtained ethyl acetate layer was washed with saturated brine, and dried over anhydrous magnesium sulfate. The solvent was evaporated under reduced pressure. The obtained residue was purified by silica gel column chromatography to give the title compound as colorless crystals (0.61 g, 99%).

$^1$H NMR (300 MHz, CDCl$_3$)δ0.08 (6H, s), 0.90 (9H, s), 1.29(3H, t, J=7.2), 2.76 (2H, q, J=7.2), 4.39-4.47 (4H, m), 4.84 (2H, s), 5.12(2H, s), 6.83 (1H, s), 6.88 (1H, s), 7.00 (1H, s), 7.39-7.56 (6H, m), 7.61-7.67(1H, m), 7.75 (1H, d, J=7.8)

Reference Example 43

3-(2,4-dimethoxybenzyl)-6-ethylthieno[2,3-d]pyrimidine-2,4(1H,3H)-dione

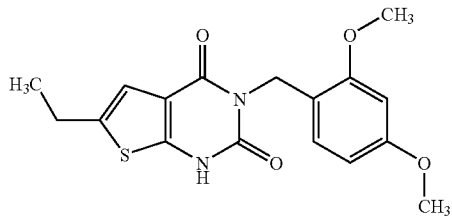 [SMILES: CCc1cc2c(=O)n(Cc3ccc(OC)cc3OC)c(=O)[nH]c2s1]

To a solution (1.5 L) of methyl 2-amino-5-ethylthiophene-3-carboxylate (30 g) in methylene chloride were added triphosgene (20.8 g) and triethylamine (58.6 mL), and the mixture was stirred at room temperature for 2 hr. To the reaction mixture was added 1-(2,4-dimethoxyphenyl)methanamine (48.6 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (1.5 L), sodium methoxide (21.9 g) was added, and the mixture was stirred at 60° C. for 2 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The precipitated solid was collected by filtration to give the title compound as a colorless solid (55.9 g, 100%).

$^1$H NMR (300 MHz, CDCl$_3$)δ1.29 (3H, t, J=7.5), 2.75 (2H,q, J=7.5), 3.76 (3H, s), 3.84 (3H, s), 5.18 (2H, s), 6.35-6.45 (2H, m),6.94-6.98 (2H, m), 10.7 (1H, br)

Reference Example 44 methyl 2-amino-5-(2,2,2-trifluoroethyl)thiophene-3-carboxylate

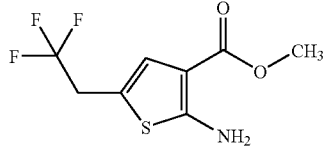

To a mixture of methyl cyanoacetate (4.1 mL), sulfur (1.5 g) and N,N-dimethylformamide (10 mL) was added a solution of 4,4,4-trifluorobutanal (5 g) in N,N-dimethylformamide (5 mL), and the mixture was stirred at room temperature for 3 hr. The reaction mixture was diluted with water, washed successively with water and saturated brine, and dried over anhydrous magnesium sulfate. The solvent was evaporated under reduced pressure. The obtained residue was purified by silica gel column chromatography to give the title compound as colorless crystals (1.07 g, 11%).

¹H NMR (300 MHz, CDCl₃)δ3.34 (2H, q, J=10.2), 3.80 (3H,s), 5.94 (2H, br), 6.88 (1H, s)

Reference Example 45

4'-{[2,4-dioxo-3-(2-phenylethyl)-3,4-dihydrothieno[2,3-d]pyrimidin-1(2H)-yl]methyl}biphenyl-2-carbonitrile

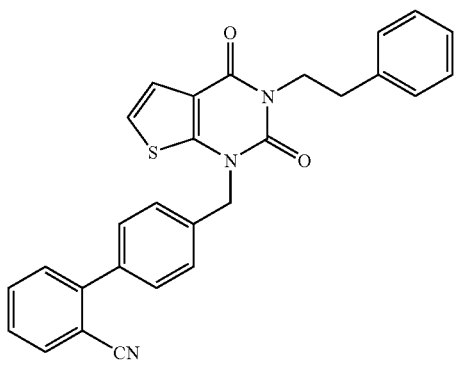 [SMILES: N#Cc1ccccc1-c1ccc(Cn2c(=O)n(CCc3ccccc3)c(=O)c3ccsc32)cc1]

A mixture of 3-(2-phenylethyl)thieno[2,3-d]pyrimidine-2,4(1H,3H)-dione (2.9 g), 4'-(bromomethyl)biphenyl-2-carbonitrile (3.2 g), potassium carbonate (2.9 g) and acetonitrile (150 mL) was stirred at room temperature for 2 hr. Insoluble material was filtered off, and the filtrate was concentrated. The obtained residue was purified by silica gel column chromatography to give the title compound as a pale-yellow solid (4.8 g, 97%).

¹H NMR (300 MHz, DMSO-d₆)δ2.94 (2H, t, J=7.7), 4.18 (2H, t, J=7.5), 5.26 (2H, s), 7.19-7.37 (6H, m), 7.37-7.50 (2H, m), 7.51-7.70(5H, m), 7.70-7.87 (1H, m), 7.98 (1H, d, J=9.5)

Reference Example 46

4'-{[6-formyl-2,4-dioxo-3-(2-phenylethyl)-3,4-dihydrothieno[2,3-d]pyrimidin-1(2H)-yl]methyl}biphenyl-2-carbonitrile

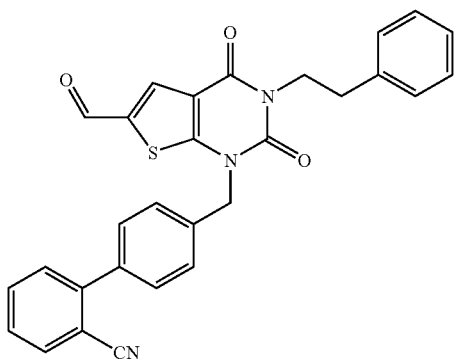 [SMILES: N#Cc1ccccc1-c1ccc(Cn2c(=O)n(CCc3ccccc3)c(=O)c3cc(C=O)sc32)cc1]

A mixture of 4'-{[2,4-dioxo-3-(2-phenylethyl)-3,4-dihydrothieno[2,3-d]pyrimidin-1(2H)-yl]methyl}biphenyl-2-carbonitrile (2 g), phosphorus oxychloride (30 mL) and N,N-dimethylformamide (10 mL) was stirred at 50° C. for 2 hr. The reaction mixture was diluted with chloroform, washed successively with saturated aqueous sodium hydrogencarbonate solution and saturated brine, and dried over anhydrous sodium sulfate. The solvent was evaporated under reduced pressure. The precipitated solid was collected by filtration to give the title compound as a colorless solid (1.96 g, 92%).

¹H NMR (300 MHz, DMSO-d₆)δ2.94 (2H, t, J=7.5), 4.18 (2H,t, J=7.5), 5.30 (2H, s), 7.16-7.38 (5H, m), 7.41-7.53 (2H, m), 7.53-7.70 (4H,m), 7.72-7.85 (1H, m), 7.95 (1H, d, J=7.5), 8.31 (1H, s), 9.85 (1H, s)

Reference Example 47

4'-{[6-(hydroxymethyl)-2,4-dioxo-3-(2-phenylethyl)-3,4-dihydrothieno[2,3-d]pyrimidin-1(2H)-yl]methyl}biphenyl-2-carbonitrile

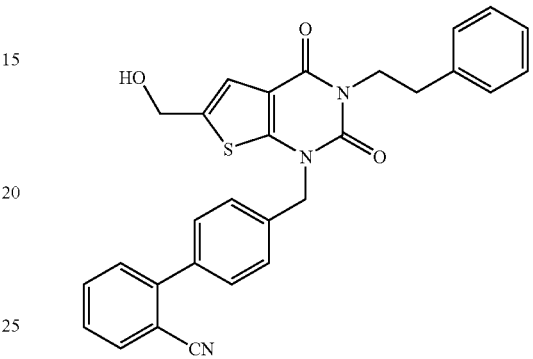

To a mixture of 4'-{[6-formyl-2,4-dioxo-3-(2-phenylethyl)-3,4-dihydrothieno[2,3-d]pyrimidin-1(2H)-yl]methyl}biphenyl-2-carbonitrile (0.5 g), tetrahydrofuran (20 mL) and methanol (20 mL) was added sodium borohydride (0.088 g), and the mixture was stirred at room temperature for 1 hr. The reaction mixture was concentrated, and the residue was extracted with chloroform and saturated aqueous ammonium chloride solution. The chloroform layer was washed with saturated brine, and dried over anhydrous sodium sulfate. The solvent was evaporated under reduced pressure. The obtained residue was purified by silica gel column chromatography to give the title compound as a colorless amorphous solid (0.45 g, 89%).

¹H NMR (300 MHz, DMSO-d₆)δ2.93 (2H, t, J=7.8), 4.18 (2H, t, J=7.8), 4.56 (2H, d, J=5.7), 5.23 (2H, s), 5.36 (1H, t, J=5.7),7.11 (1H, s), 7.16-7.48 (7H, m), 7.48-7.70 (4H, m), 7.73-7.83 (1H, m), 7.96(1H, d, J=7.8)

Reference Example 48

4'-{[6-(methoxymethyl)-2,4-dioxo-3-(2-phenylethyl)-3,4-dihydrothieno[2,3-d]pyrimidin-1(2H)-yl]methyl}biphenyl-2-carbonitrile

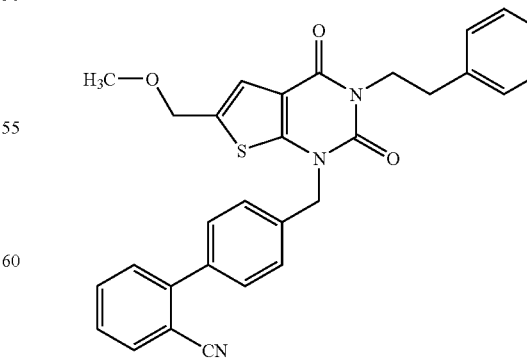

To a mixture of 4'-{[6-(hydroxymethyl)-2,4-dioxo-3-(2-phenylethyl)-3,4-dihydrothieno[2,3-d]pyrimidin-1(2H)-yl]methyl}biphenyl-2-carbonitrile (0.45 g), methyl iodide (0.11 mL) and N,N-dimethylformamide (5 mL) was added 60% sodium hydride (0.05 g), and the mixture was stirred at room temperature for 2 hr. The reaction mixture was diluted with ethyl acetate, washed successively with 1N hydrochloric acid and saturated brine, and dried over anhydrous sodium sulfate. The solvent was evaporated under reduced pressure. The obtained residue was purified by silica gel column chromatography to give the title compound as a colorless amorphous solid (0.35 g, 77%).

$^1$H NMR (300 MHz, DMSO-$d_6$)δ2.93 (2H, t, J=7.5), 3.25 (3H, s), 4.18 (2H, t, J=7.5), 4.52 (2H, s), 5.23 (2H, s), 7.15-7.35 (6H, m), 7.38-7.48 (2H, m), 7.50-7.70 (4H, m), 7.75-7.85 (1H, m), 7.95 (1H, d, J=7.5).

Reference Example 49

6-ethyl-3-[2-(4-fluorophenyl)ethyl]thieno[2,3-d]pyrimidine-2,4(1H,3H)-dione

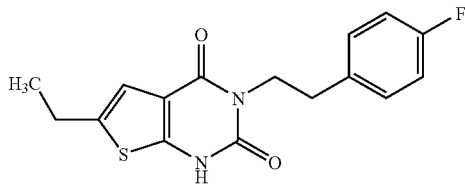 [SMILES: CCc1cc2c(=O)n(CCc3ccc(F)cc3)c(=O)[nH]c2s1]

To a solution (20 mL) of methyl 2-amino-5-ethylthiophene-3-carboxylate (0.5 g) in methylene chloride were added triphosgene (0.35 g) and triethylamine (0.6 mL), and the mixture was stirred at room temperature for 2 hr. To the reaction mixture was added 2-(4-fluorophenyl)ethanamine (1.06 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (20 mL), sodium methoxide (0.73 g) was added, and the mixture was stirred at 60° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (859 g, 100%).

$^1$H NMR (300 MHz, CDCl$_3$)δ1.40 (3H, t, J=7.8), 3.02 (4H,m), 4.28 (2H, m), 7.20-7.32 (5H, m), 11.2 (1H, br)

Reference Example 50

4'-{[3-(2,4-dimethoxybenzyl)-2,4-dioxo-6-(2,2,2-trifluoroethyl)-3,4-dihydrothieno[2,3-d]pyrimidin-1(2H)-yl]methyl}biphenyl-2-carbonitrile

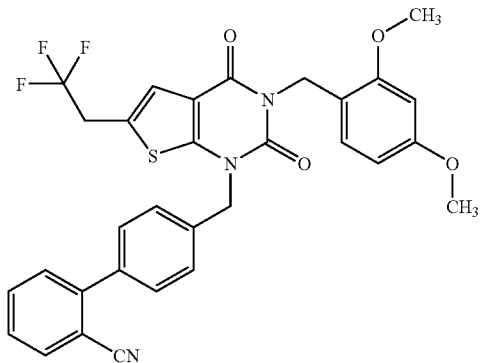 [SMILES: COc1ccc(Cn2c(=O)c3cc(CC(F)(F)F)sc3n(Cc3ccc(-c4ccccc4C#N)cc3)c2=O)c(OC)c1]

To a solution (100 mL) of methyl 2-amino-5-(2,2,2-trifluoroethyl)thiophene-3-carboxylate (1.08 g) in methylene chloride were added triphosgene (0.58 g) and triethylamine (0.97 mL), and the mixture was stirred at room temperature for 2 hr. To the reaction mixture was added 1-(2,4-dimethoxyphenyl)methanamine (2.03 mL), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in methanol (100 mL), sodium methoxide (1.2 g) was added, and the mixture was stirred at 60° C. for 1 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The obtained residue was dissolved in acetonitrile (200 mL), 4'-(bromomethyl)biphenyl-2-carbonitrile (1.23 g) and potassium carbonate (1.25 g) were added, and the mixture was stirred at 50° C. for 2 hr. Insoluble material was filtered off, and the solvent was evaporated under reduced pressure. The obtained residue was purified by silica gel column chromatography to give the title compound as a colorless amorphous solid (2.4 g, 90%).

$^1$H NMR (300 MHz, CDCl$_3$)δ3.50 (2H, q, J=10.2), 3.76 (3H,s), 3.81 (3H, s), 5.20 (2H, s), 5.23 (2H, s), 6.34-6.45 (2H, m), 7.00 (1H, d, J=8.1), 7.26-7.28 (1H, m), 7.42-7.56 (6H, m), 7.61-7.67 (1H, m), 7.76 (1H, d, J=7.8)

Reference Example 51

4'-{[2,4-dioxo-6-(2,2,2-trifluoroethyl)-3,4-dihydrothieno[2,3-d]pyrimidin-1(2H)-yl]methyl}biphenyl-2-carbonitrile

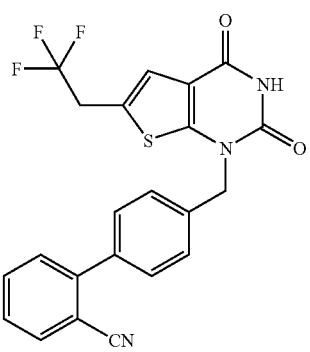 [SMILES: N#Cc1ccccc1-c1ccc(Cn2c(=O)[nH]c(=O)c3cc(CC(F)(F)F)sc32)cc1]

A mixture of 4'-{[3-(2,4-dimethoxybenzyl)-2,4-dioxo-6-(2,2,2-trifluoroethyl)-3,4-dihydrothieno[2,3-d]pyrimidin-1(2H)-yl]methyl}biphenyl-2-carbonitrile (1.68 g) and trifluoroacetic acid (30 mL) was stirred at 50° C. for 2 hr. To the reaction mixture was added toluene (30 mL), under reduced pressure, and concentrated. The precipitated solid was collected by filtration to give the title compound as a colorless solid (1.8 g, 100%).

$^1$H NMR (300 MHz, DMSO-$d_6$)δ3.94 (2H, q, J=11.1), 5.20(2H, s), 7.24-7.32 (1H, m), 7.42-7.55 (2H, m), 7.55-7.68 (4H, m), 7.70-7.86(1H, m), 7.95 (1H, d, J=7.9), 11.7 (1H, s)

Reference Example 52

4'-{[3-[2-(4-fluorophenyl)-2-oxoethyl]-2,4-dioxo-6-(2,2,2-trifluoroethyl)-3,4-dihydrothieno[2,3-d]pyrimidin-1(2H)-yl]methyl}biphenyl-2-carbonitrile

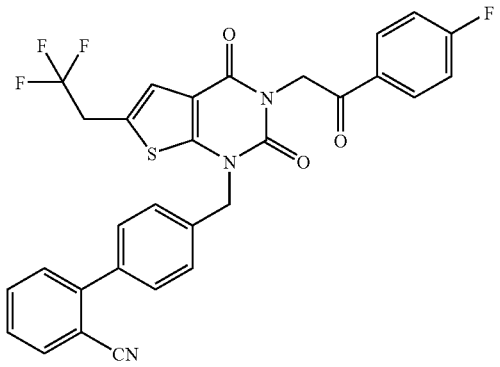 [SMILES: N#Cc1ccccc1-c1ccc(Cn2c(=O)n(CC(=O)c3ccc(F)cc3)c(=O)c3cc(CC(F)(F)F)sc32)cc1]

To a mixture of 4'-{[2,4-dioxo-6-(2,2,2-trifluoroethyl)-3,4-dihydrothieno[2,3-d]pyrimidin-1(2H)-yl]methyl}biphenyl-2-carbonitrile (1.5 g), 2-bromo-1-(4-fluorophenyl)ethanone (0.89 g) and N,N-dimethylformamide (50 mL) was added 60% sodium hydride (0.16 g), and the mixture was stirred at room temperature for 2 hr. The reaction mixture was diluted with ethyl acetate, washed successively with 1N hydrochloric acid and saturated brine, and dried over anhydrous sodium sulfate. The solvent was evaporated under reduced pressure. The obtained residue was recrystallized from tetrahydrofuran to give the title compound as colorless crystals (1.08 g, 55%).

$^1$H NMR (300 MHz, CDCl$_3$)δ3.47 (2H, q, J=16.5), 5.20 (2H,s), 5.45 (2H, s), 7.11-7.26 (4H, m), 7.38-7.75 (9H, m)

Reference Example 53

4'-{[3-[2-(4-fluorophenyl)-2-hydroxyethyl]-2,4-dioxo-6-(2,2,2-trifluoroethyl)-3,4-dihydrothieno[2,3-d]pyrimidin-1(2H)-yl]methyl}biphenyl-2-carbonitrile

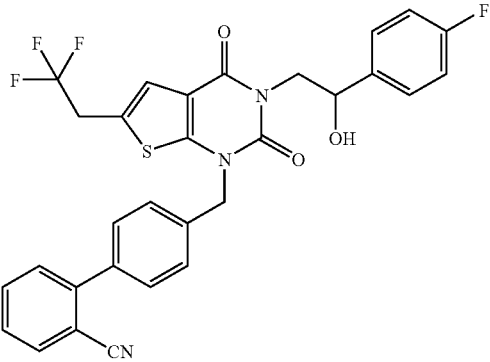 [SMILES: N#Cc1ccccc1-c1ccc(Cn2c(=O)n(CC(O)c3ccc(F)cc3)c(=O)c3cc(CC(F)(F)F)sc32)cc1]

To a mixture of 4'-{[3-[2-(4-fluorophenyl)-2-oxoethyl]-2,4-dioxo-6-(2,2,2-trifluoroethyl)-3,4-dihydrothieno[2,3-d]pyrimidin-1(2H)-yl]methyl}biphenyl-2-carbonitrile (0.9 g), tetrahydrofuran (20 mL) and methanol (20 mL) was added sodium borohydride (0.19 g), and the mixture was stirred at room temperature for 1 hr. The reaction mixture was concentrated, and the residue was extracted with ethyl acetate and saturated aqueous ammonium chloride solution. The ethyl acetate layer was washed with saturated brine, and dried over anhydrous sodium sulfate. The solvent was evaporated under reduced pressure. The obtained residue was purified by silica gel column chromatography to give the title compound as a colorless oil (0.41 g, 45%).

$^1$H NMR (300 MHz, CDCl$_3$)δ3.47-3.57 (3H, m), 4.30-4.48 (2H,m), 5.09-5.15 (1H, m), 5.15-5.26 (2H, m), 7.03-7.10 (3H, m), 7.26-7.29 (1H, m),7.43-7.58 (7H, m), 7.65 (1H, t, J=7.8), 7.76 (1H, d, J=7.8)

Reference Example 54

6-cyclopropyl-3-(2,4-dimethoxybenzyl)thieno[2,3-d]pyrimidine-2,4(1H,3H)-dione

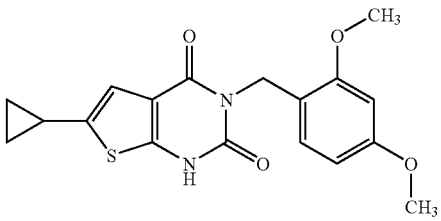 [SMILES: COc1ccc(Cn2c(=O)[nH]c3sc(C4CC4)cc3c2=O)c(OC)c1]

To a solution (300 mL) of methyl 2-amino-5-cyclopropylthiophene-3-carboxylate (4.7 g) in methylene chloride were added triphosgene (3.06 g) and triethylamine (8.6 mL), and the mixture was stirred at room temperature for 2 hr. To the reaction mixture was added 1-(2,4-dimethoxyphenyl)methanamine (7.2 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (300 mL), sodium methoxide (6.4 g) was added, and the mixture was stirred at 60° C. for 2 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The precipitated solid was collected by filtration to give the title compound as a colorless solid (8.53 g, 100%).

$^1$H NMR (300 MHz, DMSO-d$_6$)δ0.67-0.72 (2H, m), 0.91-0.98(2H, m), 2.00-2.08 (1H, m), 3.70 (3H, s), 3.80 (3H, s), 4.87 (2H, s), 6.35-6.39(1H, m), 6.54 (1H, s), 6.62 (1H, d, J=8.1), 6.83 (1H, s), 12.2 (1H, s)

Reference Example 55

4'-{[6-cyclopropyl-3-(2,4-dimethoxybenzyl)-2,4-dioxo-3,4-dihydrothieno[2,3-d]pyrimidin-1(2H)-yl]methyl}biphenyl-2-carbonitrile

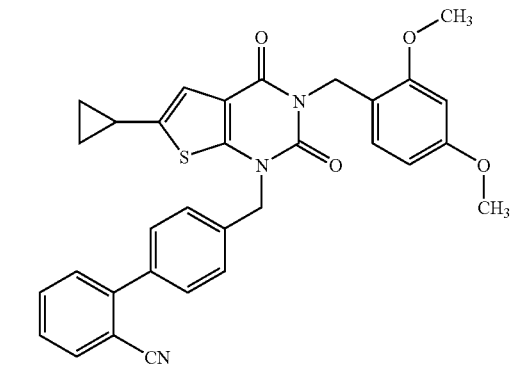 [SMILES: COc1ccc(Cn2c(=O)c3cc(C4CC4)sc3n(Cc3ccc(-c4ccccc4C#N)cc3)c2=O)c(OC)c1]

A mixture of 6-cyclopropyl-3-(2,4-dimethoxybenzyl)thieno[2,3-d]pyrimidine-2,4(1H,3H)-dione (1.82 g), 4'-(bromomethyl)biphenyl-2-carbonitrile (1.38 g) and potassium carbonate (1.4 g) and acetonitrile (100 mL) was stirred at 50°

C. for 2 hr. Insoluble material was filtered off, and the solvent was evaporated under reduced pressure. The obtained residue was purified by silica gel column chromatography to give the title compound as a colorless amorphous solid (2.4 g, 86%).

$^1$H NMR (300 MHz, CDCl$_3$)δ0.69-0.75 (2H, m), 0.93-0.10 (2H,m), 1.89-1.98 (1H, m), 3.86 (3H, s), 3.80 (3H, s), 5.17 (2H, s), 5.22 (3H, s),6.37-6.44 (2H, m), 6.95-6.98 (1H, m), 7.42-7.56 (6H, m), 7.46 (1H, t, J=7.8),7.76 (1H, d, J=7.5)

Reference Example 56

4'-{[3-(2,4-dimethoxybenzyl)-6-ethyl-2,4-dioxo-3,4-dihydrothieno[2,3-d]pyrimidin-1(2H)-yl]methyl}biphenyl-2-carbonitrile

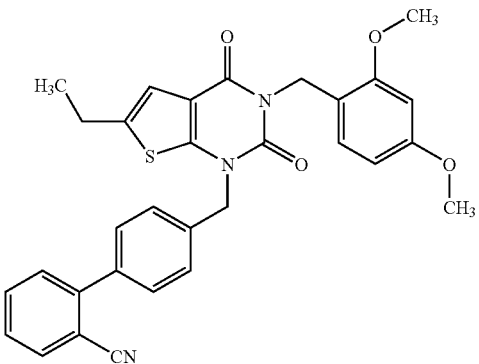 [SMILES: CCc1cc2c(=O)n(Cc3ccc(OC)cc3OC)c(=O)n(Cc3ccc(-c4ccccc4C#N)cc3)c2s1]

A mixture of 3-(2,4-dimethoxybenzyl)-6-ethylthieno[2,3-d]pyrimidine-2,4(1H,3H)-dione (45 g), 4'-(bromomethyl)biphenyl-2-carbonitrile (42.5 g), potassium carbonate (27 g) and acetonitrile (1 L) was stirred at 50° C. for 2 hr. The precipitated solid was collected by filtration, washed with water and diethyl ether, and dried under reduced pressure to give the title compound as a colorless solid (64 g, 92%).

$^1$H NMR (300 MHz, CDCl$_3$)δ1.30 (3H, t, J=7.6), 2.76 (2H,q, J=7.6), 3.77 (3H, s), 3.82 (3H, s), 5.19 (2H,s), 5.23 (2H, s), 6.37-6.45(2H, m), 6.98 (1H, d, J=8.4), 7.03 (1H, s), 7.42-7.56 (6H, m), 7.61-7.67 (1H,m), 7.75 (1H, d, J=7.8)

Reference Example 57

4'-[(6-ethyl-2,4-dioxo-3,4-dihydrothieno[2,3-d]pyrimidin-1(2H)-yl)methyl]biphenyl-2-carbonitrile

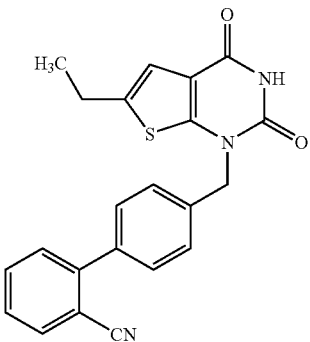 [SMILES: CCc1cc2c(=O)[nH]c(=O)n(Cc3ccc(-c4ccccc4C#N)cc3)c2s1]

A mixture of 4'-{[3-(2,4-dimethoxybenzyl)-6-ethyl-2,4-dioxo-3,4-dihydrothieno[2,3-d]pyrimidin-1(2H)-yl]methyl}biphenyl-2-carbonitrile (64 g) and trifluoroacetic acid (300 mL) was stirred at 50° C. for 2 hr. To the reaction mixture was added toluene (300 mL), and the mixture was concentrated under reduced pressure. To the obtained residue was added ethyl acetate (150 mL), and the mixture was concentrated under reduced pressure. The precipitated solid was collected by filtration to give the title compound as a colorless solid (46.1 g, 100%).

$^1$H NMR (300 MHz, DMSO-d$_6$)δ1.17 (3H, t, J=7.5), 2.71 (2H, q, J=7.5), 5.15 (2H, s), 6.95 (1H, s), 7.45 (2H, d, J=8.1), 7.57 (4H,m), 7.77 (1H, t, J=7.2), 7.93 (1H, d, J=7.8), 11.5 (1H, s)

Reference Example 58

4'-{[6-ethyl-3-[2-(4-methoxyphenyl)-2-oxoethyl]-2,4-dioxo-3,4-dihydrothieno[2,3-d]pyrimidin-1(2H)-yl]methyl}biphenyl-2-carbonitrile

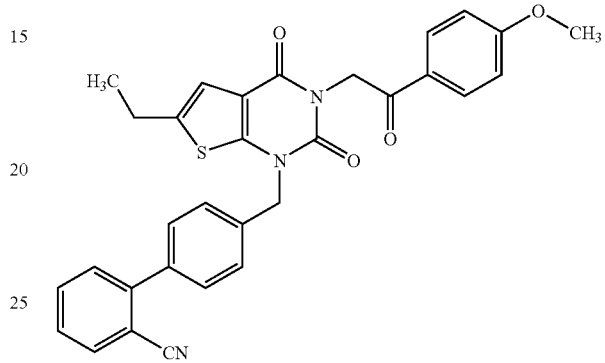

To a mixture of 4'-[(6-ethyl-2,4-dioxo-3,4-dihydrothieno[2,3-d]pyrimidin-1(2H)-yl)methyl]biphenyl-2-carbonitrile (1 g), 2-bromo-1-(4-methoxyphenyl)ethanone (0.71 g) and N,N-dimethylformamide (30 mL) was added 60% sodium hydride (0.12 g), and the mixture was stirred at room temperature for 2 hr. The reaction mixture was diluted with chloroform, washed with 5% potassium hydrogensulfate and then saturated brine, and dried over anhydrous magnesium sulfate. The solvent was evaporated under reduced pressure. The precipitated solid was collected by filtration to give the title compound as colorless crystals (1.38 g, 100%).

$^1$H NMR (300 MHz, CDCl$_3$)δ1.30 (3H, t, J=7.6), 2.69-2.85 (2H, m), 3.89 (3H, s), 5.12-5.30 (2H, m), 5.48 (2H, s), 6.97 (2H, d, J=9.1),7.04 (1H, s), 7.38-7.61 (6H, m), 7.60-7.68 (1H, m), 7.76 (1H, d, J=7.6), 8.02(2H, d, J=8.7)

Reference Example 59

4'-{[6-ethyl-3-[2-(2-methoxyphenyl)-2-oxoethyl]-2,4-dioxo-3,4-dihydrothieno[2,3-d]pyrimidin-1(2H)-yl]methyl}biphenyl-2-carbonitrile

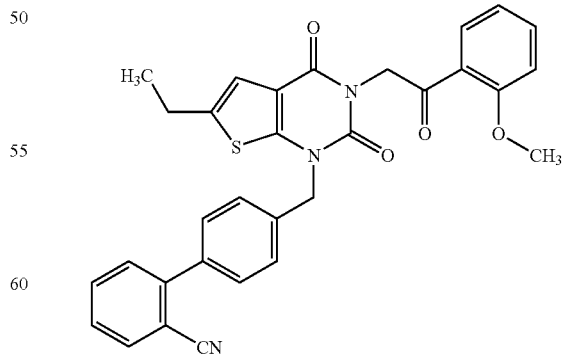

To a mixture of 4'-[(6-ethyl-2,4-dioxo-3,4-dihydrothieno[2,3-d]pyrimidin-1(2H)-yl)methyl]biphenyl-2-carbonitrile (5 g), 2-bromo-1-(2-methoxyphenyl)ethanone (3.3 g) and N,N-dimethylformamide (200 mL) was added 60% sodium hydride (1 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as colorless crystals (4.12 g, 60%).

¹H NMR (300 MHz, CDCl₃)δ1.25 (3H, t, J=7.8), 2.72 (2H,q, J=7.8), 3.95 (3H, s), 5.17 (2H, s), 5.42 (2H, s), 7.00 (3H, m), 7.36-7.64(8H, m), 7.72 (2H, m), 7.91 (1H, m)

Reference Example 60 methyl 5-chloro-2-(6-ethyl-2,4-dioxo-1,4-dihydrothieno[2,3-d]pyrimidin-3(2H)-yl)benzoate

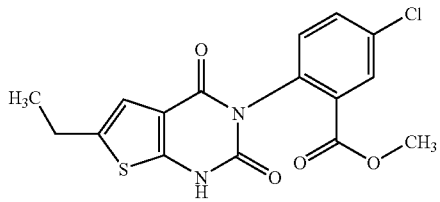 [SMILES: CCc1cc2c(=O)n(-c3ccc(Cl)cc3C(=O)OC)c(=O)[nH]c2s1]

To a solution (40 mL) of methyl 2-amino-5-ethylthiophene-3-carboxylate (0.4 g) in methylene chloride were added triphosgene (0.28 g) and triethylamine (0.48 mL), and the mixture was stirred at room temperature for 2 hr. To the reaction mixture was added methyl 2-amino-5-chlorobenzoate (1 mL), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in methanol (40 mL), sodium methoxide (0.58 g) was added, and the mixture was stirred at 60° C. for 1 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The precipitated solid was collected by filtration to give the title compound as a colorless solid (0.67 g, 85%).

¹H NMR (300 MHz, DMSO-d₆)δ1.26 (3H, t, J=7.5), 2.83 (2H, q, J=7.5), 3.61 (1H, s), 7.17 (1H, s), 7.25 (1H, d, J=8.7), 7.75-7.79(1H, m), 7.85 (1H, s), 11.8 (1H, s)

Reference Example 61

4'-{[3-[2-(2,4-dimethoxyphenyl)-2-oxoethyl]-6-ethyl-2,4-dioxo-3,4-dihydrothieno[2,3-d]pyrimidin-1(2H)-yl]methyl}biphenyl-2-carbonitrile

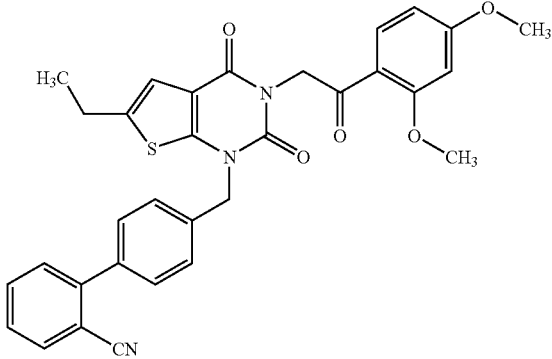 [SMILES: CCc1cc2c(=O)n(CC(=O)c3ccc(OC)cc3OC)c(=O)n(Cc3ccc(-c4ccccc4C#N)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (1 g), 2-bromo-1-(2,4-dimethoxyphenyl)ethanone (0.83 g) and N,N-dimethylformamide (50 mL) was added 60% sodium hydride (0.15 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as a colorless amorphous solid (0.91 g, 62%).

¹H NMR (300 MHz, CDCl₃)δ1.29 (3H, t, J=7.5), 2.76 (2H,q, J=7.5), 3.76 (3H, s), 3.81 (3H, s), 5.19 (2H, s), 5.23 (2H, s), 6.38-6.45(2H, m), 6.98 (1H, d, J=8.1), 7.03 (1H, s), 7.42-7.56 (6H, m), 7.64 (1H, t, J=7.2), 7.76 (1H, d, J=7.8)

Reference Example 62

4'-{[6-ethyl-3-[2-(2-fluoro-4-methoxyphenyl)-2-oxoethyl]-2,4-dioxo-3,4-dihydrothieno[2,3-d]pyrimidin-1(2H)-yl]methyl}biphenyl-2-carbonitrile

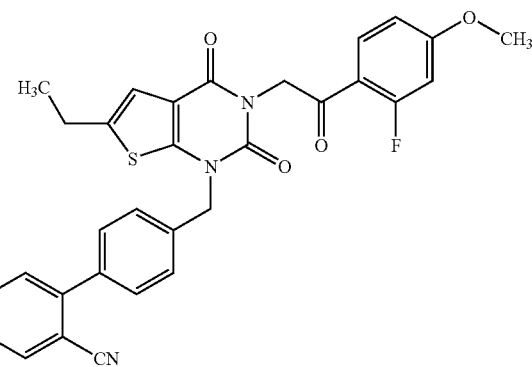

To a solution (100 mL) of 1-(2-fluoro-4-methoxyphenyl)ethanone (1.5 g) in diethyl ether was added a solution (10 mL) of bromine (0.46 mL) in diethyl ether. The reaction mixture was stirred at room temperature for 8 hr, and concentrated under reduced pressure. To a mixture of the obtained residue, 4'-[(6-ethyl-2,4-dioxo-3,4-dihydrothieno[2,3-d]pyrimidin-1(2H)-yl)methyl]biphenyl-2-carbonitrile (1 g) and N,N-dimethylformamide (50 mL) was added 60% sodium hydride (0.21 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as a colorless amorphous solid (1 g, 70%).

¹H NMR (300 MHz, CDCl₃)δ1.30 (3H, t, J=7.5), 2.76 (2H,q, J=7.5), 3.88 (3H, s), 5.22 (2H, s), 5.40 (2H, d, J=3.6), 6.64-6.80 (2H,m), 7.03 (1H, s), 7.42-7.64 (7H, m), 7.75 (1H, d, J=7.8), 7.97 (1H, t, J=8.7)

Reference Example 63

4'-{[3-[2-(3,4-dimethoxyphenyl)-2-oxoethyl]-6-ethyl-2,4-dioxo-3,4-dihydrothieno[2,3-d]pyrimidin-1(2H)-yl]methyl}biphenyl-2-carbonitrile

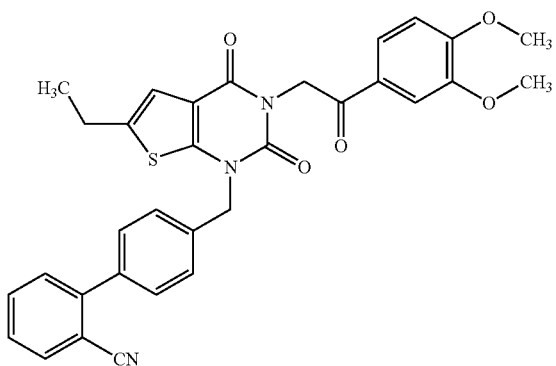 [SMILES: CCc1cc2c(=O)n(CC(=O)c3ccc(OC)c(OC)c3)c(=O)n(Cc3ccc(-c4ccccc4C#N)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (1 g), 2-bromo-1-(3,4-dimethoxyphenyl)ethanone (0.8 g) and N,N-dimethylformamide (25 mL) was added 60% sodium hydride (0.16 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as a colorless amorphous solid (1.25 g, 86%).

$^1$H NMR (300 MHz, CDCl$_3$)δ1.30 (3H, t, J=7.2), 2.77 (2H,q, J=7.2), 3.93 (3H, s), 3.97 (3H, s), 5.22 (2H, m), 5.50 (2H, s), 6.93 (1H,d, J=8.1), 7.03 (1H, s), 7.40-7.77 (10H, m).

Reference Example 64

4'-{[6-ethyl-3-[2-(4-methoxy-2-methylphenyl)-2-oxoethyl]-2,4-dioxo-3,4-dihydrothieno[2,3-d]pyrimidin-1(2H)-yl]methyl}biphenyl-2-carbonitrile

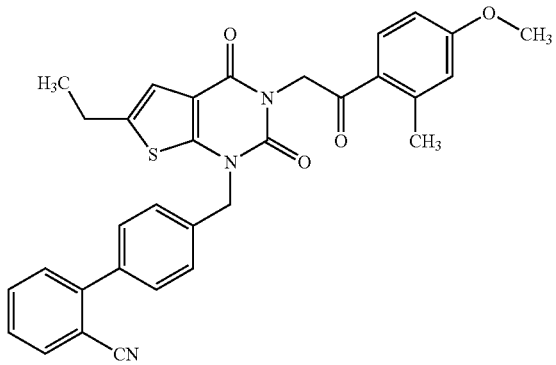 [SMILES: CCc1cc2c(=O)n(CC(=O)c3ccc(OC)cc3C)c(=O)n(Cc3ccc(-c4ccccc4C#N)cc3)c2s1]

To a mixture of 1-methoxy-3-methylbenzene (5 mL), acetylchloride (2.82 mL) and methylene chloride (150 mL) was added aluminum chloride (5.8 g) at 0° C. The reaction mixture was extracted with ice water and ethyl acetate. The ethyl acetate layer was successively washed with 1N hydrochloric acid and saturated brine, and dried over anhydrous magnesium sulfate. The solvent was evaporated under reduced pressure. The obtained residue was dissolved in diethyl ether (100 mL), and a solution (10 mL) of bromine (2.2 mL) in diethyl ether was added. The reaction mixture was stirred at room temperature for 1 hr, washed successively with water and saturated brine, and dried over anhydrous magnesium sulfate. The solvent was evaporated under reduced pressure. To a mixture of the obtained residue, 4'-[(6-ethyl-2,4-dioxo-3,4-dihydrothieno[2,3-d]pyrimidin-1(2H)-yl)methyl]biphenyl-2-carbonitrile (2 g) and N,N-dimethylformamide (50 mL) was added 60% sodium hydride (0.31 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as colorless crystals (1.1 g, 39%).

$^1$H NMR (300 MHz, CDCl$_3$)δ1.30 (3H, t, J=7.5), 2.56 (3H,s), 2.77 (2H, q, J=7.5), 3.86 (3H, s), 5.21 (2H, s), 5.39 (2H, s), 6.77-6.82(2H, m), 7.03 (1H, s), 7.42-7.57 (6H, m), 7.64 (1H, t, J=7.5), 7.75 (1H, m),7.89 (1H, d, J=8.4)

Reference Example 65

4'-{[3-(2,4-dimethoxybenzyl)-6-ethyl-2,4-dioxo-3,4-dihydrothieno[2,3-d]pyrimidin-1(2H)-yl]methyl}-3'-fluorobiphenyl-2-carbonitrile

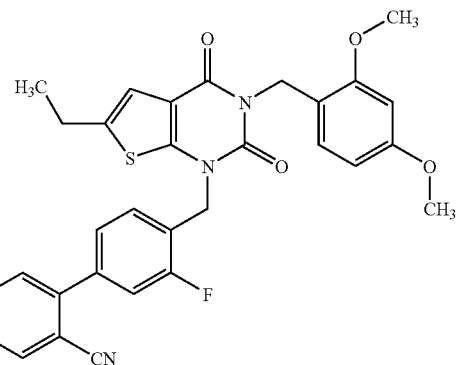

A mixture of 3-(2,4-dimethoxybenzyl)-6-ethylthieno[2,3-d]pyrimidine-2,4(1H,3H)-dione (2 g), 4'-(bromomethyl)-3'-fluorobiphenyl-2-carbonitrile (2 g), potassium carbonate (1.2 g) and acetonitrile (50 mL) was stirred at 50° C. for 2 hr. Insoluble material was filtered off, and the solvent was evaporated under reduced pressure. The obtained residue was purified by silica gel column chromatography to give the title compound as a colorless amorphous solid (1.3 g, 41%).

$^1$H NMR (300 MHz, CDCl$_3$)δ1.29 (3H, t, J=7.2), 2.76 (2H,q, J=7.2), 3.77 (3H, s), 3.82 (3H, s), 5.24 (2H, s), 5.27 (2H, s), 6.38-6.45(2H, m), 6.98-7.04 (2H, m), 7.28-7.39 (3H, m), 7.45-7.50 (2H, m), 7.65 (1H, t,J=7.8), 7.76 (1H, d, J=7.8)

Reference Example 66

4'-[(6-ethyl-2,4-dioxo-3,4-dihydrothieno[2,3-d]pyrimidin-1(2H)-yl)methyl]-3'-fluorobiphenyl-2-carbonitrile

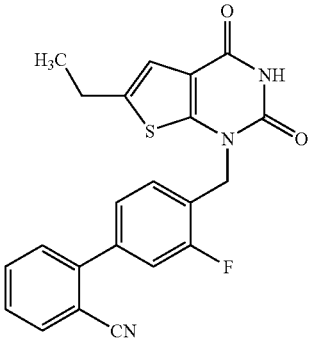 [SMILES: CCc1cc2c(=O)[nH]c(=O)n(Cc3ccc(-c4ccccc4C#N)cc3F)c2s1]

A mixture of 4'-{[3-(2,4-dimethoxybenzyl)-6-ethyl-2,4-dioxo-3,4-dihydrothieno[2,3-d]pyrimidin-1(2H)-yl]methyl}-3'-fluorobiphenyl-2-carbonitrile (1.3 g) and trifluoroacetic acid (20 mL) was stirred at 50° C. for 2 hr. To the reaction mixture was added toluene (20 mL), and the mixture was concentrated under reduced pressure. To the obtained residue was added ethyl acetate (10 mL), and the mixture was concentrated under reduced pressure. The precipitated solid was collected by filtration to give the title compound as a colorless solid (0.95 g, 100%).

$^1$H NMR (300 MHz, DMSO-$d_6$)δ1.17 (3H, t, J=7.5), 2.72 (2H, q, J=7.5), 5.18 (2H, s), 6.96 (1H, s), 7.36-7.42 (2H, m), 7.51-7.64 (3H,m), 7.78 (1H, t, J=7.5), 7.95 (1H, d, J=7.8)

Reference Example 67

4'-{[6-ethyl-3-[2-(4-methoxyphenyl)-2-oxoethyl]-2,4-dioxo-3,4-dihydrothieno[2,3-d]pyrimidin-1(2H)-yl]methyl}-3'-fluorobiphenyl-2-carbonitrile

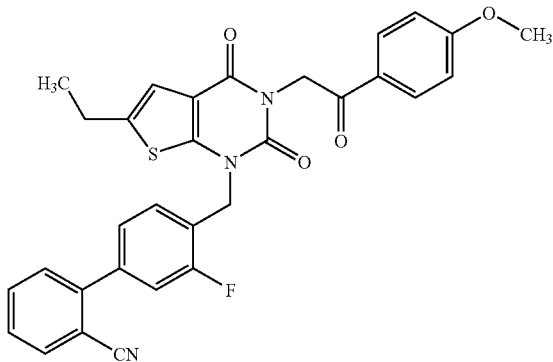 [SMILES: CCc1cc2c(=O)n(CC(=O)c3ccc(OC)cc3)c(=O)n(Cc3ccc(-c4ccccc4C#N)cc3F)c2s1]

To a mixture of 4'-[(6-ethyl-2,4-dioxo-3,4-dihydrothieno[2,3-d]pyrimidin-1(2H)-yl)methyl]-3'-fluorobiphenyl-2-carbonitrile (1.17 g), 2-bromo-1-(4-methoxyphenyl)ethanone (0.64 g) and N,N-dimethylformamide (20 mL) was added 60% sodium hydride (0.11 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as colorless crystals (0.9 g, 69%).

$^1$H NMR (300 MHz, CDCl$_3$)δ1.30 (3H, t, J=7.5), 2.76 (2H,q, J=7.5), 3.89 (3H, s), 5.29 (2H, s), 5.49 (2H, s), 6.95-6.98 (2H, m), 7.04(1H, s), 7.31-7.34 (2H, m), 7.40-7.49 (3H, m), 7.66 (1H, t, J=7.8), 7.76-7.79(1H, m), 8.00-8.03 (2H, m)

Reference Example 68

4'-{[6-ethyl-3-{[1-(4-methoxyphenyl)cyclopropyl]methyl}-2,4-dioxo-3,4-dihydrothieno[2,3-d]pyrimidin-1(2H)-yl]methyl}biphenyl-2-carbonitrile

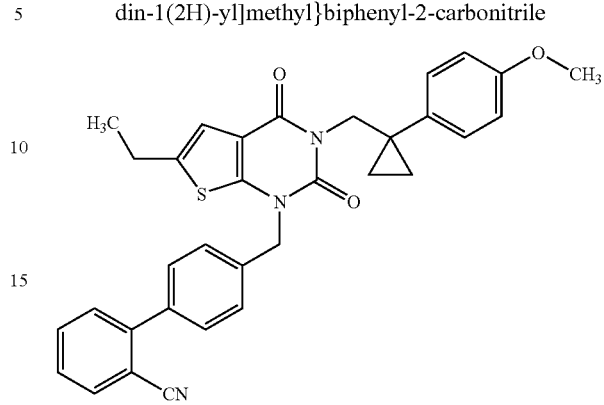

A mixture of 4'-[(6-ethyl-2,4-dioxo-3,4-dihydrothieno[2,3-d]pyrimidin-1(2H)-yl)methyl]biphenyl-2-carbonitrile (1 g), 1,1'-(azodicarbonyl)dipiperidine (1.3 g), tributylphosphine (1.6 mL), [1-(4-methoxyphenyl)cyclopropyl]methanol (0.46 g) and tetrahydrofuran (30 mL) was stirred at room temperature for 3 hr. The reaction mixture was concentrated under reduced pressure, to the residue was added diisopropyl ether (50 mL), and the mixture was stirred at room temperature for 1 hr. Insoluble material was filtered off, and the solvent was evaporated under reduced pressure. The obtained residue was purified by silica gel column chromatography to give the title compound as a colorless amorphous solid (0.71 g, 50%).

$^1$H NMR (300 MHz, CDCl$_3$)δ0.81-0.85 (2H, m), 1.04-1.08 (2H,m), 1.29 (3H, t, J=7.2), 2.74 (2H, q, J=7.2), 3.72 (3H, s), 4.29 (2H, s),5.04 (2H, s), 6.74-6.78 (2H, m), 6.98 (1H, s), 7.19-7.27 (4H, m), 7.42-7.73(4H, m), 7.62-7.68 (1H, m), 7.76 (1H, d, J=7.8)

Reference Example 69

4'-{[3-[2-(3,5-dimethoxyphenyl)-2-oxoethyl]-6-ethyl-2,4-dioxo-3,4-dihydrothieno[2,3-d]pyrimidin-1(2H)-yl]methyl}biphenyl-2-carbonitrile

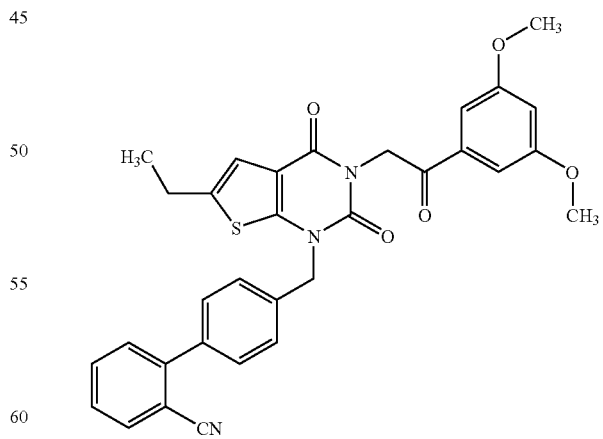

To a mixture of 4'-[(6-ethyl-2,4-dioxo-3,4-dihydrothieno[2,3-d]pyrimidin-1(2H)-yl)methyl]biphenyl-2-carbonitrile (1.5 g), 2-bromo-1-(3,5-dimethoxyphenyl)ethanone (1 g) and N,N-dimethylformamide (20 mL) was added 60% sodium hydride (0.19 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as colorless crystals (1.14 g, 52%).

$^1$H NMR (300 MHz, DMSO-$d_6$)δ1.20 (3H, t, J=7.8), 2.76 (2H, q, J=7.8), 3.87 (3H, s), 3.99 (3H, s), 5.21 (2H, s), 5.25 (2H, s), 6.66(1H, dd, J=8.7, 1.8), 6.23-6.73 (1H, m), 7.01 (1H, s), 7.45-7.48 (2H, m), 7.54-7.62 (4H, m), 7.75-7.80 (2H, m), 7.93 (1H, d, J=6.9)

Reference Example 70

4'-{[6-ethyl-3-[2-(2-naphthyl)-2-oxoethyl]-2,4-dioxo-3,4-dihydrothieno[2,3-d]pyrimidin-1(2H)-yl]methyl}biphenyl-2-carbonitrile

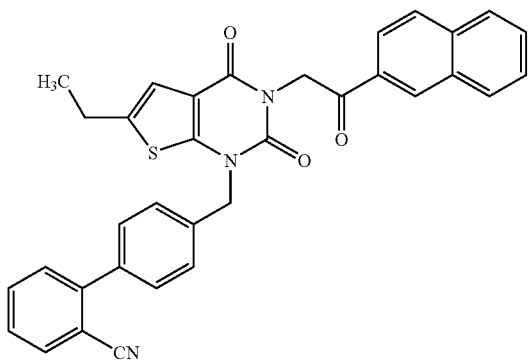 [SMILES: CCc1cc2c(=O)n(CC(=O)c3ccc4ccccc4c3)c(=O)n(Cc3ccc(-c4ccccc4C#N)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (1.5 g), 2-bromo-1-(2-naphthyl)ethanone (1.16 g) and N,N-dimethylformamide (20 mL) was added 60% sodium hydride (0.19 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as colorless crystals (0.84 g, 39%).

$^1$H NMR (300 MHz, DMSO-$d_6$)δ1.21 (3H, t, J=7.5), 2.77 (2H, q, J=7.5), 5.28 (2H, s), 5.62 (2H, s), 7.05 (1H, s), 7.50-7.78 (9H, m), 7.94 (2H, d, J=7.8), 8.02-8.09 (3H, m), 8.15 (1H, d, J=8.4), 8.89 (1H, s)

Reference Example 71

4'-{[3-[2-(3-bromo-4-methoxyphenyl)-2-oxoethyl]-6-ethyl-2,4-dioxo-3,4-dihydrothieno[2,3-d]pyrimidin-1(2H)-yl]methyl}biphenyl-2-carbonitrile

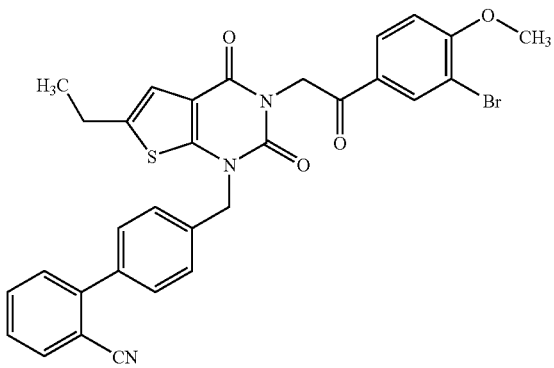 [SMILES: CCc1cc2c(=O)n(CC(=O)c3ccc(OC)c(Br)c3)c(=O)n(Cc3ccc(-c4ccccc4C#N)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (5 g), 2-bromo-1-(3-bromo-4-methoxyphenyl)ethanone (4.4 g) and N,N-dimethylformamide (300 mL) was added 60% sodium hydride (0.57 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as colorless crystals (3.4 g, 43%).

$^1$H NMR (300 MHz, CDCl$_3$)δ1.30 (3H, t, J=7.8), 2.77 (2H,q, J=7.8), 3.98 (3H, s), 5.21 (2H, s), 5.45 (2H, s), 6.97 (2H, d, J=8.4), 7.04 (1H, s), 7.42-7.67 (6H, m), 7.76 (1H, d, J=7.8), 8.00 (1H, dd, J=8.4,1.8), 8.25 (1H, d, J=2.1)

Reference Example 72

4'-{[6-ethyl-3-[2-(4-methoxy-3-methylphenyl)-2-oxoethyl]-2,4-dioxo-3,4-dihydrothieno[2,3-d]pyrimidin-1(2H)-yl]methyl}biphenyl-2-carbonitrile

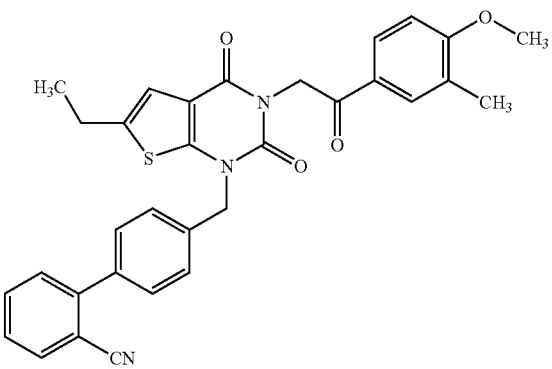 [SMILES: CCc1cc2c(=O)n(CC(=O)c3ccc(OC)c(C)c3)c(=O)n(Cc3ccc(-c4ccccc4C#N)cc3)c2s1]

A mixture of 4'-{[3-[2-(3-bromo-4-methoxyphenyl)-2-oxoethyl]-6-ethyl-2,4-dioxo-3,4-dihydrothieno[2,3-d]pyrimidin-1(2H)-yl]methyl}biphenyl-2-carbonitrile (1.3 g), methylboronic acid (0.25 g), [1,1'-bis(diphenylphosphino)ferrocene]dichloropalladium (0.086 g), potassium carbonate (0.88 g), tetrahydrofuran (50 mL) and water (5 mL) was stirred under argon atmosphere at 50° C. for 2 days. The reaction mixture was diluted with ethyl acetate, and insoluble material was filtered off through celite. The filtrate was concentrated under reduced pressure and the obtained residue was purified by silica gel column chromatography to give the title compound as a colorless amorphous solid (0.94 g, 81%).

$^1$H NMR (300 MHz, CDCl$_3$)δ1.30 (3H, t, J=7.5), 2.26 (3H,s), 2.76 (2H, q, J=7.5), 3.91 (3H, s), 5.21 (2H, s), 5.48 (2H, s), 6.87 (2H,d, J=8.7), 7.03 (1H, s), 7.42-7.67 (6H, m), 7.76 (1H, d, J=8.1), 7.84 (1H,s), 7.90 (1H, dd, J=8.4, 2.1)

Reference Example 73

4'-[(6-cyclopropyl-2,4-dioxo-3,4-dihydrothieno[2,3-d]pyrimidin-1(2H)-yl)methyl]-3'-fluorobiphenyl-2-carbonitrile

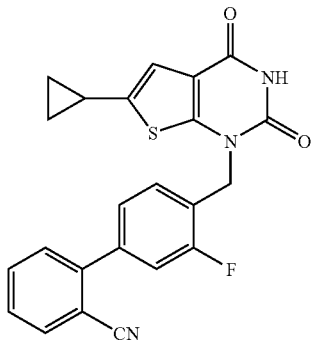 [SMILES: N#Cc1ccccc1-c1ccc(Cn2c(=O)[nH]c(=O)c3cc(C4CC4)sc32)c(F)c1]

A mixture of 6-cyclopropyl-3-(2,4-dimethoxybenzyl)thieno[2,3-d]pyrimidine-2,4(1H,3H)-dione (2 g), 4'-(bromomethyl)-3'-fluorobiphenyl-2-carbonitrile (1.8 g), potassium carbonate (1.5 g) and acetonitrile (200 mL) was stirred at 50° C. for 2 hr. Insoluble material was filtered off, and the solvent was evaporated under reduced pressure. The obtained residue was dissolved in trifluoroacetic acid (50 mL), and the mixture was stirred at 50° C. for 2 hr. To the reaction mixture was added toluene (50 mL), and the mixture was concentrated under reduced pressure. To the obtained residue was added ethyl acetate (50 mL), and the mixture was concentrated under reduced pressure. The precipitated solid was collected by filtration to give the title compound as a colorless solid (1.5 g, 64%).

$^1$H NMR (300 MHz, DMSO-$d_6$)δ0.64-0.69 (2H, m), 0.89-0.95(2H, m), 1.97-2.07 (1H, m), 5.16 (2H, s), 6.90 (1H, s), 7.36-7.42 (2H, m),7.51-7.65 (3H, m), 7.79 (1H, t, J=7.5), 7.95 (1H, d, J=7.8), 11.5 (1H, s)

Reference Example 74

4'-{[6-cyclopropyl-3-[2-(4-methoxyphenyl)-2-oxoethyl]-2,4-dioxo-3,4-dihydrothieno[2,3-d]pyrimidin-1(2H)-yl]methyl}-3'-fluorobiphenyl-2-carbonitrile

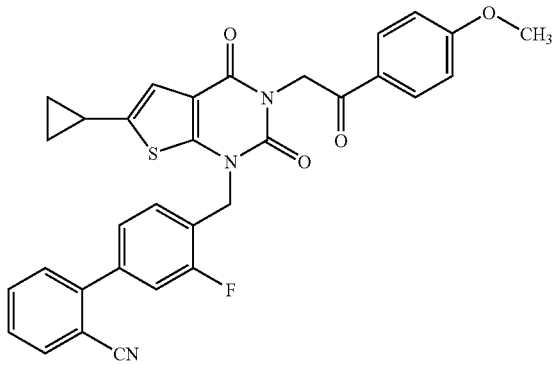 [SMILES: COc1ccc(C(=O)Cn2c(=O)c3cc(C4CC4)sc3n(Cc3ccc(-c4ccccc4C#N)cc3F)c2=O)cc1]

To a mixture of 4'-[(6-cyclopropyl-2,4-dioxo-3,4-dihydrothieno[2,3-d]pyrimidin-1(2H)-yl)methyl]-3'-fluorobiphenyl-2-carbonitrile (1.5 g), 2-bromo-1-(4-methoxyphenyl)ethanone (0.99 g) and N,N-dimethylformamide (40 mL) was added 60% sodium hydride (0.17 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as colorless crystals (0.95 g, 47%).

$^1$H NMR (300 MHz, CDCl$_3$)δ0.71-0.76 (2H, m), 0.95-1.01 (2H,m), 1.91-1.99 (1H, m), 3.89 (3H, s), 5.28 (2H, s), 5.48 (2H, s), 6.95-6.98 (3H,m), 7.31-7.50 (5H, m), 7.66 (1H, t, J=7.5), 7.76-7.79 (1H, m), 7.99-8.03 (2H,m)

Reference Example 75

4'-{[6-ethyl-3-[2-(2-methoxyphenyl)-2-oxoethyl]-2,4-dioxo-3,4-dihydrothieno[2,3-d]pyrimidin-1(2H)-yl]methyl}biphenyl-2-carbonitrile

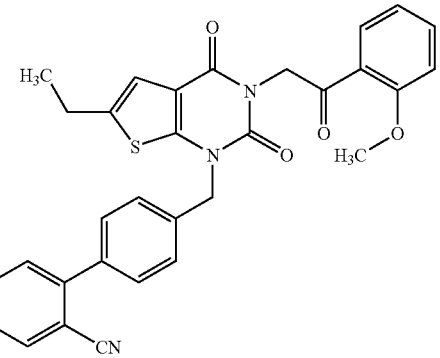

To a mixture of 4'-[(6-ethyl-2,4-dioxo-3,4-dihydrothieno[2,3-d]pyrimidin-1(2H)-yl)methyl]biphenyl-2-carbonitrile (5 g), 2-bromo-1-(2-methoxyphenyl)ethanone (3.3 g) and N,N-dimethylformamide (200 mL) was added 60% sodium hydride (1 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as colorless crystals (4.12 g, 60%).

$^1$H NMR (200 MHz, CDCl$_3$)δ1.25 (3H, t, J=7.8), 2.72 (2H,q, J=7.8), 3.95 (3H, s), 5.17 (2H, s), 5.42 (2H, s), 6.95-7.02 (3H, m),7.36-7.64 (8H, m), 7.72 (1H, d, J=7.6), 7.91 (1H, d, J=7.2)

Reference Example 76 methyl 2-(6-ethyl-2,4-dioxo-1,4-dihydrothieno[2,3-d]pyrimidin-3(2H)-yl)propanoate

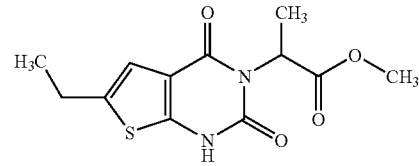 [SMILES: CCc1cc2c(=O)n(C(C)C(=O)OC)c(=O)[nH]c2s1]

To a solution (500 mL) of methyl 2-amino-5-ethylthiophene-3-carboxylate (15 g) in methylene chloride were added triphosgene (10.4 g) and triethylamine (29.4 mL), and the mixture was stirred at room temperature for 2 hr. To the reaction mixture were further added triethylamine (24.8 mL) and DL-alanine methyl ester hydrochloride (22.6 g), and the mixture was further stirred at room temperature for 1 hr, washed with water and saturated brine, and dried over anhydrous magnesium sulfate. The solvent was evaporated under reduced pressure. The obtained residue was dissolved in methanol (500 mL), sodium methoxide (21.9 g) was added, and the mixture was stirred at 60° C. for 1 hr. The reaction

Reference Example 77 methyl 2-[1-[(2'-cyanobiphenyl-4-yl)methyl]-6-ethyl-2,4-dioxo-1,4-dihydrothieno[2,3-d]pyrimidin-3(2H)-yl]propanoate

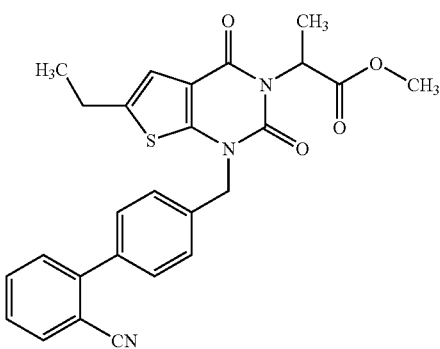 [SMILES: CCc1cc2c(=O)n(C(C)C(=O)OC)c(=O)n(Cc3ccc(-c4ccccc4C#N)cc3)c2s1]

A mixture of methyl 2-(6-ethyl-2,4-dioxo-1,4-dihydrothieno[2,3-d]pyrimidin-3(2H)-yl)propanoate (9.9 g), 4'-(bromomethyl)biphenyl-2-carbonitrile (11.5 g), potassium carbonate (9.7 g) and acetonitrile (500 mL) was stirred at 50° C. for 2 hr. Insoluble material was filtered off, and the solvent was evaporated under reduced pressure. The obtained residue was purified by silica gel column chromatography to give the title compound as a colorless amorphous solid (15 g, 90%).

$^1$H NMR (300 MHz, CDCl$_3$)δ1.29 (3H, t, J=7.2), 1.66 (3H,d, J=6.9), 2.76 (2H, q, J=7.2), 3.72 (3H, s), 5.17 (2H, dd, J=43.2,15.6), 5.63 (1H, q, J=6.9), 7.02 (1H, s), 7.42-7.57 (6H, m), 7.64 (1H, t, J=7.8), 7.75 (1H, d, J=7.8)

Reference Example 78

4'-{[6-ethyl-3-(2-hydroxy-1-methylethyl)-2,4-dioxo-3,4-dihydrothieno[2,3-d]pyrimidin-1(2H)-yl]methyl}biphenyl-2-carbonitrile

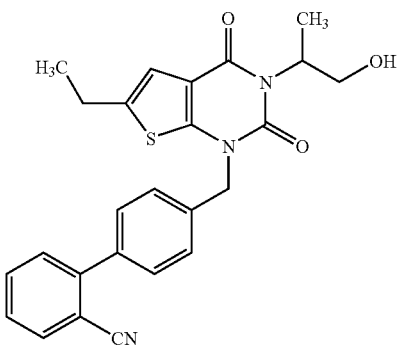 [SMILES: CCc1cc2c(=O)n(C(C)CO)c(=O)n(Cc3ccc(-c4ccccc4C#N)cc3)c2s1]

To a mixture of methyl 2-[1-[(2'-cyanobiphenyl-4-yl)methyl]-6-ethyl-2,4-dioxo-1,4-dihydrothieno[2,3-d]pyrimidin-3(2H)-yl]propanoate (3 g), N-methylmorpholine (0.86 mL) and tetrahydrofuran (50 mL) was added ethyl chlorocarbonate (0.75 mL) at 0° C., and the mixture was stirred at the same temperature for 2 hr. The reaction mixture was cooled to −15° C., sodium borohydride (0.74 g) and methanol (12 mL) were added, and the mixture was allowed to gradually warm to room temperature. The reaction mixture was extracted with saturated aqueous ammonium chloride solution and ethyl acetate. The ethyl acetate layer was washed with saturated brine, and dried over anhydrous magnesium sulfate. The solvent was evaporated under reduced pressure. The obtained residue was purified by silica gel column chromatography to give the title compound as a colorless amorphous solid (2 g, 69%).

$^1$H NMR (300 MHz, CDCl$_3$)δ1.29 (3H, t, J=7.5), 1.49 (3H,d, J=7.2), 2.75 (2H, q, J=7.5), 3.90 (1H, dd, J=12.3, 2.7), 4.04-4.10(2H, m), 5.12-5.24 (2H, m), 5.32-5.38 (1H, m), 7.01 (1H, s), 7.43-7.57 (6H, m),7.65 (1H, t, J=8.1), 7.76 (1H, d, J=7.8)

Reference Example 79

4'-{[6-ethyl-3-(1-methyl-2-oxoethyl)-2,4-dioxo-3,4-dihydrothieno[2,3-d]pyrimidin-1(2H)-yl]methyl}biphenyl-2-carbonitrile

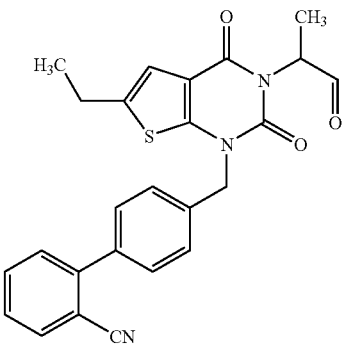 [SMILES: CCc1cc2c(=O)n(C(C)C=O)c(=O)n(Cc3ccc(-c4ccccc4C#N)cc3)c2s1]

To a mixture of oxalylchloride (0.43 mL) and methylene chloride (10 mL) were added a solution (10 mL) of dimethyl sulfoxide (0.35 mL) in methylene chloride and a solution (10 mL) of 4'-{[6-ethyl-3-(2-hydroxy-1-methylethyl)-2,4-dioxo-3,4-dihydrothieno[2,3-d]pyrimidin-1(2H)-yl]methyl}biphenyl-2-carbonitrile (2 g) in methylene chloride at −78° C., and the mixture was stirred at the same temperature for 15 min. Triethylamine (3.14 mL) was added, and the mixture was allowed to warm to room temperature. The reaction mixture was washed with water and saturated brine, and dried over anhydrous magnesium sulfate. The solvent was evaporated under reduced pressure. The obtained residue was purified by silica gel column chromatography to give the title compound as a colorless amorphous solid (1.7 g, 85%).

$^1$H NMR (300 MHz, CDCl$_3$)δ1.30 (3H, t, J=7.5), 1.58 (3H,d, J=6.9), 2.77 (2H, q, J=7.5), 5.19 (2H, s), 5.26 (1H, q, J=6.9), 7.02(1H, s), 7.43-7.58 (6H, m), 7.65 (1H, t, J=7.5), 7.76 (1H, d, J=7.8), 9.59(1H, s)

Reference Example 80

4'-{[6-ethyl-3-[2-hydroxy-2-(4-methoxyphenyl)-1-methylethyl]-2,4-dioxo-3,4-dihydrothieno[2,3-d]pyrimidin-1(2H)-yl]methyl}biphenyl-2-carbonitrile

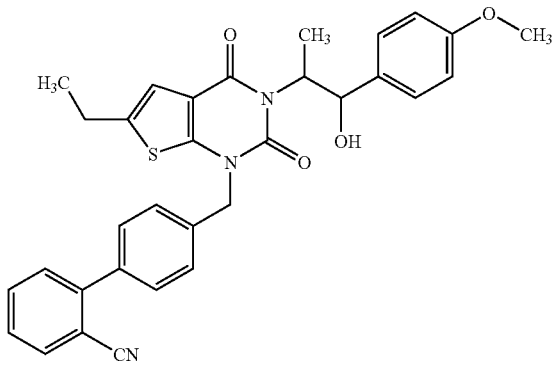 [SMILES: CCc1cc2c(=O)n(C(C)C(O)c3ccc(OC)cc3)c(=O)n(Cc3ccc(-c4ccccc4C#N)cc3)c2s1]

To a mixture of 4'-{[6-ethyl-3-(1-methyl-2-oxoethyl)-2,4-dioxo-3,4-dihydrothieno[2,3-d]pyrimidin-1(2H)-yl]methyl}biphenyl-2-carbonitrile (1.7 g) and tetrahydrofuran (100 mL) was added 4-methoxyphenyl-magnesium bromide (12.6 mL), and the mixture was stirred at 50° C. for 16 hr. The reaction mixture was extracted with saturated aqueous ammonium chloride solution and ethyl acetate. The ethyl acetate layer was washed with saturated brine, and dried over anhydrous magnesium sulfate. The solvent was evaporated under reduced pressure. The obtained residue was purified by silica gel column chromatography to give the title compound as a colorless amorphous solid (0.68 g, 32%).

$^1$H NMR (300 MHz, CDCl$_3$)δ1.27 (3H, t, J=7.5), 1.45-1.60 (3H, m), 2.71-2.74 (2H, m), 3.76 (3H, s), 4.81-5.38 (5H, m), 6.80-6.85 (2H, m),3.95-6.98 (1H, m), 7.30-7.55 (8H, m), 7.65 (1H, t, J=7.8), 7.77 (1H, d, J=7.8)

Reference Example 81

4'-{[6-ethyl-3-[2-(4-methoxyphenyl)-1-methyl-2-oxoethyl]-2,4-dioxo-3,4-dihydrothieno[2,3-d]pyrimidin-1(2H)-yl]methyl}biphenyl-2-carbonitrile

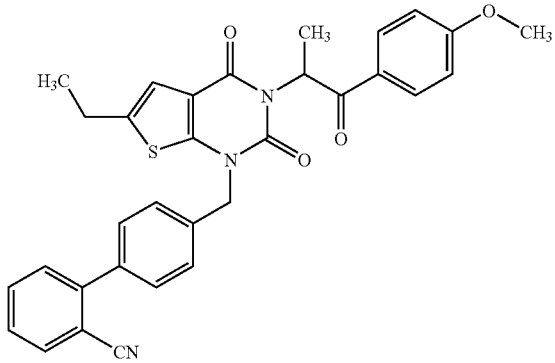 [SMILES: CCc1cc2c(=O)n(C(C)C(=O)c3ccc(OC)cc3)c(=O)n(Cc3ccc(-c4ccccc4C#N)cc3)c2s1]

To a mixture of oxalylchloride (0.12 mL) and methylene chloride (10 mL) were added a solution (5 mL) of dimethyl sulfoxide (0.096 mL) in methylene chloride and a solution (5 mL) of 4'-{[6-ethyl-3-[2-hydroxy-2-(4-methoxyphenyl)-1-methylethyl]-2,4-dioxo-3,4-dihydrothieno[2,3-d]pyrimidin-1(2H)-yl]methyl}biphenyl-2-carbonitrile (0.68 g) in methylene chloride at −78° C., and the mixture was stirred at the same temperature for 15 min. Triethylamine (0.86 mL) was added, and the mixture was allowed to warm to room temperature. The reaction mixture was washed with water and saturated brine, and dried over anhydrous magnesium sulfate. The solvent was evaporated under reduced pressure. The obtained residue was purified by silica gel column chromatography to give the title compound as colorless crystals (0.27 g, 40%).

$^1$H NMR (300 MHz, CDCl$_3$)δ1.27 (3H, t, J=7.2), 1.66 (3H,d, J=6.6), 2.73 (2H, q, J=7.2), 3.76 (3H, s), 4.77 (1H, d, J=15.9), 5.30(1H, d, J=15.9), 6.07 (1H, q, J=6.9), 6.83 (2H, d, J=8.7), 6.99-7.02 (3H,m), 7.38 (2H, d, J=7.8), 7.43-7.48 (2H, m), 7.63-7.78 (4H, m)

Reference Example 82 methyl (6-ethyl-2,4-dioxo-1,4-dihydrothieno[2,3-d]pyrimidin-3(2H)-yl)acetate

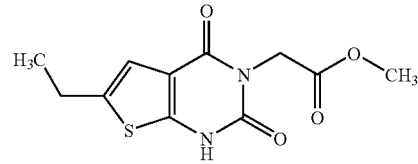 [SMILES: CCc1cc2c(=O)n(CC(=O)OC)c(=O)[nH]c2s1]

To a solution (400 mL) of methyl 2-amino-5-ethylthiophene-3-carboxylate (10 g) in methylene chloride were added triphosgene (6.9 g) and triethylamine (12 mL), and the mixture was stirred at room temperature for 2 hr. To the reaction mixture were further added triethylamine (24.8 mL) and glycine methyl ester hydrochloride (20.3 g), and the mixture was further stirred at room temperature for 1 hr, washed with water and saturated brine, and dried over anhydrous magnesium sulfate. The solvent was evaporated under reduced pressure. The obtained residue was dissolved in methanol (500 mL), sodium methoxide (14.6 g) was added, and the mixture was stirred at 60° C. for 1 hr. The reaction mixture was concentrated under reduced pressure, and the obtained residue was extracted with 1N hydrochloric acid and ethyl acetate. The ethyl acetate layer was washed with saturated brine, and dried over anhydrous magnesium sulfate. The solvent was evaporated under reduced pressure. The precipitated solid was collected by filtration to give the title compound as a colorless solid (8.69 g, 60%).

$^1$H NMR (300 MHz, DMSO-d$_6$)δ1.21 (3H, t, J=7.5), 2.74 (2H, q, J=7.5), 3.65 (3H, s), 4.57 (2H, s), 6.87 (1H, s), 12.3 (1H, s)

Reference Example 83 methyl [1-[(2'-cyanobiphenyl-4-yl)methyl]-6-ethyl-2,4-dioxo-1,4-dihydrothieno[2,3-d]pyrimidin-3(2H)-yl]acetate

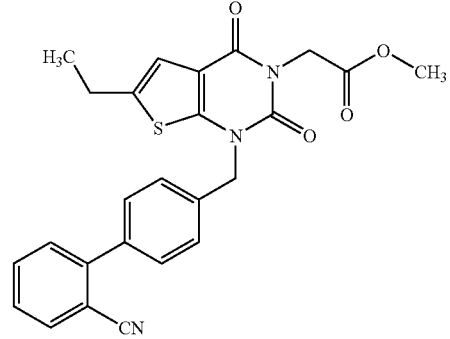 [SMILES: CCc1cc2c(=O)n(CC(=O)OC)c(=O)n(Cc3ccc(-c4ccccc4C#N)cc3)c2s1]

A mixture of methyl (6-ethyl-2,4-dioxo-1,4-dihydrothieno[2,3-d]pyrimidin-3(2H)-yl)acetate (3.7 g), 4'-(bromomethyl)

biphenyl-2-carbonitrile (4.3 g), potassium carbonate (3.6 g) and acetonitrile (200 mL) was stirred at 50° C. for 2 hr. Insoluble material was filtered off, and the solvent was evaporated under reduced pressure. The precipitated solid was collected by filtration, washed with water and diethyl ether, and dried under reduced pressure to give the title compound as a colorless solid (3.4 g, 57%).

$^1$H NMR (300 MHz, CDCl$_3$)δ1.29 (3H, t, J=7.2), 2.76 (2H,d, J=7.2), 3.78 (3H, s), 4.83 (2H, s), 5.20 (2H, s), 7.03 (1H, s), 7.42-7.57(6H, m), 7.64 (1H, t, J=7.5), 7.75 (1H, d, J=8.1)

Reference Example 84

4'-{[3-(3,3-dimethyl-2-oxobutyl)-2,4-dioxo-6-propoxy-3,4-dihydropyrimidin-1(2H)-yl]methyl}biphenyl-2-carbonitrile

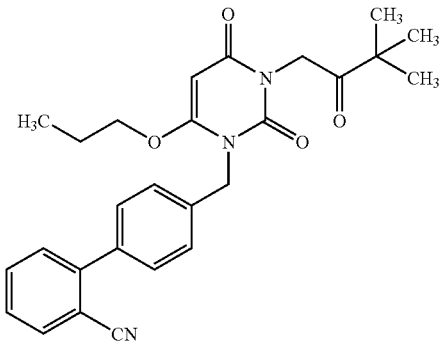 [SMILES: CCCOc1cc(=O)n(CC(=O)C(C)(C)C)c(=O)n1Cc1ccc(-c2ccccc2C#N)cc1]

To a mixture of 4'-[(2,4-dioxo-6-propoxy-3,4-dihydropyrimidin-1(2H)-yl)methyl]-biphenyl-2-carbonitrile (1 g), 1-bromo-3,3-dimethylbutan-2-one (0.59 g) and N,N-dimethylformamide (15 mL) was added 60% sodium hydride (0.17 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as a colorless amorphous solid (0.8 g, 26%).

$^1$H NMR (300 MHz, CDCl$_3$)δ0.95 (3H, t, J=7.3), 1.24-1.31 (9H, m), 1.73-1.88 (2H, m), 3.98 (2H, t, J=6.4), 4.94 (2H, s), 5.14 (3H, d, J=4.1), 7.36-7.57 (6H, m), 7.63 (1H, dd, J=7.6, 1.2), 7.71-7.80 (1H, m)

Reference Example 85

4'-{[6-ethyl-3-(2-morpholin-4-ylethyl)-2,4-dioxo-3,4-dihydrothieno[2,3-d]pyrimidin-1(2H)-yl]methyl}-3'-fluorobiphenyl-2-carbonitrile

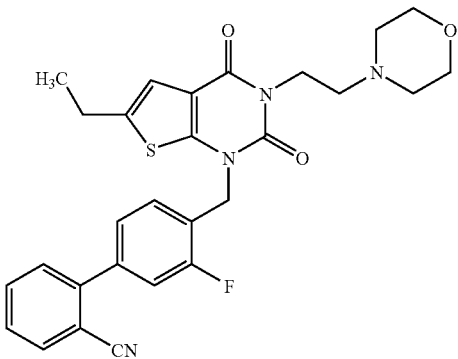 [SMILES: CCc1cc2c(=O)n(CCN3CCOCC3)c(=O)n(Cc3ccc(-c4ccccc4C#N)cc3F)c2s1]

To a solution (350 mL) of methyl 2-amino-5-ethylthiophene-3-carboxylate (10 g) in methylene chloride were added triphosgene (6.9 g) and triethylamine (19.5 mL), and the mixture was stirred at room temperature for 2 hr. To the reaction mixture was added 2-morpholin-4-ylethanamine (14.2 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (500 mL), sodium methoxide (14.9 g) was added, and the mixture was stirred at 60° C. for 2 hr. The reaction mixture was concentrated under reduced pressure, and the obtained residue was dissolved in water (300 mL). 1N Hydrochloric acid was added to adjust to pH 4, and the precipitated solid was collected by filtration. The obtained solid was dissolved in acetonitrile (50 mL), 4'-(bromomethyl)-3'-fluorobiphenyl-2-carbonitrile (1.03 g) and potassium carbonate (0.49 g) were added, and the mixture was stirred at 50° C. for 3 hr. Insoluble material was filtered off, and the solvent was evaporated under reduced pressure. The obtained residue was purified by silica gel column chromatography to give the title compound as colorless crystals (1.22 g, 73%).

$^1$H NMR (300 MHz, CDCl$_3$)δ1.23 (3H, t, J=7.6), 2.56-2.64 (2H, m), 2.75 (2H, q, J=7.6), 3.27-3.37 (4H, m), 3.46-3.61 (4H, m), 4.09 (2H,t, J=6.6), 5.19 (2H, s), 7.00 (1H, s), 7.22-7.34 (2H, m), 7.34-7.40 (1H, m),7.55 (2H, dd, J=17.4, 7.2), 7.61-7.75 (2H, m)

Reference Example 86

4-[(2-methoxyethoxy)methyl]-3-(4'-methylbiphenyl-2-yl)-1,2,4-oxadiazol-5(4H)-one

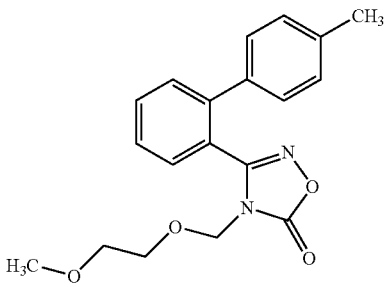

To a mixture of 3-(4'-methylbiphenyl-2-yl)-1,2,4-oxadiazol-5(4H)-one (44.1 g), 1-(chloromethoxy)-2-methoxyethane (24 g) and methylene chloride (500 mL) was added a solution (30 mL) of diisopropylethylamine (36.2 mL) in methylene chloride was added, and the mixture was stirred at room temperature for 3 hr. The reaction mixture was washed with water and saturated brine, and dried over anhydrous magnesium sulfate. The solvent was evaporated under reduced pressure. The precipitated solid was collected by filtration to give the title compound as a colorless solid (46.6 g, 78%).

$^1$H NMR (300 MHz, CDCl$_3$)δ3.27 (3H, s), 3.29-3.32 (2H, m),3.45-3.48 (2H, m), 4.47 (2H, s), 4.54 (2H, s), 7.16-7.26 (4H, m), 4.46-7.68(4H, m)

Reference Example 87

3-[4'-(bromomethyl)biphenyl-2-yl]-4-[(2-methoxyethoxy)methyl]-1,2,4-oxadiazol-5(4H)-one

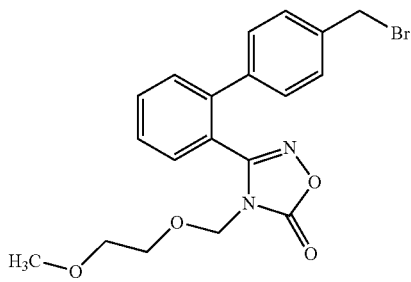 [SMILES: COCCOCn1c(-c2ccccc2-c2ccc(CBr)cc2)noc1=O]

A mixture of 4-[(2-methoxyethoxy)methyl]-3-(4'-methylbiphenyl-2-yl)-1,2,4-oxadiazol-5(4H)-one (46.6 g), N-bromosuccinimide (26.9 g), α,α'-azobisisobutyronitrile (2.2 g) and carbon tetrachloride (500 mL) was stirred at 80° C. for 6 hr. Insoluble material was filtered off, and the solvent was evaporated under reduced pressure. The obtained residue was purified by silica gel column chromatography to give the title compound as colorless oil (30.5 g, 53%).

$^1$H NMR (300 MHz, CDCl$_3$)δ3.27 (3H, s), 3.30-3.33 (2H, m),3.46-3.49 (2H, m), 4.49 (2H, s), 4.54 (2H, s), 7.33-7.43 (4H, m), 7.49-7.69(4H, m)

Reference Example 88

4'-{[3-(2-cyclohexyl-2-oxoethyl)-6-ethyl-2,4-dioxo-3,4-dihydrothieno[2,3-d]pyrimidin-1(2H)-yl]methyl}biphenyl-2-carbonitrile

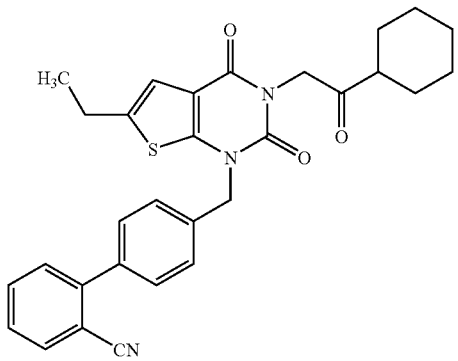 [SMILES: CCc1cc2c(=O)n(CC(=O)C3CCCCC3)c(=O)n(Cc3ccc(-c4ccccc4C#N)cc3)c2s1]

A mixture of 4'-[(6-ethyl-2,4-dioxo-3,4-dihydrothieno[2,3-d]pyrimidin-1(2H)-yl)methyl]biphenyl-2-carbonitrile (1 g), 2-cyclohexyloxirane (0.98 g), potassium carbonate (0.71 g) and N,N-dimethylformamide (13 mL) was stirred at 80° C. for 20 hr. After allowing to cool to room temperature, ethyl acetate and water were added to the reaction mixture, and the mixture was extracted with ethyl acetate. The organic layer was successively washed with water and saturated brine, and dried over anhydrous magnesium sulfate. The solvent was evaporated under reduced pressure. The residue obtained by silica gel column chromatography was dissolved in methylene chloride (8 mL), 4-methylmorpholine-N-oxide (0.34 g), tetrapropylammonium perruthenate (0.026 g) and molecular sieves 4A (0.15 g) were added, and the mixture was stirred at room temperature for 3 hr. The reaction mixture was concentrated under reduced pressure, and silica gel column chromatography gave the title compound as a colorless solid (0.68 g, 52%).

$^1$H NMR (300 MHz, CDCl$_3$)δ1.14-2.11 (13H, m), 2.44-2.62(2H, m), 2.65-2.85 (2H, m), 4.94 (2H, s), 5.19 (2H, s), 7.00 (1H, t, J=1.2),7.36-7.84 (8H, m)

Reference Example 89

4'-{[6-ethyl-3-[2-(4-ethylphenyl)-2-oxoethyl]-2,4-dioxo-3,4-dihydrothieno[2,3-d]pyrimidin-1(2H)-yl]methyl}biphenyl-2-carbonitrile

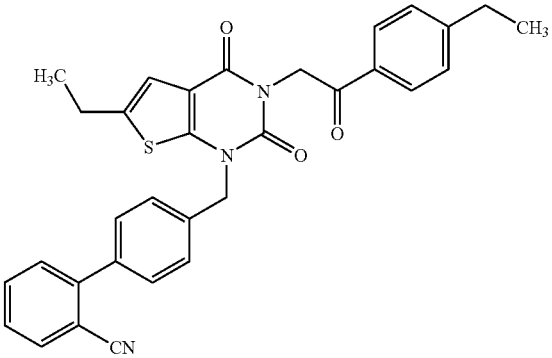 [SMILES: CCc1ccc(C(=O)Cn2c(=O)c3cc(CC)sc3n(Cc3ccc(-c4ccccc4C#N)cc3)c2=O)cc1]

To a mixture of 4'-[(6-ethyl-2,4-dioxo-3,4-dihydrothieno[2,3-d]pyrimidin-1(2H)-yl)methyl]biphenyl-2-carbonitrile (1 g), 2-bromo-1-(4-ethylphenyl)ethanone (0.88 g) and N,N-dimethylformamide (40 mL) was added 60% sodium hydride (0.15 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as colorless crystals (0.87 g, 63%).

$^1$H NMR (300 MHz, CDCl$_3$)δ1.24-1.32 (6H, m), 2.69-2.80 (4H,m), 5.21 (2H, s), 5.50 (2H, s), 7.03 (1H, s), 7.32 (2H, d, J=8.1), 7.42-7.66(7H, m), 7.75 (2H, dd, J=7.5, 1.2), 7.96 (2H, d, J=8.4)

Reference Example 90

4'-{[3-(2,4-dimethoxybenzyl)-2,4-dioxo-6-(2,2,2-trifluoroethyl)-3,4-dihydrothieno[2,3-d]pyrimidin-1(2H)-yl]methyl}-3',5'-difluorobiphenyl-2-carbonitrile

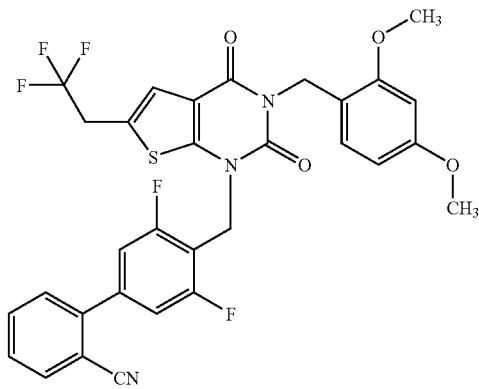 [SMILES: COc1ccc(Cn2c(=O)c3cc(CC(F)(F)F)sc3n(Cc3c(F)cc(-c4ccccc4C#N)cc3F)c2=O)c(OC)c1]

To a solution (70 mL) of methyl 2-amino-5-(2,2,2-trifluoroethyl)thiophene-3-carboxylate (0.71 g) in methylene chloride were added triphosgene (0.36 g) and triethylamine (0.64 mL) was added, and the mixture was stirred at room temperature for 2 hr. To the reaction mixture was added 1-(2,4-dimethoxyphenyl)methanamine (1.35 mL), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in methanol (70 mL), sodium methoxide (0.8 g) was added, and the mixture was stirred at 60° C. for 1 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The obtained residue was dissolved in acetonitrile (50 mL), 4'-(bromomethyl)-3',5'-difluorobiphenyl-2-carbonitrile (1 g) and potassium carbonate (0.83 g) was added, and the mixture was stirred at 50° C. for 2 hr. Insoluble material was filtered off, and the solvent was evaporated under reduced pressure. The obtained residue was purified by silica gel column chromatography to give the title compound as a colorless amorphous solid (1.71 g, 91%).

$^1$H NMR (300 MHz, CDCl$_3$)δ3.51 (2H, q, J=10.2), 3.76 (3H,s), 3.80 (3H, s), 5.21 (2H, s), 5.35 (2H, s), 6.38-6.44 (2H, m), 6.97 (1H, d, J=8.4), 7.11-7.16 (2H, m), 7.37 (1H, d, J=7.8), 7.49-7.54 (2H, m), 7.68 (1H,t, J=7.8), 7.78 (1H, d, J=6.9)

Reference Example 91

4'-{[2,4-dioxo-6-(2,2,2-trifluoroethyl)-3,4-dihydrothieno[2,3-d]pyrimidin-1(2H)-yl]methyl}-3',5'-difluorobiphenyl-2-carbonitrile

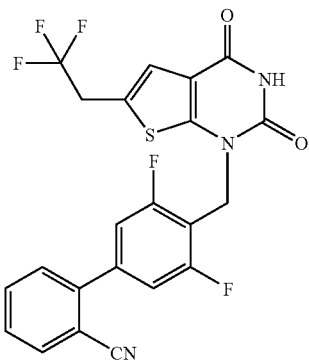 [SMILES: N#Cc1ccccc1-c1cc(F)c(Cn2c(=O)[nH]c(=O)c3cc(CC(F)(F)F)sc32)c(F)c1]

A mixture of 4'-{[3-(2,4-dimethoxybenzyl)-2,4-dioxo-6-(2,2,2-trifluoroethyl)-3,4-dihydrothieno[2,3-d]pyrimidin-1(2H)-yl]methyl}-3',5'-difluorobiphenyl-2-carbonitrile (1.71 g) and trifluoroacetic acid (20 mL) was stirred at 50° C. for 2 hr. To the reaction mixture was added toluene (20 mL), and the mixture was concentrated under reduced pressure. To the obtained residue was added ethyl acetate (20 mL), and the mixture was concentrated under reduced pressure. The precipitated solid was collected by filtration to give the title compound as a colorless solid (1.3 g, 100%).

$^1$H NMR (300 MHz, DMSO-d$_6$)δ3.95 (2H, q, J=10.8), 5.23(2H, s), 7.24 (1H, s), 7.42 (2H, d, J=8.7), 7.59-7.67 (2H, m), 7.80 (1H, t, J=7.5), 7.96 (1H, d, J=10.5), 11.6 (1H, s)

Reference Example 92

3',5'-difluoro-4'-{[3-[2-(4-methoxyphenyl)-2-oxoethyl]-2,4-dioxo-6-(2,2,2-trifluoroethyl)-3,4-dihydrothieno[2,3-d]pyrimidin-1(2H)-yl]methyl}biphenyl-2-carbonitrile

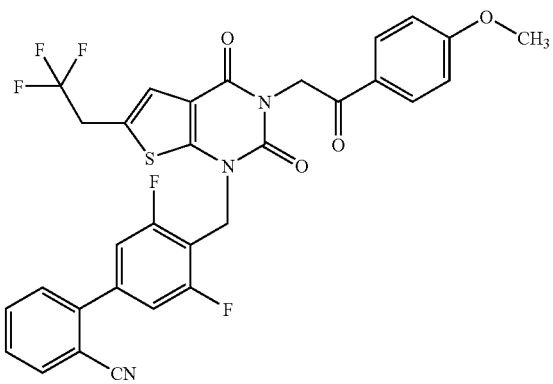 [SMILES: COc1ccc(C(=O)Cn2c(=O)c3cc(CC(F)(F)F)sc3n(Cc3c(F)cc(-c4ccccc4C#N)cc3F)c2=O)cc1]

To a mixture of 4'-{[2,4-dioxo-6-(2,2,2-trifluoroethyl)-3,4-dihydrothieno[2,3-d]pyrimidin-1(2H)-yl]methyl}-3',5'-difluorobiphenyl-2-carbonitrile (0.65 g), 2-bromo-1-(4-methoxyphenyl)ethanone (0.34 g) and N,N-dimethylformamide (15 mL) was added 60% sodium hydride (0.082 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as a colorless solid (0.5 g, 59%).

$^1$H NMR (300 MHz, CDCl$_3$)δ3.52 (2H, q, J=10.1), 3.89 (3H,s), 5.34 (2H, s), 5.46 (2H, s), 6.91-7.01 (2H, m), 7.11-7.20 (2H, m), 7.30 (1H,s), 7.45-7.55 (2H, m), 7.62-7.72 (1H, m), 7.79 (1H, dd, J=7.7, 1.1),7.95-8.05 (2H, m)

Reference Example 93

3',5'-difluoro-4'-{[3-[2-(2-methoxyphenyl)-2-oxoethyl]-2,4-dioxo-6-(2,2,2-trifluoroethyl)-3,4-dihydrothieno[2,3-d]pyrimidin-1(2H)-yl]methyl}biphenyl-2-carbonitrile

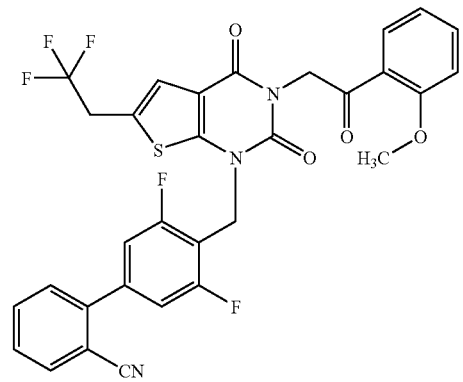 [SMILES: COc1ccccc1C(=O)Cn1c(=O)c2cc(CC(F)(F)F)sc2n(Cc2c(F)cc(-c3ccccc3C#N)cc2F)c1=O]

To a mixture of 4'-{[2,4-dioxo-6-(2,2,2-trifluoroethyl)-3,4-dihydrothieno[2,3-d]pyrimidin-1(2H)-yl]methyl}-3',5'-difluorobiphenyl-2-carbonitrile (0.65 g), 2-bromo-1-(2-methoxyphenyl)ethanone (0.34 g) and N,N-dimethylformamide (15 mL) was added 60% sodium hydride (0.082 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as a colorless solid (0.48 g, 59%).

$^1$H NMR (300 MHz, CDCl$_3$)δ3.51 (2H, q, J=10.2), 3.98 (3H,s), 5.33 (2H, s), 5.43 (2H, s), 6.96-7.05 (2H, m), 7.11-7.19 (2H, m), 7.30 (1H,s), 7.43-7.56 (3H, m), 7.62-7.71 (1H, m), 7.75-7.81 (1H, m), 7.92-7.96 (1H, m)

Reference Example 94

4'-{[3-[2-(2,4-difluorophenyl)-2-oxoethyl]-2,4-dioxo-6-(2,2,2-trifluoroethyl)-3,4-dihydrothieno[2,3-d]pyrimidin-1(2H)-yl]methyl}biphenyl-2-carbonitrile

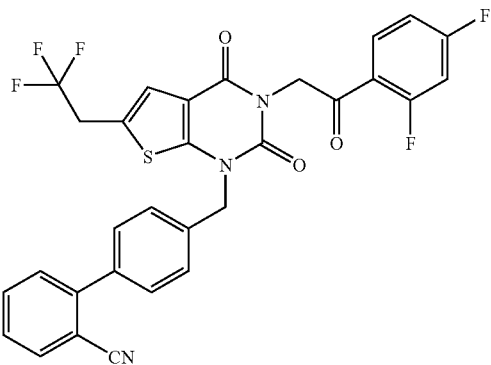 [SMILES: N#Cc1ccccc1-c1ccc(Cn2c(=O)n(CC(=O)c3ccc(F)cc3F)c(=O)c3cc(CC(F)(F)F)sc32)cc1]

To a mixture of 4'-{[2,4-dioxo-6-(2,2,2-trifluoroethyl)-3,4-dihydrothieno[2,3-d]pyrimidin-1(2H)-yl]methyl}biphenyl-2-carbonitrile (1.5 g), 2-bromo-1-(2,4-difluorophenyl)ethanone (0.88 g) and N,N-dimethylformamide (30 mL) was added 60% sodium hydride (0.16 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as a colorless solid (0.98 g, 49%).

$^1$H NMR (300 MHz, CDCl$_3$)δ3.52 (2H, q, J=9.9), 5.24 (2H,s), 5.42 (2H, d, J=4.0), 6.89-7.06 (2H, m), 7.30 (1H, s), 7.41-7.69 (7H, m), 7.77(1H, dd, J=7.7, 0.9), 8.01-8.12 (1H, m)

Reference Example 95

4'-{[6-cyclopropyl-3-[2-(4-fluoro-2-methoxyphenyl)-2-oxoethyl]-2,4-dioxo-3,4-dihydrothieno[2,3-d]pyrimidin-1(2H)-yl]methyl}-3'-fluorobiphenyl-2-carbonitrile

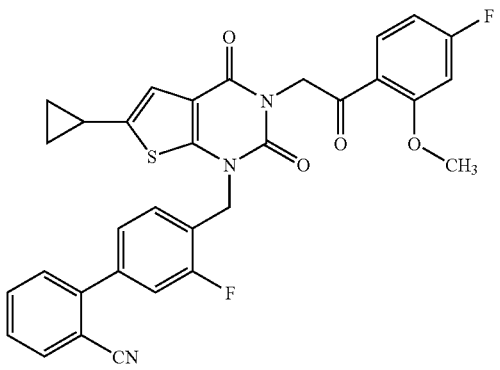 [SMILES: COc1cc(F)ccc1C(=O)Cn1c(=O)c2cc(C3CC3)sc2n(Cc2ccc(-c3ccccc3C#N)cc2F)c1=O]

To a mixture of 4'-[(6-cyclopropyl-2,4-dioxo-3,4-dihydrothieno[2,3-d]pyrimidin-1(2H)-yl)methyl]-3'-fluorobiphenyl-2-carbonitrile (0.32 g), 2-bromo-1-(4-fluoro-2-methoxyphenyl)ethanone (0.25 g) and N,N-dimethylformamide (15 mL) was added 60% sodium hydride (0.046 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as a colorless amorphous solid (0.3 g, 67%).

$^1$H NMR (300 MHz, CDCl$_3$)δ0.67-0.80 (2H, m), 0.95-1.05 (2H,m), 1.87-2.00 (1H, m), 3.98 (3H, s), 5.27 (2H, s), 5.41 (2H, s), 6.67-6.79 (2H,m), 6.99 (1H, s), 7.29-7.53 (5H, m), 7.63-7.71 (1H, m), 7.72-7.82 (1H, m),7.94-8.08 (1H, m)

Reference Example 96

4'-{[6-cyclopropyl-3-[2-(4-fluoro-2-methoxyphenyl)-2-oxoethyl]-2,4-dioxo-3,4-dihydrothieno[2,3-d]pyrimidin-1(2H)-yl]methyl}biphenyl-2-carbonitrile

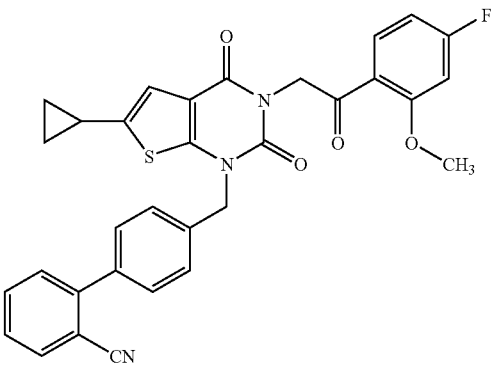 [SMILES: COc1cc(F)ccc1C(=O)Cn1c(=O)c2cc(C3CC3)sc2n(Cc2ccc(-c3ccccc3C#N)cc2)c1=O]

A mixture of 4'-{[6-cyclopropyl-3-(2,4-dimethoxybenzyl)-2,4-dioxo-3,4-dihydrothieno[2,3-d]pyrimidin-1(2H)-yl]methyl}biphenyl-2-carbonitrile (1.2 g) and trifluoroacetic acid (10 mL) was stirred at 50° C. for 2 hr. To the reaction mixture was added toluene (10 mL), and the mixture was concentrated under reduced pressure. The obtained residue was dissolved in N,N-dimethylformamide (30 mL), 2-bromo-1-(4-fluoro-2-methoxyphenyl)ethanone (0.8 g) and sodium hydride (0.15 g) were added, and the mixture was stirred at room temperature for 3 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.94 g, 66%).

$^1$H NMR (300 MHz, CDCl$_3$)δ0.67-0.79 (2H, m), 0.91-1.08 (2H,m), 1.85-2.02 (1H, m), 3.98 (3H, s), 5.19 (2H, s), 5.40 (2H, s), 6.65-6.85 (2H,m), 6.98 (1H, d, J=0.9), 7.38-7.59 (6H, m), 7.60-7.69 (1H, m), 7.76 (1H, dd,J=7.7, 0.9), 7.94-8.06 (1H, m)

Reference Example 97

4'-{[3-(3,3-dimethyl-2-oxobutyl)-6-ethyl-2,4-dioxo-3,4-dihydrothieno[2,3-d]pyrimidin-1(2H)-yl]methyl}biphenyl-2-carbonitrile

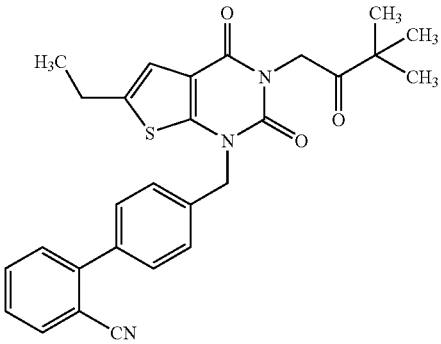 [SMILES: CCc1cc2c(=O)n(CC(=O)C(C)(C)C)c(=O)n(Cc3ccc(-c4ccccc4C#N)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (1.0 g), 1-bromo-3,3-dimethylbutan-2-one (0.52 mL) and N,N-dimethylformamide (8 mL) was added 60% sodium hydride (0.16 g), and the mixture was stirred at room temperature for 24 hr. The reaction mixture was diluted with ethyl acetate, washed with water and saturated brine, and dried over anhydrous magnesium sulfate. The solvent was evaporated under reduced pressure. The obtained residue was purified by silica gel column chromatography to give the title compound as a pale-yellow amorphous solid (0.76 g, 61%).

$^1$H NMR (300 MHz, CDCl$_3$)δ1.21-1.39 (12H, m), 2.63-2.86(2H, m), 5.05 (2H, s), 5.20 (2H, s), 7.00 (1H, s), 7.33-7.99 (8H, m)

Reference Example 98

4'-{[3-[2-(1-adamantyl)-2-oxoethyl]-6-ethyl-2,4-dioxo-3,4-dihydrothieno[2,3-d]pyrimidin-1(2H)-yl]methyl}biphenyl-2-carbonitrile

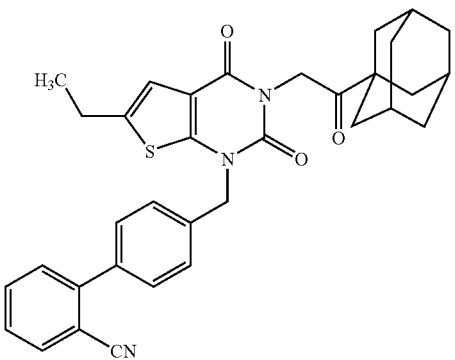 [SMILES: CCc1cc2c(=O)n(CC(=O)C34CC5CC(CC(C5)C3)C4)c(=O)n(Cc3ccc(-c4ccccc4C#N)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (1.0 g), 1-(1-adamantyl)-2-bromoethanone (1.0 g) and N,N-dimethylformamide (8 mL) was added 60% sodium hydride (0.16 g), and the mixture was stirred at room temperature for 24 hr. The reaction mixture was diluted with ethyl acetate, successively washed with water and saturated brine and then saturated brine, and dried over anhydrous magnesium sulfate. The solvent was evaporated under reduced pressure. The obtained residue was purified by silica gel column chromatography to give the title compound as a pale-yellow amorphous solid (0.68 g, 47%).

$^1$H NMR (300 MHz, CDCl$_3$)δ1.28 (3H, t, J=7.5), 1.65-2.21 (15H, m), 2.75 (2H, dq, J=7.5, 0.9), 5.01 (2H, s), 5.19 (2H, s), 7.00 (1H, s), 7.36-7.94 (8H, m)

Reference Example 99

4'-{[6-ethyl-3-[2-(4-hydroxyphenyl)-2-oxoethyl]-2,4-dioxo-3,4-dihydrothieno[2,3-d]pyrimidin-1(2H)-yl]methyl}biphenyl-2-carbonitrile

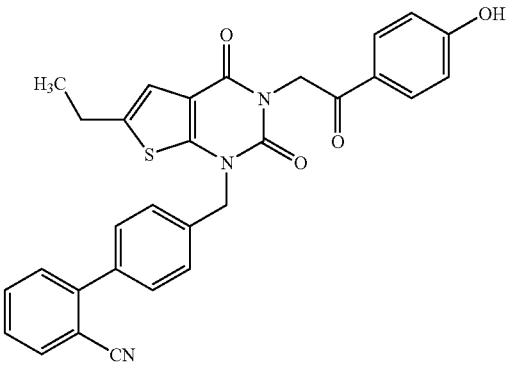 [SMILES: CCc1cc2c(=O)n(CC(=O)c3ccc(O)cc3)c(=O)n(Cc3ccc(-c4ccccc4C#N)cc3)c2s1]

To a solution of 4'-{[6-ethyl-3-[2-(4-methoxyphenyl)-2-oxoethyl]-2,4-dioxo-3,4-dihydrothieno[2,3-d]pyrimidin-1(2H)-yl]methyl}biphenyl-2-carbonitrile (1.0 g) in methylene chloride (6 mL) was added tribromide boron (5.6 mL, 1.0M methylene chloride solution), and the mixture was stirred at room temperature for 24 hr. To the reaction mixture were added ethyl acetate and water, and the mixture was extracted with ethyl acetate. The organic layer was washed with water and saturated brine, and dried over anhydrous magnesium sulfate. The solvent was evaporated under reduced pressure. The obtained residue was purified by silica gel column chromatography to give the title compound as a pale-yellow amorphous solid (0.49 g, 50%).

$^1$H NMR (300 MHz, CDCl$_3$)δ1.29 (3H, t, J=7.5), 2.77 (2H,q, J=7.4), 5.22 (3H, s), 5.43 (1H, s), 7.31-7.90 (11H, m)

Reference Example 100

4'-[(6-cyclopropyl-2,4-dioxo-3,4-dihydrothieno[2,3-d]pyrimidin-1(2H)-yl)methyl]-3',5'-difluorobiphenyl-2-carbonitrile

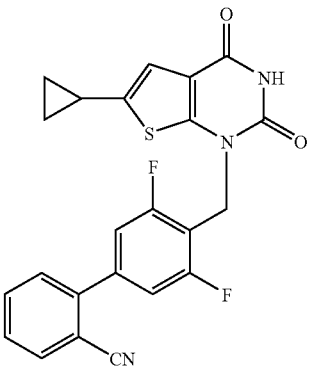 [SMILES: N#Cc1ccccc1-c1cc(F)c(Cn2c(=O)[nH]c(=O)c3cc(C4CC4)sc32)c(F)c1]

A mixture of 6-cyclopropyl-3-(2,4-dimethoxybenzyl)thieno[2,3-d]pyrimidine-2,4(1H,3H)-dione (0.37 g), 4'-(bromomethyl)-3',5'-difluorobiphenyl-2-carbonitrile (0.38 g), potassium carbonate (0.29 g) and acetonitrile (30 mL) was stirred at 50° C. for 2 hr. Insoluble material was filtered off, and the solvent was evaporated under reduced pressure. The obtained residue was dissolved in trifluoroacetic acid (10 mL), and the mixture was stirred at 50° C. for 2 hr. To the reaction mixture was added toluene (10 mL), and the mixture was concentrated under reduced pressure. To the obtained residue was added ethyl acetate (10 mL), and the mixture was concentrated under reduced pressure. The precipitated solid was collected by filtration to give the title compound as a colorless solid (0.42 g, 94%).

$^1$H NMR (300 MHz, DMSO-d$_6$)δ0.65-0.73 (2H, m), 0.90-0.99(2H, m), 1.99-2.11 (1H, m), 5.23 (2H, s), 6.90 (1H, d, J=0.8), 7.44 (2H, d, J=8.7), 7.59-7.73 (2H, m), 7.81 (1H, dd, J=7.6, 1.2), 7.99 (1H, dd, J=7.7,0.9), 11.49 (1H, s)

Reference Example 101

4'-{[3-(2-cyclohexyl-2-oxoethyl)-2,4-dioxo-6-(2,2,2-trifluoroethyl)-3,4-dihydrothieno[2,3-d]pyrimidin-1(2H)-yl]methyl}biphenyl-2-carbonitrile

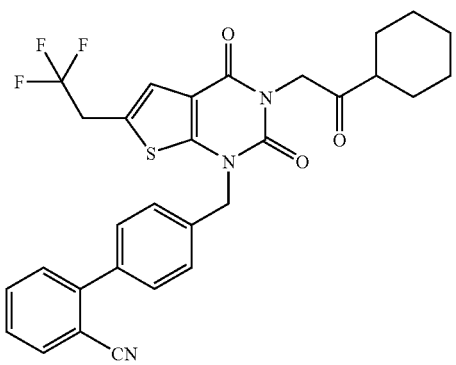 [SMILES: N#Cc1ccccc1-c1ccc(Cn2c(=O)n(CC(=O)C3CCCCC3)c(=O)c3cc(CC(F)(F)F)sc32)cc1]

To a mixture of 4'-{[2,4-dioxo-6-(2,2,2-trifluoroethyl)-3,4-dihydrothieno[2,3-d]pyrimidin-1(2H)-yl]methyl}biphenyl-2-carbonitrile (1.0 g), 2-cyclohexyloxirane (0.98 g) and N,N-dimethylformamide (7 mL) was added potassium carbonate (0.63 g), and the mixture was stirred at 80° C. for 24 hr. To the reaction mixture was added ethyl acetate and water, and the mixture was extracted with ethyl acetate. The organic layer was washed with water and saturated brine, and dried over anhydrous magnesium sulfate. The solvent was evaporated under reduced pressure. A mixture of the obtained residue, tetrapropylammonium perruthenate (0.011 g), 4-methylmorpholine-N-oxide (0.15 g), molecular sieves 4A (0.12 g) and methylene chloride (3 mL) was stirred at room temperature for 24 hr. The reaction mixture was purified by silica gel column chromatography to give the title compound as a pale-yellow amorphous solid (0.29 g, 79%).

$^1$H NMR (300 MHz, CDCl$_3$)δ1.16-2.08 (10H, m), 2.48-2.64(1H, m), 3.50 (2H, q, J=10.1), 4.94 (2H, s), 5.21 (2H, s), 7.40-7.80 (8H, m)

Reference Example 102

4'-{[6-ethyl-2,4-dioxo-3-(2-oxo-2-pyridin-4-ylethyl)-3,4-dihydrothieno[2,3-d]pyrimidin-1(2H)-yl]methyl}biphenyl-2-carbonitrile

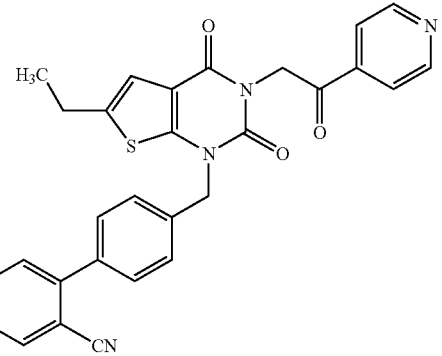

To a mixture of 4'-[(6-ethyl-2,4-dioxo-3,4-dihydrothieno[2,3-d]pyrimidin-1(2H)-yl)methyl]biphenyl-2-carbonitrile (1.0 g), 2-bromo-1-pyridin-4-yl-ethanone hydrogen bromide (1.09 g) and N,N-dimethylformamide (8 mL) was added 60% sodium hydride (0.31 g), and the mixture was stirred at room temperature for 20 hr. After allowing to cool to room temperature, ethyl acetate and water were added to the reaction mixture, and the mixture was extracted with ethyl acetate. The organic layer was successively washed with water and saturated brine, and dried over anhydrous magnesium sulfate. The solvent was evaporated under reduced pressure. The obtained residue was purified by silica gel column chromatography to give the title compound as a pale-yellow amorphous solid (0.20 g, 15%).

$^1$H NMR (300 MHz, CDCl$_3$)δ1.31 (3H, t, J=7.5), 2.78 (2H,dd, J=7.5, 1.1), 5.22 (2H, s), 7.04 (1H, d, J=1.1), 7.33-9.00 (12H, m)

Reference Example 103

4'-{[3-{2-[4-(cyclopropylmethoxy)phenyl]-2-oxoethyl}-6-ethyl-2,4-dioxo-3,4-dihydrothieno[2,3-d]pyrimidin-1(2H)-yl]methyl}biphenyl-2-carbonitrile

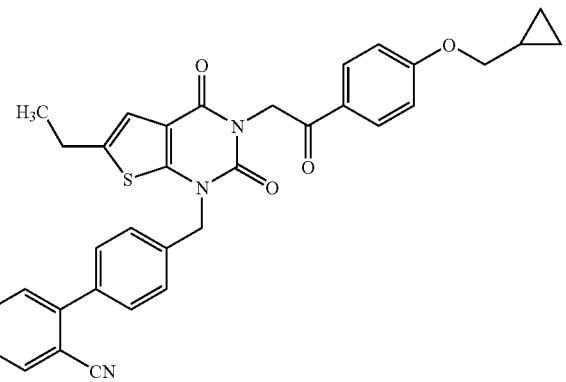

To a mixture of 4'-{[6-ethyl-3-[2-(4-hydroxyphenyl)-2-oxoethyl]-2,4-dioxo-3,4-dihydrothieno[2,3-d]pyrimidin-1(2H)-yl]methyl}biphenyl-2-carbonitrile, (bromomethyl)cyclopropane (0.42 mL) and N,N-dimethylformamide (7 mL) was added cesium carbonate (0.94 g), and the mixture was stirred at 60° C. for 12 hr. After allowing to cool to room temperature, ethyl acetate and water were added to the reaction mixture, and the mixture was extracted with ethyl acetate. The organic layer was successively washed with water and saturated brine, and dried over anhydrous magnesium sulfate. The solvent was evaporated under reduced pressure. The obtained residue was purified by silica gel column chromatography to give the title compound as a pale-yellow amorphous solid (0.61 g, 73%).

¹H NMR (300 MHz, CDCl₃) δ0.34-0.42 (2H, m), 0.62-0.72 (2H,m), 1.24-1.37 (1H, m,), 1.30 (3H, t, J=7.4 Hz), 2.72-2.82 (2H, m), 3.89 (2H,d, J=6.8), 5.22 (2H, s), 5.48 (2H, s), 6.92-8.05 (13H, m)

Reference Example 104

4'-{[3-(2-{4-[2-(dimethylamino)ethoxy]phenyl}-2-oxoethyl)-6-ethyl-2,4-dioxo-3,4-dihydrothieno[2,3-d]pyrimidin-1(2H)-yl]methyl}biphenyl-2-carbonitrile

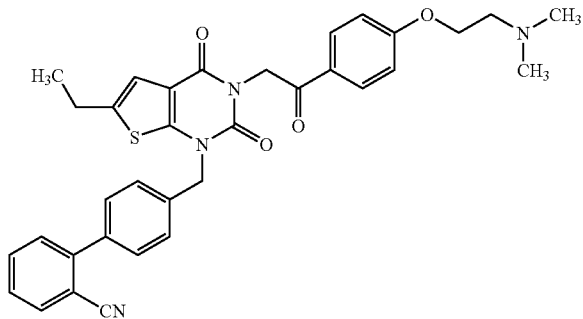 [SMILES: CCc1cc2c(=O)n(CC(=O)c3ccc(OCCN(C)C)cc3)c(=O)n(Cc3ccc(-c4ccccc4C#N)cc3)c2s1]

To a mixture of 4'-{[6-ethyl-3-[2-(4-hydroxyphenyl)-2-oxoethyl]-2,4-dioxo-3,4-dihydrothieno[2,3-d]pyrimidin-1(2H)-yl]methyl}biphenyl-2-carbonitrile, 2-chloro-N,N-dimethylethanamine hydrochloride (0.62 g) and N,N-dimethylformamide (7 mL) was added cesium carbonate (2.8 g), and the mixture was stirred at 60° C. for 12 hr. After allowing to cool to room temperature, ethyl acetate and water were added to the reaction mixture, and the mixture was extracted with ethyl acetate. The organic layer was successively washed with water and saturated brine, and dried over anhydrous magnesium sulfate. The solvent was evaporated under reduced pressure. The obtained residue was purified by silica gel column chromatography to give the title compound as a pale-yellow amorphous solid (0.41 g, 48%).

¹H NMR (300 MHz, CDCl₃) δ1.30 (3H, t, J=7.5), 2.35 (6H,s), 2.68-2.84 (4H, m), 4.09-4.20 (2H, m), 5.22 (2H, s), 5.48 (2H, s), 6.90-8.23(13H, m)

Reference Example 105

4'-{[6-ethyl-3-[2-(1-methyl-1H-benzoimidazol-2-yl)-2-oxoethyl]-2,4-dioxo-3,4-dihydrothieno[2,3-d]pyrimidin-1(2H)-yl]methyl}biphenyl-2-carbonitrile

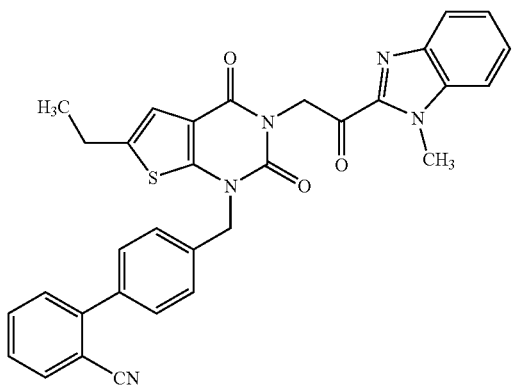 [SMILES: CCc1cc2c(=O)n(CC(=O)c3nc4ccccc4n3C)c(=O)n(Cc3ccc(-c4ccccc4C#N)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (1.0 g), 2-bromo-1-(1-methyl-1H-benzoimidazol-2-yl)ethanone (1.0 g) and N,N-dimethylformamide (10 mL) was added 60% sodium hydride (0.16 g), and the mixture was stirred at 50° C. for 24 hr. After allowing to cool to room temperature, ethyl acetate and water were added to the reaction mixture, and the mixture was extracted with ethyl acetate. The organic layer was successively washed with water and saturated brine, and dried over anhydrous magnesium sulfate. The solvent was evaporated under reduced pressure. The obtained residue was purified by silica gel column chromatography to give the title compound as a pale-yellow amorphous solid (0.28 g, 19%).

¹H NMR (300 MHz, CDCl₃) δ1.30 (3H, t, J=7.4), 2.77 (2H,dq, J=7.5, 1.1), 4.15 (3H, s), 5.23 (2H, s), 5.85 (2H, s), 7.05 (1H, s),7.33-7.96 (12H, m)

Reference Example 106

4'-{[3-(3,3-dimethyl-2-oxobutyl)-6-ethyl-2,4-dioxo-3,4-dihydrothieno[2,3-d]pyrimidin-1(2H)-yl]methyl}biphenyl-2-carbonitrile

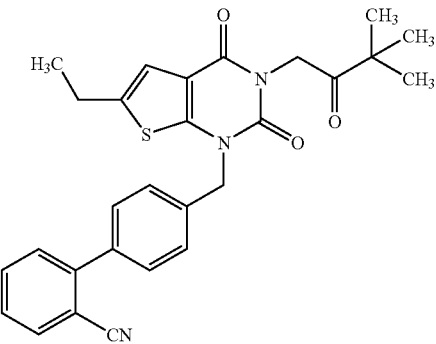 [SMILES: CCc1cc2c(=O)n(CC(=O)C(C)(C)C)c(=O)n(Cc3ccc(-c4ccccc4C#N)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (1.0 g), 1-bromo-3,3-dimethylbutan-2-one (0.52 mL) and N,N-dimethylformamide (8 mL) was added 60% sodium hydride (0.16 g), and the mixture was stirred at room temperature for 24 hr. To the reaction mixture was added ethyl acetate and water, and the mixture was extracted with ethyl acetate. The organic layer was successively washed with water and saturated brine, and dried over anhydrous magnesium sulfate. The solvent was evaporated under reduced pressure. The obtained residue was purified by silica gel column chromatography to give the title compound as a pale-yellow amorphous solid (0.76 g, 61%).

¹H NMR (300 MHz, CDCl₃) δ1.21-1.39 (12H, m), 2.63-2.86(2H, m), 5.05 (2H, s), 5.20 (2H, s), 7.00 (1H, s), 7.33-7.99 (8H, m)

Reference Example 107

3'-fluoro-4'-{[3-[2-(4-methoxyphenyl)-2-oxoethyl]-2,4-dioxo-6-propoxy-3,4-dihydropyrimidin-1(2H)-yl]methyl}biphenyl-2-carbonitrile

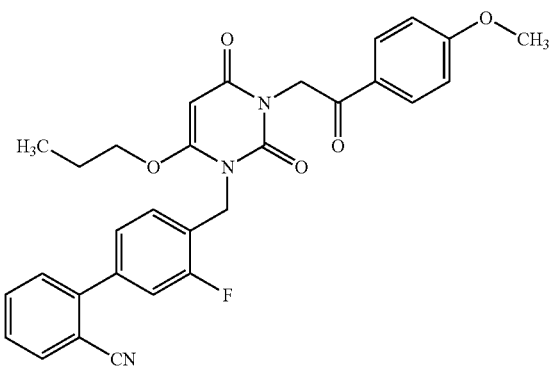 [SMILES: CCCOc1cc(=O)n(CC(=O)c2ccc(OC)cc2)c(=O)n1Cc1ccc(-c2ccccc2C#N)cc1F]

To a mixture of 4'-[(2,4-dioxo-6-propoxy-3,4-dihydropyrimidin-1(2H)-yl)methyl]-3'-fluorobiphenyl-2-carbonitrile (0.55 g), 2-bromo-1-(4-methoxyphenyl)ethanone (0.4 g) and N,N-dimethylformamide (25 mL) was added 60% sodium hydride (0.087 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as a colorless amorphous solid (0.45 g, 59%).

$^1$H NMR (300 MHz, CDCl$_3$)δ0.93 (3H, t, J=7.4), 1.79 (2H,q, J=6.6), 3.88 (3H, s), 3.99 (2H, t, J=6.4), 5.20 (1H, s), 5.26 (2H, s),5.39 (2H, s), 6.88-7.01 (2H, m), 7.22-7.51 (5H, m), 7.61-7.72 (1H, m), 7.77(1H, dd, J=8.1, 1.3), 7.97-8.07 (2H, m)

Reference Example 108

4'-{[6-ethyl-3-[(3-methyloxetan-3-yl)methyl]-2,4-dioxo-3,4-dihydrothieno[2,3-d]pyrimidin-1(2H)-yl]methyl}biphenyl-2-carbonitrile

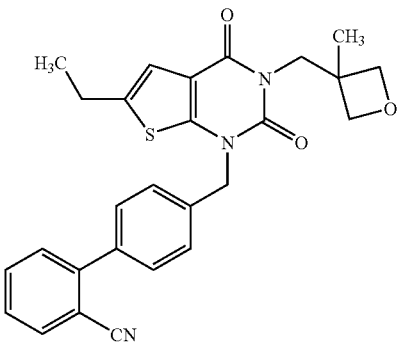 [SMILES: CCc1cc2c(=O)n(CC3(C)COC3)c(=O)n(Cc3ccc(-c4ccccc4C#N)cc3)c2s1]

A mixture of 4'-[(6-ethyl-2,4-dioxo-3,4-dihydrothieno[2,3-d]pyrimidin-1(2H)-yl)methyl]biphenyl-2-carbonitrile (1 g), 1,1'-(azodicarbonyl)dipiperidine (1.3 g), tributylphosphine (1.6 mL), (3-methyloxetan-3-yl)methanol (0.29 g) and tetrahydrofuran (30 mL) was stirred at room temperature for 3 hr. The reaction mixture was extracted with water and ethyl acetate. The ethyl acetate layer was washed with saturated brine, and dried over anhydrous magnesium sulfate. The solvent was evaporated under reduced pressure. The obtained residue was purified by silica gel column chromatography to give the title compound as a colorless amorphous solid (0.68 g, 56%).

$^1$H NMR (300 MHz, CDCl$_3$)δ1.30 (3H, t, J=7.5), 1.41 (3H,s), 2.71-2.82 (6H, m), 4.20 (2H, s), 4.27 (2H, d, J=6.6), 4.77 (2H, d, J=6.2), 5.20 (2H, s), 7.02 (1H, t, J=1.2), 7.40-7.60 (6H, m), 7.59-7.69 (1H,m), 7.77 (1H, dd, J=7.7, 0.9)

Reference Example 109

4'-{[6-ethyl-3-[(4-hydroxytetrahydro-2H-pyran-4-yl)methyl]-2,4-dioxo-3,4-dihydrothieno[2,3-d]pyrimidin-1(2H)-yl]methyl}biphenyl-2-carbonitrile

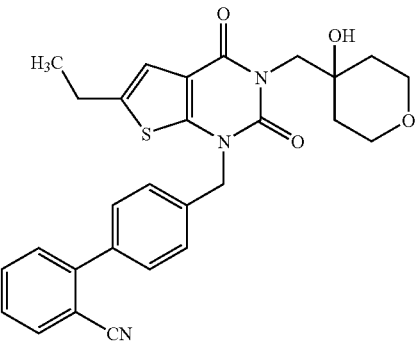 [SMILES: CCc1cc2c(=O)n(CC3(O)CCOCC3)c(=O)n(Cc3ccc(-c4ccccc4C#N)cc3)c2s1]

To a mixture of tetrahydro-4H-pyran-4-one (1.2 g), diiodomethane (1.45 mL) and tetrahydrofuran (40 mL) was added methyllithium (2.1M diethyl ether solution, 11.4 mL) at 0° C., and the mixture was stirred at room temperature for 4 hr. The reaction mixture was extracted with diethyl ether and saturated aqueous ammonium chloride solution. The diethyl ether layer was washed with saturated brine, and dried over anhydrous magnesium sulfate. The solvent was evaporated under reduced pressure. The obtained residue was dissolved in N,N-dimethylformamide (15 mL), 4'-[(6-ethyl-2,4-dioxo-3,4-dihydrothieno[2,3-d]pyrimidin-1(2H)-yl)methyl]biphenyl-2-carbonitrile (1.5 g) and potassium carbonate (1.07 g) was added, and the mixture was stirred at 80° C. for 16 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as a colorless amorphous solid (0.16 g, 8%).

$^1$H NMR (300 MHz, CDCl$_3$)δ1.30 (3H, t, J=7.5), 1.50-1.56 (2H, m), 1.77-1.87 (2H, m), 1.77 (2H, q, J=7.8), 3.77-3.81 (2H, m), 4.26 (2H,s), 5.20 (2H, s), 7.02 (1H, s), 7.43-7.57 (6H, m), 7.64 (1H, t, J=7.5), 7.75(1H, d, J=7.8)

Reference Example 110

4'-{[3-(4-{[tert-butyl(dimethyl)silyl]oxy}-2-hydroxy-3,3-dimethylbutyl)-6-ethyl-2,4-dioxo-3,4-dihydrothieno[2,3-d]pyrimidin-1(2H)-yl]methyl}biphenyl-2-carbonitrile

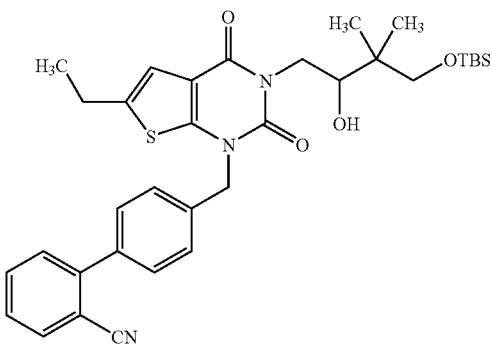 [SMILES: CCc1cc2c(=O)n(CC(O)C(C)(C)CO[Si](C)(C)C(C)(C)C)c(=O)n(Cc3ccc(-c4ccccc4C#N)cc3)c2s1]

A mixture of 4'-[(6-ethyl-2,4-dioxo-3,4-dihydrothieno[2,3-d]pyrimidin-1(2H)-yl)methyl]biphenyl-2-carbonitrile (2.0 g), tert-butyl(dimethyl) (2-methyl-2-oxirane-2-ylpropoxy)silane (3.75 g), potassium carbonate (1.38 g) and N,N-dimethylformamide (15 mL) was stirred at 80° C. for 24 hr. After allowing to cool to room temperature, ethyl acetate and water were added to the reaction mixture, and the mixture was extracted with ethyl acetate. The organic layer was successively washed with water and saturated brine, and dried over anhydrous magnesium sulfate. The solvent was evaporated under reduced pressure. The obtained residue was purified by silica gel column chromatography to give the title compound as a pale-yellow amorphous solid (1.36 g, 43%).

$^1$H NMR (300 MHz, CDCl$_3$)δ0.08 (6H, s), 0.90 (9H, s), 1.02(6H, s), 1.28 (3H, t, J=7.4), 2.75 (2H, dq, J=1.0, 7.5), 3.37 (1H, d, J=5.8), 3.48-3.59 (2H, m), 3.77-3.87 (1H, m), 4.17-4.25 (1H, m), 4.30-4.43 (1H,m), 5.10-5.28 (2H, m), 7.01 (2H, s), 7.39-7.80 (8H, m)

Reference Example 111

4'-{[3-(3,3-dimethyl-2-oxo-4-{[(1,1,2,2-tetramethylpropyl)silyl]oxy}butyl)-6-ethyl-2,4-dioxo-3,4-dihydrothieno[2,3-d]pyrimidin-1(2H)-yl]methyl}biphenyl-2-carbonitrile

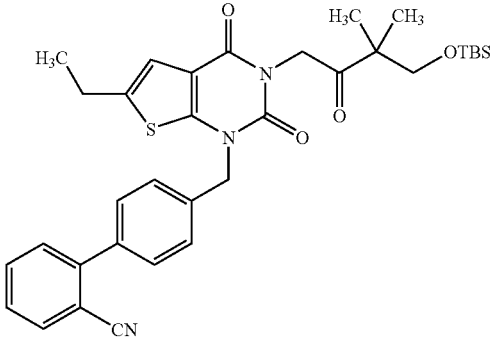 [SMILES: CCc1cc2c(=O)n(CC(=O)C(C)(C)CO[Si](C)(C)C(C)(C)C)c(=O)n(Cc3ccc(-c4ccccc4C#N)cc3)c2s1]

A mixture of 4'-{[3-(4-{[tert-butyl(dimethyl)silyl]oxy}-2-hydroxy-3,3-dimethylbutyl)-6-ethyl-2,4-dioxo-3,4-dihydrothieno[2,3-d]pyrimidin-1(2H)-yl]methyl}biphenyl-2-carbonitrile (1.0 g), tetrapropylammonium perruthenate (0.056 g), 4-methylmorpholine-N-oxide (0.38 g), molecular sieves 4A (0.32 g) and methylene chloride (8 mL) was stirred at room temperature for 12 hr. The reaction mixture was purified by silica gel column chromatography to give the title compound as a pale-yellow amorphous solid (0.92 g, 92%).

$^1$H NMR (300 MHz, CDCl$_3$)δ0.09 (6H, s), 0.93 (9H, s), 1.25(6H, s), 1.28 (3H, t, J=7.4), 2.68-2.80 (2H, m), 3.68 (2H, s), 5.08 (2H, s),5.19 (2H, s), 7.00 (1H, s), 7.38-7.82 (8H, m)

Reference Example 112

4'-{[6-ethyl-3-(2-hydroxy-3,3-dimethylbutyl)-2,4-dioxo-3,4-dihydrothieno[2,3-d]pyrimidin-1(2H)-yl]methyl}biphenyl-2-carbonitrile

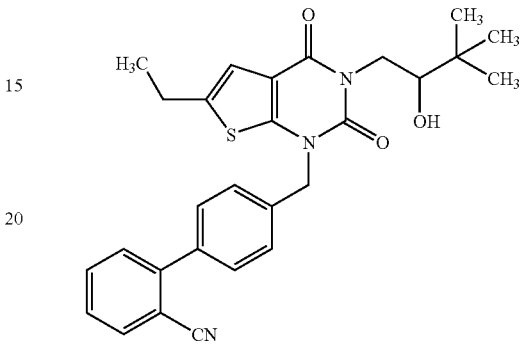

A mixture of 4'-[(6-ethyl-2,4-dioxo-3,4-dihydrothieno[2,3-d]pyrimidin-1(2H)-yl)methyl]biphenyl-2-carbonitrile (1.0 g), 2-tert-butyloxirane (0.78 g), potassium carbonate (1.1 g) and N,N-dimethylformamide (10 mL) was stirred at 80° C. for 20 hr. After allowing to cool to room temperature, ethyl acetate and water were added to the reaction mixture, and the mixture was extracted with ethyl acetate. The organic layer was successively washed with water and saturated brine, and dried over anhydrous magnesium sulfate. The solvent was evaporated under reduced pressure. The obtained residue was purified by silica gel column chromatography to give the title compound as a pale-yellow amorphous solid (0.63 g, 50%).

$^1$H NMR (300 MHz, CDCl$_3$)δ1.04 (9H, s), 1.30 (3H, t, J=7.4), 2.77 (2H, dq, J=7.5, 1.0), 2.87 (1H, d, J=6.4), 3.57 (1H, ddd, J=9.8, 6.5, 2.2), 4.12 (1H, dd, J=13.8, 10.0), 4.38 (1H, dd, J=13.7, 2.2),5.11-5.29 (2H, m), 7.01 (1H, t, J=1.1), 7.41-7.81 (8H, m)

Reference Example 113

4'-{[3-[2-(5-chloro-2-thienyl)-2-oxoethyl]-6-ethyl-2,4-dioxo-3,4-dihydrothieno[2,3-d]pyrimidin-1(2H)-yl]methyl}biphenyl-2-carbonitrile

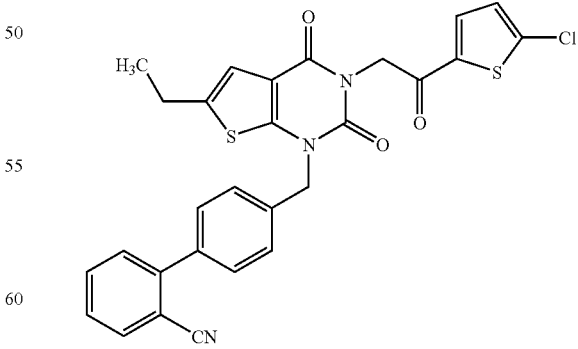

To a mixture of 4'-[(6-ethyl-2,4-dioxo-3,4-dihydrothieno[2,3-d]pyrimidin-1(2H)-yl)methyl]biphenyl-2-carbonitrile (1 g), 2-bromo-1-(5-chloro-2-thienyl)ethanone (0.74 g) and N,N-dimethylformamide (15 mL) was added 60% sodium hydride (0.15 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as a colorless amorphous solid (0.79 g, 56%).

$^1$H NMR (300 MHz, CDCl$_3$)δ1.29 (3H, t, J=7.5), 2.77 (2H,q, J=7.5), 5.21 (2H, s), 5.38 (2H, s), 6.97-7.05 (2H, m), 7.40-7.59 (6H, m),7.61-7.69 (2H, m), 7.76 (1H, d, J=7.7)

Reference Example 114

3-[2-(4-methoxyphenyl)-2-oxoethyl]-6-methylthieno[2,3-d]pyrimidine-2,4(1H,3H)-dione

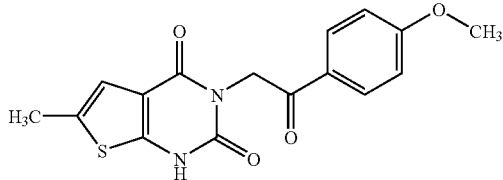

To a solution (100 mL) of methyl 2-amino-5-methylthiophene-3-carboxylate (2 g) in methylene chloride were added triphosgene (1.5 g) and triethylamine (4.24 mL), and the mixture was stirred at room temperature for 2 hr. To the reaction mixture were further added triethylamine (1.8 mL) and 2-amino-1-(4-methoxyphenyl)ethanone hydrochloride (2.6 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (100 mL), sodium methoxide (3.16 g) was added, and the mixture was stirred at 60° C. for 2 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The precipitated solid was collected by filtration to give the title compound as a colorless solid (2.94 g, 76%).

$^1$H NMR (300 MHz, DMSO-d$_6$)δ1.23 (3H, t, J=7.5), 2.77 (2H, q, J=7.5), 3.87 (3H, s), 5.30 (2H, s), 6.91 (1H, s), 7.10 (2H, d, J=8.7), 8.06 (2H, d, J=8.7), 12.32 (1H, br)

Reference Example 115

4'-{[6-cyclopropyl-3-(3,3-dimethyl-2-oxobutyl)-2,4-dioxo-3,4-dihydrothieno[2,3-d]pyrimidin-1(2H)-yl]methyl}biphenyl-2-carbonitrile

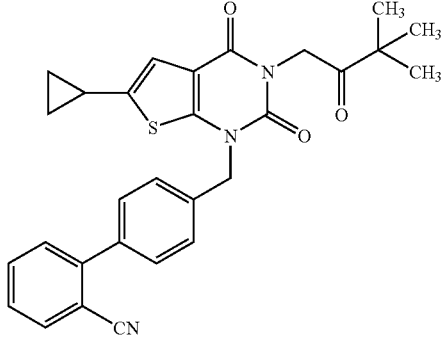 [SMILES: CC(C)(C)C(=O)Cn1c(=O)c2cc(C3CC3)sc2n(Cc2ccc(-c3ccccc3C#N)cc2)c1=O]

A mixture of 4'-{[6-cyclopropyl-3-(2,4-dimethoxybenzyl)-2,4-dioxo-3,4-dihydrothieno[2,3-d]pyrimidin-1(2H)-yl]methyl}biphenyl-2-carbonitrile (1.0 g) and trifluoroacetic acid (5.3 mL) was stirred at 50° C. for 2 hr. To the reaction mixture was added toluene (30 mL), and the mixture was concentrated under reduced pressure. The obtained residue was dissolved in N,N-dimethylformamide (10 mL), 1-bromo-3,3-dimethylbutan-2-one (0.52 mL) and sodium hydride (0.16 g) were added, and the mixture was stirred at room temperature for 5 hr. To the reaction mixture were added ethyl acetate and water, and the mixture was extracted with ethyl acetate. The organic layer was successively washed with water and saturated brine, and dried over anhydrous magnesium sulfate. The solvent was evaporated under reduced pressure. The obtained residue was purified by silica gel column chromatography to give the title compound as a colorless amorphous solid (0.76 g, 86%).

$^1$H NMR (300 MHz, CDCl$_3$)δ0.68-0.75 (2H, m), 0.93-1.01 (2H,m), 1.29 (9H, s), 1.88-1.99 (1H, m), 5.04 (2H, s), 5.18 (2H, s), 6.91-6.96 (1H,m), 7.39-7.81 (8H, m)

Reference Example 116

4'-{[6-cyclopropyl-3-(2-hydroxy-3,3-dimethylbutyl)-2,4-dioxo-3,4-dihydrothieno[2,3-d]pyrimidin-1(2H)-yl]methyl}biphenyl-2-carbonitrile

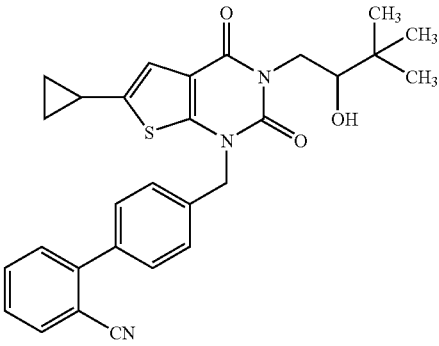 [SMILES: CC(C)(C)C(O)Cn1c(=O)c2cc(C3CC3)sc2n(Cc2ccc(-c3ccccc3C#N)cc2)c1=O]

A mixture of 4'-{[6-cyclopropyl-3-(2,4-dimethoxybenzyl)-2,4-dioxo-3,4-dihydrothieno[2,3-d]pyrimidin-1(2H)-yl]methyl}biphenyl-2-carbonitrile (1.0 g) and trifluoroacetic acid (5.3 mL) was stirred at 50° C. for 2 hr. To the reaction mixture was added toluene (30 mL), and the mixture was concentrated under reduced pressure. The obtained residue was dissolved in N,N-dimethylformamide (10 mL), 2-tert-butyloxirane (0.78 g) and potassium carbonate (1.1 g) was added, and the mixture was stirred at 80° C. for 15 hr. After allowing to cool to room temperature, ethyl acetate and water were added to the reaction mixture, and the mixture was extracted with ethyl acetate. The organic layer was successively washed with water and saturated brine, and dried over anhydrous magnesium sulfate. The solvent was evaporated under reduced pressure. The obtained residue was purified by silica gel column chromatography to give the title compound as a pale-yellow amorphous solid (0.46 g, 50%).

$^1$H NMR (300 MHz, CDCl$_3$)δ0.69-0.77 (2H, m), 0.94-1.01 (2H,m), 1.04 (9H, s), 1.89-2.00 (1H, m), 2.85 (1H, d, J=6.4), 3.51-3.60 (1H, m),4.11 (2H, dd, J=13.6, 10.0), 4.37 (2H, dd, J=13.7, 2.2), 5.08-5.30 (2H, m),6.91-6.99 (1H, m), 7.40-7.81 (8H, m)

Reference Example 117

4'-{[6-ethyl-3-[2-(3-fluoro-4-methoxyphenyl)-2-oxoethyl]-2,4-dioxo-3,4-dihydrothieno[2,3-d]pyrimidin-1(2H)-yl]methyl}-3'-fluorobiphenyl-2-carbonitrile

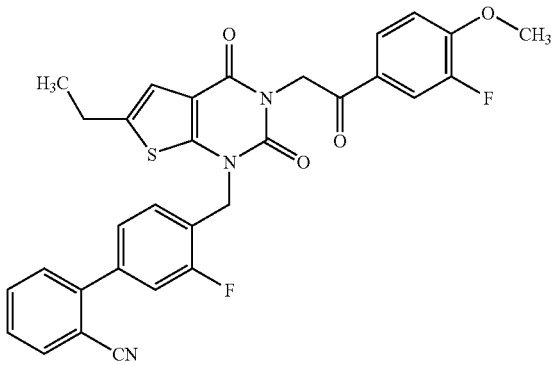 [SMILES: CCc1cc2c(=O)n(CC(=O)c3ccc(OC)c(F)c3)c(=O)n(Cc3ccc(-c4ccccc4C#N)cc3F)c2s1]

To a mixture of 4'-[(6-ethyl-2,4-dioxo-3,4-dihydrothieno[2,3-d]pyrimidin-1(2H)-yl)methyl]-3'-fluorobiphenyl-2-carbonitrile (1 g), 2-bromo-1-(3-fluoro-4-methoxyphenyl)ethanone (0.67 g) and N,N-dimethylformamide (10 mL) was added 60% sodium hydride (0.15 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The precipitated solid was collected by filtration to give the title compound as colorless crystals (0.9 g, 64%).

$^1$H NMR (300 MHz, CDCl$_3$)δ1.26-1.33 (3H, m), 2.77 (2H, qd, J=7.5, 1.1), 3.98 (3H, s), 5.29 (2H, s), 5.46 (2H, s), 6.99-7.08 (2H, m), 7.30-7.34 (1H, m), 7.35 (1H, s), 7.39-7.52 (3H, m), 7.66 (1H, td, J=7.7, 1.3), 7.74-7.86 (3H, m)

Reference Example 118

3-(2,4-dimethoxybenzyl)-6-propylthieno[2,3-d]pyrimidine-2,4(1H,3H)-dione

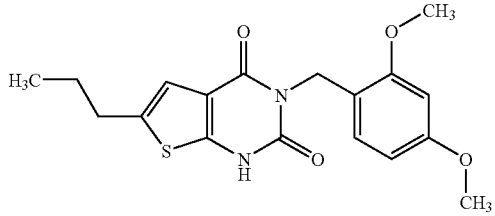 [SMILES: CCCc1cc2c(=O)n(Cc3ccc(OC)cc3OC)c(=O)[nH]c2s1]

To a solution (800 mL) of methyl 2-amino-5-propylthiophene-3-carboxylate (2 g) in methylene chloride were added triphosgene (1.27 g) and triethylamine (3.6 mL), and the mixture was stirred at room temperature for 2 hr. To the reaction mixture was added 1-(2,4-dimethoxyphenyl)methanamine (1.95 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (100 mL), sodium methoxide (2.7 g) was added, and the mixture was stirred at 60° C. for 2 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The precipitated solid was collected by filtration to give the title compound as a colorless solid (2.7 g, 75%)

$^1$H NMR (300 MHz, DMSO-d$_6$)δ0.92 (3H, t, J=7.3),1.52-1.70 (2H, m), 2.71 (2H, t, J=7.2), 3.71 (3H, s), 3.81 (3H, s), 4.90 (2H,s), 6.39 (1H, dd, J=8.5, 2.4), 6.56 (1H, d, J=2.4), 6.65 (1H, d, J=8.5),6.89 (1H, s), 12.20 (1H, s)

Reference Example 119

4'-[(2,4-dioxo-6-propyl-3,4-dihydrothieno[2,3-d]pyrimidin-1(2H)-yl)methyl]-3'-fluorobiphenyl-2-carbonitrile

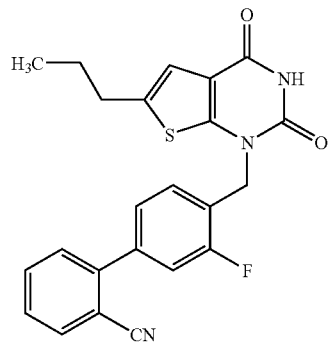 [SMILES: CCCc1cc2c(=O)[nH]c(=O)n(Cc3ccc(-c4ccccc4C#N)cc3F)c2s1]

A mixture of 3-(2,4-dimethoxybenzyl)-6-propylthieno[2,3-d]pyrimidine-2,4(1H,3H)-dione (2.7 g), 4'-(bromomethyl)-3'-fluorobiphenyl-2-carbonitrile (2.6 g), potassium carbonate (2.1 g) and acetonitrile (100 mL) was stirred at 50° C. for 2 hr. Insoluble material was filtered off, and the solvent was evaporated under reduced pressure. The obtained residue was dissolved in trifluoroacetic acid (50 mL), and the mixture was stirred at 50° C. for 2 hr. To the reaction mixture was added toluene (50 mL), and the mixture was concentrated under reduced pressure. To the obtained residue was added ethyl acetate (50 mL), and the mixture was concentrated under reduced pressure. The precipitated solid was collected by filtration to give the title compound as a colorless solid (2 g, 64%).

$^1$H NMR (300 MHz, DMSO-d$_6$)δ0.79-0.97 (3H, m), 1.44-1.67(2H, m), 2.59-2.82 (2H, m), 5.20 (2H, s), 6.97 (1H, s), 7.35-7.45 (2H, m),7.49-7.71 (3H, m), 7.69-7.85 (1H, m), 7.97 (1H, d, J=7.7), 11.57 (1H, s)

Reference Example 120 ethyl 5-amino-2-ethyl-1,3-thiazole-4-carboxylate

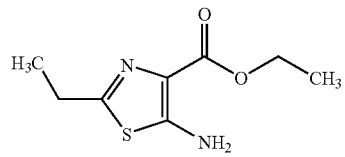

A mixture of ethyl 3-nitrilo-N-propionylalaninate (10 g), 2,4-bis(4-methoxyphenyl)-1,3,2,4-dithiadiphosphetane 2,4-disulfide (24.1 g) and tetrahydrofuran (150 mL) was stirred at 70° C. for 16 hr. The reaction mixture was concentrated under reduced pressure, and the obtained residue was extracted with ethyl acetate and saturated aqueous sodium hydrogencarbonate solution. The ethyl acetate layer was washed with saturated brine, and dried over anhydrous magnesium sulfate. The solvent was evaporated under reduced pressure. After purification by silica gel column chromatography, the obtained residue was recrystallized from ethyl acetate-hexane to give the title compound as colorless crystals (3.8 g, 38%).

$^1$H NMR (300 MHz, CDCl$_3$)δ1.29 (3H, t, J=7.5), 1.37 (3H,t, J=7.2), 2.86 (2H, q, J=7.5), 4.37 (2H, q, J=7.2), 5.91 (2H, br)

Reference Example 121

2-ethyl-6-(2-phenylethyl)[1,3]thiazolo[5,4-d]pyrimidine-5,7(4H,6H)-dione

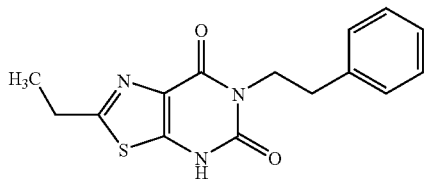 [SMILES: CCc1nc2c(=O)n(CCc3ccccc3)c(=O)[nH]c2s1]

To a solution (30 mL) of ethyl 5-amino-2-ethyl-1,3-thiazole-4-carboxylate (0.5 g) in methylene chloride were added triphosgene (0.32 g) and triethylamine (0.23 mL), and the mixture was stirred at room temperature for 2 hr. To the reaction mixture was added 2-phenylethanamine (0.95 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in ethanol (40 mL), sodium ethoxide (20% ethanol solution, 2.2 g) was added, and the mixture was stirred at 80° C. for 2 hr. The reaction mixture was concentrated under reduced pressure, and the obtained residue was extracted with 1N hydrochloric acid and ethyl acetate. The ethyl acetate layer was washed with saturated brine, and dried over anhydrous magnesium sulfate. The solvent was evaporated under reduced pressure. The precipitated solid was collected by filtration to give the title compound as a colorless solid (0.48 g, 64%).

$^1$H NMR (300 MHz, CDCl$_3$)δ1.40 (3H, t, J=7.8), 3.02 (4H,m), 4.28 (2H, m), 7.20-7.32 (5H, m), 11.2 (1H, br)

Reference Example 122

4'-[(6-ethyl-2,4-dioxo-2H-thieno[2,3-d][1,3]oxazine-1(4H)-yl)methyl]biphenyl-2-carbonitrile

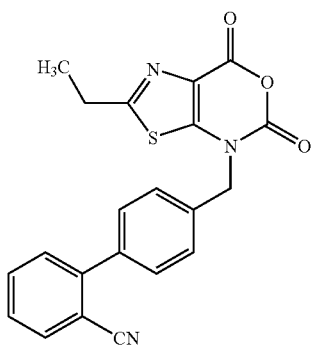 [SMILES: CCc1nc2c(=O)oc(=O)n(Cc3ccc(-c4ccccc4C#N)cc3)c2s1]

A mixture of methyl 2-amino-5-ethylthiophene-3-carboxylate (4.33 g), 2N aqueous sodium hydroxide solution (45 mL) and ethanol (80 mL) was stirred at 80° C. for 2 hr. The reaction mixture was concentrated under reduced pressure, adjusted to pH 7 with water and 1N hydrochloric acid, and the mixture was extracted with ethyl acetate. The ethyl acetate layer was washed with saturated brine, and dried over anhydrous magnesium sulfate. The solvent was evaporated under reduced pressure. The obtained residue was dissolved in 1,4-dioxane, triphosgene (6 g) was added, and the mixture was stirred at 100° C. for 16 hr. The reaction mixture was concentrated under reduced pressure, and extracted with water and ethyl acetate. The obtained ethyl acetate layer was washed with saturated brine, and dried over anhydrous magnesium sulfate. The solvent was evaporated under reduced pressure. The precipitated solid was dissolved in acetonitrile (100 mL), 4'-(bromomethyl)biphenyl-2-carbonitrile (4.9 g) and potassium carbonate (2.5 g) was added, and the mixture was stirred at 50° C. for 2 hr. Insoluble material was filtered off, and the solvent was evaporated under reduced pressure. The obtained residue was purified by silica gel column chromatography to give the title compound as colorless crystals (3.7 g, 41%).

$^1$H NMR (300 MHz, CDCl$_3$)δ1.30 (3H, t, J=7.4), 2.64-2.90 (2H, m), 5.14 (2H, s), 6.91-7.02 (1H, m), 7.41-7.70 (7H, m), 7.77 (1H, d, J=7.7)

Reference Example 123

4'-[(5-ethyl-2-oxo-1,2-dihydro-3H-thieno[2,3-d]imidazol-3-yl)methyl]biphenyl-2-carbonitrile

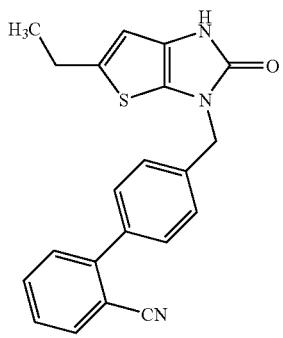 [SMILES: CCc1cc2[nH]c(=O)n(Cc3ccc(-c4ccccc4C#N)cc3)c2s1]

A mixture of 4'-[(6-ethyl-2,4-dioxo-2H-thieno[2,3-d][1,3]oxazine-1(4H)-yl)methyl]biphenyl-2-carbonitrile (3.5 g), sodium azide (0.88 g) and N,N-dimethylformamide (50 mL) was stirred at 50° C. for 1 hr. The reaction mixture was diluted with ethyl acetate, washed successively with water and saturated brine, and dried over anhydrous magnesium sulfate. The solvent was evaporated under reduced pressure. The obtained residue was dissolved in toluene (30 mL), and the mixture was stirred at 110° C. for 20 hr. The reaction mixture was concentrated under reduced pressure, and the residue was purified by silica gel column chromatography to give the title compound as colorless crystals (1.5 g, 46%).

$^1$H NMR (300 MHz, DMSO-d$_6$)δ1.17 (3H, t, J=7.6), 2.72 (2H, q, J=7.6), 4.94 (2H, s), 6.60 (1H, s), 7.45 (2H, d, J=8.0), 7.49-7.66(2H, m), 7.71-7.87 (1H, m), 7.95 (1H, d, J=7.6), 10.8 (1H, s)

Reference Example 124

4'-{[5-ethyl-2-oxo-1-(2-phenylethyl)-1,2-dihydro-3H-thieno[2,3-d]imidazol-3-yl]methyl}biphenyl-2-carbonitrile

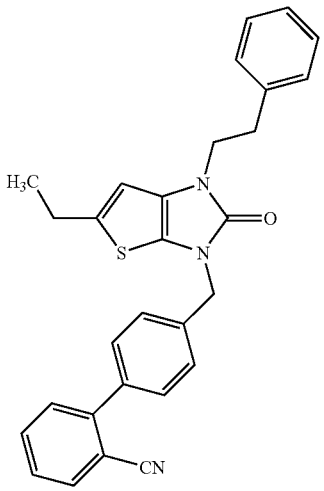 [SMILES: CCc1cc2c(s1)n(Cc1ccc(-c3ccccc3C#N)cc1)c(=O)n2CCc1ccccc1]

To a mixture of 4'-[(5-ethyl-2-oxo-1,2-dihydro-3H-thieno[2,3-d]imidazol-3-yl)methyl]biphenyl-2-carbonitrile (0.5 g), (2-bromoethyl)benzene (0.23 mL) and N,N-dimethylformamide (20 mL) was added 60% sodium hydride (0.066 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as a colorless amorphous solid (0.58 g, 87%).

$^1$H NMR (200 MHz, CDCl$_3$)δ1.17 (3H, t, J=7.4), 2.67 (2H,q, J=7.4), 3.01 (2H, t, J=7.6), 4.03 (2H, t, J=7.6), 4.93 (2H, s), 6.17(1H, s), 7.12-7.26 (5H, m), 7.36-7.66 (7H, m), 7.72 (1H, d, J=7.6)

Reference Example 125

4'-{[5-ethyl-1-(4-fluorobenzyl)-2-oxo-1,2-dihydro-3H-thieno[2,3-d]imidazol-3-yl]methyl}biphenyl-2-carbonitrile

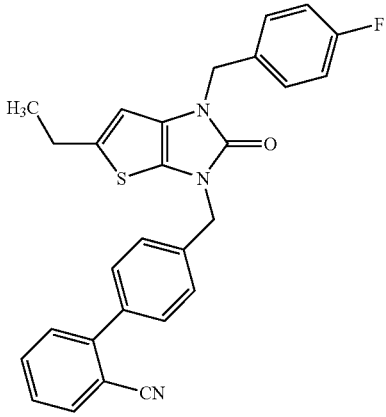 [SMILES: CCc1cc2c(s1)n(Cc1ccc(-c3ccccc3C#N)cc1)c(=O)n2Cc1ccc(F)cc1]

To a mixture of 4'-[(5-ethyl-2-oxo-1,2-dihydro-3H-thieno[2,3-d]imidazol-3-yl)methyl]biphenyl-2-carbonitrile (0.35 g), 1-(bromomethyl)-4-fluorobenzene (0.18 mL) and N,N-dimethylformamide (15 mL) was added 60% sodium hydride (0.057 g), and the mixture was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.36 g, 80%).

$^1$H NMR (300 MHz, CDCl$_3$)δ1.19 (3H, t, J=7.2), 2.69 (2H,q, J=7.2), 4.97 (2H, s), 5.02 (2H, s), 6.22 (1H, s), 7.00-7.06 (2H, m),7.30-7.35 (2H, m), 7.42-7.57 (6H, m), 7.62-7.67 (1H, m), 7.76 (1H, d, J=7.8)

Reference Example 126

4'-[(2-ethoxy-5-ethyl-3H-thieno[2,3-d]imidazol-3-yl)methyl]biphenyl-2-carbonitrile

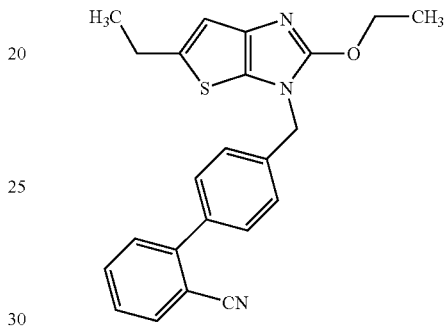

To a mixture of 4'-[(5-ethyl-2-oxo-1,2-dihydro-3H-thieno[2,3-d]imidazol-3-yl)methyl]biphenyl-2-carbonitrile (0.5 g) and 1,4-dioxane was added triethyloxonium tetrafluoroborate (1M methylene chloride solution, 4.2 mL), and the mixture was stirred at room temperature for 4 hr. The reaction mixture was extracted with chloroform and water. The obtained chloroform layer was successively washed with saturated aqueous sodium hydrogencarbonate solution and saturated brine, and dried over anhydrous magnesium sulfate. The solvent was evaporated under reduced pressure. The obtained residue was purified by silica gel column chromatography to give the title compound as a colorless amorphous solid (0.48 g, 92%).

$^1$H NMR (300 MHz, CDCl$_3$)δ1.23-1.32 (3H, m), 1.46 (3H, t, J=7.1), 2.80 (2H, q, J=7.4), 4.53 (2H, q, J=7.), 5.07 (2H, s), 6.74 (1H,s), 7.33-7.59 (6H, m), 7.58-7.71 (1H, m), 7.76 (1H, d, J=7.7)

Reference Example 127

4'-[(7-ethyl-2,5-dioxo-2,3,4,5-tetrahydro-1H-thieno[2,3-e][1,4]diazepin-1-yl)methyl]biphenyl-2-carbonitrile

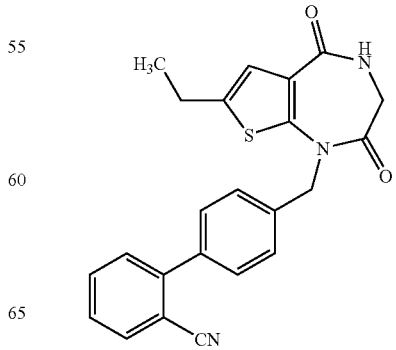

A mixture of 4'-[(6-ethyl-2,4-dioxo-2H-thieno[2,3-d][1,3]oxazine-1(4H)-yl)methyl]biphenyl-2-carbonitrile (2 g), glycine (0.46 g) and acetic acid (20 mL) was stirred at 100° C. for 2 days. The reaction mixture was concentrated under reduced pressure, and purified by silica gel column chromatography to give the title compound as a colorless amorphous solid (1 g, 48%).

$^1$H NMR (300 MHz, CDCl$_3$)δ1.26 (3H, t, J=7.8), 2.72 (2H,q, J=7.8), 4.04 (2H, d, J=5.7), 5.13 (2H, s), 6.91 (1H, s), 7.36-7.53 (6H,m), 7.61-7.66 (1H, m), 7.76 (1H, d, J=7.8)

Reference Example 128

4'-{[7-ethyl-2,5-dioxo-4-(2-phenylethyl)-2,3,4,5-tetrahydro-1H-thieno[2,3-e][1,4]diazepin-1-yl]methyl}biphenyl-2-carbonitrile

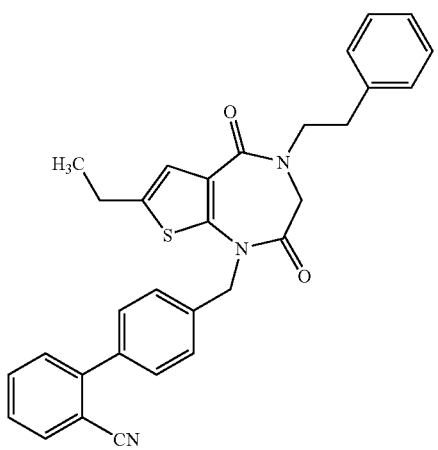 [SMILES: CCc1cc2c(s1)N(Cc1ccc(-c3ccccc3C#N)cc1)C(=O)CN(CCc1ccccc1)C2=O]

To a mixture of 4'-[(7-ethyl-2,5-dioxo-2,3,4,5-tetrahydro-1H-thieno[2,3-e][1,4]diazepin-1-yl)methyl]biphenyl-2-carbonitrile (0.5 g), (2-bromoethyl)benzene (0.19 mL) and N,N-dimethylformamide (20 mL) was added 60% sodium hydride (0.055 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as a colorless amorphous solid (0.27 g, 43%).

$^1$H NMR (300 MHz, CDCl$_3$)δ1.25 (3H, t, J=7.5), 2.70 (2H,q, J=7.5), 2.98 (2H, t, J=7.8), 3.88 (2H, t, J=7.8), 3.99 (1H, br), 5.06(2H, s), 6.91 (1H, s), 7.00-7.31 (7H, m), 7.41-7.50 (4H, m), 7.63 (1H, m), 7.77(1H, d, J=7.5)

Reference Example 129

4'-[(2-ethyl-4,9-dioxo-7,8,8a,9-tetrahydro-4H-pyrrolo[1,2-a]thieno[2,3-e][1,4]diazepin-10(6H)-yl)methyl]biphenyl-2-carbonitrile

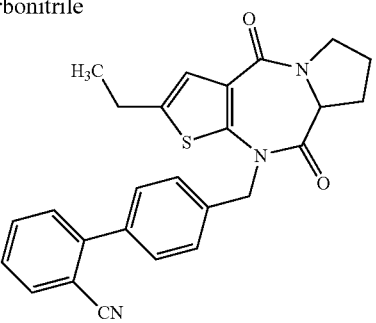

A mixture of 4'-[(6-ethyl-2,4-dioxo-2H-thieno[2,3-d][1,3]oxazine-1(4H)-yl)methyl]biphenyl-2-carbonitrile (1 g), D,L-proline (0.44 g) and acetic acid (50 mL) was stirred at 100° C. for 2 days. The reaction mixture was concentrated under reduced pressure, and purified by silica gel column chromatography to give the title compound as a colorless amorphous solid (0.74 g, 65%).

$^1$H NMR (300 MHz, CDCl$_3$)δ1.25 (3H, t, J=7.8), 2.72 (2H,q, J=7.8), 2.01-2.13 (3H, m), 2.79-2.83 (1H, m), 3.63-3.67 (2H, m), 4.04 (1H,d, J=5.7), 5.13 (2H, s), 6.91 (1H, s), 7.36-7.53 (6H, m), 7.61-7.66 (1H, m),7.76 (1H, d, J=7.8)

Reference Example 130

4'-{[7-ethyl-4-(4-fluorobenzyl)-2,5-dioxo-2,3,4,5-tetrahydro-1H-thieno[2,3-e][1,4]diazepin-1-yl]methyl}biphenyl-2-carbonitrile

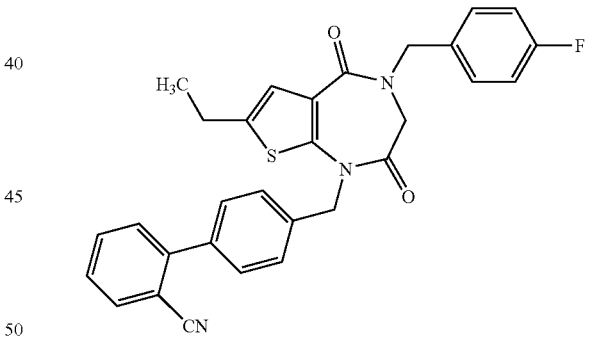

To a mixture of 4'-[(7-ethyl-2,5-dioxo-2,3,4,5-tetrahydro-1H-thieno[2,3-e][1,4]diazepin-1-yl)methyl]biphenyl-2-carbonitrile (0.52 g), 1-(bromomethyl)-4-fluorobenzene (0.24 mL) and N,N-dimethylformamide (15 mL) was added 60% sodium hydride (0.078 g), and the mixture was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography to give the title compound as a colorless amorphous solid (0.38 g, 58%).

$^1$H NMR (300 MHz, CDCl$_3$)δ1.27 (3H, t, J=7.8), 2.72 (2H,q, J=7.8), 4.03 (2H, s), 4.76 (2H, s), 5.07 (2H, s), 6.96-7.04 (3H, m),7.26-7.35 (4H,m), 7.41-7.50 (4H,m), 7.62-7.67 (1H, m), 7.75 (1H, d, J=7.5)

Reference Example 131 methyl 5-ethyl-2-[(4-phenylbutanoyl)amino]thiophene-3-carboxylate

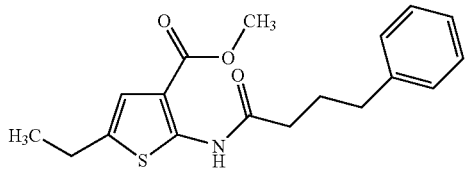 [SMILES: CCc1cc(C(=O)OC)c(NC(=O)CCCc2ccccc2)s1]

To a mixture of 4-phenylbutanoic acid (18.6 g), oxalylchloride (11.7 mL) and tetrahydrofuran (350 mL) was added N,N-dimethylformamide (one drop), and the mixture was stirred at room temperature for 2 hr. The reaction mixture was concentrated under reduced pressure, and the obtained residue was dissolved in tetrahydrofuran (50 mL), and added dropwise to a mixture of methyl 2-amino-5-ethylthiophene-3-carboxylate (19 g), triethylamine (21.6 mL) and tetrahydrofuran (300 mL) at 0° C. The reaction mixture was stirred at room temperature for 16 hr, and the solvent was evaporated under reduced pressure. The obtained residue was extracted with ethyl acetate and saturated aqueous sodium hydrogencarbonate solution. The ethyl acetate layer was washed with saturated brine, and dried over anhydrous magnesium sulfate. The solvent was evaporated under reduced pressure. The obtained residue was purified by silica gel column chromatography to give the title compound as a colorless oil (32.2 g, 94%).

$^1$H NMR (300 MHz, CDCl$_3$)δ1.29 (3H, t, J=7.8), 2.05-2.14 (2H, m), 2.49 (3H, t, J=7.5), 2.70-2.77 (4H, m), 3.86 (3H, s), 7.17-7.21 (3H,m), 7.26-7.31 (2H, m)

Reference Example 132

4'-{[2-ethyl-4-hydroxy-6-oxo-5-(2-phenylethyl)thieno[2,3-b]pyridin-7(6H)-yl]methyl}biphenyl-2-carbonitrile

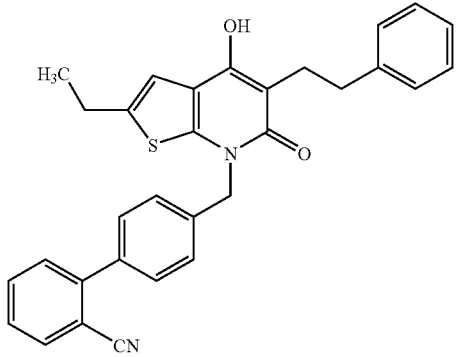 [SMILES: CCc1cc2c(O)c(CCc3ccccc3)c(=O)n(Cc3ccc(-c4ccccc4C#N)cc3)c2s1]

To a mixture of methyl 5-ethyl-2-[(4-phenylbutanoyl)amino]thiophene-3-carboxylate (15 g) and N,N-dimethylformamide (150 mL) was added 60% sodium hydride (2.17 g), and the mixture was stirred at room temperature for 15 min. To the reaction mixture was added 4'-(bromomethyl)biphenyl-2-carbonitrile (14.8 g), and the mixture was further stirred for 3 hr. The reaction mixture was diluted with ethyl acetate, washed with 5% potassium hydrogensulfate and then saturated brine, and dried over anhydrous magnesium sulfate. The solvent was evaporated under reduced pressure. After purification by silica gel column chromatography, the obtained residue was dissolved in tetrahydrofuran (200 mL), potassium tert-butoxide (5.3 g) was added, and the mixture was stirred at room temperature for 16 hr. The reaction mixture was extracted with saturated aqueous ammonium chloride solution and ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless oil (4.89 g, 22%).

$^1$H NMR (300 MHz, CDCl$_3$)δ1.27 (3H, t, J=7.5), 2.75 (2H,q, J=7.5), 2.89-2.97 (4H, m), 5.37 (2H, s), 5.67 (1H, br), 6.83 (1H, s),7.00-7.30 (5H, m), 7.40-7.53 (6H, m), 7.59-7.62 (1H, m), 7.74 (1H, d, J=7.5)

Reference Example 133

4'-{[2-ethyl-5-methyl-4,6-dioxo-5-(2-phenylethyl)-5,6-dihydrothieno[2,3-b]pyridin-7(4H)-yl]methyl}biphenyl-2-carbonitrile

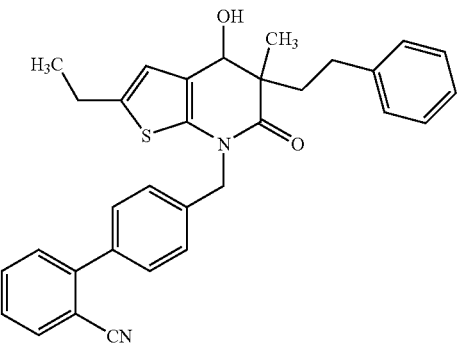 [SMILES: CCc1cc2c(s1)N(Cc1ccc(-c3ccccc3C#N)cc1)C(=O)C(C)(CCc1ccccc1)C2O]

A mixture of 4'-{[2-ethyl-4-hydroxy-6-oxo-5-(2-phenylethyl)thieno[2,3-b]pyridin-7(6H)-yl]methyl}biphenyl-2-carbonitrile (0.5 g), iodomethane (0.076 mL), 60% sodium hydride (0.049 g) and tetrahydrofuran (15 mL) was stirred at room temperature for 20 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography to give the title compound as a colorless amorphous solid (0.32 g, 62%).

$^1$H NMR (300 MHz, CDCl$_3$)δ1.30 (3H, t, J=7.2), 1.54 (3H,s), 2.32-2.52 (4H, m), 2.72 (2H, q, J=7.2), 5.06 (2H, dd, J=38.1, 15.9),6.95 (1H, s), 7.08-7.26 (5H, m), 7.41-7.56 (6H, m), 7.60-7.66 (1H, m), 7.75(1H, d, J=7.5)

Reference Example 134

4'-{[2-ethyl-4-methoxy-6-oxo-5-(2-phenylethyl)thieno[2,3-b]pyridin-7(6H)-yl]methyl}biphenyl-2-carbonitrile

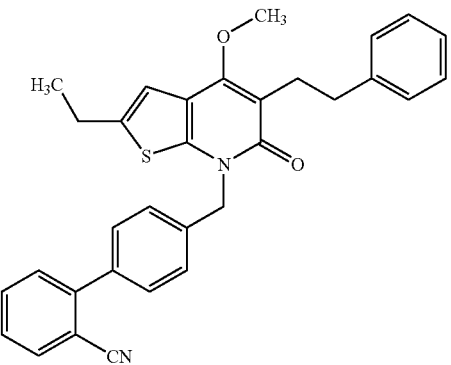 [SMILES: CCc1cc2c(OC)c(CCc3ccccc3)c(=O)n(Cc3ccc(-c4ccccc4C#N)cc3)c2s1]

To a mixture of 4'-{[2-ethyl-4-hydroxy-6-oxo-5-(2-phenylethyl)thieno[2,3-b]pyridin-7(6H)-yl]methyl}biphenyl-2-carbonitrile (0.5 g), diisopropylethylamine (0.72 mL), methanol (2 mL) and acetonitrile (18 mL) was added trimethylsilyldiazomethane (2M hexane solution, 0.72 mL), and the mixture was stirred at room temperature for 6 hr. The reaction mixture was concentrated under reduced pressure, and the obtained residue was extracted with water and ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as a colorless amorphous solid (0.28 g, 62%).

$^1$H NMR (300 MHz, CDCl$_3$)δ1.31 (3H, t, J=6.9), 2.80 (2H,q, J=6.9), 2.89-2.98 (4H, m), 3.81 (3H, s), 5.40 (2H, s), 6.84 (1H, s),7.14-7.29 (5H, m), 7.40-7.55 (6H, m), 7.60-7.65 (1H, m), 7.75 (1H, d, J=7.8)

Reference Example 135

7-[(2'-cyanobiphenyl-4-yl)methyl]-2-ethyl-6-oxo-5-(2-phenylethyl)-6,7-dihydrothieno[2,3-b]pyridin-4-yl trifluoromethanesulfonate

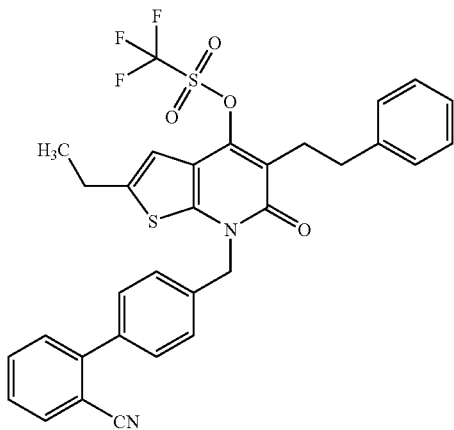 [SMILES: CCc1cc2c(OS(=O)(=O)C(F)(F)F)c(CCc3ccccc3)c(=O)n(Cc3ccc(-c4ccccc4C#N)cc3)c2s1]

To a mixture of 4'-{[2-ethyl-4-hydroxy-6-oxo-5-(2-phenylethyl)thieno[2,3-b]pyridin-7(6H)-yl]methyl}biphenyl-2-carbonitrile (3 g) and pyridine (50 mL) was added trifluoromethanesulfonic anhydride (1.13 mL) at 0° C., and the mixture was stirred at room temperature for 4 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The precipitated solid was collected by filtration to give the title compound as colorless crystals (3.3 g, 87%).

$^1$H NMR (300 MHz, CDCl$_3$)δ1.32 (3H, t, J=7.5), 2.83 (2H,q, J=7.5), 2.90-3.35 (4H, m), 5.42 (2H, s), 6.86 (1H, s), 7.18-7.29 (6H, m),7.42-7.56 (2H, m), 7.64 (3H, t, J=7.5), 7.75 (2H, d, J=7.8)

Reference Example 136

4'-{[2-ethyl-6-oxo-5-(2-phenylethyl)thieno[2,3-b]pyridin-7(6H)-yl]methyl}biphenyl-2-carbonitrile

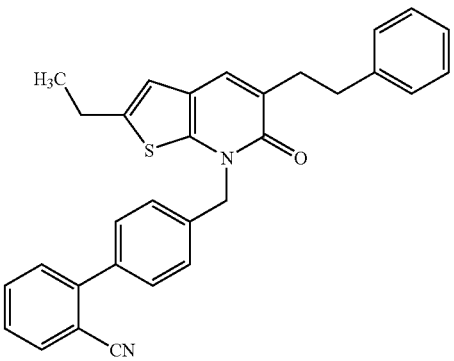 [SMILES: CCc1cc2cc(CCc3ccccc3)c(=O)n(Cc3ccc(-c4ccccc4C#N)cc3)c2s1]

To a mixture of 7-[(2'-cyanobiphenyl-4-yl)methyl]-2-ethyl-6-oxo-5-(2-phenylethyl)-6,7-dihydrothieno[2,3-b]pyridin-4-yl trifluoromethanesulfonate (1 g), palladium acetate (0.018 g), triphenylphosphine (0.042 g), tributylamine (1.18 mL) and N,N-dimethylformamide (20 mL) was added formic acid (0.12 mL), and the mixture was stirred under argon atmosphere at 70° C. for 1 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography to give the title compound as colorless crystals (0.34 g, 45%).

$^1$H NMR (300 MHz, CDCl$_3$)δ1.30 (3H, t, J=7.2), 2.79 (2H,q, J=7.2), 2.92-3.02 (4H, m), 5.42 (2H, s), 6.67 (1H, s), 7.15-7.30 (5H, m),7.40-7.54 (7H, m), 7.59-7.65 (1H, m), 7.74 (1H, d, J=7.8)

Reference Example 137

4'-{[2-ethyl-4-methyl-6-oxo-5-(2-phenylethyl)thieno[2,3-b]pyridin-7(6H)-yl]methyl}biphenyl-2-carbonitrile

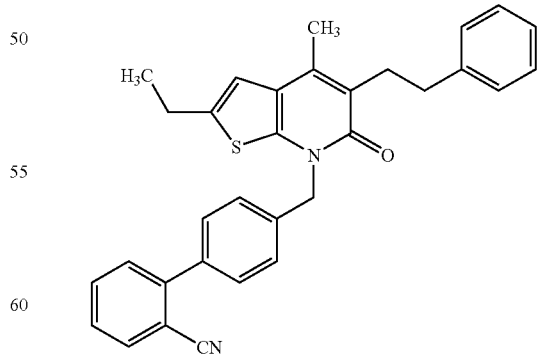

A mixture of 7-[(2'-cyanobiphenyl-4-yl)methyl]-2-ethyl-6-oxo-5-(2-phenylethyl)-6,7-dihydrothieno[2,3-b]pyridin-4-yl trifluoromethanesulfonate (1 g), palladium acetate (0.018 g), tris(2-methylphenyl)phosphine (0.049 g), triethylamine (0.27 mL), tetramethyltin (0.27 mL) and N,N-dimethylformamide (10 mL) was stirred under argon atmosphere at 100° C. for 1 hr. The reaction mixture was diluted with ethyl acetate, successively washed with 20% aqueous potassium fluoride solution and saturated brine, and dried over anhydrous magnesium sulfate. The solvent was evaporated under reduced pressure. The obtained residue was purified by silica gel column chromatography to give the title compound as a colorless amorphous solid (0.69 g, 88%).

$^1$H NMR (300 MHz, CDCl$_3$)δ1.30 (3H, t, J=7.), 2.22 (3H, s), 2.77-2.88 (4H, m), 2.95-3.02 (2H, m), 5.42 (2H, s), 6.77 (1H, s), 7.16-7.28(5H, m), 7.40-7.54 (6H, m), 7.59-7.65 (1H, m), 7.74 (1H, d, J=7.5)

Reference Example 138

6-iodo-3-(2-phenylethyl)quinazoline-2,4(1H,3H)-dione

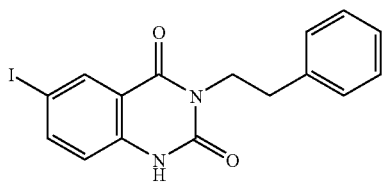 [SMILES: O=c1[nH]c2ccc(I)cc2c(=O)n1CCc1ccccc1]

To a solution (40 mL) of methyl 2-amino-5-iodobenzoate (2.3 g) in methylene chloride were added triphosgene (3.2 g) and triethylamine (3.9 g), and the mixture was stirred at room temperature for 2 hr. To the reaction mixture was added 2-phenylethanamine (3.0 g), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (30 mL), 60% sodium hydride (0.5 g) was added, and the mixture was stirred at 70° C. for 2 hr. The reaction mixture was neutralized with hydrochloric acid (10% methanol solution), insoluble material was filtered off, and the solvent was evaporated under reduced pressure. The precipitated solid was collected by filtration to give the title compound as a colorless solid (2.1 g, 65%).

$^1$H NMR (300 MHz, DMSO-d$_6$)δ2.83-2.88 (2H, m), 4.05-4.10(2H, m), 6.99 (1H, d, J=8.7), 7.17-7.31 (5H, m), 7.92 (1H, dd, J=2.1, 8.7),8.14 (1H, d, J=2.1)

Reference Example 139

3-(2-phenylethyl)-6-vinylquinazoline-2,4(1H,3H)-dione

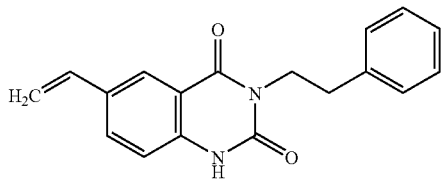

A solution (40 mL) of 6-iodo-3-(2-phenylethyl)quinazoline-2,4(1H,3H)-dione (2.0 g), tributylvinyltin (1.9 g), lithium chloride (1.1 g), dichlorobis(triphenylphosphine)palladium (0.18 g) in N,N-dimethylformamide was stirred under argon atmosphere at 90° C. for 12 hr. The reaction mixture was allowed to cool to room temperature, ethyl acetate and 15% potassium fluoride solution were added, and the mixture was stirred for 2 hr. Insoluble material was filtered off through celite. The organic layer of the filtrate was separated, washed with 1N hydrochloric acid and saturated brine, dried over anhydrous sodium sulfate, and concentrated under reduced pressure. The obtained residue was purified by silica gel column chromatography to give the title compound as a pale-yellow solid (4.8 g, 97%).

$^1$H NMR (300 MHz, DMSO-d$_6$)δ2.48-2.90 (2H, m), 4.07-4.13(2H, m), 5.26 (1H, d, J=11.1), 5.82 (1H, d, J=17.7), 6.79 (1H, dd, J=17.7, 11.1), 7.13-7.32 (6H, m), 7.83 (1H, dd, J=8.4, 2.1), 7.93 (1H, d, J=2.1), 11.49 (1H, s)

Reference Example 140

6-ethyl-3-(2-phenylethyl)quinazoline-2,4(1H,3H)-dione

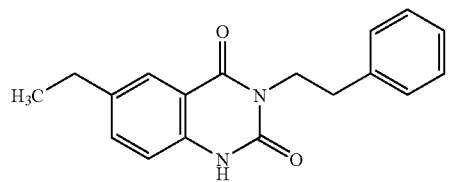 [SMILES: CCc1ccc2[nH]c(=O)n(CCc3ccccc3)c(=O)c2c1]

To a solution (20 mL) of 3-(2-phenylethyl)-6-vinylquinazoline-2,4(1H,3H)-dione (0.6 g) in tetrahydrofuran-methanol (1:1) was added palladium carbon (10%, 0.06 g), and the mixture was stirred under hydrogen atmosphere for 4 hr. Insoluble material was filtered off, and the filtrate was concentrated to give the title compound as a brown solid (0.47 g, 78%).

$^1$H NMR (300 MHz, DMSO-d$_6$)δ1.18 (3H, t, J=7.8), 2.64 (2H, q, J=7.8), 2.87 (2H, t, J=8.1), 4.10 (2H, t, J=8.1), 7.11 (1H, d, J=8.4), 7.20-7.33 (5H, m), 7.53 (1H, d, J=8.1), 7.75 (1H, s), 11.36 (1H, s)

Reference Example 141

4'-{[6-ethyl-3-(4-isopropoxyphenyl)-2,4-dioxo-3,4-dihydrothieno[2,3-d]pyrimidin-1(2H)-yl]methyl}-3'-fluorobiphenyl-2-carbonitrile

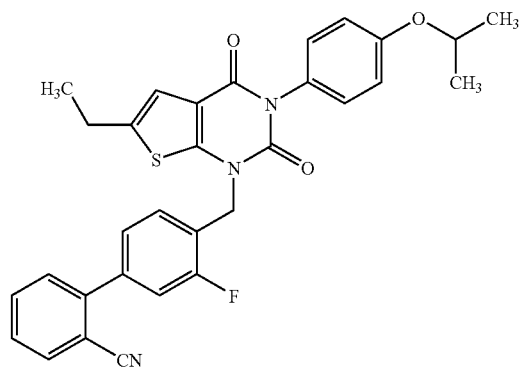 [SMILES: CCc1cc2c(=O)n(-c3ccc(OC(C)C)cc3)c(=O)n(Cc3ccc(-c4ccccc4C#N)cc3F)c2s1]

To a suspension (20 mL) of 4'-[(6-ethyl-2,4-dioxo-3,4-dihydrothieno[2,3-d]pyrimidin-1(2H)-yl)methyl]-3'-fluorobiphenyl-2-carbonitrile (0.5 g), (4-isopropoxyphenyl)boronic acid (0.43 g), triethylamine (0.86 mL), pyridine (0.48 mL) and molecular sieves 4A (1 g) in dichloromethane was added copper(II) acetate (0.45 g) and the mixture was stirred for 2 days. The reaction mixture was diluted with ethyl acetate, insoluble material was filtered off through celite, and the filtrate was concentrated. The residue was purified by silica gel column chromatography to give the title compound as a pale-yellow solid (0.5 g, 75%).

$^1$H NMR (300 MHz, DMSO-$d_6$)δ1.21 (3H, t, J=7.2), 1.30 (6H, d, J=6.0), 2.77 (2H, q, J=7.2), 4.57-4.72 (1H, m), 5.26 (2H, s), 6.99(2H, d, J=9.3), 7.05 (1H, s), 7.21 (2H, d, J=9.3), 7.38-7.45 (1H, m), 7.50-7.69 (4H, m), 7.76-7.85 (1H, m), 7.97 (1H, d, J=7.8)

Reference Example 142

4'-{[3-(2,2-dimethyl-2,3-dihydro-1-benzofuran-5-yl)-6-ethyl-2,4-dioxo-3,4-dihydrothieno[2,3-d]pyrimidin-1(2H)-yl]methyl}-3'-fluorobiphenyl-2-carbonitrile

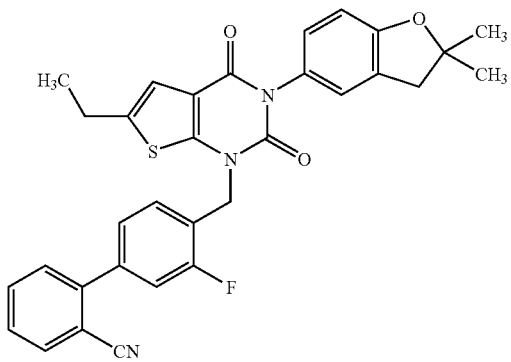 [SMILES: CCc1cc2c(=O)n(-c3ccc4c(c3)CC(C)(C)O4)c(=O)n(Cc3ccc(-c4ccccc4C#N)cc3F)c2s1]

To a suspension (20 mL) of 4'-[(6-ethyl-2,4-dioxo-3,4-dihydrothieno[2,3-d]pyrimidin-1(2H)-yl)methyl]-3'-fluorobiphenyl-2-carbonitrile (0.5 g), (2,2-dimethyl-2,3-dihydro-1-benzofuran-5-yl)boronic acid (0.47 g), triethylamine (0.86 mL), pyridine (0.48 mL) and molecular sieves 4A (1 g) in dichloromethane was added copper(II) acetate (0.45 g) and the mixture was stirred for 2 days. The reaction mixture was diluted with ethyl acetate, insoluble material was filtered off through celite, and the filtrate was concentrated. The residue was purified by silica gel column chromatography to give the title compound as a pale-yellow solid (0.54 g, 79%).

$^1$H NMR (300 MHz, DMSO-$d_6$)δ1.20 (3H, t, J=7.2), 1.45 (6H,s), 2.77 (2H, q, J=7.2), 3.05 (2H, s), 5.25 (2H, s), 6.76 (1H, d, J=8.4), 6.98-7.06 (2H, m), 7.12 (1H, s), 7.38-7.46 (1H, m), 7.49-7.69 (4H, m), 7.77-7.85 (1H, m), 7.97 (1H, d, J=8.1)

Reference Example 143

4'-[(2,4-dioxo-6-propyl-3,4-dihydropyrimidin-1(2H)-yl)methyl]biphenyl-2-carbonitrile

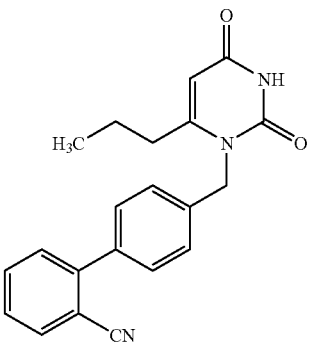 [SMILES: CCCc1cc(=O)[nH]c(=O)n1Cc1ccc(-c2ccccc2C#N)cc1]

A mixture of 6-propylpyrimidine-2,4(1H,3H)-dione (3.08 g) and 1,1,1,3,3,3-hexamethyldisilasane (12 mL) was stirred at 130° C. for 16 hr. The reaction mixture was concentrated under reduced pressure, the obtained residue was dissolved in dichloroethane (40 mL), 4'-(bromomethyl)biphenyl-2-carbonitrile (6.52 g) and iodine (0.06 g) were added, and the mixture was stirred at 80° C. for 24 hr. The reaction mixture was concentrated under reduced pressure, and purified by silica gel column chromatography to give the title compound as colorless crystals (1.14 g, 12%).

$^1$H NMR (300 MHz, CDCl$_3$)δ0.99 (3H, t, J=6.9), 1.55-1.68 (2H, m), 2.44 (2H, t, J=7.2), 5.17 (2H, s), 5.64 (1H, s), 7.26-7.31 (2H, m), 7.43-7.57 (4H, m), 7.65 (1H, t, J=7.8), 7.76 (1H, d, J=7.8)

Reference Example 144

4'-{[3-[2-(4-methoxyphenyl)-2-oxoethyl]-2,4-dioxo-6-propyl-3,4-dihydropyrimidin-1(2H)-yl]methyl}biphenyl-2-carbonitrile

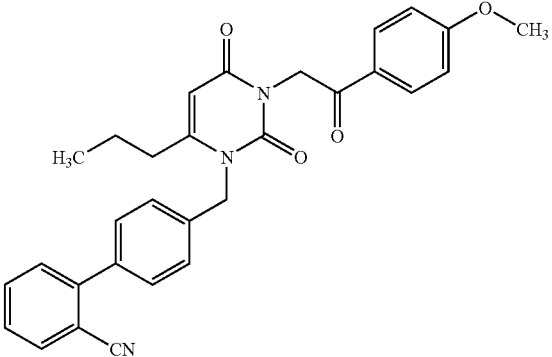 [SMILES: CCCc1cc(=O)n(CC(=O)c2ccc(OC)cc2)c(=O)n1Cc1ccc(-c2ccccc2C#N)cc1]

To a mixture of 4'-[(2,4-dioxo-6-propyl-3,4-dihydropyrimidin-1(2H)-yl)methyl]biphenyl-2-carbonitrile (0.5 g), 2-bromo-1-(4-methoxyphenyl)ethanone (0.4 g) and N,N-dimethylformamide (10 mL) was added 60% sodium hydride (0.076 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as colorless crystals (0.63 g, 81%).

¹H NMR (300 MHz, CDCl₃) δ1.01 (3H, t, J=7.2), 1.58-1.68 (2H, m), 2.46 (2H, t, J=7.5), 3.87 (3H, s), 5.20 (2H, s), 5.41 (2H, s), 5.75(1H, s), 6.95 (2H, d, J=9.0), 7.31 (2H, d, J=8.1), 7.41-7.67 (5H, m), 7.76(1H, d, J=7.5), 7.98 (2H, d, J=9.0)

Reference Example 145

4'-[(6-chloro-2,4-dioxo-3,4-dihydropyrimidin-1(2H)-yl)methyl]biphenyl-2-carbonitrile

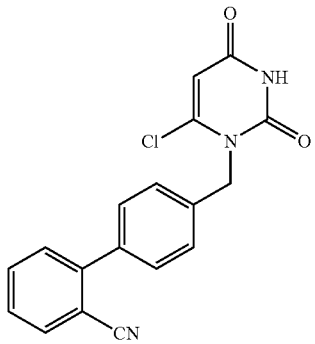 [SMILES: N#Cc1ccccc1-c1ccc(Cn2c(Cl)cc(=O)[nH]c2=O)cc1]

A mixture of 6-chloropyrimidine-2,4(1H,3H)-dione (10 g), 4'-(bromomethyl)biphenyl-2-carbonitrile (4.71 g), potassium carbonate (27.8 g) and dimethyl sulfoxide (100 mL) was stirred at 65° C. for 2 hr. To the reaction mixture were added 1N aqueous sodium hydroxide solution (70 mL) and toluene (50 mL), and the mixture was cooled to 0° C. The precipitated solid was recrystallized from methanol to give the title compound as colorless crystals (3.3 g, 14%).

¹H NMR (300 MHz, DMSO-d₆) δ5.18 (2H, s), 5.65 (1H, s),7.35 (2H, d, J=7.5), 7.53-7.62 (4H, m), 7.77 (1H, t, J=7.8), 7.92 (1H, d, J=7.8)

Reference Example 146

4'-[(2,4-dioxo-6-propoxy-3,4-dihydropyrimidin-1(2H)-yl)methyl]biphenyl-2-carbonitrile

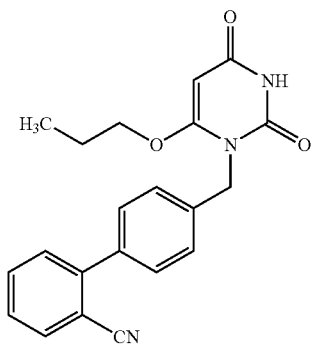 [SMILES: CCCOc1cc(=O)[nH]c(=O)n1Cc1ccc(-c2ccccc2C#N)cc1]

To a mixture of 4'-[(6-chloro-2,4-dioxo-3,4-dihydropyrimidin-1(2H)-yl)methyl]biphenyl-2-carbonitrile (2.3 g) and n-propanol (70 mL) was added a solution of sodium (0.24 g) in n-propanol (10 mL), and the mixture was stirred at 100° C. for 4 hr. The reaction mixture was concentrated under reduced pressure, and the obtained residue was dissolved in water (100 mL). 1N Hydrochloric acid was added to adjust to pH 4, and the precipitated solid was recrystallized from methanol to give the title compound as colorless crystals (1.17 g, 47%).

¹H NMR (300 MHz, DMSO-d₆) δ0.80 (3H, t, J=7.2),1.58-1.70 (2H, m), 3.40 (2H, t, J=6.0), 5.00-5.02 (2H, m), 5.09 (1H, s), 7.37(2H, d, J=8.4), 7.53-7.60 (4H, m), 7.76 (1H, t, J=7.2), 7.92 (1H, d, J=7.8), 11.2 (1H, s)

Reference Example 147

4'-{[3-[2-(4-methoxyphenyl)-2-oxoethyl]-2,4-dioxo-6-propoxy-3,4-dihydropyrimidin-1(2H)-yl]methyl}biphenyl-2-carbonitrile

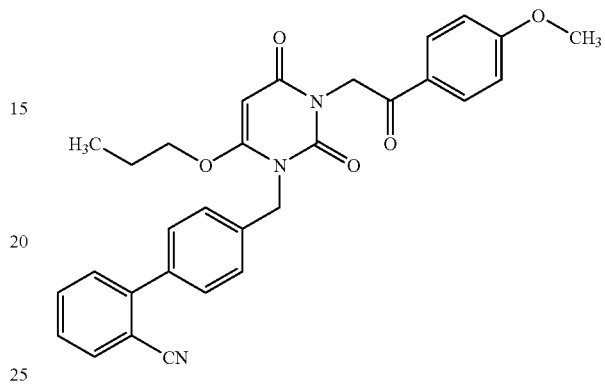

To a mixture of 4'-[(2,4-dioxo-6-propoxy-3,4-dihydropyrimidin-1(2H)-yl)methyl]biphenyl-2-carbonitrile (0.55 g), 2-bromo-1-(4-methoxyphenyl)ethanone (0.38 g) and N,N-dimethylformamide (15 mL) was added 60% sodium hydride (0.073 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as a colorless amorphous solid (0.7 g, 90%).

¹H NMR (300 MHz, CDCl₃) δ0.97 (3H, t, J=7.4), 1.76-1.87 (2H, m), 3.88 (3H, s), 4.01 (2H, t, J=6.4), 5.18 (3H, d, J=5.5), 5.38 (2H,s), 6.88-7.01 (2H, m), 7.40-7.56 (6H, m), 7.61-7.68 (1H, m), 7.76 (1H, d, J=7.7), 7.95-8.06 (2H, m)

Reference Example 148

4'-{[2,4-dioxo-6-(2,2,2-trifluoroethoxy)-3,4-dihydropyrimidin-1(2H)-yl]methyl}biphenyl-2-carbonitrile

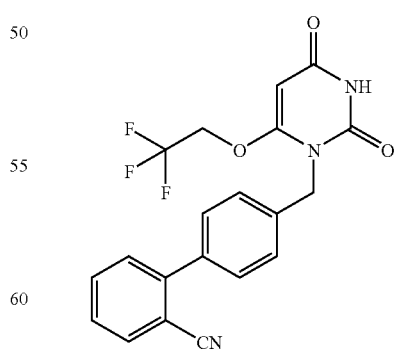

To a mixture of 4'-[(6-chloro-2,4-dioxo-3,4-dihydropyrimidin-1(2H)-yl)methyl]biphenyl-2-carbonitrile (2.7 g) and 2,2,2-trifluoroethanol (70 mL) was added a solution of sodium (0.28 g) in 2,2,2-trifluoroethanol (10 mL), and the mixture was stirred at 100° C. for 4 hr. The reaction mixture was concentrated under reduced pressure, and the obtained residue was extracted with chloroform and 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as colorless crystals (1.3 g, 30%).

$^1$H NMR (300 MHz, DMSO-d$_6$)δ4.92 (2H, dd, J=8.2, 3.1), 5.01 (2H, s), 5.24-5.35 (1H, m), 7.40 (2H, d, J=8.3), 7.51-7.64 (4H, m), 7.74-7.84 (1H, m), 7.89-7.99 (1H, m), 11.37 (1H, s)

Reference Example 149

4'-{[3-[2-(4-methoxyphenyl)-2-oxoethyl]-2,4-dioxo-6-(2,2,2-trifluoroethoxy)-3,4-dihydropyrimidin-1(2H)-yl]methyl}biphenyl-2-carbonitrile

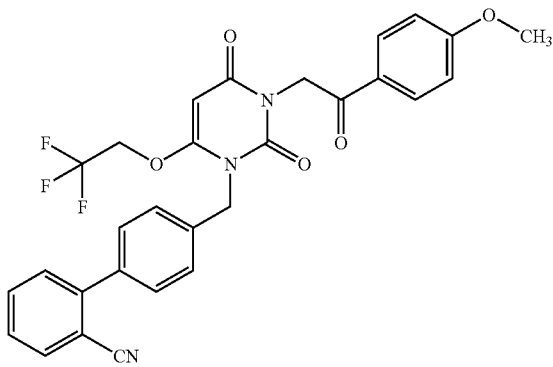 [SMILES: COc1ccc(C(=O)Cn2c(=O)cc(OCC(F)(F)F)n(Cc3ccc(-c4ccccc4C#N)cc3)c2=O)cc1]

To a mixture of 4'-{[2,4-dioxo-6-(2,2,2-trifluoroethoxy)-3,4-dihydropyrimidin-1(2H)-yl]methyl}biphenyl-2-carbonitrile (0.65 g), 2-bromo-1-(4-methoxyphenyl)ethanone (0.33 g) and N,N-dimethylformamide (20 mL) was added 60% sodium hydride (0.071 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as a colorless amorphous solid (0.59 g, 91%).

$^1$H NMR (300 MHz, CDCl$_3$)δ3.87 (3H, s), 5.03 (2H, q, J=8.5), 5.12 (2H, s), 5.31 (2H, s), 5.59 (1H, s), 7.10 (2H, d, J=9.0), 7.43(2H, d, J=8.3), 7.54-7.66 (4H, m), 7.74-7.84 (1H, m), 7.90-8.01 (1H, m), 8.06(2H, d, J=8.9)

Reference Example 150

4'-[(2,4-dioxo-6-propoxy-3,4-dihydropyrimidin-1(2H)-yl)methyl]-3'-fluorobiphenyl-2-carbonitrile

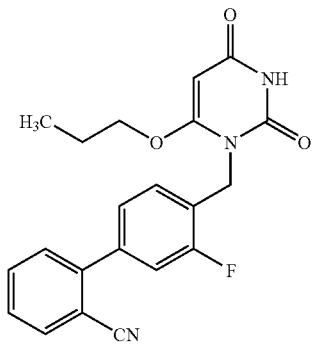 [SMILES: CCCOc1cc(=O)[nH]c(=O)n1Cc1ccc(-c2ccccc2C#N)cc1F]

A mixture of 6-chloropyrimidine-2,4(1H,3H)-dione (5 g), 4'-(bromomethyl)-3'-fluorobiphenyl-2-carbonitrile (9.9 g), potassium carbonate (2.36 g) and dimethyl sulfoxide (35 mL) was stirred at 65° C. for 2 hr. To the reaction mixture were added 1N aqueous sodium hydroxide solution (35 mL) and toluene (30 mL), and the mixture was cooled to 0° C. The precipitated solid was dissolved in chloroform, and the mixture was extracted with 1N hydrochloric acid. The obtained chloroform layer was washed with saturated brine, and dried over anhydrous magnesium sulfate. The solvent was evaporated under reduced pressure. The obtained residue was dissolved in n-propanol (60 mL), a solution of sodium (0.58 g) in n-propanol (30 mL) was added, and the mixture was stirred at 100° C. for 16 hr. The reaction mixture was concentrated under reduced pressure, and the obtained residue was extracted with 1N aqueous sodium hydroxide solution (50 mL) and ethyl acetate. The ethyl acetate layer was washed with saturated brine, and dried over anhydrous magnesium sulfate. The solvent was evaporated under reduced pressure. The obtained residue was purified by preparative HPLC to give the title compound as a colorless solid (0.55 g, 26%).

$^1$H NMR (300 MHz, DMSO-d$_6$)δ0.78 (3H, t, J=7.3),1.50-1.70 (2H, m), 4.00 (2H, t, J=6.2), 5.07 (2H, s), 5.13 (1H, d, J=1.9),7.25-8.03 (7H, m), 11.21 (1H, s)

Reference Example 151

3'-butyl-4'-{[6-ethyl-3-[2-(4-methoxyphenyl)-2-oxoethyl]-2,4-dioxo-3,4-dihydrothieno[2,3-d]pyrimidin-1(2H)-yl]methyl}biphenyl-2-carbonitrile

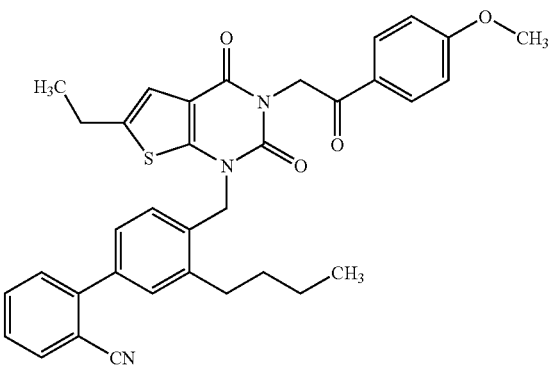 [SMILES: CCCCc1cc(-c2ccccc2C#N)ccc1Cn1c(=O)n(CC(=O)c2ccc(OC)cc2)c(=O)c2cc(CC)sc21]

A mixture of 3'-bromo-4'-{[3-(2,4-dimethoxybenzyl)-6-ethyl-2,4-dioxo-3,4-dihydrothieno[2,3-d]pyrimidin-1(2H)-yl]methyl}biphenyl-2-carbonitrile (1.28 g) and trifluoroacetic acid (20 mL) was stirred at 50° C. for 2 hr. To the reaction mixture was added toluene (20 mL), and the mixture was concentrated under reduced pressure. The obtained residue was dissolved in N,N-dimethylformamide (30 mL), 2-bromo-1-(4-methoxyphenyl)ethanone (0.73 g) and sodium hydride (0.16 g) were added, and the mixture was stirred at room temperature for 16 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The precipitated solid was dissolved in tetrahydrofuran (50 mL) and water (5 mL), n-butylboronic acid (0.33 g), [1,1'-bis(diphenylphosphino)ferrocene]dichloropalladium (0.067 g) and potassium carbonate (0.68 g) were added, and the mixture was stirred under argon atmosphere at 50° C. for 2 days. The reaction mixture was diluted with ethyl acetate, and insoluble material was filtered off through celite. The filtrate was concentrated under reduced pressure and the obtained residue was purified by silica gel column chromatography to give the title compound as a colorless amorphous solid (0.75 g, 62%).

$^1$H NMR (300 MHz, CDCl$_3$)δ0.98 (3H, t, J=7.2), 1.28 (3H,t, J=7.5), 1.40-1.53 (2H, m), 1.63-1.73 (2H, m), 2.71-2.81 (4H,m), 3.88 (3H,s), 5.28 (2H, s), 5.49 (2H, s), 6.96 (2H, m), 7.05 (1H, s), 7.15 (1H, d, J=8.0), 7.33-7.50 (4H, m), 7.63 (1H, t, J=7.8), 7.75 (1H, d, J=7.5),7.99-8.04 (2H, m)

Reference Example 152

4'-{[6-ethyl-3-[2-(4-methoxyphenyl)-2-oxoethyl]-2,4-dioxo-3,4-dihydrothieno[2,3-d]pyrimidin-1(2H)-yl]methyl}-3'-methylbiphenyl-2-carbonitrile

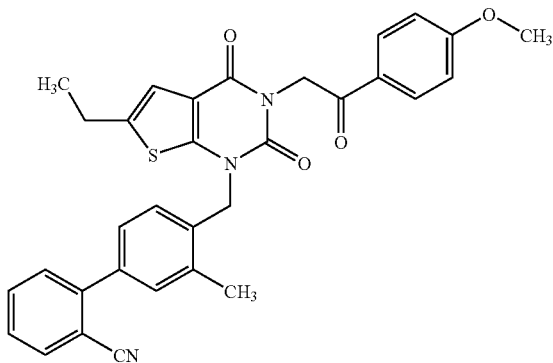 [SMILES: CCc1cc2c(=O)n(CC(=O)c3ccc(OC)cc3)c(=O)n(Cc3ccc(-c4ccccc4C#N)cc3C)c2s1]

A mixture of 3'-bromo-4'-{[3-(2,4-dimethoxybenzyl)-6-ethyl-2,4-dioxo-3,4-dihydrothieno[2,3-d]pyrimidin-1(2H)-yl]methyl}biphenyl-2-carbonitrile (1.28 g) and trifluoroacetic acid (20 mL) was stirred at 50° C. for 2 hr. To the reaction mixture was added toluene (20 mL), and the mixture was concentrated under reduced pressure. The obtained residue was dissolved in N,N-dimethylformamide (30 mL), 2-bromo-1-(4-methoxyphenyl)ethanone (0.73 g) and sodium hydride (0.16 g) were added, and the mixture was stirred at room temperature for 16 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The precipitated solid was dissolved in tetrahydrofuran (50 mL) and water (5 mL), methylboronic acid (0.2 g), [1,1'-bis(diphenylphosphino)ferrocene]dichloropalladium (0.067 g) and potassium carbonate (0.68 g) were added, and the mixture was stirred under argon atmosphere at 50° C. for 2 days. The reaction mixture was diluted with ethyl acetate, and insoluble material was filtered off through celite. The filtrate was concentrated under reduced pressure and the obtained residue was purified by silica gel column chromatography to give the title compound as a colorless amorphous solid (0.67 g, 60%).

$^1$H NMR (300 MHz, CDCl$_3$)δ1.27 (3H, t, J=7.5), 2.47 (3H,s), 2.74 (2H, q, J=7.5), 3.88 (3H, s), 5.22 (2H, s), 5.49 (2H, s), 6.96 (2H,d, J=8.4), 7.05 (1H, s), 7.18 (1H, d, J=8.1), 7.35-7.49 (4H, m), 7.62 (1H,t, J=7.5), 7.75 (1H, d, J=7.8), 8.01 (2H, d, J=8.4)

Reference Example 153

4'-{[6-ethyl-3-[2-(4-fluorophenyl)-2-oxoethyl]-2,4-dioxo-3,4-dihydrothieno[2,3-d]pyrimidin-1(2H)-yl]methyl}biphenyl-2-carbonitrile

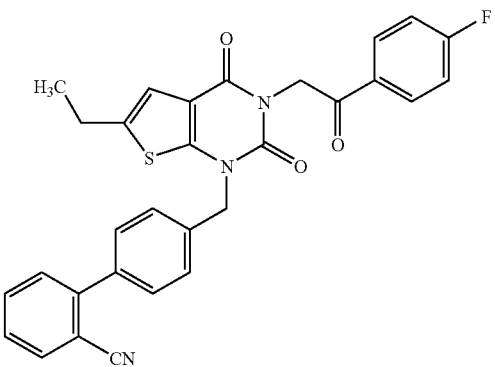 [SMILES: CCc1cc2c(=O)n(CC(=O)c3ccc(F)cc3)c(=O)n(Cc3ccc(-c4ccccc4C#N)cc3)c2s1]

To a solution of 4'-[(6-ethyl-2,4-dioxo-3,4-dihydrothieno[2,3-d]pyrimidin-1(2H)-yl)methyl]biphenyl-2-carbonitrile (1.50 g), 2-bromo-1-(4-fluorophenyl)ethanone (1.01 g) in DMF (50 ml) was added under ice-cooling 60% sodium hydride (0.093 g) and the mixture was stirred at 70° C. for 1 hr. The solvent was concentrated, water was added, and the mixture was extracted with ethyl acetate and dried over anhydrous magnesium sulfate. The solvent was evaporated under reduced pressure. Silica gel column chromatography gave the title compound as a colorless solid (1.40 g).

$^1$H NMR (300 MHz, DMSO-d$_6$)δ1.22 (3H, t, J=7.4), 2.78 (2H, dq, J=7.5, 0.9), 5.28 (2H, s), 5.48 (2H, s), 7.05 (1H, s), 7.40-7.52(4H, m), 7.56-7.65 (4H, m), 7.79 (1H, td, J=7.7, 1.4), 7.96 (1H, dd, J=7.7,0.9), 8.17-8.25 (2H, m)

Reference Example 154

4'-[(6-ethyl-2,4-dioxo-3,4-dihydrothieno[2,3-d]pyrimidin-1(2H)-yl)methyl]-3'-methoxybiphenyl-2-carbonitrile

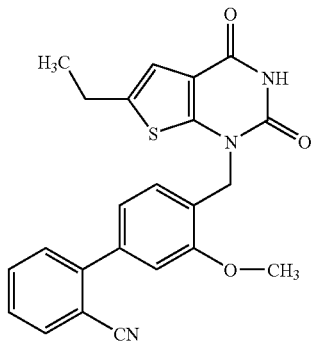 [SMILES: CCc1cc2c(=O)[nH]c(=O)n(Cc3ccc(-c4ccccc4C#N)cc3OC)c2s1]

A mixture of 3-(2,4-dimethoxybenzyl)-6-ethylthieno[2,3-d]pyrimidine-2,4(1H,3H)-dione (2 g), 4'-(hydroxymethyl)-3'-methoxybiphenyl-2-carbonitrile (1.7 g), 1,1'-(azodicarbonyl)dipiperidine (2.2 g), tributylphosphine (2.2 mL) and tetrahydrofuran (4 mL) was stirred at room temperature overnight. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was dissolved in trifluoroacetic acid (15 mL), and the mixture was stirred at 50° C. for 2 hr. The reaction mixture was concentrated under reduced pressure. To the obtained residue was added ethyl acetate, and insoluble material was filtered off. The filtrate was concentrated and recrystallized from diethyl ether to give the title compound as a colorless solid (1.9 g, 80%).

$^1$H NMR (300 MHz, DMSO-d$_6$)δ1.18 (3H, t, J=7.5),2.67-2.77 (2H, m), 3.94 (3H, s), 5.07 (2H, s), 6.97 (1H, s), 7.12 (2H, s), 7.28(1H, s), 7.55-7.63 (1H, m), 7.65-7.70 (1H, m), 7.75-7.84 (1H, m), 7.95 (1H, dd,J=7.7, 0.94), 11.53 (1H, s)

Reference Example 155

4'-{[6-ethyl-3-[2-(4-methoxyphenyl)-2-oxoethyl]-2,4-dioxo-3,4-dihydrothieno[2,3-d]pyrimidin-1(2H)-yl]methyl}-3'-methoxybiphenyl-2-carbonitrile

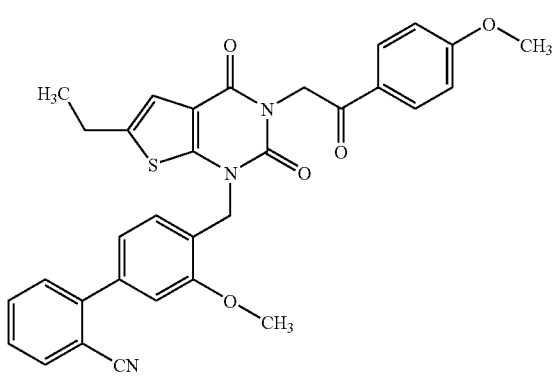 [SMILES: CCc1cc2c(=O)n(CC(=O)c3ccc(OC)cc3)c(=O)n(Cc3ccc(-c4ccccc4C#N)cc3OC)c2s1]

To a mixture of 4'-[(6-ethyl-2,4-dioxo-3,4-dihydrothieno [2,3-d]pyrimidin-1(2H)-yl]methyl]-3'-methoxybiphenyl-2-carbonitrile (1.9 g), 2-bromo-1-(4-methoxyphenyl)ethanone (1.3 g) and N,N-dimethylformamide (19 mL) was added 60% sodium hydride (0.28 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as pale-yellow crystals (1.2 g, 46%).

$^1$H NMR (300 MHz, DMSO-d$_6$)δ1.21 (3H, t, J=7.5), 2.76 (2H, q, J=7.5), 3.88 (3H, s), 3.94 (3H, s), 5.17 (2H, s), 5.42 (2H, s),7.03-7.16 (5H, m), 7.30 (1H, s), 7.59 (1H, dd, J=7.5, 1.3), 7.66-7.71 (1H, m),7.76-7.84 (1H, m), 7.96 (1H, dd, J=7.8, 1.0), 8.08 (2H, d, J=8.9)

Reference Example 156

3'-bromo-4'-{[3-(2,4-dimethoxybenzyl)-6-ethyl-2,4-dioxo-3,4-dihydrothieno[2,3-d]pyrimidin-1(2H)-yl] methyl}biphenyl-2-carbonitrile

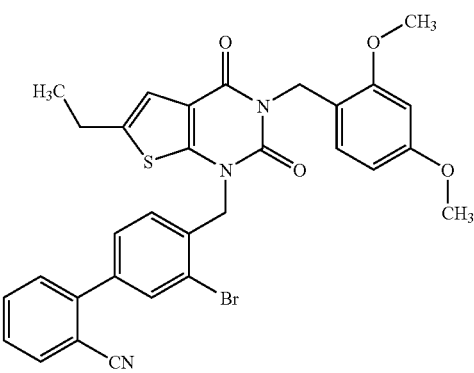 [SMILES: CCc1cc2c(=O)n(Cc3ccc(OC)cc3OC)c(=O)n(Cc3ccc(-c4ccccc4C#N)cc3Br)c2s1]

A mixture of 3-(2,4-dimethoxybenzyl)-6-ethylthieno[2,3-d]pyrimidine-2,4(1H,3H)-dione (3.4 g), 3'-bromo-4'-(bromomethyl)biphenyl-2-carbonitrile (3.8 g), potassium carbonate (2.7 g) and acetonitrile (200 mL) was stirred at 50° C. for 2 hr. Insoluble material was filtered off, and the solvent was evaporated under reduced pressure. The precipitated solid was collected by filtration to give the title compound as a colorless solid (4.92 g, 81%).

$^1$H NMR (300 MHz, CDCl$_3$)δ1.28 (3H, t, J=7.5), 2.75 (2H,d, J=7.5), 3.77 (3H, s), 3.83 (3H, s), 5.26 (2H, s), 5.30 (2H, s), 6.39-6.46(2H, m), 7.03-7.10 (3H, m), 7.44-7.51 (3H, m), 7.63-7.69 (1H, m), 7.64-7.80(2H, m)

Reference Example 157

4'-[(6-ethyl-2,4-dioxo-3,4-dihydrothieno[2,3-d]pyrimidin-1(2H)-yl)methyl]-2'-fluorobiphenyl-2-carbonitrile

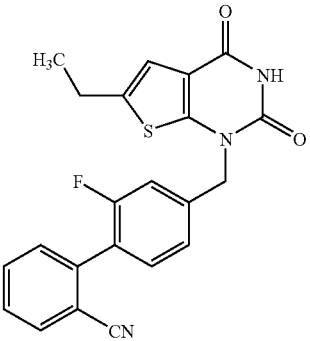 [SMILES: CCc1cc2c(=O)[nH]c(=O)n(Cc3ccc(-c4ccccc4C#N)c(F)c3)c2s1]

A mixture of 3-(2,4-dimethoxybenzyl)-6-ethylthieno[2,3-d]pyrimidine-2,4(1H,3H)-dione (2 g), 4'-(bromomethyl)-2'-fluorobiphenyl-2-carbonitrile (2 g), potassium carbonate (1.6 g) and acetonitrile (40 mL) was stirred at 50° C. for 1.5 hr. Insoluble material was filtered off, and the solvent was evaporated under reduced pressure. The obtained residue was dissolved in trifluoroacetic acid (15 mL), and the mixture was stirred at 50° C. for 2 hr. The reaction mixture was concentrated under reduced pressure. To the obtained residue was added ethyl acetate, and insoluble material was filtered off. The filtrate was concentrated and recrystallized from diethyl ether to give the title compound as a colorless solid (1.6 g, 90%).

¹H NMR (300 MHz, DMSO-d₆)δ1.20 (3H, t, J=7.4), 2.74 (2H, q, J=7.4), 5.18 (2H, s), 6.98 (1H, s), 7.30 (1H, dd, J=7.9, 1.5), 7.42(1H, dd, J=11.0, 1.2), 7.52 (1H, t, J=7.9), 7.57-7.68 (2H, m), 7.78-7.86(1H, m), 7.94-8.02 (1H, m), 11.56 (1H, s)

Reference Example 158

4'-{[6-ethyl-3-[2-(4-methoxyphenyl)-2-oxoethyl]-2,4-dioxo-3,4-dihydrothieno[2,3-d]pyrimidin-1(2H)-yl]methyl}-2'-fluorobiphenyl-2-carbonitrile

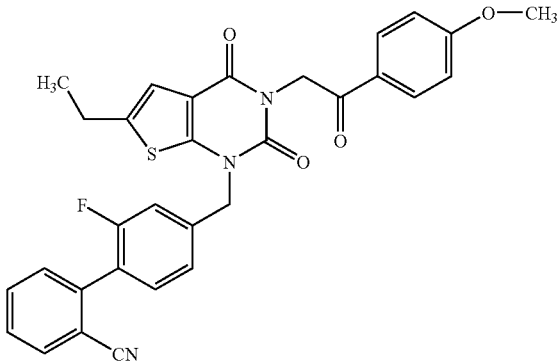 [SMILES: CCc1cc2c(=O)n(CC(=O)c3ccc(OC)cc3)c(=O)n(Cc3ccc(-c4ccccc4C#N)c(F)c3)c2s1]

To a mixture of 4'-[(6-ethyl-2,4-dioxo-3,4-dihydrothieno[2,3-d]pyrimidin-1(2H)-yl)methyl]-2'-fluorobiphenyl-2-carbonitrile (1.6 g), 2-bromo-1-(4-methoxyphenyl)ethanone (1.1 g) and N,N-dimethylformamide (19 mL) was added 60% sodium hydride (0.23 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as colorless crystals (1.8 g, 86%).
¹H NMR (300 MHz, DMSO-d₆)δ1.22 (3H, t, J=7.5), 2.79 (2H, q, J=7.5), 3.88 (3H, s), 5.29 (2H, s), 5.43 (2H, s), 7.06 (1H, s), 7.11(2H, d, J=8.9), 7.32 (1H, dd, J=8.0, 1.6), 7.39 (1H, dd, J=10.9, 1.3),7.55 (1H, t, J=7.8), 7.59-7.69 (2H, m), 7.77-7.86 (1H, m), 7.99 (1H, d, J=7.9), 8.09 (2H, d, J=9.0)

Reference Example 159

4'-[(6-ethyl-2,4-dioxo-3,4-dihydrothieno[2,3-d]pyrimidin-1(2H)-yl)methyl]-5-methylbiphenyl-2-carbonitrile

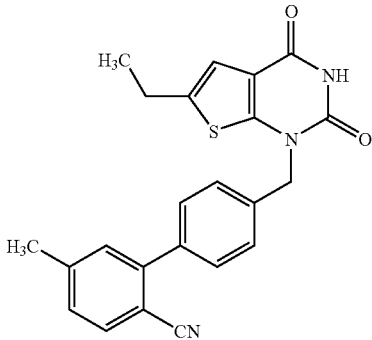 [SMILES: CCc1cc2c(=O)[nH]c(=O)n(Cc3ccc(-c4cc(C)ccc4C#N)cc3)c2s1]

A mixture of 3-(2,4-dimethoxybenzyl)-6-ethylthieno[2,3-d]pyrimidine-2,4(1H,3H)-dione (2 g), 4'-(hydroxymethyl)-5-methylbiphenyl-2-carbonitrile (1.5 g), 1,1'-(azodicarbonyl)dipiperidine (2.2 g), tributylphosphine (2.2 mL) and tetrahydrofuran (4 mL) was stirred at room temperature overnight. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was dissolved in trifluoroacetic acid (15 mL), and the mixture was stirred at 50° C. for 2 hr. The reaction mixture was concentrated under reduced pressure. To the obtained residue was added ethyl acetate, and insoluble material was filtered off. The filtrate was concentrated and recrystallized from diethyl ether to give the title compound as a colorless solid (2 g, 85%).
¹H NMR (300 MHz, DMSO-d₆)δ1.19 (3H, t, J=7.5), 2.43 (3H, s), 2.74 (2H, q, J=7.5), 5.16 (2H, s), 6.97 (1H, s), 7.35-7.61 (6H, m),7.83 (1H, d, J=7.9), 11.56 (1H, s)

Reference Example 160

4'-{[6-ethyl-3-[2-(4-methoxyphenyl)-2-oxoethyl]-2,4-dioxo-3,4-dihydrothieno[2,3-d]pyrimidin-1(2H)-yl]methyl}-5-methylbiphenyl-2-carbonitrile

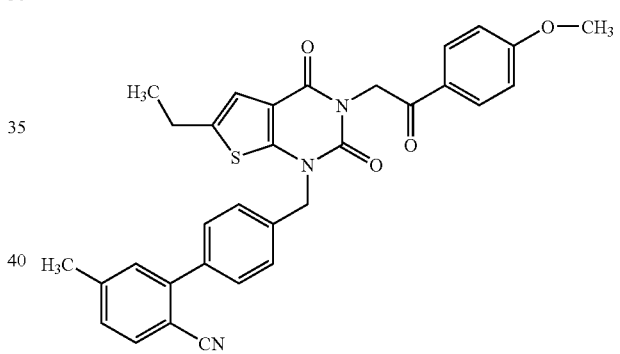

To a mixture of 4'-[(6-ethyl-2,4-dioxo-3,4-dihydrothieno[2,3-d]pyrimidin-1(2H)-yl)methyl]-5-methylbiphenyl-2-carbonitrile (2 g), 2-bromo-1-(4-methoxyphenyl)ethanone (1.4 g) and N,N-dimethylformamide (19 mL) was added 60% sodium hydride (0.3 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as colorless crystals (1.2 g, 80%).
¹H NMR (300 MHz, DMSO-d₆)δ1.22 (3H, t, J=7.4), 2.43 (3H, s), 2.77 (2H, q, J=7.4), 3.88 (3H, s), 5.27 (2H, s), 5.43 (2H, s), 7.05(1H, t, J=1.1), 7.11 (2H, d, J=9.0), 7.40 (1H, dd, J=7.9, 0.9), 7.43-7.52(3H, m), 7.58-7.62 (2H, m), 7.83 (1H, d, J=7.9), 8.09 (2H, d, J=8.9)

Reference Example 161

4'-[(6-ethyl-2,4-dioxo-3,4-dihydrothieno[2,3-d]pyrimidin-1(2H)-yl)methyl]-3',5'-difluorobiphenyl-2-carbonitrile

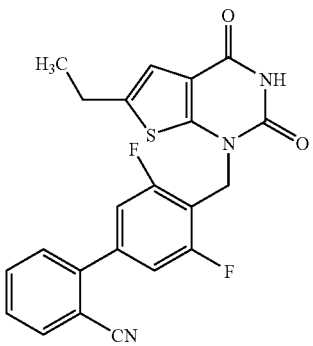 [SMILES: CCc1cc2c(=O)[nH]c(=O)n(Cc3c(F)cc(-c4ccccc4C#N)cc3F)c2s1]

A mixture of 3-(2,4-dimethoxybenzyl)-6-ethylthieno[2,3-d]pyrimidine-2,4(1H,3H)-dione (2 g), 3',5'-difluoro-4'-(hydroxymethyl)biphenyl-2-carbonitrile (1.6 g), 1,1'-(azodicarbonyl)dipiperidine (2.2 g), tributylphosphine (2.2 mL) and tetrahydrofuran (4 mL) was stirred at room temperature overnight. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was dissolved in trifluoroacetic acid (15 mL), and the mixture was stirred at 50° C. for 2 hr. The reaction mixture was concentrated under reduced pressure. To the obtained residue was added ethyl acetate, and insoluble material was filtered off. The filtrate was concentrated and recrystallized from diethyl ether to give the title compound as a colorless solid (1.5 g, 76%).

$^1$H NMR (300 MHz, DMSO-$d_6$)δ1.20 (3H, t, J=7.5),2.69-2.79 (2H, m), 5.24 (2H, s), 6.96 (1H, s), 7.44 (2H, d, J=8.9), 7.60-7.71(2H, m), 7.96-8.06 (2H, m), 11.49 (1H, s)

Reference Example 162

4'-{[6-ethyl-3-[2-(4-methoxyphenyl)-2-oxoethyl]-2,4-dioxo-3,4-dihydrothieno[2,3-d]pyrimidin-1(2H)-yl]methyl}-3',5'-difluorobiphenyl-2-carbonitrile

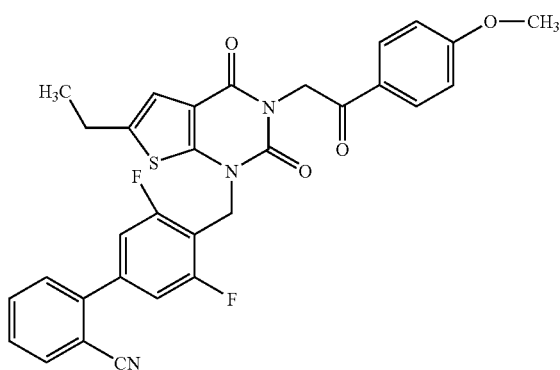 [SMILES: CCc1cc2c(=O)n(CC(=O)c3ccc(OC)cc3)c(=O)n(Cc3c(F)cc(-c4ccccc4C#N)cc3F)c2s1]

To a mixture of 4'-[(6-ethyl-2,4-dioxo-3,4-dihydrothieno[2,3-d]pyrimidin-1(2H)-yl)methyl]-3',5'-difluorobiphenyl-2-carbonitrile (1.5 g), 2-bromo-1-(4-methoxyphenyl)ethanone (0.96 g) and N,N-dimethylformamide (19 mL) was added 60% sodium hydride (0.21 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as colorless crystals (1.2 g, 59%).

$^1$H NMR (300 MHz, DMSO-$d_6$)δ1.24 (3H, t, J=7.5),2.75-2.85 (2H, m), 3.87 (3H, s), 5.32 (2H, s), 5.37 (2H, s), 7.04 (1H, s), 7.10(2H, d, J=9.0), 7.45 (2H, d, J=8.7), 7.60-7.72 (2H, m), 7.78-7.86 (1H, m),7.99 (1H, dd, J=7.7, 0.94), 8.06 (2H, d, J=8.9)

Reference Example 163

4'-[(6-ethyl-2,4-dioxo-3,4-dihydrothieno[2,3-d]pyrimidin-1(2H)-yl)methyl]-4-fluorobiphenyl-2-carbonitrile

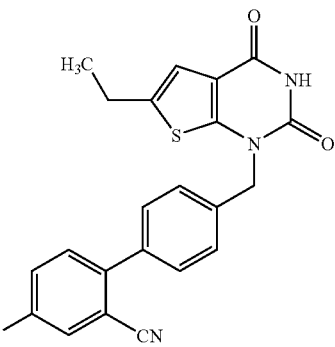

A mixture of 3-(2,4-dimethoxybenzyl)-6-ethylthieno[2,3-d]pyrimidine-2,4(1H,3H)-dione (2 g), 4-fluoro-4'-(hydroxymethyl)biphenyl-2-carbonitrile (1.4 g), 1,1'-(azodicarbonyl)dipiperidine (2.2 g), tributylphosphine (2.2 mL) and tetrahydrofuran (4 mL) was stirred at room temperature overnight. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was dissolved in trifluoroacetic acid (15 mL), and the mixture was stirred at 50° C. for 2 hr. The reaction mixture was concentrated under reduced pressure. To the obtained residue was added ethyl acetate, and insoluble material was filtered off. The filtrate was concentrated and recrystallized from diethyl ether to give the title compound as a colorless solid (2 g, 86%).

$^1$H NMR (300 MHz, DMSO-$d_6$)δ1.19 (3H, t, J=7.4), 2.73 (2H, q, J=7.4), 5.16 (2H, s), 6.97 (1H, s), 7.44-7.71 (6H, m), 7.93-8.01 (1H,m), 11.55 (1H, s)

Reference Example 164

4'-{[6-ethyl-3-[2-(4-methoxyphenyl)-2-oxoethyl]-2,4-dioxo-3,4-dihydrothieno[2,3-d]pyrimidin-1(2H)-yl]methyl}-4-fluorobiphenyl-2-carbonitrile

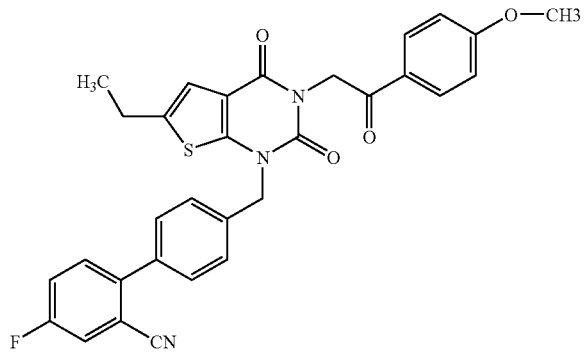 [SMILES: CCc1cc2c(=O)n(CC(=O)c3ccc(OC)cc3)c(=O)n(Cc3ccc(-c4ccc(F)cc4C#N)cc3)c2s1]

To a mixture of 4'-[(6-ethyl-2,4-dioxo-3,4-dihydrothieno[2,3-d]pyrimidin-1(2H)-yl)methyl]-4-fluorobiphenyl-2-carbonitrile (2 g), 2-bromo-1-(4-methoxyphenyl)ethanone (1.4 g) and N,N-dimethylformamide (19 mL) was added 60% sodium hydride (0.3 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as colorless crystals (2.4 g, 87%).

$^1$H NMR (300 MHz, DMSO-$d_6$)δ1.21 (3H, t, J=7.4),2.72-2.82 (2H, m), 3.88 (3H, s), 5.27 (2H, s), 5.43 (2H, s), 7.05 (1H, s), 7.11(2H, d, J=9.0), 7.46-7.52 (2H, m), 7.57-7.63 (2H, m), 7.66-7.70 (2H, m),7.95-8.00 (1H, m), 8.09 (2H, d, J=9.0)

Reference Example 165

4'-{[6-ethyl-3-[2-(4-fluorophenyl)-2-hydroxypropyl]-2,4-dioxo-3,4-dihydrothieno[2,3-d]pyrimidin-1(2H)-yl]methyl}biphenyl-2-carbonitrile

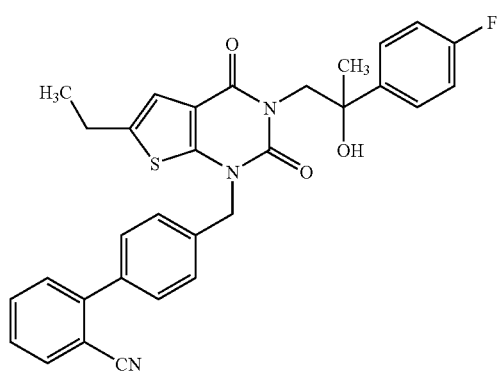 [SMILES: CCc1cc2c(=O)n(CC(C)(O)c3ccc(F)cc3)c(=O)n(Cc3ccc(-c4ccccc4C#N)cc3)c2s1]

A mixture of 4'-[(6-ethyl-2,4-dioxo-3,4-dihydrothieno[2,3-d]pyrimidin-1(2H)-yl)methyl]biphenyl-2-carbonitrile (2 g), 2-(4-fluorophenyl)-2-methyloxirane (1.2 g), potassium carbonate (1.4 g) and DMF (20 mL) was stirred at 80° C. for 16 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography to give the title compound as a colorless amorphous solid (1.8 g, 66%).

$^1$H NMR (300 MHz, DMSO-$d_6$)δ1.19 (3H, t, J=7.5), 1.48 (3H, s), 2.67-2.80 (2H, m), 4.21-4.34 (2H, m), 5.16 (2H, s), 5.30 (1H, s), 7.00(1H, s), 7.11 (2H, t, J=9.0), 7.38 (2H, d, J=8.1), 7.45-7.66 (6H, m),7.75-7.84 (1H, m), 7.96 (1H, dd, J=7.7, 0.94)

Reference Example 166

4'-{[6-ethyl-3-[2-(4-methoxyphenyl)-2-oxoethyl]-2,4-dioxo-3,4-dihydrothieno[2,3-d]pyrimidin-1(2H)-yl]methyl}-3-fluorobiphenyl-2-carbonitrile

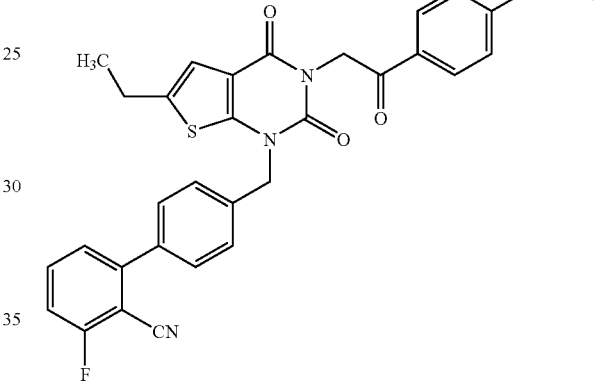

A mixture of 3-(2,4-dimethoxybenzyl)-6-ethylthieno[2,3-d]pyrimidine-2,4(1H,3H)-dione (2 g), 4'-(hydroxymethyl)-3-fluorobiphenyl-2-carbonitrile (1.4 g), 1,1'-(azodicarbonyl)dipiperidine (2.2 g), tributylphosphine (2.2 mL) and tetrahydrofuran (4 mL) was stirred at room temperature overnight. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was dissolved in trifluoroacetic acid (15 mL), and the mixture was stirred at 50° C. for 2 hr. The reaction mixture was concentrated under reduced pressure. To the obtained residue was added ethyl acetate, and insoluble material was filtered off. To a mixture of the obtained residue, 2-bromo-1-(4-methoxyphenyl)ethanone (1.2 g) and N,N-dimethylformamide (19 mL) was added 60% sodium hydride (0.26 g), and the mixture was stirred at room temperature for 2 hr. The reaction mixture was diluted with ethyl acetate, washed with 5% potassium hydrogensulfate and then saturated brine, and dried over anhydrous magnesium sulfate. The solvent was evaporated under reduced pressure. The obtained residue was purified by silica gel column chromatography to give the title compound as colorless crystals (1.1 g, 47%).

$^1$H NMR (300 MHz, DMSO-$d_6$)δ1.22 (3H, t, J=7.4),2.72-2.83 (2H, m), 3.88 (3H, s), 5.28 (2H, s), 5.43 (2H, s), 7.05 (1H, s), 7.11(2H, d, J=8.9), 7.46-7.69 (6H, m), 7.80-7.91 (1H, m), 8.09 (2H, d, J=8.9)

Reference Example 167

4'-[(6-ethyl-2,4-dioxo-3,4-dihydrothieno[2,3-d]pyrimidin-1(2H)-yl)methyl]-5-fluorobiphenyl-2-carbonitrile

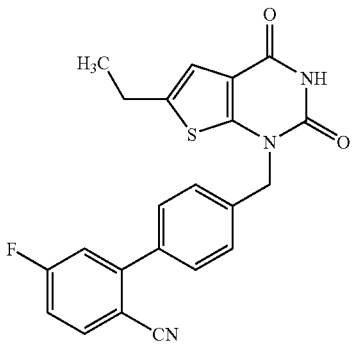 [SMILES: CCc1cc2c(=O)[nH]c(=O)n(Cc3ccc(-c4cc(F)ccc4C#N)cc3)c2s1]

A mixture of 3-(2,4-dimethoxybenzyl)-6-ethylthieno[2,3-d]pyrimidine-2,4(1H,3H)-dione (1.5 g), 4'-(hydroxymethyl)-5-fluorobiphenyl-2-carbonitrile (1.3 g), 1,1'-(azodicarbonyl)dipiperidine (1.6 g), tributylphosphine (1.3 mL) and tetrahydrofuran (16 mL) was stirred at room temperature overnight. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was dissolved in trifluoroacetic acid (15 mL) and the mixture was stirred at 50° C. for 2 hr. The reaction mixture was concentrated under reduced pressure. To the obtained residue was added ethyl acetate, and insoluble material was filtered off. The filtrate was concentrated and recrystallized from diethyl ether to give the title compound as a colorless solid (1.8 g, 100%).

$^1$H NMR (300 MHz, DMSO-$d_6$)δ1.19 (3H, t, J=7.4),2.68-2.78 (2H, m), 5.17 (2H, s), 6.97 (1H, t, J=1.1), 7.42-7.65 (6H, m), 8.06(1H, dd, J=8.7, 5.7), 11.55 (1H, s)

Reference Example 168

6-ethyl-1-({2'-[5-(trichloromethyl)-1,2,4-oxadiazol-3-yl]biphenyl-4-yl}methyl)thieno[2,3-d]pyrimidine-2,4(1H,3H)-dione

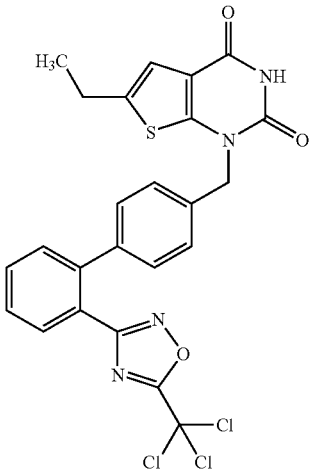 [SMILES: CCc1cc2c(=O)[nH]c(=O)n(Cc3ccc(-c4ccccc4-c4noc(C(Cl)(Cl)Cl)n4)cc3)c2s1]

A mixture of hydroxylammonium chloride (3.6 g), sodium hydrogencarbonate (5.2 g) and dimethyl sulfoxide (30 mL) was stirred at 40° C. for 30 min, 4'-[(6-ethyl-2,4-dioxo-3,4-dihydrothieno[2,3-d]pyrimidin-1(2H)-yl)methyl]biphenyl-2-carbonitrile (2 g) was added, and the mixture was stirred at 90° C. for 20 hr. After allowing to cool to room temperature, ethyl acetate and water were added to the reaction mixture, and the mixture was extracted with ethyl acetate. The organic layer was successively washed with water and saturated brine, and dried over anhydrous magnesium sulfate. The solvent was evaporated under reduced pressure. The obtained residue was dissolved in toluene (30 mL) and to the mixture was added trichloroacetic anhydride (1.8 g) and the mixture was stirred at 80° C. for 3 hr. The reaction mixture was concentrated under reduced pressure, and the obtained residue was purified by silica gel column chromatography to give the title compound as a colorless solid (1.48 g, 52%).

$^1$H NMR (300 MHz, DMSO-$d_6$)δ1.17-1.24 (3H, m), 2.68-2.79(2H, m), 5.09 (2H, s), 6.96 (1H, s), 7.18-7.25 (2H, m), 7.27-7.35 (2H, m), 7.52-7.64(2H, m), 7.71 (1H, dd, J=7.5, 1.5), 7.88 (1H, dd, J=7.6, 1.2), 11.52 (1H,s)

Example 1

3-butyl-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

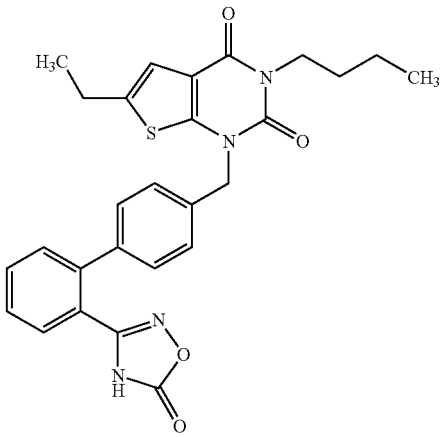 [SMILES: CCCCn1c(=O)c2cc(CC)sc2n(Cc2ccc(-c3ccccc3-c3noc(=O)[nH]3)cc2)c1=O]

To a mixture of 3-butyl-6-ethylthieno[2,3-d]pyrimidine-2,4(1H,3H)-dione (1 g), 3-[4'-(bromomethyl)biphenyl-2-yl]-5-(trichloromethyl)-1,2,4-oxadiazole (1.89 g) and N,N-dimethylformamide (50 mL) was added sodium hydride (0.17 g), and the mixture was stirred at 50° C. for 1 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. To the obtained residue was added 1N aqueous sodium hydroxide solution (50 mL), and the mixture was stirred at 60° C. for 1 hr. The reaction mixture was adjusted to pH 4 with 1N hydrochloric acid, extracted with ethyl acetate. The obtained ethyl acetate layer was washed with saturated brine, and dried over anhydrous magnesium sulfate. The solvent was evaporated under reduced pressure. The residue was purified by silica gel column chromatography, and the obtained solid was recrystallized from tetrahydrofuran-diisopropylether to give the title compound as colorless crystals (1.13 g, 58%).

$^1$H NMR (400 MHz, CDCl$_3$)δ0.92 (3H, t, J=7.2), 1.26 (3H,t, J=7.6), 1.34-1.42 (2H, m), 1.58-1.68 (2H, m), 2.74 (2H, q, J=7.2),3.98-4.04 (2H, m), 5.14 (2H, s), 6.80 (1H, s), 7.32-7.34 (2H, m), 7.41-7.52(4H, m), 7.60-7.64 (1H, m), 7.76-7.80 (1H, m)

Example 2

3-benzyl-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

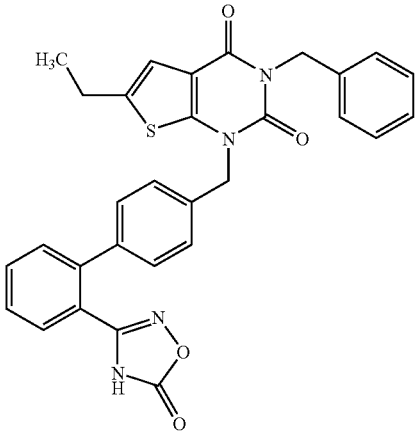 [SMILES: CCc1cc2c(=O)n(Cc3ccccc3)c(=O)n(Cc3ccc(-c4ccccc4-c4noc(=O)[nH]4)cc3)c2s1]

To a mixture of 3-benzyl-6-ethylthieno[2,3-d]pyrimidine-2,4(1H,3H)-dione (1 g), 3-[4'-(bromomethyl)biphenyl-2-yl]-5-(trichloromethyl)-1,2,4-oxadiazole (1.66 g) and N,N-dimethylformamide (50 mL) was added sodium hydride (0.15 g), and the mixture was stirred at 50° C. for 1 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. To the obtained residue was added 1N aqueous sodium hydroxide solution (50 mL), and the mixture was stirred at 60° C. for 1 hr. The reaction mixture was adjusted to pH 4 with 1N hydrochloric acid, and extracted with ethyl acetate. The obtained ethyl acetate layer was washed with saturated brine, and dried over anhydrous magnesium sulfate. The solvent was evaporated under reduced pressure. The residue was purified by silica gel column chromatography, and the obtained solid was recrystallized from tetrahydrofuran-diethyl ether to give the title compound as colorless crystals (1.12 g, 60%).

$^1$H NMR (400 MHz, CDCl$_3$)δ1.26 (3H, t, J=7.6), 2.72 (2H,d, J=7.6), 5.15 (2H, s), 5.24 (2H, s), 7.01 (1H, s), 7.22-7.35 (6H, m),7.38-7.46 (3H, m), 7.48-7.58 (3H, m), 7.93 (1H, m)

Example 3

6-ethyl-3-(2-hydroxyethyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

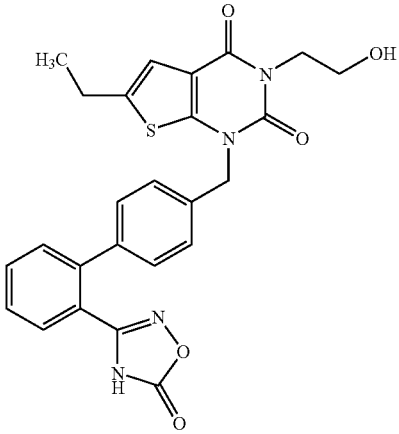 [SMILES: CCc1cc2c(=O)n(CCO)c(=O)n(Cc3ccc(-c4ccccc4-c4noc(=O)[nH]4)cc3)c2s1]

To a mixture of 3-(2-{[tert-butyl(dimethyl)silyl]oxy}ethyl)-6-ethylthieno[2,3-d]pyrimidine-2,4(1H,3H)-dione (0.14 g), 3-[4'-(bromomethyl)biphenyl-2-yl]-5-(trichloromethyl)-1,2,4-oxadiazole (0.22 g) and N,N-dimethylformamide (10 mL) was added sodium hydride (0.02 g), and the mixture was stirred at 50° C. for 1 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. To the obtained residue was added 1N aqueous sodium hydroxide solution (50 mL), and the mixture was stirred at 60° C. for 1 hr. The reaction mixture was adjusted to pH 4 with 1N hydrochloric acid, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography, and dissolved in tetrahydrofuran (10 mL). Tetrabutylammonium fluoride (1.0M tetrahydrofuran solution, 0.6 mL) was added, and the mixture was stirred at room temperature for 2 hr. The reaction mixture was diluted with ethyl acetate, washed with saturated brine, and dried over anhydrous magnesium sulfate. The solvent was evaporated under reduced pressure. The residue was purified by silica gel column chromatography to give the title compound as a colorless amorphous solid (0.07 g, 37%).

$^1$H NMR (300 MHz, CDCl$_3$)δ1.32 (3H, t, J=7.6), 2.79 (2H,q, J=7.6), 3.89 (2H, t, J=4.8), 4.27 (2H, t, J=4.8), 5.14 (2H, s), 7.03(1H, s), 7.35 (2H, d, J=8.0), 7.43-7.54 (4H, m), 7.63 (1H, t, J=7.6), 7.84(2H, d, J=7.6)

Example 4

3-cyclopropyl-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

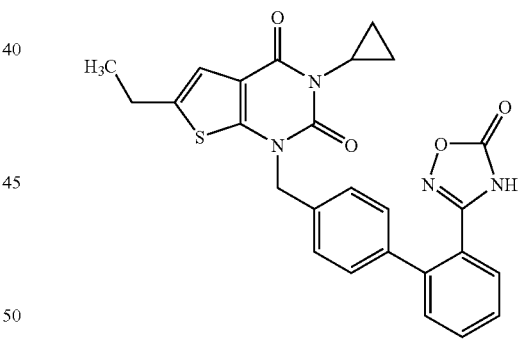

A mixture of 3-cyclopropyl-6-ethylthieno[2,3-d]pyrimidine-2,4(1H,3H)-dione (0.25 g), 3-[4'-(bromomethyl)biphenyl-2-yl]-5-(trichloromethyl)-1,2,4-oxadiazole (0.55 g), potassium carbonate (0.18 g) and N,N-dimethylformamide (10 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless amorphous solid (0.3 g, 56%).

$^1$H NMR (400 MHz, CDCl$_3$)δ0.82-0.86 (2H, m), 1.16-1.20 (2H,m), 1.29 (3H, t, J=7.6), 2.72-2.80 (3H, m), 5.14 (2H, s), 6.99 (1H, s), 7.33(2H, d, J=8.0), 7.41 (1H, d, J=7.6), 7.48-7.54 (3H, m), 7.61-7.64 (1H, m),7.83-7.86 (1H, m)

Example 5

3-[2-(3,4-dimethoxyphenyl)ethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

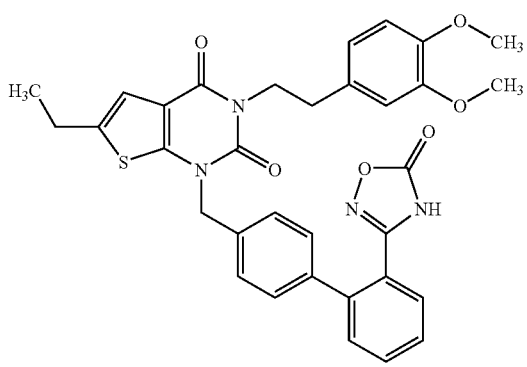 [SMILES: CCc1cc2c(=O)n(CCc3ccc(OC)c(OC)c3)c(=O)n(Cc3ccc(-c4ccccc4-c4noc(=O)[nH]4)cc3)c2s1]

A mixture of 3-[2-(3,4-dimethoxyphenyl)ethyl]-6-ethylthieno[2,3-d]pyrimidine-2,4(1H,3H)-dione (0.25 g), 3-[4'-(bromomethyl)biphenyl-2-yl]-5-(trichloromethyl)-1,2,4-oxadiazole (0.36 g), potassium carbonate (0.12 g) and N,N-dimethylformamide (10 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 1 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was recrystallized from acetone-hexane to give the title compound as colorless crystals (0.3 g, 56%).

$^1$H NMR (300 MHz, CDCl$_3$)δ1.31 (3H, t, J=7.2), 2.78 (2H,q, J=7.2), 2.98 (2H, t, J=7.2), 3.49 (3H, s), 3.53 (3H, s), 3.64 (1H, s),4.36 (2H, t, J=7.2), 5.09 (2H, s), 6.68 (2H, m), 6.78-6.81 (1H, m), 7.05 (1H,s), 7.24-7.25 (4H, m), 7.42 (1H, d, J=7.6), 7.52 (1H, t, J=8.0), 7.63 (1H,t, J=7.6), 7.84 (1H, d, J=7.6)

Example 6

6-ethyl-1-{[2'-(5-oxo-4,5-dihydro-1,2,4-oxadiazol-3-yl)biphenyl-4-yl]methyl}-3-(2-phenylethyl)thieno[2,3-d]pyrimidine-2,4(1H,3H)-dione

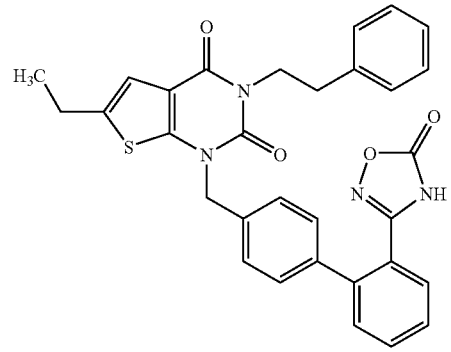 [SMILES: CCc1cc2c(=O)n(CCc3ccccc3)c(=O)n(Cc3ccc(-c4ccccc4-c4noc(=O)[nH]4)cc3)c2s1]

A mixture of 6-ethyl-3-(2-phenylethyl)thieno[2,3-d]pyrimidine-2,4(1H,3H)-dione (0.25 g), 3-[4'-(bromomethyl)biphenyl-2-yl]-5-(trichloromethyl)-1,2,4-oxadiazole (0.43 g), potassium carbonate (0.14 g) and N,N-dimethylformamide (10 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 1 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was recrystallized from acetone-diethyl ether to give the title compound as colorless crystals (0.17 g, 38%).

$^1$H NMR (300 MHz, CDCl$_3$)δ1.29 (3H, t, J=7.6), 2.77 (2H,q, J=7.6), 2.96-3.00 (2H, m), 4.25-4.30 (2H, m), 5.16 (2H, s), 7.02 (1H, s),7.20-7.25 (1H, m), 7.26-7.34 (6H, m), 7.38-7.43 (3H, m), 7.52 (1H, t, J=7.6),7.63 (1H, t, J=7.6), 7.86 (1H, d, J=7.6)

Example 7

6-ethyl-3-(2-morpholin-4-ylethyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

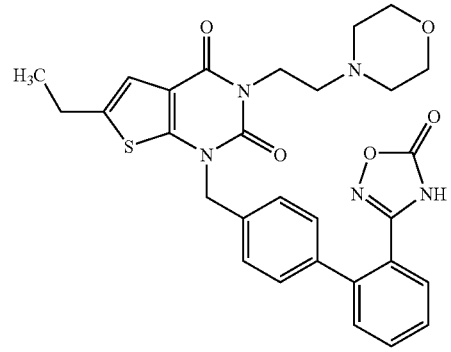 [SMILES: CCc1cc2c(=O)n(CCN3CCOCC3)c(=O)n(Cc3ccc(-c4ccccc4-c4noc(=O)[nH]4)cc3)c2s1]

A mixture of 6-ethyl-3-(2-morpholin-4-ylethyl)thieno[2,3-d]pyrimidine-2,4(1H,3H)-dione (0.25 g), 3-[4'-(bromomethyl)biphenyl-2-yl]-5-(trichloromethyl)-1,2,4-oxadiazole (0.42 g), potassium carbonate (0.13 g) and N,N-dimethylformamide (10 mL) was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 1 hr. The reaction mixture was adjusted to pH 7 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless amorphous solid (0.06 g, 13%).

$^1$H NMR (300 MHz, DMSO-$d_6$) δ1.20 (3H, t, J=7.6), 2.56-2.64 (2H, m), 2.75 (2H, q, J=7.6), 3.27-3.37 (4H, m), 3.46-3.61 (4H, m), 4.09 (2H, t, J=6.6), 5.19 (2H, s), 7.00 (1H, s), 7.24-7.35 (2H, m), 7.34-7.44 (2H, m), 7.55 (2H, dd, J=17.4, 7.2), 7.61-7.75 (2H, m), 12.2 (1H, s)

Example 8

6-ethyl-3-(2-morpholin-4-ylethyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

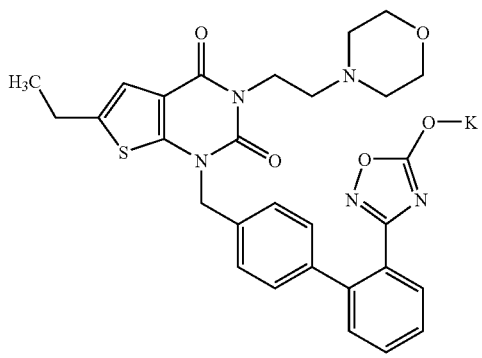

To a solution (6 mL) of 6-ethyl-3-(2-morpholin-4-ylethyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.23 g) in acetone was added a solution (1 mL) of potassium 2-ethylhexanoate (0.075 g) in acetone, and the mixture was stirred at room temperature for 1 hr. The precipitated solid was collected by filtration to give the title compound as colorless crystals (0.16 g, 63%).

$^1$H NMR (300 MHz, DMSO-$d_6$) δ1.20 (3H, t, J=7.2), 2.43 (4H, br), 2.53 (2H, m), 2.75 (2H, q, J=7.2), 3.52 (4H, br), 4.06 (2H, m), 5.14 (2H, s), 6.99 (1H, s), 7.25-7.52 (8H, m)

Example 9

6-ethyl-3-(2-morpholin-4-ylethyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione hydrochloride

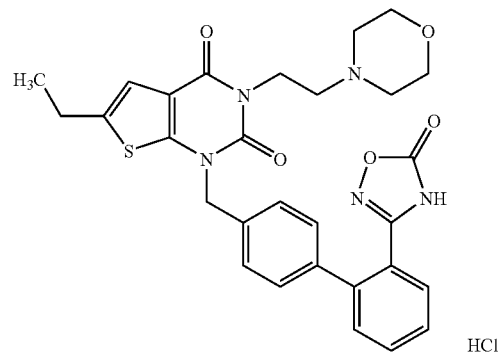 [SMILES: CCc1cc2c(=O)n(CCN3CCOCC3)c(=O)n(Cc3ccc(-c4ccccc4-c4noc(=O)[nH]4)cc3)c2s1 ; Cl]

6-Ethyl-3-(2-morpholin-4-ylethyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.26 g) was dissolved in ethyl acetate (8 mL) and acetone (2 mL), and 4N hydrochloric acid (ethyl acetate solution, 0.11 mL) was added. The precipitated solid was collected by filtration to give the title compound as colorless crystals (0.16. g, 60%).

$^1$H NMR (300 MHz, DMSO-$d_6$) δ1.20 (3H, t, J=7.2), 2.75 (2H, q, J=7.2), 3.14 (2H, br), 3.39 (2H, m), 3.50-3.70 (4H, m), 4.04 (2H, m), 4.30 (2H, m), 5.21 (2H, s), 7.03 (1H, s), 7.31 (2H, d, J=8.1), 7.45-7.71 (6H, m), 10.50 (1H, br), 12.50 (1H, br)

Example 10

3-(2-anilinoethyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

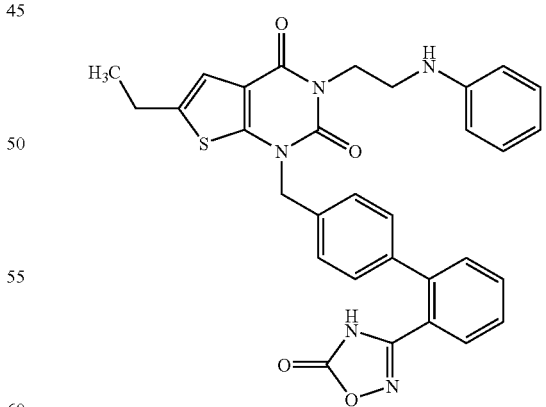

A mixture of 3-(2-anilinoethyl)-6-ethylthieno[2,3-d]pyrimidine-2,4(1H,3H)-dione (0.2 g), 3-[4'-(bromomethyl)biphenyl-2-yl]-5-(trichloromethyl)-1,2,4-oxadiazole (0.33 g), potassium carbonate (0.11 g) and N,N-dimethylformamide (10 mL) was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 1 hr. The reaction mixture was adjusted to pH 7 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was recrystallized from acetone-hexane to give the title compound as colorless crystals (0.2 g, 56%).

$^1$H NMR (400 MHz, CDCl$_3$) δ1.29 (3H, t, J=7.6), 2.76 (2H,q, J=7.6), 3.48 (2H, t, J=6.4), 4.37 (2H, t, J=6.0), 5.17 (2H, s), 6.64(3H, m), 7.01 (1H, s), 7.13 (2H, t, J=8.0), 7.32 (3H, t, J=8.0), 7.41 (1H,d, J=7.6), 7.46 (2H, d, J=8.4), 7.52 (1H, t, J=8.0), 7.62 (1H, t, J=7.6), 7.86 (1H, d, J=8.0)

Example 11

6-ethyl-1-{[2'-(5-oxo-4,5-dihydro-1,2,4-oxadiazol-3-yl)biphenyl-4-yl]methyl}-3-pyridin-2-ylthieno[2,3-d]pyrimidine-2,4(1H,3H)-dione

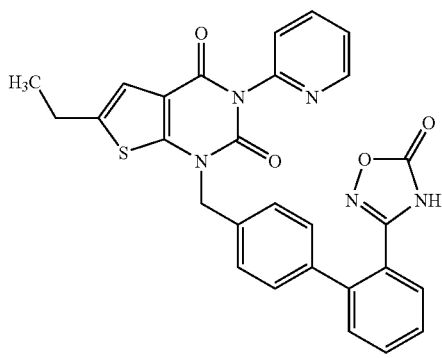 [SMILES: CCc1cc2c(=O)n(-c3ccccn3)c(=O)n(Cc3ccc(-c4ccccc4-c4noc(=O)[nH]4)cc3)c2s1]

A mixture of 6-ethyl-3-pyridin-2-ylthieno[2,3-d]pyrimidine-2,4(1H,3H)-dione (0.25 g), 3-[4'-(bromomethyl)biphenyl-2-yl]-5-(trichloromethyl)-1,2,4-oxadiazole (0.48 g), potassium carbonate (0.15 g) and N,N-dimethylformamide (10 mL) was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 1 hr. The reaction mixture was adjusted to pH 7 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as colorless crystals (0.078 g, 16%).

$^1$H NMR (300 MHz, DMSO-d$_6$) δ1.22 (3H, t, J=7.4), 2.78 (2H, d, J=7.4), 5.21 (2H, s), 6.98-7.09 (1H, m), 7.29-7.63 (8H, m), 7.64-7.76(2H, m), 7.93-8.12 (1H, m), 8.61 (1H, d, J=3.8), 12.4 (1H, s)

Example 12

6-ethyl-1-{[2'-(5-oxo-4,5-dihydro-1,2,4-oxadiazol-3-yl)biphenyl-4-yl]methyl}-3-(3-phenylpropyl)thieno[2,3-d]pyrimidine-2,4(1H,3H)-dione

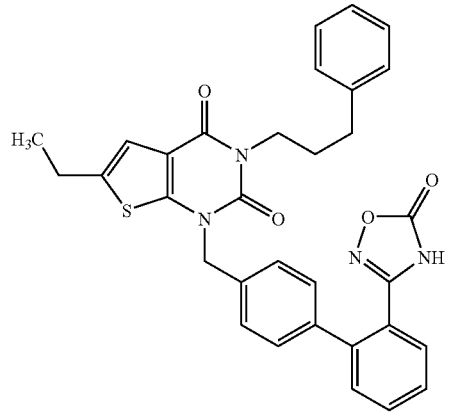 [SMILES: CCc1cc2c(=O)n(CCCc3ccccc3)c(=O)n(Cc3ccc(-c4ccccc4-c4noc(=O)[nH]4)cc3)c2s1]

A mixture of 6-ethyl-3-(3-phenylpropyl)thieno[2,3-d]pyrimidine-2,4(1H,3H)-dione (0.3 g), 3-[4'-(bromomethyl)biphenyl-2-yl]-5-(trichloromethyl)-1,2,4-oxadiazole (0.45 g), potassium carbonate (0.15 g) and N,N-dimethylformamide (10 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless amorphous solid (0.24 g, 45%).

$^1$H NMR (400 MHz, CDCl$_3$) δ1.29 (3H, t, J=7.2), 2.00-2.12 (2H, m), 2.68-2.80 (4H, m), 4.06-4.14 (2H, m), 5.16 (2H, s), 7.01 (1H, s),7.13-7.26 (4H, m), 7.32-7.36 (2H, m), 7.40-7.53 (5H, m), 7.60-7.64 (1H, m),7.82-7.86 (1H, m)

Example 13

6-ethyl-1-{[2'-(5-oxo-4,5-dihydro-1,2,4-oxadiazol-3-yl)biphenyl-4-yl]methyl}-3-(2-phenoxyethyl)thieno[2,3-d]pyrimidine-2,4(1H,3H)-dione

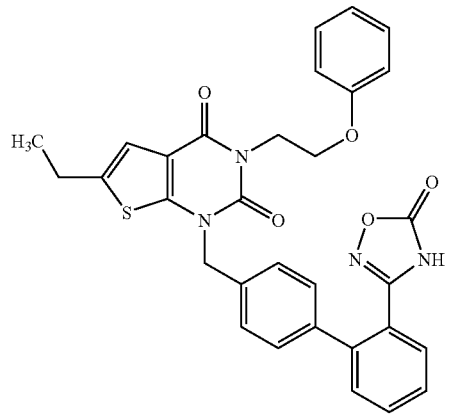 [SMILES: CCc1cc2c(=O)n(CCOc3ccccc3)c(=O)n(Cc3ccc(-c4ccccc4-c4noc(=O)[nH]4)cc3)c2s1]

To a solution (40 mL) of methyl 2-amino-5-ethylthiophene-3-carboxylate (0.5 g) in methylene chloride were added triphosgene (0.35 g) and triethylamine (0.98 mL), and the mixture was stirred at room temperature for 2 hr. To the reaction mixture was added 2-phenoxyethanamine (1 g), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in methanol (50 mL), sodium methoxide (28% methanol solution, 1.3 g) was added, and the mixture was stirred at 60° C. for 1 hr. The reaction mixture was neutralized with hydrochloric acid (10% methanol solution), and the precipitated solid was collected by filtration. The obtained solid was dissolved in N,N-dimethylformamide (10 mL), 3-[4'-(bromomethyl)biphenyl-2-yl]-5-(trichloromethyl)-1,2,4-oxadiazole (0.38 g) and potassium carbonate (0.12 g) were added, and the mixture was stirred at 50° C. for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The precipitated solid was collected by filtration to give the title compound as colorless crystals (0.24 g, 54%).

$^1$H NMR (400 MHz, CDCl$_3$)δ1.27 (3H, t, J=7.2), 2.76 (2H,d, J=7.2), 4.25 (2H, t, J=6.0), 4.48 (2H, t, J=5.6), 5.17 (2H, s),6.89-6.93 (3H, m), 7.02 (1H, s), 7.22-7.26 (2H, m), 7.32 (2H, d, J=8.4),7.40-7.54 (4H, m), 7.62 (1H, t, J=7.6), 7.84 (1H, d, J=8.0)

Example 14

6-ethyl-1-{[2'-(5-oxo-4,5-dihydro-1,2,4-oxadiazol-3-yl)biphenyl-4-yl]methyl}-3-phenylthieno[2,3-d]pyrimidine-2,4(1H,3H)-dione

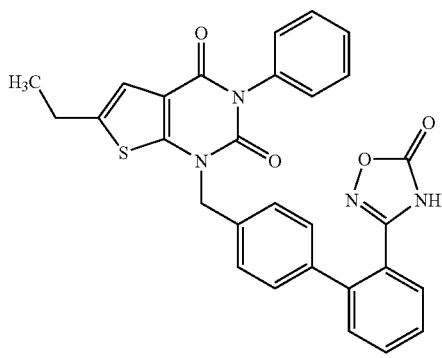 [SMILES: CCc1cc2c(=O)n(-c3ccccc3)c(=O)n(Cc3ccc(-c4ccccc4-c4noc(=O)[nH]4)cc3)c2s1]

A mixture of 6-ethyl-3-phenylthieno[2,3-d]pyrimidine-2,4(1H,3H)-dione (0.25 g), 3-[4'-(bromomethyl)biphenyl-2-yl]-5-(trichloromethyl)-1,2,4-oxadiazole (0.48 g), potassium carbonate (0.15 g) and N,N-dimethylformamide (10 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as colorless crystals (0.1 g, 21%).

$^1$H NMR (300 MHz, DMSO-d$_6$)δ1.21 (3H, t, J=7.6), 2.76 (2H, d, J=7.6), 5.21 (2H, s), 7.04 (1H, s), 7.34 (4H, t, J=7.6), 7.39-7.64(7H, m), 7.68 (2H, dd, J=6.8, 4.9), 12.42 (1H, s)

Example 15

6-ethyl-3-(2-methoxyethyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

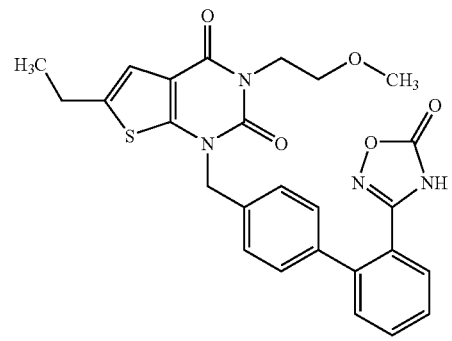 [SMILES: CCc1cc2c(=O)n(CCOC)c(=O)n(Cc3ccc(-c4ccccc4-c4noc(=O)[nH]4)cc3)c2s1]

A mixture of 6-ethyl-3-(2-methoxyethyl)thieno[2,3-d]pyrimidine-2,4(1H,3H)-dione (0.25 g), 3-[4'-(bromomethyl)biphenyl-2-yl]-5-(trichloromethyl)-1,2,4-oxadiazole (0.47 g), potassium carbonate (0.15 g) and N,N-dimethylformamide (10 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as colorless crystals (0.08 g, 16%).

$^1$H NMR (300 MHz, DMSO-d$_6$)δ1.19 (3H, t, J=7.6),2.59-2.84 (2H, m), 3.25 (3H, s), 3.55 (2H, t, J=6.1), 4.13 (2H, t, J=6.1),5.19 (2H, s), 7.00 (1H, s), 7.27-7.35 (2H, m), 7.35-7.47 (2H, m), 7.46-7.62(2H, m), 7.63-7.78 (2H, m), 12.41 (1H, s)

Example 16

3-(2-aminoethyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione hydrochloride

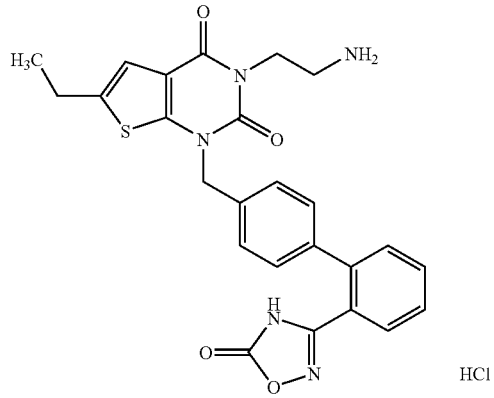 [SMILES: CCc1cc2c(=O)n(CCN)c(=O)n(Cc3ccc(-c4ccccc4-c4noc(=O)[nH]4)cc3)c2s1 ; Cl]

A mixture of tert-butyl [2-(6-ethyl-2,4-dioxo-1,4-dihydrothieno[2,3-d]pyrimidin-3(2H)-yl)ethyl]carbamate (0.5 g), 3-[4'-(bromomethyl)biphenyl-2-yl]-5-(trichloromethyl)-1,2,4-oxadiazole (0.7 g), potassium carbonate (0.22 g) and N,N-dimethylformamide (20 mL) was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 2 hr. The reaction mixture was adjusted to pH 7 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography and dissolved in ethyl acetate (5 mL). 4N Hydrochloric acid (ethyl acetate solution, 4 mL) was added, and the mixture was stirred at room temperature. The precipitated solid was collected by filtration to give the title compound as colorless crystals (0.12 g, 25%).

$^1$H NMR (400 MHz, DMSO-$d_6$)δ1.19 (3H, t, J=7.6), 2.75 (2H, d, J=7.6), 3.06-3.14 (2H, m), 4.20 (2H, d, J=5.6), 5.21 (2H, s), 7.03(1H, s), 7.32 (2H, d, J=8.0), 7.45 (2H, d, J=8.4), 7.52-7.60 (2H, m),7.67-7.62 (2H, m), 7.85 (2H, br), 12.46 (1H, s)

Example 17

6-ethyl-1-{[2'-(5-oxo-4,5-dihydro-1,2,4-oxadiazol-3-yl)biphenyl-4-yl]methyl}-3-(2-pyridin-2-ylethyl)thieno[2,3-d]pyrimidine-2,4(1H,3H)-dione

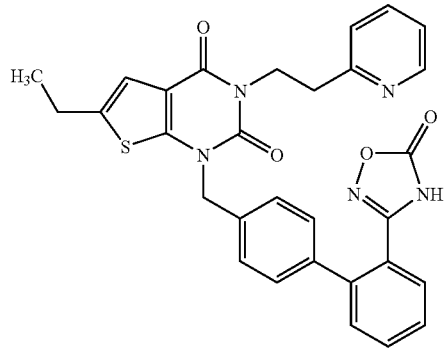 [SMILES: CCc1cc2c(=O)n(CCc3ccccn3)c(=O)n(Cc3ccc(-c4ccccc4-c4noc(=O)[nH]4)cc3)c2s1]

A mixture of 6-ethyl-3-(2-pyridin-2-ylethyl)thieno[2,3-d]pyrimidine-2,4(1H,3H)-dione (0.4 g), 3-[4'-(bromomethyl)biphenyl-2-yl]-5-(trichloromethyl)-1,2,4-oxadiazole (0.58 g), potassium carbonate (0.18 g) and N,N-dimethylformamide (10 mL) was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 1 hr. The reaction mixture was adjusted to pH 7 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless amorphous solid (0.1 g, 14%).

$^1$H NMR (300 MHz, DMSO-$d_6$)δ1.19 (3H, t, J=7.4),2.66-2.81 (2H, m), 3.25 (2H, s), 4.32 (2H, t, J=6.3), 5.12 (2H, s), 6.83-7.11(1H, m), 7.19-7.45 (4H, m), 7.45-7.79 (6H, m), 8.16 (1H, s), 8.64 (1H, s), 12.5(1H, s)

Example 18

5-methyl-1-{[2'-(5-oxo-4,5-dihydro-1,2,4-oxadiazol-3-yl)biphenyl-4-yl]methyl}-3-(2-phenylethyl)thieno[2,3-d]pyrimidine-2,4(1H,3H)-dione

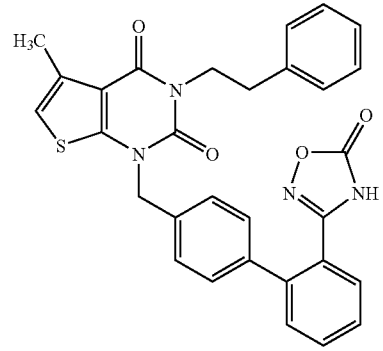 [SMILES: Cc1csc2c1c(=O)n(CCc1ccccc1)c(=O)n2Cc1ccc(-c2ccccc2-c2noc(=O)[nH]2)cc1]

A mixture of 5-methyl-3-(2-phenylethyl)thieno[2,3-d]pyrimidine-2,4(1H,3H)-dione (1.5 g), 3-[4'-(bromomethyl)biphenyl-2-yl]-5-(trichloromethyl)-1,2,4-oxadiazole (2.49 g), potassium carbonate (0.8 g) and N,N-dimethylformamide (30 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (15 mL) and methanol (15 mL). 1N Aqueous sodium hydroxide solution (15 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as colorless crystals (1.27 g, 46%).

$^1$H NMR (400 MHz, CDCl$_3$)δ2.51 (3H, s), 3.99-3.03 (2H, m),4.27-4.31 (2H, m), 5.22 (2H, s), 6.47 (1H, s), 7.21-7.35 (7H, m), 7.40-7.45(3H, m), 7.51-7.55 (1H, m), 7.63 (1H, t, J=8.0), 7.88 (1H, d, J=7.6)

Example 19

6-ethyl-3-[(5-methylpyrazin-2-yl)methyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

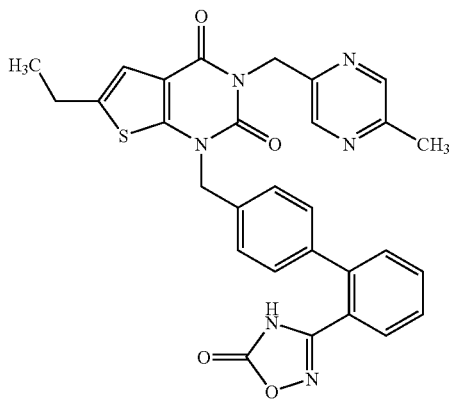 [SMILES: CCc1cc2c(=O)n(Cc3cnc(C)cn3)c(=O)n(Cc3ccc(-c4ccccc4-c4noc(=O)[nH]4)cc3)c2s1]

A mixture of 6-ethyl-3-[(5-methylpyrazin-2-yl)methyl]thieno[2,3-d]pyrimidine-2,4(1H,3H)-dione (0.3 g), 3-[4'-(bromomethyl)biphenyl-2-yl]-5-(trichloromethyl)-1,2,4-oxadiazole (0.47 g), potassium carbonate (0.27 g) and N,N-dimethylformamide (10 mL) was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 1 hr. The reaction mixture was adjusted to pH 7 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The precipitated solid was collected by filtration to give the title compound as colorless crystals (0.076 g, 14%).

$^1$H NMR (400 MHz, DMSO-d$_6$)δ1.20 (3H, t, J=7.6), 2.46 (3H, s), 2.75 (2H, d, J=7.6), 5.21 (2H, s), 5.28 (2H, s), 7.01 (1H, s), 7.32(2H, d, J=8.0), 7.39 (2H, d, J=8.0), 7.53-7.59 (2H, m), 7.67-7.72 (2H, m),8.41 (1H, s), 8.78 (1H, s), 12.41 (1H, s)

Example 20

1-{[2'-(5-oxo-4,5-dihydro-1,2,4-oxadiazol-3-yl)biphenyl-4-yl]methyl}-3-(2-phenylethyl)thieno[2,3-d]pyrimidine-2,4(1H,3H)-dione

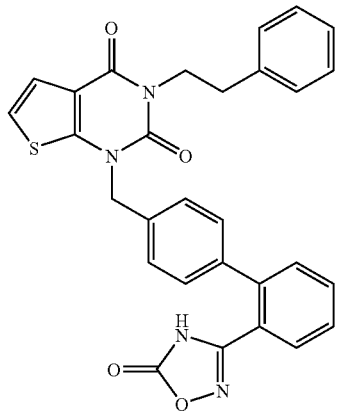 [SMILES: O=c1[nH]c(-c2ccccc2-c2ccc(Cn3c(=O)n(CCc4ccccc4)c(=O)c4ccsc43)cc2)no1]

A mixture of 3-(2-phenylethyl)thieno[2,3-d]pyrimidine-2,4(1H,3H)-dione (4.0 g), 3-[4'-(bromomethyl)biphenyl-2-yl]-5-(trichloromethyl)-1,2,4-oxadiazole (6.3 g), potassium carbonate (2 g) and N,N-dimethylformamide (50 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (15 mL) and methanol (15 mL). 1N Aqueous sodium hydroxide solution (15 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The precipitated solid was collected by filtration to give the title compound as colorless crystals (0.75 g, 10%).

$^1$H NMR (400 MHz, DMSO-d$_6$)δ2.98-3.02 (2H, m), 4.28-4.31(2H, m), 5.22 (2H, s), 6.84 (1H, d, J=5.6), 7.20-7.35 (7H, m), 7.40-7.43 (3H,m), 7.50-7.55 (1H, m), 7.60-7.65 (2H, m), 7.84 (1H, d, J=7.6)

Example 21

3-benzyl-6-methoxy-5-methyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

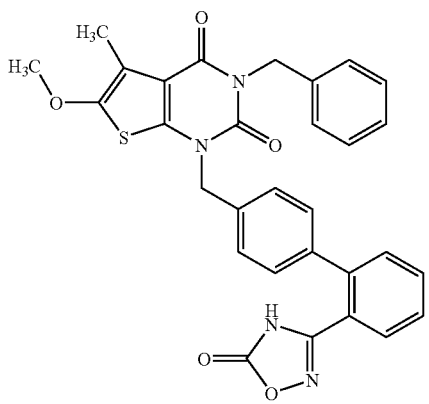 [SMILES: COc1sc2c(c1C)c(=O)n(Cc1ccccc1)c(=O)n2Cc1ccc(-c2ccccc2-c2noc(=O)[nH]2)cc1]

A mixture of 3-benzyl-6-methoxy-5-methylthieno[2,3-d]pyrimidine-2,4(1H,3H)-dione (0.50 g), 3-[4'-(bromomethyl)biphenyl-2-yl]-5-(trichloromethyl)-1,2,4-oxadiazole (0.82 g), potassium carbonate (0.46 g) and N,N-dimethylformamide (20 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (4 mL) and methanol (4 mL). 1N Aqueous sodium hydroxide solution (4 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (0.90 g, 97%).

$^1$H NMR (300 MHz, DMSO-d$_6$)δ2.22 (3H, s), 3.81 (3H, s),5.11 (2H, s), 5.17 (2H, s), 7.18-7.44 (9H, m), 7.47-7.62 (2H, m), 7.63-7.75(2H, m), 12.42 (1H, br)

Example 22

6-methoxy-5-methyl-1-{[2'-(5-oxo-4,5-dihydro-1,2,4-oxadiazol-3-yl)biphenyl-4-yl]methyl}-3-(2-phenylethyl)thieno[2,3-d]pyrimidine-2,4(1H,3H)-dione

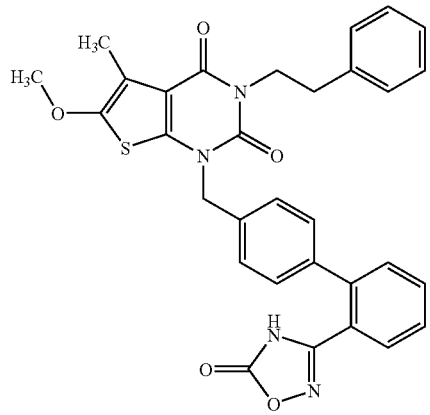 [SMILES: COc1sc2c(c1C)c(=O)n(CCc1ccccc1)c(=O)n2Cc1ccc(-c2ccccc2-c2noc(=O)[nH]2)cc1]

A mixture of 6-methoxy-5-methyl-3-(2-phenylethyl)thieno[2,3-d]pyrimidine-2,4(1H,3H)-dione (0.50 g), 3-[4'-(bromomethyl)biphenyl-2-yl]-5-(trichloromethyl)-1,2,4-oxadiazole (0.78 g), potassium carbonate (0.46 g) and N,N-dimethylformamide (20 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (4 mL) and methanol (4 mL). 1N Aqueous sodium hydroxide solution (4 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (0.86 g, 99%).

$^1$H NMR (300 MHz, DMSO-d$_6$)δ2.36 (3H, s), 2.90 (3H, s),3.80 (2H, t, J=8.1), 4.14 (2H, t, J=8.1), 5.13 (2H, s), 7.18-7.36 (9H, m),7.48-7.63 (2H, m), 7.69-7.75 (2H, m), 12.42 (1H, br)

Example 23

6-methoxy-5-methyl-1-{[2'-(5-oxo-4,5-dihydro-1,2,4-oxadiazol-3-yl)biphenyl-4-yl]methyl}-3-[(1S)-1-phenylethyl]thieno[2,3-d]pyrimidine-2,4(1H,3H)-dione

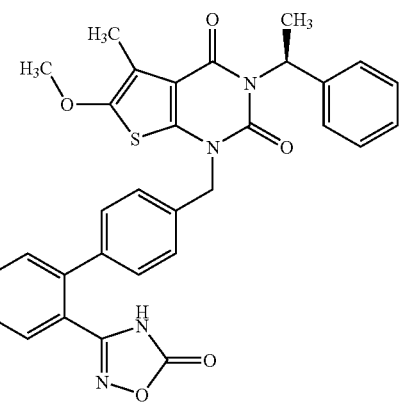

A mixture of 6-methoxy-5-methyl-3-[(1S)-1-phenylethyl]thieno[2,3-d]pyrimidine-2,4(1H,3H)-dione (0.43 g), 3-[4'-(bromomethyl)biphenyl-2-yl]-5-(trichloromethyl)-1,2,4-oxadiazole (0.67 g), potassium carbonate (0.38 g) and N,N-dimethylformamide (20 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (4 mL) and methanol (4 mL). 1N Aqueous sodium hydroxide solution (4 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (0.74 g, 94%).

$^1$H NMR (300 MHz, DMSO-d$_6$)δ1.83 (3H, d, J=7.2), 2.21 (3H, s), 3.80 (3H, s), 5.09 (2H, s), 6.25 (1H, m), 6.98-7.36 (9H, m), 7.42-7.52(2H, m), 7.60-7.65 (2H, m)

Example 24

6-methoxy-5-methyl-1-{[2'-(5-oxo-4,5-dihydro-1,2,4-oxadiazol-3-yl)biphenyl-4-yl]methyl}-3-[(1R)-1-phenylethyl]thieno[2,3-d]pyrimidine-2,4(1H,3H)-dione

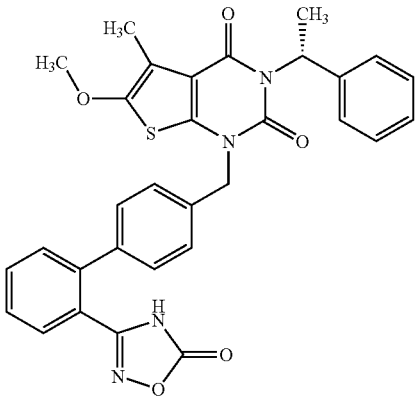 [SMILES: COc1sc2c(c1C)c(=O)n([C@H](C)c1ccccc1)c(=O)n2Cc1ccc(-c2ccccc2-c2noc(=O)[nH]2)cc1]

A mixture of 6-methoxy-5-methyl-3-[(1R)-1-phenylethyl]thieno[2,3-d]pyrimidine-2,4(1H,3H)-dione (0.62 g), 3-[4'-(bromomethyl)biphenyl-2-yl]-5-(trichloromethyl)-1,2,4-oxadiazole (0.97 g), potassium carbonate (0.54 g) and N,N-dimethylformamide (20 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (4 mL) and methanol (4 mL). 1N Aqueous sodium hydroxide solution (4 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (1.0 g, 91%).

$^1$H NMR (300 MHz, DMSO-$d_6$)δ1.83 (3H, d, J=6.9), 2.21 (3H, s), 3.80 (3H, s), 5.10 (2H, s), 6.25 (1H, m), 7.11-7.33 (9H, m), 7.51-7.60(2H, m), 7.63-7.74 (2H, m)

Example 25

6-methoxy-5-methyl-3-(2-morpholin-4-ylethyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

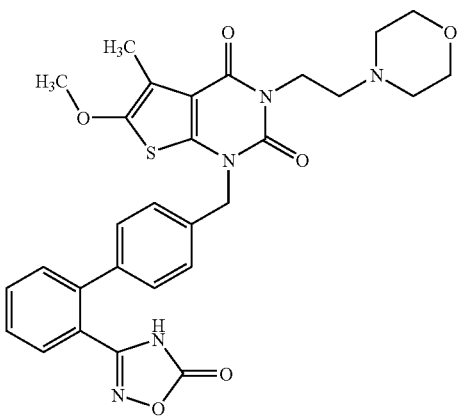 [SMILES: COc1sc2c(c1C)c(=O)n(CCN1CCOCC1)c(=O)n2Cc1ccc(-c2ccccc2-c2noc(=O)[nH]2)cc1]

A mixture of 6-methoxy-5-methyl-3-(2-morpholin-4-ylethyl)thieno[2,3-d]pyrimidine-2,4(1H,3H)-dione (0.51 g), 3-[4'-(bromomethyl)biphenyl-2-yl]-5-(trichloromethyl)-1,2,4-oxadiazole (0.78 g), potassium carbonate (0.43 g) and N,N-dimethylformamide (20 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (4 mL) and methanol (4 mL). 1N Aqueous sodium hydroxide solution (4 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (0.76 g, 84%).

$^1$H NMR (300 MHz, DMSO-$d_6$)δ2.22 (3H, s), 2.47 (4H, br),2.55 (2H, t, J=3.3), 3.54 (4H, br), 3.80 (3H, s), 4.06 (2H, t, J=3.3), 5.15(2H, s), 7.29-7.40 (4H, m), 7.46-7.62 (2H, m), 7.65-7.71 (2H, m)

Example 26

6-methyl-1-{[2'-(5-oxo-4,5-dihydro-1,2,4-oxadiazol-3-yl)biphenyl-4-yl]methyl}-3-(2-phenylethyl)thieno[2,3-d]pyrimidine-2,4(1H,3H)-dione

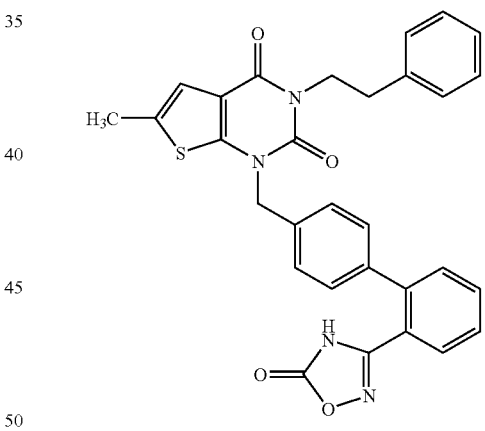

A mixture of 6-methyl-3-(2-phenylethyl)thieno[2,3-d]pyrimidine-2,4(1H,3H)-dione (0.25 g), 3-[4'-(bromomethyl)biphenyl-2-yl]-5-(trichloromethyl)-1,2,4-oxadiazole (0.45 g), potassium carbonate (0.15 g) and N,N-dimethylformamide (10 mL) was stirred at room temperature for 2 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 2 hr. The reaction mixture was adjusted to pH 4 with water and 1N hydrochloric acid, and extracted with chloroform. The obtained chloroform layer was washed with saturated

Example 27

3-(5-chloropyridin-2-yl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

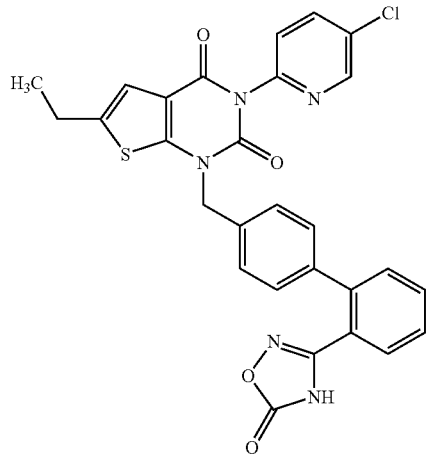 [SMILES: CCc1cc2c(=O)n(-c3ccc(Cl)cn3)c(=O)n(Cc3ccc(-c4ccccc4-c4noc(=O)[nH]4)cc3)c2s1]

To a solution (75 mL) of methyl 2-amino-5-ethylthiophene-3-carboxylate (1.0 g) in methylene chloride were added triphosgene (0.69 g) and triethylamine (1.19 mL), and the mixture was stirred at room temperature for 2 hr. To the reaction mixture was added 5-chloropyridin-2-amine (1.04 g), and the mixture was further stirred at room temperature for 1 hr, and the precipitated solid was collected by filtration. The obtained solid was dissolved in methanol (5 mL), sodium methoxide (28% methanol solution, 5.0 g) was added, and the mixture was stirred at 60° C. for 1 hr. The reaction mixture was neutralized with hydrochloric acid (10% methanol solution), and the precipitated solid was collected by filtration. The obtained solid was dissolved in N,N-dimethylformamide (10 mL), 3-[4'-(bromomethyl)biphenyl-2-yl]-5-(trichloromethyl)-1,2,4-oxadiazole (0.45 g) and potassium carbonate (0.15 g) were added, and the mixture was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and methanol (5 mL). 1N Aqueous sodium hydroxide solution (5 mL) was added, and the mixture was stirred at room temperature for 2 hr. The reaction mixture was adjusted to pH 7 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.16 g, 3%).

$^1$H NMR (300 MHz, DMSO-d$_6$)δ1.22 (3H, t, J=7.6), 2.77 (2H, q, J=7.6), 5.22 (2H, s), 7.05 (1H, s), 7.34 (2H, d, J=8.0), 7.45 (2H, d, J=8.0), 7.53-7.59 (2H, m), 7.65-7.72 (3H, m), 8.18 (1H, d, J=8.8), 8.69(1H, s), 12.40 (1H, s)

Example 28

2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]ethyl methanesulfonate

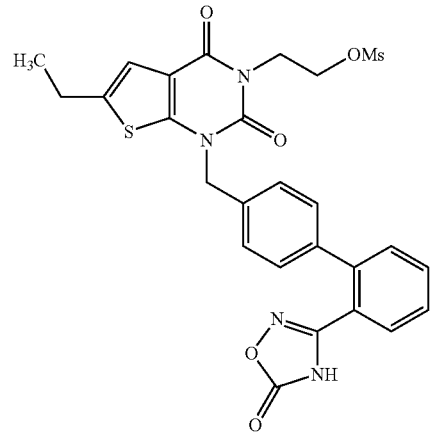 [SMILES: CCc1cc2c(=O)n(CCOS(C)(=O)=O)c(=O)n(Cc3ccc(-c4ccccc4-c4noc(=O)[nH]4)cc3)c2s1]

To a solution (450 ml) of methyl 2-amino-5-ethylthiophene-3-carboxylate (18 g) in methylene chloride were added triphosgene (12.5 g) and triethylamine (21.4 mL), and the mixture was stirred at room temperature for 2 hr. To the reaction mixture was added 2-aminoethanol (17.6 mL), and the mixture was further stirred at room temperature for 1 hr. The reaction mixture was washed with water and saturated brine, and dried over anhydrous magnesium sulfate. The solvent was evaporated under reduced pressure. The obtained residue was dissolved in methanol (200 mL), sodium methoxide (21.7 g) was added, and the mixture was stirred at 60° C. for 2 hr. The reaction mixture was neutralized with hydrochloric acid (10% methanol solution), insoluble material was filtered off, and the solvent was evaporated under reduced pressure. The obtained residue was dissolved in N,N-dimethylformamide (150 mL), 3-[4'-(bromomethyl)biphenyl-2-yl]-5-(trichloromethyl)-1,2,4-oxadiazole (12 g) and potassium carbonate (7.7 g) were added, and the mixture was stirred at room temperature for 3 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was purified by silica gel column chromatography and dissolved in methylene chloride (100 mL). Triethylamine (2.23 mL), methanesulfonylchloride (1.24 mL) and N,N-dimethylpyridin-4-amine (0.16 g) were added, and the mixture was stirred at room temperature for 1 hr. The reaction mixture was washed successively with water and saturated brine, and dried over anhydrous magnesium sulfate. The solvent was evaporated under reduced pressure. The obtained residue was dissolved in tetrahydrofuran (30 mL) and acetone (30 mL). 1N Aqueous sodium hydroxide solution (20 mL) was added, and the mixture was stirred at room temperature for 30 min. The reaction mixture was adjusted to pH 4 with water and 1N hydrochloric acid, and extracted with chloroform. The obtained chloroform layer was washed with saturated brine, and dried over anhydrous magnesium sulfate. The solvent was evaporated under reduced pressure. The residue was purified by silica gel column chromatography to give the title compound as colorless crystals (3.5 g, 6%).

$^1$H NMR (300 MHz, DMSO-d$_6$)δ1.20 (3H, t, J=7.6), 2.74 (2H, q, J=7.6), 3.16 (3H, s), 4.29 (2H, t, J=5.2), 4.46 (2H, t, J=5.2),5.21 (2H, s), 7.02 (1H, s), 7.29-7.31 (2H, m), 7.40-7.42 (2H, m), 7.52-7.57(2H, m), 7.66-7.70 (2H, m), 12.4 (1H, s)

brine, and dried over anhydrous magnesium sulfate. The solvent was evaporated under reduced pressure. The precipitated solid was collected by filtration to give the title compound as colorless crystals (0.18 g, 38%).

$^1$H NMR (300 MHz, DMSO-d$_6$)δ2.38 (3H, s), 2.78-3.01 (2H,m), 4.08-4.24 (2H, m), 5.16 (2H, s), 6.97 (1H, s), 7.18-7.36 (9H, m), 7.56 (2H,dd, J=14.0, 7.6), 7.65-7.78 (2H, m), 12.42 (1 H, s)

Example 29

6-ethyl-1-{[2'-(5-oxo-4,5-dihydro-1,2,4-oxadiazol-3-yl)biphenyl-4-yl]methyl}-3-(2-piperidin-1-ylethyl)thieno[2,3-d]pyrimidine-2,4(1H,3H)-dione hydrochloride

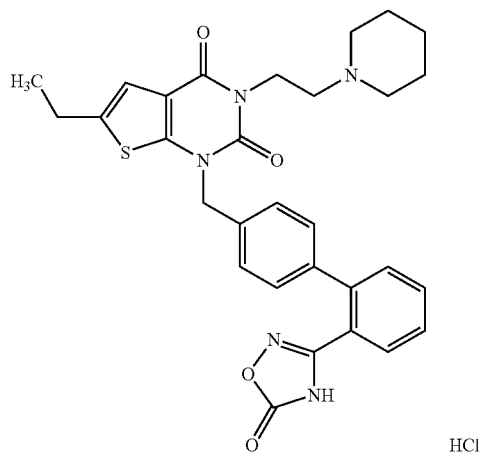 [SMILES: CCc1cc2c(=O)n(CCN3CCCCC3)c(=O)n(Cc3ccc(-c4ccccc4-c4noc(=O)[nH]4)cc3)c2s1 ; Cl]

A mixture of 2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]ethyl methanesulfonate (0.3 g), potassium iodide (0.087 g), piperidine (0.26 mL) and acetonitrile (20 mL) was stirred at 80° C. for 2 hr. Insoluble material was filtered off, and the solvent was evaporated under reduced pressure. The obtained residue was purified by preparative HPLC, and dissolved in ethyl acetate (10 mL). Hydrochloric acid (4N ethyl acetate solution, 0.5 mL) was added, and the mixture was stirred at room temperature. The precipitated solid was collected by filtration to give the title compound as a colorless amorphous solid (0.14 g, 45%).

$^1$H NMR (300 MHz, DMSO-$d_6$)δ1.20 (3H, t, J=7.4), 1.31-1.88 (6H, m), 2.76 (2H, q, J=7.4), 2.86-3.04.(2H, m), 3.29-3.42 (2H, m), 3.63 (2H, s), 4.29 (2H, t, J=5.7), 5.21 (2H, s), 7.05 (1H, s), 7.32 (2H, d, J=8.1), 7.46 (2H, d, J=8.3), 7.51-7.62 (2H, m), 7.66-7.75 (2H, m), 12.49 (1H,s)

Example 30

6-ethyl-3-[2-(4-methylpiperazin-1-yl)ethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione hydrochloride

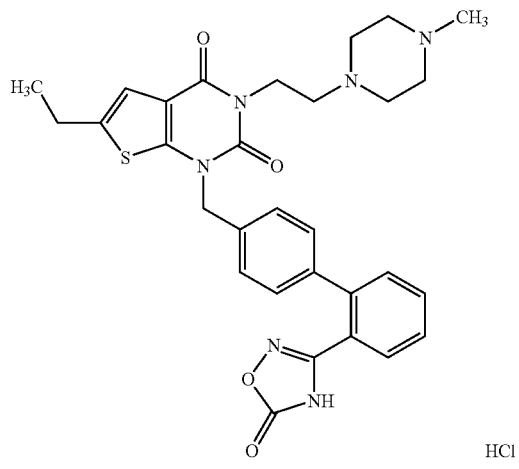 [SMILES: CCc1cc2c(=O)n(CCN3CCN(C)CC3)c(=O)n(Cc3ccc(-c4ccccc4-c4noc(=O)[nH]4)cc3)c2s1 ; Cl]

A mixture of 2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]ethyl methanesulfonate (0.3 g), potassium iodide (0.087 g), N-methylpiperazine (0.29 mL) and acetonitrile (20 mL) was stirred at 80° C. for 2 hr. Insoluble material was filtered off, and the solvent was evaporated under reduced pressure. The obtained residue was purified by preparative HPLC and dissolved in ethyl acetate (10 mL). Hydrochloric acid (4N ethyl acetate solution, 0.5 mL) was added, and the mixture was stirred at room temperature. The precipitated solid was collected by filtration to give the title compound as a colorless amorphous solid (0.13 g, 40%). $^1$H NMR (300 MHz, DMSO-$d_6$)δ1.20 (3H, t, J=7.6), 1.95-2.10 (3H, m), 2.68-2.83 (2H, m), 2.83-3.80 (10H, m), 4.31 (2H, t, J=5.7), 5.21 (2H, s), 6.95-7.13 (1H, m), 7.32 (2H, d, J=8.3), 7.41-7.62 (4H,m), 7.64-7.76 (2H, m), 12.4 (1H, br)

Example 31

3-[2-(4-acetylpiperazin-1-yl)ethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione hydrochloride

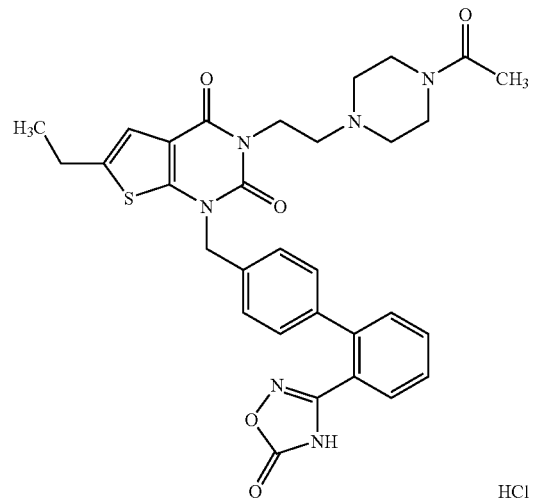 [SMILES: CCc1cc2c(=O)n(CCN3CCN(C(C)=O)CC3)c(=O)n(Cc3ccc(-c4ccccc4-c4noc(=O)[nH]4)cc3)c2s1 ; Cl]

A mixture of 2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]ethyl methanesulfonate (0.3 g), potassium iodide (0.087 g), N-acetylpiperazine (0.39 g) and acetonitrile (20 mL) was stirred at 80° C. for 2 hr. Insoluble material was filtered off, and the solvent was evaporated under reduced pressure. The obtained residue was purified by preparative HPLC and dissolved in ethyl acetate (10 mL). Hydrochloric acid (4N ethyl acetate solution, 0.5 mL) was added, and the mixture was stirred at room temperature. The precipitated solid was collected by filtration to give the title compound as a colorless amorphous solid (0.13 g, 39%).

$^1$H NMR (300 MHz, DMSO-$d_6$)δ1.20 (3H, t, J=7.6), 1.95-2.10 (3H, m), 2.68-2.83 (2H, m), 2.83-3.80 (10H, m), 4.31 (2H, t, J=5.7), 5.21 (2H, s), 6.95-7.13 (1H, m), 7.32 (2H, d, J=8.3), 7.41-7.62 (4H,m), 7.64-7.76 (2H, m), 12.48 (1H, s)

Example 32

6-ethyl-3-(6-methoxypyridazin-3-yl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

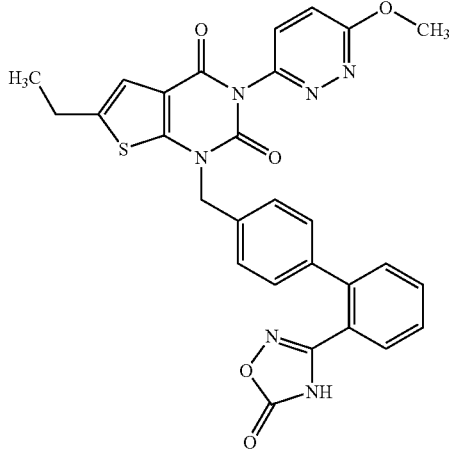 [SMILES: CCc1cc2c(=O)n(-c3ccc(OC)nn3)c(=O)n(Cc3ccc(-c4ccccc4-c4noc(=O)[nH]4)cc3)c2s1]

A mixture of 6-ethyl-3-(6-methoxypyridazin-3-yl)thieno[2,3-d]pyrimidine-2,4(1H,3H)-dione (0.3 g), 3-[4'-(bromomethyl)biphenyl-2-yl]-5-(trichloromethyl)-1,2,4-oxadiazole (0.86 g), potassium carbonate (0.27 g) and N,N-dimethylformamide (10 mL) was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and acetone (5 mL). 1N Aqueous sodium hydroxide solution (2 mL) was added, and the mixture was stirred at room temperature for 2 hr. The reaction mixture was adjusted to pH 7 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The obtained residue was purified by silica gel column chromatography to give the title compound as colorless crystals (0.17 g, 30%).

$^1$H NMR (300 MHz, DMSO-$d_6$)δ1.22 (3H, s), 2.73-2.81 (2H,m), 4.10 (3H, s), 5.16-5.30 (2H, m), 7.08 (1H, s), 7.34 (2H, d, J=8.3), 7.48(3H, d, J=9.1), 7.52-7.61 (2H, m), 7.66-7.74 (2H, m), 7.86 (1H, d, J=9.5),12.41 (1H, s)

Example 33

6-ethyl-1-{[2'-(5-oxo-4,5-dihydro-1,2,4-oxadiazol-3-yl)biphenyl-4-yl]methyl}-3-[2-(2-thienyl)ethyl]thieno[2,3-d]pyrimidine-2,4(1H, 3H)-dione

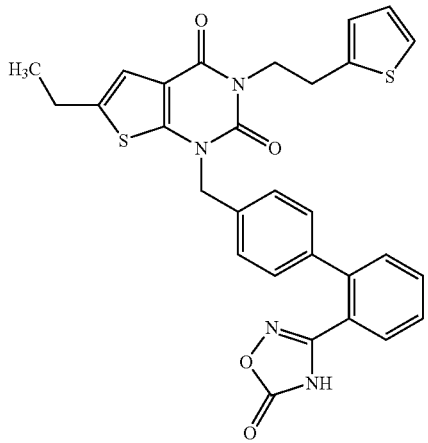 [SMILES: CCc1cc2c(=O)n(CCc3cccs3)c(=O)n(Cc3ccc(-c4ccccc4-c4noc(=O)[nH]4)cc3)c2s1]

A mixture of 6-ethyl-3-[2-(2-thienyl)ethyl]thieno[2,3-d]pyrimidine-2,4(1H,3H)-dione (0.36 g), 3-[4'-(bromomethyl)biphenyl-2-yl]-5-(trichloromethyl)-1,2,4-oxadiazole (0.76 g), potassium carbonate (0.32 g) and N,N-dimethylformamide (10 mL) was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and acetone (5 mL). 1N Aqueous sodium hydroxide solution (2 mL) was added, and the mixture was stirred at room temperature for 2 hr. The reaction mixture was adjusted to pH 7 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as colorless crystals (0.32 g, 49%).

$^1$H NMR (300 MHz, DMSO-$d_6$)δ1.19 (3H, t, J=7.4),2.65-2.83 (2H, m), 3.15 (2H, t, J=7.4), 4.18 (2H, t, J=7.6), 5.18 (2H, s),6.85-7.05 (3H, m), 7.22-7.45 (5H, m), 7.48-7.61 (2H, m), 7.63-7.83 (2H, m),12.4 (1H, s)

Example 34

6-ethyl-3-(5-methylisoxazol-3-yl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

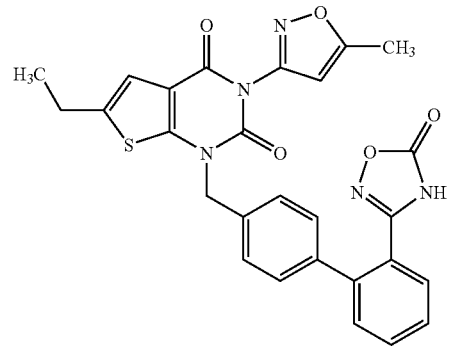 [SMILES: CCc1cc2c(=O)n(-c3cc(C)on3)c(=O)n(Cc3ccc(-c4ccccc4-c4noc(=O)[nH]4)cc3)c2s1]

A mixture of 6-ethyl-3-(5-methylisoxazol-3-yl)thieno[2,3-d]pyrimidine-2,4(1H,3H)-dione (0.6 g), 3-[4'-(bromomethyl)biphenyl-2-yl]-5-(trichloromethyl)-1,2,4-oxadiazole (1.1 g), potassium carbonate (0.6 g) and N,N-dimethylformamide (20 mL) was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and acetone (5 mL). 1N Aqueous sodium hydroxide solution (2 mL) was added, and the mixture was stirred at room temperature for 2 hr. The reaction mixture was adjusted to pH 7 with water and 1N hydrochloric acid, and the mixture was extracted with ethyl s acetate. The obtained ethyl s acetate layer was washed with saturated brine, and dried over anhydrous magnesium sulfate. The solvent was evaporated under reduced pressure. The residue was purified by silica gel column chromatography to give the title compound as colorless crystals (0.25 g, 22%).

$^1$H NMR (300 MHz, DMSO-$d_6$)δ1.21 (3H, t, J=7.4), 2.68-2.85(2H, m), 5.20 (2H, s), 6.46 (1H, s), 7.02-7.10 (1H, m), 7.27-7.38 (2H, m),7.42-7.50 (2H, m), 7.49-7.63 (2H, m), 7.63-7.76 (2H, m), 12.4 (1H, s)

Example 35

6-ethyl-1-{[2'-(5-oxo-4,5-dihydro-1,2,4-oxadiazol-3-yl)biphenyl-4-yl]methyl}-3-quinolin-3-ylthieno[2,3-d]pyrimidine-2,4(1H,3H)-dione

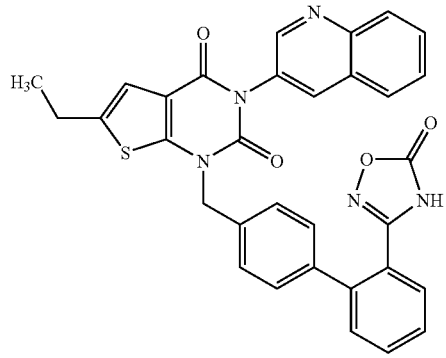 [SMILES: CCc1cc2c(=O)n(-c3cnc4ccccc4c3)c(=O)n(Cc3ccc(-c4ccccc4-c4noc(=O)[nH]4)cc3)c2s1]

A mixture of 6-ethyl-3-quinolin-3-ylthieno[2,3-d]pyrimidine-2,4(1H,3H)-dione (0.6 g), 3-[4'-(bromomethyl)biphenyl-2-yl]-5-(trichloromethyl)-1,2,4-oxadiazole (0.8 g), potassium carbonate (0.6 g) and N,N-dimethylformamide (20 mL) was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and acetone (5 mL). 1N Aqueous sodium hydroxide solution (2 mL) was added, and the mixture was stirred at room temperature for 2 hr. The reaction mixture was adjusted to pH 7 with water and 1N hydrochloric acid, and extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as colorless crystals (0.37 g, 35%).

$^1$H NMR (300 MHz, DMSO-$d_6$)δ1.22 (3H, t, J=7.4), 2.70-2.88 (2H, m), 5.26 (2H, s), 7.09 (1H, s), 7.35 (2H, d, J=8.3), 7.43-7.63(4H, m), 7.65-7.77 (3H, m), 7.82-7.91 (1H, m), 8.00-8.17 (2H, m), 8.47 (1H, d,J=2.5), 8.89 (1H, d, J=2.5), 12.42 (1H, s)

Example 36

3-(4,6-dimethoxypyrimidin-2-yl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

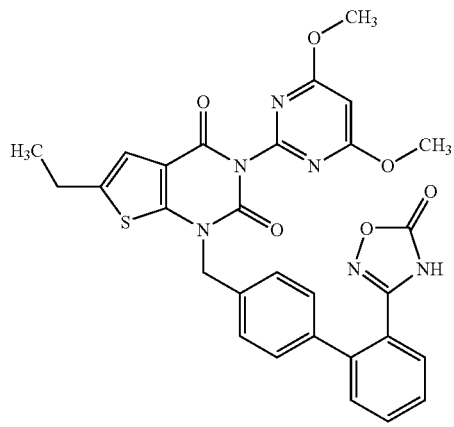 [SMILES: CCc1cc2c(=O)n(-c3nc(OC)cc(OC)n3)c(=O)n(Cc3ccc(-c4ccccc4-c4noc(=O)[nH]4)cc3)c2s1]

A mixture of 3-(4,6-dimethoxypyrimidin-2-yl)-6-ethylthieno[2,3-d]pyrimidine-2,4(1H,3H)-dione (0.3 g), 3-[4'-(bromomethyl)biphenyl-2-yl]-5-(trichloromethyl)-1,2,4-oxadiazole (0.24 g), potassium carbonate (0.25 g) and N,N-dimethylformamide (10 mL) was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (5 mL) and acetone (5 mL). 1N Aqueous sodium hydroxide solution (2 mL) was added, and the mixture was stirred at room temperature for 2 hr. The reaction mixture was adjusted to pH 7 with water and 1N hydrochloric acid, and extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as colorless crystals (0.17 g, 31%).

$^1$H NMR (300 MHz, DMSO-$d_6$)δ1.16-1.29 (3H, m), 2.69-2.88(2H, m), 3.91 (6H, s), 5.21 (2H, s), 6.48 (1H, s), 7.05 (1H, s), 7.32-7.40 (2H,m), 7.39-7.49 (2H, m), 7.53-7.66 (2H, m), 7.63-7.77 (2H, m), 12.41 (1H, s)

Example 37

3-(2-morpholin-4-ylethyl)-1-{[2'-(5-oxo-4,5-dihydro-1,2,4-oxadiazol-3-yl)biphenyl-4-yl]methyl}-6-propylthieno[2,3-d]pyrimidine-2,4(1H,3H)-dione

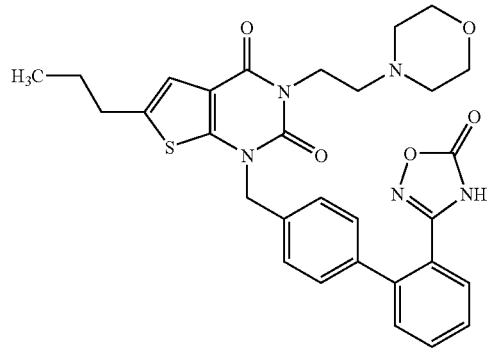 [SMILES: CCCc1cc2c(=O)n(CCN3CCOCC3)c(=O)n(Cc3ccc(-c4ccccc4-c4noc(=O)[nH]4)cc3)c2s1]

A mixture of 3-(2-morpholin-4-ylethyl)-6-propylthieno[2,3-d]pyrimidine-2,4(1H,3H)-dione (0.5 g), 3-[4'-(bromomethyl)biphenyl-2-yl]-5-(trichloromethyl)-1,2,4-oxadiazole (0.83 g), potassium carbonate (0.43 g) and acetonitrile (20 mL) was stirred at room temperature for 2 hr. Insoluble material was filtered off, and the filtrate was concentrated. The obtained residue was purified by silica gel column chromatography and dissolved in tetrahydrofuran (4 mL) and methanol (4 mL). 1N Aqueous sodium hydroxide solution (4 ml) was added, and the mixture was stirred at room temperature for 2 hr. The reaction mixture was adjusted to pH 4 with water and 1N hydrochloric acid, and extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (0.29 g, 32%).

$^1$H NMR (300 MHz, DMSO-d$_6$)δ0.90 (3H, t, J=7.2), 1.58 (2H, m), 2.67-2.84 (8H, m), 3.61 (4H, br), 4.14 (2H, br), 5.20 (2H, s), 7.01(1H, s), 7.31 (2H, d, J=8.4), 7.41 (2H, d, J=8.4), 7.50-7.73 (4H, m)

Example 38

6-isopropyl-3-(2-morpholin-4-ylethyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

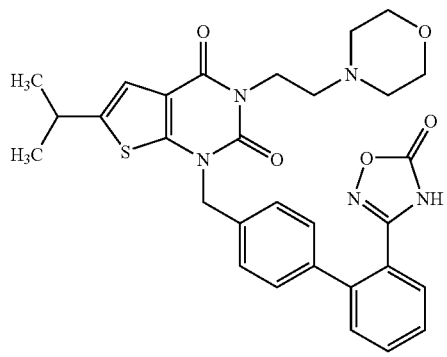 [SMILES: CC(C)c1cc2c(=O)n(CCN3CCOCC3)c(=O)n(Cc3ccc(-c4ccccc4-c4noc(=O)[nH]4)cc3)c2s1]

A mixture of 6-isopropyl-3-(2-morpholin-4-ylethyl)thieno[2,3-d]pyrimidine-2,4(1H,3H)-dione (0.5 g), 3-[4'-(bromomethyl)biphenyl-2-yl]-5-(trichloromethyl)-1,2,4-oxadiazole (0.83 g), potassium carbonate (0.43 g) and acetonitrile (20 mL) was stirred at room temperature for 2 hr. Insoluble material was filtered off, and the filtrate was concentrated. The obtained residue was purified by silica gel column chromatography and dissolved in tetrahydrofuran (4 mL) and methanol (4 mL). 1N Aqueous sodium hydroxide solution (4 mL) was added, and the mixture was stirred at room temperature for 2 hr. The reaction mixture was adjusted to pH 4 with water and 1N hydrochloric acid, and extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (0.46 g, 51%).

$^1$H NMR (300 MHz, DMSO-d$_6$)δ1.23 (6H, d, J=6.9), 2.64 (4H, br), 2.75 (2H, m), 3.10 (1H, m), 3.59 (4H, m), 4.12 (2H, m), 5.20 (2H, s),7.00 (1H, s), 7.31 (2H, d, J=8.1), 7.41 (2H, d, J=8.1), 7.50-7.72 (4H, m)

Example 39

6-cyclopropyl-1-{[2'-(5-oxo-4,5-dihydro-1,2,4-oxadiazol-3-yl)biphenyl-4-yl]methyl}-3-(2-phenylethyl)thieno[2,3-d]pyrimidine-2,4(1H,3H)-dione

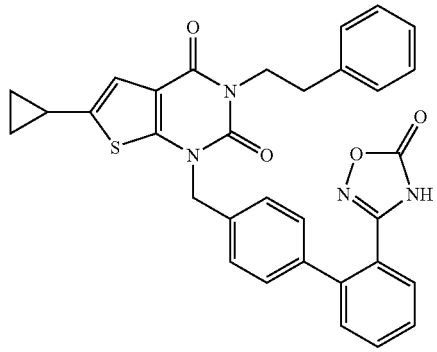 [SMILES: O=c1[nH]c(-c2ccccc2-c2ccc(Cn3c(=O)n(CCc4ccccc4)c(=O)c4cc(C5CC5)sc43)cc2)no1]

A mixture of 6-cyclopropyl-3-(2-morpholin-4-ylethyl)thieno[2,3-d]pyrimidine-2,4(1H,3H)-dione (0.50 g), 3-[4'-(bromomethyl)biphenyl-2-yl]-5-(trichloromethyl)-1,2,4-oxadiazole (0.86 g), potassium carbonate (0.44 g) and acetonitrile (20 mL) was stirred at room temperature for 2 hr. Insoluble material was filtered off, and the filtrate was concentrated. The obtained residue was purified by silica gel column chromatography and dissolved in tetrahydrofuran (4 mL) and methanol (4 mL). 1N Aqueous sodium hydroxide solution (4 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (0.76 g, 84%).

$^1$H NMR (300 MHz, DMSO-d$_6$)δ0.62-0.77 (2H, m), 0.86-1.02(2H, m), 2.05 (1H, m), 2.91 (2H, t, J=8.1), 4.16 (2H, t, J=8.1), 5.15 (2H,s), 6.94 (1H, s), 7.14-7.39 (9H, m), 7.49-7.63 (2H, m), 7.63-7.75 (2H, m),12.43 (1H, br)

Example 40

6-cyclopropyl-3-(2-morpholin-4-ylethyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

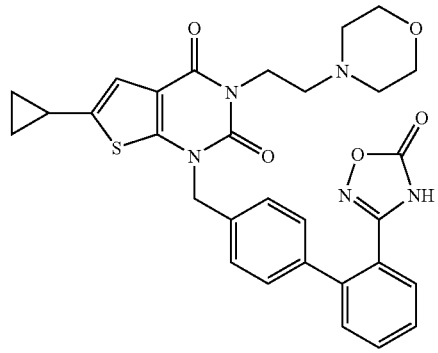 [SMILES: O=c1[nH]c(-c2ccccc2-c2ccc(Cn3c(=O)n(CCN4CCOCC4)c(=O)c4cc(C5CC5)sc43)cc2)no1]

A mixture of 6-cyclopropyl-3-(2-phenylethyl)thieno[2,3-d]pyrimidine-2,4(1H,3H)-dione (0.50 g), 3-[4'-(bromomethyl)biphenyl-2-yl]-5-(trichloromethyl)-1,2,4-oxadiazole (0.84 g), potassium carbonate (0.44 g) and acetonitrile (10 mL) was stirred at room temperature for 2 hr. Insoluble material was filtered off, and the filtrate was concentrated. The obtained residue was purified by silica gel column chromatography and dissolved in tetrahydrofuran (4 mL) and methanol (4 mL). 1N Aqueous sodium hydroxide solution (4 mL) was added, and the mixture was stirred at room temperature for 2 hr. The reaction mixture was adjusted to pH 4 with water and 1N hydrochloric acid, and extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (0.56 g, 62%).

$^1$H NMR (300 MHz, DMSO-d$_6$)δ0.66-0.72 (2H, m), 0.91-0.98(2H, m), 2.06 (1H, m), 2.55-2.75 (6H, m), 3.56 (4H, br), 4.10 (2H, t, J=3.0),5.18 (2H, s), 6.95 (1H, s), 7.31 (2H, d, J=8.1), 7.40 (2H, d, J=8.1),7.50-7.62 (2H, m), 7.66-7.72 (2H, m), 12.1 (1H, br)

Example 41

3-(5-chloropyridin-2-yl)-6-cyclopropyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

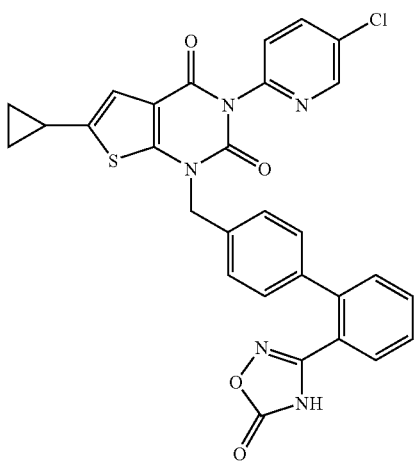 [SMILES: O=c1[nH]c(-c2ccccc2-c2ccc(Cn3c(=O)n(-c4ccc(Cl)cn4)c(=O)c4cc(C5CC5)sc43)cc2)no1]

To a solution (30 mL) of methyl 2-amino-5-cyclopropylthiophene-3-carboxylate (0.3 g) in methylene chloride were added triphosgene (0.2 g) and triethylamine (0.32 mL), and the mixture was stirred at room temperature for 2 hr. To the reaction mixture was added 5-chloropyridin-2-amine (0.59 g), the mixture was further stirred at room temperature for 1 hr, and the precipitated solid was collected by filtration. The obtained solid was dissolved in methanol (30 mL), sodium methoxide (28% methanol solution, 0.73 g) was added, and the mixture was stirred at 60° C. for 1 hr. The reaction mixture was neutralized with hydrochloric acid (10% methanol solution), and the precipitated solid was collected by filtration. The obtained solid was dissolved in N,N-dimethylformamide (10 mL), 3-[4'-(bromomethyl)biphenyl-2-yl]-5-(trichloromethyl)-1,2,4-oxadiazole (0.42 g) and potassium carbonate. (0.21 g) were added, and the mixture was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (2 mL) and acetone (2 mL). 1N Aqueous sodium hydroxide solution (1 mL) was added, and the mixture was stirred at room temperature for 2 hr. The reaction mixture was adjusted to pH 7 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.056 g, 15%).

$^1$H NMR (300 MHz, DMSO-$d_6$)δ1.22 (3H, t, J=7.6), 2.77 (2H, q, J=7.6), 5.22 (2H, s), 7.05 (1H, s), 7.34 (2H, d, J=8.0), 7.45 (2H,d, J=8.0), 7.53-7.59 (2H, m), 7.65-7.72 (3H, m), 8.18 (1H, m), 8.69 (1H, m),12.43 (1H, s)

Example 42

6-cyclopropyl-3-[2-(4-fluorophenyl)ethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

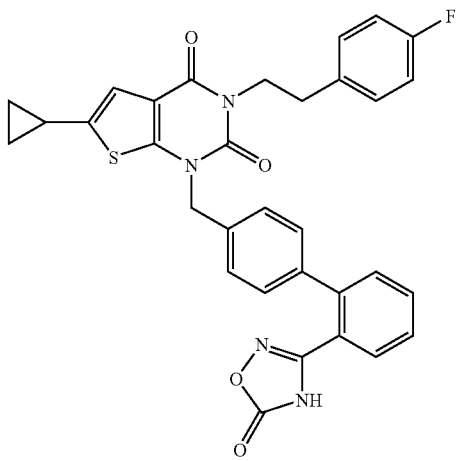 [SMILES: O=c1[nH]c(-c2ccccc2-c2ccc(Cn3c(=O)n(CCc4ccc(F)cc4)c(=O)c4cc(C5CC5)sc43)cc2)no1]

To a solution (30 mL) of methyl 2-amino-5-cyclopropylthiophene-3-carboxylate (0.3 g) in methylene chloride were added triphosgene (0.2 g) and triethylamine (0.32 mL), and the mixture was stirred at room temperature for 2 hr. To the reaction mixture was added 2-(4-fluorophenyl)ethanamine (0.59 mL), and the mixture was further stirred at room temperature for 1 hr. The precipitated solid was collected by filtration. The obtained solid was dissolved in methanol (30 mL), sodium methoxide (28% methanol solution, 0.73 g) was added, and the mixture was stirred at 60° C. for 1 hr. The reaction mixture was neutralized with hydrochloric acid (10% methanol solution), and the precipitated solid was collected by filtration. The obtained solid was dissolved in N,N-dimethylformamide (10 mL), 3-[4'-(bromomethyl)biphenyl-2-yl]-5-(trichloromethyl)-1,2,4-oxadiazole (0.42 g) and potassium carbonate (0.21 g) were added, and the mixture was stirred at room temperature for 2 hr. The reaction mixture was diluted with ethyl acetate, washed successively with water and saturated brine, and dried over anhydrous magnesium sulfate. The solvent was evaporated under reduced pressure. The obtained residue was purified by silica gel column chromatography and dissolved in tetrahydrofuran (4 mL) and acetone (4 mL). 1N Aqueous sodium hydroxide solution (2 mL) was added, and the mixture was stirred at room temperature for 2 hr. The reaction mixture was adjusted to pH 4 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.51 g, 56%).

$^1$H NMR (300 MHz, CDCl$_3$)δ0.71-0.75 (2H, m), 0.94-1.00 (2H,m), 1.91-1.97 (1H, m), 2.90-2.95 (2H, m), 4.19-4.24 (2H, m), 5.09 (2H, s),6.91-6.97 (3H, m), 7.19-7.23 (2H, m), 7.30-7.37 (4H, m), 7.42-7.62 (3H, m), 7.81 (1H, d, J=7.5)

Example 43

1-{[2'-(5-oxo-4,5-dihydro-1,2,4-oxadiazol-3-yl)biphenyl-4-yl]methyl}-3-(2-phenylethyl)-6-propylthieno[2,3-d]pyrimidine-2,4(1H,3H)-dione

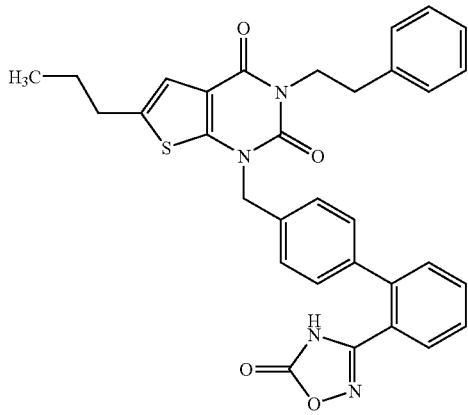 [SMILES: CCCc1cc2c(=O)n(CCc3ccccc3)c(=O)n(Cc3ccc(-c4ccccc4-c4noc(=O)[nH]4)cc3)c2s1]

A mixture of 3-(2-phenylethyl)-6-propylthieno[2,3-d]pyrimidine-2,4(1H,3H)-dione (0.40 g), 3-[4'-(bromomethyl)biphenyl-2-yl]-5-(trichloromethyl)-1,2,4-oxadiazole (0.68 g), potassium carbonate (0.35 g) and acetonitrile (16 mL) was stirred at room temperature for 2 hr. Insoluble material was filtered off, and the filtrate was concentrated. The obtained residue was purified by silica gel column chromatography and dissolved in tetrahydrofuran (4 mL) and methanol (4 mL). 1N Aqueous sodium hydroxide solution (4 mL) was added, and the mixture was stirred at room temperature for 2 hr. The reaction mixture was adjusted to pH 4 with water and 1N hydrochloric acid, and extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (0.44 g, 61%).

$^1$H NMR (300 MHz, DMSO-$d_6$)δ0.89 (3H, t, J=7.4),1.45-1.69 (2H, m), 2.69 (2H, t, J=7.2), 2.91 (2H, t, J=7.8), 4.17 (2H, t, J=7.8), 5.16 (2H, s), 6.99 (1H, s), 7.08-7.41 (9H, m), 7.44-7.73 (4H, m), 12.42(1H, br)

Example 44

6-isopropyl-1-{[2'-(5-oxo-4,5-dihydro-1,2,4-oxadiazol-3-yl)biphenyl-4-yl]methyl}-3-(2-phenylethyl)thieno[2,3-d]pyrimidine-2,4(1H,3H)-dione

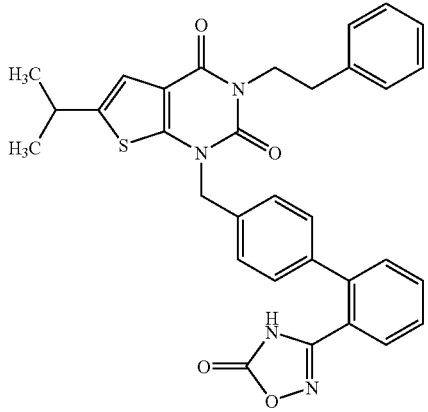 [SMILES: CC(C)c1cc2c(=O)n(CCc3ccccc3)c(=O)n(Cc3ccc(-c4ccccc4-c4noc(=O)[nH]4)cc3)c2s1]

A mixture of 6-isopropyl-3-(2-phenylethyl)thieno[2,3-d]pyrimidine-2,4(1H,3H)-dione (0.40 g), 3-[4'-(bromomethyl)biphenyl-2-yl]-5-(trichloromethyl)-1,2,4-oxadiazole (0.68 g), potassium carbonate (0.35 g) and acetonitrile (16 mL) was stirred at room temperature for 2 hr. Insoluble material was filtered off, and the filtrate was concentrated. The obtained residue was purified by silica gel column chromatography and dissolved in tetrahydrofuran (4 mL) and methanol (4 mL). 1N Aqueous sodium hydroxide solution (4 mL) was added, and the mixture was stirred at room temperature for 2 hr. The reaction mixture was adjusted to pH 4 with water and 1N hydrochloric acid, and extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (0.46 g, 64%).

$^1$H NMR (300 MHz, DMSO-$d_6$)δ1.23 (6H, d, J=6.6), 2.91 (2H, t, J=7.8), 3.83 (1H, m), 4.17 (2H, t, J=7.8), 5.17 (2H, s), 6.99 (1H,s), 7.07-7.39 (9H, m), 7.50-7.62 (2H, m), 7.64-7.72 (2H, m), 12.41 (1H, br)

Example 45

6-ethyl-3-{2-[2-(methoxymethyl)-1H-imidazol-1-yl]ethyl}-1-{[2'-(5-oxo-4,5-dihydro-1,2,4-oxadiazol-3-yl)biphenyl-4-yl]methyl}thieno[2,3-d]pyrimidine-2,4(1H,3H)-dione

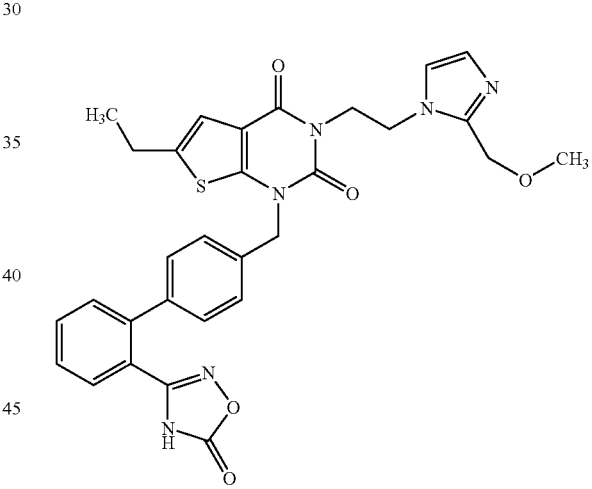

To a mixture of 4'-{[6-ethyl-3-{2-[2-(hydroxymethyl)-1H-imidazol-1-yl]ethyl}-2,4-dioxo-3,4-dihydrothieno[2,3-d]pyrimidin-1(2H)-yl]methyl}biphenyl-2-carbonitrile (0.5 g), methyl iodide (0.08 mL) and N,N-dimethylformamide (10 mL) was added 60% sodium hydride (0.047 g), and the mixture was stirred at room temperature for 2 hr. Water was added to the reaction mixture, and the mixture was extracted with methylene chloride. The organic layer was washed with saturated brine, dried over anhydrous magnesium sulfate, and the solvent was evaporated. The residue obtained by silica gel column chromatography was dissolved in dimethyl sulfoxide (5 mL), and the mixture was added to a mixture of hydroxylammonium chloride (0.57 g), sodium hydrogencarbonate (0.82 g) and dimethyl sulfoxide (10 mL), which had been stirred at 40° C. for 30 min in advance. The reaction mixture was stirred at 90° C. for 16 hr, diluted with ethyl acetate, washed successively with water and saturated brine, and dried over anhydrous magnesium sulfate. The solvent was evaporated under reduced pressure. The residue was dissolved in methylene chloride (15 mL), washed with N,N'-carbonyldiimidazole (0.18 g). Then 1,8-diazabicyclo[5.4.0]undec-7-ene (0.16 mL) was added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The residue was purified by silica gel column chromatography to give the title compound as colorless crystals (0.14 gm, 26%).

$^1$H NMR (300 MHz, DMSO-d$_6$)δ1.19 (3H, t, J=7.4),2.66-2.80 (2H, m), 3.11 (3H, s), 4.28 (4H, s), 4.38 (2H, s), 5.14 (2H, s), 6.82(1H, s), 6.98 (1H, s), 7.16 (1H, s), 7.32 (4H, s), 7.52-7.59 (2H, m), 7.63-7.76(2H, m)

Example 46

6-ethyl-3-{2-[2-(hydroxymethyl)-1H-imidazol-1-yl]ethyl}-1-{[2'-(5-oxo-4,5-dihydro-1,2,4-oxadiazol-3-yl)biphenyl-4-yl]methyl}thieno[2,3-d]pyrimidine-2,4 (1H,3H)-dione

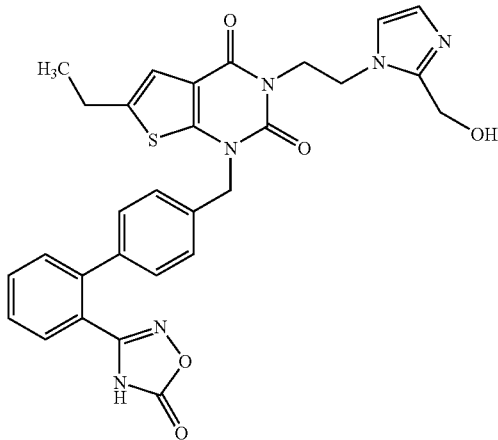 [SMILES: CCc1cc2c(=O)n(CCn3ccnc3CO)c(=O)n(Cc3ccc(-c4ccccc4-c4noc(=O)[nH]4)cc3)c2s1]

A mixture of hydroxylammonium chloride (0.57 g), sodium hydrogencarbonate (0.82 g) and dimethyl sulfoxide (15 mL) was stirred at 40° C. for 30 min, 4'-{[3-{2-[2-({[tert-butyl(dimethyl)silyl]oxy}methyl)-1H-imidazol-1-yl]ethyl}-6-ethyl-2,4-dioxo-3,4-dihydrothieno[2,3-d]pyrimidin-1 (2H)-yl]methyl}biphenyl-2-carbonitrile (0.61 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was dissolved in methylene chloride (15 mL), N,N'-carbonyldiimidazole (0.18 g) and then 1,8-diazabicyclo[5.4.0]undec-7-ene (0.16 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The residue obtained by silica gel column chromatography was dissolved in tetrahydrofuran (10 mL), tetrabutylammoniumbromide (1.0M tetrahydrofuran solution, 2.0 mL) was added, and the mixture was stirred at room temperature for 2 hr. The reaction mixture was extracted with 1N hydrochloric acid and chloroform, and the ethyl acetate layer was washed with saturated brine, and concentrated. The residue was purified by silica gel column chromatography to give the title compound as colorless crystals (0.2 g, 35%).

$^1$H NMR (300 MHz, DMSO-d$_6$)δ1.19 (3H, t, J=7.4), 2.73 (2H, q, J=7.2), 4.31 (4H, dd, J=7.0, 4.0), 4.49 (2H, s), 5.13 (2H, s), 6.84(1H, s), 6.98 (1H, s), 7.10 (1H, s), 7.32 (4H, s), 7.50-7.62 (2H, m), 7.62-7.75(2H, m)

Example 47

6-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]nicotinonitrile

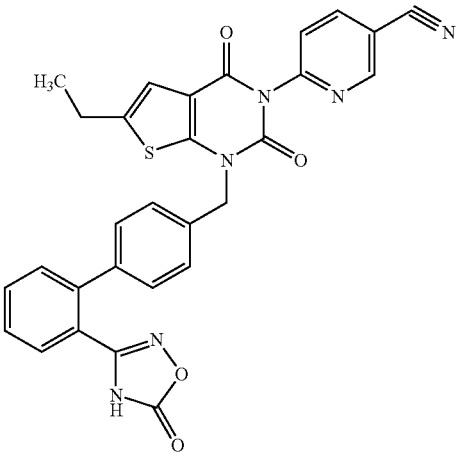 [SMILES: CCc1cc2c(=O)n(-c3ccc(C#N)cn3)c(=O)n(Cc3ccc(-c4ccccc4-c4noc(=O)[nH]4)cc3)c2s1]

To a solution (40 mL) of methyl 2-amino-5-ethylthiophene-3-carboxylate (1 g) in methylene chloride were added triphosgene (0.69 g) and triethylamine (1.2 mL), and the mixture was stirred at room temperature for 2 hr. To the reaction mixture was added 4-aminobenzonitrile (1.28 g), and the mixture was further stirred at room temperature for 1 hr, and the precipitated solid was collected by filtration. The obtained solid was dissolved in methanol (40 mL), sodium methoxide (0.73 g) was added, and the mixture was stirred at 60° C. for 1 hr. The reaction mixture was neutralized with hydrochloric acid (10% methanol solution), and the precipitated solid was collected by filtration. The obtained to solid was dissolved in acetonitrile (50 mL), 3-[4'-(bromomethyl)biphenyl-2-yl]-5-(trichloromethyl)-1,2,4-oxadiazole (2.3 g) and potassium carbonate (1.5 g) were added, and the mixture was stirred at 50° C. for 2 hr. Insoluble material was filtered off, and the solvent was evaporated under reduced pressure. The obtained residue was purified by silica gel column chromatography and dissolved in tetrahydrofuran (4 mL) and acetone (4 mL). 1N Aqueous sodium hydroxide solution (2 mL) was added, and the mixture was stirred at room temperature for 1 hr. The reaction mixture was adjusted to pH 7 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.18 g, 6%).

$^1$H NMR (300 MHz, DMSO-d$_6$)δ1.16-1.29 (3H, m), 2.65-2.84(2H, m), 5.22 (2H, s), 7.07 (1H, s), 7.34 (2H, d, J=8.3), 7.41-7.51 (2H, m), 7.50-7.62 (2H, m), 7.63-7.76 (2H, m), 7.88 (1H, d, J=8.7), 8.58 (1H, dd, J=8.3, 2.3), 9.13 (1H, d, J=1.5), 12.42 (1H, s)

Example 48

6-ethyl-1-{[2'-(5-oxo-4,5-dihydro-1,2,4-oxadiazol-3-yl)biphenyl-4-yl]methyl}-3-(1-phenyl-1H-pyrazol-5-yl)thieno[2,3-d]pyrimidine-2,4(1H,3H)-dione

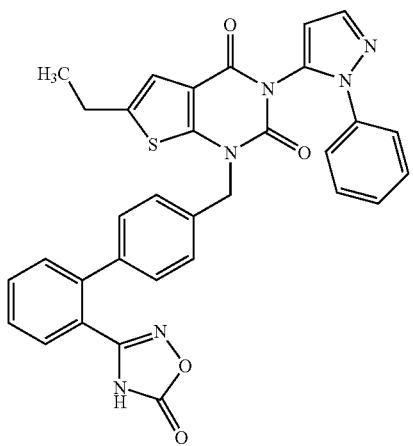 [SMILES: CCc1cc2c(=O)n(-c3ccnn3-c3ccccc3)c(=O)n(Cc3ccc(-c4ccccc4-c4noc(=O)[nH]4)cc3)c2s1]

To a solution (20 mL) of 2-amino-5-ethylthiophene-3-carboxylate (0.5 g) in methylene chloride were added triphosgene (0.35 g) and triethylamine (0.6 mL), and the mixture was stirred at room temperature for 2 hr. To the reaction mixture was added 1-phenyl-1H-pyrazole-5-amine (1.1 g), and the mixture was further stirred at room temperature for 1 hr, and the precipitated solid was collected by filtration. The obtained solid was dissolved in methanol (20 ml), sodium methoxide (0.58 g) was added, and the mixture was stirred at 60° C. for 1 hr. The reaction mixture was neutralized with hydrochloric acid (10% methanol solution), and the precipitated solid was collected by filtration. The obtained solid was dissolved in acetonitrile (30 mL), 3-[4'-(bromomethyl)biphenyl-2-yl]-5-(trichloromethyl)-1,2,4-oxadiazole (1.17 g) and potassium carbonate (0.75 g) were added, and the mixture was stirred at 50° C. for 2 hr. Insoluble material was filtered off, and the solvent was evaporated under reduced pressure. The obtained residue was purified by silica gel column chromatography and dissolved in tetrahydrofuran (4 mL) and acetone (4 mL). 1N Aqueous sodium hydroxide solution (2 mL) was added, and the mixture was stirred at room temperature for 1 hr. The reaction mixture was adjusted to pH 7 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.4 g, 25%).

$^1$H NMR (300 MHz, DMSO-$d_6$) δ1.12-1.24 (3H, m), 2.73 (2H, d, J=7.6), 4.90 (1H, d, J=17.0), 5.37 (1H, d, J=16.7), 6.63 (1H, d, J=1.9), 6.99-7.11 (3H, m), 7.21-7.36 (4H, m), 7.39-7.51 (3H, m), 7.57 (2H, dd, J=17.4, 6.8), 7.65-7.76 (2H, m), 7.85 (1H, d, J=1.9), 12.46 (1H, s)

Example 49

3-(2,4-dimethoxybenzyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

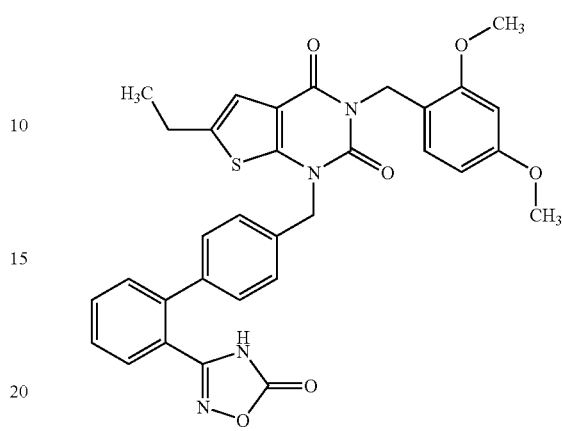

A mixture of 3-(2,4-dimethoxybenzyl)-6-ethylthieno[2,3-d]pyrimidine-2,4(1H,3H)-dione (1 g), 3-[4'-(bromomethyl)biphenyl-2-yl]-5-(trichloromethyl)-1,2,4-oxadiazole (1.43 g), potassium carbonate (0.8 g) and acetonitrile (40 mL) was stirred at room temperature for 2 hr. Insoluble material was filtered off, and the filtrate was concentrated. The obtained residue was purified by silica gel column chromatography and dissolved in tetrahydrofuran (8 mL) and methanol (8 mL). 1N Aqueous sodium hydroxide solution (8 mL) was added, and the mixture was stirred at room temperature for 2 hr. The reaction mixture was adjusted to pH 4 with water and 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as a colorless solid (0.74 g, 45%).

$^1$H NMR (300 MHz, DMSO-$d_6$) δ1.21 (3H, t, J=7.5), 2.75 (2H, q, J=7.5), 3.72 (3H, s), 3.81 (3H, s), 5.01 (2H, s), 5.20 (2H, s), 6.42(1H, d, J=8.4), 6.57 (1H, s), 6.74 (1H, d, J=8.4), 7.01 (1H, s), 7.32 (2H, d, J=8.1), 7.39 (2H, d, J=8.1), 7.50-7.61 (2H, m), 7.62-7.76 (2H, m), 12.41(1H, br)

Example 50

6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

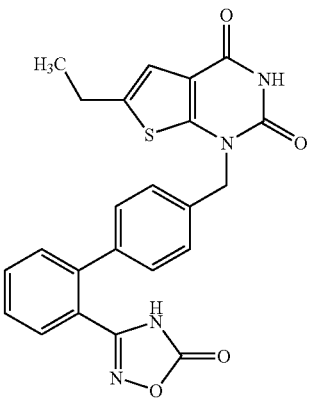 [SMILES: CCc1cc2c(=O)[nH]c(=O)n(Cc3ccc(-c4ccccc4-c4noc(=O)[nH]4)cc3)c2s1]

A mixture of 3-(2,4-dimethoxybenzyl)-6-ethyl-1-{[2'-(5-oxo-4,5-dihydro-1,2,4-oxadiazol-3-yl)biphenyl-4-yl]

methyl}thieno[2,3-d]pyrimidine-2,4(1H,3H)-dione (0.3 g) and trifluoroacetic acid (5 mL) was stirred at 50° C. for 2 hr. To the reaction mixture was added toluene (10 mL), and the mixture was concentrated under reduced pressure. The obtained residue was dissolved in 1N aqueous sodium hydroxide solution, washed with chloroform, and adjusted to pH 4 with 1N hydrochloric acid. The precipitated solid was collected by filtration to give the title compound as colorless crystals (0.21 g, 93%).

$^1$H NMR (300 MHz, DMSO-$d_6$)δ1.19 (3H, t, J=7.5), 2.72 (2H, q, J=7.5), 5.13 (2H, s), 6.95 (1H, s), 7.26-7.42 (4H, m), 7.49-7.62 (2H,m), 7.64-7.74 (2H, m), 11.54 (1H, s), 12.40 (1H, br)

Example 51

3-[2-(4-fluorophenyl)ethyl]-1-{[2'-(5-oxo-4,5-dihydro-1,2,4-oxadiazol-3-yl)biphenyl-4-yl]methyl}-6-(2,2,2-trifluoroethyl)thieno[2,3-d]pyrimidine-2,4(1H,3H)-dione

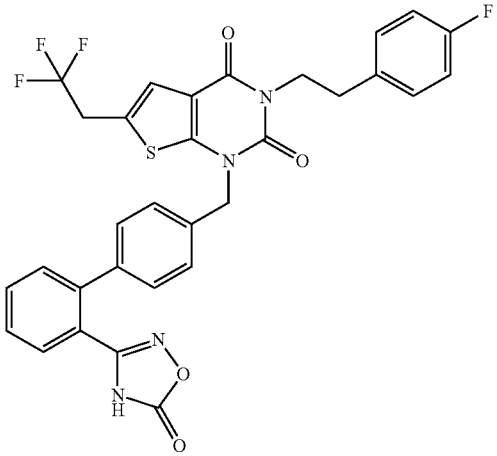 [SMILES: O=c1[nH]c(-c2ccccc2-c2ccc(Cn3c(=O)n(CCc4ccc(F)cc4)c(=O)c4cc(CC(F)(F)F)sc43)cc2)no1]

To a solution (30 mL) of methyl 2-amino-5-(2,2,2-trifluoroethyl)thiophene-3-carboxylate (0.3 g) in methylene chloride were added triphosgene (0.16 g) and triethylamine (0.26 mL), and the mixture was stirred at room temperature for 2 hr. To the reaction mixture was added 2-(4-fluorophenyl)ethanamine (0.49 g), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in methanol (40 mL), sodium methoxide (0.37 g) was added, and the mixture was stirred at 60° C. for 1 hr. The reaction mixture was neutralized with hydrochloric acid (10% methanol solution), and the precipitated solid was collected by filtration. The obtained solid was dissolved in acetonitrile (40 mL), 3-[4'-(bromomethyl)biphenyl-2-yl]-5-(trichloromethyl)-1,2,4-oxadiazole (0.65 g) and potassium carbonate (0.35 g) were added, and the mixture was stirred at 50° C. for 2 hr. Insoluble material was filtered off, and the solvent was evaporated under reduced pressure. The obtained residue was purified by silica gel column chromatography and dissolved in tetrahydrofuran (4 mL) and acetone (4 mL). 1N Aqueous sodium hydroxide solution (2 mL) was added, and the mixture was stirred at room temperature for 1 hr. The reaction mixture was adjusted to pH 4 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.57 g, 57%).

$^1$H NMR (300 MHz, DMSO-$d_6$)δ2.92 (2H, t, J=7.4), 3.96 (2H, d, J=11.0), 4.11-4.18 (2H, m), 5.19 (2H, s), 7.11 (2H, t, J=8.9),7.20-7.37 (7H, m), 7.56 (2H, dd, J=17.8, 7.2), 7.63-7.78 (2H, m), 12.4 (1H,s)

Example 52

3-(2-morpholin-4-ylethyl)-1-{[2'-(5-oxo-4,5-dihydro-1,2,4-oxadiazol-3-yl)biphenyl-4-yl]methyl}-6-(2,2,2-trifluoroethyl)thieno[2,3-d]pyrimidine-2,4(1H,3H)-dione

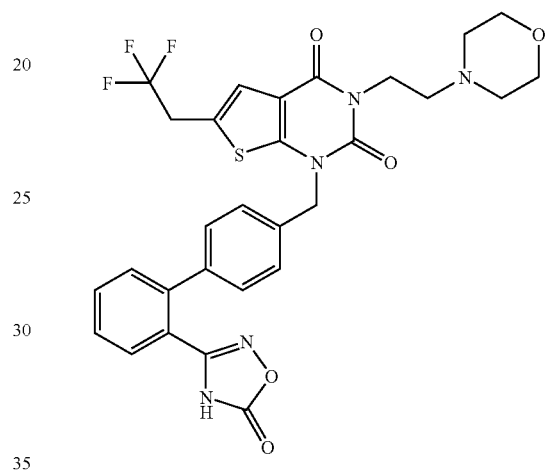

To a solution (50 mL) of methyl 2-amino-5-(2,2,2-trifluoroethyl)thiophene-3-carboxylate (0.5 g) in methylene chloride were added triphosgene (0.27 g) and triethylamine (0.44 mL), and the mixture was stirred at room temperature for 2 hr. To the reaction mixture was added 2-morpholin-4-ylethanamine (0.82 g), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in methanol (50 mL), sodium methoxide (0.58 g) was added, and the mixture was stirred at 60° C. for 1 hr. The reaction mixture was neutralized with hydrochloric acid (10% methanol solution), and the precipitated solid was collected by filtration. The obtained solid was dissolved in acetonitrile (40 mL), 3-[4'-(bromomethyl)biphenyl-2-yl]-5-(trichloromethyl)-1,2,4-oxadiazole (1.1 g) and potassium carbonate (0.58 g) were added, and the mixture was stirred at 50° C. for 2 hr. Insoluble material was filtered off, and the solvent was evaporated under reduced pressure. The obtained residue was purified by silica gel column chromatography and dissolved in tetrahydrofuran (4 mL) and acetone (4 mL). 1N Aqueous sodium hydroxide solution (2 mL) was added, and the mixture was stirred at room temperature for 1 hr. The reaction mixture was adjusted to pH 7 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.76 g, 55%).

$^1$H NMR (300 MHz, CDCl$_3$)δ2.57 (4H, s), 2.68 (2H, t, J=6.0), 3.41-3.66 (6H, m), 4.21 (2H, t, J=6.0), 5.19 (2H, s), 7.23-7.36 (3H,m), 7.36-7.56 (4H, m), 7.61-7.64 (1H, m), 7.76-7.79 (1H, m)

Example 53

6-ethyl-3-(6-methoxypyridin-3-yl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

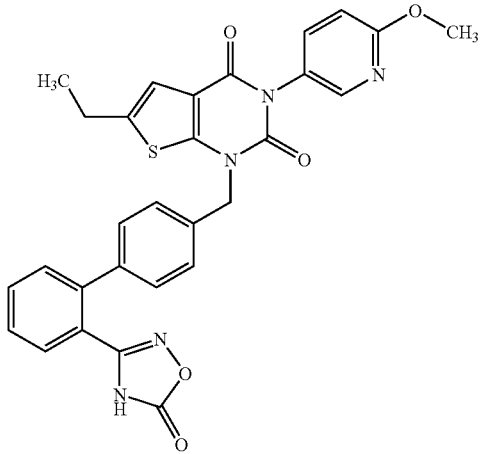 [SMILES: CCc1cc2c(=O)n(-c3ccc(OC)nc3)c(=O)n(Cc3ccc(-c4ccccc4-c4noc(=O)[nH]4)cc3)c2s1]

To a solution (30 mL) of methyl 2-amino-5-ethylthiophene-3-carboxylate (0.36 g) in methylene chloride were added triphosgene (0.25 g) and triethylamine (0.4 mL), and the mixture was stirred at room temperature for 2 hr. To the reaction mixture was added 6-bromopyridin-3-amine (1 g), and the mixture was further stirred at room temperature for 1 hr, and the precipitated solid was collected by filtration. The obtained solid was dissolved in methanol (20 mL), sodium methoxide (0.52 g) was added, and the mixture was stirred at 60° C. for 1 hr. The reaction mixture was neutralized with hydrochloric acid (10% methanol solution), and the precipitated solid was collected by filtration. The obtained solid was dissolved in acetonitrile (40 3-[4'-(bromomethyl)biphenyl-2-yl]-5-(trichloromethyl)-1,2,4-oxadiazole (0.83 g) and potassium carbonate (0.53 g) was added, and the mixture was stirred at 50° C. for 2 hr. Insoluble material was filtered off, and the solvent was evaporated under reduced pressure. The obtained residue was purified by silica gel column chromatography and dissolved in tetrahydrofuran (4 mL) and acetone (4 mL). 1N Aqueous sodium hydroxide solution (2 mL) was added, and the mixture was stirred at room temperature for 1 hr. The reaction mixture was adjusted to pH 7 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.58 g, 54%).

$^1$H NMR (300 MHz, DMSO-d$_6$)δ1.20 (3H, t, J=7.4), 2.76 (2H, q, J=7.4), 3.90 (3H, s), 5.22 (2H, s), 6.96 (1H, d, J=8.7), 7.05 (1H,$), 7.33 (2H, d, J=8.3), 7.42-7.63 (4H, m), 7.63-7.79 (3H, m), 8.17 (1H, d, J=2.3), 12.4 (1H, s)

Example 54

6-(methoxymethyl)-1-{[2'-(5-oxo-4,5-dihydro-1,2,4-oxadiazol-3-yl)biphenyl-4-yl]methyl}-3-(2-phenylethyl)thieno[2,3-d]pyrimidine-2,4(1H,3H)-dione

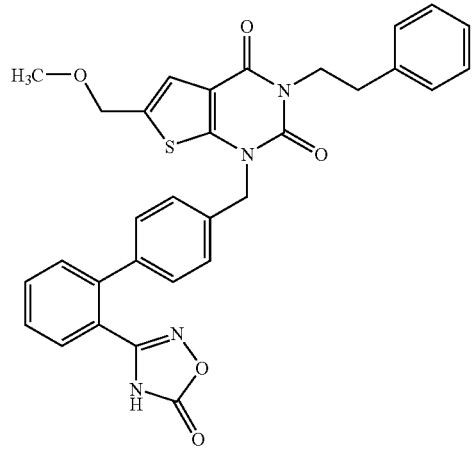 [SMILES: COCc1cc2c(=O)n(CCc3ccccc3)c(=O)n(Cc3ccc(-c4ccccc4-c4noc(=O)[nH]4)cc3)c2s1]

A mixture of hydroxylammonium chloride (0.40 g), sodium hydrogencarbonate (0.58 g) and dimethyl sulfoxide (10 mL) was stirred at 40° C. for 30 min, 4'-{[6-(methoxymethyl)-2,4-dioxo-3-(2-phenylethyl)-3,4-dihydrothieno[2,3-d]pyrimidin-1(2H)-yl]methyl}biphenyl-2-carbonitrile (0.35 g) was added, and the mixture was stirred at 90° C. for 16 hr. The reaction mixture was diluted with ethyl acetate, washed successively with water and saturated brine, and dried over anhydrous magnesium sulfate. The solvent was evaporated under reduced pressure. The residue was dissolved in tetrahydrofuran (10 mL), N,N'-carbonyldiimidazole (0.17 g) and then 1,8-diazabicyclo[5.4.0]undec-7-ene (0.16 mL) were added, and the mixture was stirred at room temperature for 2 hr. The reaction mixture was diluted with ethyl acetate, washed successively with saturated aqueous potassium hydrogensulfate solution and saturated brine, and dried over anhydrous magnesium sulfate. The solvent was evaporated under reduced pressure. The residue was purified by silica gel column chromatography to give the title compound as pale-yellow crystals (0.26 g, 67%).

$^1$H NMR (300 MHz, DMSO-d$_6$)δ2.92 (2H, t, J=7.5), 3.24 (3H, s), 4.17 (2H, t, J=7.5), 4.51 (2H, s), 5.19 (2H, s), 7.17-7.34 (10H, m),7.50-7.61 (2H, m), 7.64-7.75 (2H, m), 12.43 (1H, br)

Example 55

6-(hydroxymethyl)-1-{[2'-(5-oxo-4,5-dihydro-1,2,4-oxadiazol-3-yl)biphenyl-4-yl]methyl}-3-(2-phenylethyl)thieno[2,3-d]pyrimidine-2,4(1H,3H)-dione

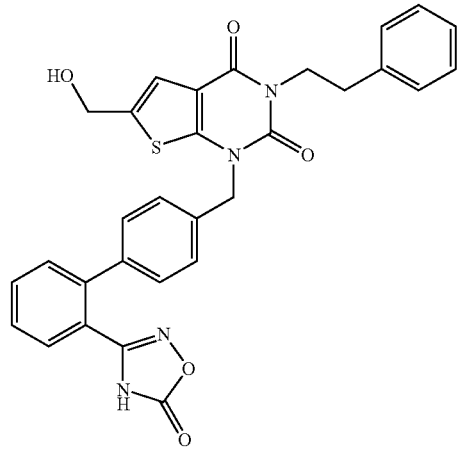 [SMILES: O=c1[nH]c(-c2ccccc2-c2ccc(Cn3c(=O)n(CCc4ccccc4)c(=O)c4cc(CO)sc43)cc2)no1]

To a mixture of 4'-{[6-(hydroxymethyl)-2,4-dioxo-3-(2-phenylethyl)-3,4-dihydrothieno[2,3-d]pyrimidin-1(2H)-yl]methyl}biphenyl-2-carbonitrile (0.4 g), N,N-dimethylpyridin-4-amine (0.25 g) and methylene chloride (10 mL) was added tert-butyl(dimethyl)silyl trifluoromethanesulfonate (0.32 mL), and the mixture was stirred at room temperature for 2 hr. The reaction mixture was washed with 1N hydrochloric acid, saturated aqueous sodium hydrogencarbonate solution and saturated brine, and dried over anhydrous sodium sulfate. The solvent was evaporated under reduced pressure. The obtained residue was dissolved in dimethyl sulfoxide (5 mL), and added to a mixture of hydroxylammonium chloride (0.44 g), sodium hydrogencarbonate (0.68 g) and dimethyl sulfoxide (10 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was dissolved in methylene chloride (15 mL), N,N'-carbonyldiimidazole (0.16 g) and then 1,8-diazabicyclo[5.4.0]undec-7-ene (0.15 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (10 mL). Tetrabutylammonium fluoride (1.0M tetrahydrofuran solution, 2 mL) was added, and the mixture was stirred at room temperature for 12 hr. The reaction mixture was diluted with ethyl acetate, washed with saturated brine, and dried over anhydrous magnesium sulfate. The solvent was evaporated under reduced pressure. The residue was purified by silica gel column chromatography to give the title compound as colorless crystals (0.28 g, 61%).

$^1$H NMR (300 MHz, DMSO-$d_6$)δ2.93 (2H, t, J=7.8), 4.18 (2H, t, J=7.8), 4.52 (2H, t, J=7.8), 5.18 (2H, s), 5.62 (1H, t, J=4.2),7.10 (1H, s), 7.15-7.38 (9H, m), 7.44-7.78 (4H, m), 12.45 (1H, br)

Example 56

6-ethyl-3-[2-(4-fluorophenyl)ethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

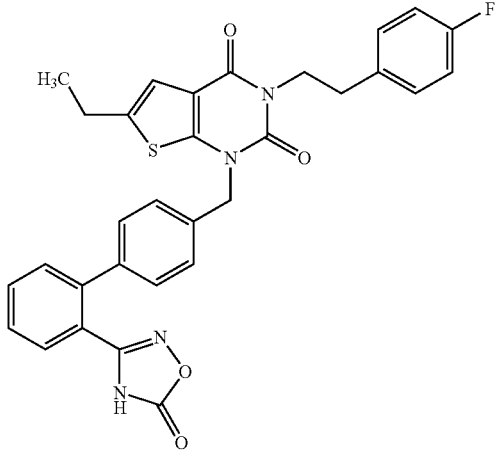 [SMILES: CCc1cc2c(=O)n(CCc3ccc(F)cc3)c(=O)n(Cc3ccc(-c4ccccc4-c4noc(=O)[nH]4)cc3)c2s1]

A mixture of 6-ethyl-3-[2-(4-fluorophenyl)ethyl]thieno[2,3-d]pyrimidine-2,4(1H,3H)-dione (0.3 g), 3-[4'-(bromomethyl)biphenyl-2-yl]-5-(trichloromethyl)-1,2,4-oxadiazole (0.49 g), potassium carbonate (0.16 g) and acetonitrile (30 mL) was stirred at 50° C. for 2 hr. Insoluble material was filtered off, and the solvent was evaporated under reduced pressure. The obtained residue was purified by silica gel column chromatography and dissolved in tetrahydrofuran (5 mL) and acetone (5 mL). 1N Aqueous sodium hydroxide solution (2 mL) was added, and the mixture was stirred at room temperature for 2 hr. The reaction mixture was adjusted to pH 7 with water and 1N hydrochloric acid, and extracted with ethyl acetate. The obtained ethyl acetate layer was washed with saturated brine, and dried over anhydrous magnesium sulfate. The solvent was evaporated under reduced pressure. The residue was purified by silica gel column chromatography to give the title compound as colorless crystals (0.23 g, 43%).

$^1$H NMR (300 MHz, DMSO-$d_6$)δ1.19 (3H, t, J=7.4),2.64-2.78 (2H, m), 2.91 (2H, t, J=7.2), 4.06-4.22 (2H, m), 5.16 (2H, s), 6.99(1H, s), 7.04-7.16 (2H, m), 7.17-7.36 (6H, m), 7.45-7.62 (2H, m), 7.62-7.77(2H, m), 12.4 (1H, s)

Example 57

3-(4'-{[3-[2-(4-fluorophenyl)ethyl]-2,4-dioxo-6-(2,2,2-trifluoroethyl)-3,4-dihydrothieno[2,3-d]pyrimidin-1(2H)-yl]methyl}biphenyl-2-yl)-1,2,4-oxadiazol-5-olate potassium salt

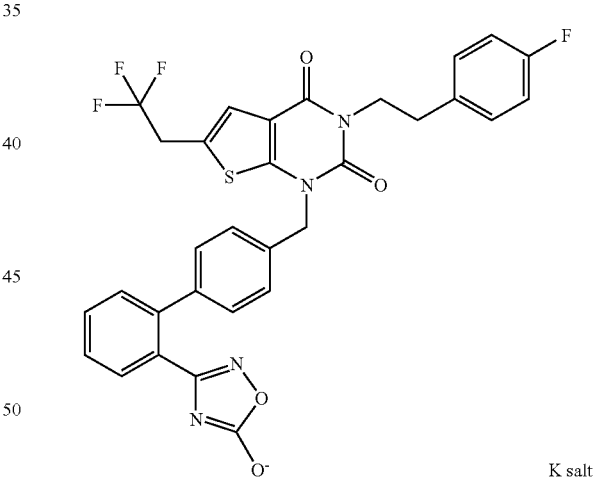

To a solution (2 mL) of 3-[2-(4-fluorophenyl)ethyl]-1-{[2'-(5-oxo-4,5-dihydro-1,2,4-oxadiazol-3-yl)biphenyl-4-yl]methyl}-6-(2,2,2-trifluoroethyl)thieno[2,3-d]pyrimidine-2,4(1H,3H)-dione (0.3 g) in methylene chloride was added a solution (2 mL) of potassium 2-ethylhexanoate (0.11 g) in diethyl ether, and the mixture was stirred at room temperature for 1 hr. The precipitated solid was collected by filtration to give the title compound as colorless crystals (0.2 g, 64%).

$^1$H NMR (300 MHz, DMSO-$d_6$)δ2.89 (2H, t, J=7.8), 3.96 (2H, q, J=10.8), 4.13 (2H, t, J=7.8), 5.13 (2H, s), 7.07-7.49 (13H, m)

Example 58

3-[2-(4-chlorophenyl)ethyl]-1-{[2'-(5-oxo-4,5-dihydro-1,2,4-oxadiazol-3-yl)biphenyl-4-yl]methyl}-6-(2,2,2-trifluoroethyl)thieno[2,3-d]pyrimidine-2,4(1H,3H)-dione

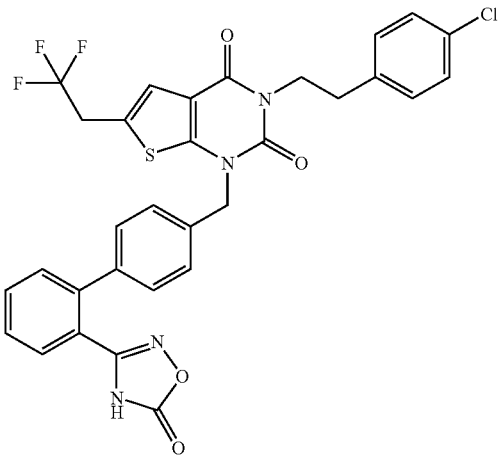 [SMILES: O=c1[nH]c(-c2ccccc2-c2ccc(Cn3c(=O)n(CCc4ccc(Cl)cc4)c(=O)c4cc(CC(F)(F)F)sc43)cc2)no1]

To a solution (50 mL) of methyl 2-amino-5-(2,2,2-trifluoroethyl)thiophene-3-carboxylate (0.5 g) in methylene chloride were added triphosgene (0.27 g) and triethylamine (0.47 mL), and the mixture was stirred at room temperature for 2 hr. To the reaction mixture was added 2-(4-chlorophenyl)ethanamine (0.88 mL), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in methanol (50 mL), sodium methoxide (0.56 g) was added, and the mixture was stirred at 60° C. for 1 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The obtained residue was dissolved in acetonitrile (50 mL), 3-[4'-(bromomethyl)biphenyl-2-yl]-5-(trichloromethyl)-1,2,4-oxadiazole (1.08 g) and potassium carbonate (0.58 g) were added, and the mixture was stirred at 50° C. for 2 hr. Insoluble material was filtered off, and the solvent was evaporated under reduced pressure. The obtained residue was purified by silica gel column chromatography and dissolved in tetrahydrofuran (10 mL) and acetone (10 mL). 1N Aqueous sodium hydroxide solution (4 mL) was added, and the mixture was stirred at room temperature for 1 hr. The reaction mixture was adjusted to pH 4 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.8 g, 60%).

$^1$H NMR (300 MHz, DMSO-$d_6$) δ2.92 (2H, t, J=7.4), 3.96 (2H, q, J=10.9), 4.16 (2H, t, J=7.0), 5.18 (2H, s), 7.15-7.41 (9H, m), 7.56 (2H, dd, J=17.6, 7.4), 7.62-7.79 (2H, m), 12.4 (1H, s)

Example 59

3-[2-(4-methylphenyl)ethyl]-1-{[2'-(5-oxo-4,5-dihydro-1,2,4-oxadiazol-3-yl)biphenyl-4-yl]methyl}-6-(2,2,2-trifluoroethyl)thieno[2,3-d]pyrimidine-2,4(1H,3H)-dione

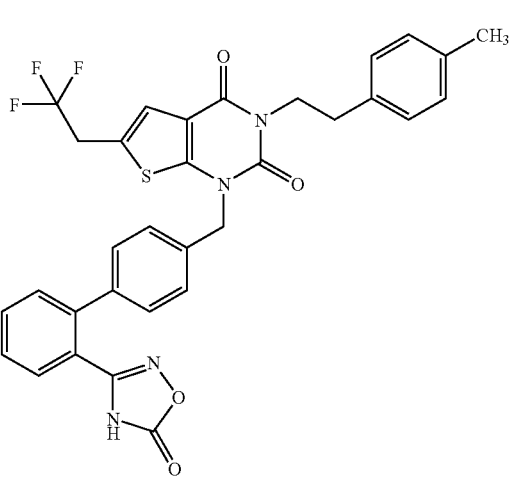 [SMILES: Cc1ccc(CCn2c(=O)c3cc(CC(F)(F)F)sc3n(Cc3ccc(-c4ccccc4-c4noc(=O)[nH]4)cc3)c2=O)cc1]

To a solution (50 mL) of methyl 2-amino-5-(2,2,2-trifluoroethyl)thiophene-3-carboxylate (0.5 g) in methylene chloride were added triphosgene (0.27 g) and triethylamine (0.47 mL), and the mixture was stirred at room temperature for 2 hr. To the reaction mixture was added 2-(4-methylphenyl)ethanamine (0.91 mL), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in methanol (50 mL), sodium methoxide (0.56 g) was added, and the mixture was stirred at 60° C. for 1 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The obtained residue was dissolved in acetonitrile (50 mL), 3-[4'-(bromomethyl)biphenyl-2-yl]-5-(trichloromethyl)-1,2,4-oxadiazole (1.08 g) and potassium carbonate (0.58 g) were added, and the mixture was stirred at 50° C. for 2 hr. Insoluble material was filtered off, and the solvent was evaporated under reduced pressure. The obtained residue was purified by silica gel column chromatography and dissolved in tetrahydrofuran (10 mL) and acetone (10 mL). 1N Aqueous sodium hydroxide solution (4 mL) was added, and the mixture was stirred at room temperature for 1 hr. The reaction mixture was adjusted to pH 4 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.44 g, 28%).

$^1$H NMR (300 MHz, DMSO-$d_6$) δ2.26 (3H, s), 2.79-2.91 (2H, m), 3.96 (2H, q, J=11.1), 4.07-4.19 (2H, m), 5.20 (2H, s), 7.09-7.17 (4H, m),7.27-7.39 (5H, m), 7.55 (2H, dd, J=17.8, 7.6), 7.60-7.73 (2H, m), 12.4 (1H,s)

Example 60

3-[2-(3-fluorophenyl)ethyl]-1-{[2'-(5-oxo-4,5-dihydro-1,2,4-oxadiazol-3-yl)biphenyl-4-yl]methyl}-6-(2,2,2-trifluoroethyl)thieno[2,3-d]pyrimidine-2,4(1H,3H)-dione

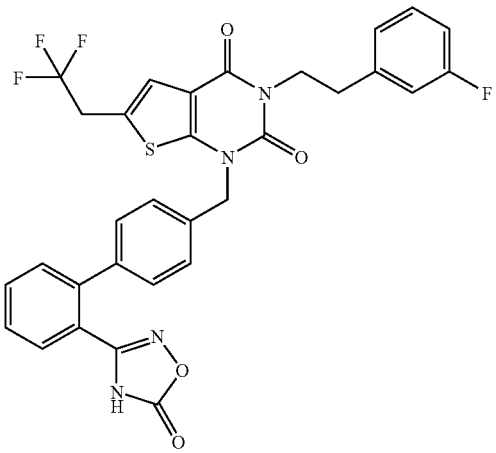 [SMILES: O=c1[nH]c(-c2ccccc2-c2ccc(Cn3c(=O)n(CCc4cccc(F)c4)c(=O)c4cc(CC(F)(F)F)sc43)cc2)no1]

To a solution (50 mL) of methyl 2-amino-5-(2,2,2-trifluoroethyl)thiophene-3-carboxylate (0.5 g) in methylene chloride were added triphosgene (0.27 g) and triethylamine (0.47 mL), and the mixture was stirred at room temperature for 2 hr. To the reaction mixture was added 2-(3-fluorophenyl)ethanamine (0.82 mL), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in methanol (50 mL), sodium methoxide (0.56 g) was added, and the mixture was stirred at 60° C. for 1 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The obtained residue was dissolved in acetonitrile (50 mL), 3-[4'-(bromomethyl)biphenyl-2-yl]-5-(trichloromethyl)-1,2,4-oxadiazole (1.08 g) and potassium carbonate (0.58 g) were added, and the mixture was stirred at 50° C. for 2 hr. Insoluble material was filtered off, and the solvent was evaporated under reduced pressure. The obtained residue was purified by silica gel column chromatography and dissolved in tetrahydrofuran (10 mL) and acetone (10 mL). 1N Aqueous sodium hydroxide solution (4 mL) was added, and the mixture was stirred at room temperature for 1 hr. The reaction mixture was adjusted to pH 4 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.59 g, 37%).

$^1$H NMR (300 MHz, DMSO-d$_6$)δ2.95 (2H, t, J=7.2),3.85-4.07 (2H, m), 4.18 (2H, t, J=7.2), 5.20 (2H, s), 6.94-7.17 (3H, m),7.21-7.42 (6H, m), 7.56 (2H, dd, J=16.1, 7.8), 7.61-7.76 (2H, m), 12.4 (1H,s)

Example 61

3-[2-(4-fluorophenyl)-2-hydroxyethyl]-1-{[2'-(5-oxo-4,5-dihydro-1,2,4-oxadiazol-3-yl)biphenyl-4-yl]methyl}-6-(2,2,2-trifluoroethyl)thieno[2,3-d]pyrimidine-2,4(1H,3H)-dione

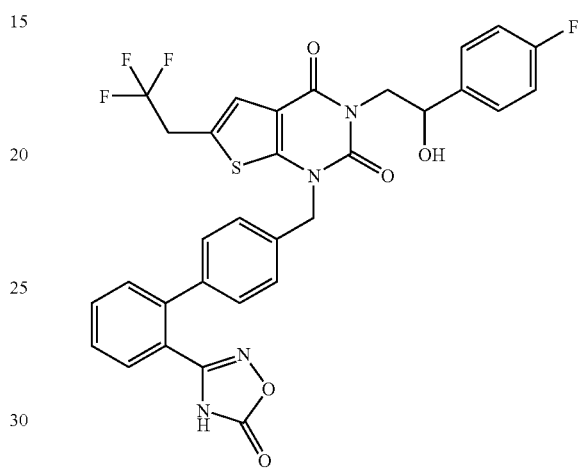

To a mixture of 4'-{[3-[2-(4-fluorophenyl)-2-hydroxyethyl]-2,4-dioxo-6-(2,2,2-trifluoroethyl)-3,4-dihydrothieno[2,3-d]pyrimidin-1(2H)-yl]methyl}biphenyl-2-carbonitrile (0.41 g), N,N-dimethylpyridin-4-amine (0.52 g) and methylene chloride (30 mL) was added tert-butyl(dimethyl)silyl trifluoromethanesulfonate (0.95 mL), and the mixture was stirred at room temperature for 2 days. The reaction mixture was washed with water and saturated brine, and dried over anhydrous magnesium sulfate. The solvent was evaporated under reduced pressure. The obtained residue was dissolved in dimethyl sulfoxide (5 mL), and added to a mixture of hydroxylammonium chloride (0.98 g), sodium hydrogencarbonate (1.42 g) and dimethyl sulfoxide (10 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was dissolved in methylene chloride (15 mL), N,N'-carbonyldiimidazole (0.14 g) and then 1,8-diazabicyclo[5.4.0]undec-7-ene (0.01 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography and dissolved in tetrahydrofuran (10 mL). Tetrabutylammonium fluoride (1.0M tetrahydrofuran solution, 0.5 mL) was added, and the mixture was stirred at room temperature for 2 hr. The reaction mixture was diluted with ethyl acetate, washed with saturated brine, and dried over anhydrous magnesium sulfate. The solvent was evaporated under reduced pressure. The residue was purified by silica gel column chromatography to give the title compound as colorless crystals (0.035 g, 8%).

$^1$H NMR (300 MHz, DMSO-d$_6$)δ3.89-4.00 (3H, m), 4.18-4.25(1H, m), 4.95-5.01 (1H, m), 5.16 (2 H, dd, J=40.5, 16.5), 5.59 (1H, d,J=4.2), 7.13 (2H, m), 7.26-7.39 (7H, m), 7.53 (2H, m), 7.66 (2H, m), 12.40 (1H,s)

Example 62

3-[2-(4-fluorophenyl)-2-oxoethyl]-1-{[2'-(5-oxo-4,5-dihydro-1,2,4-oxadiazol-3-yl)biphenyl-4-yl]methyl}-6-(2,2,2-trifluoroethyl)thieno[2,3-d]pyrimidine-2,4(1H,3H)-dione

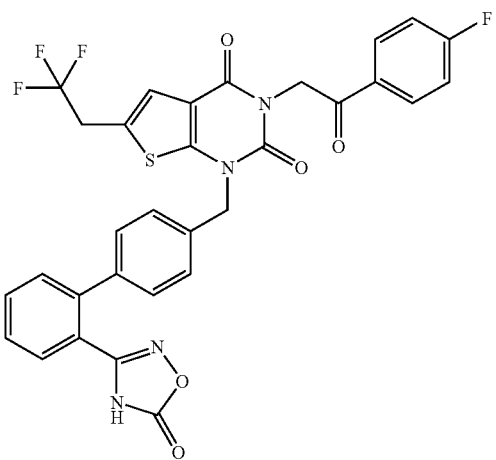 [SMILES: O=C(Cn1c(=O)c2cc(CC(F)(F)F)sc2n(Cc2ccc(-c3ccccc3-c3noc(=O)[nH]3)cc2)c1=O)c1ccc(F)cc1]

A mixture of hydroxylammonium chloride (0.97 g), sodium hydrogencarbonate (1.4 g) and dimethyl sulfoxide (15 mL) was stirred at 40° C. for 30 min, 4'-{[3-[2-(4-fluorophenyl)-2-oxoethyl]-2,4-dioxo-6-(2,2,2-trifluoroethyl)-3,4-dihydrothieno[2,3-d]pyrimidin-1(2H)-yl]methyl}biphenyl-2-carbonitrile (0.8 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was dissolved in methylene chloride (15 mL), N,N'-carbonyldiimidazole (0.23 g) and then 1,8-diazabicyclo[5.4.0]undec-7-ene (0.19 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The residue obtained by silica gel column chromatography was dissolved in methylene chloride (50 mL), iodine acid (0.34 g) was added, and the mixture was stirred at 35° C. for 16 hr. The reaction mixture was washed successively with water and saturated brine, and dried over anhydrous magnesium sulfate. The solvent was evaporated under reduced pressure. The obtained residue was purified by preparative HPLC to give the title compound as a colorless amorphous solid (0.12 g, 14%).

$^1$H NMR (300 MHz, DMSO-d$_6$)δ3.97 (2H, d, J=10.5), 5.25(2H, s), 5.47 (2H, s), 7.32-7.45 (7H, m), 7.50-7.59 (3H, m), 7.61-7.71 (3H, m),12.4 (1H, s)

Example 63

6-cyclopropyl-3-[2-(4-fluorophenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

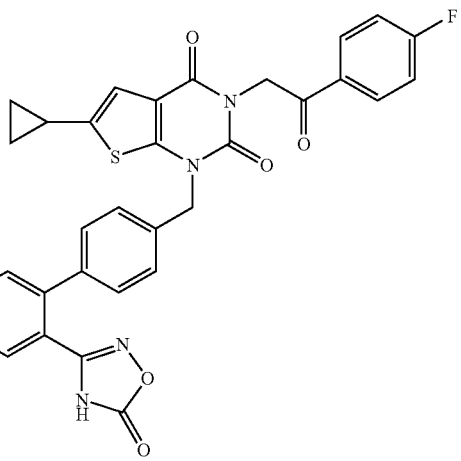

A mixture of 4'-{[6-cyclopropyl-3-(2,4-dimethoxybenzyl)-2,4-dioxo-3,4-dihydrothieno[2,3-d]pyrimidin-1(2H)-yl]methyl}biphenyl-2-carbonitrile (1.18 g) and trifluoroacetic acid (10 mL) was stirred at 50° C. for 2 hr. To the reaction mixture was added toluene (10 mL), and the mixture was s concentrated under reduced pressure. The obtained residue was dissolved in N,N-dimethylformamide (30 mL), 2-bromo-1-(4-fluorophenyl)ethanone (0.56 g) and sodium hydride (0.11 g) were added, and the mixture was stirred at room temperature for 3 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. After purification by silica gel column chromatography, the obtained residue was dissolved in dimethyl sulfoxide (5 mL), and the mixture was added to a mixture of hydroxylammonium chloride (2.34 g), sodium hydrogencarbonate (3.4 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was dissolved in methylene chloride (15 mL), N,N'-carbonyldiimidazole (0.3 g) and then 1,8-diazabicyclo[5.4.0]undec-7-ene (0.25 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The residue obtained by silica gel column chromatography was dissolved in methylene chloride (30 mL), iodine acid (0.73 g) was added, and the mixture was stirred at 35° C. for 8 hr. The reaction mixture was washed successively with water and saturated brine, and dried over anhydrous magnesium sulfate. The solvent was evaporated under reduced pressure. The obtained residue was purified by preparative HPLC to give the title compound as colorless crystals (0.18 g, 13%).

$^1$H NMR (300 MHz, DMSO-d$_6$)δ0.67-0.78 (2H, m), 0.91-1.02(2H, m), 2.02-2.15 (1H, m), 5.22 (2H, s), 5.47 (2H, s), 6.98 (1H, s), 7.30-7.49(6H, m), 7.50-7.64 (2H, m), 7.65-7.77 (2H, m), 8.05-8.28 (2H, m), 12.43 (1H, s)

Example 64

6-cyclopropyl-3-[2-(4-fluorophenyl)-2-hydroxy-ethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

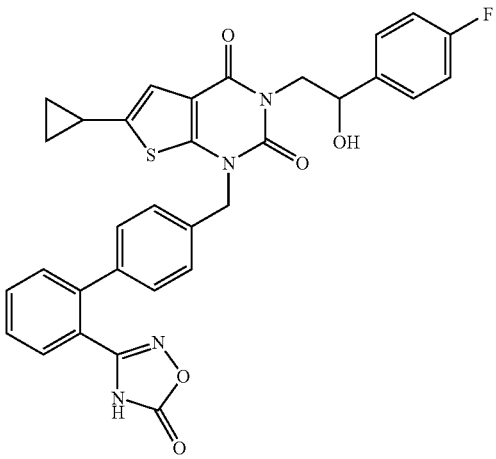 [SMILES: O=c1[nH]c(-c2ccccc2-c2ccc(Cn3c(=O)n(CC(O)c4ccc(F)cc4)c(=O)c4cc(C5CC5)sc43)cc2)no1]

To a mixture of 6-cyclopropyl-3-[2-(4-fluorophenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.1 g), tetrahydrofuran (10 mL) and methanol (10 mL) was added sodium borohydride-(0.038 g), and the mixture was stirred at room temperature for 1 hr. The reaction mixture was concentrated, and the residue was extracted with chloroform and saturated aqueous ammonium chloride solution. The chloroform layer was washed with saturated brine, and dried over anhydrous magnesium sulfate. The solvent was evaporated under reduced pressure. The precipitated solid was collected by filtration to give the title compound as colorless crystals (0.074 g, 74%).

$^1$H NMR (300 MHz, DMSO-$d_6$)δ0.61-0.76 (2H, m), 0.89-1.03(2H, m), 1.98-2.12 (1H, m), 3.97 (1H, dd, J=12.9, 5.7), 4.21 (1H, dd, J=12.9, 8.0), 4.92-5.28 (3H, m), 5.57-5.64 (1H, m), 6.94 (1H, s), 7.14 (2H, t, J=8.9), 7.21-7.42 (6H, m), 7.49-7.63 (2H, m), 7.63-7.75 (2H, m), 12.45 (1H, s)

Example 65

6-ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

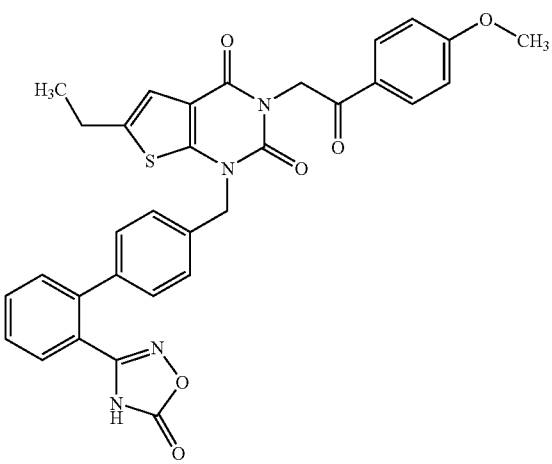 [SMILES: CCc1cc2c(=O)n(CC(=O)c3ccc(OC)cc3)c(=O)n(Cc3ccc(-c4ccccc4-c4noc(=O)[nH]4)cc3)c2s1]

A mixture of hydroxylammonium chloride (1.8 g), sodium hydrogencarbonate (2.8 g) and dimethyl sulfoxide (15 mL) was stirred at 40° C. for 30 min, 4'-{[6-ethyl-3-[2-(4-methoxyphenyl)-2-oxoethyl]-2,4-dioxo-3,4-dihydrothieno[2,3-d]pyrimidin-1(2H)-yl]methyl}biphenyl-2-carbonitrile (1.38 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was dissolved in methylene chloride (15 mL), N,N'-carbonyldiimidazole (0.28 g) and then 1,8-diazabicyclo[5.4.0]undec-7-ene (0.23 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.27 g, 17%).

$^1$H NMR (300 MHz, DMSO-$d_6$)δ1.21 (3H, t, J=7.5), 2.75 (2H, q, J=7.5), 3.87 (3H, s), 5.22 (2H, s), 5.41 (2H, s), 7.01 (1H, s), 7.09(2H, d, J=8.4), 7.30-7.39 (6H, m), 7.51-7.58 (2H, m), 7.64-7.70 (2H, m), 12.4(1H, s)

Example 66

6-ethyl-3-[2-(2-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

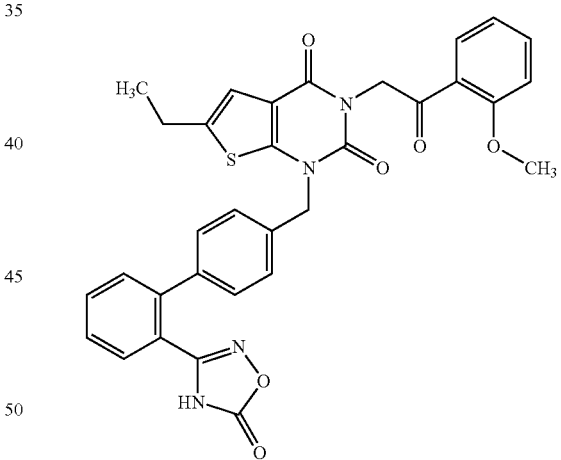

A mixture of hydroxylammonium chloride (8.3 g), sodium hydrogencarbonate (13 g) and dimethyl sulfoxide (100 mL) was stirred at 40° C. for 30 min, 4'-{[6-ethyl-3-[2-(2-methoxyphenyl)-2-oxoethyl]-2,4-dioxo-3,4-dihydrothieno[2,3-d]pyrimidin-1(2H)-yl]methyl}biphenyl-2-carbonitrile (4.12 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was dissolved in methylene chloride (150 mL), N,N'-carbonyldiimidazole (1.25 g) and then 1,8-diazabicyclo[5.4.0]undec-7-ene (1.06 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained solid was recrystallized from chloroform to give the title compound as colorless crystals (1.19 g, 26%).

$^1$H NMR (300 MHz, DMSO-d$_6$)δ1.19 (3H, t, J=7.5), 2.74 (2H, q, J=7.5), 3.98 (3H, s), 5.21 (2H, s), 5.26 (2H, s), 7.00 (1H, s), 7.08(1H, t, J=7.8), 7.25-7.38 (5H, m), 7.50-7.58 (2H, m), 7.62-7.74 (4H, m), 12.4(1H, s)

Example 67 methyl 5-chloro-2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]benzoate

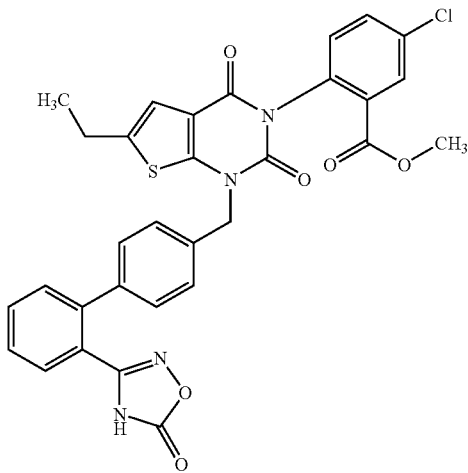 [SMILES: CCc1cc2c(=O)n(-c3ccc(Cl)cc3C(=O)OC)c(=O)n(Cc3ccc(-c4ccccc4-c4noc(=O)[nH]4)cc3)c2s1]

A mixture of methyl 5-chloro-2-(6-ethyl-2,4-dioxo-1,4-dihydrothieno[2,3-d]pyrimidin-3(2H)-yl)benzoate (0.67 g), 3-[4'-(bromomethyl)biphenyl-2-yl]-5-(trichloromethyl)-1,2,4-oxadiazole (0.96 g), potassium carbonate (0.38 g) and acetonitrile (80 mL) was stirred at 50° C. for 2 hr. Insoluble material was filtered off, and the solvent was evaporated under reduced pressure. The obtained residue was purified by silica gel column chromatography and dissolved in tetrahydrofuran (10 mL) and acetone (10 mL). 1N Aqueous potassium carbonate solution (20 mL) was added, and the mixture was stirred at room temperature for 3 hr. The reaction mixture was adjusted to pH 5 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.43 g, 38%).

$^1$H NMR (300 MHz, DMSO-d$_6$)δ1.29 (3H, t, J=7.6), 2.88 (2H, q, J=7.6), 3.64 (3H, s), 5.45 (2H, br), 7.22 (1H, s), 7.27-7.36 (2H, m),7.36-7.46 (3H, m), 7.55 (2H, dd, J=12.7, 7.4), 7.62-7.73 (2H, m), 7.81 (1H,dd, J=8.9, 2.5), 8.02 (1H, d, J=2.7), 12.43 (1H, s).

Example 68

5-chloro-2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]benzoic acid

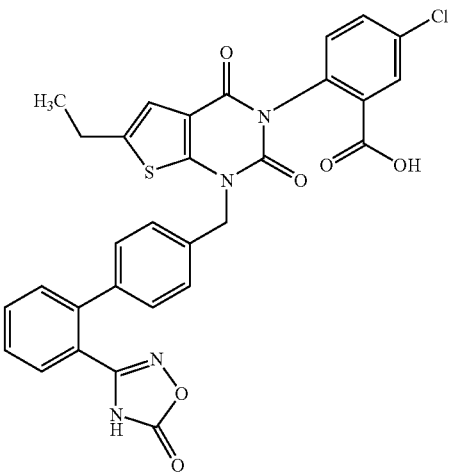 [SMILES: CCc1cc2c(=O)n(-c3ccc(Cl)cc3C(=O)O)c(=O)n(Cc3ccc(-c4ccccc4-c4noc(=O)[nH]4)cc3)c2s1]

A mixture of methyl 5-chloro-2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]benzoate (0.2 g), 1N aqueous sodium hydroxide solution (10 mL) and tetrahydrofuran (10 mL) was stirred at 100° C. for 2 hr. Tetrahydrofuran was evaporated under reduced pressure, and the residue was adjusted to pH 5 with chloroform and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.13 g, 65%).

$^1$H NMR (300 MHz, DMSO-d$_6$)δ1.17 (3H, t, J=7.8), 2.64 (2H, q, J=7.8), 4.20 (1H, d, J=15.3), 5.39 (1H, d, J=15.3), 6.67 (1H, s),7.04 (2H, d, J=8.1), 7.23-7.33 (4H, m), 7.50-7.57 (2H, m), 7.63-7.71 (2H, m),7.99 (1H, d, J=2.4)

Example 69

6-ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

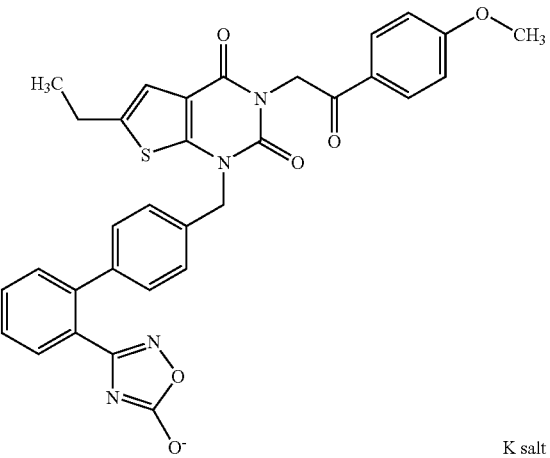 [SMILES: CCc1cc2c(=O)n(CC(=O)c3ccc(OC)cc3)c(=O)n(Cc3ccc(-c4ccccc4-c4noc([O-])n4)cc3)c2s1 ; "K salt"]

K salt

A mixture of 6-ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.25 g), potassium 2-ethylhexanoate (0.092 g), tetrahydrofuran (10 mL) and ethyl acetate (10 mL) was stirred at room temperature for 16 hr. The precipitated solid was collected by filtration to give the title compound as colorless crystals (0.18 g, 66%).

$^1$H NMR (300 MHz, DMSO-d$_6$) δ1.22 (3H, t, J=7.4), 2.78 (2H, q, J=7.4), 3.88 (3H, s), 5.18 (2H, s), 5.42 (2H, s), 7.03. (1H, s), 7.11(2H, d, J=8.3), 7.22-7.35 (5H, m), 7.34-7.53 (3H, m), 8.09 (2H, d, J=8.3)

Example 70

6-ethyl-3-[2-methoxy-2-(4-methoxyphenyl)ethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

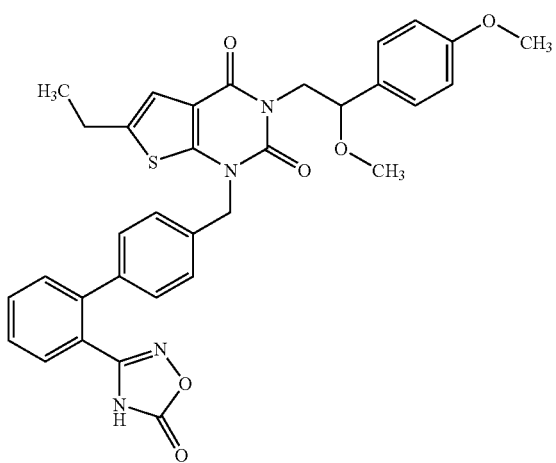 [SMILES: CCc1cc2c(=O)n(CC(OC)c3ccc(OC)cc3)c(=O)n(Cc3ccc(-c4ccccc4-c4noc(=O)[nH]4)cc3)c2s1]

To a mixture of 4'-{[6-ethyl-3-[2-(4-methoxyphenyl)-2-oxoethyl]-2,4-dioxo-3,4-dihydrothieno[2,3-d]pyrimidin-1(2H)-yl]methyl}biphenyl-2-carbonitrile (0.33 g) and tetrahydrofuran (20 mL) was added sodium borohydride (0.047 g), and the mixture was stirred at room temperature for 2 days. The reaction mixture was concentrated, and the residue was extracted with ethyl acetate and saturated aqueous ammonium chloride solution. The ethyl acetate layer was washed with saturated brine, and dried over anhydrous magnesium sulfate. The solvent was evaporated under reduced pressure. The obtained residue was dissolved in N,N-dimethylformamide (20 mL), sodium hydride (0.037 g) was added, and the mixture was stirred at room temperature for 10 min. Methyl iodide (0.046 mL) was added to the reaction mixture, and the mixture was further stirred at room temperature for 1 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. To the obtained residue was added 1N aqueous sodium hydroxide solution (50 mL), and the mixture was stirred at 60° C. for 1 hr. The reaction mixture was adjusted to pH 4 with 1N hydrochloric acid, and the mixture was extracted with ethyl acetate. The obtained ethyl acetate layer was washed with saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.46 g), sodium hydrogencarbonate (0.7 g) and dimethyl sulfoxide (10 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was dissolved in methylene chloride (30 mL), N,N'-carbonyldiimidazole (0.068 g) and then 1,8-diazabicyclo[5.4.0]undec-7-ene (0.057 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The precipitated solid was collected by filtration to give the title compound as colorless crystals (0.14 g, 36%).

$^1$H NMR (300 MHz, DMSO-d$_6$) δ1.18 (3H, t, J=7.5), 2.72 (2H, q, J=7.5), 3.04 (3H, s), 3.72 (3H, s), 3.95-4.02 (1H, m), 4.28-4.35 (1H,m), 4.55-4.59 (1H, m), 5.06 (1H, d, J=16.5), 5.20 (1H, d, J=16.5),6.90-6.96 (3H, m), 7.20-7.29 (6H, m), 7.49-7.58 (2H, m), 7.64-7.71 (2H, m),12.38 (1H, s)

Example 71

6-ethyl-3-[2-hydroxy-2-(4-methoxyphenyl)ethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

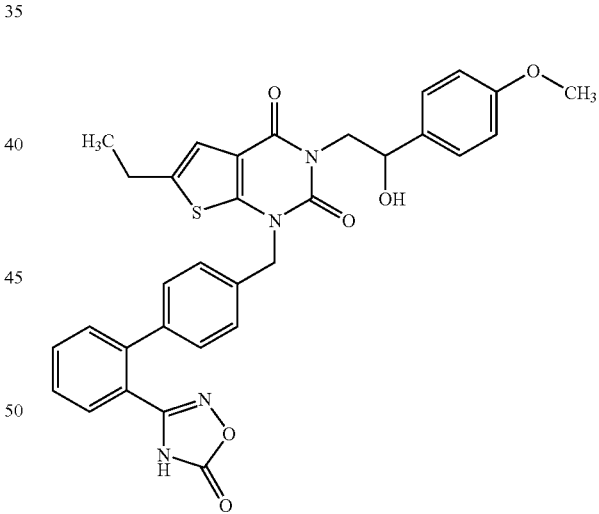

To a mixture of 6-ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g) and methanol (15 mL) was added sodium borohydride (0.025 g), and the mixture was stirred at room temperature for 2 hr. The reaction mixture was concentrated, and the residue was extracted with chloroform and saturated aqueous ammonium chloride solution. The chloroform layer was washed with saturated brine, and dried over anhydrous magnesium sulfate. The solvent was evaporated under reduced pressure. The precipitated solid was collected by filtration to give the title compound as colorless crystals (0.12 g, 61%).

¹H NMR (300 MHz, DMSO-d₆)δ1.18 (3H, t, J=7.5), 2.72 (2H, q, J=7.5), 3.70 (3H, s), 3.92-4.03 (1H, m), 4.17-4.24 (1H, m), 4.90-4.96(1H, m), 5.07 (1H, d, J=16.5), 5.20 (1H, d, J=16.5), 5.39 (1H, d, J=4.5),6.86 (2H, d, J=8.4), 6.97 (1H, s), 7.21-7.30 (6H, m), 7.49-7.58 (2H, m),7.64-7.71 (2H, m), 12.38 (1H, s)

Example 72

3-[2-(2,4-dimethoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

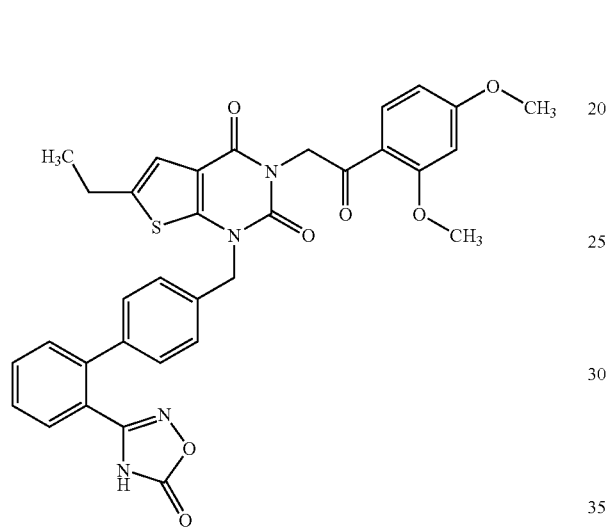

A mixture of hydroxylammonium chloride (0.89 g), sodium hydrogencarbonate (1.35 g) and dimethyl sulfoxide (10 mL) was stirred at 40° C. for 30 min, 4'-{[3-[2-(2,4-dimethoxyphenyl)-2-oxoethyl]-6-ethyl-2,4-dioxo-3,4-dihydrothieno[2,3-d]pyrimidin-1(2H)-yl]methyl}biphenyl-2-carbonitrile (0.91 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was dissolved in methylene chloride (30 mL), N,N'-carbonyldiimidazole (0.26 g) and then 1,8-diazabicyclo[5.4.0]undec-7-ene (0.22 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.35 g, 35%).

¹H NMR (300 MHz, DMSO-d₆)δ1.20 (3H, t, J=7.5), 2.74 (2H,q, J=7.5), 3.88 (3H, s), 4.00 (3H, s), 5.21 (4H, s), 6.66 (1H, d, J=8.7),6.73 (1H, s), 7.00 (1H, s), 7.34 (4H, dd, J=11.1, 8.1), 7.50-7.57 (2H, m),7.64-7.70 (2H, m), 7.77 (1H, d, J=8.7), 12.37 (1H, s)

Example 73

6-ethyl-3-[2-(2-fluoro-4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

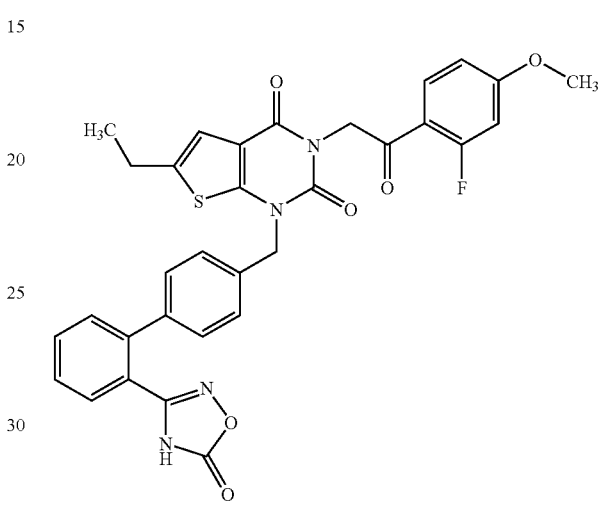

A mixture of hydroxylammonium chloride (1 g), sodium hydrogencarbonate (1.5 g) and dimethyl sulfoxide (15 mL) was stirred at 40° C. for 30 min, 4'-{[6-ethyl-3-[2-(2-fluoro-4-methoxyphenyl)-2-oxoethyl]-2,4-dioxo-3,4-dihydrothieno[2,3-d]pyrimidin-1(2H)-yl]methyl}biphenyl-2-carbonitrile (1 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by preparative HPLC and dissolved in methylene chloride (20 mL). N,N'-Carbonyldiimidazole (0.11 g) and then 1,8-diazabicyclo[5.4.0]undec-7-ene (0.096 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as a colorless amorphous solid (0.084 g, 8%).

¹H NMR (300 MHz, DMSO-d₆)δ1.20 (3H, t, J=7.5), 2.74 (2H, q, J=7.5), 3.88 (3H, s), 5.22-5.25 (4H, m), 6.93-7.07 (3H, m), 7.34 (4H,dd, J=20.4, 8.1), 7.51-7.58 (2H, m), 7.64-7.70 (2H, m), 7.89 (1H, t, J=8.7), 12.37 (1H, s)

Example 74

3-[2-(3,4-dimethoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

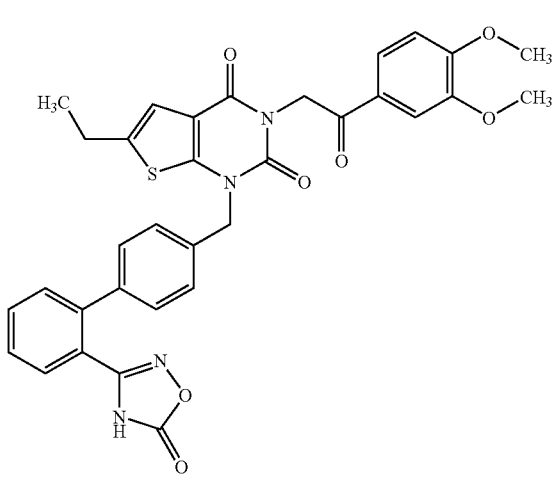 [SMILES: CCc1cc2c(=O)n(CC(=O)c3ccc(OC)c(OC)c3)c(=O)n(Cc3ccc(-c4ccccc4-c4noc(=O)[nH]4)cc3)c2s1]

A mixture of hydroxylammonium chloride (1.23 g), sodium hydrogencarbonate (1.86 g) and dimethyl sulfoxide (15 ml) was stirred at 40° C. for 30 min, 4'-{[3-[2-(3,4-dimethoxyphenyl)-2-oxoethyl]-6-ethyl-2,4-dioxo-3,4-dihydrothieno[2,3-d]pyrimidin-1(2H)-yl]methyl}biphenyl-2-carbonitrile (1.25 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL), N,N'-carbonyldiimidazole (0.36 g) and then 1,8-diazabicyclo[5.4.0]undec-7-ene (0.3 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC, and the title compound was obtained as colorless crystals from a fraction with a shorter retention time (0.42 g, 31%).

$^1$H NMR (300 MHz, DMSO-$d_6$)δ1.21 (3H, t, J=7.2), 2.75 (2H, q, J=7.2), 3.83 (3H, s), 3.87 (3H, s), 5.22 (2H, s), 5.44 (2H, s), 7.01(1H, s), 7.12 (1H, d, J=8.1), 7.34 (4H, dd, J=18.0, 8.1), 7.51-7.57 (3H,m), 7.64-7.70 (2H, m), 7.79 (1H, d, J=8.1), 12.4 (1H, s)

Example 75

3-[2-(3,4-dimethoxyphenyl)-2-(hydroxyimino)ethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

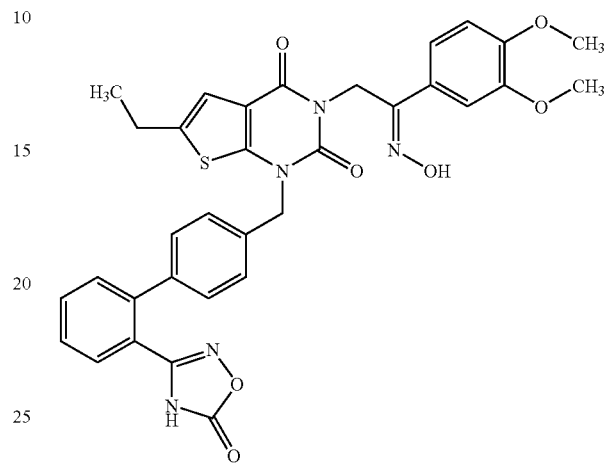

In Example 74, purification by preparative HPLC was successively perform to give the title compound as a stereoisomer mixture from a fraction with a longer retention time (0.11 g, 8%).

$^1$H NMR (300 MHz, DMSO-$d_6$)δ1.14-1.21 (3H, m), 2.68-2.77(2H, m), 3.66-3.76 (6H, m), 4.70, 4.97 (combined 2H, s),5.08, 5.20 (combined 2H, s), 6.86-7.22 (5H, m), 7.29 (4H, s), 7.49-7.68 (4H, m)

Example 76

6-ethyl-3-[2-(4-methoxy-2-methylphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

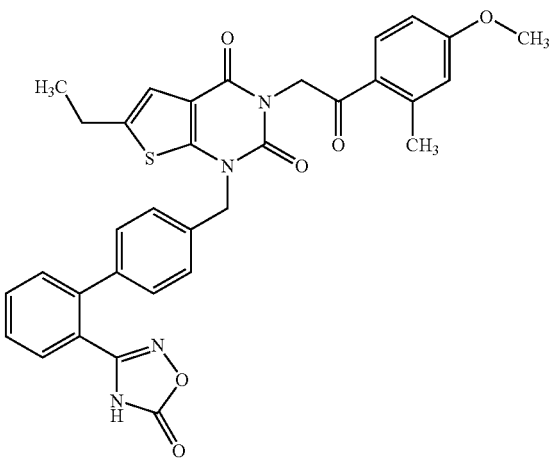 [SMILES: CCc1cc2c(=O)n(CC(=O)c3ccc(OC)cc3C)c(=O)n(Cc3ccc(-c4ccccc4-c4noc(=O)[nH]4)cc3)c2s1]

A mixture of hydroxylammonium chloride (1 g), sodium hydrogencarbonate (1.5 g) and dimethyl sulfoxide (15 mL)

was stirred at 40° C. for 30 min, 4'-{[6-ethyl-3-[2-(4-methoxy-2-methylphenyl)-2-oxoethyl]-2,4-dioxo-3,4-dihydrothieno[2,3-d]pyrimidin-1(2H)-yl]methyl}biphenyl-2-carbonitrile (1 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL), N,N'-carbonyldiimidazole (0.3 g) and then 1,8-diazabicyclo[5.4.0]undec-7-ene (0.25 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as a colorless amorphous solid (0.28 g, 25%).

$^1$H NMR (300 MHz, DMSO-$d_6$)δ1.21 (3H, t, J=7.5), 2.44 (3H, s), 2.67-2.84 (2H, m), 3.84 (3H, s), 5.23 (2H, s), 5.31 (2H, s), 6.86-6.98(2H, m), 6.96-7.09 (1H, m), 7.35 (4H, q, J=8.5), 7.49-7.63 (2H, m), 7.64-7.76(2H, m), 8.07 (1H, d, J=9.2), 12.4 (1H, s)

Example 77

6-ethyl-1-{[2'-(5-oxo-4,5-dihydro-1,2,4-oxadiazol-3-yl)biphenyl-4-yl]methyl}-3-{2-oxo-2-[4-(trifluoromethoxy)phenyl]ethyl}thieno[2,3-d]pyrimidine-2,4(1H,3H)-dione

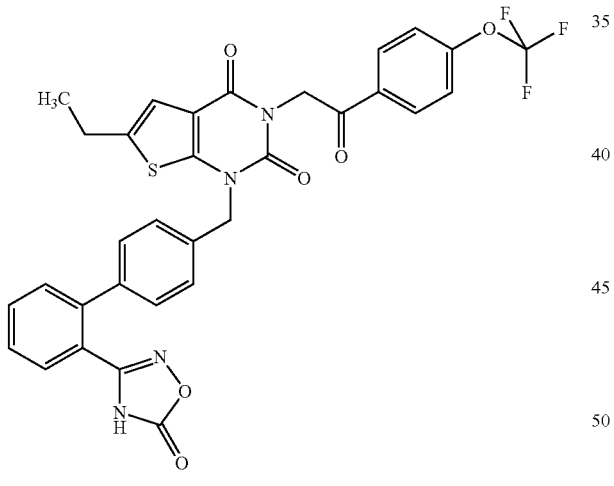

To a mixture of 4'-[(6-ethyl-2,4-dioxo-3,4-dihydrothieno[2,3-d]pyrimidin-1(2H)-yl)methyl]biphenyl-2-carbonitrile (0.9 g), 2-bromo-1-[4-(trifluoromethoxy)phenyl]ethanone (0.79 g) and N,N-dimethylformamide (50 mL) was added sodium hydride (0.14 g), and the mixture was stirred at room temperature for 1 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (1.75 g), sodium hydrogencarbonate (2.6 g) and dimethyl sulfoxide (20 ml), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.26 g) and then 1,8-diazabicyclo[5.4.0]undec-7-ene (0.22 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was dissolved in methylene chloride (30 mL), iodine acid (0.57 g) was added, and the mixture was stirred at room temperature for 5 hr. The reaction mixture was washed successively with water and saturated brine, and dried over anhydrous magnesium sulfate. The solvent was evaporated under reduced pressure. The obtained residue was purified by preparative HPLC to give the title compound as a colorless amorphous solid (0.19 g, 8%).

$^1$H NMR (300 MHz, DMSO-$d_6$)δ1.21 (3H, t, J=7.2), 2.76 (2H, q, J=7.2), 5.21 (2H, s), 5.48 (2H, s), 7.01 (1H, s), 7.28-7.64 (10H, m),8.23 (2H, d, J=8.7), 12.36 (1H, br)

Example 78

6-ethyl-3-[2-(3-fluoro-4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

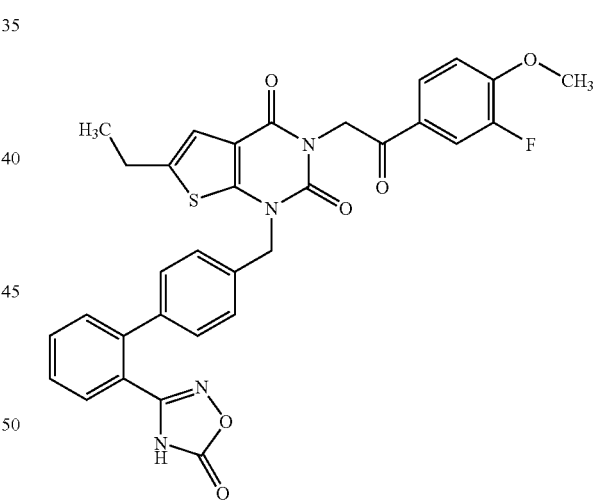

To a mixture of 4'-[(6-ethyl-2,4-dioxo-3,4-dihydrothieno[2,3-d]pyrimidin-1(2H)-yl)methyl]biphenyl-2-carbonitrile (1.5 g), 2-bromo-1-(3-fluoro-4-methoxyphenyl)ethanone (1.16 g) and N,N-dimethylformamide (30 mL) was added sodium hydride (0.19 g), and the mixture was stirred at room temperature for 1 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (1.2 g), sodium hydrogencarbonate (1.8 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.35 g) and then 1,8-diazabicyclo[5.4.0]undec-7-ene (0.29 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as a colorless amorphous solid (0.18 g, 29%).

$^1$H NMR (300 MHz, DMSO-$d_6$) δ1.21 (3H, t, J=7.5), 2.75 (2H, q, J=7.5), 3.95 (3H, s), 5.22 (2H, s), 5.42 (2H, s), 7.01 (1H, s), 7.29-7.39 (5H, m), 7.53 (2H, m), 7.66 (2H, m), 7.89-8.00 (2H, m), 12.37 (1H, s)

Example 79

6-ethyl-3-[2-(3-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

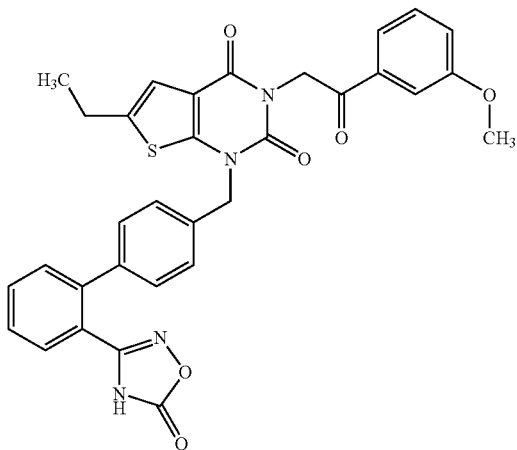 [SMILES: CCc1cc2c(=O)n(CC(=O)c3cccc(OC)c3)c(=O)n(Cc3ccc(-c4ccccc4-c4noc(=O)[nH]4)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (0.9 g), 2-bromo-1-(3-methoxyphenyl)ethanone (0.64 g) and N,N-dimethylformamide (30 mL) was added sodium hydride (0.14 g), and the mixture was stirred at room temperature for 1 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (1.51 g), sodium hydrogencarbonate (2.28 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography and dissolved in methylene chloride (10 ml). N,N'-Carbonyldiimidazole (0.057 g) and then 1,8-diazabicyclo[5.4.0]undec-7-ene (0.05 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as a colorless amorphous solid (0.055 g, 4%).

$^1$H NMR (300 MHz, DMSO-$d_6$) δ1.21 (3H, t, J=7.8), 2.74 (2H, q, J=7.8), 3.84 (3H, s), 5.22 (2H, s), 5.46 (2H, s), 7.02 (1H, s), 7.27-7.38 (4H, m), 7.48-7.55 (4H, m), 7.62-7.71 (3H, m), 12.37 (1H, s)

Example 80

6-ethyl-3-[2-(3-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

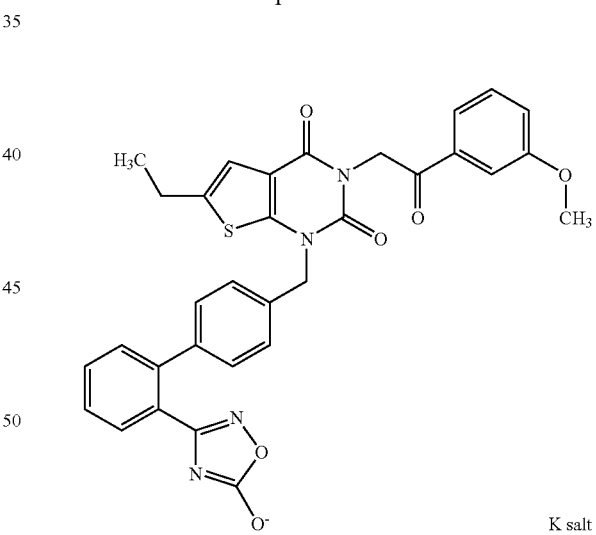

A mixture of 6-ethyl-3-[2-(3-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.045 g), potassium 2-ethylhexanoate (0.017 g), and ethyl acetate (5 mL) was stirred at room temperature for 16 hr. The precipitated solid was collected by filtration to give the title compound as colorless crystals (0.032 g, 66%).

$^1$H NMR (300 MHz, DMSO-$d_6$) δ1.22 (3H, t, J=6.9), 2.77 (2H, q, J=6.9), 3.84 (3H, s), 5.17 (2H, s), 5.45 (2H, s), 7.00 (1H, s), 7.22-7.55 (11H, m), 7.69 (1H, d, J=7.2)

Example 81

3-[2-(4-ethoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

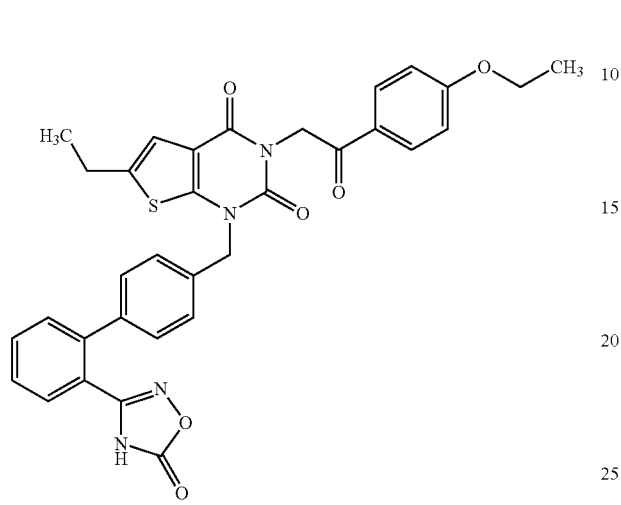

To a mixture of 4'-[(6-ethyl-2,4-dioxo-3,4-dihydrothieno[2,3-d]pyrimidin-1(2H)-yl)methyl]biphenyl-2-carbonitrile (1.5 g), 2-bromo-1-(4-ethoxyphenyl)ethanone (1.14 g) and N,N-dimethylformamide (30 mL) was added sodium hydride (0.19 g), and the mixture was stirred at room temperature for 1 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (1 g), sodium hydrogencarbonate (1.15 g) and dimethyl sulfoxide (10 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.3 g) and then 1,8-diazabicyclo[5.4.0]undec-7-ene (0.25 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.38 g, 16%).

$^1$H NMR (300 MHz,. DMSO-$d_6$)δ1.21 (3H, t, J=7.5), 1.36 (3H, t, J=6.9), 2.75 (2H, q, J=7.5), 4.14 (2H, q, J=6.9), 5.22 (2H, s),5.40 (2H, s), 7.01 (1H, s), 7.06 (2H, d, J=6.0), 7.30-7.39 (4H, m), 7.51-7.58(2H, m), 7.64-7.70 (2H, m), 8.05 (2H, d, J=8.4), 12.37 (1H, s)

Example 82

3-[2-(4-ethoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

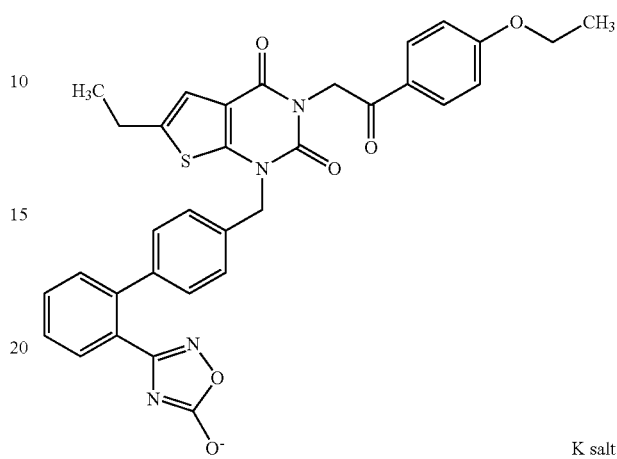

A mixture of 3-[2-(4-ethoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.38 g), potassium 2-ethylhexanoate (0.14 g), tetrahydrofuran (10 mL) and ethyl acetate (15 mL) was stirred at room temperature for 16 hr. The precipitated solid was collected by filtration to give the title compound as colorless crystals (0.35 g, 87%).

$^1$H NMR (300 MHz, DMSO-$d_6$)δ1.21 (3H, t, J=7.5), 1.36 (3H, t, J=6.9), 2.76 (2H, q, J=7.5), 4.14 (2H, q, J=6.9), 5.16 (2H, s),5.40 (2H, s), 7.00 (1H, s), 7.06 (2H, d, J=7.2), 7.23-7.49 (10H, m)

Example 83

6-ethyl-1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione

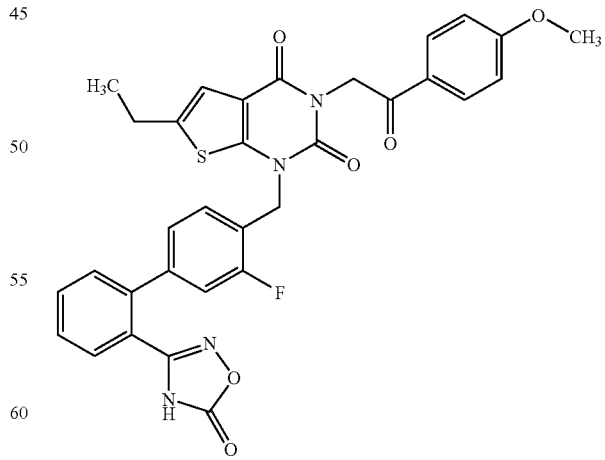

A mixture of hydroxylammonium chloride (0.9 g), sodium hydrogencarbonate (1.37 g) and dimethyl sulfoxide (15 mL) was stirred at 40° C. for 30 min, 4'-{[6-ethyl-3-[2-(4-methoxyphenyl)-2-oxoethyl]-2,4-dioxo-3,4-dihydrothieno[2,3-d]pyrimidin-1(2H)-yl]methyl}-3'-fluorobiphenyl-2-carbonitrile (0.9 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.26 g) and then 1,8-diazabicyclo[5.4.0]undec-7-ene (0.22 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.4 g, 40%).

$^1$H NMR (300 MHz, DMSO-d$_6$)δ1.20 (3H, t, J=7.2), 2.76 (2H, q, J=7.2), 3.86 (3H, s), 5.26 (2H, s), 5.39 (2H, s), 7.02 (1H, s),7.07-7.13 (3H, m), 7.22-7.32 (2H, m), 7.53-7.61 (2H, m), 7.66-7.72 (2H, m),8.06 (2H, d, J=9.0), 12.46 (1H, s)

Example 84

3-[2-(3,4-dimethoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

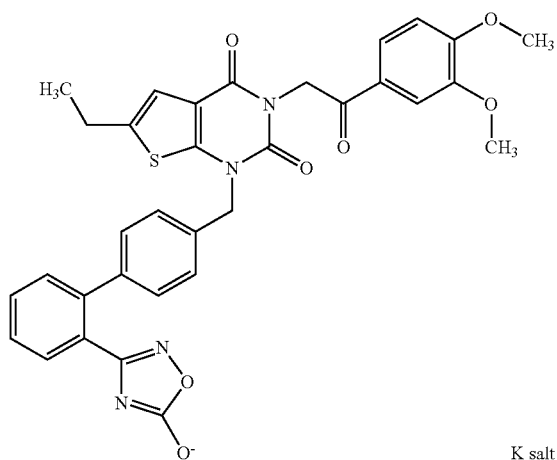

A mixture of 3-[2-(3,4-dimethoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.1 g), potassium 2-ethylhexanoate (0.035 g), tetrahydrofuran (5 mL) and ethyl acetate (5 mL) was stirred at room temperature for 16 hr. The precipitated solid was collected by filtration to give the title compound as colorless crystals (0.056 g, 53%).

$^1$H NMR (300 MHz, DMSO-d$_6$)δ1.22 (3H, t, J=7.4), 2.78 (2H, q, J=7.4), 3.85. (3H, s), 3.88 (3H, s), 5.18 (2H, s), 5.45 (2H, s), 7.03(1H, s), 7.14 (1H, d, J=8.3), 7.22-7.46 (7H, m), 7.47-7.58 (2H, m), 7.74-7.89(1H, m)

Example 85

6-ethyl-1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione potassium salt

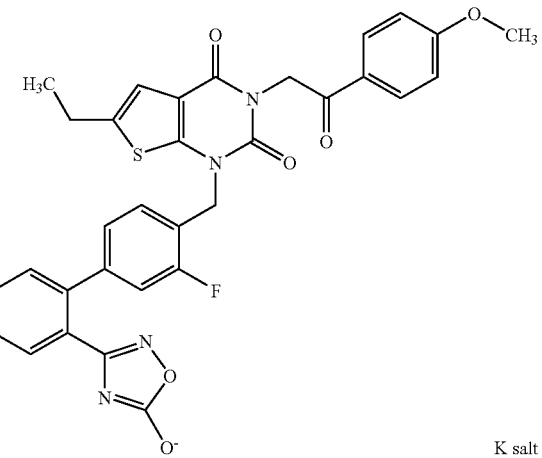

A mixture of 6-ethyl-1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H, 3H)-dione (0.4 potassium 2-ethylhexanoate (0.14 g), tetrahydrofuran (5 mL) and ethyl acetate (10 mL) was stirred at room temperature for 16 hr. The precipitated solid was collected by filtration to give the title compound as is colorless crystals (0.34 g, 80%).

$^1$H NMR (300 MHz, DMSO-d$_6$)δ1.22 (3H, t, J=7.4),2.71-2.84 (2H, m), 3.88 (3H, s), 5.23 (2H, s), 5.41 (2H, s), 7.04 (1H, s),7.07-7.24 (5H, m), 7.30-7.59 (4H, m), 8.09 (2H, d, J=8.7)

Example 86

6-ethyl-3-[2-(3-fluoro-4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4 (1H,3H)-dione potassium salt

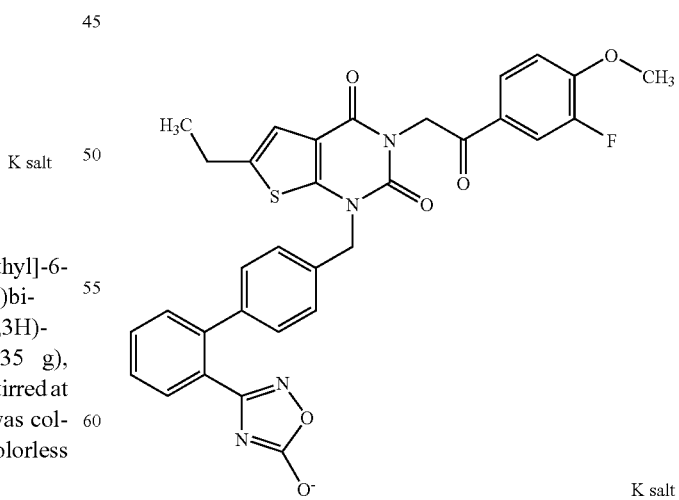

A mixture of 6-ethyl-3-[2-(3-fluoro-4-methoxyphenyl)-2-oxoethyl]-1-{[2'-(5-oxo-4,5-dihydro-1,2,4-oxadiazol-3-yl) biphenyl-4-yl]methyl}thieno[2,3-d]pyrimidine-2,4(1H,3H)- dione (0.06 g), potassium 2-ethylhexanoate (0.021 g), tetrahydrofuran (5 mL) and ethyl acetate (5 mL) was stirred at room temperature for 16 hr. The precipitated solid was collected by filtration to give the title compound as colorless crystals (0.047 g, 73%).

$^1$H NMR (300 MHz, DMSO-$d_6$) δ1.20 (3H, t, J=7.5), 2.76 (2H, q, J=7.5), 3.95 (3H, s), 5.16 (2H, s), 5.41 (2H, s), 7.00 (1H, s), 7.22-7.49 (9H, m), 7.88-8.00 (2H, m)

Example 87

6-ethyl-3-[2-(4-methoxyphenyl)-2-pyrrolidin-1-yl-ethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

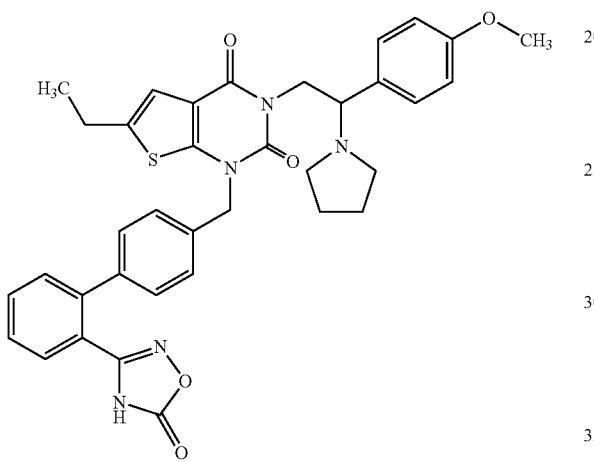 [SMILES: CCOc1ccc(C(=O)Cn2c(=O)c3cc(CC)sc3n(Cc3ccc(-c4ccccc4-c4noc(=O)[nH]4)cc3)c2=O)cc1]

To a solution (50 mL) of methyl 2-amino-5-ethylthiophene-3-carboxylate (0.5 g) in methylene chloride were added triphosgene (0.35 g) and triethylamine (0.98 mL), and the mixture was stirred at room temperature for 2 hr. To the reaction mixture was added 2-(4-methoxyphenyl)-2-pyrrolidin-1-ylethanamine (1.19 g), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in methanol (50 mL), sodium methoxide (0.73 g) was added, and the mixture was stirred at 60° C. for 1 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The obtained residue was dissolved in acetonitrile (50 mL), 3-[4'-(bromomethyl)biphenyl-2-yl]-5-(trichloromethyl)-1,2,4-oxadiazole (1.16 g) and potassium carbonate (1.49 g) were added, and the mixture was stirred at 50° C. for 2 hr. Insoluble material was filtered off, and the solvent was evaporated under reduced pressure. The obtained residue was purified by silica gel column chromatography and dissolved in tetrahydrofuran (10 mL) and acetone (10 mL). 1N Aqueous sodium hydroxide solution (5 mL) was added, and the mixture was stirred at room temperature for 1 hr. The reaction mixture was adjusted to pH 4 with water and 1N hydrochloric acid, and extracted with chloroform. The obtained chloroform layer was washed with saturated brine, and dried over anhydrous magnesium sulfate. The solvent was evaporated under reduced pressure. The residue was purified by silica gel column chromatography to give the title compound as colorless crystals (0.53 g, 30%).

$^1$H NMR (300 MHz, DMSO-$d_6$) δ1.17 (3H, t, J=7.6), 1.67 (4H, s), 2.56-2.81 (4H, m), 3.35 (2H, d, J=13.6), 3.68 (3H, s), 3.87-4.06(1H, m), 4.24-4.55 (2H, m), 4.98 (1H, s), 5.19 (1H, d, J=16.7), 6.83 (2H, d, J=8.7), 6.93 (1H, s), 7.06 (2H, d, J=8.0), 7.18 (2H, d, J=8.3), 7.26 (2H, d, J=8.0), 7.45-7.62 (2H, m), 7.61-7.75 (2H, m)

Example 88

6-ethyl-3-{[1-(4-methoxyphenyl)cyclopropyl]methyl}-1-{[2'-(5-oxo-4,5-dihydro-1,2,4-oxadiazol-3-yl)biphenyl-4-yl]methyl}thieno[2,3-d]pyrimidine-2,4(1H,3H)-dione

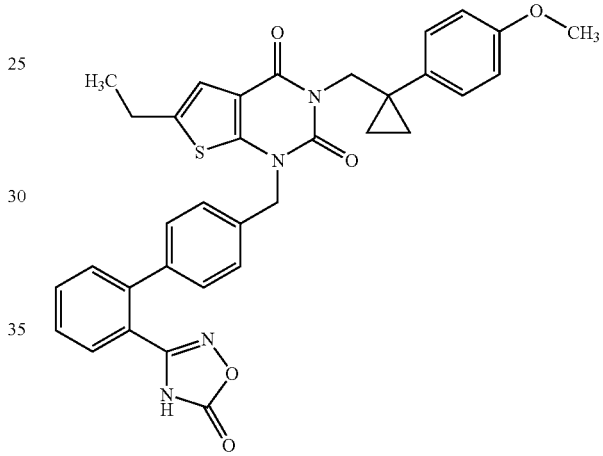

A mixture of hydroxylammonium chloride (1.44 g), sodium hydrogencarbonate (2.2 g) and dimethyl sulfoxide (15 mL) was stirred at 40° C. for 30 min, 4'-{[6-ethyl-3-{[1-(4-methoxyphenyl)cyclopropyl]methyl}-2,4-dioxo-3,4-dihydrothieno[2,3-d]pyrimidin-1(2H)-yl]methyl}biphenyl-2-carbonitrile (0.71 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was dissolved in methylene chloride (20 mL), N,N'-carbonyldiimidazole (0.21 g) and then 1,8-diazabicyclo[5.4.0]undec-7-ene (0.18 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The residue was purified by silica gel column chromatography to give the title compound as a colorless amorphous solid (0.3 g, 38%).

$^1$H NMR (300 MHz, DMSO-$d_6$) δ0.66-0.72 (2H, m), 0.94-0.99(2H, m), 0.17 (3H, t, J=7.5), 2.70 (2H, q, J=7.5), 3.64 (3H, s), 4.16 (2H,s), 5.04 (2H, s), 6.75 (2H, d, J=7.8), 6.93 (1H, s), 7.08-7.15 (4H, m),7.25-7.27 (2H, m), 7.50-7.58 (2H, m), 7.64-7.72 (2H, m), 12.4 (1H, s)

Example 89

6-ethyl-3-{[1-(4-methoxyphenyl)cyclopropyl]methyl}-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

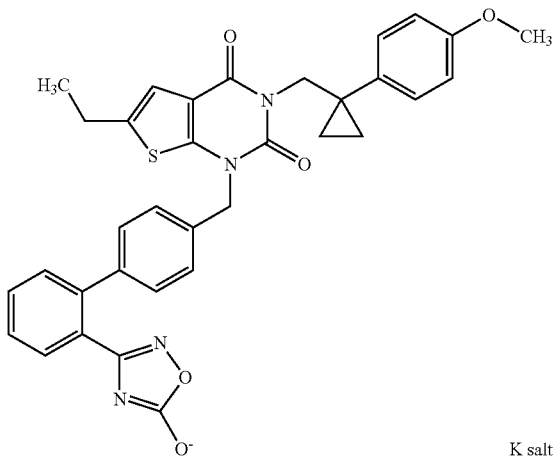 [SMILES: CCc1cc2c(=O)n(CC3(c4ccc(OC)cc4)CC3)c(=O)n(Cc3ccc(-c4ccccc4-c4noc([O-])n4)cc3)c2s1 ; "K salt"]

K salt

A mixture of 6-ethyl-3-{[1-(4-methoxyphenyl)cyclopropyl]methyl}-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.3 g), potassium 2-ethylhexanoate (0.11 g) and ethyl acetate (10 mL) was stirred at room temperature for 16 hr. The precipitated solid was collected by filtration to give the title compound as colorless crystals (0.28 g, 85%).

$^1$H NMR (300 MHz, DMSO-$d_6$)δ0.60-0.76 (2H, m), 0.88-1.03(2H, m), 1.19 (3H, t, J=7.4), 2.72 (2H, q, J=7.4), 3.66 (3H, s), 4.17 (2H,s), 5.01 (2H, s), 6.78 (2H, d, J=8.3), 6.94 (1H, s), 7.02 (2H, d, J=8.0),7.16 (2H, d, J=8.3), 7.22-7.48 (5H, m), 7.51 (1H, d, J=7.2)

Example 90

3-[2-(3,5-dimethoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H, 3H)-dione

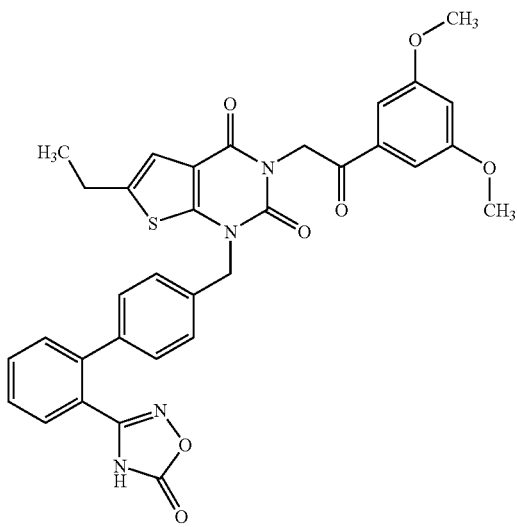 [SMILES: CCc1cc2c(=O)n(CC(=O)c3cc(OC)cc(OC)c3)c(=O)n(Cc3ccc(-c4ccccc4-c4noc(=O)[nH]4)cc3)c2s1]

A mixture of hydroxylammonium chloride (2.26 g), sodium hydrogencarbonate (3.4 g) and dimethyl sulfoxide (20 mL) was stirred at 40° C. for 30 min, 4'-{[3-[2-(3,5-dimethoxyphenyl)-2-oxoethyl]-6-ethyl-2,4-dioxo-3,4-dihydrothieno[2,3-d]pyrimidin-1(2H)-yl]methyl}biphenyl-2-carbonitrile (1.14 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (30 mL). N,N'-Carbonyldiimidazole (0.33 g) and then 1,8-diazabicyclo[5.4.0]undec-7-ene (0.28 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.6 g, 48%).

$^1$H NMR (300 MHz, DMSO-$d_6$)δ1.20 (3H, t, J=7.5), 2.74 (2H, q, J=7.5), 3.87 (3H, s), 3.99 (3H, s), 5.17 (2H, s), 5.21 (2H, s), 6.66(1H, d, J=9.0), 6.73 (1H, s), 7.00 (1H, s), 7.30-7.39 (4H, m), 7.48-7.57 (2H,m), 7.62-7.70 (2H, m), 7.77 (1H, d, J=9.0), 12.4 (1H, s)

Example 91

3-[2-(3,5-dimethoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H, 3H)-dione potassium salt

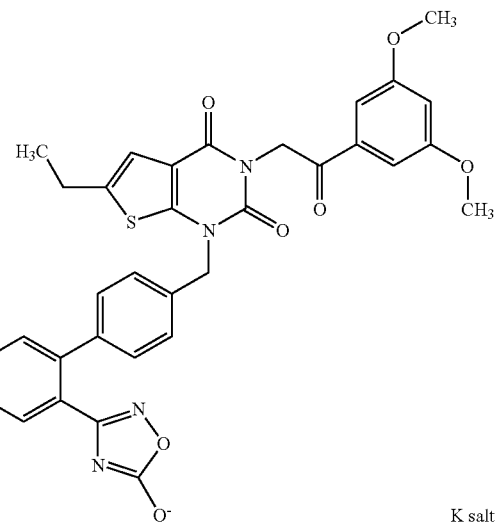

K salt

A mixture of 3-[2-(3,5-dimethoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.6 g), potassium 2-ethylhexanoate (0.21 g), tetrahydrofuran (10 mL) and ethyl acetate (10 mL) was stirred at room temperature for 16 hr. The precipitated solid was collected by filtration to give the title compound as colorless crystals (0.53 g, 84%).

$^1$H NMR (300 MHz, DMSO-$d_6$)δ1.22 (3H, t, J=7.4), 2.77 (2H, q, J=7.4), 3.88 (3H, s), 4.00 (3H, s), 5.17 (2H, s), 5.21

(2H, s), 6.68(1H, dd, J=8.7, 2.3), 6.74 (1H, d, J=2.3), 7.01 (1H, s), 7.21-7.47 (7H, m),7.46-7.53 (1H, m), 7.79 (1H, d, J=8.7)

Example 92

6-ethyl-1-{[2'-(5-oxo-4,5-dihydro-1,2,4-oxadiazol-3-yl)biphenyl-4-yl]methyl}-3-(2-oxopropyl)thieno[2,3-d]pyrimidine-2,4(1H,3H)-dione

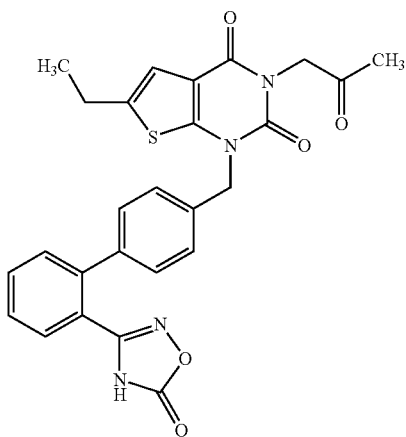 [SMILES: CCc1cc2c(=O)n(CC(C)=O)c(=O)n(Cc3ccc(-c4ccccc4-c4noc(=O)[nH]4)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (1 g), 1-bromoacetone (0.26 mL) and N,N-dimethylformamide (20 mL) was added sodium hydride (0.15 g), and the mixture was stirred at 50° C. for 3 hr. The reaction mixture was diluted with chloroform, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (1.88 g), sodium hydrogencarbonate (2.84 g) and dimethyl sulfoxide (20 ml,), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent-was evaporated under reduced pressure. The residue was purified by silica gel column chromatography and dissolved in methylene chloride (30 mL). N,N'-Carbonyldiimidazole (0.27 g) and then 1,8-diazabicyclo[5.4.0]undec-7-ene (0.23 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was dissolved in methylene chloride (50 mL), iodine acid (0.73 g) was added, and the mixture was stirred at room temperature for 24 hr. The reaction mixture was washed successively with water and saturated brine, and dried over anhydrous magnesium sulfate. The solvent was evaporated under reduced pressure. The obtained residue was purified by preparative HPLC to give the title compound as colorless crystals (0.15 g, 12%).

$^1$H NMR (300 MHz, DMSO-d$_6$)δ1.20 (3H, t, J=7.2), 2.24 (3H, s), 2.75 (2H, q, J=7.2), 4.83 (2H, s), 5.20 (2H, s), 7.01 (1H, s),7.29-7.42 (4H, m), 7.49-7.61 (2H, m), 7.64-7.74 (2H, m), 12.39 (1H, br)

Example 93

6-ethyl-1-{[2'-(5-oxo-4,5-dihydro-1,2,4-oxadiazol-3-yl)biphenyl-4-yl]methyl}-3-(2-oxopropyl)thieno[2,3-d]pyrimidine-2,4(1H,3H)-dione potassium salt

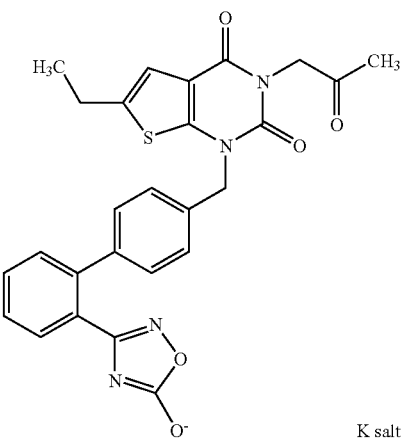 [SMILES: CCc1cc2c(=O)n(CC(C)=O)c(=O)n(Cc3ccc(-c4ccccc4-c4noc([O-])n4)cc3)c2s1 ; "K salt"]

A mixture of 6-ethyl-1-{[2'-(5-oxo-4,5-dihydro-1,2,4-oxadiazol-3-yl)biphenyl-4-yl]methyl}-3-(2-oxopropyl)thieno[2,3-d]pyrimidine-2,4(1H,3H)-dione (0.15 g), potassium 2-ethylhexanoate (0.065 g) and ethyl acetate (15 mL) was stirred at room temperature for 16 hr. The precipitated solid was collected by filtration to give the title compound as colorless crystals (0.14 g, 83%).

$^1$H NMR (300 MHz, DMSO-d$_6$)δ1.21 (3H, t, J=7.6), 2.23 (3H, s), 2.76 (2H, q, J=7.6), 4.82 (2H, s), 5.15 (2H, s), 7.00 (1H, s),7.20-7.54 (8H, m)

Example 94

6-ethyl-3-[2-(2-naphthyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

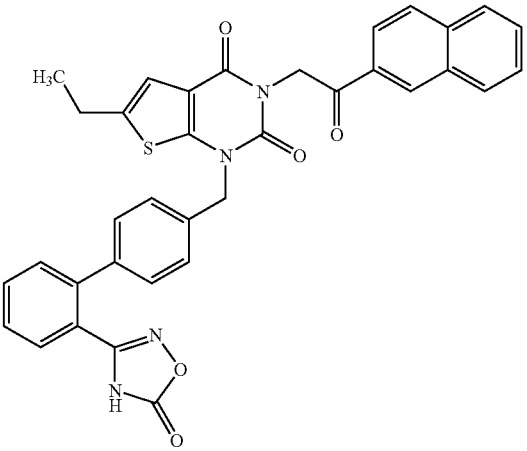 [SMILES: CCc1cc2c(=O)n(CC(=O)c3ccc4ccccc4c3)c(=O)n(Cc3ccc(-c4ccccc4-c4noc(=O)[nH]4)cc3)c2s1]

A mixture of hydroxylammonium chloride (0.83 g), sodium hydrogencarbonate (1.26 g) and dimethyl sulfoxide (10 mL) was stirred at 40° C. for 30 min, 4'-{[6-ethyl-3-[2-(2-naphthyl)-2-oxoethyl]-2,4-dioxo-3,4-dihydrothieno[2,3- d]pyrimidin-1(2H)-yl]methyl}biphenyl-2-carbonitrile (0.84 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (30 mL). N,N'-Carbonyldiimidazole (0.24 g) and then 1,8-diazabicyclo[5.4.0]undec-7-ene (0.21 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was dissolved in methylene chloride (50 mL), iodine acid (0.84 g) was added, and the mixture was stirred at room temperature for 16 hr. The reaction mixture was washed successively with water and saturated brine, and dried over anhydrous magnesium sulfate. The solvent was evaporated under reduced pressure. The obtained residue was purified by preparative HPLC to give the title compound as colorless crystals (0.26 g, 19%).

$^1$H NMR (300 MHz, DMSO-$d_6$) δ 1.21 (3H, t, J=7.2), 2.76 (2H, q, J=7.2), 5.24 (2H, s), 5.61 (2H, s), 7.04 (1H, s), 7.35 (4H, dd, J=22.5, 8.1), 7.51-7.58 (2H, m), 7.65-7.71 (4H, m), 8.02-8.09 (3H, m), 8.16 (1H, d, J=7.8), 8.90 (1H, s), 12.4 (1H, s)

Example 95

6-ethyl-3-[2-(2-naphthyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

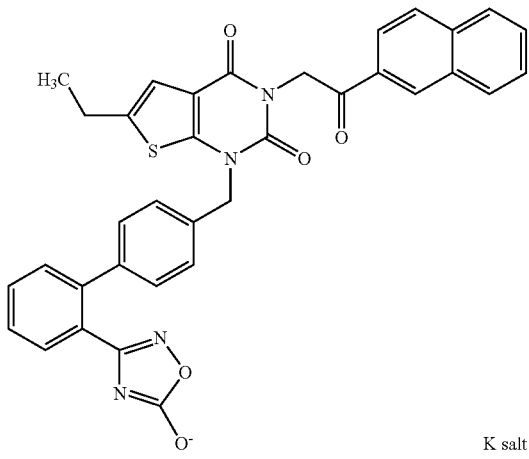 [SMILES: CCc1cc2c(=O)n(CC(=O)c3ccc4ccccc4c3)c(=O)n(Cc3ccc(-c4ccccc4-c4noc([O-])n4)cc3)c2s1 ; "K salt"]

A mixture of 6-ethyl-3-[2-(2-naphthyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.26 g), potassium 2-ethylhexanoate (0.093 g) and tetrahydrofuran (20 mL) was stirred at room temperature for 16 hr. The precipitated solid was collected by filtration to give the title compound as colorless crystals (0.23 g, 83%).

$^1$H NMR (300 MHz, DMSO-$d_6$) δ 1.23 (3H, t, J=7.6), 2.70-2.89 (2H, m), 5.20 (2H, s), 5.62 (2H, s), 7.05 (1H, s), 7.20-7.54 (8H, m), 7.61-7.79 (2H, m), 7.99-8.14 (3H, m), 8.19 (1H, d, J=7.6), 8.92 (1H, s)

Example 96

3-[2-(3-bromo-4-methoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

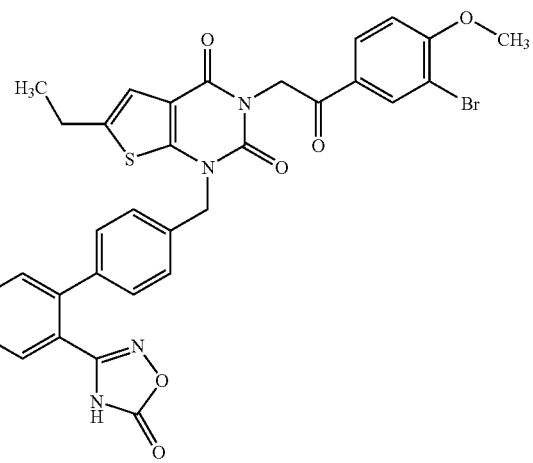

A mixture of hydroxylammonium chloride (1.8 g), sodium hydrogencarbonate (2.75 g) and dimethyl sulfoxide (20 mL) was stirred at 40° C. for 30 min, 4'-{[3-[2-(3-bromo-4-methoxyphenyl)-2-oxoethyl]-6-ethyl-2,4-dioxo-3,4-dihydrothieno[2,3-d]pyrimidin-1(2H)-yl]methyl}biphenyl-2-carbonitrile (1 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (40 mL). N,N'-Carbonyldiimidazole (0.26 g) and then 1,8-diazabicyclo[5.4.0]undec-7-ene (0.22 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was dissolved in methylene chloride (50 mL), iodine acid (0.51 g) was added, and the mixture was stirred at room temperature for 16 hr. The reaction mixture was washed successively with water and saturated brine, and dried over anhydrous magnesium sulfate. The solvent was evaporated under reduced pressure. The obtained residue was purified by preparative HPLC to give the title compound as a colorless amorphous solid (0.17 g, 16%).

$^1$H NMR (200 MHz, DMSO-$d_6$) δ 1.16 (3H, t, J=7.4), 2.72 (2H, q, J=7.4), 3.94 (3H, s), 5.15 (2H, s), 5.39 (2H, s), 6.97 (1H, s), 7.18-7.46 (9H, m), 8.08-8.22 (2H, m), 12.4 (1H, s)

Example 97

3-[2-(3-bromo-4-methoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

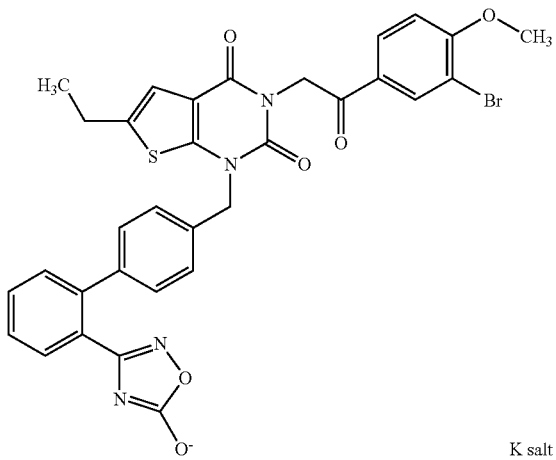

A mixture of 3-[2-(3-bromo-4-methoxyphenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.18 g), potassium 2-ethylhexanoate (0.058 g), tetrahydrofuran (10 mL) and ethyl acetate (10 mL) was stirred at room temperature for 16 hr. The precipitated solid was collected by filtration to give the title compound as colorless crystals (0.14 g, 75%).

$^1$H NMR (200 MHz, DMSO-d$_6$)δ1.16 (3H, t, J=7.4), 2.72 (2H, q, J=7.4), 3.92 (3H, s), 5.12 (2H, s), 5.38 (2H, s), 6.97 (1H, s),7.18-7.46 (9H, m), 8.08-8.22 (2H, m)

Example 98

6-cyclopropyl-3-[2-(2-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione A mixture of 4'-{[6-cyclopropyl-3-(2,4-dimethoxybenzyl)-2,4-dioxo-3,4-dihydrothieno[2,3-d]pyrimidin-1(2H)-yl]methyl}biphenyl-2-carbonitrile (1.68 g) and trifluoroacetic acid (20 mL) was stirred at 50° C. for 2 hr. To the reaction mixture was added toluene (20 mL), and the mixture was concentrated under reduced pressure. The obtained residue was dissolved in N,N-dimethylformamide (30 mL), 2-bromo-1-(2-methoxyphenyl)ethanone (1 g) and sodium hydride (0.18 g) was added, and the mixture was stirred at room temperature for 5 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was dissolved in dimethyl sulfoxide (5 mL), and added to a mixture of hydroxylammonium chloride (2.04 g), sodium hydrogencarbonate (3.09 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography and dissolved in methylene chloride (30 mL). N,N'-Carbonyldiimidazole (0.38 g) and then 1,8-diazabicyclo[5.4.0]undec-7-ene (0.33 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.4 g, 22%).

$^1$H NMR (300 MHz, DMSO-d$_6$)δ0.68-0.73 (2H, m), 0.91-0.97(2H, m), 2.02-2.11 (1H, m), 3.98 (3H, s), 5.19 (2H, s), 5.25 (2H, s), 6.95 (1H,s), 7.08 (1H, t, J=7.2), 7.28-7.38 (5H, m), 7.52-7.74 (6H, m), 12.4 (1H, s)

Example 99

6-cyclopropyl-3-[2-(2-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

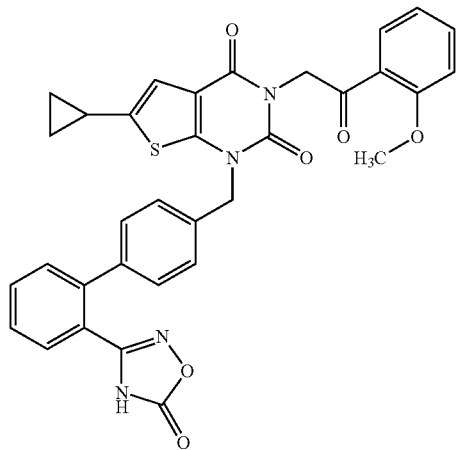 [SMILES: COc1ccccc1C(=O)Cn1c(=O)c2cc(C3CC3)sc2n(Cc2ccc(-c3ccccc3-c3noc(=O)[nH]3)cc2)c1=O]

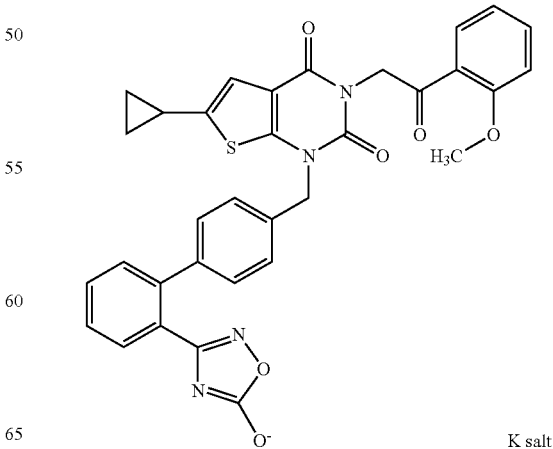

A mixture of 6-cyclopropyl-3-[2-(2-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.4 g), potassium 2-ethylhexanoate (0.14 g), tetrahydrofuran (15 mL) and ethyl acetate (15 mL) was stirred at room temperature for 16 hr. The precipitated solid was collected by filtration to give the title compound as colorless crystals (0.39 g, 91%).

$^1$H NMR (300 MHz, DMSO-$d_6$)δ0.69-0.74 (2H, m), 0.90-0.97(2H, m), 2.03-2.12 (1H, m), 3.97 (3H, s), 5.13 (2H, s), 5.24 (2H, s), 6.93 (1H,s), 7.08 (1H, t, J=7.5), 7.22-7.50 (9H, m), 7.64 (1H, t, J=6.9), 7.72 (1H,d, J=9.6)

Example 100

6-ethyl-3-[2-(4-fluoro-3-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

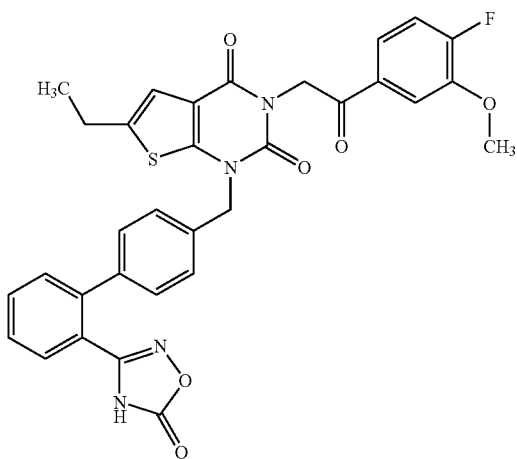 [SMILES: CCc1cc2c(=O)n(CC(=O)c3ccc(F)c(OC)c3)c(=O)n(Cc3ccc(-c4ccccc4-c4noc(=O)[nH]4)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (1.3 g), 2-bromo-1-(4-fluoro-3-methoxyphenyl)ethanone (0.99 g) and N,N-dimethylformamide (30 mL) was added sodium hydride (0.16 g), and the mixture was stirred at 50° C. for 3 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (10 ml), and the mixture was added to a mixture of hydroxylammonium chloride (1.69 g), sodium hydrogencarbonate (2.6 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.25 g) and then 1,8-diazabicyclo[5.4.0]undec-7-ene (0.21 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was dissolved in methylene chloride (20 mL), iodine acid (1.38 g) was added, and the mixture was stirred at room temperature for 24 hr. The reaction mixture was washed successively with water and saturated brine, and dried over anhydrous magnesium sulfate. The solvent was evaporated under reduced pressure. The obtained residue was purified by preparative HPLC to give the title compound as colorless crystals (0.21 g, 10%).

$^1$H NMR (300 MHz, DMSO-$d_6$)δ1.22 (3H, t, J=7.4),2.66-2.90 (2H, m), 3.97 (3H, s), 5.18 (2H, s), 5.50 (2H, s), 7.03 (1H, s),7.16-7.92 (11H, m), 12.41 (1H, s)

Example 101

6-ethyl-3-[2-(4-fluoro-3-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

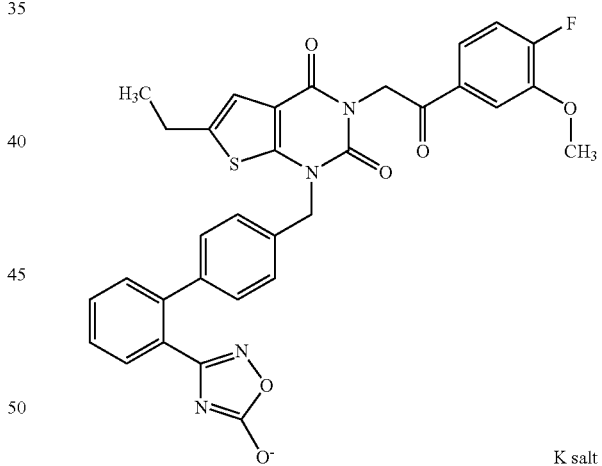

A mixture of 6-ethyl-3-[2-(4-fluoro-3-methoxyphenyl)-2-oxoethyl]-1-{[2'-(5-oxo-4,5-dihydro-1,2,4-oxadiazol-3-yl)biplienyl-4-yl]methyl}thieno[2,3-d]pyrimidine-2,4(1H,3H)-dione (0.21 g), potassium 2-ethylhexanoate (0.075 g), tetrahydrofuran (5 mL) and ethyl acetate (5 mL) was stirred at room temperature for 16 hr. The precipitated solid was collected by filtration to give the title compound as colorless crystals (0.16 g, 70%).

$^1$H NMR (300 MHz, DMSO-$d_6$)δ1.22 (3H, t, J=7.4),2.66-2.90 (2H, m), 3.95 (3H, s), 5.18 (2H, s), 5.50 (2H, s), 7.03 (1H, s),7.18-7.56 (9H, m), 7.69-7.89 (2H, m)

Example 102

6-ethyl-3-[2-(4-methoxy-3-methylphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

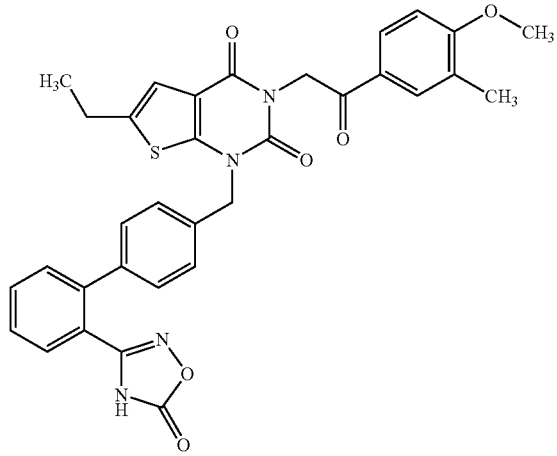

A mixture of hydroxylammonium chloride (1.9 g), sodium hydrogencarbonate (2.8 g) and dimethyl sulfoxide (20 mL) was stirred at 40° C. for 30 min, 4'-{[6-ethyl-3-[2-(4-methoxy-3-methylphenyl)-2-oxoethyl]-2,4-dioxo-3,4-dihydrothieno[2,3-d]pyrimidin-1(2H)-yl]methyl}biphenyl-2-carbonitrile (0.94 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.28 g) and then 1,8-diazabicyclo[5.4.0]undec-7-ene (0.23 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The residue was purified by silica gel column chromatography to give the title compound as a colorless amorphous solid (0.4 g, 38%).

$^1$H NMR (300 MHz, DMSO-d$_6$)δ1.20 (3H, t, J=7.2), 2.75 (2H, q, J=7.2), 3.31 (3H, s), 3.89 (3H, s), 5.21 (2H, s), 5.40 (2H, s), 7.01(1H, s), 7.10 (1H, d, J=8.7), 7.30-7.40 (4H, m), 7.51-7.58 (2H, m), 7.65-7.71(2H, m), 7.89 (1H, s), 7.98 (1H, d, J=8.7), 12.4 (1H, s)

Example 103

6-ethyl-3-[2-(4-methoxy-3-methylphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

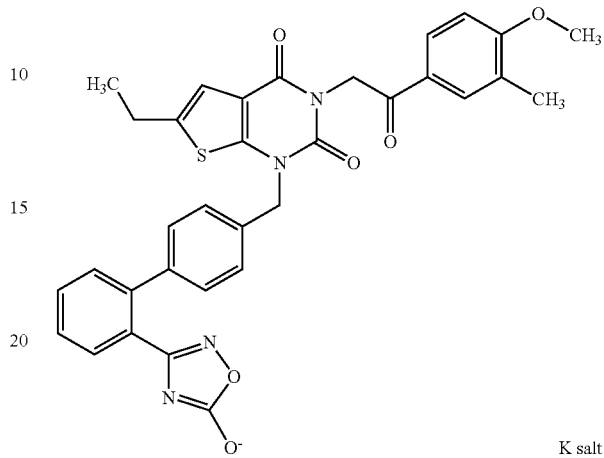

A mixture of 6-ethyl-3-[2-(4-methoxy-3-methylphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.38 g), potassium 2-ethylhexanoate (0.14 g), tetrahydrofuran (10 mL) and ethyl acetate (10 mL) was stirred at room temperature for 16 hr. The precipitated solid was collected by filtration to give the title compound as colorless crystals (0.35 g, 84%).

$^1$H NMR (300 MHz, DMSO-d$_6$)δ1.22 (3H, t, J=7.4), 2.78 (2H, q, J=7.4), 3.31 (3H, s), 3.91 (3H, s), 5.18 (2H, s), 5.41 (2H, s), 7.02(1H, s), 7.11 (1H, d, J=8.7), 7.21-7.57 (8H, m), 7.92 (1H, s), 7.93-8.05 (1H,m)

Example 104

6-cyclopropyl-1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione

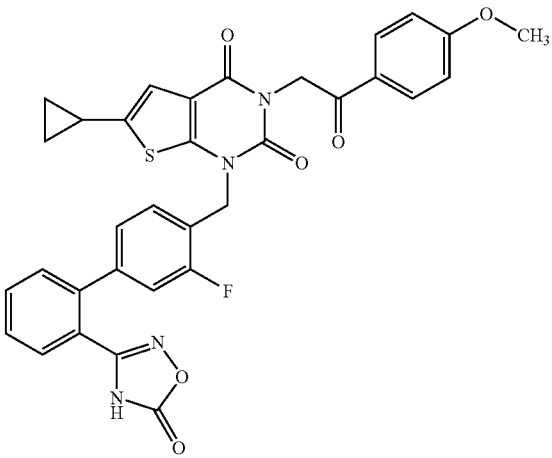 [SMILES: COc1ccc(C(=O)Cn2c(=O)c3cc(C4CC4)sc3n(Cc3ccc(-c4ccccc4-c4noc(=O)[nH]4)cc3F)c2=O)cc1]

A mixture of hydroxylammonium chloride (0.93 g), sodium hydrogencarbonate (1.4 g) and dimethyl sulfoxide (20 mL) was stirred at 40° C. for 30 min, 4'-{[6-cyclopropyl-3-[2-(4-methoxyphenyl)-2-oxoethyl]-2,4-dioxo-3,4-dihydrothieno[2,3-d]pyrimidin-1(2H)-yl]methyl}-3'-fluorobiphenyl-2-carbonitrile (0.95 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (40 mL). N,N'-Carbonyldiimidazole (0.27 g) and then 1,8-diazabicyclo[5.4.0]undec-7-ene (0.21 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.44 g, 42%).

$^1$H NMR (300 MHz, DMSO-$d_6$)δ0.67-0.78 (2H, m), 0.87-1.03(2H, m), 2.03-2.14 (1H, m), 3.88 (3H, s), 5.26 (2H, s), 5.41 (2H, s), 6.99 (1H,s), 7.06-7.20 (3H, m), 7.22-7.39 (2H, m), 7.53-7.66 (2H, m), 7.66-7.77 (2H, m),8.04-8.16 (2H, m), 12.50 (1H, br)

Example 105

6-cyclopropyl-1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione potassium salt

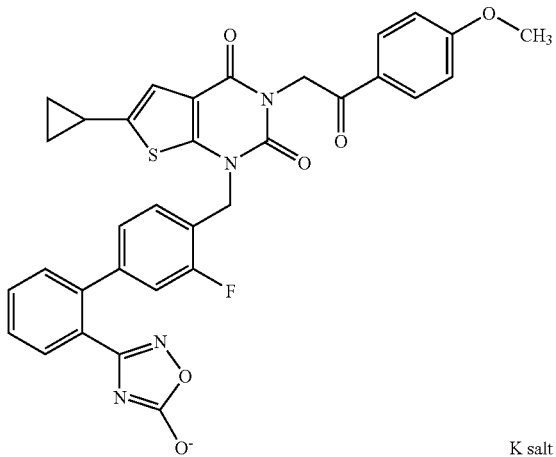 [SMILES: COc1ccc(C(=O)Cn2c(=O)c3cc(C4CC4)sc3n(Cc3ccc(-c4ccccc4-c4noc([O-])n4)cc3F)c2=O)cc1 ; "K salt"]

K salt

A mixture of 6-cyclopropyl-1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione (0.44 g), potassium 2-ethylhexanoate (0.16 g), tetrahydrofuran (10 mL) and ethyl acetate (10 mL) was stirred at room temperature for 16 hr. The precipitated solid was collected by filtration to give the title compound as colorless crystals (0.49 g, 100%).

$^1$H NMR (300 MHz, DMSO-$d_6$)δ0.66-0.79 (2H, m), 0.87-1.05(2H, m), 2.02-2.18 (1H, m), 3.87 (3H, s), 5.21 (2H, s), 5.40 (2H, s), 6.97 (1H,s), 7.03-7.27 (5H, m), 7.29-7.48 (3H, m), 7.48-7.59 (1H, m), 8.08 (2H, d, J=8.7)

Example 106

6-cyclopropyl-3-[2-(3-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

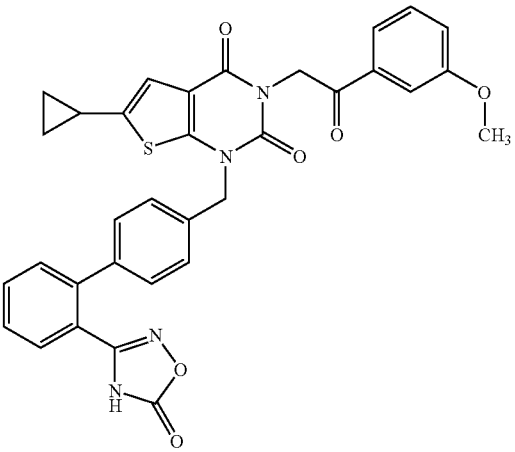 [SMILES: COc1cccc(C(=O)Cn2c(=O)c3cc(C4CC4)sc3n(Cc3ccc(-c4ccccc4-c4noc(=O)[nH]4)cc3)c2=O)c1]

A mixture of 4'-{[6-cyclopropyl-3-(2,4-dimethoxybenzyl)-2,4-dioxo-3,4-dihydrothieno[2,3-d]pyrimidin-1(2H)-yl]methyl}biphenyl-2-carbonitrile (1.68 g) and trifluoroacetic acid (20 mL) was stirred at 50° C. for 2 hr. To the reaction mixture was added toluene (20 mL), and the mixture was concentrated under reduced pressure. The obtained residue was dissolved in N,N-dimethylformamide (30 mL), 2-bromo-1-(3-methoxyphenyl)ethanone (1 g) and sodium hydride (0.18 g) were added, and the mixture was stirred at room temperature for 5 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was dissolved in dimethyl sulfoxide (5 mL), and added to a mixture of hydroxylammonium chloride (1.32 g), sodium hydrogencarbonate (1.99 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica column gel chromatography, and dissolved in methylene chloride (30 mL). N,N'-Carbonyldiimidazole (0.46 g) and then 1,8-diazabicyclo[5.4.0]undec-7-ene (0.39 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was dissolved in methylene chloride (30 mL), iodine acid (1.9 g) was added, and the mixture was stirred at room temperature for 24 hr. The reaction mixture was washed successively with water and saturated brine, and dried over anhydrous magnesium sulfate. The solvent was evaporated under reduced pressure. The obtained residue was purified by preparative HPLC to give the title compound as colorless crystals (0.21 g, 9%).

$^1$H NMR (300 MHz, DMSO-$d_6$)δ0.68-0.73 (2H, m), 0.91-0.98(2H, m), 2.03-2.16 (1H, m), 3.83 (3H, s), 5.20 (2H, s), 5.45 (2H, s), 6.96 (1H,s), 7.26-7.39 (5H, m), 7.47-7.58 (4H, m), 7.65-7.71 (3H, m)

Example 107

6-cyclopropyl-3-[2-(3-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

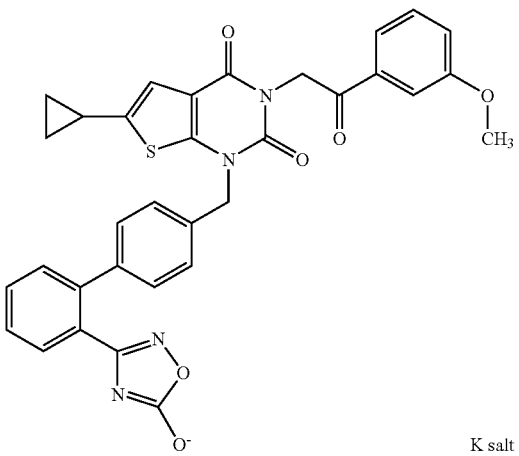 [SMILES: COc1cccc(C(=O)Cn2c(=O)c3cc(C4CC4)sc3n(Cc3ccc(-c4ccccc4-c4noc([O-])n4)cc3)c2=O)c1 ; "K salt"]

A mixture of 6-cyclopropyl-3-[2-(3-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.17 g), potassium 2-ethylhexanoate (0.062 g), tetrahydrofuran (10 mL) and ethyl acetate (10 mL) was stirred at room temperature for 16 hr. The precipitated solid was collected by filtration to give the title compound as colorless crystals (0.17 g, 93%).

$^1$H NMR (300 MHz, DMSO-$d_6$) δ 0.68-0.81 (2H, m), 0.88-1.02 (2H, m), 2.03-2.16 (1H, m), 3.85 (3H, s), 5.16 (2H, s), 5.46 (2H, s), 6.97 (1H, s), 7.21-7.60 (11H, m), 7.71 (1H, d, J=7.6)

Example 108

6-ethyl-3-[2-(2-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

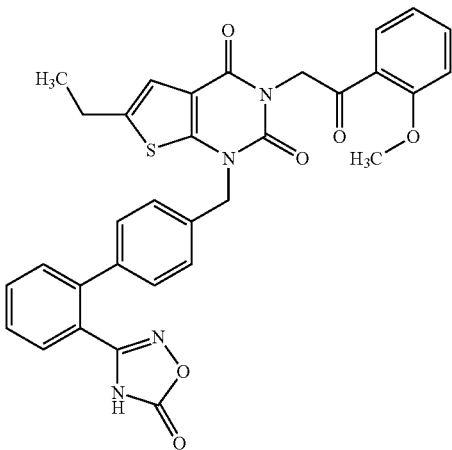 [SMILES: CCc1cc2c(=O)n(CC(=O)c3ccccc3OC)c(=O)n(Cc3ccc(-c4ccccc4-c4noc(=O)[nH]4)cc3)c2s1]

A mixture of hydroxylammonium chloride (8.6 g), sodium hydrogencarbonate (13 g) and dimethyl sulfoxide (100 mL) was stirred at 40° C. for 30 min, 4'-{[6-ethyl-3-[2-(2-methoxyphenyl)-2-oxoethyl]-2,4-dioxo-3,4-dihydrothieno[2,3-d]pyrimidin-1(2H)-yl]methyl}biphenyl-2-carbonitrile (4.12 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (150 ml). N,N'-Carbonyldiimidazole (1.25 g) and then 1,8-diazabicyclo[5.4.0]undec-7-ene (1.06 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was recrystallized from chloroform to give the title compound as colorless crystals (1.19 g, 26%).

$^1$H NMR (300 MHz, DMSO-$d_6$) δ 1.19 (3H, t, J=7.5), 2.74 (2H, q, J=7.5), 3.98 (3H, s), 5.21 (2H, s), 5.26 (2H, s), 7.00 (1H, s), 7.08 (1H, t, J=6.9), 7.25-7.38 (5H, m), 7.51-7.74 (6H, m), 12.4 (1H, s)

Example 109

6-ethyl-3-[2-(2-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

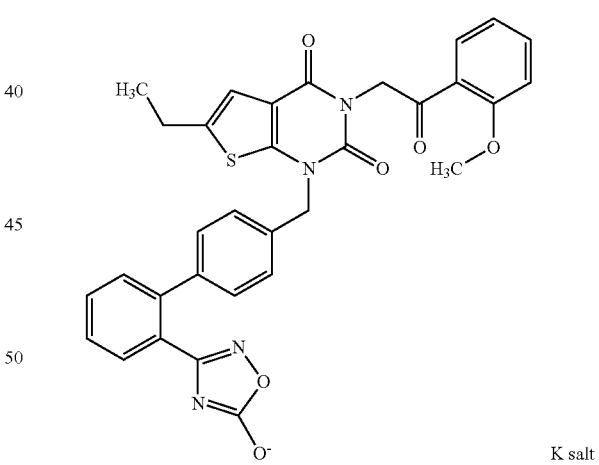

A mixture of 6-ethyl-3-[2-(2-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (1.1 g), potassium 2-ethylhexanoate (0.41 g), tetrahydrofuran (50 mL) and acetone (50 mL) was stirred at room temperature for 16 hr. The precipitated solid was collected by filtration to give the title compound as colorless crystals (0.96 g, 82%).

$^1$H NMR (300 MHz, DMSO-$d_6$) δ 1.22 (3H, t, J=7.6), 2.77 (2H, q, J=7.6), 3.99 (3H, s), 5.17 (2H, s), 5.27 (2H, s), 7.02 (1H, s), 7.10 (1H, t, J=7.6), 7.19-7.35 (6H, m), 7.34-7.53 (3H, m), 7.61-7.70 (1H, m), 7.69-7.78 (1H, m)

Example 110

6-ethyl-3-[2-(4-methoxyphenyl)-1-methyl-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

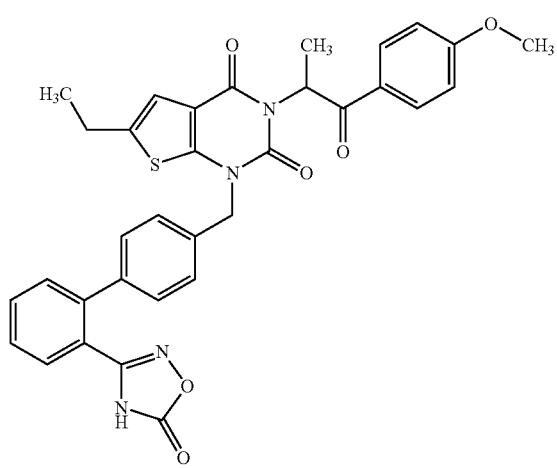 [SMILES: CCc1cc2c(=O)n(C(C)C(=O)c3ccc(OC)cc3)c(=O)n(Cc3ccc(-c4ccccc4-c4noc(=O)[nH]4)cc3)c2s1]

A mixture of hydroxylammonium chloride (0.54 g), sodium hydrogencarbonate (0.82 g) and dimethyl sulfoxide (15 mL) was stirred at 40° C. for 30 min, 4'-{[6-ethyl-3-[2-(4-methoxyphenyl)-1-methyl-2-oxoethyl]-2,4-dioxo-3,4-dihydrothieno[2,3-d]pyrimidin-1(2H)-yl]methyl}biphenyl-2-carbonitrile (0.27 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (20 ml). N,N'-Carbonyldiimidazole (0.079 g) and then 1,8-diazabicyclo[5.4.0]undec-7-ene (0.067 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The precipitated solid was collected by filtration to give the title compound as colorless crystals (0.2 g, 65%).

$^1$H NMR (300 MHz, DMSO-$d_6$)δ1.15 (3H, t, J=7.5), 1.47 (3H, d, J=6.3), 2.69 (2H, q, J=7.5), 3.71 (3H, s), 4.84 (1H, d, J=16.8),5.26 (1H, d, J=16.8), 5.96-6.06 (1H, m), 6.83 (2H, d, J=7.8), 6.93 (2H, d,J=8.7), 6.99 (1H, s), 7.10 (2H, d, J=8.4), 7.45-7.58 (4H, m), 7.64-7.72(2H, m), 12.4 (1H, s)

Example 111

6-ethyl-3-[2-(4-methoxyphenyl)-1-methyl-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

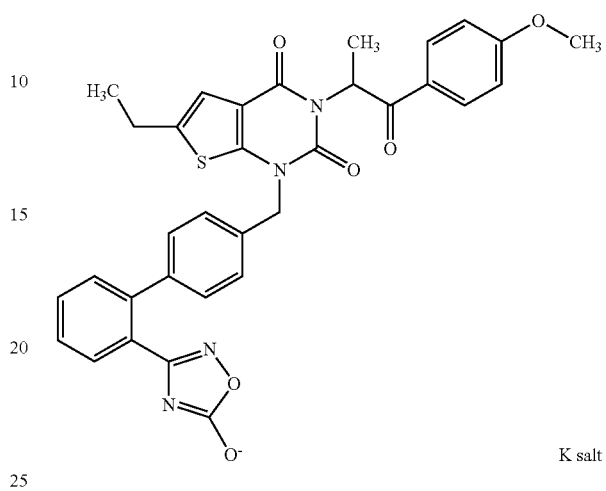

K salt

A mixture of 6-ethyl-3-[2-(4-methoxyphenyl)-1-methyl-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), potassium 2-ethylhexanoate (0.07 g) and ethyl acetate (5 mL) was stirred at room temperature for 16 hr. The precipitated solid was collected by filtration to give the title compound as colorless crystals (0.17 g, 84%).

$^1$H NMR (300 MHz, DMSO-$d_6$)δ1.16 (3H, t, J=7.5), 1.48 (3H, d, J=6.3), 2.70 (2H, q, J=7.5), 3.74 (3H, s), 4.78 (1H, d, J=17.1),5.24 (1H, d, J=17.1), 6.00 (1H, q, J=6.3), 6.71 (2H, d, J=7.5), 6.93-6.99(3H, m), 7.09 (2H, d, J=7.8), 7.23 (1H, d, J=7.5), 7.32-7.52 (5H, m)

Example 112

6-ethyl-3-(2-morpholin-4-yl-2-oxoethyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

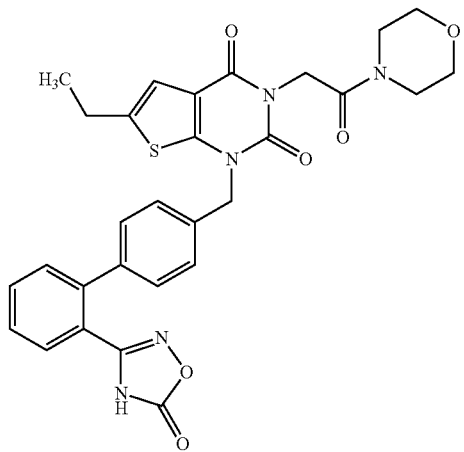 [SMILES: CCc1cc2c(=O)n(CC(=O)N3CCOCC3)c(=O)n(Cc3ccc(-c4ccccc4-c4noc(=O)[nH]4)cc3)c2s1]

A mixture of methyl [1-[(2'-cyanobiphenyl-4-yl)methyl]-6-ethyl-2,4-dioxo-1,4-dihydrothieno[2,3-d]pyrimidin-3

(2H)-yl]acetate (0.99 g), tetrahydrofuran (10 mL), methanol (10 ml) and 1N aqueous sodium hydroxide solution (10 mL) was stirred at 50° C. for 3 hr. The solvent was evaporated under reduced pressure, and the obtained residue was adjusted to pH 5 with 1N hydrochloric acid. The precipitated solid was dissolved in N,N-dimethylformamide (20 mL), morpholine (0.15 g), diethyl s cyanophosphate (0.28 g) and triethylamine (0.24 mL) were added, and the mixture was stirred at room temperature for 5 hr. The reaction mixture was diluted with ethyl acetate, washed successively with water and saturated brine, and dried over anhydrous magnesium sulfate. The solvent was evaporated under reduced pressure. The residue was purified by silica gel column chromatography, and added to a mixture of hydroxylammonium chloride (0.83 g), sodium hydrogencarbonate (1.26 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The obtained residue was dissolved in methylene chloride (40 mL), N,N'-carbonyldiimidazole (0.24 g) and then 1,8-diazabicyclo[5.4.0]undec-7-ene (0.21 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The residue was purified by silica gel column chromatography to give the title compound as a colorless amorphous solid (0.58 g, 46%).

$^1$H NMR (300 MHz, DMSO-$d_6$)δ1.19 (3H, t, J=7.2), 2.74 (2H, q, J=7.2), 3.40-3.43 (2H, m), 3.55-3.63 (6H, m), 4.79 (2H, s), 5.19 (2H,s), 6.99 (1H, s), 7.28-7.38 (4H, m), 7.50-7.67 (4H, m), 12.38 (1H, s)

Example 113

2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]-N-(4-methoxyphenyl)acetamide

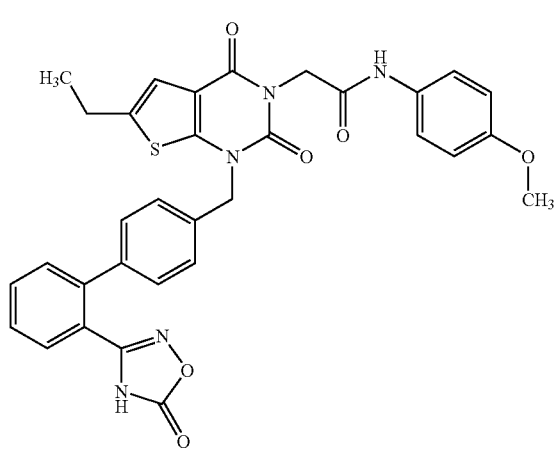 [SMILES: CCc1cc2c(=O)n(CC(=O)Nc3ccc(OC)cc3)c(=O)n(Cc3ccc(-c4ccccc4-c4noc(=O)[nH]4)cc3)c2s1]

A mixture of methyl [1-[(2'-cyanobiphenyl-4-yl)methyl]-6-ethyl-2,4-dioxo-1,4-dihydrothieno[2,3-d]pyrimidin-3(2H)-yl]acetate (0.99 g), tetrahydrofuran (10 mL), methanol (10 mL) and 1N aqueous sodium hydroxide solution (10 mL) was stirred at 50° C. for 3 hr. The solvent was evaporated under reduced pressure, and the obtained residue was adjusted to pH 5 with 1N hydrochloric acid. The precipitated solid was dissolved in N,N-dimethylformamide (20 mL), 4-methoxyaniline (0.21 g), diethyl cyanophosphate (0.28 g) and triethylamine (0.24 mL) were added, and the mixture was stirred at room temperature for 5 hr. The reaction mixture was diluted with ethyl acetate, washed successively with water and saturated brine, and dried over anhydrous magnesium sulfate. The solvent was evaporated under reduced pressure. The residue was purified by silica gel column chromatography, and added to a mixture of hydroxylammonium chloride (0.62 g), sodium hydrogencarbonate (1.07 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The obtained residue was purified by silica gel column chromatography and dissolved in methylene chloride (40 mL). N,N'-Carbonyldiimidazole (0.21 g) and then 1,8-diazabicyclo[5.4.0]undec-7-ene (0.17 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The residue was purified by silica gel column chromatography to give the title compound as colorless crystals (0.54 g, 40%).

$^1$H NMR (300 MHz, DMSO-$d_6$)δ1.19 (3H, t, J=7.8), 2.74 (2H, q, J=7.8), 3.70 (3H, s), 4.70 (2H, s), 5.21 (2H, s), 6.87 (2H, d, J=9.3), 7.01 (1H, s), 7.30-7.70 (10H, m)

Example 114

6-ethyl-1-{[2'-(5-oxo-4,5-dihydro-1,2,4-oxadiazol-3-yl)biphenyl-4-yl]methyl}-3-[2-(trifluoromethyl)phenyl]thieno[2,3-d]pyrimidine-2,4(1H,3H)-dione

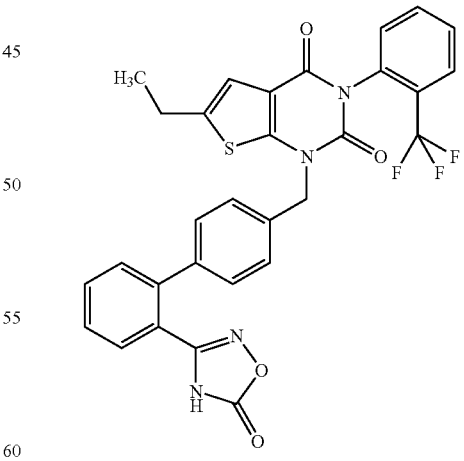

To a solution (40 mL) of methyl 2-amino-5-ethylthiophene-3-carboxylate (0.5 g) in methylene chloride were added triphosgene (0.35 g) and triethylamine (0.98 mL), and the mixture was stirred at room temperature for 2 hr. To the reaction mixture was added 2-(trifluoromethyl)aniline (0.67 mL), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in methanol (50 mL), sodium methoxide (0.73 g) was added, and the mixture was stirred at 60° C. for 1 hr. The reaction mixture was concentrated under reduced pressure, and the obtained residue was extracted with 1N hydrochloric acid and chloroform. The chloroform layer was washed with saturated brine, and dried over anhydrous magnesium sulfate. The solvent was evaporated under reduced pressure. The obtained residue was dissolved in acetonitrile (50 mL), 3-[4'-(bromomethyl)biphenyl-2-yl]-5-(trichloromethyl)-1,2,4-oxadiazole (0.94 g) and potassium carbonate (0.55 g) was added, and the mixture was stirred at 50° C. for 2 hr. Insoluble material was filtered off, and the solvent was evaporated under reduced pressure. The obtained residue was purified by silica gel column chromatography and dissolved in tetrahydrofuran (10 mL) and acetone (10 mL). 1N Aqueous sodium hydroxide solution (10 mL) was added, and the mixture was stirred at room temperature for 1 hr. The reaction mixture was adjusted to pH 4 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.87 g, 75%).

$^1$H NMR (300 MHz, DMSO-d$_6$)δ1.21 (3H, t, J=7.6), 2.76 (2H, q, J=7.4), 5.10 (1H, d, J=16.7), 5.37 (1H, d, J=16.7), 7.05 (1H, s),7.29-7.38 (2H, m), 7.37-7.46 (2H, m), 7.56 (2H, dd, J=12.3, 7.8), 7.63-7.78(4H, m), 7.79-7.96 (2H, m), 12.41 (1H, s)

Example 115

6-ethyl-3-[2-(4-methoxyphenyl)-2-oxoethyl]-1-{[3-methyl-2'-(5-oxo-4,5-dihydro-1,2,4-oxadiazol-3-yl)biphenyl-4-yl]methyl}thieno[2,3-d]pyrimidine-2,4 (1H,3H)-dione

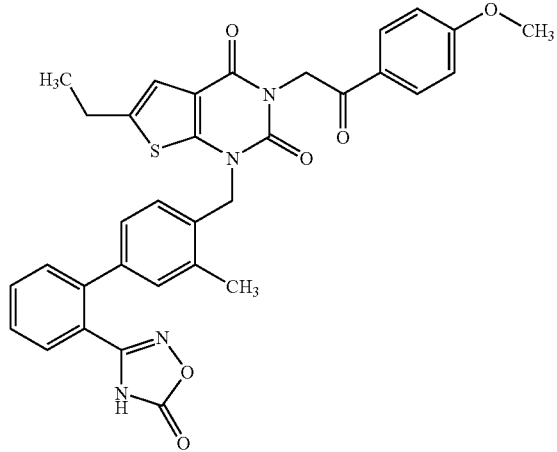 [SMILES: CCc1cc2c(=O)n(CC(=O)c3ccc(OC)cc3)c(=O)n(Cc3ccc(-c4ccccc4-c4noc(=O)[nH]4)cc3C)c2s1]

A mixture of hydroxylammonium chloride (0.68 g), sodium hydrogencarbonate (1.02 g) and dimethyl sulfoxide (15 mL) was stirred at 40° C. for 30 min, 4'-{[6-ethyl-3-[2-(4-methoxyphenyl)-2-oxoethyl]-2,4-dioxo-3,4-dihydrothieno[2,3-d]pyrimidin-1(2H)-yl]methyl}-3'-methylbiphenyl-2-carbonitrile (0.67 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (40 mL). N,N'-Carbonyldiimidazole (0.2 g) and then 1,8-diazabicyclo[5.4.0]undec-7-ene (0.17 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The precipitated solid was collected by filtration to give the title compound as colorless crystals (0.32 g, 44%).

$^1$H NMR (300 MHz, DMSO-d$_6$)δ1.20 (3H, t, J=7.5), 2.39 (3H, s), 2.76 (2H, q, J=7.5), 3.88 (3H, s), 5.23 (2H, s), 5.43 (2H, s),6.98-7.14 (5H, m), 7.24 (1H, s), 7.49-7.59 (2H, m), 7.62-7.74 (2H, m),8.04-8.14 (2H, m), 12.35 (1H, br)

Example 116

6-ethyl-3-[2-(4-methoxyphenyl)-2-oxoethyl]-1-{[3-methyl-2'-(5-oxo-4,5-dihydro-1,2,4-oxadiazol-3-yl)biphenyl-4-yl]methyl}thieno[2,3-d]pyrimidine-2,4 (1H,3H)-dione potassium salt

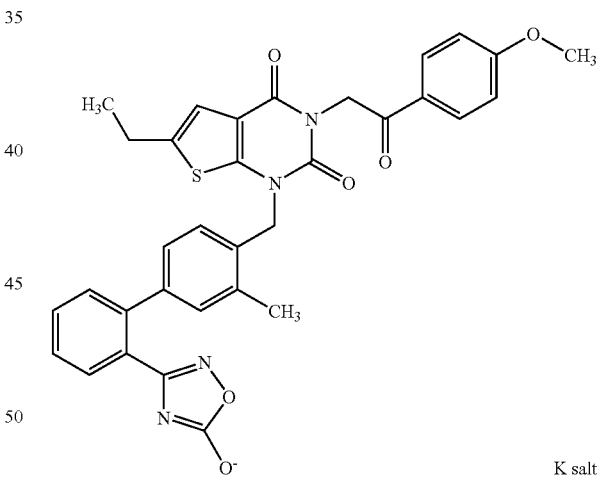

A mixture of 6-ethyl-3-[2-(4-methoxyphenyl)-2-oxoethyl]-1-{[3-methyl-2'-(5-oxo-4,5-dihydro-1,2,4-oxadiazol-3-yl)biphenyl-4-yl]methyl}thieno[2,3-d]pyrimidine-2,4(1H, 3H)-dione (0.32 g), potassium 2-ethylhexanoate (0.11 g), tetrahydrofuran (5 mL) and ethyl acetate (5 mL) was stirred at room temperature for 16 hr. The precipitated solid was collected by filtration to give the title compound as colorless crystals (0.28 g, 84%).

$^1$H NMR (300 MHz, DMSO-d$_6$)δ1.19 (3H, t, J=7.8), 2.75 (2H, q, J=7.8), 3.32 (3H, s), 3.86 (3H, s), 5.16 (2H, s), 5.41 (2H, s), 6.84(1H, d, J=8.4), 7.02-7.10 (4H, m), 7.18 (1H, s), 7.27-7.49 (4H, m), 8.07 (2H,d, J=8.4)

Example 117

6-ethyl-1-{[3-fluoro-2'-(5-oxo-4,5-dihydro-1,2,4-oxadiazol-3-yl)biphenyl-4-yl]methyl}-3-(2-morpholin-4-ylethyl)thieno[2,3-d]pyrimidine-2,4(1H,3H)-dione

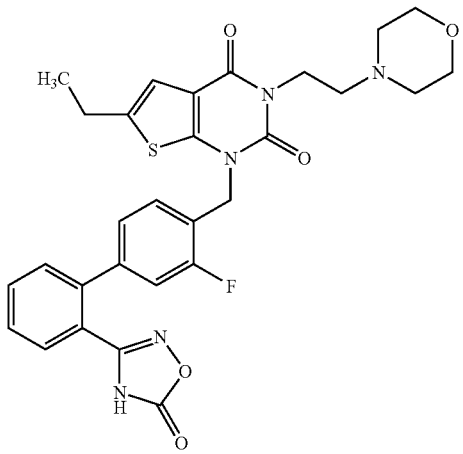 [SMILES: CCc1cc2c(=O)n(CCN3CCOCC3)c(=O)n(Cc3ccc(-c4ccccc4-c4noc(=O)[nH]4)cc3F)c2s1]

A mixture of hydroxylammonium chloride (1.63 g), sodium hydrogencarbonate (2.37 g) and dimethyl sulfoxide (20 mL) was stirred at 40° C. for 30 min, 4'-{[6-ethyl-3-(2-morpholin-4-ylethyl)-2,4-dioxo-3,4-dihydrothieno[2,3-d]pyrimidin-1(2H)-yl]methyl}-3'-fluorobiphenyl-2-carbonitrile (1.22 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was dissolved in methylene chloride (50 mL), N,N'-carbonyldiimidazole (0.42 g) and then 1,8-diazabicyclo[5.4.0]undec-7-ene (0.35 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The precipitated solid was collected by filtration to give the title compound as a colorless amorphous solid (0.77 g, 57%).

$^1$H NMR (300 MHz, DMSO-$d_6$)δ1.20 (3H, t, J=7.6),2.56-2.64 (2H, m), 2.75 (2H, q, J=7.6), 3.27-3.37 (4H, m), 3.46-3.61 (4H, m),4.09 (2H, t, J=6.6), 5.19 (2H, s), 7.00 (1H, s), 7.24-7.35 (2H, m), 7.34-7.44(1H, m), 7.55 (2H, dd, J=17.4, 7.2), 7.61-7.75 (2H, m), 12.2 (1H, s)

Example 118

3-(2,4-dimethoxybenzyl)-6-ethyl-1-[(2'-{4-[(2-methoxyethoxy)methyl]-5-oxo-4,5-dihydro-1,2,4-oxadiazol-3-yl}biphenyl-4-yl)methyl]thieno[2,3-d]pyrimidine-2,4(1H,3H)-dione

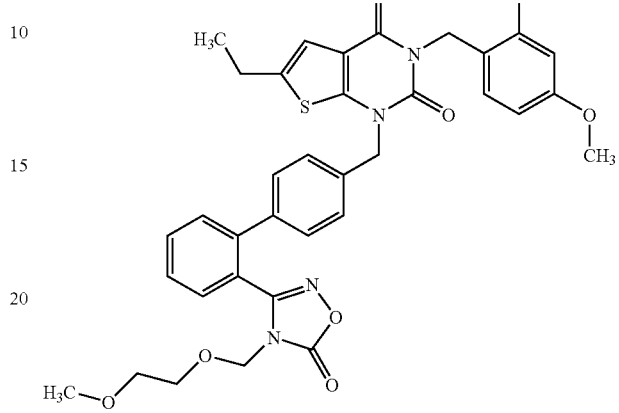

A mixture of 3-(2,4-dimethoxybenzyl)-6-ethylthieno[2,3-d]pyrimidine-2,4(1H,3H)-dione (10 g), 3-[4'-(bromomethyl)biphenyl-2-yl]-4-[(2-methoxyethoxy)methyl]-1,2,4-oxadiazol-5(4H)-one (14.5 g), potassium carbonate (8 g) and acetonitrile (500 mL) was stirred at 50° C. for 4 hr. Insoluble material was filtered off, and the solvent was evaporated under reduced pressure. The obtained residue was purified by silica gel column chromatography to give the title compound as colorless crystals (15.5 g, 79%).

$^1$H NMR (300 MHz, CDCl$_3$)δ1.29 (3H, t, J=7.5), 2.76 (2H,q, J=7.2), 3.17 (3H, s), 3.27-3.30 (2H, m), 3.43-3.46 (2H, m), 3.76 (3H, s),3.82 (3H, s), 4.49 (2H, s), 5.15 (2H, s), 5.23 (2H, s), 6.39 (1H, dd, J=8.7,2.4), 6.44-6.45 (1H, m), 6.97 (1H, d, J=8.7), 7.02 (1H, s), 7.33-7.41 (4H,m), 7.49-7.68 (4H, m)

Example 119

6-ethyl-1-[(2'-{4-[(2-methoxyethoxy)methyl]-5-oxo-4,5-dihydro-1,2,4-oxadiazol-3-yl}biphenyl-4-yl)methyl]thieno[2,3-d]pyrimidine-2,4(1H,3H)-dione

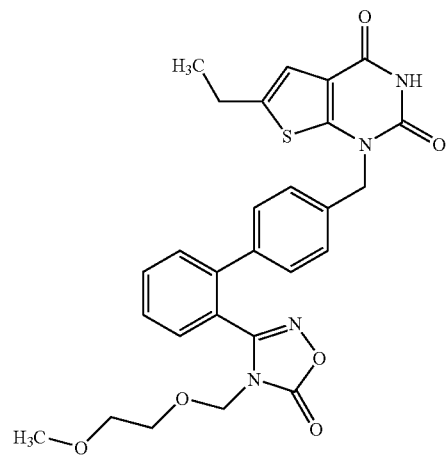 [SMILES: CCc1cc2c(=O)[nH]c(=O)n(Cc3ccc(-c4ccccc4-c4noc(=O)n4COCCOC)cc3)c2s1]

A mixture of 3-(2,4-dimethoxybenzyl)-6-ethyl-1-[(2'-{4-[(2-methoxyethoxy)methyl]-5-oxo-4,5-dihydro-1,2,4-oxadiazol-3-yl}biphenyl-4-yl)methyl]thieno[2,3-d]pyrimidine-2,4(1H,3H)-dione (15.5 g) and trifluoroacetic acid (100 mL) was stirred at 50° C. for 3 hr. To the reaction mixture was added toluene (100 mL), and the mixture was concentrated under reduced pressure. The precipitated solid was collected by filtration to give the title compound as colorless crystals (11.7 g, 99%).

$^1$H NMR (300 MHz, DMSO-d$_6$)δ1.16 (3H, t, J=7.2), 2.70 (2H, q, J=7.5), 3.10 (3H, s), 3.20-3.23 (2H, m), 3.35-3.38 (2H, m), 4.64 (2H,s), 5.10 (2H, s), 6.93 (1H, s), 7.35 (4H, s), 7.60 (2H, t, J=7.2), 7.70-7.77(2H, m), 11.52 (1H, s)

Example 120

2-{[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]acetyl}benzoic acid

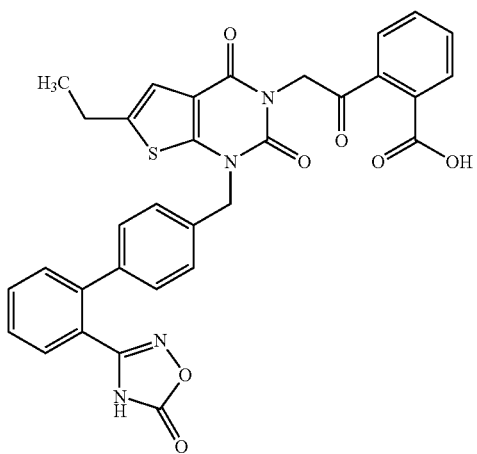 [SMILES: CCc1cc2c(=O)n(CC(=O)c3ccccc3C(=O)O)c(=O)n(Cc3ccc(-c4ccccc4-c4noc(=O)[nH]4)cc3)c2s1]

To a mixture of 6-ethyl-1-[(2'-{4-[(2-methoxyethoxy)methyl]-5-oxo-4,5-dihydro-1,2,4-oxadiazol-3-yl}biphenyl-4-yl)methyl]thieno[2,3-d]pyrimidine-2,4(1H,3H)-dione (2 g), methyl 2-(bromoacetyl)benzoate (1.06 g) and N,N-dimethylformamide (50 mL) was added sodium hydride (0.18 g), and the mixture was stirred at room temperature for 16 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue was purified by silica gel column chromatography, tetrahydrofuran (15 mL), methanol (15 mL) and 1N aqueous sodium hydroxide solution (10 mL) were added, and the mixture was stirred at room temperature for 2 hr. The reaction mixture was concentrated under reduced pressure, adjusted to pH 4 with 1N hydrochloric acid, and extracted with ethyl acetate. The ethyl acetate layer was washed with saturated brine, and dried over anhydrous magnesium sulfate. The solvent was evaporated under reduced pressure. The residue was dissolved in tetrahydrofuran (100 mL), N,N'-carbonyldiimidazole (0.2 g) and then 1,8-diazabicyclo[5.4.0]undec-7-ene (0.17 mL) were added, and the mixture was stirred at room temperature for 1 hr. The reaction mixture was diluted with ethyl acetate, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as a colorless amorphous solid (0.18 g, 30%).

$^1$H NMR (300 MHz, DMSO-d$_6$)δ1.18 (3H, t, J=7.5), 2.72 (2H, q, J=7.5), 5.17 (4H, br), 6.99 (1H, s), 7.29 (4H, br), 7.50-7.72 (7H,m), 7.82 (1H, d, J=7.2)

Example 121

3-[2-(4-chlorophenyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

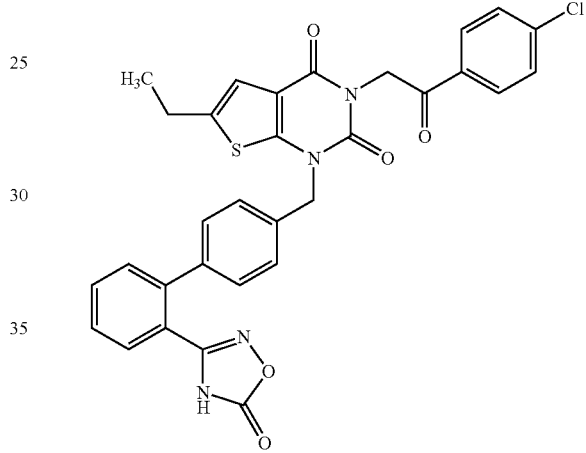

To a mixture of 6-ethyl-1-[(2'-{4-[(2-methoxyethoxy)methyl]-5-oxo-4,5-dihydro-1,2,4-oxadiazol-3-yl}biphenyl-4-yl)methyl]thieno[2,3-d]pyrimidine-2,4(1H,3H)-dione (0.42 g), 2-bromo-1-(4-chlorophenyl)ethanone (0.2 g) and N,N-dimethylformamide (20 mL) was added sodium hydride (0.04 g), and the mixture was stirred at room temperature for 4 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue was purified by silica gel column chromatography, 50% sulfuric acid (5 mL) and 1-butanol (15 mL) were added, and the mixture was stirred at 100° C. for 4 days. The reaction mixture was diluted with ethyl acetate, washed with saturated brine, and dried over anhydrous magnesium sulfate. The solvent was evaporated under reduced pressure. The obtained residue was purified by preparative HPLC to give the title compound as colorless crystals (0.058 g, 17%).

$^1$H NMR (300 MHz, DMSO-d$_6$)δ1.16-1.29 (3H, m), 2.69-2.87(2H, m), 5.23 (2H, s), 5.48 (2H, s), 7.04 (1H, s), 7.25-7.42 (4H, m), 7.56 (2H,dd, J=13.4, 7.4), 7.62-7.73 (4H, m), 8.13 (2H, d, J=8.7), 12.4 (1H, s)

Example 122

6-ethyl-3-[2-(methoxyimino)-2-(4-methoxyphenyl)ethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

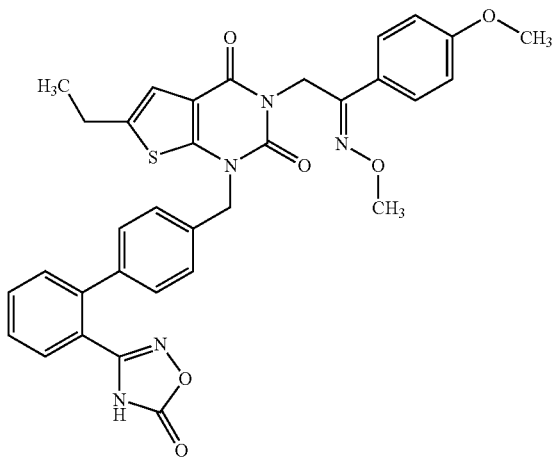 [SMILES: CCc1cc2c(=O)n(C/C(=N/OC)c3ccc(OC)cc3)c(=O)n(Cc3ccc(-c4ccccc4-c4noc(=O)[nH]4)cc3)c2s1]

A mixture of 6-ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.13 g), (aminooxy)methane hydrochloride (0.06 g), pyridine (5 mL) and ethanol (5 mL) was stirred at 100° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.06 g, 40%).

$^1$H NMR (300 MHz, DMSO-$d_6$)δ1.12-1.22 (3H, m), 2.64-2.79(2H, m), 3.64, 3.75 (combined 3H, s), 3.66, 3.88 (combined 3H, s), 4.95, 5.20 (combined 2H, s), 5.08, 5.15 (combined 2H, s), 6.82-7.69 (12H, m), 8.07 (1H, d, J=8.1), 12.4 (1H, s)

Example 123

6-ethyl-3-[2-(4-ethylphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

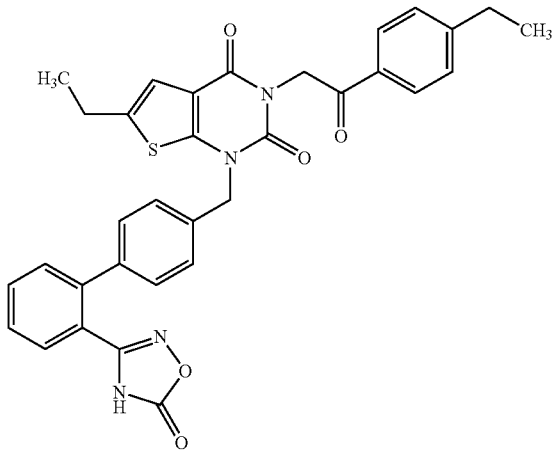 [SMILES: CCc1ccc(C(=O)Cn2c(=O)c3cc(CC)sc3n(Cc3ccc(-c4ccccc4-c4noc(=O)[nH]4)cc3)c2=O)cc1]

A mixture of hydroxylammonium chloride (1.13 g), sodium hydrogencarbonate (1.65 g) and dimethyl sulfoxide (20 mL) was stirred at 40° C. for 30 min, 4'-{[6-ethyl-3-(2-(4-ethylphenyl)-2-oxoethyl)-2,4-dioxo-3,4-dihydrothieno[2,3-d]pyrimidin-1(2H)-yl]methyl}biphenyl-2-carbonitrile (0.87 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was dissolved in methylene chloride (50 mL), N,N'-carbonyldiimidazole (0.26 g) and then 1,8-diazabicyclo[5.4.0]undec-7-ene (0.22 ml) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The precipitated solid was collected by filtration to give the title compound as a colorless amorphous solid (0.59 g, 61%).

$^1$H NMR (300 MHz, DMSO-$d_6$)δ1.20 (6H, t, J=7.8),2.66-2.79 (4H, m), 5.22 (2H, s), 5.43 (2H, s), 7.01 (1H, s), 7.30-7.43 (6H, m),7.51-7.58 (2H, m), 7.64-7.71 (2H, m), 8.00 (2H, d, J=8.4), 12.37 (1H, s)

Example 124

1-{[3,5-difluoro-2'-(5-oxo-4,5-dihydro-1,2,4-oxadiazol-3-yl)biphenyl-4-yl]methyl}-3-[2-(4-methoxyphenyl)-2-oxoethyl]-6-(2,2,2-trifluoroethyl)thieno[2,3-d]pyrimidine-2,4(1H,3H)-dione

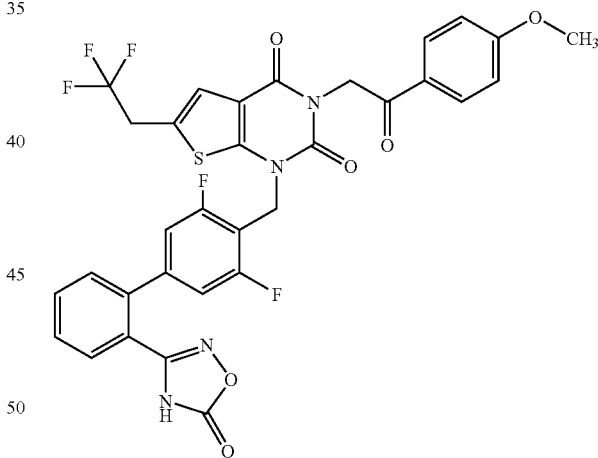

A mixture of hydroxylammonium chloride (0.56 g), sodium hydrogencarbonate (0.81 g) and dimethyl sulfoxide (10 mL) was stirred at 40° C. for 30 min, 3',5'-difluoro-4'-{[3-[2-(4-methoxyphenyl)-2-oxoethyl]-2,4-dioxo-6-(2,2,2-trifluoroethyl)-3,4-dihydrothieno[2,3-d]pyrimidin-1(2H)-yl]methyl}biphenyl-2-carbonitrile (0.5 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (30 mL), N,N'-carbonyldiimidazole (0.16 g) and then 1,8-diazabicyclo[5.4.0]undec-7-ene (0.13 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 25% sulfuric acid (5 mL) and 1-butanol (5 ml), and the mixture was stirred at 100° C. for 1 hr. The precipitated solid was collected by filtration to give the title compound as a colorless amorphous solid (0.15 g, 26%).

$^1$H NMR (300 MHz, DMSO-d$_6$)δ3.88 (3H, s), 3.96-4.10 (2H,m), 5.33 (2H, s), 5.38 (2H, s), 7.07-7.19 (4H, m), 7.33 (1H, s), 7.51-7.75 (4H,m), 8.01-8.11 (2H, m), 12.55 (1H, br)

Example 125

1-{[3,5-difluoro-2'-(5-oxo-4,5-dihydro-1,2,4-oxadiazol-3-yl)biphenyl-4-yl]methyl}-3-[2-(4-methoxyphenyl)-2-oxoethyl]-6-(2,2,2-trifluoroethyl)thieno[2,3-d]pyrimidine-2,4(1H,3H)-dione potassium salt

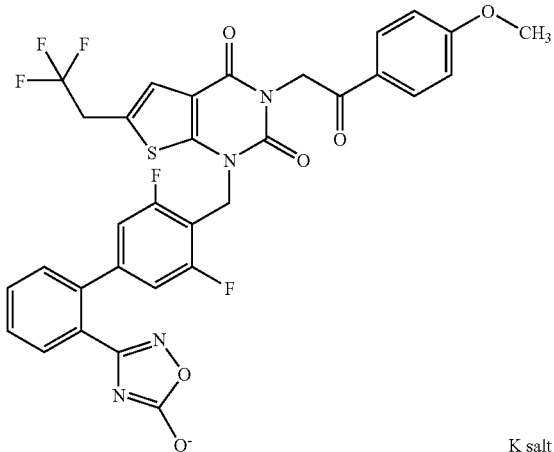 [SMILES: COc1ccc(C(=O)Cn2c(=O)c3cc(CC(F)(F)F)sc3n(Cc3c(F)cc(-c4ccccc4-c4noc([O-])n4)cc3F)c2=O)cc1 ; "K salt"]

K salt

A mixture of 1-{[3,5-difluoro-2'-(5-oxo-4,5-dihydro-1,2,4-oxadiazol-3-yl)biphenyl-4-yl]methyl}-3-[2-(4-methoxyphenyl)-2-oxoethyl]-6-(2,2,2-trifluoroethyl)thieno[2,3-d]pyrimidine-2,4(1H,3H)-dione (0.15 g), potassium 2-ethylhexanoate (0.047 g) and ethyl acetate (5 mL) was stirred at room temperature for 16 hr. The precipitated solid was collected by filtration to give the title compound as colorless crystals (0.13 g, 83%).

$^1$H NMR (300 MHz, DMSO-d$_6$)δ3.87 (3H, s), 3.93-4.15 (2H,m), 5.29 (2H, s), 5.38 (2H, s), 7.07 (4H, dd, J=17.0, 9.1), 7.31 (1H, s),7.34-7.52 (3H, m), 7.51-7.61 (1H, m), 8.07 (2H, d, J=8.7)

Example 126

1-{[3,5-difluoro-2'-(5-oxo-4,5-dihydro-1,2,4-oxadiazol-3-yl)biphenyl-4-yl]methyl}-3-[2-(2-methoxyphenyl)-2-oxoethyl]-6-(2,2,2-trifluoroethyl)thieno[2,3-d]pyrimidine-2,4(1H,3H)-dione

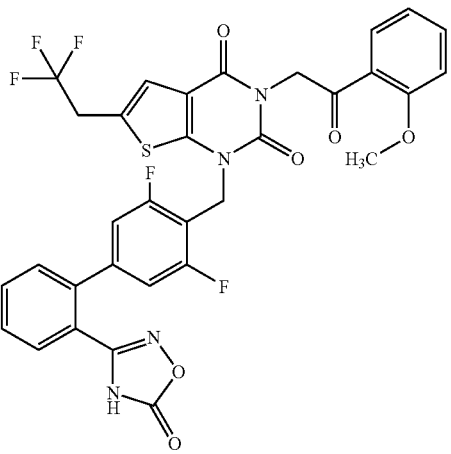 [SMILES: COc1ccccc1C(=O)Cn1c(=O)c2cc(CC(F)(F)F)sc2n(Cc2c(F)cc(-c3ccccc3-c3noc(=O)[nH]3)cc2F)c1=O]

A mixture of hydroxylammonium chloride (0.53 g), sodium hydrogencarbonate (0.77 g) and dimethyl sulfoxide (10 mL) was stirred at 40° C. for 30 min, 3',5'-difluoro-4'-{[3-[2-(2-methoxyphenyl)-2-oxoethyl]-2,4-dioxo-6-(2,2,2-trifluoroethyl)-3,4-dihydrothieno[2,3-d]pyrimidin-1(2H)-yl]methyl}biphenyl-2-carbonitrile (0.48 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (30 mL), N,N'-carbonyldiimidazole (0.14 g) and then 1,8-diazabicyclo[5.4.0]undec-7-ene (0.12 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 20% sulfuric acid (5 mL) and ethanol (10 ml). The mixture was stirred at 100° C. for 1 hr and extracted with chloroform and water. The chloroform layer was washed with saturated brine, and dried over anhydrous magnesium sulfate. The solvent was evaporated under reduced pressure. The obtained residue was purified by silica gel column chromatography to give the title compound as colorless crystals (0.23 g, 43%).

$^1$H NMR (300 MHz, DMSO-d$_6$)δ3.94-4.10 (5H, m), 5.23 (2H,s), 5.33 (2H, s), 7.04-7.18 (3H, m), 7.28 (1H, d, J=8.1 Hz), 7.33 (1H, s),7.53-7.77 (6H, m), 12.55 (1H, br)

Example 127

1-{[3,5-difluoro-2'-(5-oxo-4,5-dihydro-1,2,4-oxadiazol-3-yl)biphenyl-4-yl]methyl}-3-[2-(2-methoxyphenyl)-2-oxoethyl]-6-(2,2,2-trifluoroethyl)thieno[2,3-d]pyrimidine-2,4(1H,3H)-dione potassium salt

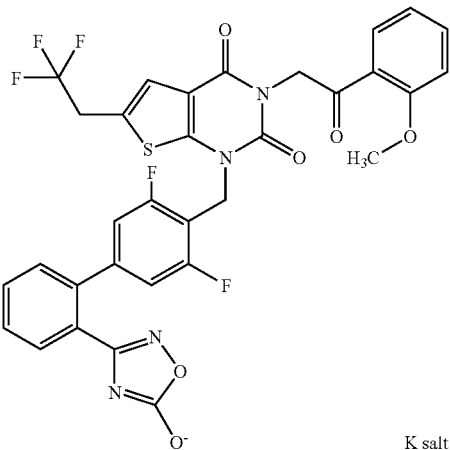 [SMILES: COc1ccccc1C(=O)Cn1c(=O)c2cc(CC(F)(F)F)sc2n(Cc2c(F)cc(-c3ccccc3-c3noc([O-])n3)cc2F)c1=O ; "K salt"]

A mixture of 1-{[3,5-difluoro-2'-(5-oxo-4,5-dihydro-1,2,4-oxadiazol-3-yl)biphenyl-4-yl]methyl}-3-[2-(2-methoxyphenyl)-2-oxoethyl]-6-(2,2,2-trifluoroethyl)thieno[2,3-d]pyrimidine-2,4(1H,3H)-dione (0.15 g), potassium 2-ethylhexanoate (0.047 g) and ethyl acetate (5 mL) was stirred at room temperature for 16 hr. The precipitated solid was collected by filtration to give the title compound as colorless crystals (0.13 g, 82%).

$^1$H NMR (300 MHz, DMSO-$d_6$)δ3.96-4.07 (5H, m), 4.20 (2H,s), 5.26 (2H, s), 7.00-7.09 (3H, m), 7.23-7.28 (2H, m), 7.33-7.36 (1H, m), 7.41-7.48 (2H, m), 7.52-7.56 (1H, m), 7.60-7.65 (1H, m), 7.70 (1H, d, J=7.8)

Example 128

3-[(6-fluoro-1,2-benzoisoxazol-3-yl)methyl]-1-{[2'-(5-oxo-4,5-dihydro-1,2,4-oxadiazol-3-yl)biphenyl-4-yl]methyl}-6-(2,2,2-trifluoroethyl)thieno[2,3-d]pyrimidine-2,4(1H,3H)-dione

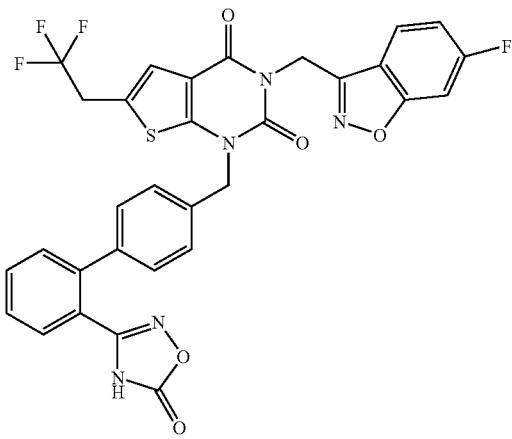 [SMILES: O=c1[nH]c(-c2ccccc2-c2ccc(Cn3c(=O)n(Cc4noc5cc(F)ccc45)c(=O)c4cc(CC(F)(F)F)sc43)cc2)no1]

A mixture of hydroxylammonium chloride (1.15 g), sodium hydrogencarbonate (1.66 g) and dimethyl sulfoxide (20 mL) was stirred at 40° C. for 30 min, 4'-{[3-[2-(2,4-difluorophenyl)-2-oxoethyl]-2,4-dioxo-6-(2,2,2-trifluoroethyl)-3,4-dihydrothieno[2,3-d]pyrimidin-1(2H)-yl]methyl}biphenyl-2-carbonitrile (0.98 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (20 mL), N,N'-carbonyldiimidazole (0.3 g) and then 1,8-diazabicyclo[5.4.0]undec-7-ene (0.25 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as a colorless amorphous solid (0.04 g, 4%).

$^1$H NMR (300 MHz, DMSO-$d_6$)δ4.01 (2H, q, J=11.1), 5.22-5.70 (4H, m), 7.29-7.47 (6H, m), 7.48-7.61 (2H, m), 7.64-7.81 (3H, m),7.89-8.03 (1H, m), 12.41 (1H, br)

Example 129

6-cyclopropyl-3-[2-(4-fluoro-2-methoxyphenyl)-2-oxoethyl]-1-{[3-fluoro-2'-(5-oxo-4,5-dihydro-1,2,4-oxadiazol-3-yl)biphenyl-4-yl]methyl}thieno[2,3-d]pyrimidine-2,4(1H,3H)-dione

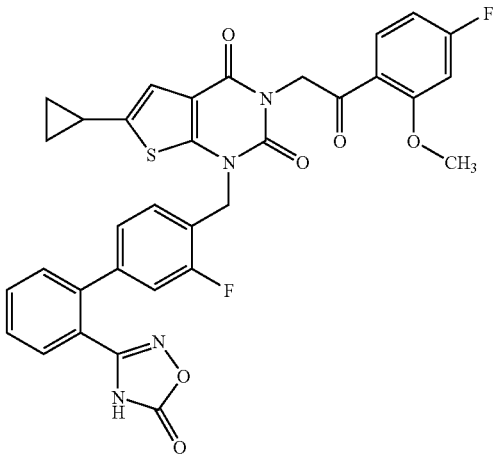 [SMILES: COc1cc(F)ccc1C(=O)Cn1c(=O)c2cc(C3CC3)sc2n(Cc2ccc(-c3ccccc3-c3noc(=O)[nH]3)cc2F)c1=O]

A mixture of hydroxylammonium chloride (0.36 g), sodium hydrogencarbonate (0.65 g) and dimethyl sulfoxide (10 mL) was stirred at 40° C. for 30 min, 4'-{[6-cyclopropyl-3-[2-(4-fluoro-2-methoxyphenyl)-2-oxoethyl]-2,4-dioxo-3,4-dihydrothieno[2,3-d]pyrimidin-1(2H)-yl]methyl}-3'-fluorobiphenyl-2-carbonitrile (0.3 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (15 mL), N,N'-carbonyldiimidazole (0.1 g) and then 1,8-diazabicyclo[5.4.0]undec-7-ene (0.085 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 25% sulfuric acid (5 mL) and 1-butanol (10 ml), and the mixture was stirred at 100° C. for 1 hr, and extracted with chloroform and water. The chloroform layer was washed with saturated brine, and dried over anhydrous magnesium sulfate. The solvent was evaporated under reduced pressure. The obtained residue was purified by silica gel column chromatography to give the title compound as colorless crystals (0.14 g, 42%).

$^1$H NMR (300 MHz, DMSO-$d_6$)δ0.67-0.79 (2H, m), 0.88-1.03(2H, m), 2.02-2.15 (1H, m), 3.96-4.02 (3H, m), 5.17-5.31 (4H, m), 6.90-7.01(2H, m), 7.03-7.16 (1H, m), 7.16-7.35 (3H, m), 7.52-7.77 (4H, m), 7.83 (1H, dd, J=8.7, 6.8), 12.50 (1H, s)

Example 130

6-cyclopropyl-3-[2-(4-fluoro-2-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

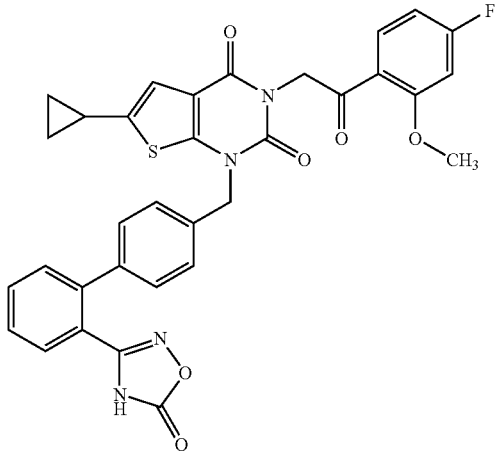 [SMILES: COc1cc(F)ccc1C(=O)Cn1c(=O)c2cc(C3CC3)sc2n(Cc2ccc(-c3ccccc3-c3noc(=O)[nH]3)cc2)c1=O]

A mixture of hydroxylammonium chloride (1.15 g), sodium hydrogencarbonate (2.09 g) and dimethyl sulfoxide (20 mL) was stirred at 40° C. for 30 min, 4'-{[6-cyclopropyl-3-[2-(4-fluoro-2-methoxyphenyl)-2-oxoethyl]-2,4-dioxo-3,4-dihydrothieno[2,3-d]pyrimidin-1(2H)-yl]methyl}biphenyl-2-carbonitrile (0.94 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (30 mL), N,N'-carbonyldiimidazole (0.32 g) and then 1,8-diazabicyclo[5.4.0]undec-7-ene (0.027 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 25% sulfuric acid (10 mL) and 1-butanol (25 ml), and the mixture was stirred at 100° C. for 1 hr, and extracted with chloroform and water. The chloroform layer was washed with saturated brine, and dried over anhydrous magnesium sulfate. The solvent was evaporated under reduced pressure. The obtained residue was purified by silica gel column chromatography to give the title compound as colorless crystals (0.16 g, 15%).

$^1$H NMR (300 MHz, DMSO-$d_6$)δ0.66-0.79 (2H, m), 0.87-1.02(2H, m), 2.02-2.13 (1H, m), 4.00 (3H, d, J=6.1), 5.12-5.36 (4H, m), 6.84-7.13(2H, m), 7.14-7.47 (5H, m), 7.57 (2H, dd, J=12.1, 7.6), 7.61-7.89 (3H, m),12.43 (1H, s)

Example 131

3-(3,3-dimethyl-2-oxobutyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

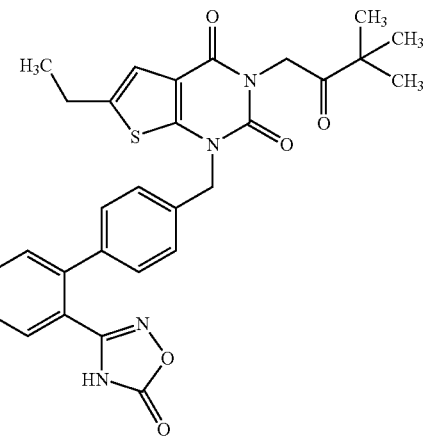

A mixture of hydroxylammonium chloride (0.87 g), sodium hydrogencarbonate (1.3 g) and dimethyl sulfoxide (8 mL) was stirred at 40° C. for 30 min, 4'-{[3-(3,3-dimethyl-2-oxobutyl)-6-ethyl-2,4-dioxo-3,4-dihydrothieno[2,3-d]pyrimidin-1(2H)-yl]methyl}biphenyl-2-carbonitrile (0.77 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (8 mL). N,N'-Carbonyldiimidazole (0.32 g) and then 1,8-diazabicyclo[5.4.0]undec-7-ene (0.3 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was purified by silica gel column chromatography to give the title compound as a colorless amorphous solid (0.64 g, 74%).

$^1$H NMR (300 MHz, DMSO-$d_6$)δ1.18-1.24 (12H, m), 2.69-2.83(2H, m), 4.96-5.01 (2H, m), 5.20 (2H, s), 6.97-7.71 (9H, m), 12.5 (1H, br)

Example 132

3-[2-(1-adamantyl)-2-oxoethyl]-6-ethyl-1-{[2'-(5-oxo-4,5-dihydro-1,2,4-oxadiazol-3-yl]biphenyl-4-yl]methyl}thieno[2,3-d]pyrimidine-2,4(1H,3H)-dione

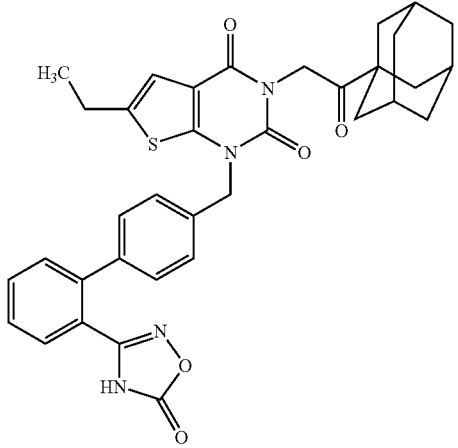 [SMILES: CCc1cc2c(=O)n(CC(=O)C34CC5CC(CC(C5)C3)C4)c(=O)n(Cc3ccc(-c4ccccc4-c4noc(=O)[nH]4)cc3)c2s1]

A mixture of hydroxylammonium chloride (0.67 g), sodium hydrogencarbonate (1.02 g) and dimethyl sulfoxide (6 mL) was stirred at 50° C. for 30 min, 4'-{[3-[2-(1-adamantyl)-2-oxoethyl]-6-ethyl-2,4-dioxo-3,4-dihydrothieno[2,3-d]pyrimidin-1(2H)-yl]methyl}biphenyl-2-carbonitrile (0.68 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (6 mL). N,N'-Carbonyldiimidazole (0.24 g) and then 1,8-diazabicyclo[5.4.0]undec-7-ene (0.23 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was purified by silica gel column chromatography to give the title compound as a colorless amorphous solid (0.46 g, 62%).

$^1$H NMR (300 MHz, DMSO-$d_6$) δ1.20 (3H, t, J=7.4),1.54-2.22 (15H, m), 2.62-2.93 (2H, m, J=7.3), 4.94 (2H, s), 5.20 (2H, s),6.75-7.89 (9H, m), 12.38 (1H, s)

Example 133

6-ethyl-3-{2-[4-(2-hydroxyethoxy)phenyl]-2-oxoethyl}-1-{[2'-(5-oxo-4,5-dihydro-1,2,4-oxadiazol-3-yl)biphenyl-4-yl]methyl}thieno[2,3-d]pyrimidine-2,4(1H,3H)-dione

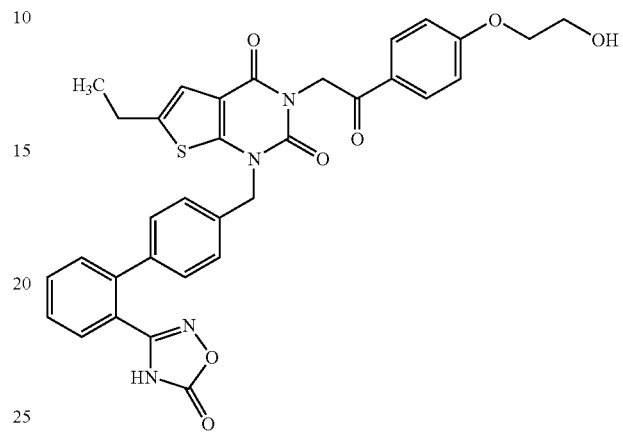

To a mixture of 4'-{[6-ethyl-3-[2-(4-hydroxyphenyl)-2-oxoethyl]-2,4-dioxo-3,4-dihydrothieno[2,3-d]pyrimidin-1(2H)-yl]methyl}biphenyl-2-carbonitrile (0.49 g), (2-bromoethoxy)(tert-butyl)dimethylsilane (0.40 mL) and N,N-dimethylformamide (5 mL) was added cesium carbonate (0.6 g), and the mixture was stirred at 60° C. for 5 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The obtained residue was purified by silica gel column chromatography, and added to a mixture of hydroxylammonium chloride (0.52 g), sodium hydrogencarbonate (0.78 g) and dimethyl sulfoxide (5 mL) stirred at 50° C. for 30 min, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (3 mL). N,N'-Carbonyldiimidazole (0.11 g) and then 1,8-diazabicyclo[5.4.0]undec-7-ene (0.1 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was dissolved in tetrahydrofuran (3 mL), tetrabutylammonium fluoride (0.2 g) was added, and the mixture was stirred at room temperature for 3 hr. To the reaction mixture were added ethyl acetate and water, and the mixture was extracted with ethyl acetate. The organic layer was washed successively with water and saturated brine, and dried over anhydrous magnesium sulfate. The solvent was evaporated under reduced pressure. The obtained residue was purified by silica gel column chromatography to give the title compound as a colorless solid (0.18 g, 31%).

¹H NMR (300 MHz, DMSO-d₆)δ1.22 (3H, t, J=7.4) 2.71-2.83(2H, m), 3.69-3.81 (2H, m), 4.12 (2H, s), 4.88-5.00 (1H, m), 5.23 (2H, s), 5.42(2H, s), 6.93-8.16 (13H, m), 12.40 (1H, s)

Example 134

6-cyclopropyl-1-{[3,5-difluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione

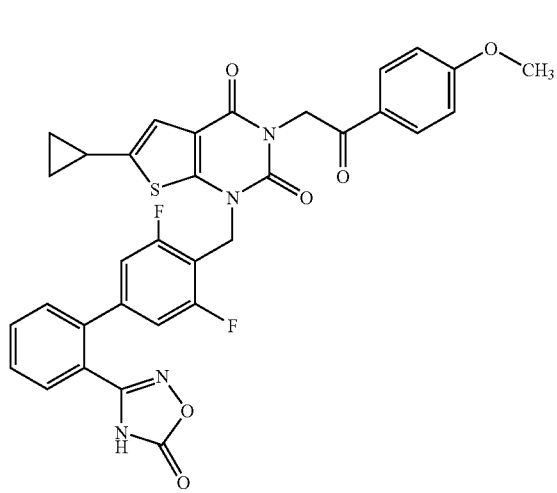 [SMILES: COc1ccc(C(=O)Cn2c(=O)c3cc(C4CC4)sc3n(Cc3c(F)cc(-c4ccccc4-c4noc(=O)[nH]4)cc3F)c2=O)cc1]

To a mixture of 4'-[(6-cyclopropyl-2,4-dioxo-3,4-dihydrothieno[2,3-d]pyrimidin-1(2H)-yl)methyl]-3',5'-difluorobiphenyl-2-carbonitrile (0.42 g), 2-bromo-1-(4-methoxyphenyl)ethanone (0.27 g) and N,N-dimethylformamide (20 mL) was added sodium hydride (0.058 g), and the mixture was stirred at 50° C. for 3 hr. The reaction mixture was diluted with chloroform, washed successively with 5% aqueous potassium hydrogensulfate solution and saturated brine, and dried over anhydrous magnesium sulfate. The solvent was evaporated under reduced pressure. The obtained residue was dissolved in dimethyl sulfoxide (5 mL), and added to a mixture of hydroxylammonium chloride (0.54 g), sodium hydrogencarbonate (0.78 g) and dimethyl sulfoxide (10 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography and dissolved in methylene chloride (30 mL). N,N'-Carbonyldiimidazole (0.15 g) and then 1,8-diazabicyclo[5.4.0]undec-7-ene (0.13 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 20% sulfuric acid (2 mL) and ethanol (10 ml). The mixture was stirred at 100° C. for 1 hr, and extracted with chloroform and water. The chloroform layer was washed with saturated brine, and dried over anhydrous magnesium sulfate. The solvent was evaporated under reduced pressure. The obtained residue was purified by silica gel column chromatography to give the title compound as colorless crystals (0.33 g, 53%).

¹H NMR (300 MHz, DMSO-d₆)δ0.69-0.78 (2H, m), 0.92-1.02(2H, m), 2.05-2.15 (1H, m), 3.87 (3H, s), 5.29 (2H, s), 5.37 (2H, s), 6.96 (1H,s), 7.04-7.16 (4H, m), 7.54-7.77 (4H, m), 8.01-8.10 (2H, m)

Example 135

6-cyclopropyl-1-{[3,5-difluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione potassium salt

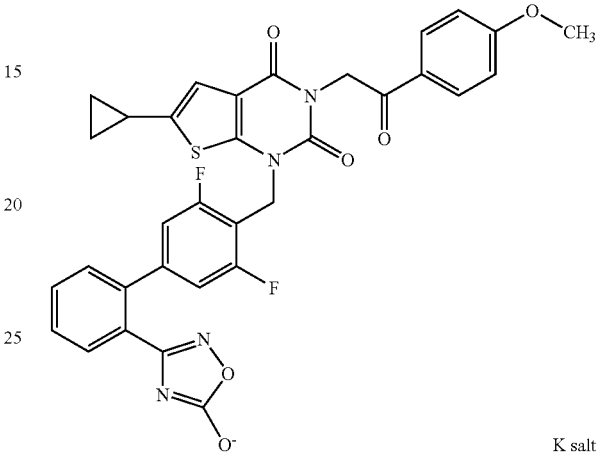

A mixture of 6-cyclopropyl-1-{[3,5-difluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione (0.33 g), potassium 2-ethylhexanoate (0.11 g) and ethyl acetate (10 mL) was stirred at room temperature for 16 hr. The precipitated solid was collected by filtration to give the title compound as colorless crystals (0.22 g, 63%).

¹H NMR (300 MHz, DMSO-d₆)δ0.67-0.80 (2H, m), 0.92-1.06(2H, m), 2.05-2.21 (1H, m), 3.87 (3H, s), 5.24 (2H, s), 5.36 (2H, s), 6.95 (1H,s), 6.99-7.15 (4H, m), 7.31-7.51 (3H, m), 7.52-7.60 (1H, m), 8.06 (2H, d, J=9.1)

Example 136

3-(2-cyclohexyl-2-oxoethyl)-1-{[2'-(5-oxo-4,5-dihydro-1,2,4-oxadiazol-3-yl)biphenyl-4-yl]methyl}-6-(2,2,2-trifluoroethyl)thieno[2,3-d]pyrimidine-2,4(1H,3H)-dione

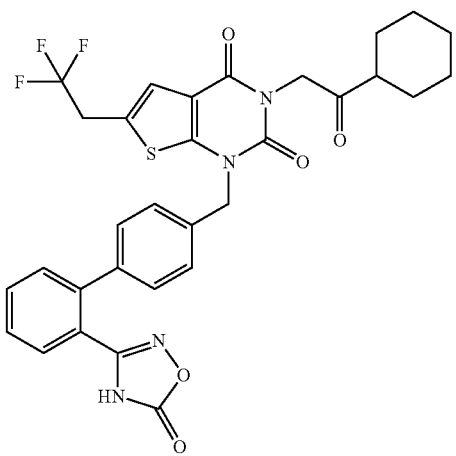 [SMILES: O=C(Cn1c(=O)c2cc(CC(F)(F)F)sc2n(Cc2ccc(-c3ccccc3-c3noc(=O)[nH]3)cc2)c1=O)C1CCCCC1]

A mixture of hydroxylammonium chloride (0.28 g), sodium hydrogencarbonate (0.43 g) and dimethyl sulfoxide (2.5 mL) was stirred at 50° C. for 30 min, 4'-{[3-(2-cyclohexyl-2-oxoethyl)-2,4-dioxo-6-(2,2,2-trifluoroethyl)-3,4-dihydrothieno[2,3-d]pyrimidin-1(2H)-yl]methyl}biphenyl-2-carbonitrile (0.29 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (2 mL). N,N'-Carbonyldiimidazole (0.061 g) and then 1,8-diazabicyclo[5.4.0]undec-7-ene (0.056 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was purified by silica gel column chromatography to give the title compound as a colorless amorphous solid (0.095 g, 30%).

$^1$H NMR (300 MHz, DMSO-$d_6$)δ1.11-1.96 (10H, m), 2.57-2.70(1H, m), 3.88-4.08 (2H, m), 4.89 (2H, s), 5.24 (2H, s), 7.04-7.77 (9H, m),12.40 (1H, s)

Example 137

6-ethyl-1-{[2'-(5-oxo-4,5-dihydro-1,2,4-oxadiazol-3-yl)biphenyl-4-yl]methyl}-3-(2-oxo-2-pyridin-4-yl-ethyl)thieno[2,3-d]pyrimidine-2,4(1H,3H)-dione

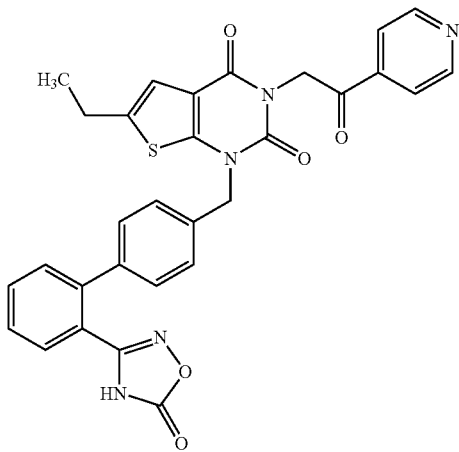 [SMILES: CCc1cc2c(=O)n(CC(=O)c3ccncc3)c(=O)n(Cc3ccc(-c4ccccc4-c4noc(=O)[nH]4)cc3)c2s1]

A mixture of hydroxylammonium chloride (0.22 g), sodium hydrogencarbonate (0.33 g) and dimethyl sulfoxide (2 mL) was stirred at 40° C. for 30 min, 4'-{[6-ethyl-2,4-dioxo-3-(2-oxo-2-pyridin-4-ylethyl)-3,4-dihydrothieno[2,3-d]pyrimidin-1(2H)-yl]methyl}biphenyl-2-carbonitrile (0.20 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (2 ml). N,N'-Carbonyldiimidazole (0.076 g) and then 1,8-diazabicyclo[5.4.0]undec-7-ene (0.070 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was purified by silica gel column chromatography to give the title compound as a pale-yellow amorphous solid (0.070 g, 32%).

$^1$H NMR (300 MHz, CDCl$_3$)δ1.29 (3H, t, J=7.4), 2.71-2.82 (2H, m), 5.16 (2H, s), 5.43 (2H, s), 6.93-9.14 (13H, m)

Example 138

3-{2-[4-(cyclopropylmethoxy)phenyl]-2-oxoethyl}-6-ethyl-1-{[2'-(5-oxo-4,5-dihydro-1,2,4-oxadiazol-3-yl)biphenyl-4-yl]methyl}thieno[2,3-d]pyrimidine-2,4 (1H,3H)-dione

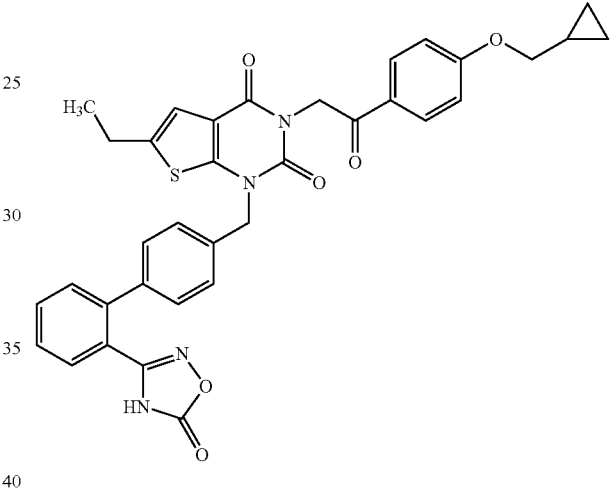

A mixture of hydroxylammonium chloride (0.58 g), sodium hydrogencarbonate (0.88 g) and dimethyl sulfoxide (5 mL) was stirred at 50° C. for 30 min, 4'-{[3-{2-[4-(cyclopropylmethoxy)phenyl]-2-oxoethyl}-6-ethyl-2,4-dioxo-3,4-dihydrothieno[2,3-d]pyrimidin-1(2H)-yl]methyl}phenyl-2-carbonitrile (0.61 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (5 mL). N,N'-Carbonyldiimidazole (0.20 g) and then 1,8-diazabicyclo[5.4.0]undec-7-ene (0.19 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was purified by silica gel column chromatography to give the title compound as a pale-yellow amorphous solid (0.46 g, 70%).

$^1$H NMR (300 MHz, DMSO-$d_6$)δ0.32-0.39 (2H, m), 0.54-0.64(2H, m), 1.21 (3H, t, J=7.5), 1.20-1.33 (1H, m), 2.69-2.83 (2H, m), 3.95 (2H,d, J=7.0), 5.23 (2H, s), 5.42 (2H, s), 7.00-8.13 (13H, m), 12.40 (1H, s)

Example 139

3-(2-{4-[2-(dimethylamino)ethoxy]phenyl}-2-oxoethyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

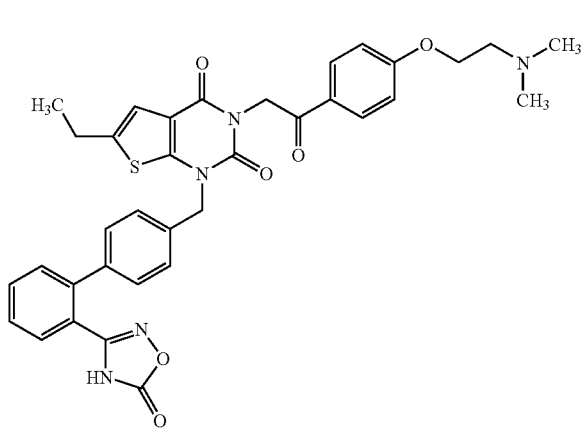 [SMILES: CCc1cc2c(=O)n(CC(=O)c3ccc(OCCN(C)C)cc3)c(=O)n(Cc3ccc(-c4ccccc4-c4noc(=O)[nH]4)cc3)c2s1]

A mixture of hydroxylammonium chloride (0.38 g), sodium hydrogencarbonate (0.58 g) and dimethyl sulfoxide (4 mL) was stirred at 50° C. for 30 min, 4'-{[3-(2-{4-[2-(dimethylamino)ethoxy]phenyl}-2-oxoethyl)-6-ethyl-2,4-dioxo-3,4-dihydrothieno[2,3-d]pyrimidin-1(2H)-yl]methyl}biphenyl-2-carbonitrile (0.41 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (4 mL). N,N'-Carbonyldiimidazole (0.13 g) and then 1,8-diazabicyclo[5.4.0]undec-7-ene (0.12 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was purified by silica gel column chromatography to give the title compound as a pale-yellow amorphous solid (0.26 g, 57%).

$^1$H NMR (300 MHz, DMSO-$d_6$)δ1.21 (3H, t, J=7.4), 2.38 (6H, s), 2.77 (2H, q, J=7.5), 2.88 (2H, t, J=5.6), 4.25 (2H, t, J=5.5),5.22 (2H, s), 5.42 (2H, s), 6.95-8.14 (13H, m)

Example 140

6-ethyl-3-[2-(1-methyl-1H-benzoimidazol-2-yl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

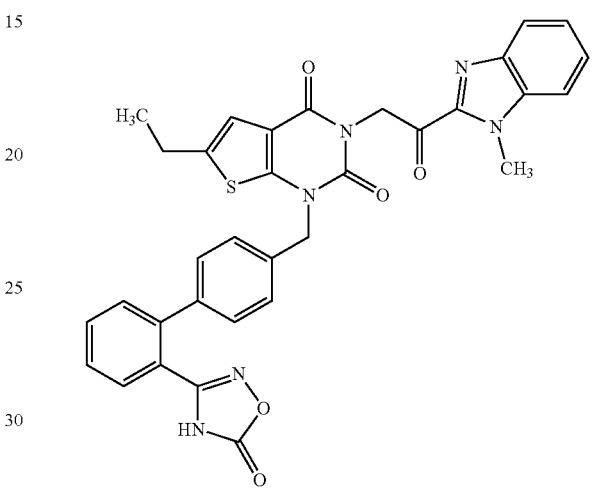

A mixture of hydroxylammonium chloride (0.28 g), sodium hydrogencarbonate (0.42 g) and dimethyl sulfoxide (3 mL) was stirred at 50° C. for 30 min, 4'-{[6-ethyl-3-[2-(1-methyl-1H-benzoimidazol-2-yl)-2-oxoethyl]-2,4-dioxo-3,4-dihydrothieno[2,3-d]pyrimidin-1(2H)-yl]methyl}biphenyl-2-carbonitrile (0.28 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (3 mL). N,N'-Carbonyldiimidazole (0.097 g) and then 1,8-diazabicyclo[5.4.0]undec-7-ene (0.090 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was purified by silica gel column chromatography to give the title compound as a pale-yellow amorphous solid (0.051 g, 16%).

$^1$H NMR (300 MHz, DMSO-$d_6$)δ1.22 (3H, t, J=7.4),2.67-2.86 (2H, m), 4.10 (3H, s), 5.25 (2H, s), 5.64 (2H, s), 7.05 (1H, s),7.24-7.97 (12H, m), 12.40 (1H, s)

Example 141

3-(3,3-dimethyl-2-oxobutyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

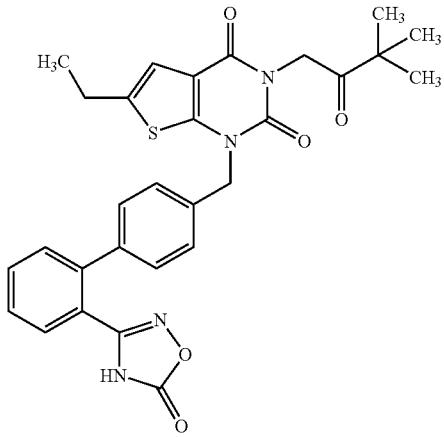 [SMILES: CCc1cc2c(=O)n(CC(=O)C(C)(C)C)c(=O)n(Cc3ccc(-c4ccccc4-c4noc(=O)[nH]4)cc3)c2s1]

A mixture of hydroxylammonium chloride (0.87 g), sodium hydrogencarbonate (1.3 g) and dimethyl sulfoxide (8 mL) was stirred at 50° C. for 30 min, 4'-{[3-(3,3-dimethyl-2-oxobutyl)-6-ethyl-2,4-dioxo-3,4-dihydrothieno[2,3-d]pyrimidin-1(2H)-yl]methyl}biphenyl-2-carbonitrile (0.77 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (8 mL). N,N'-Carbonyldiimidazole (0.32 g) and then 1,8-diazabicyclo[5.4.0]undec-7-ene (0.3 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was purified by silica gel column chromatography to give the title compound as a colorless amorphous solid (0.64 g, 74%).

$^1$H NMR (300 MHz, DMSO-d$_6$)δ1.18-1.24 (12H, m), 2.69-2.83(2H, m), 4.96-5.01 (2H, m), 5.20 (2H, s), 6.97-7.71 (9H, m), 12.4 (1H, br)

Example 142

6-ethyl-3-[2-(methoxyimino)-3,3-dimethylbutyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

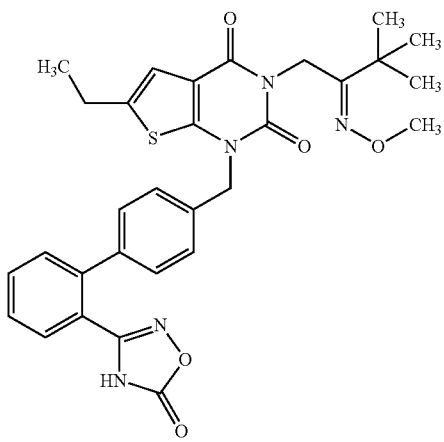 [SMILES: CCc1cc2c(=O)n(C/C(=N/OC)C(C)(C)C)c(=O)n(Cc3ccc(-c4ccccc4-c4noc(=O)[nH]4)cc3)c2s1]

A mixture of 3-(3,3-dimethyl-2-oxobutyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.20 g), (aminooxy)methane hydrochloride (0.15 g), pyridine (2 mL) and ethanol (2 mL) was stirred at 100° C. for 16 hr. To the reaction mixture were added ethyl acetate and water, and the mixture was adjusted to pH 4 with 1N hydrochloric acid. The organic layer was washed with saturated brine, and dried over anhydrous magnesium sulfate. The solvent was evaporated under reduced pressure. The obtained residue was purified by silica gel column chromatography to give the title compound as a colorless amorphous solid (0.077 g, 36%).

$^1$H NMR (300 MHz, DMSO-d$_6$)δ1.16 (9H, s), 1.20 (3H, t, J=7.5), 2.74 (2H, q, J=7.2), 3.47 (3H, s), 4.76 (2H, s), 5.20 (2H, s), 7.00(1H, s), 7.25-7.76 (8H, m), 12.41 (1H, s)

Example 143

6-cyclopropyl-3-(2-hydroxy-3,3-dimethylbutyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

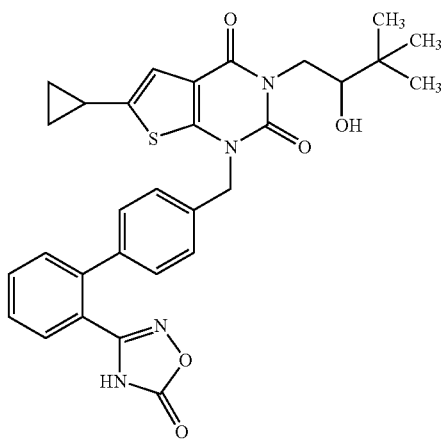 [SMILES: CC(C)(C)C(O)Cn1c(=O)c2cc(C3CC3)sc2n(Cc2ccc(-c3ccccc3-c3noc(=O)[nH]3)cc2)c1=O]

A mixture of hydroxylammonium chloride (0.51 g), sodium hydrogencarbonate (0.76 g) and dimethyl sulfoxide (5 mL) was stirred at 50° C. for 30 min, 4'-{[6-cyclopropyl-3-(2-hydroxy-3,3-dimethylbutyl)-2,4-dioxo-3,4-dihydrothieno[2,3-d]pyrimidin-1(2H)-yl]methyl}biphenyl-2-carbonitrile (0.46 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (5 mL). N,N'-Carbonyldiimidazole (0.18 g) and then 1,8-diazabicyclo[5.4.0]undec-7-ene (0.17 ml) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was purified by silica gel column chromatography to give the title compound as a colorless solid (0.29 g, 58%).

$^1$H NMR (300 MHz, CDCl$_3$)δ0.69-0.78 (2H, m), 0.96 (9H, s), 0.97-1.05 (2H, m), 1.91-2.03 (1H, m), 3.16 (1H, d, J=4.0), 3.51 (1H, d, J=9.2), 4.01 (1H, dd, J=13.6, 10.2), 4.22 (1H, dd, J=13.6, 2.1), 4.95-5.22(2H, m), 6.94 (1H, d, J=0.8), 7.30-7.84 (8H, m), 8.96 (1H, s)

Example 144

6-ethyl-3-[(3-methyloxetan-3-yl)methyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

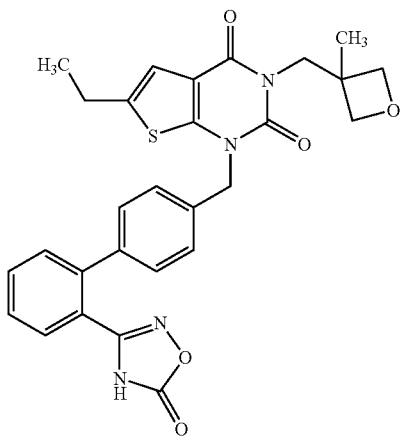 [SMILES: CCc1cc2c(=O)n(CC3(C)COC3)c(=O)n(Cc3ccc(-c4ccccc4-c4noc(=O)[nH]4)cc3)c2s1]

A mixture of hydroxylammonium chloride (1.2 g), sodium hydrogencarbonate (1.81 g) and dimethyl sulfoxide (20 mL) was stirred at 40° C. for 30 min, 4'-{[6-ethyl-3-[(3-methyloxetan-3-yl)methyl]-2,4-dioxo-3,4-dihydrothieno[2,3-d]pyrimidin-1(2H)-yl]methyl}biphenyl-2-carbonitrile (0.68 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was dissolved in methylene chloride (40 mL), N,N'-carbonyldiimidazole (0.28 g) and then 1,8-diazabicyclo[5.4.0]undec-7-ene (0.24 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.44 g, 57%).

$^1$H NMR (300 MHz, DMSO-d$_6$)δ1.20 (3H, t, J=7.4), 1.27 (3H, s), 2.69-2.79 (2H, m), 4.07-4.14 (4H, m), 4.60 (2H, d, J=6.0), 5.20 (2H,s), 7.02 (1H, s), 7.29-7.35 (2H, m), 7.35-7.42 (2H, m), 7.50-7.61 (2H, m),7.64-7.73 (2H, m), 12.4 (1H, s)

Example 145

6-ethyl-3-[(4-hydroxytetrahydro-2H-pyran-4-yl)methyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

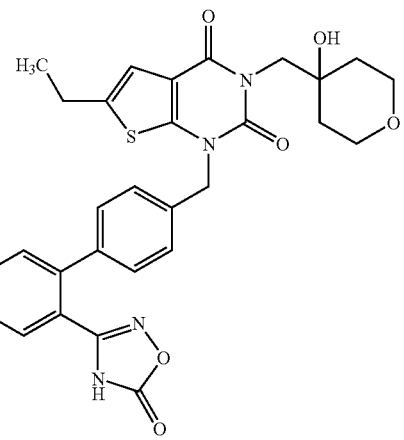

A mixture of hydroxylammonium chloride (0.27 g), sodium hydrogencarbonate (0.4 g) and dimethyl sulfoxide (10 mL) was stirred at 40° C. for 30 min, 4'-{[6-ethyl-3-[(4-hydroxytetrahydro-2H-pyran-4-yl)methyl]-2,4-dioxo-3,4-dihydrothieno[2,3-d]pyrimidin-1(2H)-yl]methyl}biphenyl-2-carbonitrile (0.16 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was dissolved in methylene chloride (10 mL), N,N'-carbonyldiimidazole (0.046 g) and then 1,8-diazabicyclo[5.4.0]undec-7-ene (0.038 ml) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as a colorless amorphous solid (0.04 g, 22%).

$^1$H NMR (300 MHz, DMSO-d$_6$)δ1.20 (3H, t, J=7.4), 1.41 (2H, d, J=13.2), 1.48-1.67 (2H, m), 2.74 (2H, q, J=7.4), 3.58 (4H, d, J=7.2), 4.04 (2H, s), 4.54 (1H, s), 5.20 (2H, s), 7.00 (1H, s), 7.27-7.35 (2H,m), 7.37-7.47 (2H, m), 7.49-7.61 (2H, m), 7.62-7.73 (2H, m), 12.40 (1H, br)

Example 146

3-(2,4-dihydroxy-3,3-dimethylbutyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

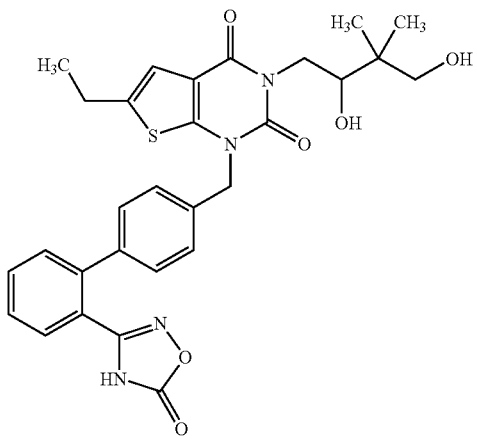 [SMILES: CCc1cc2c(=O)n(CC(O)C(C)(C)CO)c(=O)n(Cc3ccc(-c4ccccc4-c4noc(=O)[nH]4)cc3)c2s1]

A mixture of hydroxylammonium chloride (0.32 g), sodium hydrogencarbonate (0.49 g) and dimethyl sulfoxide (3 mL) was stirred at 50° C. for 30 min, 4'-{[3-(4-{[tert-butyl(dimethyl)silyl]oxy}-2-hydroxy-3,3-dimethylbutyl)-6-ethyl-2,4-dioxo-3,4-dihydrothieno[2,3-d]pyrimidin-1(2H)-yl]methyl}biphenyl-2-carbonitrile (0.36 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The, residue was purified by silica gel column chromatography and dissolved in tetrahydrofuran (8 mL). N,N'-Carbonyldiimidazole (0.097 g) and then 1,8-diazabicyclo[5.4.0]undec-7-ene (0.09 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was dissolved in tetrahydrofuran (3 mL), tetrabutylammonium fluoride (0.2 g) was added, and the mixture was stirred at room temperature for 3 hr. To the reaction mixture were added ethyl acetate and water, and the mixture was extracted with ethyl acetate. The organic layer was washed successively with water and saturated brine, and dried over anhydrous magnesium sulfate. The solvent was evaporated under reduced pressure. The obtained residue was purified by silica gel column chromatography to give the title compound as a colorless amorphous solid (0.061 g, 19%).

$^1$H NMR (300 MHz, DMSO-$d_6$)δ0.86 (3H, s), 0.89 (3H, s),1.04 (1H, d, J=6.2), 1.19 (3H, t, J=7.2), 2.74 (2H, q, J=7.3), 3.14-3.27(1H, m), 3.69-3.85 (2H, m), 4.27 (1H, t, J=13.8), 4.40-4.53 (2H, m),5.09-5.29 (2H, m), 6.98 (1H, s), 7.25-7.76 (8H, m), 12.41 (1H, s)

Example 147

6-ethyl-3-(4-hydroxy-3,3-dimethyl-2-oxobutyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

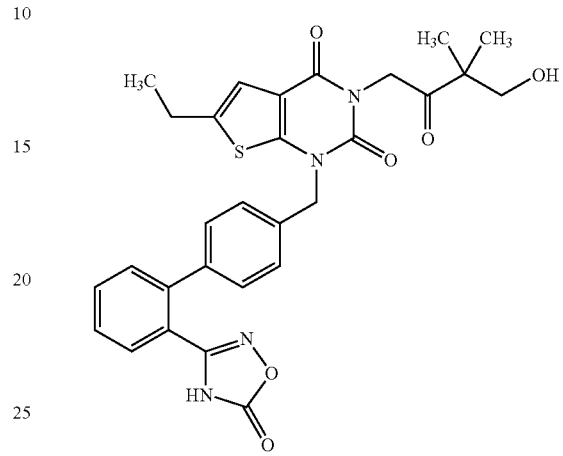

A mixture of hydroxylammonium chloride (0.83 g), sodium hydrogencarbonate (1.26 g) and dimethyl sulfoxide (8 mL) was stirred at 50° C. for 30 min, 4'-{[3-(3,3-dimethyl-2-oxo-4-{[(1,1,2,2-tetramethylpropyl)silyl]oxy}butyl)-6-ethyl-2,4-dioxo-3,4-dihydrothieno[2,3-d]pyrimidin-1(2H)-yl]methyl}biphenyl-2-carbonitrile (0.92 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (8 ml). N,N'-Carbonyldiimidazole (0.29 g) and then 1,8-diazabicyclo[5.4.0]undec-7-ene (0.27 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was dissolved in tetrahydrofuran (7 mL), tetrabutylammonium fluoride (0.51 g) was added, and the mixture was stirred at room temperature for 3 hr. To the reaction mixture were added ethyl acetate and water, and the mixture was extracted with ethyl acetate. The organic layer was washed successively with water and saturated brine, and dried over anhydrous magnesium sulfate. The solvent was evaporated under reduced pressure. The obtained residue was purified by silica gel column chromatography to give the title compound as a colorless amorphous solid (0.21 g, 25%).

$^1$H NMR (300 MHz, DMSO-$d_6$)δ1.12 (6H, s), 2.70-2.80 (2H,m), 3.56 (2H, d, J=5.1), 5.01 (2H, s), 5.05 (1H, t, J=5.0), 5.26 (2H, s),6.99 (1H, s), 7.28-7.75 (8H, m), 12.40 (1H, s)

Example 148

4-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]-2,2-dimethyl-3-oxobutyl acetate

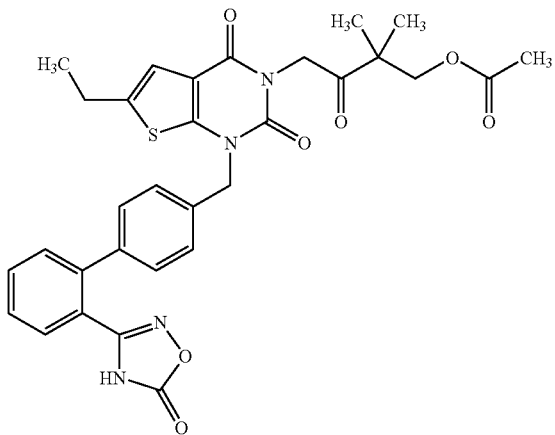 [SMILES: CCc1cc2c(=O)n(CC(=O)C(C)(C)COC(C)=O)c(=O)n(Cc3ccc(-c4ccccc4-c4noc(=O)[nH]4)cc3)c2s1]

To a solution of 6-ethyl-3-(4-hydroxy-3,3-dimethyl-2-oxobutyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.1 g) in pyridine (0.5 mL) was added acetic anhydride (0.034 mL), and the mixture was stirred at room temperature for 15 hr. To the reaction mixture were added ethyl acetate and water, and the mixture was extracted with ethyl acetate.

The organic layer was washed successively with water and saturated brine, and dried over anhydrous magnesium sulfate. The solvent was evaporated under reduced pressure. The obtained residue was purified by silica gel column chromatography to give the title compound as a colorless amorphous solid (0.086 g, 80%).

$^1$H NMR (300 MHz, DMSO-$d_6$)δ1.15-1.28 (9H, m), 2.03 (3H, s), 2.76 (2H, q, J=7.5), 4.17 (2H, s), 5.00 (2H, s), 5.21 (2H, s), 7.00 (1H, s), 7.26-7.77 (8H, m), 12.4 (1H, s)

Example 149

6-ethyl-3-(2-hydroxy-3,3-dimethylbutyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

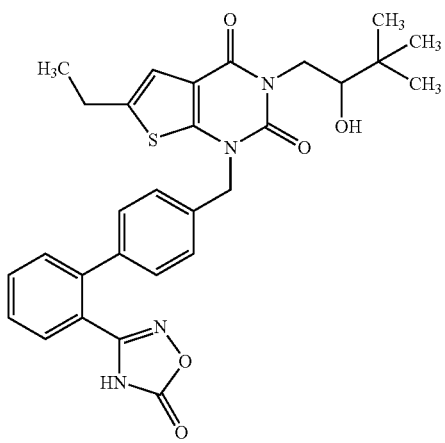 [SMILES: CCc1cc2c(=O)n(CC(O)C(C)(C)C)c(=O)n(Cc3ccc(-c4ccccc4-c4noc(=O)[nH]4)cc3)c2s1]

A mixture of hydroxylammonium chloride (0.69 g), sodium hydrogencarbonate (1.1 g) and dimethyl sulfoxide (6 mL) was stirred at 50° C. for 30 min, 4'-{[6-ethyl-3-(2-hydroxy-3,3-dimethylbutyl)-2,4-dioxo-3,4-dihydrothieno[2,3-d]pyrimidin-1(2H)-yl]methyl}biphenyl-2-carbonitrile (0.62 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (10 mL). N,N'-Carbonyldiimidazole (0.24 g) and then 1,8-diazabicyclo[5.4.0]undec-7-ene (0.22 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was purified by silica gel column chromatography to give the title compound as a colorless solid (0.42 g, 61%).

$^1$H NMR (300 MHz, DMSO-$d_6$)δ0.93 (9H, s), 1.19 (3H, t, J=7.4), 2.74 (2H, q, J=7.5), 3.54 (1H, d, J=9.2), 3.79 (1H, dd, J=12.8, 2.3), 4.21 (1H, dd, J=12.8, 10.2), 4.58 (1H, s), 5.08-5.28 (2H, m), 6.98 (1H, s), 7.24-7.76 (8H, m), 12.33 (1H, s)

Example 150

3-[2-(5-chloro-2-thienyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

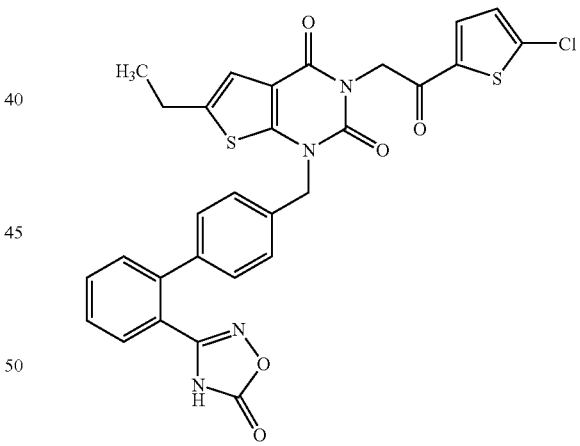

A mixture of hydroxylammonium chloride (1.21 g), sodium hydrogencarbonate (1.83 g) and dimethyl sulfoxide (20 mL) was stirred at 40° C. for 30 min, 4'-{[3-[2-(5-chloro-2-thienyl)-2-oxoethyl]-6-ethyl-2,4-dioxo-3,4-dihydrothieno[2,3-d]pyrimidin-1(2H)-yl]methyl}biphenyl-2-carbonitrile (0.79 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (20 mL), N,N'-carbonyldiimidazole (0.28 g) and then 1,8-diazabicyclo[5.4.0]undec-7-ene (0.24 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 20% sulfuric acid (10 mL) and ethanol (50 ml). The mixture was stirred at 100° C. for 1 hr, and extracted with chloroform and water. The chloroform layer was washed with saturated brine, and dried over anhydrous magnesium sulfate. The solvent was evaporated under reduced pressure. The obtained residue was purified by preparative HPLC to give the title compound as colorless crystals (0.32 g, 36%).

$^1$H NMR (300 MHz, DMSO-$d_6$)δ1.20 (3H, t, J=7.5), 2.75 (2H, q, J=7.5), 5.21 (2H, s), 5.38 (2H, s), 7.01 (1H, s), 7.30-7.41 (5H, m), 7.50-7.58 (2H, m), 7.64-7.70 (2H, m), 8.17 (1H, d, J=4.2), 12.37 (1H, s)

Example 151

1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]-6-methylthieno[2,3-d]pyrimidine-2,4(1H,3H)-dione

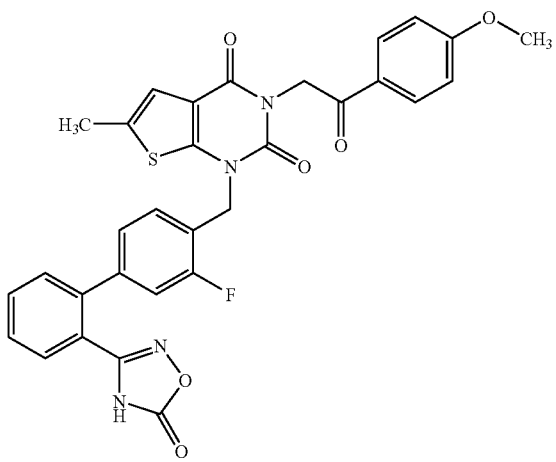 [SMILES: COc1ccc(C(=O)Cn2c(=O)c3cc(C)sc3n(Cc3ccc(-c4ccccc4-c4noc(=O)[nH]4)cc3F)c2=O)cc1]

A mixture of 3-[2-(4-methoxyphenyl)-2-oxoethyl]-6-methylthieno[2,3-d]pyrimidine-2,4(1H,3H)-dione (1 g), 4'-(bromomethyl)-3'-fluorobiphenyl-2-carbonitrile (1.06 g), potassium carbonate (0.84 g) and acetonitrile (50 mL) was stirred at 50° C. for 2 hr. Insoluble material was filtered off, and the obtained filtrate was concentrated under reduced pressure. The obtained residue was dissolved in dimethyl sulfoxide (5 mL), and added to a mixture of hydroxylammonium chloride (1.81 g), sodium hydrogencarbonate (2.73 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography and dissolved in methylene chloride (40 mL). N,N'-Carbonyldiimidazole (0.42 g) and then 1,8-diazabicyclo[5.4.0]undec-7-ene (0.36 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 20% sulfuric acid (5 mL) and ethanol (20 ml). The mixture was stirred at 100° C. for 1 hr, and extracted with chloroform and water. The chloroform layer was washed with saturated brine, and dried over anhydrous magnesium sulfate. The solvent was evaporated under reduced pressure. The obtained residue was purified by silica gel column chromatography to give the title compound as colorless crystals (0.51 g, 39%).

$^1$H NMR (300 MHz, DMSO-$d_6$)δ2.42 (3H, d, J=1.1), 3.88 (3H, s), 5.28 (2H, s), 5.41 (2H, s), 7.02 (1H, d, J=1.3), 7.08-7.17 (3H, m), 7.22-7.36 (2H, m), 7.55-7.66 (2H, m), 7.68-7.76 (2H, m), 8.08 (2H, d, J=9.0), 12.47 (1H, s)

Example 152

6-ethyl-1-{[3-fluoro-2'-(5-oxo-4,5-dihydro-1,2,4-oxadiazol-3-yl)biphenyl-4-yl]methyl}-3-[2-hydroxy-2-(4-methoxyphenyl)ethyl]thieno[2,3-d]pyrimidine-2,4(1H,3H)-dione

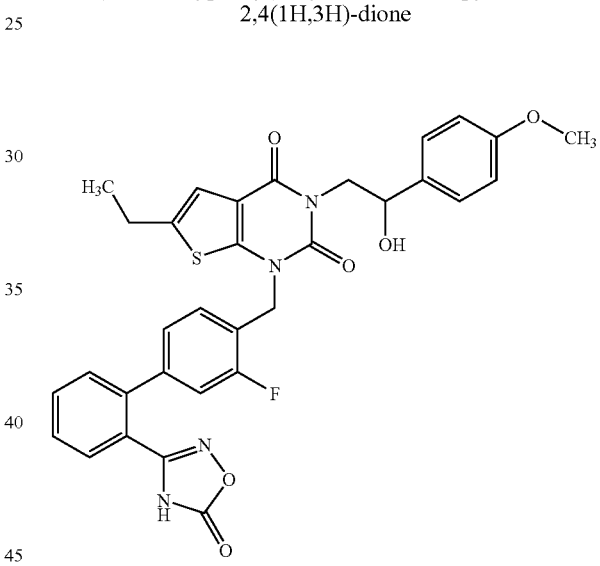

To a mixture of 6-ethyl-1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione (0.77 g) and methanol (20 mL) was added sodium borohydride (0.14 g), and the mixture was stirred at room temperature for 1 hr. The reaction mixture was concentrated, and the residue was extracted with chloroform and saturated aqueous ammonium chloride solution. The chloroform layer was washed with saturated brine, and dried over anhydrous magnesium sulfate. The solvent was evaporated under reduced pressure. The precipitated solid was collected by filtration to give the title compound as colorless crystals (0.6 g, 77%).

$^1$H NMR (300 MHz, DMSO-$d_6$)δ1.20 (3H, t, J=7.6), 2.67-2.85 (2H, m), 3.71 (3H, s), 3.93 (1H, dd, J=12.7, 5.1), 4.20 (1H, dd, J=12.9, 8.7), 4.84-5.01 (1H, m), 5.12-5.29 (2H, m), 5.41 (1H, d, J=4.9), 6.83-6.94 (2H, m), 6.99-7.16 (3H, m), 7.19-7.36 (3H, m), 7.56 (2H, dd, J=17.4, 6.8), 7.64-7.76 (2H, m), 12.54 (1H, s)

Example 153

2-[6-ethyl-1-{[3-fluoro-2'-(5-oxo-4,5-dihydro-1,2,4-oxadiazol-3-yl)biphenyl-4-yl]methyl}-2,4-dioxo-1,4-dihydrothieno[2,3-d]pyrimidin-3(2H)-yl]-1-(4-methoxyphenyl)ethyl acetate

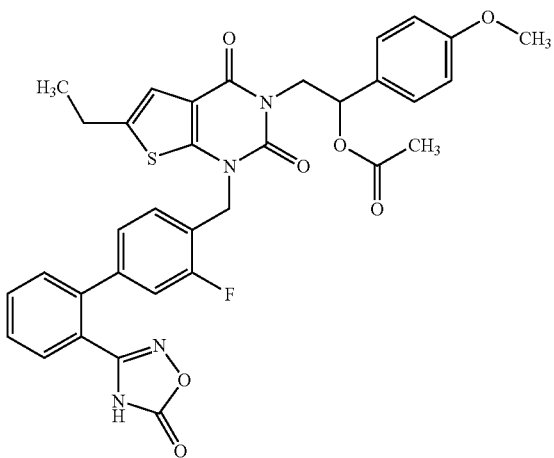 [SMILES: CCc1cc2c(=O)n(CC(OC(C)=O)c3ccc(OC)cc3)c(=O)n(Cc3ccc(-c4ccccc4-c4noc(=O)[nH]4)cc3F)c2s1]

A mixture of 6-ethyl-1-{[3-fluoro-2'-(5-oxo-4,5-dihydro-1,2,4-oxadiazol-3-yl)biphenyl-4-yl]methyl}-3-[2-hydroxy-2-(4-methoxyphenyl)ethyl]thieno[2,3-d]pyrimidine-2,4(1H,3H)-dione (0.3 g), acetic anhydride (0.07 mL), triethylamine (0.1 mL), N,N-dimethylpyridin-4-amine (0.006 g) and methylene chloride (20 mL) was stirred at room temperature for 16 hr. The reaction mixture was washed successively with water and saturated brine, and dried over anhydrous magnesium sulfate. The solvent was evaporated under reduced pressure. The precipitated solid was collected by filtration to give the title compound as colorless crystals (0.23 g, 71%).
$^1$H NMR (300 MHz, DMSO-$d_6$)δ1.20 (3H, t, J=7.5), 1.90 (3H, s), 2.75 (2H, q, J=7.5), 3.74 (3H, s), 3.99-4.10 (1H, m), 4.50 (1H, dd,J=13.6, 9.0), 5.11-5.34 (2H, m), 6.08 (1H, dd, J=9.0, 3.8), 6.95 (2H, d, J=8.7), 7.02 (1H, s), 7.05-7.10 (1H, m), 7.14-7.21 (1H, m), 7.23-7.36 (3H, m),7.59 (2H, dd, J=17.9, 7.2), 7.68-7.78 (2H, m), 12.49 (1H, s)

Example 154

3-(2,2-dimethylpropyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

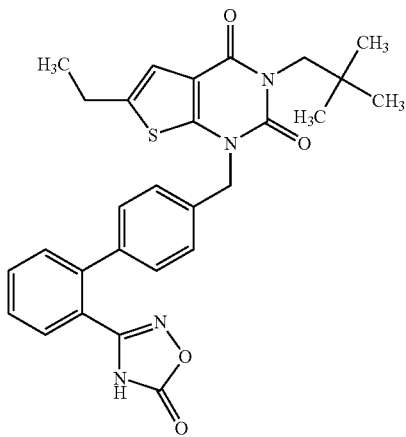 [SMILES: CCc1cc2c(=O)n(CC(C)(C)C)c(=O)n(Cc3ccc(-c4ccccc4-c4noc(=O)[nH]4)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (0.8 g), 1-iodo-2,2-dimethylpropane (0.33 mL) and N,N-dimethylformamide (20 mL) was added sodium hydride (0.12 g), and the mixture was stirred at 100° C. for 1 day. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (0.24 g), sodium hydrogencarbonate (0.35 g) and dimethyl sulfoxide (5 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was dissolved in methylene chloride (10 mL), N,N'-carbonyldiimidazole (0.055 g) and then 1,8-diazabicyclo[5.4.0]undec-7-ene (0.047 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.057 g, 39%).
$^1$H NMR (300 MHz, CDCl$_3$)δ0.91 (9H, s), 1.26 (3H, t, J=7.4), 2.73 (2H, q, J=7.4), 3.89 (2H, s), 5.10 (2H, s), 6.95 (1H, s), 7.25-7.33 (2H, m), 7.33-7.53 (4H, m), 7.61 (1H, t, J=7.4), 7.72 (1H, d, J=7.5)

Example 155

3-[2-(4-methoxyphenyl)-2-oxoethyl]-1-{[2'-(5-oxo-4,5-dihydro-1,2,4-oxadiazol-3-yl)biphenyl-4-yl]methyl}-6-propoxypyrimidine-2,4(1H,3H)-dione potassium salt

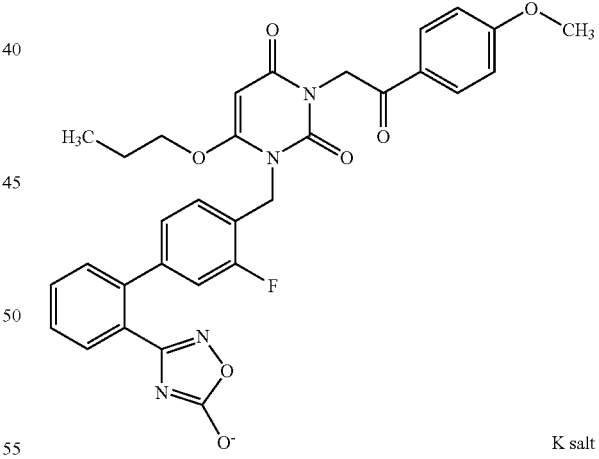

A mixture of 1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]-6-propoxypyrimidine-2,4(1H,3H)-dione (0.15 g), potassium 2-ethylhexanoate (0.056 g) and ethyl acetate (10 mL) was stirred at room temperature for 16 hr. The precipitated solid was collected by filtration to give the title compound as a colorless amorphous solid (0.12 g, 75%).
$^1$H NMR (300 MHz, DMSO-$d_6$)δ0.85 (3H, t, J=7.2),1.61-1.75 (2H, m), 3.87 (3H, s), 4.08 (2H, t, J=6.1), 5.11 (2H, s), 5.29 (2H,s), 5.35 (1H, s), 7.03-7.19 (5H, m), 7.28-7.59 (4H, m), 8.05 (2H, d, J=8.7)

Example 156

3-(3,3-dimethyl-2-oxobutyl)-1-{[2'-(5-oxo-4,5-dihydro-1,2,4-oxadiazol-3-yl)biphenyl-4-yl]methyl}-6-propoxypyrimidine-2,4(1H,3H)-dione

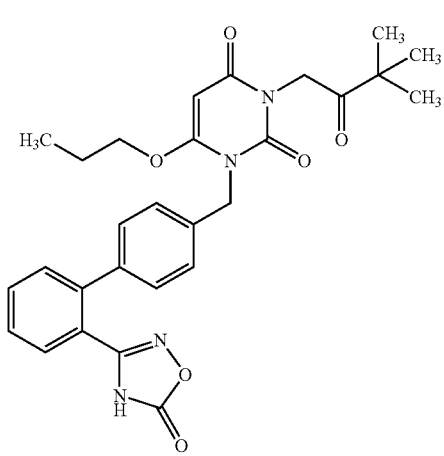 [SMILES: CCCOc1cc(=O)n(CC(=O)C(C)(C)C)c(=O)n1Cc1ccc(-c2ccccc2-c2noc(=O)[nH]2)cc1]

A mixture of hydroxylammonium chloride (1.45 g), sodium hydrogencarbonate (2.18 g) and dimethyl sulfoxide (20 mL) was stirred at 40° C. for 30 min, 4'-{[3-(3,3-dimethyl-2-oxobutyl)-2,4-dioxo-6-propoxy-3,4-dihydropyrimidin-1(2H)-yl]methyl}biphenyl-2-carbonitrile (0.8 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The obtained residue was dissolved in methylene chloride (30 mL), N,N'-carbonyldiimidazole (0.33 g) and then 1,8-diazabicyclo[5.4.0]undec-7-ene (0.28 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as a colorless amorphous solid (0.17 g, 19%).

$^1$H NMR (300 MHz, DMSO-$d_6$)δ0.82 (3H, t, J=7.3), 1.18 (9H, s), 1.65 (2H, d, J=7.3), 4.04 (2H, t, J=6.2), 4.85 (2H, s), 5.06 (2H,s), 5.29 (1H, s), 7.30 (4H, s), 7.46-7.61 (2H, m), 7.60-7.76 (2H, m), 12.40(1H, s)

Example 157

6-ethyl-3-[2-(3-fluoro-4-methoxyphenyl)-2-oxoethyl]-1-{[3-fluoro-2'-(5-oxo-4,5-dihydro-1,2,4-oxadiazol-3-yl)biphenyl-4-yl]methyl}thieno[2,3-d]pyrimidine-2,4(1H,3H)-dione

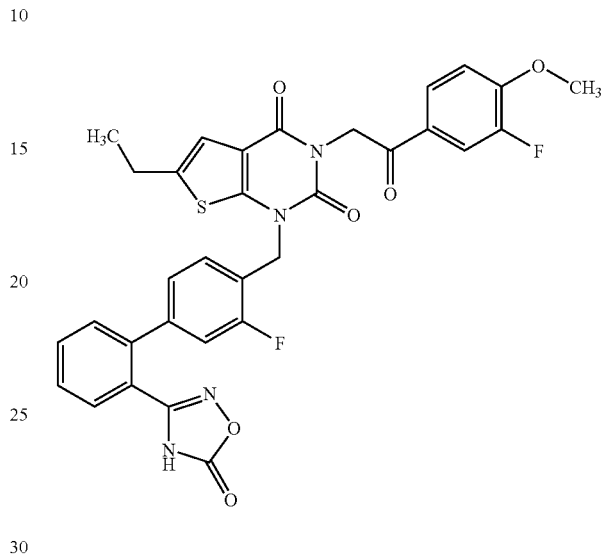

A mixture of hydroxylammonium chloride (1.31 g), sodium hydrogencarbonate (1.98 g) and dimethyl sulfoxide (20 mL) was stirred at 40° C. for 30 min, 4'-{[6-ethyl-3-[2-(3-fluoro-4-methoxyphenyl)-2-oxoethyl]-2,4-dioxo-3,4-dihydrothieno[2,3-d]pyrimidin-1(2H)-yl]methyl}-3'-fluorobiphenyl-2-carbonitrile (0.9 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (40 mL), N,N'-carbonyldiimidazole (0.3 g) and then 1,8-diazabicyclo[5.4.0]undec-7-ene (0.26 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 20% sulfuric acid (10 mL) and ethanol (20 ml), and the mixture was stirred at 100° C. for 1 hr, and extracted with chloroform and water. The chloroform layer was washed with saturated brine, and dried over anhydrous magnesium sulfate. The solvent was evaporated under reduced pressure. The obtained residue was purified by silica gel column chromatography to give the title compound as colorless crystals (0.5 g, 51%).

$^1$H NMR (300 MHz, DMSO-$d_6$)δ1.22 (3H, t, J=7.4),2.70-2.85 (2H, m), 3.97 (3H, s), 5.28 (2H, s), 5.43 (2H, s), 7.04 (1H, s), 7.13(1H, dd, J=7.9, 1.7), 7.22-7.41 (3H, m), 7.54-7.65 (2H, m), 7.66-7.75 (2H,m), 7.92 (1H, dd, J=12.1, 2.1), 7.97-8.02 (1H, m), 12.47 (1H, s)

Example 158

1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]-6-propylthieno[2,3-d]pyrimidine-2,4(1H,3H)-dione

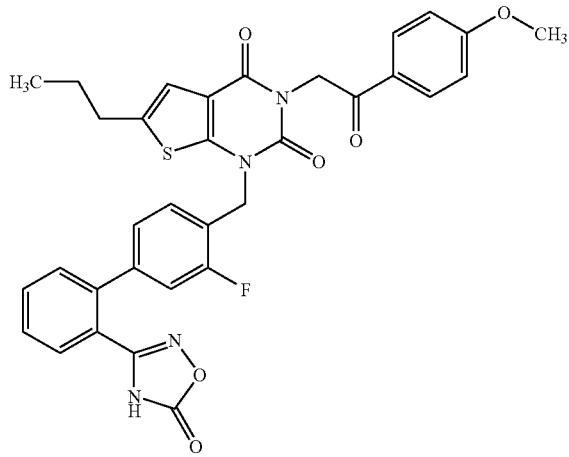 [SMILES: CCCc1cc2c(=O)n(CC(=O)c3ccc(OC)cc3)c(=O)n(Cc3ccc(-c4ccccc4-c4noc(=O)[nH]4)cc3F)c2s1]

To a mixture of 4'-[(2,4-dioxo-6-propyl-3,4-dihydrothieno[2,3-d]pyrimidin-1(2H)-yl)methyl]-3'-fluorobiphenyl-2-carbonitrile (1 g), 2-bromo-1-(4-methoxyphenyl)ethanone (0.67 g) and N,N-dimethylformamide (15 mL) was added sodium hydride (0.14 g), and the mixture was stirred at room temperature for 4 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was dissolved in dimethyl sulfoxide (5 mL), and added to a mixture of hydroxylammonium chloride (1.41 g), sodium hydrogencarbonate (2.13 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was dissolved in methylene chloride (40 mL), N,N'-carbonyldiimidazole (0.33 g) and then 1,8-diazabicyclo[5.4.0]undec-7-ene (0.28 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 20% sulfuric acid (10 mL) and ethanol (20 ml), and the mixture was stirred at 100° C. for 1 hr, and extracted with chloroform and water. The chloroform layer was washed with saturated brine, and dried over anhydrous magnesium sulfate. The solvent was evaporated under reduced pressure. The obtained residue was purified by silica gel column chromatography to give the title compound as colorless crystals (0.57 g, 53%).

$^1$H NMR (300 MHz, DMSO-$d_6$)δ0.91 (3H, t, J=7.3),1.54-1.67 (2H, m), 2.74 (2H, t, J=7.4), 3.88 (3H, s), 5.28 (2H, s), 5.41 (2H,s), 7.04 (1H, s), 7.08-7.16 (3H, m), 7.23-7.35 (2H, m), 7.54-7.64 (2H, m),7.67-7.75 (2H, m), 8.08 (2H, d, J=8.9), 12.48 (1H, s)

Example 159

1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]-6-propylthieno[2,3-d]pyrimidine-2,4(1H,3H)-dione potassium salt

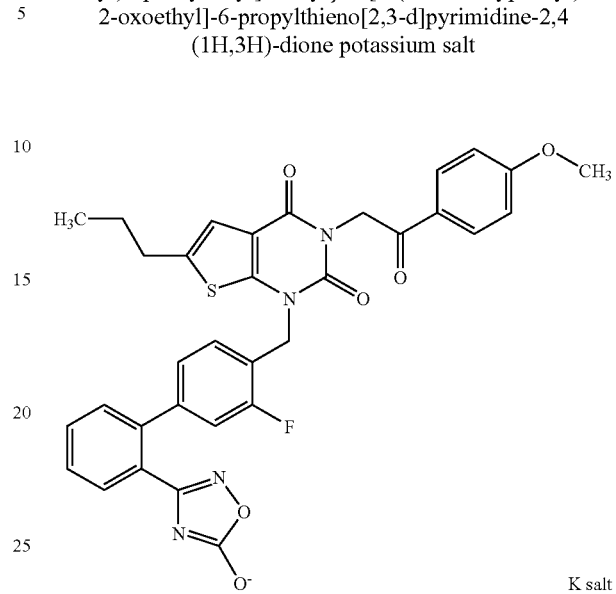

A mixture of 1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]-6-propylthieno[2,3-d]pyrimidine-2,4(1H,3H)-dione (0.3 g), potassium 2-ethylhexanoate (0.1 g) and ethyl acetate (15 mL) was stirred at room temperature for 16 hr. The precipitated solid was collected by filtration to give the title compound as colorless crystals (0.27 g, 85%).

$^1$H NMR (300 MHz, DMSO-$d_6$)δ0.92 (3H, t, J=7.3), 1.55-1.68 (2H, m), 2.74 (2H, t, J=7.3), 3.88 (3H, s), 5.23 (2H, s), 5.41 (2H,s), 7.04 (1H, s), 7.08-7.22 (5H, m), 7.32-7.48 (3H, m), 7.51-7.56 (1H, m),8.05-8.12 (2H, m)

Example 160

6-cyclopropyl-3-(3,3-dimethyl-2-oxobutyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

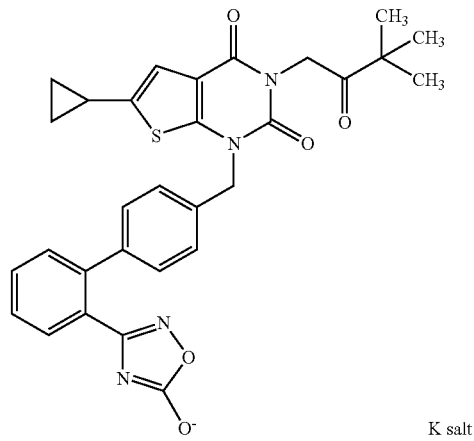 [SMILES: CC(C)(C)C(=O)Cn1c(=O)c2cc(C3CC3)sc2n(Cc2ccc(-c3ccccc3-c3noc([O-])n3)cc2)c1=O ; "K salt"]

A mixture of 6-cyclopropyl-3-(3,3-dimethyl-2-oxobutyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.56 g), potassium 2-ethylhexanoate (0.22 g) and ethyl acetate (5 mL) was stirred at room temperature for 2 hr. The precipitated solid was collected by filtration to give the title compound as colorless crystals (0.56 g, 93%).

$^1$H NMR (300 MHz, DMSO-$d_6$)δ0.68-0.76 (2H, m), 0.91-1.00(2H, m), 1.21 (9H, s), 2.04-2.14 (1H, m), 4.97 (2H, s), 5.13 (2H, s), 6.93 (1H,d, J=0.9), 7.20-7.54 (8H, m)

Example 161

2-ethyl-4-{[2'-(5-oxo-4,5-dihydro-1,2,4-oxadiazol-3-yl)biphenyl-4-yl]methyl}-6-(2-phenylethyl)[1,3]thiazolo[5,4-d]pyrimidine-5,7(4H,6H)-dione

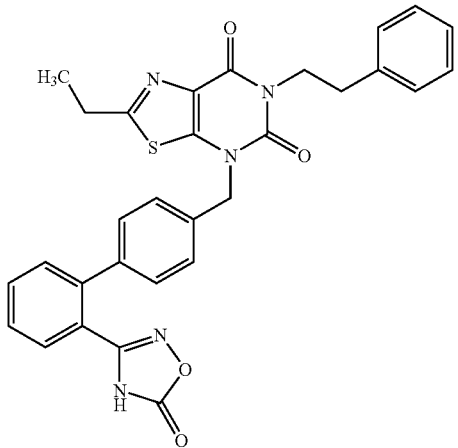 [SMILES: CCc1nc2c(=O)n(CCc3ccccc3)c(=O)n(Cc3ccc(-c4ccccc4-c4noc(=O)[nH]4)cc3)c2s1]

A mixture of 2-ethyl-6-(2-phenylethyl)[1,3]thiazolo[5,4-d]pyrimidine-5,7(4H,6H)-dione (0.25 g), 3-[4'-(bromomethyl)biphenyl-2-yl]-5-(trichloromethyl)-1,2,4-oxadiazole (0.54 g), potassium carbonate (0.17 g) and acetonitrile (15 mL) was stirred at 50° C. for 2 hr. Insoluble material was filtered off, and the solvent was evaporated under reduced pressure. The obtained residue was purified by silica gel column chromatography and dissolved in tetrahydrofuran (5 mL) and acetone (5 mL). 1N Aqueous sodium hydroxide solution (2 mL) was added, and the mixture was stirred at room temperature for 1 hr. The reaction mixture was adjusted to pH 4 with water and 1N hydrochloric acid, and extracted with chloroform. The obtained chloroform layer was washed with saturated brine, and dried over anhydrous magnesium sulfate. The solvent was evaporated under reduced pressure. The precipitated solid was collected by filtration to give the title compound as colorless crystals (0.25 g, 55%).

$^1$H NMR (300 MHz, CDCl$_3$)δ1.37 (3H, t, J=7.5), 2.96-3.03 (4H, m), 4.26-4.38 (2H, m), 5.16 (2H, s), 7.14-7.38 (8H, m), 7.43 (1H, d, J=7.5), 7.49-7.59 (1H, m), 7.59-7.67 (1H, m), 7.73 (1H, s), 7.85 (1H, dd, J=7.7, 1.3)

Example 162

2-ethyl-6-(2-morpholin-4-ylethyl)-4-{[2'-(5-oxo-4,5-dihydro-1,2,4-oxadiazol-3-yl)biphenyl-4-yl]methyl}[1,3]thiazolo[5,4-d]pyrimidine-5,7(4H,6H)-dione

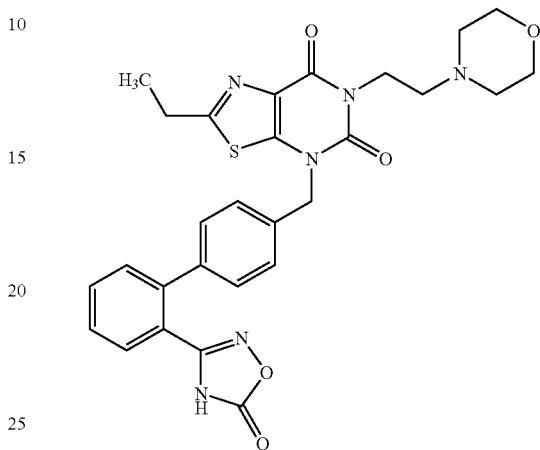

To a solution (60 mL) of ethyl 5-amino-2-ethyl-1,3-thiazole-4-carboxylate (1 g) in methylene chloride were added triphosgene (0.64 g) and triethylamine (0.45 mL), and the mixture was stirred at room temperature for 2 hr. To the reaction mixture was added 2-morpholin-4-ylethanamine (2 mL), and the mixture was further stirred at room temperature for 1 hr, and extracted with water and chloroform. The chloroform layer was washed with saturated brine, and dried over anhydrous magnesium sulfate. The solvent was evaporated under reduced pressure. The obtained residue was dissolved in ethanol (80 mL), sodium ethoxide (20% ethanol solution, 4.3 g) was added, and the mixture was stirred at 80° C. for 2 hr. The reaction mixture was neutralized with hydrochloric acid (10% methanol solution), the precipitated solid was collected by filtration. The obtained solid was dissolved in acetonitrile (40 mL), 3-[4'-(bromomethyl)biphenyl-2-yl]-5-(trichloromethyl)-1,2,4-oxadiazole (2.2 g) and potassium carbonate (0.69 g) was added, and the mixture was stirred at 50° C. for 2 hr. Insoluble material was filtered off, and the solvent was evaporated under reduced pressure. The obtained residue was purified by silica gel column chromatography and dissolved in tetrahydrofuran (10 mL) and acetone (10 mL). 1N Aqueous sodium hydroxide solution (5 mL) was added, and the mixture was stirred at room temperature for 1 hr. The reaction mixture was adjusted to pH 7 with water and 1N hydrochloric acid, and extracted with chloroform. The obtained chloroform layer was washed with saturated brine, and dried over anhydrous magnesium sulfate. The solvent was evaporated under reduced pressure. The obtained residue was purified by preparative HPLC to give the title compound as colorless crystals (0.34 g, 12%).

$^1$H NMR (300 MHz, DMSO-$d_6$)δ1.25 (3H, t, J=7.6),2.54-2.86 (6H, m), 2.96 (2H, q, J=7.6), 3.59 (4H, s), 4.14 (2H, s), 5.23 (2H,s), 7.21-7.35 (2H, m), 7.35-7.46 (2H, m), 7.46-7.61 (2H, m), 7.63-7.75 (2H, m)

Example 163

5-ethyl-3-{[2'-(5-oxo-4,5-dihydro-1,2,4-oxadiazol-3-yl)biphenyl-4-yl]methyl}-1-(2-phenylethyl)-1,3-dihydro-2H-thieno[2,3-d]imidazol-2-one

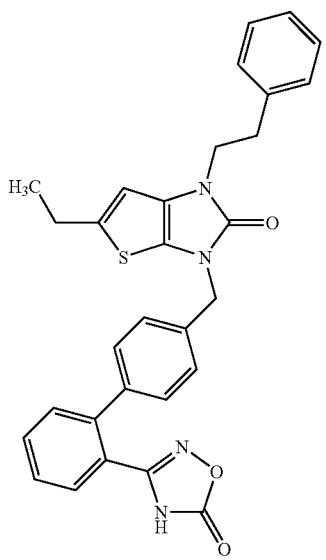 [SMILES: CCc1cc2c(s1)n(Cc1ccc(-c3ccccc3-c3noc(=O)[nH]3)cc1)c(=O)n2CCc1ccccc1]

A mixture of hydroxylammonium chloride (0.71 g), sodium hydrogencarbonate (1 g) and dimethyl sulfoxide (20 mL) was stirred at 40° C. for 30 min, 4'-{[5-ethyl-2-oxo-1-(2-phenylethyl)-1,2-dihydro-3H-thieno[2,3-d]imidazol-3-yl]methyl}biphenyl-2-carbonitrile (0.58 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (20 mL), N,N'-carbonyldiimidazole (0.22 g) and then 1,8-diazabicyclo[5.4.0]undec-7-ene (0.18 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The precipitated solid was collected by filtration to give the title compound as colorless crystals (0.23 g, 36%).

$^1$H NMR (300 MHz, DMSO-d$_6$)δ1.16 (3H, t, J=7.4), 2.71 (2H, q, J=7.4), 2.97 (2H, t, J=7.2), 4.01 (2H, t, J=7.2), 4.91 (2H, s), 6.68 (1H, s), 7.17-7.36 (9H, m), 7.47-7.62 (2H, m), 7.62-7.77 (2H, m), 12.41(1H, s)

Example 164

5-ethyl-1-(4-fluorobenzyl)-3-{[2'-(5-oxo-4,5-dihydro-1,2,4-oxadiazol-3-yl)biphenyl-4-yl]methyl}-1,3-dihydro-2H-thieno[2,3-d]imidazol-2-one

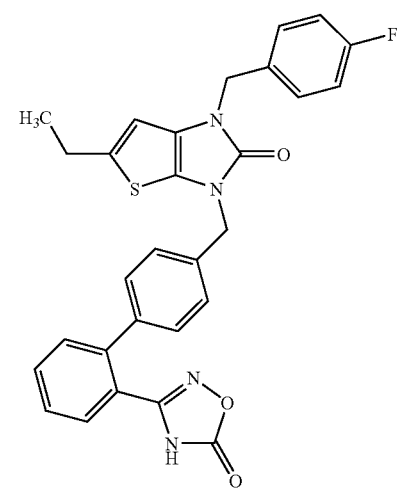 [SMILES: CCc1cc2c(s1)n(Cc1ccc(-c3ccccc3-c3noc(=O)[nH]3)cc1)c(=O)n2Cc1ccc(F)cc1]

A mixture of hydroxylammonium chloride (0.44 g), sodium hydrogencarbonate (0.65 g) and dimethyl sulfoxide (20 mL) was stirred at 40° C. for 30 min, 4'-{[5-ethyl-1-(4-fluorobenzyl)-2-oxo-1,2-dihydro-3H-thieno[2,3-d]imidazol-3-yl]methyl}biphenyl-2-carbonitrile (0.36 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (30 mL), N,N'-carbonyldiimidazole (0.14 g) and then 1,8-diazabicyclo[5.4.0]undec-7-ene (0.12 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.12 g, 29%).

$^1$H NMR (300 MHz, DMSO-d$_6$)δ1.14 (3H, t, J=7.4), 2.69 (2H, q, J=7.4), 4.96 (4H, s), 6.68 (1H, s), 7.19 (2H, t, J=8.9), 7.26-7.46(6H, m), 7.48-7.64 (2H, m), 7.62-7.75 (2H, m), 12.40 (1H, s)

Example 165

3-{4'-[(2-ethoxy-5-ethyl-3H-thieno[2,3-d]imidazol-3-yl)methyl]biphenyl-2-yl}-1,2,4-oxadiazol-5(4H)-one

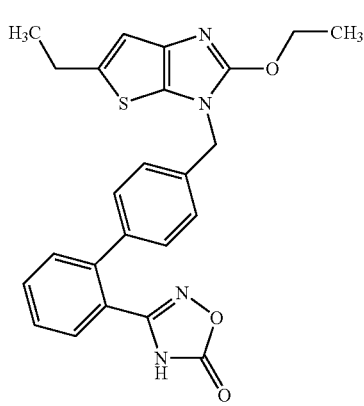 [SMILES: CCOc1nc2cc(CC)sc2n1Cc1ccc(-c2ccccc2-c2noc(=O)[nH]2)cc1]

A mixture of hydroxylammonium chloride (0.74 g), sodium hydrogencarbonate (1.07 g) and dimethyl sulfoxide (20 mL) was stirred at 40° C. for 30 min, 4'-[(2-ethoxy-5-ethyl-3H-thieno[2,3-d]imidazol-3-yl)methyl]biphenyl-2-carbonitrile (0.48 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (20 mL), N,N'-carbonyldiimidazole (0.22 g) and then 1,8-diazabicyclo[5.4.0]undec-7-ene (0.18 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The precipitated solid was collected by filtration to give the title compound as colorless crystals (0.33 g, 59%).

$^1$H NMR (300 MHz, DMSO-$d_6$)δ1.19 (3H, t, J=7.4), 1.37 (3H, t, J=7.0), 2.74 (2H, q, J=7.6), 4.43 (2H, q, J=7.2), 5.10 (2H, s),6.73 (1H, s), 7.32 (4H, s), 7.53 (2H, dd, J=18.0, 7.0), 7.61-7.76 (2H, m),12.44 (1H, s)

Example 166

7-ethyl-1-{[2'-(5-oxo-4,5-dihydro-1,2,4-oxadiazol-3-yl)biphenyl-4-yl]methyl}-4-(2-phenylethyl)-3,4-dihydro-1H-thieno[2,3-e][1,4]diazepine-2,5-dione

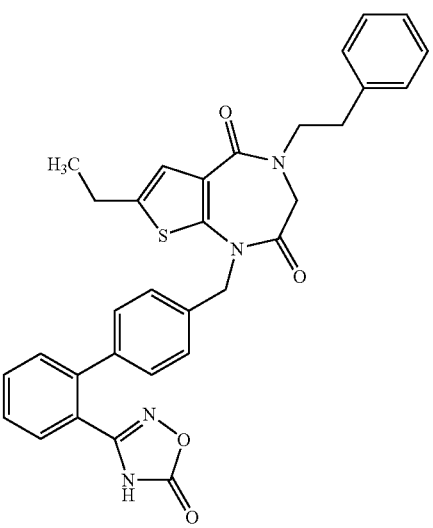 [SMILES: CCc1cc2c(s1)N(Cc1ccc(-c3ccccc3-c3noc(=O)[nH]3)cc1)C(=O)CN(CCc1ccccc1)C2=O]

A mixture of hydroxylammonium chloride (0.61 g), sodium hydrogencarbonate (0.89 g) and dimethyl sulfoxide (20 mL) was stirred at 40° C. for 30 min, 4'-{[7-ethyl-2,5-dioxo-4-(2-phenylethyl)-2,3,4,5-tetrahydro-1H-thieno[2,3-e][1,4]diazepin-1-yl]methyl}biphenyl-2-carbonitrile (0.27 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (20 mL), N,N'-carbonyldiimidazole (0.096 g) and then 1,8-diazabicyclo[5.4.0]undec-7-ene (0.08 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.13 g, 41%).

$^1$H NMR (300 MHz, CDCl$_3$)δ1.26 (3H, t, J=7.2), 2.72 (2H, q, J=7.2), 2.96 (2H, t, J=7.8), 3.83 (2H, t, J=7.8), 3.95 (2H, br), 5.02(2H, br), 6.91 (1H, s), 7.18-7.31 (9H, m), 7.38-7.63 (3H, m), 7.81 (1H, d, J=7.5)

Example 167

2-ethyl-10-{[2'-(5-oxo-4,5-dihydro-1,2,4-oxadiazol-3-yl)biphenyl-4-yl]methyl}-6,7,8,8a-tetrahydro-4H-pyrrolo[1,2-a]thieno[2,3-e][1,4]diazepine-4,9(10H)-dione

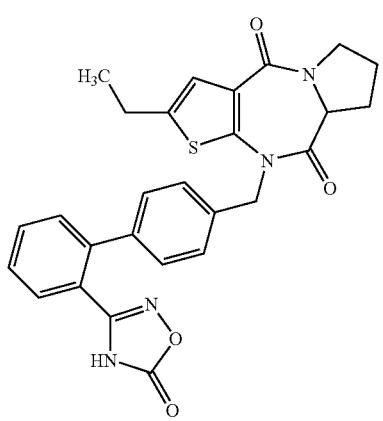 [SMILES: CCc1cc2c(s1)N(Cc1ccc(-c3ccccc3-c3noc(=O)[nH]3)cc1)C(=O)C1CCCN1C2=O]

A mixture of hydroxylammonium chloride (0.45 g), sodium hydrogencarbonate (0.66 g) and dimethyl sulfoxide (20 mL) was stirred at 40° C. for 30 min, 4'-[(2-ethyl-4,9-dioxo-7,8,8a,9-tetrahydro-4H-pyrrolo[1,2-a]thieno[2,3-e][1,4]diazepin-10(6H)-yl)methyl]biphenyl-2-carbonitrile (0.35 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (20 mL), N,N'-carbonyldiimidazole (0.14 g) and then 1,8-diazabicyclo[5.4.0]undec-7-ene (0.12 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.21 g, 52%).

$^1$H NMR (300 MHz, DMSO-d$_6$)δ1.17 (3H, t, J=7.4),1.80-1.98 (2H, m), 1.99-2.13 (1H, m), 2.53-2.61 (1H, m), 2.68 (2H, q, J=7.6),3.48 (2H, dd, J=8.1, 5.1), 4.48 (1H, dd, J=8.0, 2.3), 4.92-5.26 (2H, m),6.84 (1H, s), 7.20-7.38 (4H, m), 7.56 (2H, dd, J=9.5, 7.6), 7.62-7.78 (2H, m), 12.40 (1H, s)

Example 168

7-ethyl-4-(4-fluorobenzyl)-1-{[2'-(5-oxo-4,5-dihydro-1,2,4-oxadiazol-3-yl)biphenyl-4-yl]methyl}-3,4-dihydro-1H-thieno[2,3-e][1,4]diazepine-2,5-dione

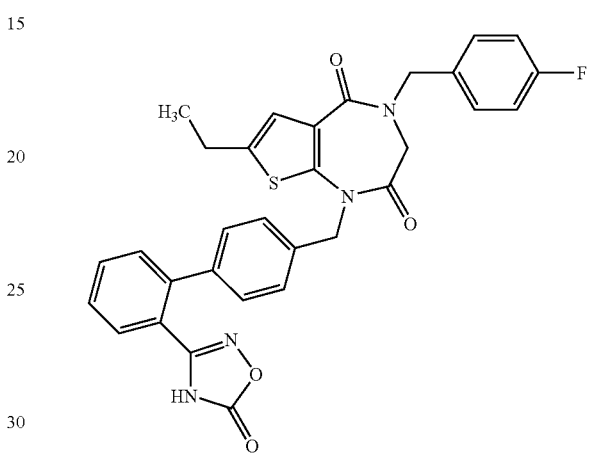

A mixture of hydroxylammonium chloride (0.43 g), sodium hydrogencarbonate (0.63 g) and dimethyl sulfoxide (20 mL) was stirred at 40° C. for 30 min, 4'-{[7-ethyl-4-(4-fluorobenzyl)-2,5-dioxo-2,3,4,5-tetrahydro-1H-thieno[2,3-e][1,4]diazepin-1-yl]methyl}biphenyl-2-carbonitrile (0.38 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (20 mL), N,N'-carbonyldiimidazole (0.13 g) and then 1,8-diazabicyclo[5.4.0]undec-7-ene (0.11 mL) were added, and the mixture was stirred at room temperature for 2 hr. The reaction Mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.19 g, 49%).

$^1$H NMR (300 MHz, DMSO-d$_6$)δ1.18 (3H, t, J=7.6), 2.70 (2H, q, J=7.6), 4.20 (2H, s), 4.72 (2H, s), 5.01 (2H, s), 6.87 (1H, s),7.06-7.22 (4H, m), 7.19-7.29 (2H, m), 7.36 (2H, dd, J=8.7, 5.7), 7.56 (2H, dd, J=12.5, 7.6), 7.68 (2H, dd, J=7.0, 5.1), 12.40 (1H, s)

Example 169

2-ethyl-5-methyl-7-{[2'-(5-oxo-4,5-dihydro-1,2,4-oxadiazol-3-yl)biphenyl-4-yl]methyl}-5-(2-phenyl-ethyl)thieno[2,3-b]pyridine-4,6(5H,7H)-dione

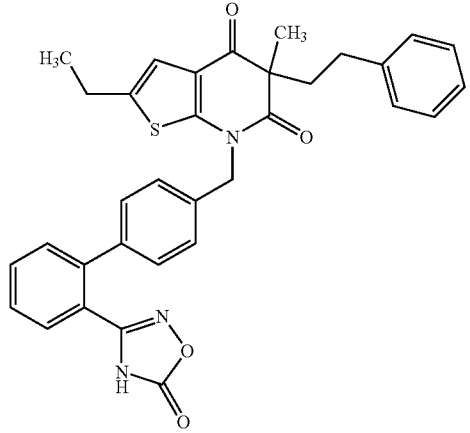 [SMILES: CCc1cc2c(s1)N(Cc1ccc(-c3ccccc3-c3noc(=O)[nH]3)cc1)C(=O)C(C)(CCc1ccccc1)C2=O]

A mixture of hydroxylammonium chloride (0.36 g), sodium hydrogencarbonate (0.53 g) and dimethyl sulfoxide (20 mL) was stirred at 40° C. for 30 min, 4'-{[2-ethyl-5-methyl-4,6-dioxo-5-(2-phenylethyl)-5,6-dihydrothieno[2,3-b]pyridin-7(4H)-yl]methyl}biphenyl-2-carbonitrile (0.32 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (20 mL), N,N'-carbonyldiimidazole (0.11 g) and then 1,8-diazabicyclo[5.4.0]undec-7-ene (0.095 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as a colorless amorphous solid (0.17 g, 48%).

$^1$H NMR (300 MHz, DMSO-$d_6$) δ1.13 (3H, t, J=7.2), 1.38 (3H, s), 2.02-2.40 (4H, m), 2.64 (2H, q, J=7.2), 5.03 (2H, m), 6.86 (1H, s), 6.98-7.35 (9H, m), 7.44-7.68 (4H, m), 12.4 (1H, br)

Example 170

2-ethyl-4-methoxy-7-{[2'-(5-oxo-4,5-dihydro-1,2,4-oxadiazol-3-yl)biphenyl-4-yl]methyl}-5-(2-phenyl-ethyl)thieno[2,3-b]pyridin-6(7H)-one

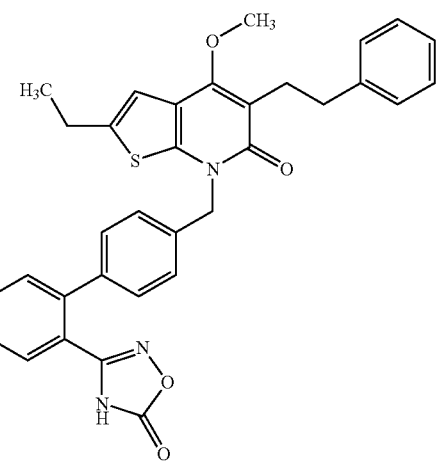

A mixture of hydroxylammonium chloride (0.32 g), sodium hydrogencarbonate (0.46 g) and dimethyl sulfoxide (20 mL) was stirred at 40° C. for 30 min, 4'-{[2-ethyl-4-methoxy-6-oxo-5-(2-phenylethyl)thieno[2,3-b]pyridin-7(6H)-yl]methyl}biphenyl-2-carbonitrile (0.28 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (20 mL), N,N'-carbonyldiimidazole (0.01 g) and then 1,8-diazabicyclo[5.4.0]undec-7-ene (0.083 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.046 g, 15%).

$^1$H NMR (300 MHz, DMSO-$d_6$) δ1.22 (3H, t, J=7.6), 2.72-2.88 (6H, m), 3.81 (3H, s), 5.34 (2H, s), 7.05 (1H, s), 7.10-7.24 (3H, m), 7.24-7.34 (6H, m), 7.48-7.61 (2H, m), 7.61-7.74 (2H, m), 12.42 (1H, s)

Example 171

2-ethyl-7-{[2'-(5-oxo-4,5-dihydro-1,2,4-oxadiazol-3-yl)biphenyl-4-yl]methyl}-5-(2-phenylethyl)thieno[2,3-b]pyridin-6(7H)-one

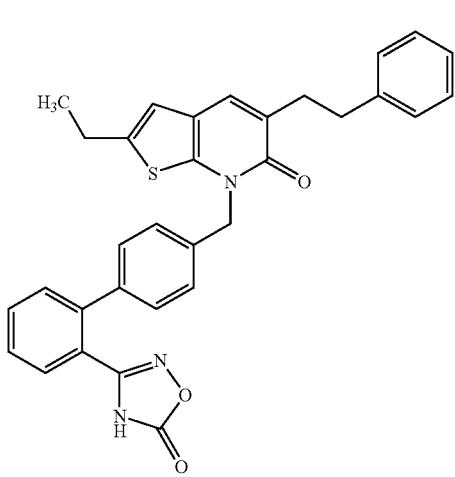 [SMILES: CCc1cc2cc(CCc3ccccc3)c(=O)n(Cc3ccc(-c4ccccc4-c4noc(=O)[nH]4)cc3)c2s1]

A mixture of hydroxylammonium chloride (0.41 g), sodium hydrogencarbonate (0.6 g) and dimethyl sulfoxide (20 mL) was stirred at 40° C. for 30 min, 4'-{[2-ethyl-6-oxo-5-(2-phenylethyl)thieno[2,3-b]pyridin-7(6H)-yl]methyl}biphenyl-2-carbonitrile (0.34 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (40 mL), N,N'-carbonyldiimidazole (0.13 g) and then 1,8-diazabicyclo[5.4.0]undec-7-ene (0.11 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was recrystallized from tetrahydrofuran to give the title compound as colorless crystals (0.23 g, 55%).

$^1$H NMR (300 MHz, DMSO-d$_6$)δ1.20 (3H, t, J=7.4), 2.66-3.04 (6H, m), 5.37 (2H, s), 6.87 (1H, s), 7.11-7.37 (9H, m), 7.55 (2H, dd, J=16.1, 7.8), 7.62-7.81 (3H, m), 12.42 (1H, s)

Example 172

2-ethyl-4-methyl-7-{[2'-(5-oxo-4,5-dihydro-1,2,4-oxadiazol-3-yl)biphenyl-4-yl]methyl}-5-(2-phenylethyl)thieno[2,3-b]pyridin-6(7H)-one

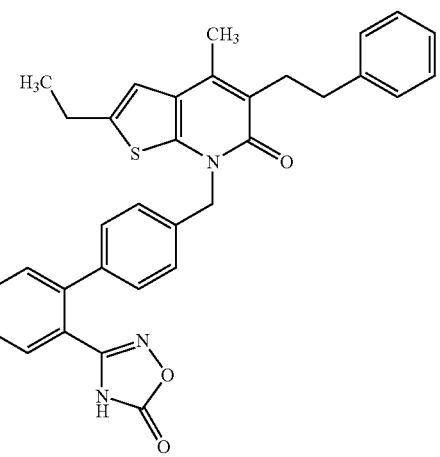

A mixture of hydroxylammonium chloride (1.62 g), sodium hydrogencarbonate (2.36 g) and dimethyl sulfoxide (20 mL) was stirred at 40° C. for 30 min, 4'-{[2-ethyl-4-methyl-6-oxo-5-(2-phenylethyl)thieno[2,3-b]pyridin-7(6H)-yl]methyl}biphenyl-2-carbonitrile (0.69 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (50 mL), N,N'-carbonyldiimidazole (0.25 g) and then 1,8-diazabicyclo[5.4.0]undec-7-ene (0.21 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.28 g, 67%).

$^1$H NMR (300 MHz, DMSO-d$_6$)δ1.22 (3H, t, J=7.4), 2.22 (3H, s), 2.69-2.83 (4H, m), 2.82-2.93 (2H, m), 5.35 (2H, s), 7.01 (1H, s), 7.13-7.35 (9H, m), 7.45-7.62 (2H, m), 7.61-7.75 (2H, m), 12.41 (1H, s)

Example 173

1-{[2'-(5-oxo-4,5-dihydro-1,2,4-oxadiazol-3-yl)biphenyl-4-yl]methyl}-3-(2-phenylethyl)-6-vinylquinazoline-2,4(1H,3H)-dione

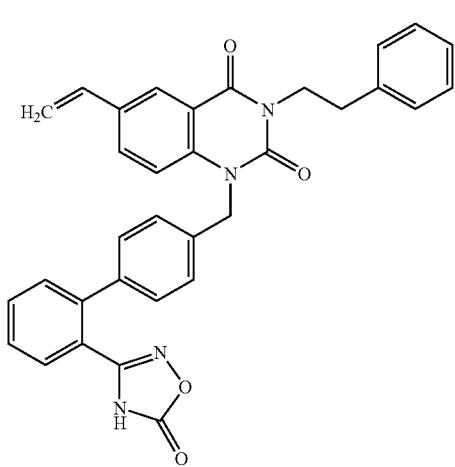 [SMILES: C=Cc1ccc2c(c1)c(=O)n(CCc1ccccc1)c(=O)n2Cc1ccc(-c2ccccc2-c2noc(=O)[nH]2)cc1]

A mixture of 3-(2-phenylethyl)-6-vinylquinazoline-2,4(1H,3H)-dione (0.40 g), 3-[4'-(bromomethyl)biphenyl-2-yl]-5-(trichloromethyl)-1,2,4-oxadiazole (0.65 g), potassium carbonate (0.38 g) and acetonitrile (16 mL) was stirred at 50° C. for 2 hr. Insoluble material was filtered off, and the solvent was evaporated under reduced pressure. The obtained residue was purified by silica gel column chromatography and dissolved in tetrahydrofuran (4 mL) and acetone (4 mL). 1N Aqueous sodium hydroxide solution (4 mL) was added, and the mixture was stirred at room temperature for 1 hr. The reaction mixture was adjusted to pH 4 with water and 1N hydrochloric acid, and extracted with chloroform. The obtained chloroform layer was washed with saturated brine, and dried over anhydrous magnesium sulfate. The solvent was evaporated under reduced pressure. The obtained residue was purified by silica gel column chromatography to give the title compound as a colorless solid (0.43 g, 57%).

$^1$H NMR (300 MHz, DMSO-$d_6$)δ2.97 (2H, t, J=7.5), 4.27 (2H, t, J=7.5), 5.29 (1H, d, J=11.4), 5.40 (2H, s), 5.86 (1H, d, J=17.4), 6.81 (1H, dd, J=11.4, 17.4), 7.19-7.31 (9H, m), 7.50-7.57 (3H, m), 7.60-7.72 (2H, m), 7.78-7.82 (1H, m), 8.09 (1H, s), 12.44 (1H, s)

Example 174

6-ethyl-1-{[2'-(5-oxo-4,5-dihydro-1,2,4-oxadiazol-3-yl)biphenyl-4-yl]methyl}-3-(2-phenylethyl)quinazoline-2,4(1H,3H)-dione

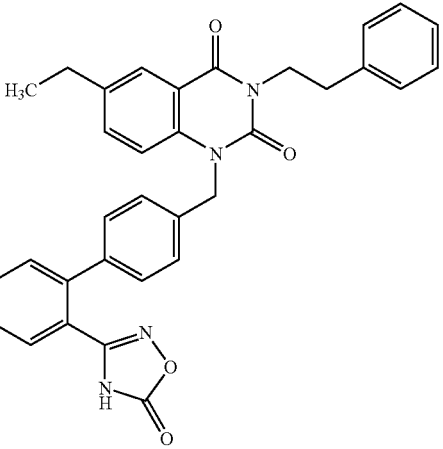

A mixture of 6-ethyl-3-(2-phenylethyl)quinazoline-2,4(1H,3H)-dione (0.40 g), 3-[4'-(bromomethyl)biphenyl-2-yl]-5-(trichloromethyl)-1,2,4-oxadiazole (0.65 g), potassium carbonate (0.38 g) and acetonitrile (16 mL) was stirred at 50° C. for 2 hr. Insoluble material was filtered off, and the solvent was evaporated under reduced pressure. The obtained residue was purified by silica gel column chromatography and dissolved in tetrahydrofuran (4 mL) and acetone (4 mL). 1N Aqueous sodium hydroxide solution (4 mL) was added, and the mixture was stirred at room temperature for 1 hr. The reaction mixture was adjusted to pH 4 with water and 1N hydrochloric acid, and extracted with chloroform. The obtained chloroform layer was washed with saturated brine, and dried over anhydrous magnesium sulfate. The solvent was evaporated under reduced pressure. The obtained residue was purified by silica gel column chromatography to give the title compound as a colorless solid (0.18 g, 24%).

$^1$H NMR (300 MHz, DMSO-$d_6$)δ1.18 (3H, t, J=7.8), 2.64 (2H, q, J=7.8), 2.97 (2H, t, J=8.1), 4.26 (2H, t, J=8.1), 5.37 (2H, s), 7.19-7.32 (10H, m), 7.50-7.60 (3H, m), 7.62-7.70 (2H, m), 7.90 (1H, s), 12.44 (1H, br)

Example 175

6-ethyl-3-[2-(4-fluorophenyl)ethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

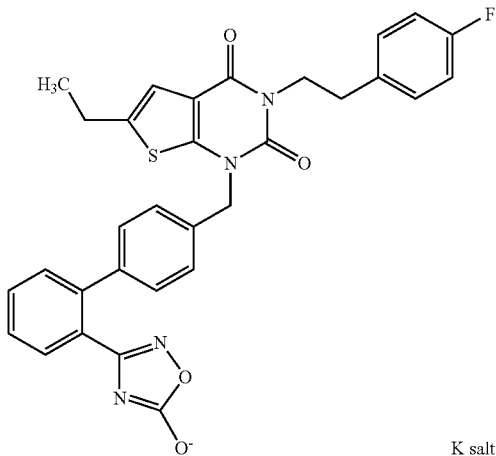 [SMILES: CCc1cc2c(=O)n(CCc3ccc(F)cc3)c(=O)n(Cc3ccc(-c4ccccc4-c4noc([O-])n4)cc3)c2s1 ; "K salt"]

A mixture of 6-ethyl-3-[2-(4-fluorophenyl)ethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.6 g), potassium 2-ethylhexanoate (0.23 g) and ethyl acetate (10 mL) was stirred at room temperature for 16 hr. The precipitated solid was collected by filtration to give the title compound as colorless crystals (0.39 g, 61%).

$^1$H NMR (300 MHz, DMSO-d$_6$)δ1.18 (3H, t, J=8.1), 2.72 (2H, q, J=8.1), 2.88 (2H, t, J=8.1), 4.13 (2H, t, J=8.1), 5.09 (2H, s),6.96 (1H, s), 7.06-7.77 (12H, m)

Example 176

2-[6-ethyl-1-{[3-fluoro-2'-(5-oxo-4,5-dihydro-1,2,4-oxadiazol-3-yl)biphenyl-4-yl]methyl}-2,4-dioxo-1,4-dihydrothieno[2,3-d]pyrimidin-3(2H)-yl]-1-(4-methoxyphenyl)ethyl acetate potassium salt

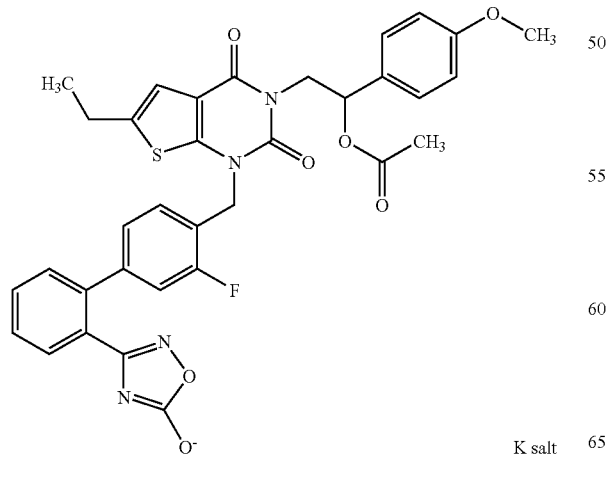

A mixture of 2-[6-ethyl-1-{[3-fluoro-2'-(5-oxo-4,5-dihydro-1,2,4-oxadiazol-3-yl)biphenyl-4-yl]methyl}-2,4-dioxo-1,4-dihydrothieno[2,3-d]pyrimidin-3(2H)-yl]-1-(4-methoxyphenyl)ethyl acetate (0.1 g), potassium 2-ethylhexanoate (0.033 g) and ethyl acetate (20 mL) was stirred at room temperature for 16 hr. The precipitated solid was collected by filtration to give the title compound as a colorless amorphous solid (0.071 g, 71%).

$^1$H NMR (300 MHz, DMSO-d$_6$)δ1.21 (3H, t, J=7.3), 1.89 (3H, s), 2.76 (2H, q, J=7.1), 3.74 (3H, s), 4.06 (1H, d, J=12.4), 4.41-4.56(1H, m), 5.07-5.28 (2H, m), 6.01-6.19 (1H, m), 6.90-7.21 (6H, m), 7.26-7.58(6H, m)

Example 177

6-ethyl-1-{[3-fluoro-2'-(5-oxo-4,5-dihydro-1,2,4-oxadiazol-3-yl)biphenyl-4-yl]methyl}-3-[2-hydroxy-2-(4-methoxyphenyl)ethyl]thieno[2,3-d]pyrimidine-2,4(1H,3H)-dione potassium salt

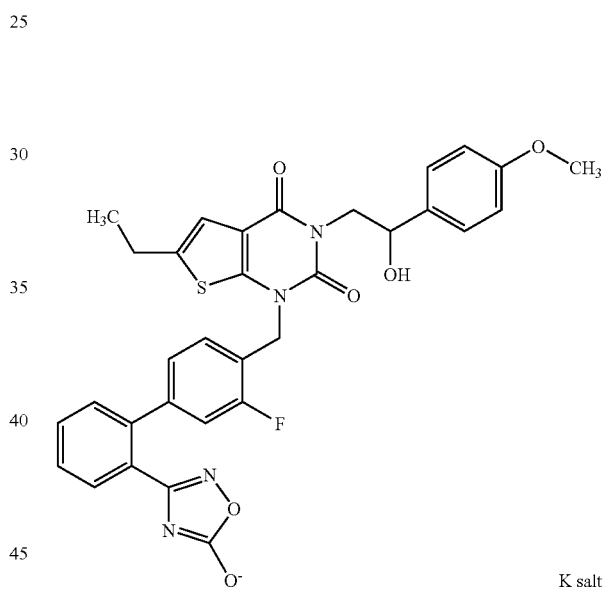

A mixture of 6-ethyl-1-{[3-fluoro-2'-(5-oxo-4,5-dihydro-1,2,4-oxadiazol-3-yl)biphenyl-4-yl]methyl}-3-[2-hydroxy-2-(4-methoxyphenyl)ethyl]thieno[2,3-d]pyrimidine-2,4(1H,3H)-dione (0.1 g), potassium 2-ethylhexanoate (0.036 g) and ethyl acetate (20 mL) was stirred at room temperature for 16 hr. The precipitated solid was collected by filtration to give the title compound as a colorless amorphous solid (0.070 g, 70%).

$^1$H NMR (300 MHz, DMSO-d$_6$)δ1.20 (3H, t, J=7.5), 2.75 (2H, q, J=7.3), 3.71 (3H, s), 3.92 (1H, dd, J=12.8, 5.1), 4.21 (1H, dd, J=12.7, 8.6), 4.90-5.01 (1H, m), 5.08-5.31 (2H, m), 5.41 (1H, d, J=4.5), 6.88(2H, d, J=8.5), 6.96-7.21 (4H, m), 7.26 (2H, d, J=8.5), 7.31-7.50 (3H, m),7.54 (1H, dd, J=7.3, 1.4)

Example 178

6-ethyl-3-[2-(3-fluoro-4-methoxyphenyl)-2-oxoethyl]-1-{[3-fluoro-2'-(5-oxo-4,5-dihydro-1,2,4-oxadiazol-3-yl)biphenyl-4-yl]methyl}thieno[2,3-d]pyrimidine-2,4(1H,3H)-dione potassium salt

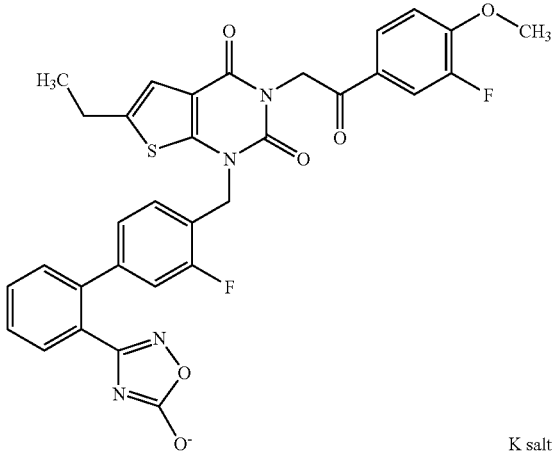

K salt

A mixture of 6-ethyl-3-[2-(3-fluoro-4-methoxyphenyl)-2-oxoethyl]-1-{[3-fluoro-2'-(5-oxo-4,5-dihydro-1,2,4-oxadiazol-3-yl)biphenyl-4-yl]methyl}thieno[2,3-d]pyrimidine-2,4(1H,3H)-dione (0.1 g), potassium 2-ethylhexanoate (0.035 g), tetrahydrofuran (5 mL) and ethyl acetate (5 mL) was stirred at room temperature for 16 hr. The precipitated solid was collected by filtration to give the title compound as a colorless amorphous solid (0.076 g, 70%).

$^1$H NMR (300 MHz, DMSO-$d_6$)δ1.22 (3H, t, J=7.5), 2.79 (2H, q, J=7.5), 3.96 (3H, s), 5.23 (2H, s), 5.42 (2H, s), 7.04 (1H, s),7.10-7.21 (3H, m), 7.32-7.47 (4H, m), 7.53 (1H, dd, J=7.3, 1.8), 7.89-8.03(2H, m)

Example 179

6-cyclopropyl-3-(2-hydroxy-3,3-dimethylbutyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

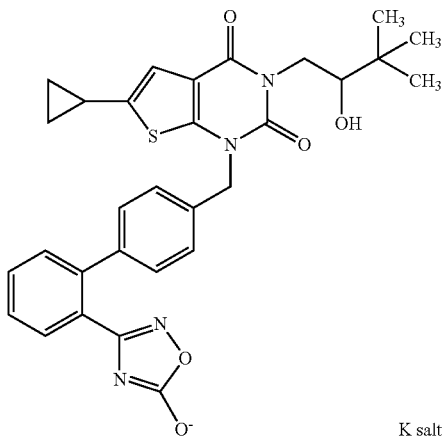 [SMILES: CC(C)(C)C(O)Cn1c(=O)c2cc(C3CC3)sc2n(Cc2ccc(-c3ccccc3-c3noc([O-])n3)cc2)c1=O ; "K salt"]

K salt

A mixture of 6-cyclopropyl-3-(2-hydroxy-3,3-dimethylbutyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.22 g), potassium 2-ethylhexanoate (0.086 g) and ethyl acetate (2 mL) was stirred at room temperature for 3 hr. The precipitated solid was collected by filtration to give the title compound as colorless crystals (0.20 g, 87%).

$^1$H NMR (300 MHz, DMSO-$d_6$)δ0.66-0.73 (2H, m), 0.92 (9H,s), 0.93-0.98 (2H, m), 2.01-2.14 (1H, m), 3.49-3.57 (1H, m), 3.77 (1H, dd, J=12.81, 2.26), 4.20 (1H, dd, J=12.8, 10.2), 4.59 (1H, d, J=5.7), 5.03-5.20(2H, m), 6.91 (1H, d, J=0.94), 7.26-7.55 (8H, m)

Example 180

6-ethyl-1-{[3-fluoro-2'-(5-oxo-4,5-dihydro-1,2,4-oxadiazol-3-yl)biphenyl-4-yl]methyl}-3-(4-isopropoxyphenyl)thieno[2,3-d]pyrimidine-2,4(1H,3H)-dione

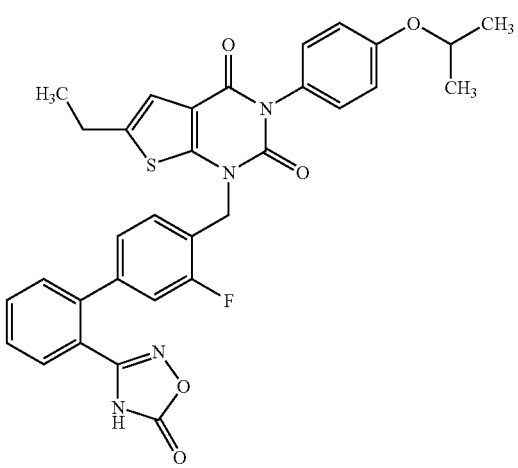 [SMILES: CCc1cc2c(=O)n(-c3ccc(OC(C)C)cc3)c(=O)n(Cc3ccc(-c4ccccc4-c4noc(=O)[nH]4)cc3F)c2s1]

A mixture of hydroxylammonium chloride (1.1 g), sodium hydrogencarbonate (1.6 g) and dimethyl sulfoxide (10 mL) was stirred at 40° C. for 30 min, 4'-{[6-ethyl-3-(4-isopropoxyphenyl)-2,4-dioxo-3,4-dihydrothieno[2,3-d]pyrimidin-1(2H)-yl]methyl}-3'-fluorobiphenyl-2-carbonitrile (0.5 g) was added, and the mixture was stirred at 90° C. for 16 hr. To the reaction mixture was added water, and the precipitated solid was collected by filtration, washed with water, and dried under reduced pressure. The solid was dissolved in tetrahydrofuran (10 mL), N,N'-carbonyldiimidazole (0.23 g) and then 1,8-diazabicyclo[5.4.0]undec-7-ene (0.21 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as a pale-yellow solid (0.37 g, 68%).

$^1$H NMR (300 MHz, DMSO-$d_6$)δ1.21 (3H, t, J=7.2), 1.30 (6H, d, J=6.0), 2.77 (2H, q, J=7.2), 4.57-4.72 (1H, m), 5.23 (2H, s),6.92-7.06 (3H, m), 7.08-7.14 (1H, m), 7.15-7.30 (3H, m), 7.40-7.49 (1H, m),7.52-7.65 (2H, m), 7.66-7.76 (2H, m), 12.48 (1H, br)

Example 181

3-(2,2-dimethyl-2,3-dihydro-1-benzofuran-5-yl)-6-ethyl-1-{[3-fluoro-2'-(5-oxo-4,5-dihydro-1,2,4-oxadiazol-3-yl)biphenyl-4-yl]methyl}thieno[2,3-d]pyrimidine-2,4(1H,3H)-dione

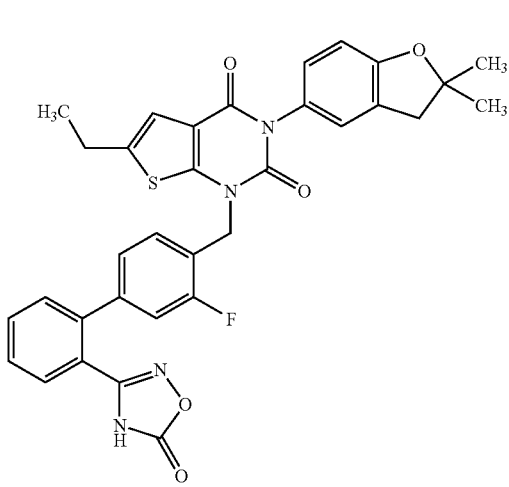 [SMILES: CCc1cc2c(=O)n(-c3ccc4c(c3)CC(C)(C)O4)c(=O)n(Cc3ccc(-c4ccccc4-c4noc(=O)[nH]4)cc3F)c2s1]

A mixture of hydroxylammonium chloride (1.2 g), sodium hydrogencarbonate (1.6 g) and dimethyl sulfoxide (10 mL) was stirred at 40° C. for 30 min, 4'-{[3-(2,2-dimethyl-2,3-dihydro-1-benzofuran-5-yl)-6-ethyl-2,4-dioxo-3,4-dihydrothieno[2,3-d]pyrimidin-1(2H)-yl]methyl}-3'-fluorobiphenyl-2-carbonitrile (0.54 g) was added, and the mixture was stirred at 90° C. for 16 hr. To the reaction mixture was added water, and the precipitated solid was collected by filtration, washed with water, and dried under reduced pressure. The solid was dissolved in tetrahydrofuran (10 mL), N,N'-carbonyldiimidazole (0.24 g) and then 1,8-diazabicyclo[5.4.0]undec-7-ene (0.22 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as a pale-yellow solid (0.43 g, 72%).

$^1$H NMR (300 MHz, DMSO-$d_6$)δ1.21 (3H, t, J=7.2), 1.45 (6H, s), 2.77 (2H, q, J=7.2), 3.05 (2H, s), 5.23 (2H, s), 6.76 (1H, d, J=8.1), 6.96-7.06 (2H, m), 7.07-7.15 (2H, m), 7.22-7.30 (1H, m), 7.39-7.48 (1H, m), 7.52-7.65 (2H, m), 7.66-7.76 (2H, m), 12.47 (1H, br)

Example 182

3-[2-(4-methoxyphenyl)-2-oxoethyl]-1-{[2'-(5-oxo-4,5-dihydro-1,2,4-oxadiazol-3-yl)biphenyl-4-yl]methyl}-6-propylpyrimidine-2,4(1H,3H)-dione

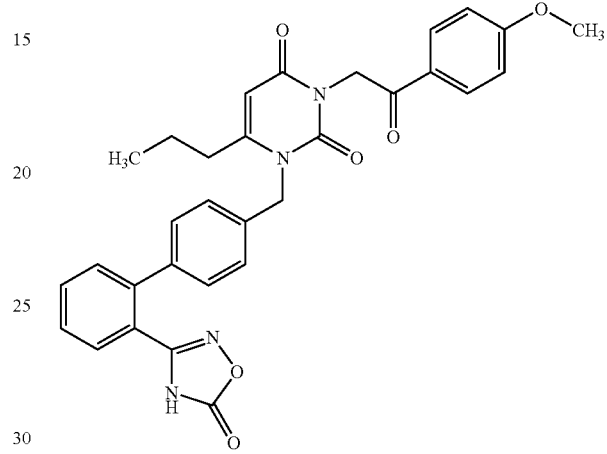

A mixture of hydroxylammonium chloride (0.89 g), sodium hydrogencarbonate (1.29 g) and dimethyl sulfoxide (20 mL) was stirred at 40° C. for 30 min, 4'-{[3-[2-(4-methoxyphenyl)-2-oxoethyl]-2,4-dioxo-6-propyl-3,4-dihydropyrimidin-1(2H)-yl]methyl}biphenyl-2-carbonitrile (0.63 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (30 mL), N,N'-carbonyldiimidazole (0.21 g) and then 1,8-diazabicyclo[5.4.0]undec-7-ene (0.18 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as a colorless amorphous solid (0.43 g, 60%).

$^1$H NMR (300 MHz, DMSO-$d_6$)δ0.88 (3H, t, J=6.9), 1.49 (2H, q, J=6.9), 2.40-2.48 (2H, m), 3.85 (3H, s), 5.18 (2H, s), 5.30 (2H, s),5.72 (1H, s), 7.07 (2H, d, J=8.7), 7.27 (4H, dd, J=22.5, 8.4), 7.51-7.58(2H, m), 7.64-7.71 (2H, m), 8.03 (2H, d, J=9.0), 12.4 (1H, s)

Example 183

3-[2-(4-methoxyphenyl)-2-oxoethyl]-1-{[2'-(5-oxo-4,5-dihydro-1,2,4-oxadiazol-3-yl)biphenyl-4-yl]methyl}-6-propoxypyrimidine-2,4(1H,3H)-dione

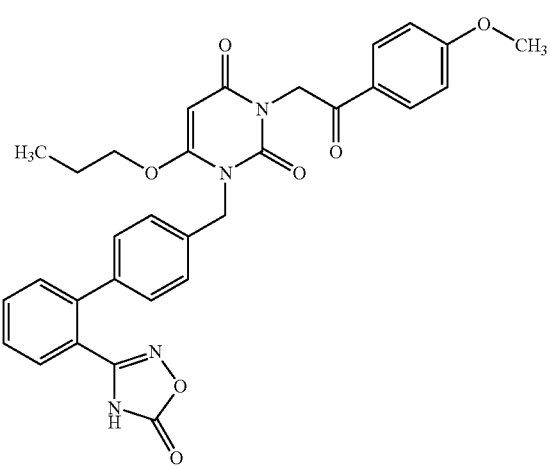 [SMILES: CCCOc1cc(=O)n(CC(=O)c2ccc(OC)cc2)c(=O)n1Cc1ccc(-c2ccccc2-c2noc(=O)[nH]2)cc1]

A mixture of hydroxylammonium chloride (0.95 g), sodium hydrogencarbonate (1.38 g) and dimethyl sulfoxide (20 mL) was stirred at 40° C. for 30 min, 4'-{[3-[2-(4-methoxyphenyl)-2-oxoethyl]-2,4-dioxo-6-propoxy-3,4-dihydropyrimidin-1(2H)-yl]methyl}biphenyl-2-carbonitrile (0.7 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (20 mL), N,N'-carbonyldiimidazole (0.25 g) and then 1,8-diazabicyclo[5.4.0]undec-7-ene (0.21 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as a colorless amorphous solid (0.2 g, 26%).

$^1$H NMR (300 MHz, DMSO-$d_6$)δ0.84 (3H, t, J=7.4), 1.67 (2H, q, J=7.4), 3.87 (3H, s), 3.99-4.12 (2H, m), 5.08 (2H, s), 5.29 (2H, s),5.35 (1H, s), 7.10 (2H, d, J=9.0), 7.32 (4H, s), 7.49-7.60 (2H, m), 7.65-7.78(2H, m), 7.95-8.12 (2H, m)

Example 184

3-[2-(4-methoxyphenyl)-2-oxoethyl]-1-{[2'-(5-oxo-4,5-dihydro-1,2,4-oxadiazol-3-yl)biphenyl-4-yl]methyl}-6-(2,2,2-trifluoroethoxy)pyrimidine-2,4(1H,3H)-dione

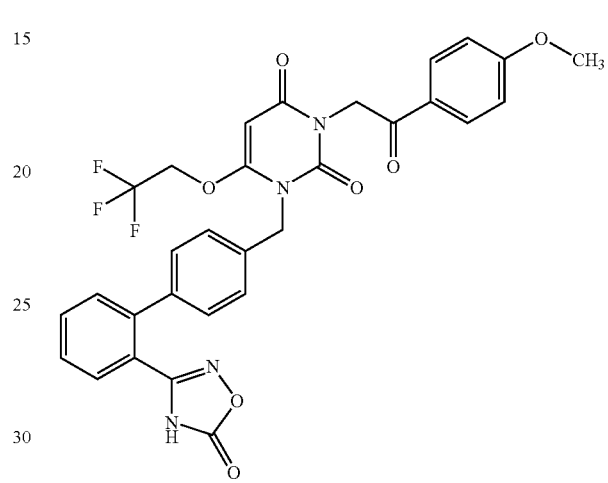

A mixture of hydroxylammonium chloride (0.74 g), sodium hydrogencarbonate (1.08 g) and dimethyl sulfoxide (20 mL) was stirred at 40° C. for 30 min, 4'-{[3-[2-(4-methoxyphenyl)-2-oxoethyl]-2,4-dioxo-6-(2,2,2-trifluoroethoxy)-3,4-dihydropyrimidin-1(2H)-yl]methyl}biphenyl-2-carbonitrile (0.59 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue obtained by silica gel column chromatography was dissolved in methylene chloride (20 mL), N,N'-carbonyldiimidazole (0.022 g) and then 1,8-diazabicyclo[5.4.0]undec-7-ene (0.019 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as a colorless amorphous solid (0.04 g, 6%).

$^1$H NMR (300 MHz, CDCl$_3$)δ3.90 (3H, s), 4.37 (2H, q, J=7.7), 5.12 (2H, s), 5.34 (3H, s), 6.97 (2H, d, J=8.9), 7.17 (2H, d, J=8.1), 7.36 (3H, d, J=7.9), 7.41-7.52 (1H, m), 7.55-7.62 (1H, m), 7.77 (1H, d, J=6.6), 7.96 (2H, d, J=8.9)

Example 185

1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]-6-propoxypyrimidine-2,4(1H,3H)-dione

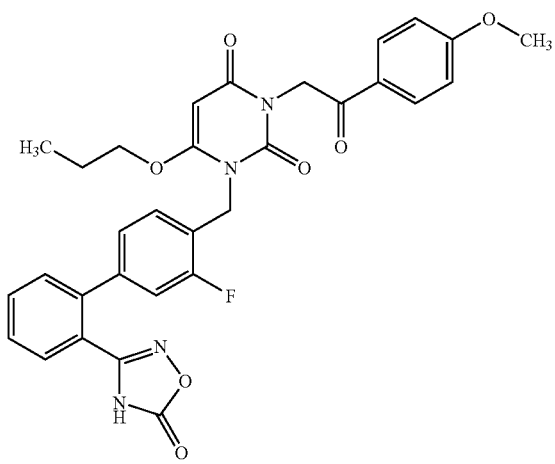 [SMILES: CCCOc1cc(=O)n(CC(=O)c2ccc(OC)cc2)c(=O)n1Cc1ccc(-c2ccccc2-c2noc(=O)[nH]2)cc1F]

A mixture of hydroxylammonium chloride (0.89 g), sodium hydrogencarbonate (1.44 g) and dimethyl sulfoxide (20 mL) was stirred at 40° C. for 30 min, 3'-fluoro-4'-{[3-[2-(4-methoxyphenyl)-2-oxoethyl]-2,4-dioxo-6-propoxy-3,4-dihydropyrimidin-1(2H)-yl]methyl}biphenyl-2-carbonitrile (0.45 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The obtained residue was dissolved in methylene chloride (20 mL), N,N'-carbonyldiimidazole (0.17 g) and then 1,8-diazabicyclo[5.4.0]undec-7-ene (0.14 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as a colorless amorphous solid (0.15 g, 30%).

$^1$H NMR (300 MHz, DMSO-$d_6$)δ0.83 (3H, t, J=7.5), 1.58-1.70 (2H, m), 3.87 (3H, s), 4.02-4.08 (2H, m), 5.15 (2H, s), 5.29 (2H, s), 5.37 (1H, s), 7.02-7.29 (5H, m), 7.50-7.64 (2H, m), 7.67-7.79 (2H, m), 8.05(2H, d, J=8.9), 12.49 (1H, br)

Example 186

6-cyclopropyl-3-(3,3-dimethyl-2-oxobutyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione A mixture of hydroxylammonium chloride (0.87 g), sodium hydrogencarbonate (1.32 g) and dimethyl sulfoxide (8 mL) was stirred at 50° C. for 30 min, 4'-{[6-cyclopropyl-3-(3,3-dimethyl-2-oxobutyl)-2,4-dioxo-3,4-dihydrothieno[2,3-d]pyrimidin-1(2H)-yl]methyl}biphenyl-2-carbonitrile (0.76 g) was added, and the mixture was stirred at 90° C. for 20 hr. After allowing to cool to room temperature, ethyl acetate and water were added to the reaction mixture, and the mixture was extracted with ethyl acetate. The organic layer was washed successively with water and saturated brine, and dried over anhydrous magnesium sulfate. The solvent was evaporated under reduced pressure. The residue was purified by silica gel column chromatography and dissolved in tetrahydrofuran (8 mL). N,N'-Carbonyldiimidazole (0.31 g) and then 1,8-diazabicyclo[5.4.0]undec-7-ene (0.28 mL) were added, and the mixture was stirred at room temperature for 2 hr. The reaction mixture was diluted with ethyl acetate, washed successively with 1N hydrochloric acid and saturated brine, and dried over anhydrous magnesium sulfate. The solvent was evaporated under reduced pressure. The residue was purified by silica gel column chromatography to give the title compound as a colorless solid (0.63 g, 72%).

$^1$H NMR (300 MHz, CDCl$_3$)δ0.66-0.77 (2H, m), 0.92-1.02 (2H,m), 1.27 (9H, s), 1.80-2.15 (1H, m), 5.02 (2H, s), 5.16 (2H, s), 6.92 (1H, s),7.31-7.90 (8H, m)

Example 187

1-{[3-butyl-2'-(5-oxo-4,5-dihydro-1,2,4-oxadiazol-3-yl)biphenyl-4-yl]methyl}-6-ethyl-3-[2-(4-methoxyphenyl)-2-oxoethyl]thieno[2,3-d]pyrimidine-2,4(1H,3H)-dione

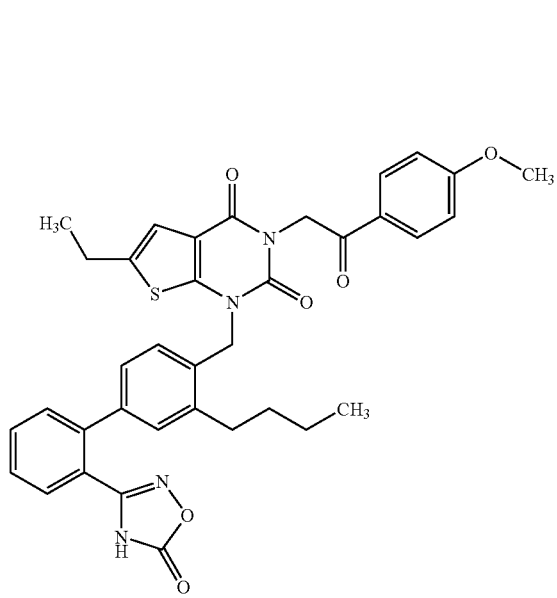 [SMILES: CCCCc1cc(-c2ccccc2-c2noc(=O)[nH]2)ccc1Cn1c(=O)n(CC(=O)c2ccc(OC)cc2)c(=O)c2cc(CC)sc21]

A mixture of hydroxylammonium chloride (0.71 g), sodium hydrogencarbonate (1.07 g) and dimethyl sulfoxide (10 mL) was stirred at 40° C. for 30 min, 3'-butyl-4'-{[6-ethyl-3-[2-(4-methoxyphenyl)-2-oxoethyl]-2,4-dioxo-3,4-dihydrothieno[2,3-d]pyrimidin-1(2H)-yl]methyl}biphenyl-2-carbonitrile (0.75 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (40 mL). N,N'-Carbonyldiimidazole (0.21 g) and then 1,8-diazabicyclo[5.4.0]undec-7-ene (0.17 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.26 g, 32%).

$^1$H NMR (300 MHz, DMSO-$d_6$)δ0.91 (3H, t, J=7.2), 1.19 (3H, t, J=7.2), 1.29-1.36 (2H, m), 1.50-1.54 (2H, m), 2.67-2.79 (4H, m), 3.86 (3H, s), 5.25 (2H, s), 5.42 (2H, s), 6.99-7.19 (2H, m), 7.54 (2H, t, J=7.5), 7.63-7.69 (2H, m), 8.07(2H, d, J=9.0), 12.47 (1H, s)

Example 188

6-ethyl-3-[2-(4-fluorophenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

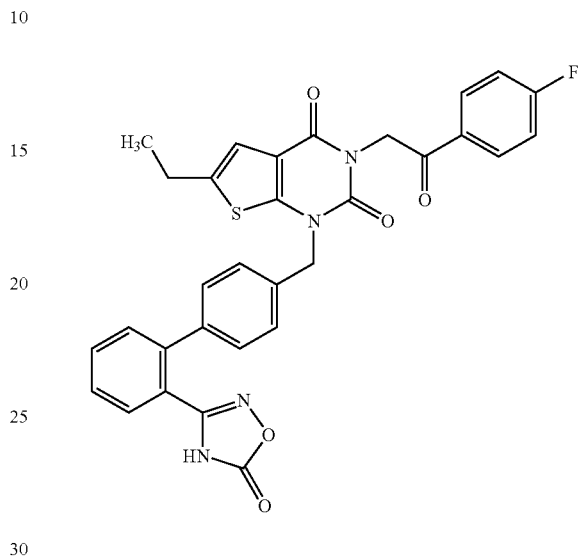

4'-{[6-Ethyl-3-[2-(4-fluorophenyl)-2-oxoethyl]-2,4-dioxo-3,4-dihydrothieno[2,3-d]pyrimidin-1(2H)-yl]methyl}biphenyl-2-carbonitrile (0.70 g) was dissolved in dimethyl sulfoxide (5 mL), and the mixture was added to a mixture of hydroxylammonium chloride (0.93 g), sodium hydrogencarbonate (1.30 g) and dimethyl sulfoxide (10 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography, dissolved in tetrahydrofuran (10 mL), N,N'-carbonyldiimidazole (0.26 g) and then 1,8-diazabicyclo[5.4.0]undec-7-ene (0.39 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was dissolved in methylene chloride (10 mL), HIO$_3$ (0.44 g) was added and the mixture was stirred at room temperature overnight. Activated carbon was added to the reaction mixture and the mixture was heated to 45° C. and filtered. The filtrate was concentrated, and purified by preparative HPLC to give the title compound as colorless crystals (0.078 g, 16%).

$^1$H NMR (300 MHz, DMSO-$d_6$)δ1.20 (3H, t, J=7.5), 2.75 (2H, q, J=7.5), 5.22 (2H, s), 5.46 (2H, s), 7.01 (1H, s), 7.30-7.45 (8H, m), 7.55 (2H, m), 7.67 (2H, m), 12.4 (1H, s)

311

Example 189

6-ethyl-3-[2-(4-fluorophenyl)-2-hydroxyethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

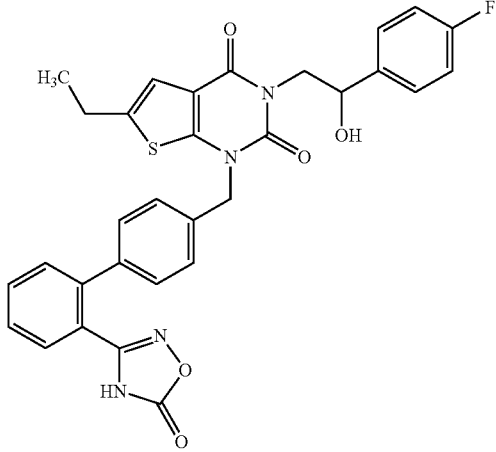 [SMILES: CCc1cc2c(=O)n(CC(O)c3ccc(F)cc3)c(=O)n(Cc3ccc(-c4ccccc4-c4noc(=O)[nH]4)cc3)c2s1]

To a solution of 6-ethyl-3-[2-(4-fluorophenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.5 g) in CHCl$_3$-methanol (1:1, 30 mL) was added NaBH$_4$ (0.039 g) at room temperature, and the mixture was stirred overnight. The reaction mixture was concentrated, water was added and the mixture was adjusted to pH 5-6 with 1N hydrochloric acid and water, extracted with ethyl acetate, and dried over anhydrous magnesium sulfate. The solvent was evaporated under reduced pressure. The residue was purified by silica gel column chromatography to give the object compound (0.50 g, 100%).

$^1$H NMR (300 MHz, DMSO-d$_6$)δ1.19 (3H, t, J=7.6), 2.73 (2H, d, J=7.6), 3.93-4.04 (1H, m, J=6.1), 4.15-4.27 (2H, m), 4.92-5.06 (1H,m), 5.10 (1H, s), 5.20 (1H, s), 6.99 (1H, s), 7.14 (2H, t, J=8.9), 7.24-7.33(4H, m), 7.33-7.40 (2H, m), 7.50-7.62 (2H, m), 7.64-7.75 (2H, m), 12.41 (1H, s)

312

Example 190

6-ethyl-3-[(6-fluoro-1,2-benzoisoxazol-3-yl)methyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

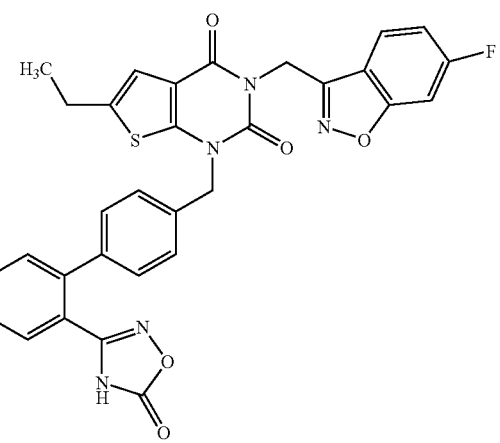

A mixture of 6-ethyl-1-({2'-[5-(trichloromethyl)-1,2,4-oxadiazol-3-yl]biphenyl-4-yl}methyl)thieno[2,3-d]pyrimidine-2,4(1H,3H)-dione (0.48 g), 3-(bromomethyl)-6-fluoro-1,2-benzoisoxazole (0.2 g), potassium carbonate (0.24 g) and acetonitrile (40 mL) was stirred at 50° C. for 2 hr. Insoluble material was filtered off, and the solvent was evaporated under reduced pressure. The obtained residue was purified by silica gel column chromatography and dissolved in tetrahydrofuran (10 mL) and acetone (10 mL). 1N Aqueous sodium hydroxide solution (4 mL) was added, and the mixture was stirred at room temperature for 1 hr. The reaction mixture was adjusted to pH 5 with water and 1N hydrochloric acid, and extracted with chloroform. The obtained chloroform layer was washed with saturated brine, and dried over anhydrous magnesium sulfate. The solvent was evaporated under reduced pressure. The residue was purified by silica gel column chromatography to give the title compound as a colorless amorphous solid (0.1 g, 19%).

$^1$H NMR (300 MHz, DMSO-d$_6$)δ1.19 (3H, t, J=7.5), 2.74 (2H, q, J=7.5), 5.21 (2H, s), 5.54 (2H, s), 7.03 (1H, s), 7.27-7.40 (5H, m),7.49-7.57 (2H, m), 7.64-7.43 (3H, m), 7.96 (1H, m)

Example 191

6-ethyl-1-{[3-methoxy-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione

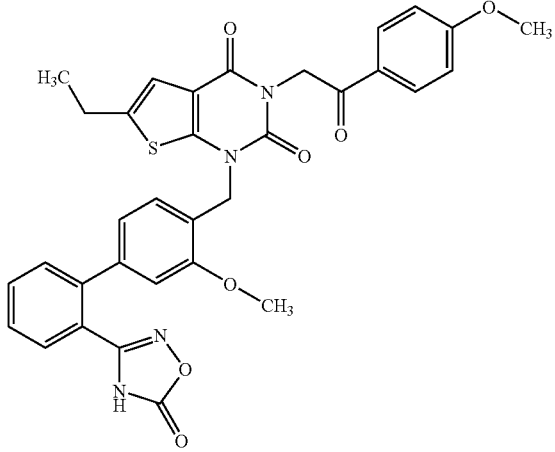 [SMILES: CCc1cc2c(=O)n(CC(=O)c3ccc(OC)cc3)c(=O)n(Cc3ccc(-c4ccccc4-c4noc(=O)[nH]4)cc3OC)c2s1]

A mixture of hydroxylammonium chloride (1.2 g), sodium hydrogencarbonate (1.8 g) and dimethyl sulfoxide (40 mL) was stirred at 40° C. for 30 min, 4'-{[6-ethyl-3-[2-(4-methoxyphenyl)-2-oxoethyl]-2,4-dioxo-3,4-dihydrothieno[2,3-d]pyrimidin-1(2H)-yl]methyl}-3'-methoxybiphenyl-2-carbonitrile (1.2 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.52 g) and then 1,8-diazabicyclo[5.4.0]undec-7-ene (0.48 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.95 g, 72%).

$^1$H NMR (300 MHz, DMSO-d$_6$)δ1.21 (3H, t, J=7.4), 2.76 (2H, q, J=7.4), 3.85 (3H, s), 3.88 (3H, s), 5.15 (2H, s), 5.41 (2H, s), 6.88(1H, dd, J=7.7, 1.5), 6.97-7.16 (5H, m), 7.53-7.76 (4H, m), 8.08 (2H, d, J=9.0), 12.40 (1H, s)

Example 192

6-ethyl-1-{[3-methoxy-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione potassium salt

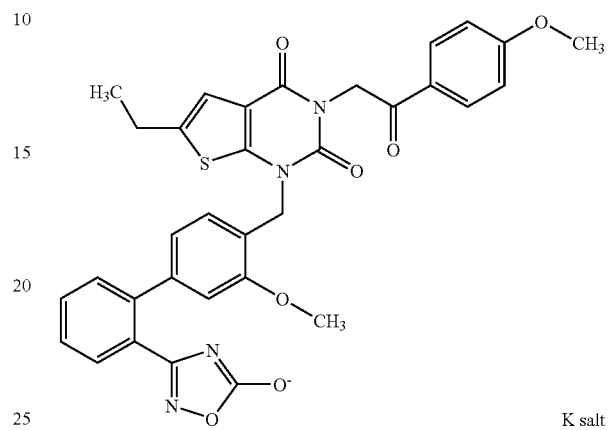

K salt

A mixture of 6-ethyl-1-{[3-methoxy-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione (0.95 g), potassium 2-ethylhexanoate (0.33 g) and ethyl acetate (20 mL) was stirred at room temperature for 16 hr. The precipitated solid was collected by filtration to give the title compound as colorless crystals (0.09 g, 9%).

$^1$H NMR (300 MHz, DMSO-d$_6$)δ1.22 (3H, t, J=7.4), 2.77 (2H, q, J=7.4), 3.78 (3H, s), 3.88 (3H, s), 5.10 (2H, s), 5.41 (2H, s),6.86-6.97 (2H, m), 7.02 (1H, s), 7.07-7.14 (3H, m), 7.33-7.49 (4H, m), 8.08(2H, d, J=9.0)

Example 193

1-{[3-bromo-2'-(5-oxo-4,5-dihydro-1,2,4-oxadiazol-3-yl)biphenyl-4-yl]methyl}-6-ethyl-3-[2-(4-methoxyphenyl)-2-oxoethyl]thieno[2,3-d]pyrimidine-2,4(1H,3H)-dione

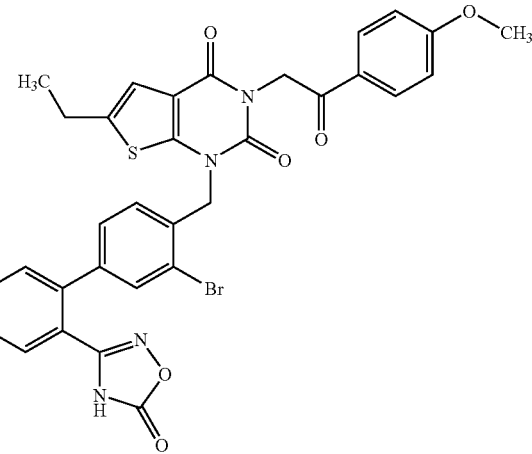

A mixture of 3'-bromo-4'-{[3-(2,4-dimethoxybenzyl)-6-ethyl-2,4-dioxo-3,4-dihydrothieno[2,3-d]pyrimidin-1(2H)-yl]methyl}biphenyl-2-carbonitrile (1.27 g) and trifluoroacetic acid (20 mL) was stirred at 50° C. for 2 hr. To the reaction mixture was added toluene (20 mL), and the mixture was concentrated under reduced pressure. The obtained residue was dissolved in N,N-dimethylformamide (30 mL), 2-bromo-1-(4-methoxyphenyl)ethanone (0.73 g) and sodium hydride (0.16 g) was added, and the mixture was stirred at room temperature for 16 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The precipitated solid was dissolved in dimethyl sulfoxide (5 mL), and the mixture was added to a mixture of hydroxylammonium chloride (0.9 g), sodium hydrogencarbonate (1.37 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.26 g) and then 1,8-diazabicyclo[5.4.0]undec-7-ene (0.22 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.41 g, 30%).

$^1$H NMR (300 MHz, DMSO-$d_6$)δ1.20 (3H, t, J=7.5),2.70-2.84 (2H, m), 3.88 (3H, s), 5.23 (2H, s), 5.43 (2H, s), 7.01-7.14 (4H, m),7.30 (1H, dd, J=7.9, 1.7), 7.43-7.68 (5H, m), 8.09 (2H, d, J=9.0)

Example 194

1-{[3-bromo-2'-(5-oxo-4,5-dihydro-1,2,4-oxadiazol-3-yl)biphenyl-4-yl]methyl}-6-ethyl-3-[2-(4-methoxyphenyl)-2-oxoethyl]thieno[2,3-d]pyrimidine-2,4(1H,3H)-dione potassium salt

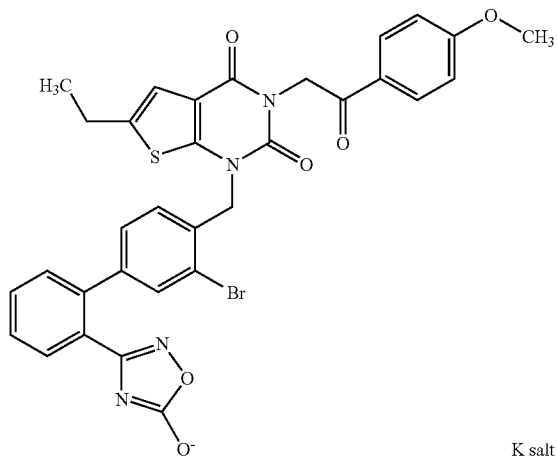

K salt

A mixture of 1-{[3-bromo-2'-(5-oxo-4,5-dihydro-1,2,4-oxadiazol-3-yl)biphenyl-4-yl]methyl}-6-ethyl-3-[2-(4-methoxyphenyl)-2-oxoethyl]thieno[2,3-d]pyrimidine-2,4(1H,3H)-dione (0.41 g), potassium 2-ethylhexanoate (0.13 g) and ethyl acetate (15 mL) was stirred at room temperature for 16 hr. The precipitated solid was collected by filtration to give the title compound as colorless crystals (0.31 g, 70%).

$^1$H NMR (300 MHz, DMSO-$d_6$)δ1.15-1.30 (3H, m), 2.77 (2H, q, J=7.3), 3.87 (3H, s), 5.20 (2H, s), 5.42 (2H, s), 6.93-7.18 (4H, m),7.21-7.50 (4H, m), 7.51-7.62 (2H, m), 8.09 (2H, d, J=8.7)

Example 195

6-ethyl-1-{[2-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione

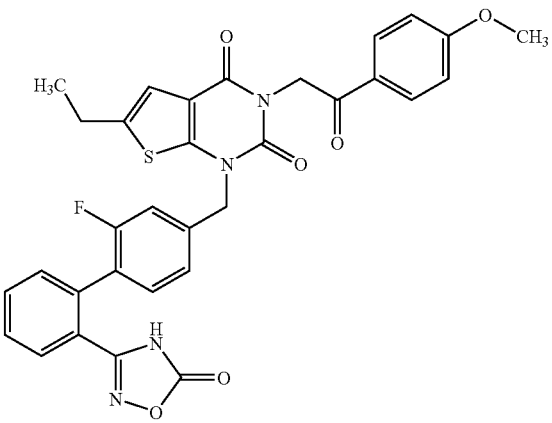 [SMILES: CCc1cc2c(=O)n(CC(=O)c3ccc(OC)cc3)c(=O)n(Cc3ccc(-c4ccccc4-c4noc(=O)[nH]4)c(F)c3)c2s1]

A mixture of hydroxylammonium chloride (1.8 g), sodium hydrogencarbonate (2.8 g) and dimethyl sulfoxide (40 mL) was stirred at 40° C. for 30 min, 4'-{[6-ethyl-3-[2-(4-methoxyphenyl)-2-oxoethyl]-2,4-dioxo-3,4-dihydrothieno[2,3-d]pyrimidin-1(2H)-yl]methyl}-2'-fluorobiphenyl-2-carbonitrile (1.8 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.31 g) and then 1,8-diazabicyclo[5.4.0]undec-7-ene (1 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.3 g, 39%).

$^1$H NMR (300 MHz, DMSO-$d_6$)δ1.22 (3H, t, J=7.9),2.74-2.83 (2H, m), 3.88 (3H, s), 5.25 (2H, s), 5.42 (2H, s), 7.04 (1H, s),7.11 (2H, d, J=9.0), 7.21-7.28 (2H, m), 7.39 (1H, t, J=8.0), 7.50-7.55 (1H,m), 7.60-7.76 (3H, m), 8.09 (2H, d, J=8.9), 12.6 (1H, s)

Example 196

6-ethyl-3-[2-(4-methoxyphenyl)-2-oxoethyl]-1-{[5'-methyl-2'-(5-oxo-4,5-dihydro-1,2,4-oxadiazol-3-yl)biphenyl-4-yl]methyl}thieno[2,3-d]pyrimidine-2,4(1H,3H)-dione

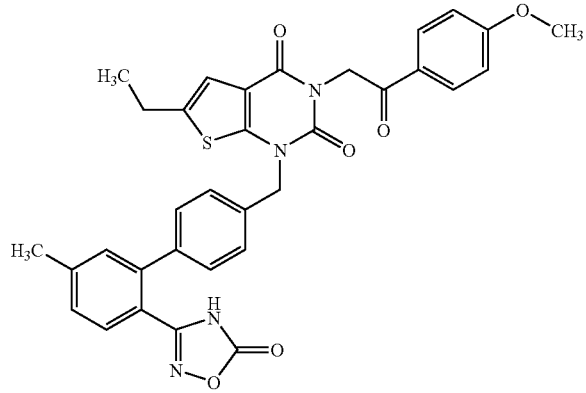

A mixture of hydroxylammonium chloride (2.2 g), sodium hydrogencarbonate (3.3 g) and dimethyl sulfoxide (40 mL) was stirred at 40° C. for 30 min, 4'-{[6-ethyl-3-[2-(4-methoxyphenyl)-2-oxoethyl]-2,4-dioxo-3,4-dihydrothieno[2,3-d]pyrimidin-1(2H)-yl]methyl}-5-methylbiphenyl-2-carbonitrile (2.2 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (1 g) and then 1,8-diazabicyclo[5.4.0]undec-7-ene (1 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (1.1 g, 45%).

$^1$H NMR (300 MHz, DMSO-$d_6$)δ1.22 (3H, t, J=7.4), 2.42 (3H, s), 2.77 (2H, q, J=7.4), 3.88 (3H, s), 5.23 (2H, s), 5.43 (2H, s), 7.03(1H, s), 7.11 (2H, d, J=8.9), 7.29-7.42 (6H, m), 7.55 (1H, d, J=7.7), 8.09(2H, d, J=8.9), 12.3 (1H, s)

Example 197

1-{[3,5-difluoro-2'-(5-oxo-4,5-dihydro-1,2,4-oxadiazol-3-yl)biphenyl-4-yl]methyl}-6-ethyl-3-[2-(4-methoxyphenyl)-2-oxoethyl]thieno[2,3-d]pyrimidine-2,4(1H,3H)-dione

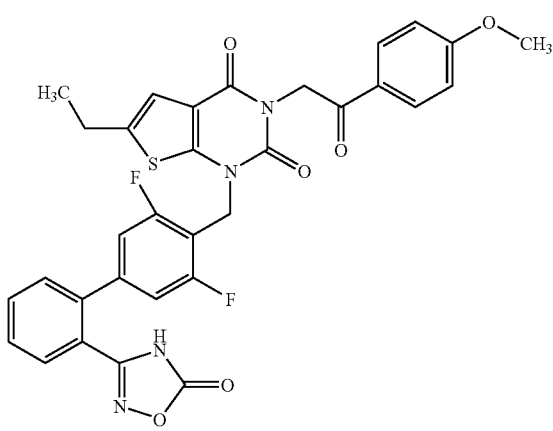 [SMILES: CCc1cc2c(=O)n(CC(=O)c3ccc(OC)cc3)c(=O)n(Cc3c(F)cc(-c4ccccc4-c4noc(=O)[nH]4)cc3F)c2s1]

A mixture of hydroxylammonium chloride (1.2 g), sodium hydrogencarbonate (1.7 g) and dimethyl sulfoxide (40 mL) was stirred at 40° C. for 30 min, 4'-{[6-ethyl-3-[2-(4-methoxyphenyl)-2-oxoethyl]-2,4-dioxo-3,4-dihydrothieno[2,3-d]pyrimidin-1(2H)-yl]methyl}-3',5'-difluorobiphenyl-2-carbonitrile (1.2 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.5 g) and then 1,8-diazabicyclo[5.4.0]undec-7-ene (0.47 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.71 g, 55%).

$^1$H NMR (300 MHz, DMSO-$d_6$)δ1.24 (3H, t, J=7.5),2.75-2.84 (2H, m), 3.88 (3H, s), 5.31 (2H, s), 5.37 (2H, s), 7.02 (1H, s),7.07-7.16 (4H, m), 7.56-7.76 (4H, m), 8.07 (2H, d, J=9.0), 12.54 (1H, s)

Example 198

6-ethyl-1-{[4'-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione

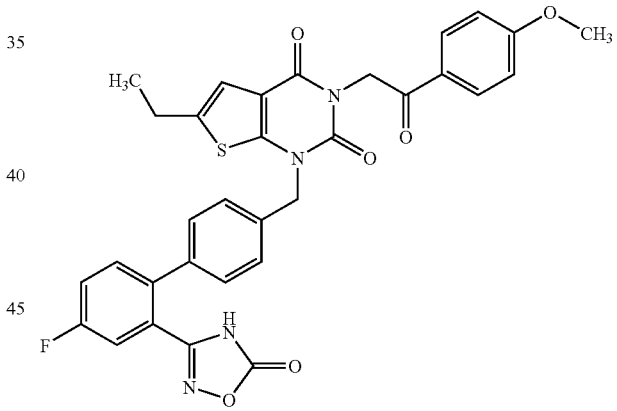

A mixture of hydroxylammonium chloride (2.4 g), sodium hydrogencarbonate (3.6 g) and dimethyl sulfoxide (40 mL) was stirred at 40° C. for 30 min, 4'-{[6-ethyl-3-[2-(4-methoxyphenyl)-2-oxoethyl]-2,4-dioxo-3,4-dihydrothieno[2,3-d]pyrimidin-1(2H)-yl]methyl}-4-fluorobiphenyl-2-carbonitrile (2.4 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (40 mL). N,N'-Carbonyldiimidazole (1.1 g) and then 1,8-diazabicyclo[5.4.0]undec-7-ene (0.99 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (1.5 g, 58%).

$^1$H NMR (300 MHz, DMSO-d$_6$)δ1.21 (3H, t, J=7.4), 2.77 (2H, q, J=7.4), 3.88 (3H, s), 5.23 (2H, s), 5.43 (2H, s), 7.03 (1H, s), 7.11(2H, d, J=8.9), 7.29-7.42 (4H, m), 7.55-7.65 (3H, m), 8.09 (2H, d, J=8.9),12.5 (1H, br)

Example 199

3-(2-cyclohexyl-2-oxoethyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione potassium salt

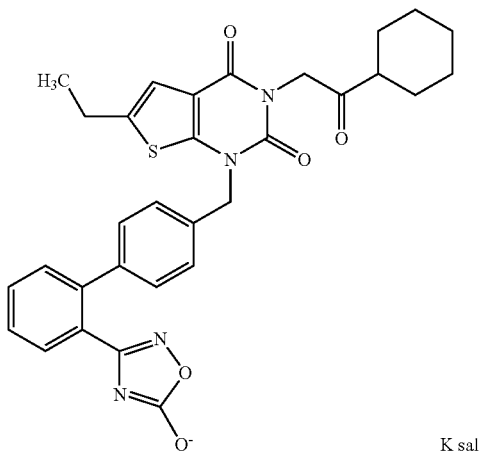

K salt

A mixture of 3-(2-cyclohexyl-2-oxoethyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.95 g), potassium 2-ethylhexanoate (0.33 g) and ethyl acetate (20 mL) was stirred at room temperature for 16 hr. The precipitated solid was collected by filtration to give the title compound as colorless crystals (0.093 g, 9%).

$^1$H NMR (300 MHz, DMSO-d$_6$)δ1.12-1.40 (8H, m), 1.56-1.95(5H, m), 2.56-2.68 (1H, m), 2.70-2.83 (2H, m), 4.87 (2H, s), 5.15 (2H, s), 6.99(1H, s), 7.21-7.53 (8H, m)

Example 200

1-{[3,5-difluoro-2'-(5-oxo-4,5-dihydro-1,2,4-oxadiazol-3-yl)biphenyl-4-yl]methyl}-6-ethyl-3-[2-(4-methoxyphenyl)-2-oxoethyl]thieno[2,3-d]pyrimidine-2,4(1H,3H)-dione potassium salt

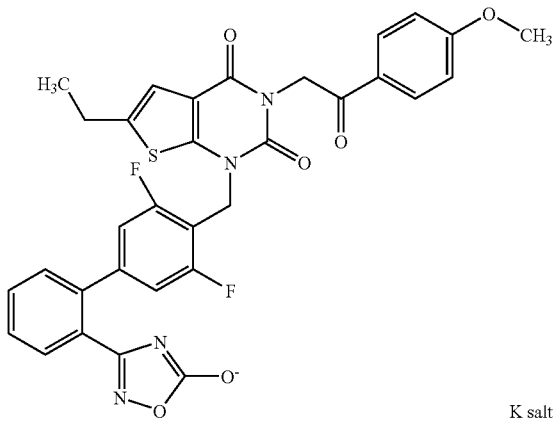 [SMILES: CCc1cc2c(=O)n(CC(=O)c3ccc(OC)cc3)c(=O)n(Cc3c(F)cc(-c4ccccc4-c4noc([O-])n4)cc3F)c2s1 ; "K salt"]

K salt

A mixture of 1-{[3,5-difluoro-2'-(5-oxo-4,5-dihydro-1,2,4-oxadiazol-3-yl)biphenyl-4-yl]methyl}-6-ethyl-3-[2-(4-methoxyphenyl)-2-oxoethyl]thieno[2,3-d]pyrimidine-2,4(1H,3H)-dione (0.46 g), potassium 2-ethylhexanoate (0.16 g), and ethyl acetate (20 mL) was stirred at room temperature for 16 hr. The precipitated solid was collected by filtration to give the title compound as colorless crystals (0.44 g, 90%).

$^1$H NMR (300 MHz, DMSO-d$_6$)δ1.24 (3H, t, J=7.4),2.73-2.86 (2H, m), 3.87 (3H, s), 5.26 (2H, s), 5.37 (2H, s), 6.99-7.14 (5H, m),7.34-7.50 (3H, m), 7.53-7.59 (1H, m), 8.07 (2H, d, J=8.9)

Example 201

6-ethyl-3-[2-(4-fluorophenyl)-2-hydroxypropyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

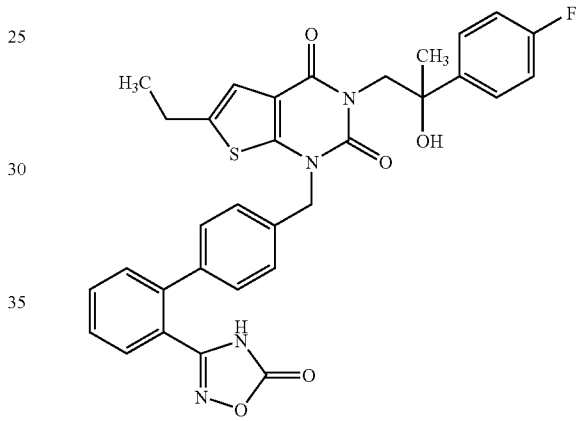

A mixture of hydroxylammonium chloride (1.9 g), sodium hydrogencarbonate (2.9 g) and dimethyl sulfoxide (40 mL) was stirred at 40° C. for 30 min, 4'-{[6-ethyl-3-[2-(4-fluorophenyl)-2-hydroxypropyl]-2,4-dioxo-3,4-dihydrothieno[2,3-d]pyrimidin-1(2H)-yl]methyl}biphenyl-2-carbonitrile (1.8 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (40 mL). N,N'-Carbonyldiimidazole (0.5 g) and then 1,8-diazabicyclo[5.4.0]undec-7-ene (0.47 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.5 g, 27%).

$^1$H NMR (300 MHz, DMSO-d$_6$)δ1.09 (3H, t, J=7.0), 1.47 (3H, s), 2.68-2.78 (2H, m), 4.19-4.34 (2H, m), 5.12 (2H, s), 5.30 (1H, s), 6.98(1H, s), 7.10 (2H, t, J=9.0), 7.23-7.33 (4H, m), 7.45-7.62 (4H, m), 7.65-7.74(2H, m), 12.42 (1H, s)

Example 202

6-ethyl-1-{[3'-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione

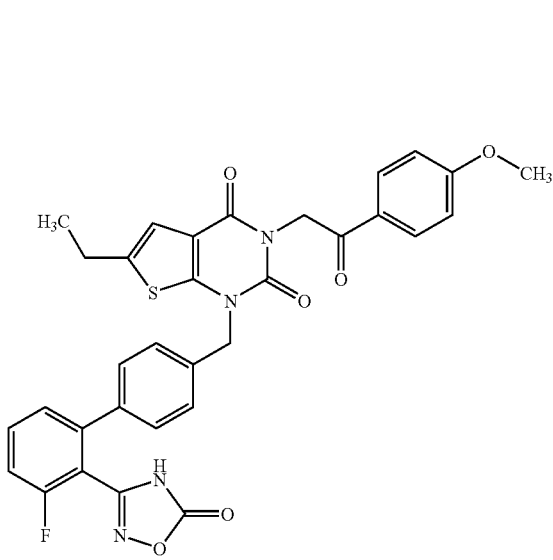 [SMILES: CCc1cc2c(=O)n(CC(=O)c3ccc(OC)cc3)c(=O)n(Cc3ccc(-c4cccc(F)c4-c4noc(=O)[nH]4)cc3)c2s1]

A mixture of hydroxylammonium chloride (1.8 g), sodium hydrogencarbonate (2.7 g) and dimethyl sulfoxide (40 mL) was stirred at 40° C. for 30 min, 4'-{[6-ethyl-3-[2-(4-methoxyphenyl)-2-oxoethyl]-2,4-dioxo-3,4-dihydrothieno[2,3-d]pyrimidin-1(2H)-yl]methyl}-3-fluorobiphenyl-2-carbonitrile (1.8 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (40 mL). N,N'-Carbonyldiimidazole (0.46 g) and then 1,8-diazabicyclo[5.4.0]undec-7-ene (0.44 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.6 g, 51%).

$^1$H NMR (300 MHz, DMSO-d$_6$)δ1.21 (3H, t, J=7.4), 2.77 (2H, q, J=7.4), 3.88 (3H, s), 5.2 (2H, s), 5.40 (2H, s), 7.00 (1H, s), 7.10(2H, d, J=8.9), 7.31-7.57 (6H, m), 7.72-7.83 (1H, m), 8.09 (2H, d, J=8.9),12.8 (1H, s)

Example 203

6-ethyl-1-{[5'-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione

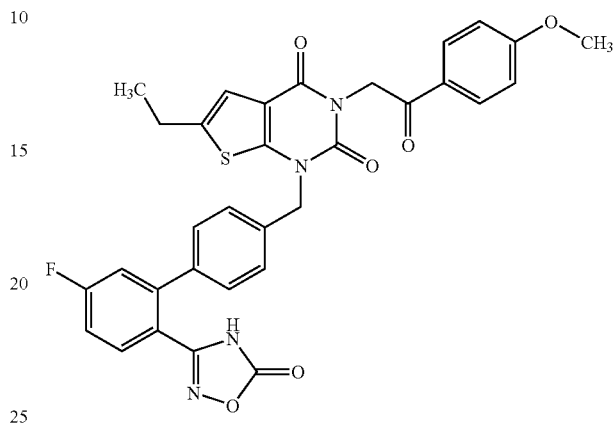

To a mixture of 4'-[(6-ethyl-2,4-dioxo-3,4-dihydrothieno[2,3-d]pyrimidin-1(2H)-yl)methyl]-5-fluorobiphenyl-2-carbonitrile (1.8 g), 2-bromo-1-(4-methoxyphenyl)ethanone (1.2 mL) and N,N-dimethylformamide (19 mL) was added sodium hydride (0.26 g), and the mixture was stirred at 50° C. for 3 hr. The reaction mixture was diluted with chloroform, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (40 mL), and the mixture was added to a mixture of hydroxylammonium chloride (1.8 g), sodium hydrogencarbonate (2.7 g) and dimethyl sulfoxide (40 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.39 g) and then 1,8-diazabicyclo[5.4.0]undec-7-ene (0.37 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.61 g, 62%).

$^1$H NMR (300 MHz, DMSO-d$_6$)δ1.22 (3H, t, J=7.5),2.70-2.83 (2H, m), 3.88 (3H, s), 5.24 (2H, s), 5.43 (2H, s), 7.03 (1H, s), 7.11(2H, d, J=9.0), 7.34-7.50 (6H, m), 7.75 (1H, dd, J=9.3, 5.8), 8.1 (2H, d, J=9.0), 12.4 (1H, s)

Example 204

6-ethyl-3-[2-(4-fluorophenyl)-2-(methoxyimino) ethyl]-1-{[2'-(5-oxo-4,5-dihydro-1,2,4-oxadiazol-3-yl)biphenyl-4-yl]methyl}thieno[2,3-d]pyrimidine-2,4 (1H,3H)-dione

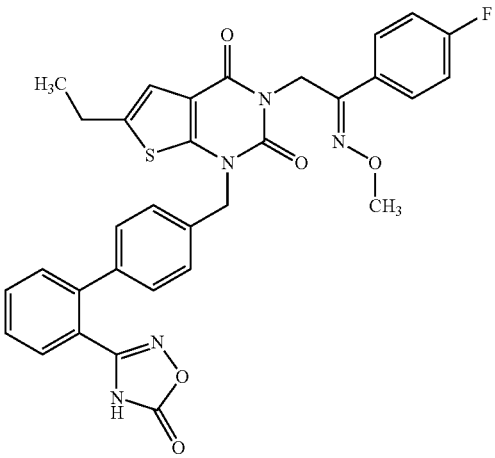 [SMILES: CCc1cc2c(=O)n(C/C(=N/OC)c3ccc(F)cc3)c(=O)n(Cc3ccc(-c4ccccc4-c4noc(=O)[nH]4)cc3)c2s1]

A mixture of 6-ethyl-3-[2-(4-fluorophenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), (aminooxy)methane hydrochloride (0.086 g), pyridine (5 mL) and ethanol (5 mL) was stirred at 100° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.15 g, 73%).

$^1$H NMR (300 MHz, DMSO-$d_6$)δ1.12-1.20 (3H, m), 2.65-2.76(2H, m), 3.64, 3.92 (combined 3H, s), 4.95, 5.19 (combined 2H, s), 5.08, 5.14 (combined 2H, s), 6.95-7.69(13H, m), 12.4 (1H, s)

Example 205

3-(2-cyclohexyl-2-oxoethyl)-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

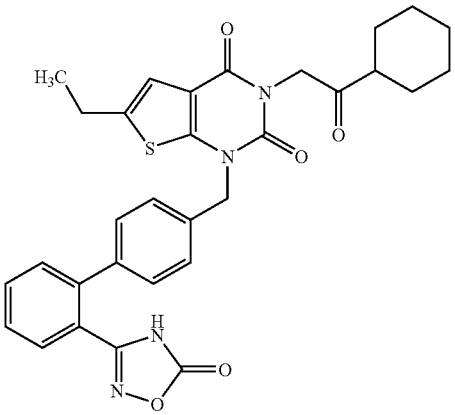 [SMILES: CCc1cc2c(=O)n(CC(=O)C3CCCCC3)c(=O)n(Cc3ccc(-c4ccccc4-c4noc(=O)[nH]4)cc3)c2s1]

A mixture of hydroxylammonium chloride (0.91 g), sodium hydrogencarbonate (1.3 g) and dimethyl sulfoxide (13 mL) was stirred at 40° C. for 30 min, 4'-{[3-(2-cyclohexyl-2-oxoethyl)-6-ethyl-2,4-dioxo-3,4-dihydrothieno[2,3-d]pyrimidin-1(2H)-yl]methyl}biphenyl-2-carbonitrile (0.67 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.32 g) and then 1,8-diazabicyclo[5.4.0]undec-7-ene (0.29 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.57 g, 76%).

$^1$H NMR (300 MHz, DMSO-$d_6$)δ1.14-1.37 (8H, m), 1.56-1.92(5H, m), 2.56-2.69 (1H, m), 2.70-2.81 (2H, m), 4.88 (2H, s), 5.20 (2H, s), 7.00(1H, s), 7.35 (4H, d, J=8.4), 7.50-7.60 (2H, m), 7.65-7.74 (2H, m), 12.4 (1H, s)

Example 206

3-[2-(ethoxyimino)-2-(4-fluorophenyl)ethyl]-6-ethyl-1-{[2'-(5-oxo-4,5-dihydro-1,2,4-oxadiazol-3-yl)biphenyl-4-yl]methyl}thieno[2,3-d]pyrimidine-2,4 (1H,3H)-dione

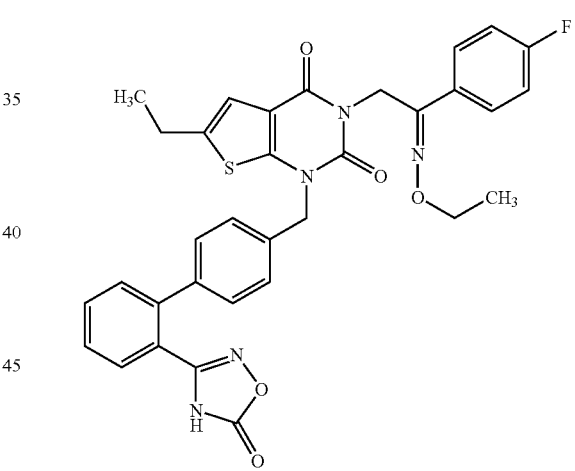

A mixture of 6-ethyl-3-[2-(4-fluorophenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), (aminooxy)ethane hydrochloride (0.04 g), pyridine (10 mL) and ethanol (10 mL) was stirred at 100° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.1 g, 48%).

$^1$H NMR (300 MHz, DMSO-$d_6$)δ1.14-1.26 (6H, m), 2.66-2.78(2H, m), 3.32-3.41 (1H, m), 3.94 (1H, q, J=7.0), 4.17 (1H, q, J=7.0), 4.99(1H, s), 5.10-5.24 (3H, m), 7.01 (2H, dd, J=8.7, 6.4), 7.16 (1H, t, J=8.8),7.23-7.33 (4H, m), 7.41 (1H, dd, J=8.6, 5.6), 7.50-7.62 (3H, m), 7.66-7.74(2H, m)

Example 207

3-[2-[(benzyloxy)imino]-2-(4-fluorophenyl)ethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

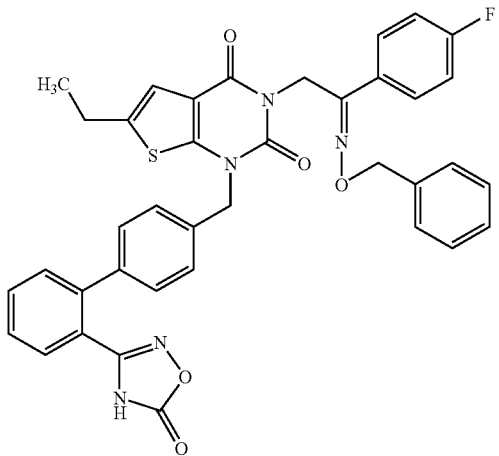 [SMILES: CCc1cc2c(=O)n(CC(=NOCc3ccccc3)c3ccc(F)cc3)c(=O)n(Cc3ccc(-c4ccccc4-c4noc(=O)[nH]4)cc3)c2s1]

A mixture of 6-ethyl-3-[2-(4-fluorophenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), [(aminooxy)methyl]benzene hydrochloride (0.07 g), pyridine (10 mL) and ethanol (10 mL) was stirred at 100° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.098 g, 42%).

$^1$H NMR (300 MHz, DMSO-$d_6$)δ1.13-1.24 (3H, m), 2.71 (2H,dt, J=14.3, 7.2), 4.99 (1H, d, J=13.8), 5.08 (1H, s), 5.18-5.28 (4H, m), 6.94-7.07 (3H, m), 7.19-7.27 (4H, m), 7.29-7.37 (4H, m), 7.41-7.52 (3H, m), 7.54-7.63 (2H, m), 7.65-7.73 (2H, m)

Example 208 ethyl ({[2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]-1-(4-fluorophenyl)ethylidene]amino}oxy)acetate

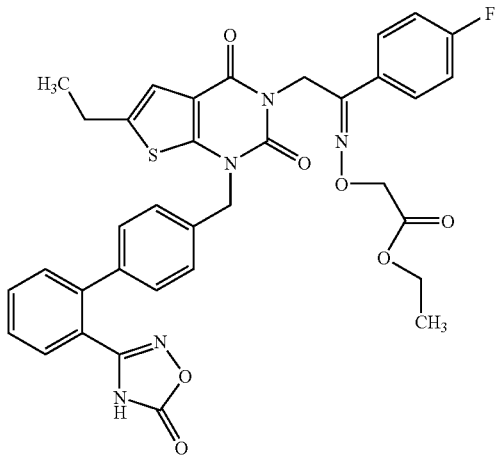 [SMILES: CCOC(=O)CON=C(Cn1c(=O)c2cc(CC)sc2n(Cc2ccc(-c3ccccc3-c3noc(=O)[nH]3)cc2)c1=O)c1ccc(F)cc1]

A mixture of 6-ethyl-3-[2-(4-fluorophenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), ethyl (aminooxy)acetate hydrochloride (0.045 g), pyridine (10 mL) and ethanol (10 mL) was stirred at 100° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.059 g, 25%).

$^1$H NMR (300 MHz, DMSO-$d_6$)δ1.14-1.25 (6H, m), 2.71 (2H, q,J=7.4), 4.12 (1H, d, J=7.0), 4.14-4.23 (2H, m), 4.52 (1H, d, J=2.4), 4.71-4.80 (2H, m), 5.11 (1H, s), 5.22 (2H, s), 6.94-7.05 (2H, m), 7.16-7.27 (3H, m), 7.29-7.33 (2H, m), 7.37 (1H, s), 7.67 (4H, d, J=0.8), 7.69 (1H, s)

Example 209

6-ethyl-1-{[2'-(5-oxo-4,5-dihydro-1,2,4-oxadiazol-3-yl)biphenyl-4-yl]methyl}-3-(2-oxo-2-phenylethyl)thieno[2,3-d]pyrimidine-2,4(1H,3H)-dione

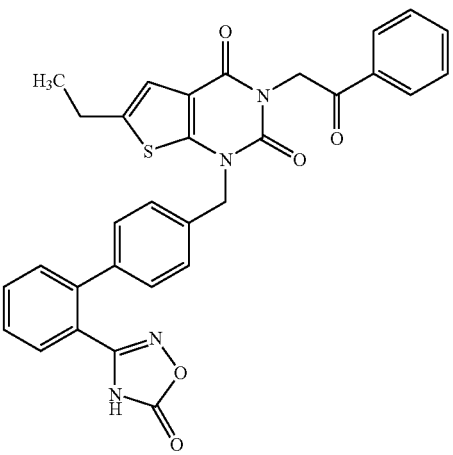 [SMILES: CCc1cc2c(=O)n(CC(=O)c3ccccc3)c(=O)n(Cc3ccc(-c4ccccc4-c4noc(=O)[nH]4)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (5.0 g) obtained in Reference Example 57, 2-bromo-1-phenylethanone (2.8 mL) and N,N-dimethylformamide (50 mL) was added sodium hydride (0.62 g), and the mixture was stirred at 50° C. for 3 hr. The reaction mixture was diluted with chloroform, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (10 mL), and the mixture was added to a mixture of hydroxylammonium chloride (4.3 g), sodium hydrogencarbonate (5.1 g) and dimethyl sulfoxide (30 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography, dissolved in tetrahydrofuran (30 mL), N,N'-carbonyldiimidazole (1.2 g)

and then 1,8-diazabicyclo[5.4.0]undec-7-ene (1.1 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.14 g, 4.2%).

$^1$H NMR (300 MHz, DMSO-$d_6$)δ1.15-1.27 (3H, m), 2.71-2.83(2H, m), 5.24 (2H, s), 5.49 (2H, s), 7.04 (1H, s), 7.31-7.43 (4H, m), 7.52-7.63(4H, m), 7.66-7.76 (3H, m), 8.08-8.14 (2H, m)

Example 210

3-[2-(ethoxyimino)-2-(4-methoxyphenyl)ethyl]-6-ethyl-1-{[2'-(5-oxo-4,5-dihydro-1,2,4-oxadiazol-3-yl)biphenyl-4-yl]methyl}thieno[2,3-d]pyrimidine-2,4 (1H,3H)-dione

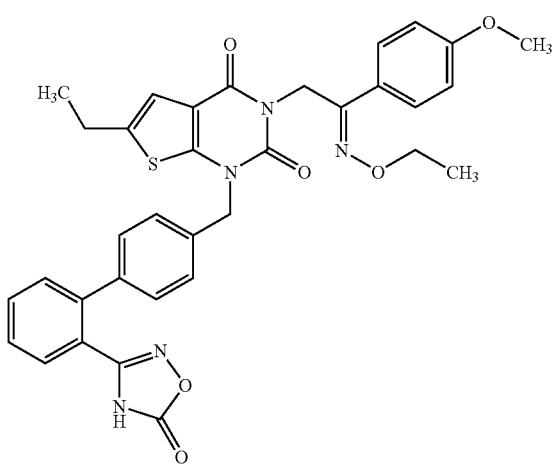 [SMILES: CCO/N=C(/Cn1c(=O)c2cc(CC)sc2n(Cc2ccc(-c3ccccc3-c3noc(=O)[nH]3)cc2)c1=O)c1ccc(OC)cc1]

A mixture of 6-ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), (aminooxy)ethane hydrochloride (0.04 g), pyridine (10 mL) and ethanol (10 mL) was stirred at 100° C. for 16 hr. To the reaction mixture were added chloroform and water and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.14 g, 63%).

$^1$H NMR (300 MHz, DMSO-$d_6$)δ1.14-1.24 (6H, m), 2.72 (2H,ddd, J=10.9, 7.5, 0.9), 3.69 (3H, s), 3.78 (1H, s), 4.14 (1H, q, J=7.0),4.97 (1H, s), 5.08-5.18 (2H, m), 5.22 (1H, s), 6.83-6.89 (1H, m), 6.96-7.02 (3H,m), 7.19-7.30 (4H, m), 7.49-7.60 (3H, m), 7.65-7.74 (2H, m)

Example 211

3-[[(benzyloxy)imino]-2-(4-methoxyphenyl)ethyl]-6-ethyl-1-{[2'-(5-oxo-4,5-dihydro-1,2,4-oxadiazol-3-yl)biphenyl-4-yl]methyl}thieno[2,3-d]pyrimidine-2,4 (1H,3H)-dione

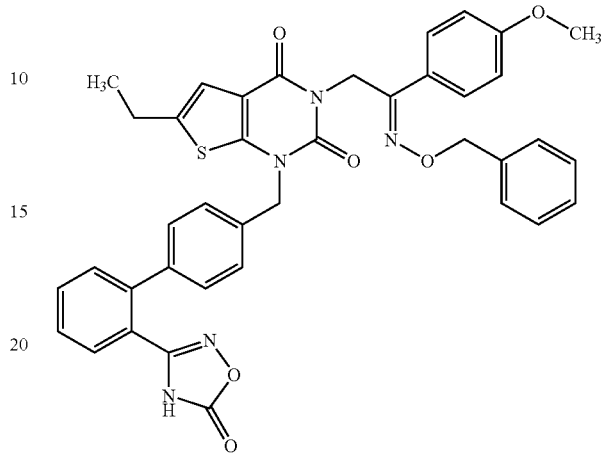

A mixture of 6-ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), [(aminooxy)methyl]benzene hydrochloride (0.066 g), pyridine (10 mL) and ethanol (10 mL) was stirred at 100° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.12 g, 51%).

$^1$H NMR (300 MHz, DMSO-$d_6$)δ1.14-1.23 (3H, m), 2.64-2.77(2H, m), 3.67 (2H, s), 3.94 (3H, s), 4.98 (1H, s), 5.09 (1H, s), 5.14-5.25 (2H,m), 6.90-7.01 (3H, m), 7.21-7.37 (7H, m), 7.40-7.46 (2H, m), 7.51-7.61 (3H, m),7.65-7.74 (3H, m)

Example 212 ethyl ({[2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]-1-(4-methoxyphenyl)ethylidene]amino}oxy)acetate

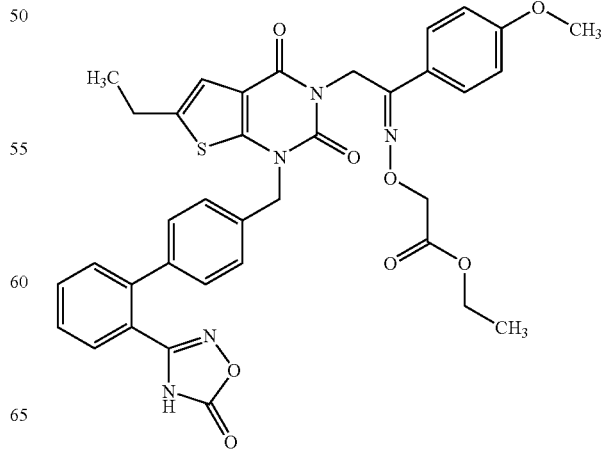

A mixture of 6-ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), ethyl (aminooxy)acetate hydrochloride (0.053 g), pyridine (10 mL) and ethanol (10 mL) was stirred at 100° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.061 g, 26%).

$^1$H NMR (300 MHz, DMSO-$d_6$)δ1.14-1.27 (6H, m), 2.65-2.79(2H, m), 3.69 (2H, s), 3.78 (1H, s), 4.01 (1H, d, J=7.2), 4.08-4.24 (2H, m), 4.43-4.55 (1H, m), 4.67-4.79 (2H, m), 5.11 (1H, s), 5.21 (2H, s), 6.81-6.92(1H, m), 6.96-7.04 (3H, m), 7.19-7.33 (4H, m), 7.49-7.63 (3H, m), 7.66-7.75(2H, m)

Example 213

6-ethyl-3-[2-(isopropoxyimino)-2-(4-methoxyphenyl)ethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

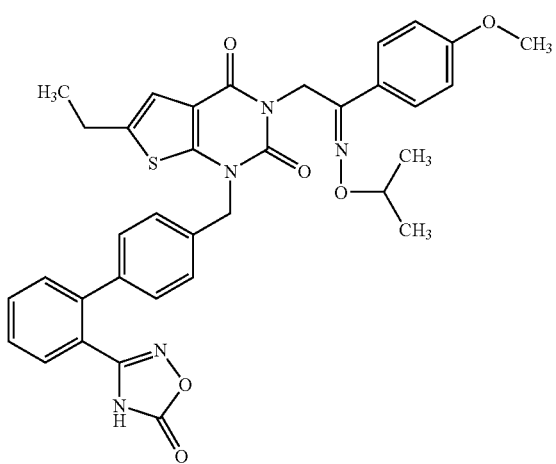 [SMILES: CCc1cc2c(=O)n(CC(=NOC(C)C)c3ccc(OC)cc3)c(=O)n(Cc3ccc(-c4ccccc4-c4noc(=O)[nH]4)cc3)c2s1]

A mixture of 6-ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), 2-(aminooxy)propane hydrochloride (0.052 g), pyridine (10 mL) and ethanol (10 mL) was stirred at 100° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.18 g, 80%).

$^1$H NMR (300 MHz, DMSO-$d_6$)δ0.78 (2H, d, J=6.8), 0.90 (4H, d, J=6.8), 1.14-1.23 (3H, m), 2.66-2.77 (2H, m), 3.69 (2H, s), 3.78 (1H,s), 3.89 (1H, d, J=6.8), 4.03 (1H, d, J=7.0), 4.97 (1H, s), 5.10-5.22 (3H,m), 6.86 (1H, d, J=8.9), 6.99 (2H, ddd, J=4.8, 2.3, 2.0), 7.02 (1H, d, J=4.1), 7.20-7.31 (4H, m), 7.49-7.54 (1H, m), 7.54-7.60 (2H, m), 7.69 (2H, ddd, J=7.3, 5.7, 1.4)

Example 214

3-[2-[(allyloxy)imino]-2-(4-methoxyphenyl)ethyl]-6-ethyl-1-{[2'-(5-oxo-4,5-dihydro-1,2,4-oxadiazol-3-yl)biphenyl-4-yl]methyl}thieno[2,3-d]pyrimidine-2,4 (1H,3H)-dione

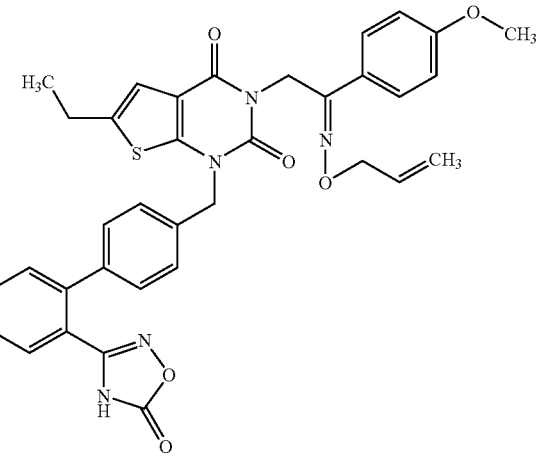

A mixture of 6-ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), 3-(aminooxy)prop-1-ene hydrochloride (0.045 g), pyridine (10 mL) and ethanol (1010 mL) was stirred at 100° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.19 g, 86%).

$^1$H NMR (300 MHz, DMSO-$d_6$)δ1.14-1.23 (3H, m), 2.70 (1H, d,J=6.6), 2.71-2.77 (1H, m), 3.68 (2H, s), 3.77 (1H, s), 4.40 (1H, d, J=5.5),4.64 (1H, d, J=5.3), 4.99 (1H, s), 5.09-5.22 (4H,m), 5.34 (1H, dd, J=17.3, 1.7), 5.97 (1H, d, J=10.5), 6.84-6.89 (1H, m), 6.99 (3H, dd, J=8.7, 1.7),7.20-7.30 (4H, m), 7.49-7.60 (3H, m), 7.66-7.74 (2H, m)

Example 215

6-ethyl-3-[2-(methoxyimino)-2-phenylethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione

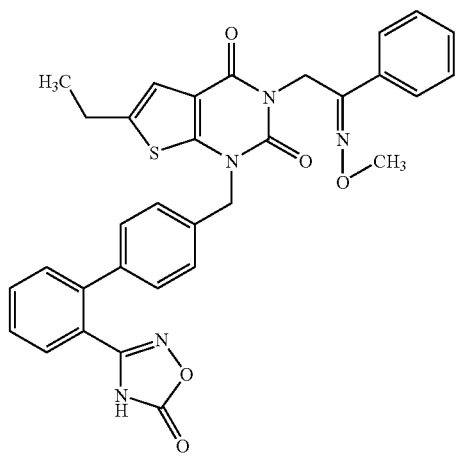 [SMILES: CCc1cc2c(=O)n(CC(=NOC)c3ccccc3)c(=O)n(Cc3ccc(-c4ccccc4-c4noc(=O)[nH]4)cc3)c2s1]

A mixture of 6-ethyl-1-{[2'-(5-oxo-4,5-dihydro-1,2,4-oxadiazol-3-yl)biphenyl-4-yl]methyl}-3-(2-oxo-2-phenylethyl)thieno[2,3-d]pyrimidine-2,4(1H,3H)-dione (0.3 g), 3-(aminooxy)prop-1-ene hydrochloride (0.05 g), pyridine (10 mL) and ethanol (10 mL) was stirred at 100° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.22 g, 74%).

$^1$H NMR (300 MHz, DMSO-d$_6$)δ1.19 (3H, dt, J=12.1, 7.5),2.66-2.79 (2H, m), 3.69 (2H, s), 3.76 (1H, s), 4.91-5.03 (1H, m), 5.08 (1H, s),5.18 (2H, d, J=8.3), 6.83-6.91 (1H, m), 6.94-7.00 (1H, m), 7.02 (1H, d, J=6.8), 7.19-7.25 (2H, m), 7.27-7.38 (5H, m), 7.45-7.60 (2H, m), 7.65-7.73 (2H,m)

Example 216

({[2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]-1-(4-fluorophenyl)ethylidene]amino}oxy)acetic acid

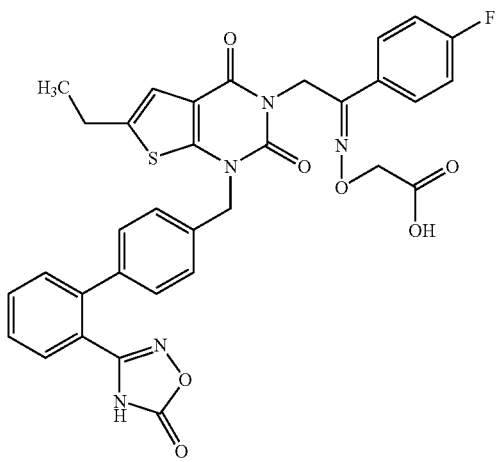 [SMILES: CCc1cc2c(=O)n(CC(=NOCC(=O)O)c3ccc(F)cc3)c(=O)n(Cc3ccc(-c4ccccc4-c4noc(=O)[nH]4)cc3)c2s1]

A mixture of 6-ethyl-3-[2-(4-fluorophenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), (aminooxy)acetic acid (0.053 g), NaHCO$_3$ (1.0 g) and ethanol (20 mL) was stirred at 80° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.062 g, 27%).

$^1$H NMR (300 MHz, DMSO-d$_6$)δ1.13-1.25 (3H, m), 2.71 (2H, td, J=7.5, 6.6), 4.68 (2H, s), 4.99 (1H, s), 5.11 (1H, s), 5.15-5.30 (2H, m),6.98 (2H, d, J=1.3), 7.01 (1H, s), 7.13-7.26 (4H, m), 7.29-7.40 (2H, m),7.49-7.62 (2H, m), 7.63-7.75 (2H, m), 12.44 (1H, s)

Example 217

({[2-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]-1-(4-methoxyphenyl)ethylidene]amino}oxy)acetic acid

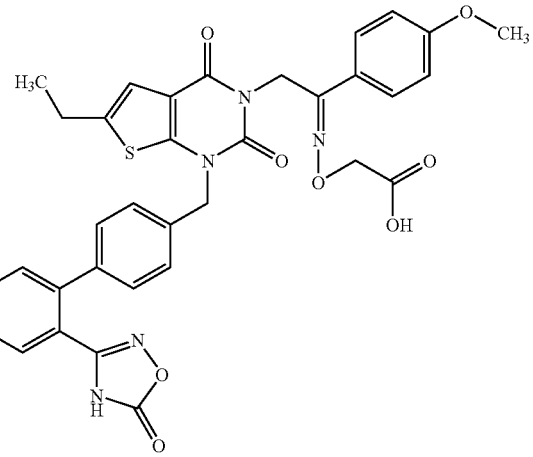

A mixture of 6-ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione (0.2 g), (aminooxy)acetic acid (0.045 g), pyridine (20 mL) was stirred at 80° C. for 16 hr. To the reaction mixture were added chloroform and water, and the mixture was adjusted to pH 4 with 1N hydrochloric acid. The chloroform layer was washed with saturated brine, and dried over anhydrous magnesium sulfate. The solvent was evaporated under reduced pressure. The obtained residue was purified by silica gel column chromatography to give the title compound as a stereoisomer mixture (0.05 g, 22%).

$^1$H NMR (300 MHz, DMSO-d$_6$)δ1.13-1.25 (3H, m), 2.65-2.78(2H, m), 3.68 (2H, s), 3.78 (1H, s), 4.44 (1H, s), 4.65 (1H, s), 4.97 (1H, s),5.10 (1H, s), 5.20 (2H, s), 6.87 (2H, d, J=8.9), 6.95-7.02 (3H, m), 7.16-7.30(4H, m), 7.49-7.63 (2H, m), 7.66-7.74 (2H, m), 12.42 (1H, s)

Example 218 ethyl 4-[6-ethyl-2,4-dioxo-1-{[2'-(5-oxo-4,5-dihydro-1,2,4-oxadiazol-3-yl)biphenyl-4-yl]methyl}-1,4-dihydrothieno[2,3-d]pyrimidin-3(2H)-yl]-3-(4-methoxyphenyl)but-2-enoate

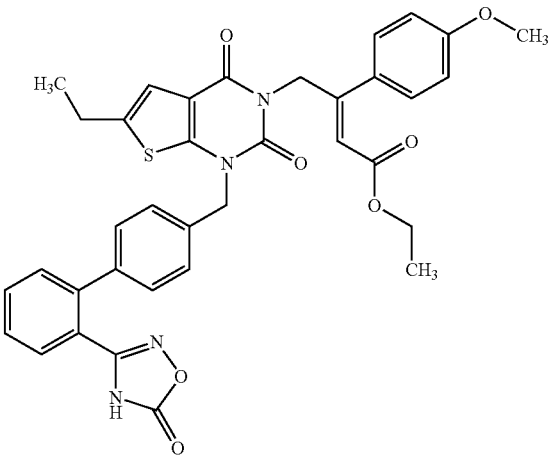 [SMILES: CCOC(=O)/C=C(/Cn1c(=O)c2cc(CC)sc2n(Cc2ccc(-c3ccccc3-c3noc(=O)[nH]3)cc2)c1=O)c1ccc(OC)cc1]

To a solution of 4'-{[6-ethyl-3-[2-(4-methoxyphenyl)-2-oxoethyl]-2,4-dioxo-3,4-dihydrothieno[2,3-d]pyrimidin-1(2H)-yl]methyl}biphenyl-2-carbonitrile (1.0 g), (diethoxyphosphoryl)ethyl acetate (0.56 ml) in THF (20 ml) was added NaH (0.1 g) under ice-cooling, and the mixture was stirred at room temperature for 1 hr. The reaction mixture was poured into water and the mixture was extracted with ethyl acetate and dried over anhydrous magnesium sulfate. The solvent was evaporated under reduced pressure. The obtained residue was purified by silica gel column chromatography to give ethyl (2E)-4-[1-[(2'-cyanobiphenyl-4-yl)methyl]-6-ethyl-2,4-dioxo-1,4-dihydrothieno[2,3-d]pyrimidin-3(2H)-yl]-3-(4-methoxyphenyl)but-2-enoate (1.0 g, 88%). This was dissolved in dimethyl sulfoxide (5 mL), and the mixture was added to a mixture of hydroxylammonium chloride (1.15 g), sodium hydrogencarbonate (1.40 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography, dissolved in tetrahydrofuran (20 mL), N,N'-carbonyldiimidazole (0.32 g) and then 1,8-diazabicyclo[5.4.0]undec-7-ene (0.30 mL) were added, and the mixture was stirred at room temperature for 2 hr. The reaction mixture was diluted with ethyl acetate, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as a stereoisomer mixture (0.078 g, 13%).

$^1$H NMR (300 MHz, DMSO-$d_6$)δ1.15 (3H, t, J=7.4), 1.26 (3H, t, J=7.1), 2.68 (2H, qd, J=7.5, 0.8), 3.67 (3H, s), 4.18 (2H, q, J=7.1), 5.07 (2H, s), 5.62 (2H, d, J=1.3), 5.95 (1H, s), 6.84 (2H, d, J=8.9), 6.93-6.97 (3H, m), 7.18-7.25 (4H, m), 7.50-7.61 (2H, m), 7.71 (2H, td, J=7.3, 6.0), 12.42 (1H, s)

Example 219

6-ethyl-3-[2-(4-methoxyphenyl)-2-oxoethyl]-1-{[2-methyl-2'-(5-oxo-4,5-dihydro-1,2,4-oxadiazol-3-yl)biphenyl-4-yl]methyl}thieno[2,3-d]pyrimidine-2,4(1H,3H)-dione

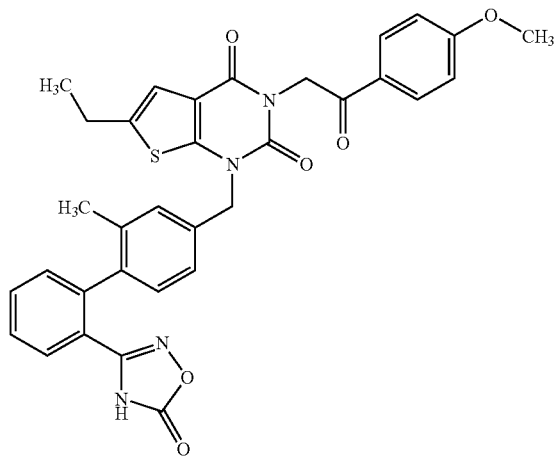 [SMILES: CCc1cc2c(=O)n(CC(=O)c3ccc(OC)cc3)c(=O)n(Cc3ccc(-c4ccccc4-c4noc(=O)[nH]4)c(C)c3)c2s1]

A mixture of 3-(2,4-dimethoxybenzyl)-6-ethylthieno[2,3-d]pyrimidine-2,4(1H,3H)-dione (1.8 g), 4'-(hydroxymethyl)-2'-methylbiphenyl-2-carbonitrile (1.4 g), 1,1'-(azodicarbonyl)dipiperidine (2 g), tributylphosphine (1.9 mL), and tetrahydrofuran (50 mL) was stirred at room temperature overnight. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was dissolved in trifluoroacetic acid (13 mL) and the mixture was stirred at 50° C. for 2 hr. To the reaction mixture was added toluene (100 mL), and the mixture was concentrated under reduced pressure. The obtained residue was dissolved in N,N-dimethylformamide (13 mL), 2-bromo-1-(4-methoxyphenyl)ethanone (0.87 g) and sodium hydride (0.19 g) were added, and the mixture was stirred at room temperature for 5 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The obtained residue was dissolved in dimethyl sulfoxide (14 mL), and the mixture was added to a mixture of hydroxylammonium chloride (1.7 g), sodium hydrogencarbonate (2.5 g) and dimethyl sulfoxide (14 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography and dissolved in methylene chloride (14 mL). N,N'-Carbonyldiimidazole (0.6 g) and then 1,8-diazabicyclo[5.4.0]undec-7-ene (0.55 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (1 g, 68%).

$^1$H NMR (300 MHz, DMSO-$d_6$)δ1.22 (3H, t, J=7.5), 2.02 (3H, s), 2.72-2.82 (2H, m), 3.88 (3H, s), 5.20 (2H, s), 5.43 (2H, s), 7.01-7.19 (5H, m), 7.23 (1H, s), 7.35-7.41 (1H, m), 7.54-7.74 (3H, m), 8.09 (2H, d, J=9.0), 12.43 (1H, s)

Example 220

6-ethyl-3-[2-(4-methoxyphenyl)-2-oxoethyl]-1-{[2-methyl-2'-(5-oxo-4,5-dihydro-1,2,4-oxadiazol-3-yl)biphenyl-4-yl]methyl}thieno[2,3-d]pyrimidine-2,4(1H,3H)-dione potassium salt

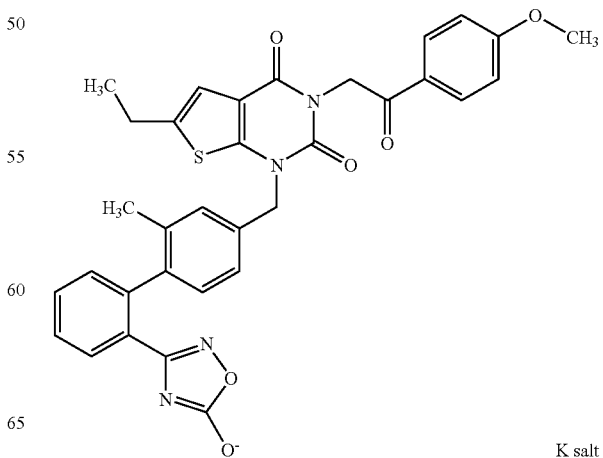

K salt

A mixture of 6-ethyl-3-[2-(4-methoxyphenyl)-2-oxoethyl]-1-{[2-methyl-2'-(5-oxo-4,5-dihydro-1,2,4-oxadiazol-3-yl)biphenyl-4-yl]methyl}thieno[2,3-d]pyrimidine-2,4(1H,3H)-dione (0.3 g), potassium 2-ethylhexanoate (0.11 g) and ethyl acetate (6 mL) was stirred at room temperature for 16 hr. The precipitated solid was collected by filtration to give the title compound as colorless crystals (0.31 g, 98%).

$^1$H NMR (300 MHz, DMSO-d$_6$)δ1.23 (3H, t, J=7.4), 2.02 (3H, s), 2.74-2.84 (2H, m), 3.88 (3H, s), 5.16 (2H, s), 5.43 (2H, s), 6.96-7.16(7H, m), 7.39 (2H, dd, J=5.8, 3.5) 7.67-7.75 (1H, m) 8.09 (2H, d, J=8.9)

Example 221

6-ethyl-1-{[2'-(5-oxo-4,5-dihydro-1,2,4-oxadiazol-3-yl)biphenyl-4-yl]methyl}-3-[2-oxo-2-(2-thienyl)ethyl]thieno[2,3-d]pyrimidine-2,4(1H,3H)-dione

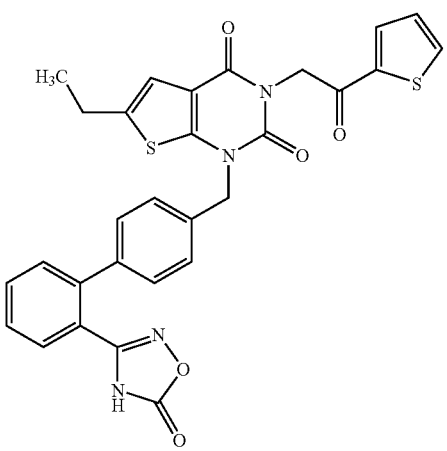 [SMILES: CCc1cc2c(=O)n(CC(=O)c3cccs3)c(=O)n(Cc3ccc(-c4ccccc4-c4noc(=O)[nH]4)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (1.5 g), 2-bromo-1-(2-thienyl)ethanone (0.87 mL) and N,N-dimethylformamide (20 mL) was added sodium hydride (0.19 g), and the mixture was stirred at room temperature for 4 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (1.63 g), sodium hydrogencarbonate (1.98 g) and dimethyl sulfoxide (30 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was dissolved in tetrahydrofuran (30 mL), N,N'-carbonyldiimidazole (0.46 g) and then 1,8-diazabicyclo[5.4.0]undec-7-ene (0.42 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 20% sulfuric acid (5 mL) and ethanol (10 ml), and the mixture was stirred at 100° C. for 1 hr, and extracted with chloroform and water. The chloroform layer was washed with saturated brine, and dried over anhydrous magnesium sulfate. The solvent was evaporated under reduced pressure. The obtained residue was purified by preparative HPLC to give the title compound as colorless crystals (0.32 g, 24%).

$^1$H NMR (300 MHz, DMSO-d$_6$)δ1.21 (3H, t, J=7.4), 2.76 (2H, q, J=7.4), 5.24 (2H, s), 5.44 (2H, s), 7.04 (1H, s), 7.31-7.44 (5H, m),7.51-7.61 (2H, m), 7.63-7.73 (2H, m), 8.09-8.16 (1H, m), 8.23-8.30 (1H, m),12.4 (1H, s)

Example 222

3-[2-(3-bromo-2-thienyl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

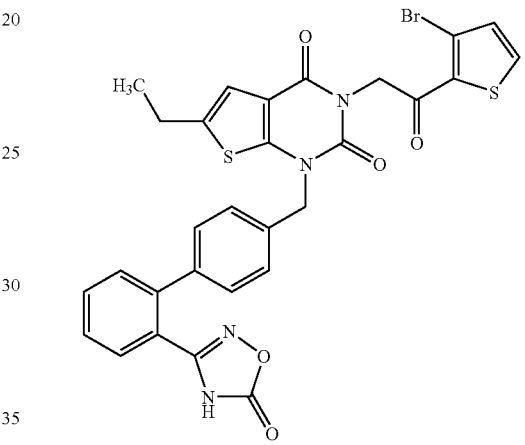

To a mixture of 4'-[(6-ethyl-2,4-dioxo-3,4-dihydrothieno[2,3-d]pyrimidin-1(2H)-yl)methyl]biphenyl-2-carbonitrile (1.5 g), 2-bromo-1-(3-bromo-2-thienyl)ethanone (1.2 mL) and N,N-dimethylformamide (20 mL) was added sodium hydride (0.19 g), and the mixture was stirred at room temperature for 4 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (1.63 g), sodium hydrogencarbonate (1.98 g) and dimethyl sulfoxide (30 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was dissolved in tetrahydrofuran (30 mL), N,N'-carbonyldiimidazole (0.46 g) and then 1,8-diazabicyclo[5.4.0]undec-7-ene (0.42 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 20% sulfuric acid (5 mL) and ethanol (10 ml), and the mixture was stirred at 100° C. for 1 hr, and extracted with chloroform and water. The chloroform layer was washed with saturated brine, and dried over anhydrous magnesium sulfate. The solvent was evaporated under reduced pressure. The obtained residue was purified by preparative HPLC to give the title compound as colorless crystals (0.13 g, 8.5%).

$^1$H NMR (300 MHz, DMSO-d$_6$)δ1.21 (3H, t, J=7.4), 2.77 (2H, q, J=7.4), 5.24 (2H, s), 5.41 (2H, s), 7.04 (1H, s), 7.31-7.45 (5H, m), 7.51-7.61 (2H, m), 7.64-7.74 (2H, m), 8.15 (1H, d, J=5.1), 12.41 (1H, s)

Example 223

6-ethyl-1-{[2'-(5-oxo-4,5-dihydro-1,2,4-oxadiazol-3-yl)biphenyl-4-yl]methyl}-3-[2-oxo-2-(5-pyridin-2-yl-2-thienyl)ethyl]thieno[2,3-d]pyrimidine-2,4(1H,3H)-dione

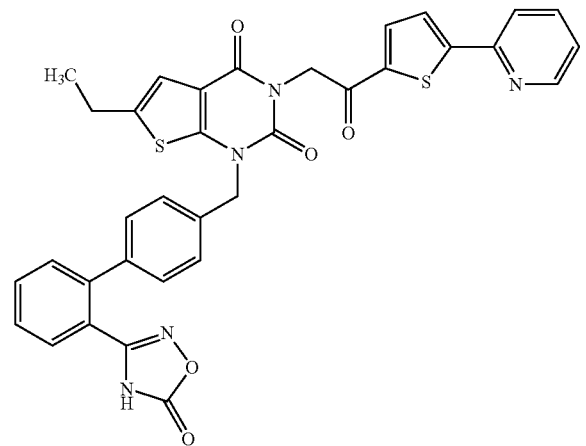 [SMILES: CCc1cc2c(=O)n(CC(=O)c3ccc(-c4ccccn4)s3)c(=O)n(Cc3ccc(-c4ccccc4-c4noc(=O)[nH]4)cc3)c2s1]

To a mixture of 4'-[(6-ethyl-2,4-dioxo-3,4-dihydrothieno[2,3-d]pyrimidin-1(2H)-yl)methyl]biphenyl-2-carbonitrile (1.5 g), 2-bromo-1-(5-pyridin-2-yl-2-thienyl)ethanone (1.2 mL) and N,N-dimethylformamide (20 mL) was added sodium hydride (0.19 g), and the mixture was stirred at room temperature for 4 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (1.2 g), sodium hydrogencarbonate (1.4 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was dissolved in tetrahydrofuran (20 mL), N,N'-carbonyldiimidazole (0.33 g) and then 1,8-diazabicyclo[5.4.0]undec-7-ene (0.30 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. To the obtained residue were added 20% sulfuric acid (5 mL) and ethanol (10 ml), and the mixture was stirred at 100° C. for 1 hr, and extracted with chloroform and water. The chloroform layer was washed with saturated brine, and dried over anhydrous magnesium sulfate.

The solvent was evaporated under reduced pressure. The obtained residue was purified by preparative HPLC to give the title compound as colorless crystals (0.17 g, 15%).

$^1$H NMR (300 MHz, DMSO-d$_6$)δ1.22 (3H, t, J=7.5), 2.72-2.82 (2H, m), 5.24 (2H, s), 5.45 (2H, s), 7.04 (1H, s), 7.32-7.44 (5H, m), 7.52-7.61 (2H, m), 7.65-7.73 (2H, m), 7.90-8.03 (2H, m), 8.12 (1H, d, J=7.9), 8.29 (1H, d, J=4.1), 8.62 (1H, d, J=4.1)

Example 224

3-[2-(1-benzofuran-2-yl)-2-oxoethyl]-6-ethyl-1-{[2'-(5-oxo-4,5-dihydro-1,2,4-oxadiazol-3-yl)biphenyl-4-yl]methyl}thieno[2,3-d]pyrimidine-2,4(1H,3H)-dione

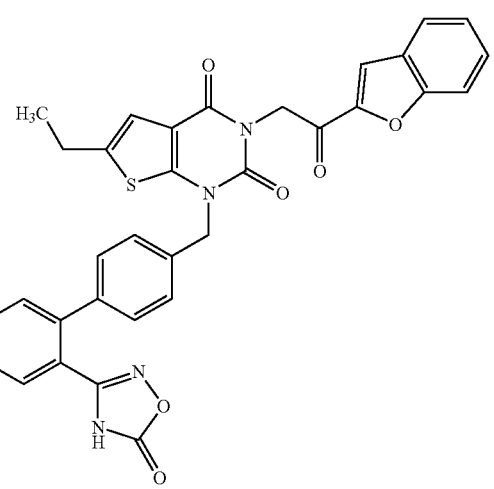

To a mixture of 4'-[(6-ethyl-2,4-dioxo-3,4-dihydrothieno[2,3-d]pyrimidin-1(2H)-yl)methyl]biphenyl-2-carbonitrile (1.5 g), 1-(1-benzofuran-2-yl)-2-bromoethanone (1.0 mL) and N,N-dimethylformamide (20 mL) was added sodium hydride (0.19 g), and the mixture was stirred at room temperature for 4 hr. The reaction mixture was diluted with ethyl acetate, washed successively with 5% aqueous potassium hydrogensulfate solution and saturated brine, and dried over anhydrous magnesium sulfate. The solvent was evaporated under reduced pressure. The residue obtained by silica gel column chromatography was dissolved in dimethyl sulfoxide (5 mL), and the mixture was added to a mixture of hydroxylammonium chloride (51.2 g), sodium hydrogencarbonate (1.4 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was dissolved in tetrahydrofuran (20 mL), N,N'-carbonyldiimidazole (0.33 g) and then 1,8-diazabicyclo[5.4.0]undec-7-ene (0.30 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. To the obtained residue were added 20% sulfuric acid (5 mL) and ethanol (10 ml), and the mixture was stirred at 100° C. for 1 hr, and extracted with chloroform and water. The chloroform layer was washed with saturated brine, and dried over anhydrous magnesium sulfate. The solvent was evaporated under reduced pressure. The obtained residue was purified by preparative HPLC to give the title compound as colorless crystals (0.17 g, 20%).

$^1$H NMR (300 MHz, DMSO-$d_6$)δ1.15-1.26 (3H, m), 2.78 (2H,qd, J=7.5, 0.9), 5.28 (2H, s), 5.44 (2H, s), 7.07 (1H, s), 7.40-7.45 (1H, m),7.48-7.54 (2H, m), 7.56-7.65 (5H, m), 7.74-7.83 (2H, m), 7.88-7.98 (2H, m),8.20 (1H, d, J=0.8)

Example 225

6-ethyl-3-(2-methyl-2-phenylpropyl)-1-{[2'-(5-oxo-4,5-dihydro-1,2,4-oxadiazol-3-yl)biphenyl-4-yl]methyl}thieno[2,3-d]pyrimidine-2,4(1H,3H)-dione

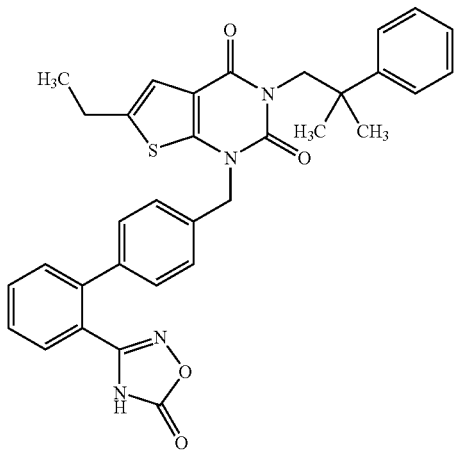 [SMILES: CCc1cc2c(=O)n(CC(C)(C)c3ccccc3)c(=O)n(Cc3ccc(-c4ccccc4-c4noc(=O)[nH]4)cc3)c2s1]

To a solution of 4'-[(6-ethyl-2,4-dioxo-3,4-dihydrothieno [2,3-d]pyrimidin-1(2H)-yl)methyl]biphenyl-2-carbonitrile (1.5 g), 2-methyl-2-phenylpropan-1-ol (0.64 g), tributylphosphine (0.86 g) in THF (50 ml) was added ADDP (1.2 g) under ice-cooling, and the mixture was stirred at room temperature overnight. The reaction mixture was poured into water, extracted with ethyl acetate and dried over anhydrous magnesium sulfate. The solvent was evaporated under reduced pressure. The obtained residue was purified by silica gel column chromatography to give 4'-{[6-ethyl-3-(2-methyl-2-phenylpropyl)-2,4-dioxo-3,4-dihydrothieno[2,3-d]pyrimidin-1(2H)-yl]methyl}biphenyl-2-carbonitrile (0.2 g). This was dissolved in dimethyl sulfoxide (2 mL), and the mixture was added to a mixture of hydroxylammonium chloride (0.27 g), sodium hydrogencarbonate (0.32 g) and dimethyl sulfoxide (20 mL), which had been stirred at 40° C. for 30 min in advance. The reaction mixture was stirred at 90° C. for 16 hr, diluted with chloroform, washed successively with water and saturated brine, and dried over anhydrous magnesium sulfate. The solvent was evaporated under reduced pressure. The residue was purified by silica gel column chromatography, dissolved in tetrahydrofuran (20 mL), N,N'-carbonyldiimidazole (0.075 g) and then 1,8-diazabicyclo[5.4.0]undec-7-ene (0.070 mL) were added, and the mixture was stirred at room temperature for 2 hr. The reaction mixture was diluted with ethyl acetate, washed successively with saturated aqueous potassium hydrogensulfate solution and saturated brine, and dried over anhydrous magnesium sulfate. The solvent was evaporated under reduced pressure. The obtained residue was purified by silica gel column chromatography to give the title compound as colorless crystals (0.073 g, 33%).

$^1$H NMR (300 MHz, DMSO-$d_6$)δ1.20 (3H, t, J=7.5), 1.31 (6H, s), 2.73 (2H, dd, J=7.4, 1.0), 4.17 (2H, s), 5.13 (2H, s), 6.99 (1H, s),7.23 (1H, d, J=7.3), 7.28-7.36 (6H, m), 7.41-7.48 (2H, m), 7.51-7.61 (2H, m),7.65-7.74 (2H, m), 12.42 (1H, s)

Example 226

6-ethyl-1-{[3-methoxy-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione

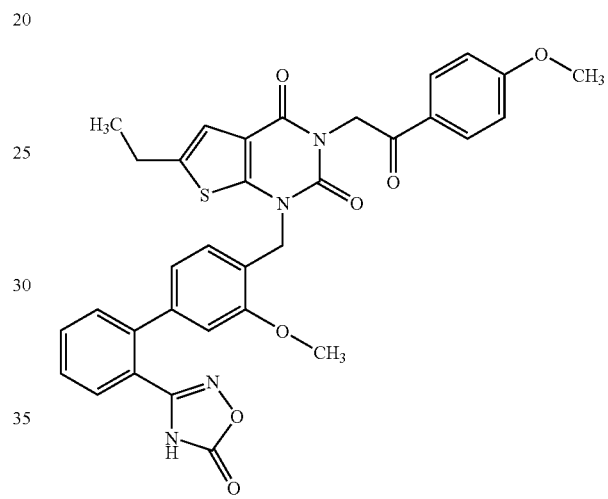

A mixture of hydroxylammonium chloride (1.2 g), sodium hydrogencarbonate (1.8 g) and dimethyl sulfoxide (40 mL) was stirred at 40° C. for 30 min, 4'-{[6-ethyl-3-[2-(4-methoxyphenyl)-2-oxoethyl]-2,4-dioxo-3,4-dihydrothieno[2,3-d] pyrimidin-1(2H)-yl]methyl}-3'-methoxybiphenyl-2-carbonitrile (1.2 g) was added, and the mixture was stirred at 90° C. for 16 hr. The reaction mixture was diluted with chloroform, washed successively with water and saturated brine, and dried over anhydrous magnesium sulfate. The solvent was evaporated under reduced pressure. The residue was purified by silica gel column chromatography and dissolved in methylene chloride (20 mL). N,N'-Carbonyldiimidazole (0.52 g) and then 1,8-diazabicyclo[5.4.0]undec-7-ene (0.48 mL) were added, and the mixture was stirred at room temperature for 2 hr. The reaction mixture was diluted with chloroform, washed successively with saturated aqueous potassium hydrogensulfate solution and saturated brine, and dried over anhydrous magnesium sulfate. The solvent was evaporated under reduced pressure. The obtained residue was purified by preparative HPLC to give the title compound as colorless crystals (0.95 g, 72%).

$^1$H NMR (300 MHz, DMSO-$d_6$)δ1.21 (3H, t, J=7.4), 2.76 (2H, q, J=7.4), 3.85 (3H, s), 3.88 (3H, s), 5.15 (2H, s), 5.41 (2H, s), 6.88(1H, dd, J=7.7, 1.5), 6.97-7.16 (5H, m), 7.53-7.76 (4H, m), 8.08 (2H, d, J=9.0), 12.40 (1H, s)

Example 227

6-ethyl-1-{[3-methoxy-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione potassium salt

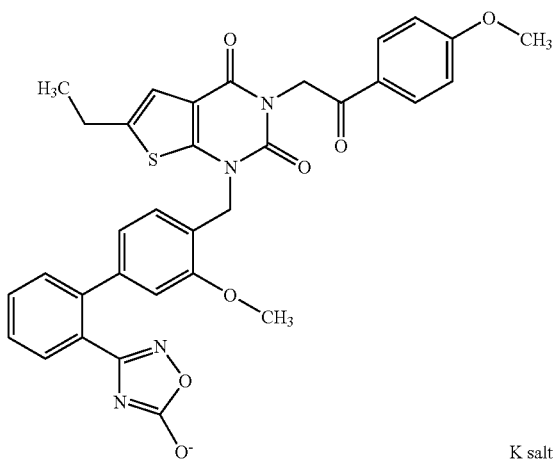 [SMILES: CCc1cc2c(=O)n(CC(=O)c3ccc(OC)cc3)c(=O)n(Cc3ccc(-c4ccccc4-c4noc([O-])n4)cc3OC)c2s1 ; "K salt"]

A mixture of 6-ethyl-1-{[3-methoxy-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione (0.95 g), potassium 2-ethylhexanoate (0.33 g) and ethyl acetate (20 mL) was stirred at room temperature for 16 hr. The precipitated solid was collected by filtration to give the title compound as colorless crystals (0.093 g, 9%).

$^1$H NMR (300 MHz, DMSO-$d_6$)δ1.22 (3H, t, J=7.4), 2.77 (2H, q, J=7.4), 3.78 (3H, s), 3.88 (3H, s), 5.10 (2H, s), 5.41 (2H, s),6.86-6.97 (2H, m), 7.02 (1H, s), 7.07-7.14 (3H, m), 7.33-7.49 (4H, m), 8.08(2H, d, J=9.0)

Experimental Example 1

Binding Assay Using Human AT1 Receptor-Expressing CHO-K1 Cellular Membrane Fraction The membrane fraction for human AT1 receptor binding assay was prepared as follows. CHO-K1 cell capable of stable expression of human AT1 receptor was cultured, recovered, suspended in homogenize buffer (10 mM $NaHCO_3$ (pH 7.4), 5 mM EDTA, 1×Complete EDTA free) [manufactured by Roche, Switzerland], and homogenized. The homogenate was centrifuged at low-speed (900×g, 10 min, 4° C.), and the supernatant was recovered and ultracentrifuged (90,000×g, 1 hr, 4° C.). The supernatant was discarded, and the pellets were resuspended in resuspension buffer (50 mM Tris (pH 7.4), 1 mM EDTA, 1×Complete EDTA free).

The binding assay was performed in the presence of 22.5 pM [$^{125}$I]-angiotensin II [manufactured by PerkinElmer, USA], 9 μg of AT1 membrane and test compound in 100 μL (total reaction volume) of reaction buffer (50 mM Tris (pH 7.4), 10 mM $MgCl_2$, supplemented or not supplemented with 0.3 mg/mL fatty acid-free bovine serum albumin [manufactured by Wako Pure Chemical Industries, Ltd., Japan]). The reaction mixture was incubated in 96 well polypropylene plate for 1 hr at room temperature, and the reaction was quenched by rapid filtration (96 well cell harvester) through a GF/C filter treated with wash buffer (50 mM Tris (pH 7.4)). Subsequently, the filter was washed 5 times with 0.3 mL of ice-cooled wash buffer. The filter was air-dried, and [$^{125}$I]-angiotensin II binding radioactivity was assayed with Top Count scintillation counter. Total binding was measured in the presence of 1% DMSO and nonspecific binding was measured in the presence of 1 μM candesartan. The binding data was analyzed by GraphPad Prism program and the $IC_{50}$ value (compound concentration showing 50% of the maximum value of inhibition percent) of the test compound was calculated. The results are shown in Tables 1 and 2.

Experimental Example 2

Evaluation of PPARγ Activating Action

PPARγ:RXR$_\alpha$:4ERPP/CHO-K1 cells obtained in the following Reference Example 5 were cultured in F12 medium [manufactured by INVITROGEN, USA] containing 10% fetal bovine serum [manufactured by MOREGATE, Australia], seeded in a 96-well half area white plate [manufactured by Corning Coster Corporation, USA] at the density of 5×10$^3$ cells/well and cultured in a $CO_2$ gas incubator at 37° C. overnight.

Then the medium was removed from the 96-well half area white plate, 45 μl of Ham's F12 medium containing 0.1% fatty acid-free bovine serum albumin (BSA) and 5 μl of test compound were added, and the cells were cultured in a $CO_2$ gas incubator at 37° C. for 1 day. The medium was removed and 20 μl of PicaGene 7.5 [manufactured by Dainippon Ink and Chemicals Corporation, Japan] diluted 2-fold with HBSS (HANKS' BALANCED SALT SOLUTION) [manufactured by BIO WHITTAKER, USA] was added. After stirring, the luciferase activity was determined using 1420 ARVO Multilabel Counter [manufactured by PerkinElmer, USA].

The percent (%) was calculated from the luciferase activity of each test compound when the luciferase activity of the control compound (compound X: 5-[3-(4-{[2-(2-furyl)-5-methyl-1,3-oxazol-4-yl]methoxy}-3-methoxyphenyl)propyl]-1,3-oxazolidine-2,4-dione) (1 μM) was 100% and that of the test compound non-administration group was 0%. The results are shown in Tables 1 and 2.

TABLE 1

| Example | AT1 receptor binding inhibitory action ($IC_{50}$ (nM)) | PPARγ activating action (activation % (1 μM)) |
|---|---|---|
| Ex. 56 | 0.34 | 65 |
| Ex. 58 | 1.6 | 27 |
| Ex. 59 | 1.2 | 58 |
| Ex. 60 | 1.0 | 42 |
| Ex. 63 | 1.1 | 31 |
| Ex. 73 | 1.5 | 35 |
| Ex. 76 | 1.0 | 27 |
| Ex. 83 | 0.77 | 37 |
| Ex. 99 | 1.2 | 56 |
| Ex. 105 | 1.0 | 34 |
| Ex. 107 | 1.1 | 43 |
| Ex. 109 | 1.4 | 64 |
| Ex. 116 | 1.8 | 38 |
| Ex. 117 | 1.8 | 62 |
| Ex. 121 | 1.7 | 28 |
| Ex. 127 | 1.4 | 53 |
| Ex. 129 | 1.6 | 61 |
| Ex. 130 | 1.6 | 56 |
| Ex. 131 | 1.2 | 72 |
| Ex. 132 | 1.7 | 50 |
| Ex. 135 | 1.5 | 71 |
| Ex. 136 | 1.5 | 36 |
| Ex. 140 | 1.7 | 26 |

TABLE 1-continued

| Example | AT1 receptor binding inhibitory action (IC$_{50}$ (nM)) | PPARγ activating action (activation % (1 μM)) |
|---|---|---|
| Ex. 142 | 1.5 | 38 |
| Ex. 143 | 1.4 | 45 |
| Ex. 144 | 1.7 | 40 |
| Ex. 145 | 1.7 | 36 |
| Ex. 148 | 1.5 | 33 |
| Ex. 149 | 1.8 | 50 |
| Ex. 150 | 1.5 | 33 |
| Ex. 152 | 1.5 | 40 |
| Ex. 153 | 1.3 | 39 |

TABLE 2

| Example | AT1 receptor binding inhibitory action (IC$_{50}$ (nM)) | PPARγ activating action (activation % (1 μM)) |
|---|---|---|
| Ex. 154 | 1.9 | 51 |
| Ex. 157 | 1.4 | 35 |
| Ex. 158 | 1.7 | 30 |
| Ex. 180 | 1.6 | 50 |
| Ex. 181 | 1.2 | 55 |
| Ex. 186 | 1.2 | 52 |
| Ex. 192 | 2.3 | 49 |
| Ex. 194 | 1.7 | 34 |
| Ex. 197 | 1.4 | 67 |
| Ex. 198 | 1.5 | 36 |
| Ex. 203 | 1.8 | 28 |
| Ex. 205 | 1.5 | 69 |
| Ex. 209 | 1.4 | 66 |
| Ex. 210 | 1.6 | 31 |
| Ex. 213 | 2.0 | 49 |
| Ex. 214 | 1.8 | 41 |
| Ex. 215 | 1.3 | 27 |
| Ex. 221 | 1.4 | 47 |
| Ex. 222 | 1.9 | 32 |
| Ex. 225 | 1.6 | 39 |

Reference Example 1

Cloning of Human PPARγ Gene

Human PPARγ gene was cloned by a PCR method using heart cDNA [manufactured by Toyobo Co., Ltd., QUICK-Clone cDNA] as a template, and a primer set shown below which was prepared by reference to the base sequence of PPARγ gene reported by Greene et al. [Gene Expr., 1995, vol. 4(4-5), pp. 281-299].

PAG-U:
(SEQ ID NO: 1)
5'-GTG GGT ACC GAA ATG ACC ATG GTT GAC ACA GAG-3'

PAG-L:
(SEQ ID NO: 2)
5'-GGG GTC GAC CAG GAC TCT CTG CTA GTA CAA GTC-3'

The PCR reaction was performed by Hot Start method using AmpliWax PCR Gem 100 [manufactured by Takara Shuzo Co., Ltd., Japan]. First, 2 μl of 10×LA PCR Buffer, 3 μl of 2.5 mM dNTP solution, 2.5 μl each of 12.5 μM primer solutions and 10 μl of sterile distilled water were mixed to obtain a bottom layer solution mixture. One μl of human heart cDNA (1 ng/ml) as a template, 3 μl of 10×LA PCR Buffer, 1 μl of 2.5 mM dNTP solution, 0.5 μl of TaKaRa LA Taq DNA polymerase [manufactured by Takara Shuzo Co., Ltd., Japan] and 24.5 μl of sterile distilled water were mixed to obtain a top layer solution mixture.

To the bottom layer solution mixture described above was added one unit of AmpliWax PCR Gem 100 [manufactured by Takara Shuzo Co., Ltd., Japan], which was treated at 70° C. for 5 minutes and then in ice for 5 minutes. Then, to the mixture was added the top layer solution mixture to prepare the reaction mixture for PCR. A tube containing the reaction mixture was set on a thermal cycler [manufactured by PerkinElmer, USA] and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 1.4 kb DNA fragment containing PPARγ gene was recovered from the gel, and then inserted into pT7 Blue-T vector [manufactured by Takara Shuzo Co., Ltd., Japan] to obtain plasmid pTBT-hPPARγ.

Reference Example 2

Cloning of Human RXR$_\alpha$ Gene

A human RXR$_\alpha$ gene was cloned by a PCR method using kidney cDNA [manufactured by Toyobo Co., Ltd., QUICK-Clone cDNA] as a template, and a primer set shown below which was prepared with reference to the base sequence of RXR$_\alpha$ gene reported by Mangelsdorf, D. J. et al. (Nature, 1990, vol. 345 (6272), pp. 224-229).

XRA-U:
(SEQ ID NO: 3)
5'-TTA GAA TTC GAC ATG GAC ACC AAA CAT TTC CTG-3'

XRA-L:
(SEQ ID NO: 4)
5'-CCC CTC GAG CTA AGT CAT TTG GTG CGG CGC CTC-3'

The PCR reaction was performed by Hot Start method using AmpliWax PCR Gem 100 [manufactured by Takara Shuzo Co., Ltd., Japan]. First, 2 μl of 10×LA PCR Buffer, 3 μl of 2.5 mM dNTP solution, 2.5 μl each of 12.5 μM primer solutions and 10 μl of sterile distilled water were mixed to obtain a bottom layer solution mixture. One μl of human kidney cDNA (1 ng/ml) as a template, 3 μl of 10×LA PCR Buffer, 1 μl of 2.5 mM dNTP solution, 0.5 μl of TaKaRa LA Taq DNA polymerase [manufactured by Takara Shuzo Co., Ltd., Japan] and 24.5 μl of sterile distilled water were mixed to obtain a top layer solution mixture.

To the bottom layer solution mixture described above was added one unit of AmpliWax PCR Gem 100 [manufactured by Takara Shuzo Co., Ltd., Japan], which was treated at 70° C. for 5 minutes and then in ice for 5 minutes. Then, to the mixture was added the top layer solution mixture to prepare the reaction mixture for PCR. A tube containing the reaction mixture was set on a thermal cycler [manufactured by PerkinElmer, USA] and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 1.4 kb DNA fragment containing RXRα gene was recovered from the gel, and then inserted into pT7 Blue-T vector [manufactured by Takara Shuzo Co., Ltd., Japan] to obtain plasmid pTBT-hRXRα.

Reference Example 3

Construction of Reporter Plasmid

A DNA fragment containing PPAR-response element (PPRE) of an acyl CoA oxidase was prepared using the following 5'-terminal phosphorylated synthetic DNA.

```
PPRE-U:
                                                     (SEQ ID NO: 5)
  5'-pTCGACAGGGGACCAGGACAAAGGTCACGTTCGGGAG-3'

PPRE-L:
                                                     (SEQ ID NO: 6)
  5'-pTCGACTCCCGAACGTGACCTTTGTCCTGGTCCCCTG-3'
```

First, PPRE-U and PPRE-L were annealed and inserted to SalI site of plasmid pBlueScript SK+. By determining the base sequence of the inserted fragment, plasmid pBSS-PPRE4, in which 4 PPREs were ligated in tandem, was selected.

An HSV thymidine kinase minimum promoter (TK promoter) region was cloned by a PCR method using pRL-TK vector [manufactured by Promega, USA] as a template, and a primer set shown below which was prepared with reference to the base sequence of the promoter region of thymidine kinase gene reported by Luckow, B et al. (Nucleic Acids Res., 1987, vol. 15(13), p. 5490)

```
                                                     (SEQ ID NO: 7)
  TK-U:  5'-CCCAGATCTCCCCAGCGTCTTGTCATTG-3'

(SEQ ID NO: 8)
  TK-L:  5'-TCACCATGGTCAAGCTTTTAAGCGGGTC-3'
```

The PCR reaction was performed by Hot Start method using AmpliWax PCR Gem 100 [manufactured by Takara Shuzo Co., Ltd., Japan]. First, 2 µl of 10×LA PCR Buffer, 3 µl of 2.5 mM dNTP solution, 2.5 µl each of 12.5 µM primer solutions and 10 µl of sterile distilled water were mixed to obtain a bottom layer solution mixture. One µl of pRL-TK vector [manufactured by Promega, USA] as a template, 3 µl of 10×LA PCR Buffer, 1 µl of 2.5 mM dNTP solution, 0.5 µl of TaKaRa A Taq DNA polymerase [manufactured by Takara Shuzo Co., Ltd., Japan] and 24.5 µl of sterile distilled water were mixed to obtain a top layer solution mixture.

To the bottom layer solution mixture described above was added one unit of AmpliWax PCR Gem 100 [manufactured by Takara Shuzo Co., Ltd., Japan], which was treated at 70° C. for 5 minutes and then in ice for 5 minutes. Then, to the mixture was added the top layer solution mixture to prepare the reaction mixture for PCR. A tube containing the reaction mixture was set on a thermal cycler [manufactured by PerkinElmer, USA] and treated at 95° C. for 2 minutes. Furthermore, after repeating the cycle of 95° C. for 15 seconds and 68° C. for 2 minutes 35 times, the tube was treated at 72° C. for 8 minutes.

The PCR product thus obtained was subjected to electrophoresis on agarose gel (1%), and 140 bp DNA fragment containing TK promoter was recovered from the gel, and then inserted into pT7 Blue-T vector [manufactured by Takara Shuzo Co., Ltd., Japan]. By digesting the plasmid thus obtained with the restriction enzymes BglII and NcoI, a fragment containing TK promoter was obtained, which was ligated to the BglII-NcoI fragment of plasmid pGL3-Basic vector [manufactured by Promega, USA] to obtain plasmid pGL3-TK.

A 4.9 kb NheI-XhoI fragment of plasmid pGL3-TK thus obtained was ligated to a 200 bp NheI-XhoI fragment of plasmid pBSS-PPRE4 to obtain plasmid pGL3-4ERPP-TK.

This plasmid pGL3-4ERPP-TK was digested with BamHI [manufactured by Takara Shuzo Co., Ltd., Japan], and then treated with T4DNA polymerase [manufactured by Takara Shuzo Co., Ltd., Japan] to form a blunt-end, whereby obtaining a DNA fragment.

On the other hand, pGFP-C1 [manufactured by Toyobo Co., Ltd., Japan] was digested with Bsu36I (manufactured by NEB, UK], and then treated with T4DNA polymerase [manufactured by Takara Shuzo Co., Ltd., Japan] to form a blunt-end whereby obtaining a 1.6 kb DNA fragment.

The both DNA fragments were ligated to construct a reporter plasmid pGL3-4ERPP-TK neo.

Reference Example 4

Preparation of Expression Plasmid for Human PPARγ and RXR$_\alpha$

A 7.8 kb FspI-NotI fragment of plasmid pVgRXR [manufactured by Invitrogen, USA] was ligated to a 0.9 kb FspI-NotI fragment containing RXR$_\alpha$ gene of plasmid pTBT-hRXR$_\alpha$ obtained in Reference Example 2 to prepare plasmid pVgRXR2. Then, pVgRXR2 was digested with BstXI, and then treated with T4DNA polymerase [manufactured by Takara Shuzo Co., Ltd., Japan] to give a blunt-ended product. Then digestion with KpnI gave a 6.5 kb DNA fragment.

On the other hand, plasmid pTBT-hPPARγ obtained in Reference Example 1 was digested with SalI, and then treated with T4DNA polymerase [manufactured by Takara Shuzo Co., Ltd.] to give a blunt-ended product. Then digestion with KpnI gave a 1.4 kb DNA fragment containing human PPARγ gene.

The both DNA fragments were ligated to construct plasmid pVgRXR2-hPPARγ.

Reference Example 5

Introduction of Human PPARγ- and RXR$_\alpha$-expression Plasmid and Reporter Plasmid into CHO-K1 Cell as Well as Establishment of Cell Expressing Same A CHO-K1 cell cultured in a 150 cm$^2$ cell culture flask [manufactured by Corning Costar Corporation, USA] containing Ham's F12 medium [manufactured by INVITROGEN, USA] supplemented with 10% fetal bovine serum [manufactured by INVITROGEN, USA] was scraped by treating with 0.5 g/L trypsin-0.2 g/L EDTA (ethylenediaminetetraacetic acid) [manufactured by Life Technologies, Inc., USA], and then the cell was washed with PBS (Phosphate-buffered saline) [manufactured by INVITROGEN, USA], centrifuged (1000 rpm, 5 minutes) and suspended in PBS. Subsequently, DNA was introduced into the cell under the conditions shown below using GENE PULSER [manufactured by Bio-Rad Laboratories, USA].

Namely, to a cuvette having a 0.4 cm gap were added 8×10$^6$ cells and 10 µg of plasmid pVgRXR2-hPPARγ obtained in Reference Example 4 and 10 µg of reporter plasmid pGL3-4ERPP-TKneo obtained in Reference Example 3, which was subjected to electroporation at the voltage of 0.25 kV under the capacitance of 960 µF. Subsequently, the cell was transferred into a F12 medium containing 10% fetal bovine serum and cultured for 24 hours, and then the cell was scraped again and centrifuged, and then suspended in Ham's F12 medium containing 10% fetal bovine serum supplemented with 500 µg/ml of Geneticin [manufactured by INVITROGEN, USA] and 250 µg/ml of Zeocin [manufactured by INVITROGEN, USA]. The obtained suspension was diluted to the density of 10$^4$ cells/ml and inoculated in a 96-well plate [manufactured by Corning Costar Corporation, USA], which was cultured in a CO$_2$ gas incubator at 37° C., whereby obtaining a Geneticin- and Zeocin-resistant transformant.

Subsequently, after the transformant strain thus obtained was cultured in a 24-well plate [manufactured by Corning Costar Corporation, USA], a strain in which the expression of luciferase was induced, i.e., PPARγ:RXRα:4ERPP/CHO-K1 cell was selected by the addition of 10 μM pioglitazone hydrochloride.

Preparation Example

When compound (I) of the present invention is used as an agent for the prophylaxis or treatment of circulatory diseases such as hypertension, cardiac disease, cerebral apoplexy, nephritis and the like or metabolic diseases such as hyperlipidemia, obesity, diabetes and the like, the compound can be used, for example, according to the following formulations. For example, using the compound of Example 1, a preparation having the following formulation can be produced.

Formulation Example 1

Capsule

| | |
|---|---|
| (1) compound of Example 1 | 10 mg |
| (2) lactose | 90 mg |
| (3) microcrystalline cellulose | 70 mg |
| (4) magnesium stearate | 10 mg |
| 1 capsule | 180 mg |

(1), (2), (3) and ½ of (4) are blended and granulated. The rest of (4) is added and the whole is encapsulated in a gelatin capsule.

Formulation Example 2

Tablet

| | |
|---|---|
| (1) the compound of Example 1 | 10 mg |
| (2) lactose | 35 mg |
| (3) cornstarch | 150 mg |
| (4) microcrystalline cellulose | 30 mg |
| (5) magnesium stearate | 5 mg |
| 1 tablet | 230 mg |

(1), (2), (3), ⅔ of (4) and ½ of (5) are blended and granulated. The rest of (4) and (5) are added to the granules and the mixture is compression molded to give tablet.

Formulation Example 3

Injection

| | |
|---|---|
| (1) the compound of Example 1 | 10 mg |
| (2) inositol | 100 mg |
| (3) benzyl alcohol | 20 mg |
| 1 ampoule | 130 mg |

(1), (2) and (3) are dissolved in distilled water for injection to the total amount of 2 mL and filled in an ampoule. All steps are performed under aseptic conditions.

[Sequencing List Free Text]
SEQ ID NO: 1: primer (PAG-U)
SEQ ID NO: 2: primer (PAG-L)
SEQ ID NO: 3: primer (XRA-U)
SEQ ID NO: 4: primer (XRA-L)
SEQ ID NO: 5: 5'-terminal phosphorylated synthetic DNA (PPRE-U)
SEQ ID NO: 6: 5'-terminal phosphorylated synthetic DNA (PPRE-L)
SEQ ID NO: 7: primer (TK-U)
SEQ ID NO: 8: primer (TK-L)

INDUSTRIAL APPLICABILITY

The compound of the present invention is useful as a medicament such as an agent for the prophylaxis or treatment of circulatory diseases such as hypertension, cardiac diseases (cardiac hypertrophy, cardiac failure, cardiac infarction and the like), arteriosclerosis, renal diseases (diabetic nephropathy, chronic glomerulonephritis and the like), cerebral apoplexy and the like and/or metabolic diseases such as hyperlipidemia (inclusive of hyper-triglyceride(TG)-emia, hypercholesterolemia, hypoHDL-emia, postprandial hyperlipemia and the like), obesity, diabetes and the like, central nervous disorders such as cerebral infarction and the like, mental diseases such as dementia, depression and the like, and the like.

This application is based on patent application No. 2007-134840 filed in Japan, and the contents disclosed therein are entirely incorporated in the present specification. In addition, the contents disclosed in patent documents and non-patent documents cited herein are hereby incorporated in their entireties by reference, to the extent that they have been disclosed herein.

The invention claimed is:

1. A compound represented by the formula (I):

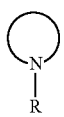

(I)

wherein a group represented by the formula:

is a group represented by the formula (a):

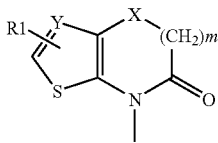

(a)

wherein,

R1 is a hydrogen atom, a $(C_1\text{-}C_6)$alkyl group optionally having substituent(s), a $(C_2\text{-}C_6)$alkenyl group optionally having substituent(s), a $(C_3\text{-}C_6)$cycloalkyl group optionally having substituent(s), a $(C_1\text{-}C_6)$alkoxy group optionally having substituent(s), a $(C_1\text{-}C_6)$alkylthio group optionally having substituent(s), a $(C_1\text{-}C_6)$alkylsulfinyl group optionally having substituent(s), or a $(C_1\text{-}C_6)$alkylsulfonyl group optionally having substituent(s);

X is a group represented by the formula: CO—X1 wherein X1 is a group represented by the formula: N(R4) wherein R4 is a hydrogen atom, a $(C_1\text{-}C_6)$alkyl group optionally having substituent(s), or a cyclic group optionally having substituent(s)

Y is a group represented by the formula: C(R7) wherein R7 is a hydrogen atom; and m is 0; and R is a group represented by the formula:

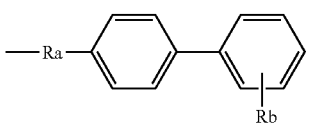

wherein,

Ra is a $(C_1\text{-}C_6)$alkylene group optionally having substituent(s), or a group represented by the formula: —O-Rc-, -Rc-O—, —N(Rd)-Rc- or -Rc-N(Rd)- wherein Rc is a bond, or a $(C_1\text{-}C_6)$alkylene group optionally having substituent(s), and Rd is a $(C_1\text{-}C_6)$alkyl group optionally having substituent(s), or a $(C_3\text{-}C_6)$cycloalkyl group optionally having substituent(s); and Rb is a group represented by the formula:

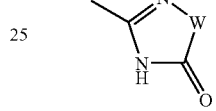

wherein W is an oxygen atom or a sulfur atom, which optionally has substituent(s), wherein the biphenyl group optionally further having substituent(s), or a salt thereof 2. The compound according to claim 1, which is represented by the formula:

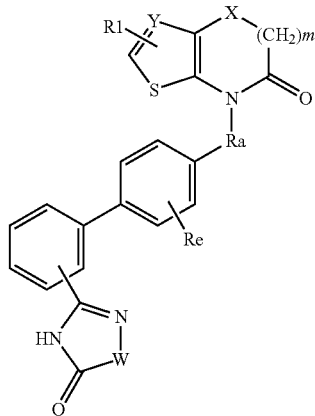

wherein R1, Ra, W, X, Y and m are each as defined in claim 1, and Re is a hydrogen atom or halogen.

3. The compound according to claim 2, wherein R1 is a $(C_1\text{-}C_6)$alkyl group optionally having substituent(s), a $(C_2\text{-}C_6)$alkenyl group optionally having substituent(s), or a $(C_3\text{-}C_6)$cycloalkyl group optionally having substituent(s);

Ra is a methylene group;

W is O; and

Re is a hydrogen atom or halogen.

4. 6-Ethyl-3-[2-(4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione or a salt thereof.

5. 6-Ethyl-3-[2-(3-fluoro-4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione or a salt thereof.

6. 6-Ethyl-3-[2-(2-fluoro-4-methoxyphenyl)-2-oxoethyl]-1-{[2'-(5-oxo-4,5-dihydro-1,2,4-oxadiazol-3-yl)biphenyl-4-yl]methyl}thieno[2,3-d]pyrimidine-2,4(1H,3H)-dione or a salt thereof.

7. 6-Ethyl-1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione or a salt thereof.

8. 6-Cyclopropyl-1-{[3-fluoro-2'-(5-oxo-4,5-dihydro-1,2,4-oxadiazol-3-yl)biphenyl-4-yl]methyl}-3-[2-(4-methoxyphenyl)-2-oxoethyl]thieno[2,3-d]pyrimidine-2,4(1H,3H)-dione or a salt thereof.

9. A pharmaceutical agent comprising the compound according to claim 1 as an active ingredient and a pharmacologically acceptable carrier.

10. The pharmaceutical agent according to claim 9, which has an angiotensin II receptor inhibitory activity and/or a peroxisomal proliferator-activated receptor agonistic activity.

* * * * *

SEQUENCE LISTING

<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: primer (PAG-U)

<400> SEQUENCE: 1
gtgggtaccg aaatgaccat ggttgacaca gag          33

<210> SEQ ID NO 2

-continued

```
<211> LENGTH: 33
<212> TYPE: DNA
<213> ORGANISM: Artificial Sequence
<220> FEATURE:
<223> OTHER INFORMATION: primer (PAG-L)

<400> SEQUENCE: 2
ggggtcgacc aggactctct gctagtacaa gtc                                33

<210> SEQ ID NO 3
<211> LENGTH: 33
<212> TYPE: DNA
<213> ORGANISM: Artificial Sequence
<220> FEATURE:
<223> OTHER INFORMATION: primer (XRA-U)

<400> SEQUENCE: 3
ttagaattcg acatggacac caaacatttc ctg                                33

<210> SEQ ID NO 4
<211> LENGTH: 33
<212> TYPE: DNA
<213> ORGANISM: Artificial Sequence
<220> FEATURE:
<223> OTHER INFORMATION: primer (XRA-L)

<400> SEQUENCE: 4
cccctcgagc taagtcattt ggtgcggcgc ctc                                33

<210> SEQ ID NO 5
<211> LENGTH: 36
<212> TYPE: DNA
<213> ORGANISM: Artificial Sequence
<220> FEATURE:
<223> OTHER INFORMATION: 5'-phosphorylated DNA (PPRE-U)
<220> FEATURE:
<221> NAME/KEY: misc_feature
<222> LOCATION: (1)..(1)
<223> OTHER INFORMATION: phosphorylated

<400> SEQUENCE: 5
tcgacagggg accaggacaa aggtcacgtt cgggag                             36

<210> SEQ ID NO 6
<211> LENGTH: 36
<212> TYPE: DNA
<213> ORGANISM: Artificial Sequence
<220> FEATURE:
<223> OTHER INFORMATION: 5'-phosphorylated DNA (PPRE-L)
<220> FEATURE:
<221> NAME/KEY: misc_feature
<222> LOCATION: (1)..(1)
<223> OTHER INFORMATION: phosphorylated

<400> SEQUENCE: 6
tcgactcccg aacgtgacct ttgtcctggt cccctg                             36

<210> SEQ ID NO 7
<211> LENGTH: 28
<212> TYPE: DNA
<213> ORGANISM: Artificial Sequence
<220> FEATURE:
<223> OTHER INFORMATION: primer (TK-U)

<400> SEQUENCE: 7
cccagatctc cccagcgtct tgtcattg                                      28

<210> SEQ ID NO 8
```

```
<211> LENGTH: 28
<212> TYPE: DNA
<213> ORGANISM: Artificial Sequence
<220> FEATURE:
<223> OTHER INFORMATION: primer (TK-L)

<400> SEQUENCE: 8
tcaccatggt caagcttta agcgggtc                                              28
```